US012005081B2

(12) United States Patent
Garrison et al.

(10) Patent No.: US 12,005,081 B2
(45) Date of Patent: Jun. 11, 2024

(54) CHIMERIC RECEPTORS AND METHODS OF USE THEREOF

(71) Applicant: Senti Biosciences, Inc., South San Francisco, CA (US)

(72) Inventors: Brian Scott Garrison, Saratoga, CA (US); Jennifer Chien, Fremont, CA (US); Kathryn Armstrong Loving, Berkeley, CA (US); Russell Morrison Gordley, San Francisco, CA (US); Michelle Elizabeth Hung, South San Francisco, CA (US)

(73) Assignee: Senti Biosciences, Inc., South San Francisco, CA (US)

( * ) Notice: Subject to any disclaimer, the term of this patent is extended or adjusted under 35 U.S.C. 154(b) by 0 days.

(21) Appl. No.: 17/338,528

(22) Filed: Jun. 3, 2021

(65) Prior Publication Data

US 2021/0299177 A1 Sep. 30, 2021

Related U.S. Application Data

(63) Continuation of application No. PCT/US2020/030640, filed on Apr. 30, 2020.

(60) Provisional application No. 62/893,106, filed on Aug. 28, 2019, provisional application No. 62/854,151, filed on May 29, 2019, provisional application No. 62/841,128, filed on Apr. 30, 2019.

(51) Int. Cl.

| | |
|---|---|
| ***A61K 35/17*** | (2015.01) |
| ***A61K 39/00*** | (2006.01) |
| ***C07K 14/725*** | (2006.01) |
| ***C07K 16/28*** | (2006.01) |
| ***C07K 16/30*** | (2006.01) |
| ***C07K 16/40*** | (2006.01) |
| ***C07K 16/46*** | (2006.01) |
| *A61K 38/00* | (2006.01) |

(52) U.S. Cl.
CPC .......... *A61K 35/17* (2013.01); *C07K 14/7051* (2013.01); *C07K 16/2803* (2013.01); *C07K 16/2863* (2013.01); *A61K 38/00* (2013.01); *C07K 2317/565* (2013.01); *C07K 2317/622* (2013.01); *C07K 2319/03* (2013.01)

(58) Field of Classification Search
None
See application file for complete search history.

(56) References Cited

U.S. PATENT DOCUMENTS

| | | | |
|---|---|---|---|
| 4,816,397 | A | 3/1989 | Boss et al. |
| 4,816,567 | A | 3/1989 | Cabilly et al. |
| 4,946,778 | A | 8/1990 | Ladner et al. |
| 5,225,539 | A | 7/1993 | Winter |
| 5,399,346 | A | 3/1995 | Anderson et al. |
| 5,589,466 | A | 12/1996 | Felgner et al. |
| 5,635,388 | A | 6/1997 | Bennett et al. |
| 5,693,761 | A | 12/1997 | Queen et al. |
| 5,693,762 | A | 12/1997 | Queen et al. |
| 5,712,149 | A | 1/1998 | Roberts |
| 5,739,116 | A | 4/1998 | Hamann et al. |
| 5,773,001 | A | 6/1998 | Hamann et al. |
| 5,777,084 | A | 7/1998 | Buhring |
| 6,083,751 | A | 7/2000 | Feldhaus et al. |
| 6,103,521 | A | 8/2000 | Capon et al. |
| 6,156,882 | A | 12/2000 | Buhring et al. |
| 6,326,193 | B1 | 12/2001 | Liu et al. |
| 6,703,199 | B1 | 3/2004 | Koide |
| 7,022,500 | B1 | 4/2006 | Queen et al. |
| 7,183,385 | B2 | 2/2007 | Comb et al. |
| 7,304,149 | B2 | 12/2007 | Murphy et al. |
| 7,446,190 | B2 | 11/2008 | Sadelain et al. |
| 7,557,189 | B2 | 7/2009 | Hoffee et al. |
| 7,695,716 | B2 | 4/2010 | Drachman et al. |
| 7,741,443 | B2 | 6/2010 | van den Oudenrijn et al. |
| 7,741,465 | B1 | 6/2010 | Eshhar et al. |
| 8,071,099 | B2 | 12/2011 | Li et al. |
| 8,759,494 | B2 | 6/2014 | Bachmann et al. |
| 9,023,996 | B2 | 5/2015 | Grosse-Hovest et al. |
| 9,045,562 | B2 | 6/2015 | Murphy et al. |
| 9,079,958 | B2 | 7/2015 | Konopitzky et al. |
| 9,212,229 | B2 | 12/2015 | Schonfeld et al. |
| 9,447,194 | B2 | 9/2016 | Jensen |
| 9,587,019 | B2 | 3/2017 | Sutherland et al. |
| 9,745,368 | B2 | 8/2017 | Milone et al. |
| 9,777,061 | B2 | 10/2017 | Ebersbach et al. |
| 9,815,908 | B2 | 11/2017 | Schonfeld et al. |
| 9,944,702 | B2 | 4/2018 | Galetto |
| 9,951,133 | B2 | 4/2018 | Yu et al. |
| 9,974,865 | B2 | 5/2018 | Lowe et al. |
| 10,071,118 | B2 | 9/2018 | Katz et al. |

(Continued)

FOREIGN PATENT DOCUMENTS

| | | | |
|---|---|---|---|
| AU | 2021200929 | A1 | 3/2021 |
| AU | 2020200751 | B2 | 7/2021 |

(Continued)

OTHER PUBLICATIONS

Albinger et al., Current status and perspective of CAR-T and CAR-NK cell therapy trials in Germany, Gene Therapy, 2020, pp. 1-15.*
Buonaguro etal, Translating Tumor Antigens into Cancer Vaccines, Clinical and Vaccine Immunology, Jan. 2011, p. 23-34.*
Hollingsworth and Jansen, Turning the corner on therapeutic cancer vaccines, npj Vaccines (2019), pp. 1-10.*

(Continued)

*Primary Examiner* — Maria Marvich
(74) *Attorney, Agent, or Firm* — Goodwin Procter LLP

(57) ABSTRACT

Provided herein are acute myeloid leukemia antigen targets for chimeric receptors and methods of using same.

28 Claims, 69 Drawing Sheets

Specification includes a Sequence Listing.

(56) References Cited

U.S. PATENT DOCUMENTS

| | | | |
|---|---|---|---|
| 10,117,896 B2 | 11/2018 | Powell, Jr. et al. | |
| 10,117,897 B2 | 11/2018 | Sadelain et al. | |
| 10,172,885 B2 | 1/2019 | Pule et al. | |
| 10,172,886 B2 | 1/2019 | Pule et al. | |
| 10,426,797 B2 | 10/2019 | Orentas et al. | |
| 10,428,305 B2 | 10/2019 | Campana et al. | |
| 10,577,417 B2 | 3/2020 | Beatty et al. | |
| 10,829,556 B2 | 11/2020 | Jensen | |
| 10,851,166 B2 | 12/2020 | Ebersbach et al. | |
| 10,865,231 B2 | 12/2020 | Maher et al. | |
| 2005/0113564 A1 | 5/2005 | Campana et al. | |
| 2006/0247191 A1 | 11/2006 | Finney et al. | |
| 2008/0160018 A1 | 7/2008 | Queen et al. | |
| 2009/0297529 A1 | 12/2009 | Li et al. | |
| 2010/0184671 A1 | 7/2010 | van den Oudenrijn et al. | |
| 2011/0091470 A1* | 4/2011 | Li | A61K 39/395 424/139.1 |
| 2012/0148552 A1 | 6/2012 | Jensen | |
| 2013/0280220 A1 | 10/2013 | Ahmed et al. | |
| 2013/0287748 A1 | 10/2013 | June et al. | |
| 2014/0120118 A1 | 5/2014 | Howard | |
| 2015/0376296 A1 | 12/2015 | Fedorov et al. | |
| 2016/0096892 A1* | 4/2016 | Brogdon | A61K 35/28 435/328 |
| 2016/0289293 A1 | 10/2016 | Pule et al. | |
| 2016/0289294 A1 | 10/2016 | Pule et al. | |
| 2016/0296562 A1 | 10/2016 | Pule et al. | |
| 2016/0303230 A1 | 10/2016 | Ahmed et al. | |
| 2017/0037149 A1 | 2/2017 | Raum et al. | |
| 2017/0209492 A1 | 7/2017 | June et al. | |
| 2017/0246278 A1 | 8/2017 | Vera Valdes et al. | |
| 2017/0281766 A1 | 10/2017 | Wiltzius | |
| 2017/0296623 A1 | 10/2017 | Juillerat et al. | |
| 2018/0002397 A1 | 1/2018 | Shah et al. | |
| 2018/0002438 A1 | 1/2018 | Kaufman et al. | |
| 2018/0021378 A1 | 1/2018 | Kang et al. | |
| 2018/0022795 A1 | 1/2018 | Milone et al. | |
| 2018/0044399 A1 | 2/2018 | Rajpal et al. | |
| 2018/0044404 A1 | 2/2018 | Oda et al. | |
| 2018/0044424 A1 | 2/2018 | June et al. | |
| 2018/0104321 A1 | 4/2018 | Pule et al. | |
| 2018/0111993 A1 | 4/2018 | Pule et al. | |
| 2018/0118838 A1 | 5/2018 | Yu et al. | |
| 2018/0280438 A1 | 10/2018 | Orentas et al. | |
| 2018/0291080 A1 | 10/2018 | Sentman et al. | |
| 2018/0305433 A1 | 10/2018 | Pule et al. | |
| 2019/0002560 A1 | 1/2019 | Monroe et al. | |
| 2019/0031759 A1 | 1/2019 | Reiter et al. | |
| 2019/0091310 A1 | 3/2019 | Wright et al. | |
| 2019/0125797 A1 | 5/2019 | Powell, Jr. et al. | |
| 2019/0134093 A1 | 5/2019 | Lim et al. | |
| 2019/0144515 A1 | 5/2019 | Sievers et al. | |
| 2019/0183931 A1 | 6/2019 | Alice et al. | |
| 2019/0192691 A1 | 6/2019 | Obsidian | |
| 2019/0225697 A1 | 7/2019 | Chien et al. | |
| 2019/0241641 A1 | 8/2019 | Orentas et al. | |
| 2019/0248869 A1 | 8/2019 | Gross et al. | |
| 2019/0255108 A1 | 8/2019 | Ma et al. | |
| 2019/0336533 A1 | 11/2019 | Hwang et al. | |
| 2019/0345218 A1 | 11/2019 | Maus | |
| 2020/0016204 A1 | 1/2020 | Pule et al. | |
| 2020/0048322 A1 | 2/2020 | Li et al. | |
| 2020/0085872 A1 | 3/2020 | Rezvani et al. | |
| 2020/0101109 A1 | 4/2020 | Orentas et al. | |
| 2020/0113940 A1 | 4/2020 | Maus et al. | |
| 2020/0129554 A1 | 4/2020 | Davila | |
| 2020/0147134 A1 | 5/2020 | Qin et al. | |
| 2020/0148767 A1 | 5/2020 | Walter et al. | |
| 2020/0216534 A1 | 7/2020 | Davila | |
| 2020/0223920 A1 | 7/2020 | Davila | |
| 2020/0261499 A1* | 8/2020 | Gross | C07K 14/70521 |
| 2020/0283729 A1 | 9/2020 | Loew et al. | |
| 2020/0316120 A1* | 10/2020 | Gross | C12Q 1/6886 |
| 2020/0317777 A1 | 10/2020 | Sadelain et al. | |
| 2020/0384029 A1 | 12/2020 | Riley et al. | |
| 2021/0017277 A1 | 1/2021 | Qin et al. | |
| 2021/0030793 A1 | 2/2021 | Geiger et al. | |
| 2021/0032661 A1 | 2/2021 | Powell et al. | |
| 2021/0038645 A1 | 2/2021 | Soon-Shiong et al. | |
| 2021/0061877 A1 | 3/2021 | Marasco | |
| 2021/0077532 A1 | 3/2021 | Xiao et al. | |
| 2021/0079061 A1 | 3/2021 | Salter et al. | |
| 2021/0101976 A1* | 4/2021 | Chang | C07K 16/2851 |
| 2021/0137983 A1 | 5/2021 | Xiao et al. | |
| 2021/0161961 A1 | 6/2021 | Xiao et al. | |
| 2021/0187026 A1 | 6/2021 | Pule et al. | |

FOREIGN PATENT DOCUMENTS

| | | | |
|---|---|---|---|
| CA | 3091224 | A1 | 9/2019 |
| CA | 2930215 | C | 4/2021 |
| CN | 105384823 | A | 3/2016 |
| CN | 105820255 | A | 8/2016 |
| CN | 106749675 | A | 5/2017 |
| CN | 107353343 | A | 11/2017 |
| CN | 107735407 | A | 2/2018 |
| CN | 108047333 | A | 5/2018 |
| CN | 108060136 | A | 5/2018 |
| CN | 104829733 | B | 6/2018 |
| CN | 105384825 | B | 6/2018 |
| CN | 108251442 | A | 7/2018 |
| CN | 108473557 | A | 8/2018 |
| CN | 104877032 | B | 12/2018 |
| CN | 109843922 | A | 6/2019 |
| CN | 110191898 | A | 8/2019 |
| CN | 110616191 | A | 12/2019 |
| CN | 112390894 | A | 2/2021 |
| CN | 112500492 | A | 3/2021 |
| CN | 112501125 | A | 3/2021 |
| CN | 108047333 | B | 5/2021 |
| EP | 0120694 | A2 | 10/1984 |
| EP | 0239400 | A2 | 9/1987 |
| EP | 0125023 | B1 | 6/1991 |
| EP | 0451216 | A1 | 10/1991 |
| EP | 0519596 | | 12/1992 |
| EP | 0194276 | B1 | 8/1993 |
| EP | 3006459 | A1 | 4/2016 |
| EP | 3331920 | A4 | 4/2019 |
| EP | 3594245 | A1 | 1/2020 |
| EP | 3597215 | A1 | 1/2020 |
| EP | 3626261 | A1 | 3/2020 |
| EP | 3593812 | | 5/2020 |
| EP | 3593812 | A3 | 5/2020 |
| EP | 3743513 | A1 | 12/2020 |
| EP | 3755348 | A1 | 12/2020 |
| EP | 3755721 | A1 | 12/2020 |
| JP | 2017522880 | A | 8/2017 |
| JP | 6673848 | B2 | 3/2020 |
| JP | 2021500882 | A | 1/2021 |
| JP | 2021042223 | A | 3/2021 |
| JP | 2021514206 | A | 6/2021 |
| KR | 100231090 | B1 | 11/1999 |
| KR | 20200131867 | A | 11/2020 |
| RU | 2017125531 | A | 1/2019 |
| RU | 2015116901 | C2 | 8/2020 |
| TW | I719942 | B | 3/2021 |
| WO | 1986/01533 | A1 | 3/1986 |
| WO | 2001/29058 | A1 | 4/2001 |
| WO | 2001/32867 | A1 | 5/2001 |
| WO | 2001/32866 | A3 | 11/2001 |
| WO | 2001/96584 | A2 | 12/2001 |
| WO | 2012/079000 | A4 | 8/2012 |
| WO | 2012/138475 | A1 | 10/2012 |
| WO | 2014/055442 | A2 | 4/2014 |
| WO | 2014/055657 | A1 | 4/2014 |
| WO | 2014/145252 | A3 | 12/2014 |
| WO | 2015/075469 | A1 | 5/2015 |
| WO | 2015/075470 | A1 | 5/2015 |
| WO | 2015075468 | A1 | 5/2015 |
| WO | 2015/142314 | | 10/2015 |
| WO | 2015/142314 | A8 | 10/2015 |
| WO | 2016/075612 | A1 | 5/2016 |
| WO | 2016/097231 | A2 | 6/2016 |
| WO | 2016/109668 | A1 | 7/2016 |

(56) References Cited

FOREIGN PATENT DOCUMENTS

| | | | | |
|---|---|---|---|---|
| WO | 2016/100985 | | 8/2016 | |
| WO | 2016/100985 | A3 | 8/2016 | |
| WO | 2016/126608 | A1 | 8/2016 | |
| WO | 2016/141357 | A1 | 9/2016 | |
| WO | 2016/174407 | A1 | 11/2016 | |
| WO | 2016/179319 | A1 | 11/2016 | |
| WO | 2016/201389 | A2 | 12/2016 | |
| WO | 2016/210293 | A1 | 12/2016 | |
| WO | 2017/011804 | A1 | 1/2017 | |
| WO | 2017/068361 | A1 | 4/2017 | |
| WO | 2017/143076 | A9 | 10/2017 | |
| WO | 2017/173410 | A1 | 10/2017 | |
| WO | 2017/176760 | A2 | 10/2017 | |
| WO | 2017/180587 | A2 | 10/2017 | |
| WO | 2017/190100 | A1 | 11/2017 | |
| WO | 2017/193059 | A1 | 11/2017 | |
| WO | 2017/205747 | A1 | 11/2017 | |
| WO | 2017/180587 | A3 | 12/2017 | |
| WO | 2017/222593 | A1 | 12/2017 | |
| WO | 2017/181119 | A3 | 1/2018 | |
| WO | 2018/027197 | A1 | 2/2018 | |
| WO | 2018/061012 | A1 | 4/2018 | |
| WO | 2018/073394 | A1 | 4/2018 | |
| WO | 2018/119279 | A1 | 6/2018 | |
| WO | 2018/102795 | | 7/2018 | |
| WO | 2018/102795 | A3 | 7/2018 | |
| WO | 2018/118494 | A9 | 7/2018 | |
| WO | 2018/132427 | A1 | 7/2018 | |
| WO | 2018/175988 | A1 | 9/2018 | |
| WO | 2018/183941 | A2 | 10/2018 | |
| WO | 2018/191748 | A1 | 10/2018 | |
| WO | 2018/195339 | A1 | 10/2018 | |
| WO | 2018/213337 | A1 | 11/2018 | |
| WO | 2018/218207 | A1 | 11/2018 | |
| WO | 2018/222935 | A1 | 12/2018 | |
| WO | 2018/223600 | A1 | 12/2018 | |
| WO | WO-2018/237022 | A1 | 12/2018 | |
| WO | 2019/010383 | A1 | 1/2019 | |
| WO | 2019/018382 | A1 | 1/2019 | |
| WO | 2019/025484 | A1 | 2/2019 | |
| WO | 2019/060174 | A1 | 3/2019 | |
| WO | 2019/068007 | A1 | 4/2019 | |
| WO | WO-2019/075395 | A1 | 4/2019 | |
| WO | 2019/051424 | A9 | 5/2019 | |
| WO | 2019/089813 | A1 | 5/2019 | |
| WO | 2019/099707 | A1 | 5/2019 | |
| WO | 2019/126724 | A1 | 6/2019 | |
| WO | 2019/164929 | A1 | 8/2019 | |
| WO | 2019/165116 | A1 | 8/2019 | |
| WO | 2019/177986 | A1 | 9/2019 | |
| WO | 2019/178382 | A1 | 9/2019 | |
| WO | 2019/178463 | A1 | 9/2019 | |
| WO | 2019/178518 | A1 | 9/2019 | |
| WO | 2019/210293 | A1 | 10/2019 | |
| WO | 2019/231920 | A1 | 12/2019 | |
| WO | WO-2020035676 | A1 * | 2/2020 | ..... A61K 39/001129 |
| WO | 2020/077356 | A1 | 4/2020 | |
| WO | 2020/065406 | A3 | 7/2020 | |
| WO | 2020/146743 | A1 | 7/2020 | |
| WO | 2020/146706 | A3 | 9/2020 | |
| WO | 2020/210719 | A1 | 10/2020 | |
| WO | 2020/219425 | A1 | 10/2020 | |
| WO | 2020/223445 | A1 | 11/2020 | |
| WO | 2020/228825 | A1 | 11/2020 | |
| WO | 2020/247837 | A1 | 12/2020 | |
| WO | 2020/261231 | A1 | 12/2020 | |
| WO | 2020/243713 | | 1/2021 | |
| WO | 2020/243713 | A3 | 1/2021 | |
| WO | 2021/027795 | A1 | 2/2021 | |
| WO | 2021/027867 | A1 | 2/2021 | |
| WO | 2021/030149 | A1 | 2/2021 | |
| WO | 2021/013274 | A3 | 3/2021 | |
| WO | 2021/096868 | A1 | 5/2021 | |
| WO | 2021/119489 | A1 | 6/2021 | |

OTHER PUBLICATIONS

Durgeau et al., Recent Advances in Targeting CD8 T-Cell Immunity for More Effective Cancer Immunotherapy, Front. Immunol., Jan. 22, 2018, pp. 1-14.*

Cadhila etal, Enabling T Cell Recruitment to Tumours as a Strategy for Improving Adoptive T Cell Therapy, European Oncology & Haematology, 2017, pp. 66-73.*

Murthy et al., Local Immunotherapy of Cancer: Innovative Approaches to Harnessing Tumor-Specific Immune Responses, JNCI J Natl Cancer Inst (2017), pp. 1-12.*

Garrison et al, Precise Targeting of AML With OR/NOT Logic Gated Gene Circuits in CAR NK Cells, ASGCT Abstract #77, May 12, 2021, pp. 1-26.*

Garrison et al., FLT3 or CD33 Not EMCN Logic Gated CAR-NK Cell Therapy (SENTI-202) for Precise Targeting of AML, Abstract: 2799, Jul. 9, 2019, p. 1.*

Kjeldsen, E, A Novel Acquired t(2;4)(q36.1;q24) with a Concurrent Submicroscopic del(4)(q23q24) in An Adult with Polycythemia Vera, Cancers 2018, pp. 1-5.*

Garrison et al., "Precise Targeting of AML With OR/NOT Logic-Gated Gene Circuits in CAR-NK Cells," Senti Bio, ASGCT-Abstract #77, 2021, 26 pages.

PCT/US2020/030640—International Search Report and Written Opinion, dated Sep. 4, 2020, 29 pages.

Gordley et al., "Modular engineering of cellular signaling proteins and networks." Current opinion in structural biology 39 (2016): 106-114.

Pule et al., "Virus-specific T cells engineered to coexpress tumor-specific receptors: persistence and antitumor activity in individuals with neuroblastoma." Nature medicine 14, No. 11 (2008): 1264-1270.

Maude et al., "Chimeric antigen receptor T cells for sustained remissions in leukemia." New England Journal of Medicine 371, No. 16 (2014): 1507-1517.

Brentjens et al., "CD19-targeted T cells rapidly induce molecular remissions in adults with chemotherapy—refractory acute lymphoblastic leukemia." Science translational medicine 5, No. 177 (2013): 177ra38-177ra38.

Stanford et al., "Regulation of TCR signalling by tyrosine phosphatases: from immune homeostasis to autoimmunity." Immunology 137, No. 1 (2012): 1-19.

Willemsen et al., "Grafting primary human T lymphocytes with cancer-specific chimeric single chain and two chain TCR." Gene therapy 7, No. 16 (2000): 1369-1377.

Zhang et al., "Transgenic TCR expression: comparison of single chain with full-length receptor constructs for T-cell function." Cancer gene therapy 11, No. 7 (2004): 487-496.

Aggen et al., "Single-chain V?V? T-cell receptors function without mispairing with endogenous TCR chains." Gene therapy 19, No. 4 (2012): 365-374.

Valton et al., "A multidrug-resistant engineered Car T cell for allogeneic combination immunotherapy." Molecular Therapy 23, No. 9 (2015): 1507-1518.

Torikai et al., "A foundation for universal T-cell based immunotherapy: T cells engineered to express a CD19-specific chimeric-antigen-receptor and eliminate expression of endogenous TCR." Blood, The Journal of the American Society of Hematology 119, No. 24 (2012): 5697-5705.

Samulowitz et al., "Human endomucin: distribution pattern, expression on high endothelial venules, and decoration with the MECA-79 epitope." The American journal of pathology 160, No. 5 (2002): 1669-1681.

Craddock et al., "Enhanced tumor trafficking of GD2 chimeric antigen receptor T cells by expression of the chemokine receptor CCR2b", Journal of immunotherapy (2010), 33(8), 780-788.

Kershaw et al., "Redirecting migration of T cells to chemokine secreted from tumors by genetic modification with CXCR2." Human gene therapy 13, No. 16 (2002): 1971-1980.

Di Stasi et al., "Inducible apoptosis as a safety switch for adoptive cell therapy." N Engl J Med 365 (2011): 1673-1683.

(56) References Cited

OTHER PUBLICATIONS

Chicaybam et al., "Car T cells generated using sleeping beauty transposon vectors and expanded with an EBV—transformed lymphoblastoid cell line display antitumor activity in vitro and in vivo." Human gene therapy 30, No. 4 (2019): 511-522.
Ptackova et al., "A new approach to CAR T-cell gene engineering and cultivation using piggyBac transposon in the presence of IL-4, IL-7 and IL-21." Cytotherapy 20, No. 4 (2018): 507-520.
Shalapour et al., "Immunosuppressive plasma cells impede T-cell-dependent immunogenic chemotherapy." Nature 621, No. 7550 (2015): 94-98.
Reiter et al., "Tyrosine kinase inhibition increases the cell surface localization of FLT3-ITD and enhances FLT3-directed immunotherapy of acute myeloid leukemia." Leukemia 32, No. 2 (2018): 313-322.
Kearney et al., "Loss of DNAM-1 ligand expression by acute myeloid leukemia cells renders them resistant to NK cell killing." Oncoimmunology 5, No. 8 (2016): e1196308.
Holliger et al., "Engineered antibody fragments and the rise of single domains." Nature biotechnology 23, No. 9 (2005): 1126-1136.
Dohner, et al., "Diagnosis and management of AML in adults: 2017 ELN recommendations from an international expert panel", Blood, Jan. 2017, vol. 129, No. 4: pp. 424-447. Epub Nov. 28, 2016. doi: 10.1182/blood-2016-08-733196.
Liu, et al., "First-in-Human CLL1-CD33 Compound CART Cell Therapy Induces Complete Remission in Patients with Refractory Acute Myeloid Leukemia: Update on Phase 1 Clinical Trial", Blood, Nov. 2018, vol. 132: p. 901 (3 pages). DOI: 10.1182/BLOOD-2018-99-110579.
EP 20798134.1—Extended European Search Report, dated Jun. 28, 2023, 32 pages.

* cited by examiner

FLT3

CD33

CLEC12A

CD312/ADGRE2

SLC22A16

CD123/ILR3RA

LAT2

PIEZO1/FAM38A

CD38

EMB

CD131/CSF2RB

P2RY8

LILRA2/CD85H

SLC17A9

MYADM

CD300LF

CD244/SLAMF4

PLAUR

CD93

SPNS3

GAPT

RASGRP4

CD117/C-Kit

CD123/ILR3RA

EMCN (Endomucin)

JAM2

MS4A15

SLC34A2

SLC2A2

TRPM1

SCTR

KCNQ2

PERP

TNF-α

IFN-γ

IL-2

TNF-α

IFN-γ

IL-2

TNF-α

IFN-γ

IL-2

TNF-α

IFN-γ

IL-2

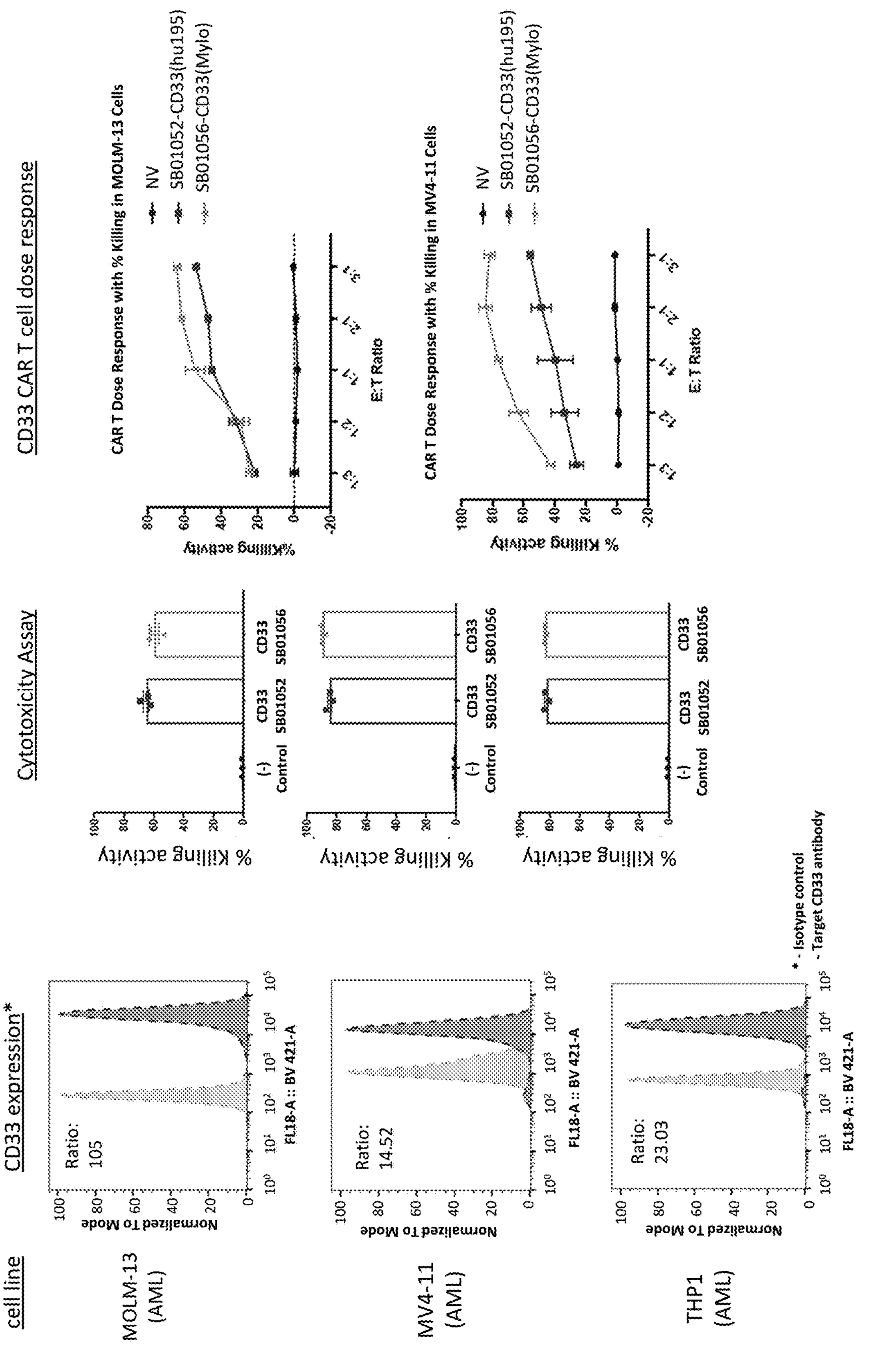
FIG. 42A
FIG. 42B
FIG. 42C
cell line
MOLM-13 (AML)
MV4-11 (AML)
THP1 (AML)
CD33 expression*
Ratio: 105
Ratio: 14.52
Ratio: 23.03
Normalized To Mode
FL18-A :: BV 421-A
* - Isotype control
- Target CD33 antibody
Cytotoxicity Assay
% Killing activity
(-) Control
CD33 SB01052
CD33 SB01056
CD33 CAR T cell dose response
CAR T Dose Response with % Killing in MOLM-13 Cells
CAR T Dose Response with % Killing in MV4-11 Cells
%Killing activity
% Killing activity
E:T Ratio
NV
SB01052-CD33(hu195)
SB01056-CD33(Mylo)

MOLM-13

MV4-11

THP-1
IL-2 (pg/ml)
IFN-γ (pg/ml)
TNF-α (pg/ml)
IFN-γ (MV4-11)
IFN-γ (THP-1)
(-) Control
SB01052
SB01056
0
2000
4000
6000
8000
10000

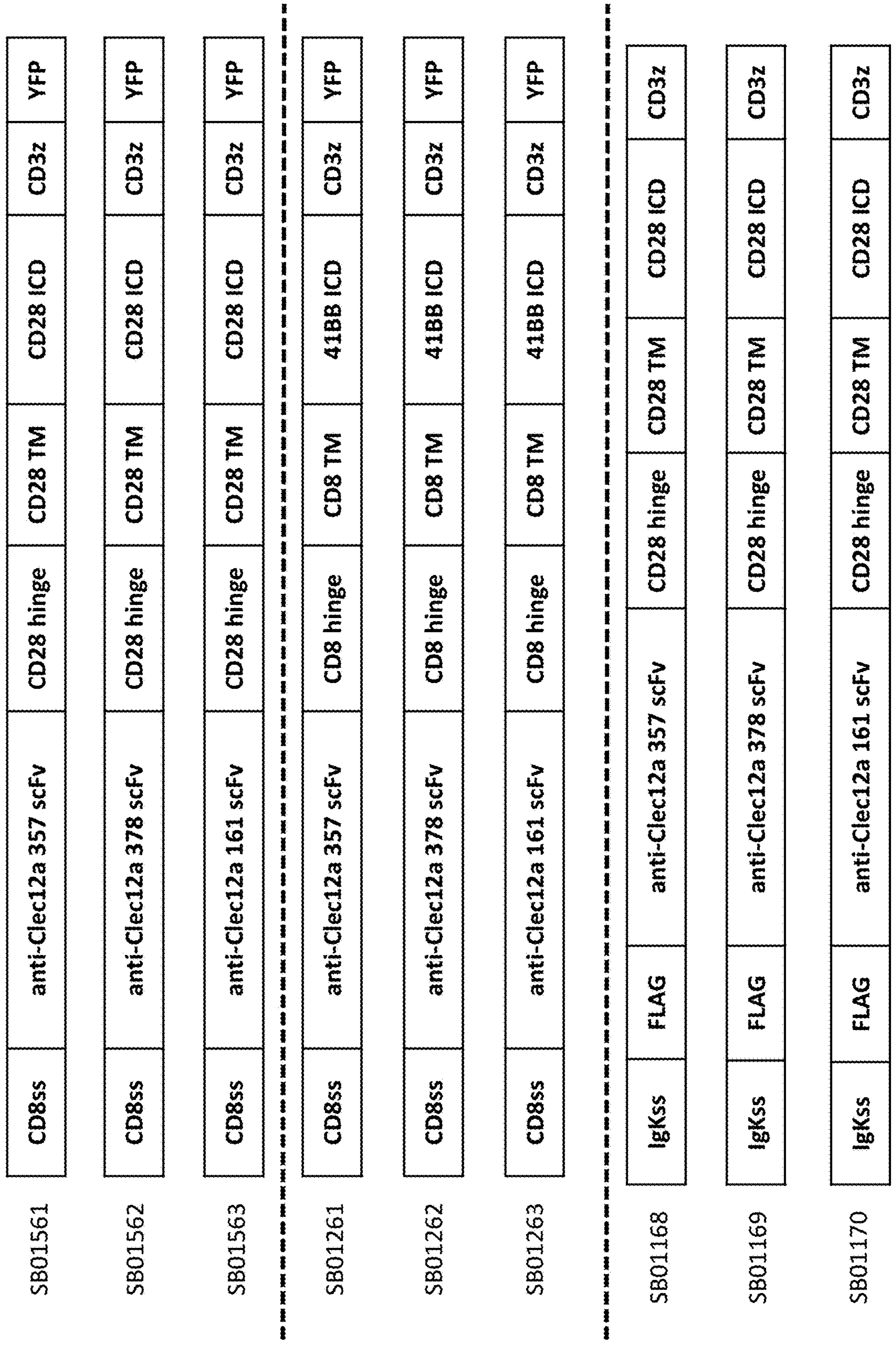

FIG. 47

| | | | | | | | |
|---|---|---|---|---|---|---|---|
| SB01561 | CD8ss | anti-Clec12a 357 scFv | CD28 hinge | CD28 TM | CD28 ICD | CD3z | YFP |
| SB01562 | CD8ss | anti-Clec12a 378 scFv | CD28 hinge | CD28 TM | CD28 ICD | CD3z | YFP |
| SB01563 | CD8ss | anti-Clec12a 161 scFv | CD28 hinge | CD28 TM | CD28 ICD | CD3z | YFP |
| SB01261 | CD8ss | anti-Clec12a 357 scFv | CD8 hinge | CD8 TM | 41BB ICD | CD3z | YFP |
| SB01262 | CD8ss | anti-Clec12a 378 scFv | CD8 hinge | CD8 TM | 41BB ICD | CD3z | YFP |
| SB01263 | CD8ss | anti-Clec12a 161 scFv | CD8 hinge | CD8 TM | 41BB ICD | CD3z | YFP |
| SB01168 | IgKss | FLAG | anti-Clec12a 357 scFv | CD28 hinge | CD28 TM | CD28 ICD | CD3z |
| SB01169 | IgKss | FLAG | anti-Clec12a 378 scFv | CD28 hinge | CD28 TM | CD28 ICD | CD3z |
| SB01170 | IgKss | FLAG | anti-Clec12a 161 scFv | CD28 hinge | CD28 TM | CD28 ICD | CD3z |

| SB0# | Hinge Source |
|---|---|
| 1071 | IgG4 minimal |
| 1072 | IgG4 minimal; No disulfides |
| 1073 | IgG4 minimal; enhanced disulfides |
| 1074 | IgG1 minimal hinge |
| 1078 | PDGFR |
| 1077 | LNGFR (truncated) |
| 1076 | LNGFR |
| 816 | Original D4 hinge |
| 819 | NC7 binder |

SEQUENCE LISTING

```
<160> NUMBER OF SEQ ID NOS: 229

<210> SEQ ID NO 1
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Ala Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Val Val Ala Ala Ala Val Ala Asp Tyr Trp Gly Gln Gly Thr
            100                 105                 110

Leu Val Thr Val Ser Ser
        115


<210> SEQ ID NO 2
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ser
```

```
                85                  90                  95

Leu Gln Thr Pro Phe Thr Phe Gly Pro Gly Thr Lys Val Asp Ile Lys
            100                 105                 110


<210> SEQ ID NO 3
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Thr Phe Ala Leu Phe Gly Phe Arg Glu Gln Ala Phe Asp Ile Trp
            100                 105                 110

Gly Gln Gly Thr Thr Val Thr Val Ser Ser
        115                 120


<210> SEQ ID NO 4
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Leu Ala Thr Tyr Tyr Cys Gln Gln Ser Tyr Ser Thr Pro Phe
                85                  90                  95

Thr Phe Gly Pro Gly Thr Lys Val Asp Ile Lys
            100                 105


<210> SEQ ID NO 5
<211> LENGTH: 119
<212> TYPE: PRT
<213> ORGANISM: Artificial Sequence
<220> FEATURE:
<223> OTHER INFORMATION: Description of Artificial Sequence: Synthetic
```

polypeptide

<400> SEQUENCE: 5

Glu Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Ser Tyr
20 25 30

Tyr Met His Trp Val Arg Gln Ala Pro Gly Gln Gly Leu Glu Trp Met
35 40 45

Gly Ile Ile Asn Pro Ser Gly Gly Ser Thr Ser Tyr Ala Gln Lys Phe
50 55 60

Gln Gly Arg Val Thr Met Thr Arg Asp Thr Ser Thr Ser Thr Val Tyr
65 70 75 80

Met Glu Leu Ser Ser Leu Arg Ser Glu Asp Thr Ala Val Tyr Tyr Cys
85 90 95

Ala Arg Gly Val Gly Ala His Asp Ala Phe Asp Ile Trp Gly Gln Gly
100 105 110

Thr Thr Val Thr Val Ser Ser
115

<210> SEQ ID NO 6
<211> LENGTH: 112
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 6

Asp Val Val Met Thr Gln Ser Pro Leu Ser Leu Pro Val Thr Pro Gly
1 5 10 15

Glu Pro Ala Ser Ile Ser Cys Arg Ser Ser Gln Ser Leu Leu His Ser
20 25 30

Asn Gly Asn Asn Tyr Leu Asp Trp Tyr Leu Gln Lys Pro Gly Gln Ser
35 40 45

Pro Gln Leu Leu Ile Tyr Leu Gly Ser Asn Arg Ala Ser Gly Val Pro
50 55 60

Asp Arg Phe Ser Gly Ser Gly Ser Asp Thr Asp Phe Thr Leu Gln Ile
65 70 75 80

Ser Arg Val Glu Ala Glu Asp Val Gly Val Tyr Tyr Cys Met Gln Gly
85 90 95

Thr His Pro Ala Ile Ser Phe Gly Gln Gly Thr Arg Leu Glu Ile Lys
100 105 110

<210> SEQ ID NO 7
<211> LENGTH: 118
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 7

Gln Val Gln Leu Gln Gln Pro Gly Ala Glu Leu Val Lys Pro Gly Ala
1 5 10 15

Ser Leu Lys Leu Ser Cys Lys Ser Ser Gly Tyr Thr Phe Thr Ser Tyr
20 25 30

Trp Met His Trp Val Arg Gln Arg Pro Gly His Gly Leu Glu Trp Ile
35 40 45

Gly Glu Ile Asp Pro Ser Asp Ser Tyr Lys Asp Tyr Asn Gln Lys Phe
    50                  55                  60

Lys Asp Lys Ala Thr Leu Thr Val Asp Arg Ser Ser Asn Thr Ala Tyr
65                  70                  75                  80

Met His Leu Ser Ser Leu Thr Ser Asp Asp Ser Ala Val Tyr Tyr Cys
                85                  90                  95

Ala Arg Ala Ile Thr Thr Thr Pro Phe Asp Phe Trp Gly Gln Gly Thr
            100                 105                 110

Thr Leu Thr Val Ser Ser
        115

<210> SEQ ID NO 8
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Asp Ile Val Leu Thr Gln Ser Pro Ala Thr Leu Ser Val Thr Pro Gly
1               5                   10                  15

Asp Ser Val Ser Leu Ser Cys Arg Ala Ser Gln Ser Ile Ser Asn Asn
            20                  25                  30

Leu His Trp Tyr Gln Gln Lys Ser His Glu Ser Pro Arg Leu Leu Ile
        35                  40                  45

Lys Tyr Ala Ser Gln Ser Ile Ser Gly Ile Pro Ser Arg Phe Ser Gly
    50                  55                  60

Ser Gly Ser Gly Thr Asp Phe Thr Leu Ser Ile Asn Ser Val Glu Thr
65                  70                  75                  80

Glu Asp Phe Gly Val Tyr Phe Cys Gln Gln Ser Asn Thr Trp Pro Tyr
                85                  90                  95

Thr Phe Gly Gly Gly Thr Lys Leu Glu Ile Lys Arg
            100                 105

<210> SEQ ID NO 9
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Gln Val Thr Leu Lys Glu Ser Gly Pro Thr Leu Val Lys Pro Thr Glu
1               5                   10                  15

Thr Leu Thr Leu Thr Cys Thr Leu Ser Gly Phe Ser Leu Asn Asn Ala
            20                  25                  30

Arg Met Gly Val Ser Trp Ile Arg Gln Pro Pro Gly Lys Cys Leu Glu
        35                  40                  45

Trp Leu Ala His Ile Phe Ser Asn Asp Glu Lys Ser Tyr Ser Thr Ser
    50                  55                  60

Leu Lys Asn Arg Leu Thr Ile Ser Lys Asp Ser Ser Lys Thr Gln Val
65                  70                  75                  80

Val Leu Thr Met Thr Asn Val Asp Pro Val Asp Thr Ala Thr Tyr Tyr
                85                  90                  95

Cys Ala Arg Ile Val Gly Tyr Gly Ser Gly Trp Tyr Gly Phe Phe Asp
            100                 105                 110

Tyr Trp Gly Gln Gly Thr Leu Val Thr Val Ser Ser
115 120

<210> SEQ ID NO 10
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 10

Asp Ile Gln Met Thr Gln Ser Pro Ser Ser Leu Ser Ala Ser Val Gly
1 5 10 15

Asp Arg Val Thr Ile Thr Cys Arg Ala Ser Gln Gly Ile Arg Asn Asp
20 25 30

Leu Gly Trp Tyr Gln Gln Lys Pro Gly Lys Ala Pro Lys Arg Leu Ile
35 40 45

Tyr Ala Ala Ser Thr Leu Gln Ser Gly Val Pro Ser Arg Phe Ser Gly
50 55 60

Ser Gly Ser Gly Thr Glu Phe Thr Leu Thr Ile Ser Ser Leu Gln Pro
65 70 75 80

Glu Asp Phe Ala Thr Tyr Tyr Cys Leu Gln His Asn Ser Tyr Pro Leu
85 90 95

Thr Phe Gly Cys Gly Thr Lys Val Glu Ile Lys
100 105

<210> SEQ ID NO 11
<211> LENGTH: 124
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 11

Gln Val Thr Leu Lys Glu Ser Gly Pro Val Leu Val Lys Pro Thr Glu
1 5 10 15

Thr Leu Thr Leu Thr Cys Thr Val Ser Gly Phe Ser Leu Arg Asn Ala
20 25 30

Arg Met Ala Val Ser Trp Ile Arg Gln Pro Pro Gly Lys Thr Leu Glu
35 40 45

Trp Leu Ala His Ile Phe Ser Asn Asp Glu Lys Ser Tyr Ser Thr Ser
50 55 60

Leu Lys Ser Arg Leu Thr Ile Ser Lys Asp Thr Ser Lys Ser Gln Val
65 70 75 80

Val Leu Thr Met Thr Asn Met Asp Pro Val Asp Thr Ala Thr Tyr Tyr
85 90 95

Cys Ala Arg Ile Val Gly Tyr Gly Ser Gly Trp Tyr Gly Tyr Phe Asp
100 105 110

Tyr Trp Gly Gln Gly Thr Leu Val Thr Val Ser Ser
115 120

<210> SEQ ID NO 12
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 12

Asp Ile Gln Met Thr Gln Ser Pro Ser Ser Val Ser Ala Ser Val Gly
1 5 10 15

Asp Arg Val Thr Ile Thr Cys Arg Ala Ser Gln Asp Ile Arg Tyr Asp
20 25 30

Leu Ala Trp Tyr Gln Gln Lys Pro Gly Lys Ala Pro Lys Arg Leu Ile
35 40 45

Tyr Ala Ala Ser Ser Leu Gln Ser Gly Val Pro Ser Arg Phe Ser Gly
50 55 60

Ser Gly Ser Gly Thr Glu Phe Thr Leu Thr Ile Ser Ser Leu Gln Pro
65 70 75 80

Glu Asp Phe Ala Thr Tyr Tyr Cys Leu Gln His Asn Phe Tyr Pro Leu
85 90 95

Thr Phe Gly Gly Gly Thr Lys Val Glu Ile Lys
100 105

<210> SEQ ID NO 13
<211> LENGTH: 116
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 13

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Ser Ser Tyr
20 25 30

Gly Met His Trp Val Arg Gln Ala Pro Gly Lys Gly Leu Glu Trp Val
35 40 45

Ala Val Ile Ser Tyr Asp Gly Ser Asn Lys Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Asn Leu Ala Pro Trp Ala Ala Tyr Trp Gly Gln Gly Thr Leu Val
100 105 110

Thr Val Ser Ser
115

<210> SEQ ID NO 14
<211> LENGTH: 112
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 14

Glu Ile Val Leu Thr Gln Ser Pro Leu Ser Leu Pro Val Thr Pro Gly
1 5 10 15

Glu Pro Ala Ser Ile Ser Cys Arg Ser Ser Gln Ser Leu Leu His Ser
20 25 30

Asn Gly Tyr Asn Tyr Leu Asp Trp Tyr Leu Gln Lys Pro Gly Gln Ser
35 40 45

Pro Gln Leu Leu Ile Tyr Leu Gly Ser Asn Arg Ala Ser Gly Val Pro
50 55 60

Asp Arg Phe Ser Gly Ser Gly Ser Gly Thr Asp Phe Thr Leu Lys Ile
65 70 75 80

Ser Arg Val Glu Ala Glu Asp Val Gly Val Tyr Tyr Cys Met Gln Ala
85 90 95

Leu Gln Thr Pro His Thr Phe Gly Gln Gly Thr Lys Leu Glu Ile Lys
100 105 110

<210> SEQ ID NO 15
<211> LENGTH: 123
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 15

Gln Val Gln Leu Lys Gln Ser Gly Pro Gly Leu Val Gln Pro Ser Gln
1 5 10 15

Ser Leu Ser Ile Thr Cys Thr Val Ser Gly Phe Ser Leu Thr Asn Tyr
20 25 30

Gly Leu His Trp Val Arg Gln Ser Pro Gly Lys Gly Leu Glu Trp Leu
35 40 45

Gly Val Ile Trp Ser Gly Gly Ser Thr Asp Tyr Asn Ala Ala Phe Ile
50 55 60

Ser Arg Leu Ser Ile Ser Lys Asp Asn Ser Lys Ser Gln Val Phe Phe
65 70 75 80

Lys Met Asn Ser Leu Gln Ala Asp Asp Thr Ala Ile Tyr Tyr Cys Ala
85 90 95

Arg Lys Gly Gly Ile Tyr Tyr Ala Asn His Tyr Tyr Ala Met Asp Tyr
100 105 110

Trp Gly Gln Gly Thr Ser Val Thr Val Ser Ser
115 120

<210> SEQ ID NO 16
<211> LENGTH: 114
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 16

Asp Ile Val Met Thr Gln Ser Pro Ser Ser Leu Ser Val Ser Ala Gly
1 5 10 15

Glu Lys Val Thr Met Ser Cys Lys Ser Ser Gln Ser Leu Leu Asn Ser
20 25 30

Gly Asn Gln Lys Asn Tyr Met Ala Trp Tyr Gln Gln Lys Pro Gly Gln
35 40 45

Pro Pro Lys Leu Leu Ile Tyr Gly Ala Ser Thr Arg Glu Ser Gly Val
50 55 60

Pro Asp Arg Phe Thr Gly Ser Gly Ser Gly Thr Asp Phe Thr Leu Thr
65 70 75 80

Ile Ser Ser Val Gln Ala Glu Asp Leu Ala Val Tyr Tyr Cys Gln Asn
85 90 95

Asp His Ser Tyr Pro Leu Thr Phe Gly Ala Gly Thr Lys Leu Glu Leu
100 105 110

Lys Arg

<210> SEQ ID NO 17
<211> LENGTH: 116
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 17

```
Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asp Tyr
            20                  25                  30

Asn Met His Trp Val Arg Gln Ala Pro Gly Gln Gly Leu Glu Trp Ile
        35                  40                  45

Gly Tyr Ile Tyr Pro Tyr Asn Gly Gly Thr Gly Tyr Asn Gln Lys Phe
    50                  55                  60

Lys Ser Lys Ala Thr Ile Thr Ala Asp Glu Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Arg Pro Ala Met Asp Tyr Trp Gly Gln Gly Thr Leu Val
            100                 105                 110

Thr Val Ser Ser
        115
```

<210> SEQ ID NO 18
<211> LENGTH: 111
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 18

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Ser Val Asp Asn Tyr
            20                  25                  30

Gly Ile Ser Phe Met Asn Trp Phe Gln Gln Lys Pro Gly Lys Ala Pro
        35                  40                  45

Lys Leu Leu Ile Tyr Ala Ala Ser Asn Gln Gly Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Asp Asp Phe Ala Thr Tyr Tyr Cys Gln Gln Ser Lys
                85                  90                  95

Glu Val Pro Trp Thr Phe Gly Gln Gly Thr Lys Val Glu Ile Lys
            100                 105                 110
```

<210> SEQ ID NO 19
<211> LENGTH: 116
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 19

Glu Val Gln Leu Val Gln Ser Gly Ala Glu Val Lys Lys Pro Gly Ser
1 5 10 15

Ser Val Lys Val Ser Cys Lys Ala Ser Gly Tyr Thr Ile Thr Asp Ser
20 25 30

Asn Ile His Trp Val Arg Gln Ala Pro Gly Gln Ser Leu Glu Trp Ile
35 40 45

Gly Tyr Ile Tyr Pro Tyr Asn Gly Gly Thr Asp Tyr Asn Gln Lys Phe
50 55 60

Lys Asn Arg Ala Thr Leu Thr Val Asp Asn Pro Thr Asn Thr Ala Tyr
65 70 75 80

Met Glu Leu Ser Ser Leu Arg Ser Glu Asp Thr Ala Phe Tyr Tyr Cys
85 90 95

Val Asn Gly Asn Pro Trp Leu Ala Tyr Trp Gly Gln Gly Thr Leu Val
100 105 110

Thr Val Ser Ser
115

<210> SEQ ID NO 20
<211> LENGTH: 112
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 20

Asp Ile Gln Leu Thr Gln Ser Pro Ser Thr Leu Ser Ala Ser Val Gly
1 5 10 15

Asp Arg Val Thr Ile Thr Cys Arg Ala Ser Glu Ser Leu Asp Asn Tyr
20 25 30

Gly Ile Arg Phe Leu Thr Trp Phe Gln Gln Lys Pro Gly Lys Ala Pro
35 40 45

Lys Leu Leu Met Tyr Ala Ala Ser Asn Gln Gly Ser Gly Val Pro Ser
50 55 60

Arg Phe Ser Gly Ser Gly Ser Gly Thr Glu Phe Thr Leu Thr Ile Ser
65 70 75 80

Ser Leu Gln Pro Asp Asp Phe Ala Thr Tyr Tyr Cys Gln Gln Thr Lys
85 90 95

Glu Val Pro Trp Ser Phe Gly Gln Gly Thr Lys Val Glu Val Lys Arg
100 105 110

<210> SEQ ID NO 21
<211> LENGTH: 118
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 21

Gln Val Gln Leu Gln Glu Ser Gly Pro Gly Leu Val Lys Pro Ser Glu
1 5 10 15

Thr Leu Ser Leu Thr Cys Val Val Ser Gly Gly Ser Ile Ser Ser Ser
20 25 30

Asn Trp Trp Ser Trp Val Arg Gln Pro Pro Gly Lys Gly Leu Glu Trp
35 40 45

Ile Gly Glu Ile Tyr His Ser Gly Ser Pro Asp Tyr Asn Pro Ser Leu
50 55 60

Lys Ser Arg Val Thr Ile Ser Val Asp Lys Ser Arg Asn Gln Phe Ser
65 70 75 80

Leu Lys Leu Ser Ser Val Thr Ala Ala Asp Thr Ala Val Tyr Tyr Cys
85 90 95

Ala Lys Val Ser Thr Gly Gly Phe Phe Asp Tyr Trp Gly Gln Gly Thr
100 105 110

Leu Val Thr Val Ser Ser
115

<210> SEQ ID NO 22
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 22

Glu Ile Glu Leu Thr Gln Ser Pro Ser Ser Leu Ser Ala Ser Val Gly
1 5 10 15

Asp Arg Val Thr Ile Thr Cys Arg Ala Ser Gln Ser Ile Ser Ser Tyr
20 25 30

Leu Asn Trp Tyr Gln Gln Lys Pro Gly Lys Ala Pro Lys Leu Leu Ile
35 40 45

Tyr Ala Ala Ser Ser Leu Gln Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Ser Tyr Ser Thr Pro Pro
85 90 95

Thr Phe Gly Pro Gly Thr Lys Val Glu Ile Lys
100 105

<210> SEQ ID NO 23
<211> LENGTH: 118
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 23

Gln Val Gln Leu Gln Glu Ser Gly Pro Gly Leu Val Lys Pro Ser Glu
1 5 10 15

Thr Leu Ser Leu Thr Cys Val Val Ser Gly Gly Ser Ile Ser Ser Ser
20 25 30

Asn Trp Trp Ser Trp Val Arg Gln Pro Pro Gly Lys Gly Leu Glu Trp
35 40 45

Ile Gly Glu Ile Tyr His Ser Gly Ser Pro Asn Tyr Asn Pro Ser Leu
50 55 60

Lys Ser Arg Val Thr Ile Ser Val Asp Lys Ser Lys Asn Gln Phe Ser
65 70 75 80

Leu Lys Leu Ser Ser Val Thr Ala Ala Asp Thr Ala Val Tyr Tyr Cys
85 90 95

Ala Arg Ser Ser Ser Gly Gly Phe Phe Asp Tyr Trp Gly Gln Gly Thr
100 105 110

Leu Val Thr Val Ser Ser
115

<210> SEQ ID NO 24
<211> LENGTH: 107
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 24

Glu Ile Glu Leu Thr Gln Ser Pro Ser Ser Leu Ser Ala Ser Val Gly
1 5 10 15

Asp Arg Val Thr Ile Thr Cys Arg Ala Ser Gln Ser Ile Ser Ser Tyr
20 25 30

Leu Asn Trp Tyr Gln Gln Lys Pro Gly Lys Ala Pro Lys Leu Leu Ile
35 40 45

Tyr Ala Ala Ser Ser Leu Gln Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Ser Tyr Ser Thr Pro Pro
85 90 95

Thr Phe Gly Gln Gly Thr Lys Val Glu Ile Lys
100 105

<210> SEQ ID NO 25
<211> LENGTH: 107
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 25

Glu Ile Glu Leu Thr Gln Ser Pro Ser Ser Leu Ser Ala Ser Val Gly
1 5 10 15

Asp Arg Val Thr Ile Thr Cys Arg Ala Ser Gln Ser Ile Ser Ser Tyr
20 25 30

Leu Asn Trp Tyr Gln Gln Lys Pro Gly Lys Ala Pro Lys Leu Leu Ile
35 40 45

Tyr Ala Ala Ser Ser Leu Gln Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Ser Tyr Ser Thr Pro Pro
85 90 95

Thr Phe Gly Gln Gly Thr Lys Val Glu Ile Lys
100 105

<210> SEQ ID NO 26
<211> LENGTH: 118
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 26

Gln Val Gln Leu Gln Glu Ser Gly Pro Gly Leu Val Lys Pro Ser Glu
1 5 10 15

-continued

```
Thr Leu Ser Leu Thr Cys Val Val Ser Gly Gly Ser Ile Ser Ser Ser
            20                  25                  30

Asn Trp Trp Ser Trp Val Arg Gln Pro Pro Gly Lys Gly Leu Glu Trp
        35                  40                  45

Ile Gly Glu Ile Tyr His Ser Gly Ser Pro Asn Tyr Asn Pro Ser Leu
    50                  55                  60

Lys Ser Arg Val Thr Ile Ser Val Asp Lys Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Gln Thr Thr Ala Gly Ser Phe Asp Tyr Trp Gly Gln Gly Thr
            100                 105                 110

Leu Val Thr Val Ser Ser
        115
```

<210> SEQ ID NO 27
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 27

```
Gly Gly Gly Gly Ser Gly Gly Gly Gly Ser Gly Gly Gly Gly Ser
1               5                   10                  15
```

<210> SEQ ID NO 28
<211> LENGTH: 354
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 28

```
gaagtgcaac ttgttcagag cggggcagaa gttaagaagc caggcgcttc cgtcaaggtg     60

agttgcaagg caagtggata cacctttacg agttattata tgcactgggc acggcaggcc    120

cctggtcagg gcctcgaatg gatggggatt ataaatcctt ctggcgggtc aaccagctac    180

gcacaaaaat ttcaaggtcg ggtgacaatg acgcgcgaca cgtcaacgag tacagtgtat    240

atggaattgt ctagcctgag gtccgaggat actgctgtct attattgtgc tcgcgtggtc    300

gctgctgctg tggcagacta ctggggtcag ggtacacttg tgacggtaag cagc          354
```

<210> SEQ ID NO 29
<211> LENGTH: 336
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 29

```
gacgtagtta tgacacagtc tccactgtca ttgccagtaa caccaggtga gcccgcctcc     60

atctcatgta gatcctccca atctctcctt cattcaaacg ggtataatta tctcgactgg    120

tatttgcaga aaccgggcca gagccctcaa ctgctcatct atttggggag caaccgggcc    180

tctggtgtcc ctgatagatt ctccgggagt ggatcaggta cggattttac actgaagatc    240

agcagggtgg aagcagaaga tgttggtgtg tattactgta tgcaatcact ccagaccccg    300
```

tttacctttg ggcctggaac aaaggtagat attaaa 336

<210> SEQ ID NO 30
<211> LENGTH: 366
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 30
gaggttcaac tggtacaaag cggagccgag gtaaagaaac cagggagtag cgtcaaagtg 60
tcctgcaaag cctcaggcgg cacattcagt agctatgcta tttcatgggt acgccaagca 120
ccaggacagg ggctggagtg gatgggcggg attatcccca tcttcggtac ggcaaactat 180
gcacaaaagt tccagggacg agtcaccatc acggctgata agtccacctc caccgcctat 240
atggagctga gttcccttcg gagcgaggat actgctgtgt attattgtgc cacgttcgca 300
ctgttcggtt ttcgggagca ggcgtttgat atttggggac aaggcacaac ggtcacggtc 360
agttca 366

<210> SEQ ID NO 31
<211> LENGTH: 321
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 31
gacattcaga tgacccagag tccctcttca ttgagtgcga gcgtcggtga tcgggttacg 60
ataacctgta gggcctccca aagtatatca tcatatttga actggtacca acagaaacct 120
gggaaagcgc cgaagctcct tatctatgct gccagctctt tgcaaagcgg tgtgccctca 180
cggttctccg gtagtgggtc cgggaccgac ttcactttga ccatcagcag ccttcagcca 240
gaggatcttg ccacttatta ctgccagcaa tcttatagca caccgtttac attcggtcca 300
ggcacaaagg tagacattaa g 321

<210> SEQ ID NO 32
<211> LENGTH: 357
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 32
gaggtacagc ttgtgcagag tggagcagaa gttaaaaaac ccggagcttc cgtgaaggta 60
agctgcaagg cttcaggata tacatttact agctactaca tgcactgggt ccgccaagct 120
ccgggccaag gccttgaatg gatgggcatc ataaatccca gtggaggctc aacgagctat 180
gcacaaaagt tccaagggcg cgttaccatg acgcgcgaca ccagcacgtc caccgtctat 240
atggaactct caagtttgcg atctgaagat acggctgtct actattgcgc acgaggggtc 300
ggagcgcatg acgccttcga catctgggga caagggacta cagtaactgt gtcaagc 357

<210> SEQ ID NO 33
<211> LENGTH: 147
<212> TYPE: DNA
<213> ORGANISM: Artificial Sequence
<220> FEATURE:

<223> OTHER INFORMATION: Description of Artificial Sequence: Synthetic
      polynucleotide

<400> SEQUENCE: 33
gatgttgtta tgacacagtc tcccctctct ttgcctgtta cgcctggcga gcccgcctct     60
atttcttgtc gatctagtca gagcctgctg cattctaatg gaaacaacta tttggactgg    120
tacttgcaaa agccgggtca aagtccc                                        147

<210> SEQ ID NO 34
<211> LENGTH: 354
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 34
caagtccaac ttcagcagcc aggcgctgag ttggttaaac cgggcgcaag cctcaaactt     60
agttgcaagt catccggata tactttcacg tcttattgga tgcattgggt acgacaaaga    120
cctggtcacg gcctcgaatg gattggcgaa atcgacccgt cagacagcta caaggattac    180
aaccagaaat tcaaagataa ggcaacactt actgtggatc gctcaagtaa cacggcttac    240
atgcacctct cttcactcac gtctgacgac agtgcggtgt attattgcgc ccgcgctatt    300
acaacaaccc ctttcgattt ctggggccag ggtactacgc tcacagtctc atcc          354

<210> SEQ ID NO 35
<211> LENGTH: 324
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 35
gatatcgtcc tcacccaatc cccggctact ttgagtgtaa caccaggcga cagcgtgtca     60
ctgtcatgcc gagcctccca gtcaatcagc aataatctgc attggtatca acagaaatca    120
cacgaatccc cccgactttt gataaagtat gcgtcacagt ccatatcagg cattcccagt    180
aggttttcag gcagtggttc aggtactgac ttcaccctct ccattaactc tgtagaaaca    240
gaggactttg gcgtctactt ctgtcagcaa tccaacacct ggccttatac attcggcggc    300
ggcactaagc tggaaattaa gaga                                           324

<210> SEQ ID NO 36
<211> LENGTH: 372
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 36
caagtaaccc ttaaagagtc cggccccact ttggttaaac ctactgaaac acttacactc     60
acatgcacat tgtccggctt ttcactcaac aacgcaagga tgggtgtgtc ctggattcgc    120
cagccccctg gaaaatgttt ggaatggctc gctcatatat ttagcaacga cgagaaaagt    180
tactcaactt cactcaagaa ccgcctcact attagcaaag attcctccaa aacccaagta    240
gttctgacaa tgacgaatgt agacccagtc gatactgcaa cttactattg cgcacgaata    300
gtcggttacg ggagtggctg gtatgggttt ttcgactatt ggggacaggg cactcttgta    360
acagtaagta gc 372

<210> SEQ ID NO 37
<211> LENGTH: 321
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 37
gacatccaga tgactcaatc tccatctagc ctctcagcgt ctgtgggcga tcgagtcacc 60
atcacctgta gggcttccca gggtataagg aatgatttgg gctggtacca gcaaaaaccg 120
ggtaaggctc cgaaacgact gatatacgca gcttctacgt tgcaatccgg ggtgccatcc 180
agatttagtg gcagcgggag cggtactgag tttacgctga ctatctcctc acttcagcca 240
gaggatttcg ccacgtacta ttgtctgcaa cacaactcct atccgctgac cttcgggtgc 300
gggacaaagg tggaaattaa a 321

<210> SEQ ID NO 38
<211> LENGTH: 372
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 38
caagtgacct tgaaggagtc agggccagtg ttggtaaaac ctactgagac tctcacgttg 60
acatgcacgg tatcaggttt cagcctgagg aacgctcgga tggccgtcag ttggatacgc 120
cagccgccag gcaaaactct tgaatggttg gcgcacatat tcagtaacga cgagaaatct 180
tactctacat cccttaagtc tcgcctcacc atttctaaag acacatccaa atcacaagtg 240
gtactcacga tgacaaacat ggaccctgtt gacactgcta catattattg tgctaggata 300
gtgggctacg gtagcggatg gtacggttat tttgattact ggggacaagg gacgcttgtt 360
acggtgtcct ca 372

<210> SEQ ID NO 39
<211> LENGTH: 321
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 39
gacattcaga tgacccagtc tccgtccagc gttagcgcaa gcgtggggga tagagtcact 60
attacgtgta gagccagtca agatatacgg tacgatcttg cttggtatca gcaaaaaccg 120
ggaaaagccc cgaagagact tatatatgca gcttcctcct tgcaaagcgg ggtcccatcc 180
cggtttagtg gtagtggttc cggaacagag ttcacgctga ctatttcatc actgcaaccc 240
gaagattttg ccacctacta ctgccttcaa cacaatttct atcctcttac cttcggcgga 300
ggtactaagg tagagattaa g 321

<210> SEQ ID NO 40
<211> LENGTH: 354
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 40
gaagtacagt tggttgagag tggtggagga ctcgttcaac ctggcggtag tttgcgactc     60
agctgcgcgg cttccggttt caccttctca tcctatggga tgcactgggt cagacaagcc    120
cctggaaagg gcctcgaatg ggttgctgtg attagctatg acggctctaa taaatactat    180
gcagatagtg taaaggggag atttacgatt tctcgcgata atagcaaaaa tacgctgtac    240
ctgcaaatgg aaaccaacag cctgcgagcg gaagatacgg cggtttatta ctgcgcgaat    300
cttgccccgt gggcagcata ctggggacag gggacgttgg tgacggtaag cagt          354

<210> SEQ ID NO 41
<211> LENGTH: 348
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 41
gagattgtgc tcacccagtc tccactcagc cttcctgtaa cgcccggtga gcctgcctct     60
atatcatgcc gaagttccca aagccttctg cactcaaacg gctataacta cttggactgg    120
tacctccaga agcccggcca aagtcctcaa ctgttgatat acctggggtc caaccgggca    180
tcaggagtac ctgatagatt ctcaggaagt gggtcaggaa ccgacttcac gctgaaaatt    240
agtcgcgtag aggcggaaga tgtaggtgtg tattactgta tgcaggcgtt gcaaacaccg    300
cacacttttg gacagggaac caaactggaa ataaagacca gtagtggt                 348

<210> SEQ ID NO 42
<211> LENGTH: 369
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 42
caggtccaac tgaaacaaag cggtcccggt cttgtccagc cctcccaatc tctcagtatt     60
acttgcactg tgtcaggttt cagcctcacg aactacggtc tgcattgggt ccgccagtct    120
ccaggaaaag gcctggagtg gctcggtgtt atctggagtg gtggaagtac ggattacaat    180
gctgccttta tctctcggct cagtatctcc aaagataact ctaagtccca agtctttttc    240
aaaatgaact ctttgcaggc agatgatacg gccatatact attgcgcacg caagggtggg    300
atctactatg caaaccacta ttacgcgatg gactactggg gccaaggcac gagtgttacc    360
gtgtcaagc                                                            369

<210> SEQ ID NO 43
<211> LENGTH: 342
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 43
gacatagtga tgactcagtc tccgtcctct ctttccgtga gtgcgggcga aaaggttacc     60
atgtcctgca aaagttcaca gtcacttctc aattctggca accaaaaaaa ttacatggca 120
tggtatcaac agaaaccagg tcagccgcca aagctcctca tatatggtgc atcaacgcga 180
gagtcaggcg tacctgacag gtttaccgga tctggcagcg gtacagactt tactcttacc 240
atatcaagtg tgcaggcaga ggacttggcg gtatactatt gtcaaaacga tcatagttac 300
cctcttacat ttggcgcggg cactaaactg gagctgaaac gc 342

<210> SEQ ID NO 44
<211> LENGTH: 348
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 44
caggttcagc tggttcagtc tggcgccgaa gtgaagaaac ctggcagcag cgtgaaggtg 60
tcctgcaagg ccagcggcta cacctttacc gactacaaca tgcactgggt ccgacaggcc 120
cctggacaag gacttgagtg gatcggctac atctacccct acaatggcgg caccggctac 180
aaccagaagt tcaagagcaa ggccaccatc accgccgacg agagcacaaa caccgcctac 240
atggaactga gcagcctgag aagcgaggac accgccgtgt actactgtgc cagaggcaga 300
cccgccatgg attattgggg acagggcacc ctggtcaccg tttctagc 348

<210> SEQ ID NO 45
<211> LENGTH: 333
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 45
gatatccaga tgacacagag ccccagcagc ctgtctgcca gcgtgggaga tagagtgacc 60
atcacctgta gagccagcga gagcgtggac aactacggca tcagcttcat gaactggttc 120
cagcagaagc ccggcaaggc ccctaagctg ctgatctacg ccgccagcaa tcaaggcagc 180
ggagtgccta gcagattttc cggctctggc agcggcaccg atttcaccct gacaatctct 240
agcctccagc ctgacgactt cgccacctac tactgccagc agagcaaaga ggtgccctgg 300
acattcggcc agggcacaaa ggtggaaatc aag 333

<210> SEQ ID NO 46
<211> LENGTH: 348
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 46
gaagtgcagc tggttcagtc tggcgccgaa gtgaagaaac ctggcagcag cgtgaaggtg 60
tcctgcaagg ccagcggcta caccatcacc gacagcaaca tccactgggt ccgacaggct 120
ccaggccagt ctcttgagtg gatcggctac atctacccct acaacggcgg caccgactac 180
aaccagaagt tcaagaaccg ggccacactg accgtggaca accctaccaa taccgcctac 240
atggaactga gcagcctgcg gagcgaggac accgcctttt actactgcgt gaacggcaac 300
ccctggctgg cctattgggg acagggaaca ctggtcacag tgtctagc 348

-continued

<210> SEQ ID NO 47
<211> LENGTH: 336
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 47
gatattcagc tgacacagag ccccagcaca ctgtctgcct ctgtgggcga cagagtgacc 60
atcacctgta gagccagcga gagcctggac aactacggca tcagatttct gacctggttc 120
cagcagaagc ccggcaaggc tcctaagctg ctgatgtacg ccgccagcaa tcaaggcagc 180
ggagtgccta gcagattttc cggctctggc agcggcacag agttcaccct gacaatctct 240
agcctccagc ctgacgactt cgccacctac tactgccagc agaccaaaga ggtgccctgg 300
tcctttggac agggcaccaa ggtggaagtg aagcgg 336

<210> SEQ ID NO 48
<211> LENGTH: 354
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 48
caggtgcagc tgcaggagtc ggggccagga ctggtgaagc cttcggagac cctgtccctc 60
acctgcgttg tctctggtgg ctccatcagc agtagtaact ggtggagctg ggtccgccag 120
cccccaggga aggggctgga gtggattggg gaaatctatc atagtgggag ccccgactac 180
aacccgtccc tcaagagtcg agtcaccata tcagtagaca agtccaggaa ccagttctcc 240
ctgaagctga gctctgtgac cgccgcggac acggccgtgt attactgtgc aaaggttagt 300
actggtggtt tctttgacta ctggggccaa ggtaccctgg tcaccgtctc gagt 354

<210> SEQ ID NO 49
<211> LENGTH: 321
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 49
gaaattgagc tcacccagtc tccatcctcc ctgtctgcat ctgtaggaga cagagtcacc 60
atcacttgcc gggcaagtca gagcattagc agctacttaa attggtatca gcagaaacca 120
gggaaagccc ctaagctcct gatctatgct gcatccagtt tgcaaagtgg ggtcccatca 180
aggttcagtg gcagtggatc tgggacagat ttcactctca ccatcagcag tctgcaacct 240
gaagattttg caacttacta ctgtcaacag agttacagta cccctccaac gttcggccca 300
gggaccaagg tggagatcaa a 321

<210> SEQ ID NO 50
<211> LENGTH: 354
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 50
caggtgcagc tgcaggagtc gggcccagga ctggtgaagc cttcggagac cctgtccctc 60
acctgcgttg tctctggtgg ctccatcagc agtagtaact ggtggagctg ggtccgccag 120
cccccaggga aggggctgga gtggattggg gaaatctatc atagtgggag ccccaactac 180
aacccgtccc tcaagagtcg agtcaccata tcagtagaca agtccaagaa ccagttctcc 240
ctgaagctga gctctgtgac cgccgcggac acggccgtgt attactgtgc aaggtcgtct 300
tctggtggtt tctttgacta ctggggccaa ggtaccctgg tcaccgtctc gagt 354

<210> SEQ ID NO 51
<211> LENGTH: 321
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 51
gaaattgagc tcacccagtc tccatcctcc ctgtctgcat ctgtaggaga cagagtcacc 60
atcacttgcc gggcaagtca gagcattagc agctacttaa attggtatca gcagaaacca 120
gggaaagccc ctaagctcct gatctatgct gcatccagtt tgcaaagtgg ggtcccatca 180
aggttcagtg gcagtggatc tgggacagat ttcactctca ccatcagcag tctgcaacct 240
gaagattttg caacttacta ctgtcaacag agttacagta cccctccaac gttcggccaa 300
gggaccaagg tggagatcaa a 321

<210> SEQ ID NO 52
<211> LENGTH: 354
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 52
caggtgcagc tgcaggagtc gggcccagga ctggtgaagc cttcggagac cctgtccctc 60
acctgcgttg tctctggtgg ctccatcagc agtagtaact ggtggagctg ggtccgccag 120
cccccaggga aggggctgga gtggattggg gaaatctatc atagtgggag ccccaactac 180
aacccgtccc tcaagagtcg agtcaccata tcagtagaca agtccaagaa ccagttctcc 240
ctgaagctga gctctgtgac cgccgcggac acggccgtgt attactgtgc aaggcagact 300
actgctgggt cctttgacta ctggggccaa ggtaccctgg tcaccgtctc gagt 354

<210> SEQ ID NO 53
<211> LENGTH: 321
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 53
gaaattgagc tcacccagtc tccatcctcc ctgtctgcat ctgtaggaga cagagtcacc 60
atcacttgcc gggcaagtca gagcattagc agctacttaa attggtatca gcagaaacca 120
gggaaagccc ctaagctcct gatctatgct gcatccagtt tgcaaagtgg ggtcccatca 180
aggttcagtg gcagtggatc tgggacagat ttcactctca ccatcagcag tctgcaacct 240
gaagattttg caacttacta ctgtcaacag agttacagta cccctccaac gttcggccaa 300
gggaccaagg tggagatcaa a 321

<210> SEQ ID NO 54
<211> LENGTH: 45
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 54
ggaggcggag gatctggtgg cggaggaagt ggcggaggcg gttct 45

<210> SEQ ID NO 55
<211> LENGTH: 42
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 55

Ala Ala Ala Ile Glu Val Met Tyr Pro Pro Pro Tyr Leu Asp Asn Glu
1 5 10 15

Lys Ser Asn Gly Thr Ile Ile His Val Lys Gly Lys His Leu Cys Pro
20 25 30

Ser Pro Leu Phe Pro Gly Pro Ser Lys Pro
35 40

<210> SEQ ID NO 56
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 56

Glu Ser Lys Tyr Gly Pro Pro Cys Pro Ser Cys Pro
1 5 10

<210> SEQ ID NO 57
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 57

Glu Ser Lys Tyr Gly Pro Pro Ala Pro Ser Ala Pro
1 5 10

<210> SEQ ID NO 58
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 58

Glu Ser Lys Tyr Gly Pro Pro Cys Pro Pro Cys Pro
1 5 10

<210> SEQ ID NO 59
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

```
Glu Pro Lys Ser Cys Asp Lys Thr His Thr Cys Pro
1               5                   10
```

<210> SEQ ID NO 60
<211> LENGTH: 86
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 60

```
Ala Ala Ala Phe Val Pro Val Phe Leu Pro Ala Lys Pro Thr Thr Thr
1               5                   10                  15

Pro Ala Pro Arg Pro Pro Thr Pro Ala Pro Thr Ile Ala Ser Gln Pro
            20                  25                  30

Leu Ser Leu Arg Pro Glu Ala Cys Arg Pro Ala Ala Gly Gly Ala Val
        35                  40                  45

His Thr Arg Gly Leu Asp Phe Ala Cys Asp Ile Tyr Ile Trp Ala Pro
    50                  55                  60

Leu Ala Gly Thr Cys Gly Val Leu Leu Leu Ser Leu Val Ile Thr Leu
65                  70                  75                  80

Tyr Cys Asn His Arg Asn
                85
```

<210> SEQ ID NO 61
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 61

```
Ala Cys Pro Thr Gly Leu Tyr Thr His Ser Gly Glu Cys Cys Lys Ala
1               5                   10                  15

Cys Asn Leu Gly Glu Gly Val Ala Gln Pro Cys Gly Ala Asn Gln Thr
            20                  25                  30

Val Cys Glu Pro Cys Leu Asp Ser Val Thr Phe Ser Asp Val Val Ser
        35                  40                  45

Ala Thr Glu Pro Cys Lys Pro Cys Thr Glu Cys Val Gly Leu Gln Ser
    50                  55                  60

Met Ser Ala Pro Cys Val Glu Ala Asp Asp Ala Val Cys Arg Cys Ala
65                  70                  75                  80

Tyr Gly Tyr Tyr Gln Asp Glu Thr Thr Gly Arg Cys Glu Ala Cys Arg
                85                  90                  95

Val Cys Glu Ala Gly Ser Gly Leu Val Phe Ser Cys Gln Asp Lys Gln
            100                 105                 110

Asn Thr Val Cys Glu Glu Cys Pro Asp Gly Thr Tyr Ser Asp Glu Ala
        115                 120                 125

Asp Ala Glu Cys
    130
```

<210> SEQ ID NO 62
<211> LENGTH: 34
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 62

Ala Cys Pro Thr Gly Leu Tyr Thr His Ser Gly Glu Cys Cys Lys Ala
1 5 10 15

Cys Asn Leu Gly Glu Gly Val Ala Gln Pro Cys Gly Ala Asn Gln Thr
20 25 30

Val Cys

<210> SEQ ID NO 63

<400> SEQUENCE: 63

000

<210> SEQ ID NO 64
<211> LENGTH: 20
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 64

Ala Val Gly Gln Asp Thr Gln Glu Val Ile Val Val Pro His Ser Leu
1 5 10 15

Pro Phe Lys Val
20

<210> SEQ ID NO 65
<211> LENGTH: 126
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 65
gcagcagcta tcgaggtgat gtatcctccg ccctacctgg ataatgaaaa gagtaatggg 60
actatcattc atgtaaaagg gaagcatctt tgtccttctc cccttttccc cggtccgtct 120
aaacct 126

<210> SEQ ID NO 66
<211> LENGTH: 36
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 66
gaaagcaagt acggtccacc ttgccctagc tgtccg 36

<210> SEQ ID NO 67
<211> LENGTH: 36
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 67
gaatccaagt acggcccccc agcgcctagt gcccca 36

<210> SEQ ID NO 68
<211> LENGTH: 36
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 68
gaatctaaat atggcccgcc atgcccgcct tgccca 36

<210> SEQ ID NO 69
<211> LENGTH: 36
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 69
gaaccgaagt cttgtgataa aactcatacg tgcccg 36

<210> SEQ ID NO 70
<211> LENGTH: 258
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 70
gctgctgctt tcgtacccgt gttcctccct gctaagccta cgactacccc cgcaccgaga 60
ccacccacgc cagcacccac gattgctagc cagcccctta gtttgcgacc agaagcttgt 120
cggcctgctg ctggtggcgc ggtacatacc cgcggccttg attttgcttg cgatatatat 180
atctgggcgc ctctggccgg aacatgcggg gtcctcctcc tttctctggt tattactctc 240
tactgtaatc acaggaat 258

<210> SEQ ID NO 71
<211> LENGTH: 396
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 71
gcctgcccga ccgggctcta cactcatagc ggggaatgtt gtaaggcatg taacttgggt 60
gagggcgtcg cacagccctg cggagctaac caaacagtgt gcgaaccctg cctcgatagt 120
gtgacgttct ctgatgttgt atcagctaca gagccttgca aaccatgtac tgagtgcgtt 180
ggacttcagt caatgagcgc tccatgtgtg gaggcagatg atgcggtctg tcgatgtgct 240
tacggatact accaagacga gacaacaggg cggtgcgagg cctgtagagt ttgtgaggcg 300
ggctccgggc tggtgttttc atgtcaagac aagcaaaata cggtctgtga agagtgccct 360
gatggcacct actcagacga agcagatgca gaatgc 396

<210> SEQ ID NO 72
<211> LENGTH: 102
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 72
gcctgcccta caggactcta cacgcatagc ggtgagtgtt gtaaagcatg caacctcggg 60
gaaggtgtag cccagccatg cggggctaac caaaccgttt gc 102

<210> SEQ ID NO 73
<211> LENGTH: 60
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 73
gctgtgggcc aggacacgca ggaggtcatc gtggtgccac actccttgcc ctttaaggtg 60

<210> SEQ ID NO 74
<211> LENGTH: 20
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 74

Glu Ala Ala Ala Lys Glu Ala Ala Ala Lys Glu Ala Ala Ala Lys Glu
1 5 10 15

Ala Ala Ala Lys
20

<210> SEQ ID NO 75
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 75

Gly Tyr Thr Phe Thr Ser Tyr Tyr Met His
1 5 10

<210> SEQ ID NO 76
<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 76

Ile Ile Asn Pro Ser Gly Gly Ser Thr Ser Tyr Ala Gln Lys Phe Gln
1 5 10 15

Gly

<210> SEQ ID NO 77
<211> LENGTH: 9

<212> TYPE: PRT
<213> ORGANISM: Artificial Sequence
<220> FEATURE:
<223> OTHER INFORMATION: Description of Artificial Sequence: Synthetic
peptide

<400> SEQUENCE: 77

Val Val Ala Ala Ala Val Ala Asp Tyr
1 5

<210> SEQ ID NO 78
<211> LENGTH: 16
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 78

Arg Ser Ser Gln Ser Leu Leu His Ser Asn Gly Tyr Asn Tyr Leu Asp
1 5 10 15

<210> SEQ ID NO 79
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 79

Leu Gly Ser Asn Arg Ala
1 5

<210> SEQ ID NO 80
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 80

Met Gln Ser Leu Gln Thr Pro Phe Thr
1 5

<210> SEQ ID NO 81
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 81

Gly Gly Thr Phe Ser Ser Tyr Ala Ile Ser
1 5 10

<210> SEQ ID NO 82
<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 82

Gly Ile Ile Pro Ile Phe Gly Thr Ala Asn Tyr Ala Gln Lys Phe Gln

-continued 1 5 10 15

Gly

<210> SEQ ID NO 83
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 83

Phe Ala Leu Phe Gly Phe Arg Glu Gln Ala Phe Asp Ile
1 5 10

<210> SEQ ID NO 84
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 84

Arg Ala Ser Gln Ser Ile Ser Ser Tyr Leu Asn
1 5 10

<210> SEQ ID NO 85
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 85

Ala Ala Ser Ser Leu Gln Ser
1 5

<210> SEQ ID NO 86
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 86

Gln Gln Ser Tyr Ser Thr Pro Phe Thr
1 5

<210> SEQ ID NO 87
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 87

Gly Tyr Thr Phe Thr Ser Tyr Tyr Met His
1 5 10

<210> SEQ ID NO 88
<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 88

Ile Ile Asn Pro Ser Gly Gly Ser Thr Ser Tyr Ala Gln Lys Phe Gln
1 5 10 15

Gly

<210> SEQ ID NO 89
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 89

Gly Val Gly Ala His Asp Ala Phe Asp Ile
1 5 10

<210> SEQ ID NO 90
<211> LENGTH: 16
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 90

Arg Ser Ser Gln Ser Leu Leu His Ser Asn Gly Asn Asn Tyr Leu Asp
1 5 10 15

<210> SEQ ID NO 91
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 91

Leu Gly Ser Asn Arg Ala
1 5

<210> SEQ ID NO 92
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 92

Met Gln Gly Thr His Pro Ala Ile Ser
1 5

<210> SEQ ID NO 93
<211> LENGTH: 5
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 93

Ser Tyr Trp Met His 1 5

<210> SEQ ID NO 94
<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 94

Glu Ile Asp Pro Ser Asp Ser Tyr Lys Asp Tyr Asn Gln Lys Phe Lys
1 5 10 15

Asp

<210> SEQ ID NO 95
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 95

Ala Ile Thr Thr Thr Pro Phe Asp Phe
1 5

<210> SEQ ID NO 96
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 96

Arg Ala Ser Gln Ser Ile Ser Asn Asn Leu His
1 5 10

<210> SEQ ID NO 97
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 97

Tyr Ala Ser Gln Ser Ile Ser
1 5

<210> SEQ ID NO 98
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 98

Gln Gln Ser Asn Thr Trp Pro Tyr Thr
1 5

<210> SEQ ID NO 99
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 99

Asn Ala Arg Met Gly Val Ser
1 5

<210> SEQ ID NO 100
<211> LENGTH: 16
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 100

His Ile Phe Ser Asn Asp Glu Lys Ser Tyr Ser Thr Ser Leu Lys Asn
1 5 10 15

<210> SEQ ID NO 101
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 101

Ile Val Gly Tyr Gly Ser Gly Trp Tyr Gly Phe Phe Asp Tyr
1 5 10

<210> SEQ ID NO 102
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 102

Arg Ala Ser Gln Gly Ile Arg Asn Asp Leu Gly
1 5 10

<210> SEQ ID NO 103
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 103

Ala Ala Ser Thr Leu Gln Ser
1 5

<210> SEQ ID NO 104
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 104

Leu Gln His Asn Ser Tyr Pro Leu Thr
1 5

-continued

<210> SEQ ID NO 105
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 105

Asn Ala Arg Met Ala Val Ser
1 5

<210> SEQ ID NO 106
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 106

His Ile Phe Ser Asn Asp Glu Lys Ser Tyr Ser Thr Ser Leu Lys Ser
1 5 10 15

<210> SEQ ID NO 107
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 107

Ile Val Gly Tyr Gly Ser Gly Trp Tyr Gly Tyr Phe Asp Tyr
1 5 10

<210> SEQ ID NO 108
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 108

Arg Ala Ser Gln Asp Ile Arg Tyr Asp Leu Ala
1 5 10

<210> SEQ ID NO 109
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 109

Ala Ala Ser Ser Leu Gln Ser
1 5

<210> SEQ ID NO 110
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 110

Leu Gln His Asn Phe Tyr Pro Leu Thr
1 5

<210> SEQ ID NO 111
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 111

Gly Phe Thr Phe Ser Ser Tyr Gly
1 5

<210> SEQ ID NO 112
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 112

Ile Ser Tyr Asp Gly Ser Asn Lys
1 5

<210> SEQ ID NO 113
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 113

Ala Asn Leu Ala Pro Trp Ala Ala Tyr Trp
1 5 10

<210> SEQ ID NO 114
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 114

Gln Ser Leu Leu His Ser Asn Gly Tyr Asn Tyr
1 5 10

<210> SEQ ID NO 115
<211> LENGTH: 3
<212> TYPE: PRT
<213> ORGANISM: Artificial Sequence
<220> FEATURE:
<223> OTHER INFORMATION: Description of Artificial Sequence: Synthetic peptide

<400> SEQUENCE: 115

Leu Gly Ser
1

<210> SEQ ID NO 116
<211> LENGTH: 9
<212> TYPE: PRT

<213> ORGANISM: Artificial Sequence
<220> FEATURE:
<223> OTHER INFORMATION: Description of Artificial Sequence: Synthetic
      peptide

<400> SEQUENCE: 116

Met Gln Ala Leu Gln Thr Pro His Thr
1               5

<210> SEQ ID NO 117
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 117

Asn Tyr Gly Leu His
1               5

<210> SEQ ID NO 118
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 118

Val Ile Trp Ser Gly Gly Ser Thr Asp Tyr Asn Ala Ala Phe Ile Ser
1               5                   10                  15

<210> SEQ ID NO 119
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 119

Lys Gly Gly Ile Tyr Tyr Ala Asn His Tyr Tyr Ala Met Asp Tyr
1               5                   10                  15

<210> SEQ ID NO 120
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 120

Lys Ser Ser Gln Ser Leu Leu Asn Ser Gly Asn Gln Lys Asn Tyr Met
1               5                   10                  15

Ala

<210> SEQ ID NO 121
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 121

```
Gly Ala Ser Thr Arg Glu Ser
1               5


<210> SEQ ID NO 122
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 122

Gln Asn Asp His Ser Tyr Pro Leu Thr
1               5


<210> SEQ ID NO 123
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 123

Asp Tyr Asn Met His
1               5


<210> SEQ ID NO 124
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 124

Tyr Ile Tyr Pro Tyr Asn Gly Gly Thr Gly Tyr Asn Gln Lys Phe Lys
1               5                   10                  15

Ser Lys Ala


<210> SEQ ID NO 125
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 125

Gly Arg Pro Ala Met Asp Tyr Trp Gly Gln
1               5                   10


<210> SEQ ID NO 126
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 126

Arg Ala Ser Glu Ser Val Asp Asn Tyr Gly Ile Ser Phe Met Asn
1               5                   10                  15


<210> SEQ ID NO 127
<211> LENGTH: 7
<212> TYPE: PRT
```

<213> ORGANISM: Artificial Sequence
<220> FEATURE:
<223> OTHER INFORMATION: Description of Artificial Sequence: Synthetic
peptide

<400> SEQUENCE: 127

Ala Ala Ser Asn Gln Gly Ser
1 5

<210> SEQ ID NO 128
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 128

Gln Gln Ser Lys Glu Val Pro Trp Thr
1 5

<210> SEQ ID NO 129
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 129

Gly Tyr Thr Ile Thr Asp Ser Asn
1 5

<210> SEQ ID NO 130
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 130

Ile Tyr Pro Tyr Asn Gly Gly Thr
1 5

<210> SEQ ID NO 131
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 131

Val Asn Gly Asn Pro Trp Leu Ala Tyr
1 5

<210> SEQ ID NO 132
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 132

Glu Ser Leu Asp Asn Tyr Gly Ile Arg Phe
1 5 10

<210> SEQ ID NO 133
<211> LENGTH: 3
<212> TYPE: PRT
<213> ORGANISM: Artificial Sequence
<220> FEATURE:
<223> OTHER INFORMATION: Description of Artificial Sequence: Synthetic peptide

<400> SEQUENCE: 133

Ala Ala Ser
1

<210> SEQ ID NO 134
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 134

Gln Gln Thr Lys Glu Val Pro Trp Ser
1 5

<210> SEQ ID NO 135
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 135

Ser Ser Asn Trp Trp Ser
1 5

<210> SEQ ID NO 136
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 136

Glu Ile Tyr His Ser Gly Ser Pro Asp Tyr Asn Pro Ser Leu Lys Ser
1 5 10 15

<210> SEQ ID NO 137
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 137

Val Ser Thr Gly Gly Phe Phe Asp Tyr
1 5

<210> SEQ ID NO 138
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 138

Arg Ala Ser Gln Ser Ile Ser Ser Tyr Leu Asn
1 5 10

<210> SEQ ID NO 139
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 139

Ala Ala Ser Ser Leu Gln Ser
1 5

<210> SEQ ID NO 140
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 140

Gln Gln Ser Tyr Ser Thr Pro Pro Thr
1 5

<210> SEQ ID NO 141
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 141

Ser Ser Asn Trp Trp Ser
1 5

<210> SEQ ID NO 142
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 142

Glu Ile Tyr His Ser Gly Ser Pro Asn Tyr Asn Pro Ser Leu Lys Ser
1 5 10 15

<210> SEQ ID NO 143
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 143

Ser Ser Ser Gly Gly Phe Phe Asp Tyr
1 5

<210> SEQ ID NO 144
<211> LENGTH: 11

<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 144

Arg Ala Ser Gln Ser Ile Ser Ser Tyr Leu Asn
1               5                   10

<210> SEQ ID NO 145
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 145

Ala Ala Ser Ser Leu Gln Ser
1               5

<210> SEQ ID NO 146
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 146

Gln Gln Ser Tyr Ser Thr Pro Pro Thr
1               5

<210> SEQ ID NO 147
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 147

Arg Ala Ser Gln Ser Ile Ser Ser Tyr Leu Asn
1               5                   10

<210> SEQ ID NO 148
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 148

Ala Ala Ser Ser Leu Gln
1               5

<210> SEQ ID NO 149
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 149

Gln Gln Ser Tyr Ser Thr Pro Pro Thr 1 5

<210> SEQ ID NO 150
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 150

Ser Ser Asn Trp Trp Ser
1 5

<210> SEQ ID NO 151
<211> LENGTH: 16
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 151

Glu Ile Tyr His Ser Gly Ser Pro Asn Tyr Asn Pro Ser Leu Lys Ser
1 5 10 15

<210> SEQ ID NO 152
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 152

Gln Thr Thr Ala Gly Ser Phe Asp Tyr
1 5

<210> SEQ ID NO 153
<211> LENGTH: 731
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 153

Met Ala Leu Pro Val Thr Ala Leu Leu Leu Pro Leu Ala Leu Leu Leu
1 5 10 15

His Ala Ala Arg Pro Asp Val Val Met Thr Gln Ser Pro Leu Ser Leu
20 25 30

Pro Val Thr Pro Gly Glu Pro Ala Ser Ile Ser Cys Arg Ser Ser Gln
35 40 45

Ser Leu Leu His Ser Asn Gly Tyr Asn Tyr Leu Asp Trp Tyr Leu Gln
50 55 60

Lys Pro Gly Gln Ser Pro Gln Leu Leu Ile Tyr Leu Gly Ser Asn Arg
65 70 75 80

Ala Ser Gly Val Pro Asp Arg Phe Ser Gly Ser Gly Ser Gly Thr Asp
85 90 95

Phe Thr Leu Lys Ile Ser Arg Val Glu Ala Glu Asp Val Gly Val Tyr
100 105 110

Tyr Cys Met Gln Ser Leu Gln Thr Pro Phe Thr Phe Gly Pro Gly Thr
115 120 125

-continued

```
Lys Val Asp Ile Lys Gly Gly Gly Gly Ser Gly Gly Gly Gly Ser Gly
    130                 135                 140

Gly Gly Gly Ser Glu Val Gln Leu Val Gln Ser Gly Ala Glu Val Lys
145                 150                 155                 160

Lys Pro Gly Ala Ser Val Lys Val Ser Cys Lys Ala Ser Gly Tyr Thr
                165                 170                 175

Phe Thr Ser Tyr Tyr Met His Trp Ala Arg Gln Ala Pro Gly Gln Gly
            180                 185                 190

Leu Glu Trp Met Gly Ile Ile Asn Pro Ser Gly Gly Ser Thr Ser Tyr
        195                 200                 205

Ala Gln Lys Phe Gln Gly Arg Val Thr Met Thr Arg Asp Thr Ser Thr
    210                 215                 220

Ser Thr Val Tyr Met Glu Leu Ser Ser Leu Arg Ser Glu Asp Thr Ala
225                 230                 235                 240

Val Tyr Tyr Cys Ala Arg Val Val Ala Ala Ala Val Ala Asp Tyr Trp
                245                 250                 255

Gly Gln Gly Thr Leu Val Thr Val Ser Ser Thr Thr Thr Pro Ala Pro
            260                 265                 270

Arg Pro Pro Thr Pro Ala Pro Thr Ile Ala Leu Gln Pro Leu Ser Leu
        275                 280                 285

Arg Pro Glu Ala Cys Arg Pro Ala Ala Gly Gly Ala Val His Thr Arg
    290                 295                 300

Gly Leu Asp Phe Ala Cys Asp Ile Tyr Ile Trp Ala Pro Leu Ala Gly
305                 310                 315                 320

Thr Cys Gly Val Leu Leu Leu Ser Leu Val Ile Thr Lys Arg Gly Arg
                325                 330                 335

Lys Lys Leu Leu Tyr Ile Phe Lys Gln Pro Phe Met Arg Pro Val Gln
            340                 345                 350

Thr Thr Gln Glu Glu Asp Gly Cys Ser Cys Arg Phe Pro Glu Glu Glu
        355                 360                 365

Glu Gly Gly Cys Glu Leu Arg Val Lys Phe Ser Arg Ser Ala Asp Ala
    370                 375                 380

Pro Ala Tyr Lys Gln Gly Gln Asn Gln Leu Tyr Asn Glu Leu Asn Leu
385                 390                 395                 400

Gly Arg Arg Glu Glu Tyr Asp Val Leu Asp Lys Arg Arg Gly Arg Asp
                405                 410                 415

Pro Glu Met Gly Gly Lys Pro Arg Arg Lys Asn Pro Gln Glu Gly Leu
            420                 425                 430

Tyr Asn Glu Leu Gln Lys Asp Lys Met Ala Glu Ala Tyr Ser Glu Ile
        435                 440                 445

Gly Met Lys Gly Glu Arg Arg Arg Gly Lys Gly His Asp Gly Leu Tyr
    450                 455                 460

Gln Gly Leu Ser Thr Ala Thr Lys Asp Thr Tyr Asp Ala Leu His Met
465                 470                 475                 480

Gln Ala Leu Pro Pro Arg Gly Ser Ser Gly Thr Gly Met Val Ser Lys
                485                 490                 495

Gly Glu Glu Leu Phe Thr Gly Val Val Pro Ile Leu Val Glu Leu Asp
            500                 505                 510

Gly Asp Val Asn Gly His Lys Phe Ser Val Ser Gly Glu Gly Glu Gly
        515                 520                 525

Asp Ala Thr Tyr Gly Lys Leu Thr Leu Lys Leu Ile Cys Thr Thr Gly
    530                 535                 540

Lys Leu Pro Val Pro Trp Pro Thr Leu Val Thr Thr Leu Gly Tyr Gly
```

545 550 555 560

Leu Gln Cys Phe Ala Arg Tyr Pro Asp His Met Lys Gln His Asp Phe
565 570 575

Phe Lys Ser Ala Met Pro Glu Gly Tyr Val Gln Glu Arg Thr Ile Phe
580 585 590

Phe Lys Asp Asp Gly Asn Tyr Lys Thr Arg Ala Glu Val Lys Phe Glu
595 600 605

Gly Asp Thr Leu Val Asn Arg Ile Glu Leu Lys Gly Ile Asp Phe Lys
610 615 620

Glu Asp Gly Asn Ile Leu Gly His Lys Leu Glu Tyr Asn Tyr Asn Ser
625 630 635 640

His Asn Val Tyr Ile Thr Ala Asp Lys Gln Lys Asn Gly Ile Lys Ala
645 650 655

Asn Phe Lys Ile Arg His Asn Ile Glu Asp Gly Gly Val Gln Leu Ala
660 665 670

Asp His Tyr Gln Gln Asn Thr Pro Ile Gly Asp Gly Pro Val Leu Leu
675 680 685

Pro Asp Asn His Tyr Leu Ser Tyr Gln Ser Ala Leu Ser Lys Asp Pro
690 695 700

Asn Glu Lys Arg Asp His Met Val Leu Leu Glu Phe Val Thr Ala Ala
705 710 715 720

Gly Ile Thr Leu Gly Met Asp Glu Leu Tyr Lys
725 730

<210> SEQ ID NO 154
<211> LENGTH: 1567
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 154
acaaaaattt caaggtcggg tgacaatgac gcgcgacacg tcaacgagta cagtgtatat 60
ggaattgtct agcctgaggt ccgaggatac tgctgtctat tattgtgctc gcgtggtcgc 120
tgctgctgtg gcagactact ggggtcaggg tacacttgtg acggtaagca gcaccacgac 180
gccggcgccc cggcctccca cccccgcacc aacgatagcc cttcagccct tgagcctccg 240
gccagaagca tgccgcccgg cagccggagg tgcagtccat acgcgcggac tggactttgc 300
atgtgacatc tacatatggg cccccctcgc cggtacttgc ggtgttttgc ttttgtcact 360
ggtgattacg aagcgcggtc gaaaaaaact cctctacatc ttcaaacaac ctttcatgcg 420
gcctgtccaa acaactcaag aagaggacgg gtgttcatgc cgctttccag aggaagagga 480
aggtggctgt gaacttaggg tcaagtttag caggtcagcg gacgcaccag cttacaagca 540
aggccaaaac cagctttata acgaattgaa tttgggacgc agggaagaat acgatgtgct 600
cgataaacgc agagggaggg acccggaaat gggaggaaag ccaaggcgga aaaacccaca 660
ggaggggttg tacaacgagc ttcaaaaaga taagatggcg gaagcatact ccgaaatagg 720
aatgaagggt gaacggagga ggggcaaggg ccacgacggc ctgtaccagg gactctcaac 780
tgctacgaag gatacttatg atgctcttca catgcaagct ctgccgccgc gcggatcgag 840
tggcaccggt atggtgagca agggcgagga gctgttcacc ggggtggtgc ccatcctggt 900
cgagctggac ggcgacgtaa acggccacaa gttcagcgtg tccggcgagg gcgagggcga 960
tgccacctac ggcaagctga ccctgaagct gatctgcacc accggcaagc tgcccgtgcc 1020

-continued

```
ctggcccacc ctcgtgacca ccctgggcta cggcctccag tgcttcgccc gctaccccga   1080

ccacatgaag cagcacgact tcttcaagtc cgccatgccc gaaggctacg tccaggagcg   1140

caccatcttc ttcaaggacg acggcaacta caagacccgc gccgaggtga agttcgaggg   1200

cgacaccctg gtgaaccgca tcgagctgaa gggcatcgac ttcaaggagg acggcaacat   1260

cctggggcac aagctggagt acaactacaa cagccacaac gtctatatca ccgccgacaa   1320

gcagaagaac ggcatcaagg ccaacttcaa gatccgccac aacatcgagg acggcggcgt   1380

gcagctcgcc gaccactacc agcagaacac ccccatcggc gacggccccg tgctgctgcc   1440

cgacaaccac tacctgagct accagtccgc cctgagcaaa gaccccaacg agaagcgcga   1500

tcacatggtc ctgctggagt tcgtgaccgc cgccgggatc actctcggca tggacgagct   1560

gtacaag                                                             1567
```

<210> SEQ ID NO 155
<211> LENGTH: 730
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 155

```
Met Ala Leu Pro Val Thr Ala Leu Leu Leu Pro Leu Ala Leu Leu Leu
1               5                   10                  15

His Ala Ala Arg Pro Glu Val Gln Leu Val Gln Ser Gly Ala Glu Val
            20                  25                  30

Lys Lys Pro Gly Ser Ser Val Lys Val Ser Cys Lys Ala Ser Gly Gly
        35                  40                  45

Thr Phe Ser Ser Tyr Ala Ile Ser Trp Val Arg Gln Ala Pro Gly Gln
    50                  55                  60

Gly Leu Glu Trp Met Gly Gly Ile Ile Pro Ile Phe Gly Thr Ala Asn
65                  70                  75                  80

Tyr Ala Gln Lys Phe Gln Gly Arg Val Thr Ile Thr Ala Asp Lys Ser
                85                  90                  95

Thr Ser Thr Ala Tyr Met Glu Leu Ser Ser Leu Arg Ser Glu Asp Thr
            100                 105                 110

Ala Val Tyr Tyr Cys Ala Thr Phe Ala Leu Phe Gly Phe Arg Glu Gln
        115                 120                 125

Ala Phe Asp Ile Trp Gly Gln Gly Thr Thr Val Thr Val Ser Ser Gly
    130                 135                 140

Gly Gly Gly Ser Gly Gly Gly Gly Ser Gly Gly Gly Gly Ser Asp Ile
145                 150                 155                 160

Gln Met Thr Gln Ser Pro Ser Ser Leu Ser Ala Ser Val Gly Asp Arg
                165                 170                 175

Val Thr Ile Thr Cys Arg Ala Ser Gln Ser Ile Ser Ser Tyr Leu Asn
            180                 185                 190

Trp Tyr Gln Gln Lys Pro Gly Lys Ala Pro Lys Leu Leu Ile Tyr Ala
        195                 200                 205

Ala Ser Ser Leu Gln Ser Gly Val Pro Ser Arg Phe Ser Gly Ser Gly
    210                 215                 220

Ser Gly Thr Asp Phe Thr Leu Thr Ile Ser Ser Leu Gln Pro Glu Asp
225                 230                 235                 240

Leu Ala Thr Tyr Tyr Cys Gln Gln Ser Tyr Ser Thr Pro Phe Thr Phe
                245                 250                 255
```

```
Gly Pro Gly Thr Lys Val Asp Ile Lys Thr Thr Thr Pro Ala Pro Arg
            260                 265                 270

Pro Pro Thr Pro Ala Pro Thr Ile Ala Leu Gln Pro Leu Ser Leu Arg
        275                 280                 285

Pro Glu Ala Cys Arg Pro Ala Ala Gly Gly Ala Val His Thr Arg Gly
    290                 295                 300

Leu Asp Phe Ala Cys Asp Ile Tyr Ile Trp Ala Pro Leu Ala Gly Thr
305                 310                 315                 320

Cys Gly Val Leu Leu Leu Ser Leu Val Ile Thr Lys Arg Gly Arg Lys
                325                 330                 335

Lys Leu Leu Tyr Ile Phe Lys Gln Pro Phe Met Arg Pro Val Gln Thr
            340                 345                 350

Thr Gln Glu Glu Asp Gly Cys Ser Cys Arg Phe Pro Glu Glu Glu Glu
        355                 360                 365

Gly Gly Cys Glu Leu Arg Val Lys Phe Ser Arg Ser Ala Asp Ala Pro
    370                 375                 380

Ala Tyr Lys Gln Gly Gln Asn Gln Leu Tyr Asn Glu Leu Asn Leu Gly
385                 390                 395                 400

Arg Arg Glu Glu Tyr Asp Val Leu Asp Lys Arg Arg Gly Arg Asp Pro
                405                 410                 415

Glu Met Gly Gly Lys Pro Arg Arg Lys Asn Pro Gln Glu Gly Leu Tyr
            420                 425                 430

Asn Glu Leu Gln Lys Asp Lys Met Ala Glu Ala Tyr Ser Glu Ile Gly
        435                 440                 445

Met Lys Gly Glu Arg Arg Arg Gly Lys Gly His Asp Gly Leu Tyr Gln
    450                 455                 460

Gly Leu Ser Thr Ala Thr Lys Asp Thr Tyr Asp Ala Leu His Met Gln
465                 470                 475                 480

Ala Leu Pro Pro Arg Gly Ser Ser Gly Thr Gly Met Val Ser Lys Gly
                485                 490                 495

Glu Glu Leu Phe Thr Gly Val Val Pro Ile Leu Val Glu Leu Asp Gly
            500                 505                 510

Asp Val Asn Gly His Lys Phe Ser Val Ser Gly Glu Gly Glu Gly Asp
        515                 520                 525

Ala Thr Tyr Gly Lys Leu Thr Leu Lys Leu Ile Cys Thr Thr Gly Lys
    530                 535                 540

Leu Pro Val Pro Trp Pro Thr Leu Val Thr Thr Leu Gly Tyr Gly Leu
545                 550                 555                 560

Gln Cys Phe Ala Arg Tyr Pro Asp His Met Lys Gln His Asp Phe Phe
                565                 570                 575

Lys Ser Ala Met Pro Glu Gly Tyr Val Gln Glu Arg Thr Ile Phe Phe
            580                 585                 590

Lys Asp Asp Gly Asn Tyr Lys Thr Arg Ala Glu Val Lys Phe Glu Gly
        595                 600                 605

Asp Thr Leu Val Asn Arg Ile Glu Leu Lys Gly Ile Asp Phe Lys Glu
    610                 615                 620

Asp Gly Asn Ile Leu Gly His Lys Leu Glu Tyr Asn Tyr Asn Ser His
625                 630                 635                 640

Asn Val Tyr Ile Thr Ala Asp Lys Gln Lys Asn Gly Ile Lys Ala Asn
                645                 650                 655

Phe Lys Ile Arg His Asn Ile Glu Asp Gly Gly Val Gln Leu Ala Asp
            660                 665                 670
```

-continued

His Tyr Gln Gln Asn Thr Pro Ile Gly Asp Gly Pro Val Leu Leu Pro
        675                 680                 685

Asp Asn His Tyr Leu Ser Tyr Gln Ser Ala Leu Ser Lys Asp Pro Asn
    690                 695                 700

Glu Lys Arg Asp His Met Val Leu Leu Glu Phe Val Thr Ala Ala Gly
705                 710                 715                 720

Ile Thr Leu Gly Met Asp Glu Leu Tyr Lys
                725                 730

<210> SEQ ID NO 156
<211> LENGTH: 1605
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 156
cagaaacctg ggaaagcgcc gaagctcctt atctatgctg ccagctcttt gcaaagcggt 60
gtgccctcac ggttctccgg tagtgggtcc gggaccgact tcactttgac catcagcagc 120
cttcagccag aggatcttgc cacttattac tgccagcaat cttatagcac accgtttaca 180
ttcggtccag gcacaaaggt agacattaag accacgacgc cggcgccccg gcctcccacc 240
cccgcaccaa cgatagccct tcagcccttg agcctccggc cagaagcatg ccgcccggca 300
gccggaggtg cagtccatac gcgcggactg gactttgcat gtgacatcta catatgggcc 360
cccctcgccg gtacttgcgg tgttttgctt ttgtcactgg tgattacgaa gcgcggtcga 420
aaaaaactcc tctacatctt caaacaacct ttcatgcggc ctgtccaaac aactcaagaa 480
gaggacgggt gttcatgccg ctttccagag gaagaggaag gtggctgtga acttagggtc 540
aagtttagca ggtcagcgga cgcaccagct tacaagcaag gccaaaacca gctttataac 600
gaattgaatt tgggacgcag ggaagaatac gatgtgctcg ataaacgcag agggagggac 660
ccggaaatgg gaggaaagcc aaggcggaaa aacccacagg aggggttgta caacgagctt 720
caaaaagata agatggcgga agcatactcc gaaataggaa tgaagggtga acggaggagg 780
ggcaagggcc acgacggcct gtaccaggga ctctcaactg ctacgaagga tacttatgat 840
gctcttcaca tgcaagctct gccgccgcgc ggatcgagtg gcaccggtat ggtgagcaag 900
ggcgaggagc tgttcaccgg ggtggtgccc atcctggtcg agctggacgg cgacgtaaac 960
ggccacaagt tcagcgtgtc cggcgagggc gagggcgatg ccacctacgg caagctgacc 1020
ctgaagctga tctgcaccac cggcaagctg cccgtgccct ggcccaccct cgtgaccacc 1080
ctgggctacg gcctccagtg cttcgcccgc taccccgacc acatgaagca gcacgacttc 1140
ttcaagtccg ccatgcccga aggctacgtc caggagcgca ccatcttctt caaggacgac 1200
ggcaactaca agacccgcgc cgaggtgaag ttcgagggcg acaccctggt gaaccgcatc 1260
gagctgaagg gcatcgactt caaggaggac ggcaacatcc tggggcacaa gctggagtac 1320
aactacaaca gccacaacgt ctatatcacc gccgacaagc agaagaacgg catcaaggcc 1380
aacttcaaga tccgccacaa catcgaggac ggcggcgtgc agctcgccga ccactaccag 1440
cagaacaccc ccatcggcga cggccccgtg ctgctgcccg acaaccacta cctgagctac 1500
cagtccgccc tgagcaaaga ccccaacgag aagcgcgatc acatggtcct gctggagttc 1560
gtgaccgccg ccgggatcac tctcggcatg gacgagctgt acaag 1605

<210> SEQ ID NO 157

<211> LENGTH: 501
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 157

```
Met Glu Thr Asp Thr Leu Leu Leu Trp Val Leu Leu Leu Trp Val Pro
1               5                   10                  15

Gly Ser Thr Gly Ala Gly Gly Ser Asp Tyr Lys Asp Asp Asp Asp Lys
            20                  25                  30

Gly Gly Ser Gln Val Gln Leu Val Gln Ser Gly Ala Glu Val Lys Lys
        35                  40                  45

Pro Gly Ser Ser Val Lys Val Ser Cys Lys Ala Ser Gly Tyr Thr Phe
    50                  55                  60

Thr Asp Tyr Asn Met His Trp Val Arg Gln Ala Pro Gly Gln Gly Leu
65                  70                  75                  80

Glu Trp Ile Gly Tyr Ile Tyr Pro Tyr Asn Gly Gly Thr Gly Tyr Asn
                85                  90                  95

Gln Lys Phe Lys Ser Lys Ala Thr Ile Thr Ala Asp Glu Ser Thr Asn
            100                 105                 110

Thr Ala Tyr Met Glu Leu Ser Ser Leu Arg Ser Glu Asp Thr Ala Val
        115                 120                 125

Tyr Tyr Cys Ala Arg Gly Arg Pro Ala Met Asp Tyr Trp Gly Gln Gly
    130                 135                 140

Thr Leu Val Thr Val Ser Ser Gly Gly Gly Gly Ser Gly Gly Gly Gly
145                 150                 155                 160

Ser Gly Gly Gly Gly Ser Asp Ile Gln Met Thr Gln Ser Pro Ser Ser
                165                 170                 175

Leu Ser Ala Ser Val Gly Asp Arg Val Thr Ile Thr Cys Arg Ala Ser
            180                 185                 190

Glu Ser Val Asp Asn Tyr Gly Ile Ser Phe Met Asn Trp Phe Gln Gln
        195                 200                 205

Lys Pro Gly Lys Ala Pro Lys Leu Leu Ile Tyr Ala Ala Ser Asn Gln
    210                 215                 220

Gly Ser Gly Val Pro Ser Arg Phe Ser Gly Ser Gly Ser Gly Thr Asp
225                 230                 235                 240

Phe Thr Leu Thr Ile Ser Ser Leu Gln Pro Asp Asp Phe Ala Thr Tyr
                245                 250                 255

Tyr Cys Gln Gln Ser Lys Glu Val Pro Trp Thr Phe Gly Gln Gly Thr
            260                 265                 270

Lys Val Glu Ile Lys Ser Gly Ala Ala Ala Ile Glu Val Met Tyr Pro
        275                 280                 285

Pro Pro Tyr Leu Asp Asn Glu Lys Ser Asn Gly Thr Ile Ile His Val
    290                 295                 300

Lys Gly Lys His Leu Cys Pro Ser Pro Leu Phe Pro Gly Pro Ser Lys
305                 310                 315                 320

Pro Phe Trp Val Leu Val Val Val Gly Gly Val Leu Ala Cys Tyr Ser
                325                 330                 335

Leu Leu Val Thr Val Ala Phe Ile Ile Phe Trp Val Arg Ser Lys Arg
            340                 345                 350

Ser Arg Leu Leu His Ser Asp Tyr Met Asn Met Thr Pro Arg Arg Pro
        355                 360                 365

Gly Pro Thr Arg Lys His Tyr Gln Pro Tyr Ala Pro Pro Arg Asp Phe
```

```
    370                 375                 380

Ala Ala Tyr Arg Ser Arg Val Lys Phe Ser Arg Ser Ala Asp Ala Pro
385                 390                 395                 400

Ala Tyr Lys Gln Gly Gln Asn Gln Leu Tyr Asn Glu Leu Asn Leu Gly
                405                 410                 415

Arg Arg Glu Glu Tyr Asp Val Leu Asp Lys Arg Arg Gly Arg Asp Pro
            420                 425                 430

Glu Met Gly Gly Lys Pro Arg Arg Lys Asn Pro Gln Glu Gly Leu Tyr
        435                 440                 445

Asn Glu Leu Gln Lys Asp Lys Met Ala Glu Ala Tyr Ser Glu Ile Gly
    450                 455                 460

Met Lys Gly Glu Arg Arg Arg Gly Lys Gly His Asp Gly Leu Tyr Gln
465                 470                 475                 480

Gly Leu Ser Thr Ala Thr Lys Asp Thr Tyr Asp Ala Leu His Met Gln
                485                 490                 495

Ala Leu Pro Pro Arg
            500


<210> SEQ ID NO 158
<211> LENGTH: 1503
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 158

atggaaacgg atactctgct gctgtgggtc ctcttgcttt gggtacctgg gagtaccggc     60

gctggcgggt ccgattacaa ggacgatgac gacaaagggg gttctcaggt tcagctggtt    120

cagtctggcg ccgaagtgaa gaaacctggc agcagcgtga aggtgtcctg caaggccagc    180

ggctacacct ttaccgacta caacatgcac tgggtccgac aggcccctgg acaaggactt    240

gagtggatcg gctacatcta cccctacaat ggcggcaccg gctacaacca gaagttcaag    300

agcaaggcca ccatcaccgc cgacgagagc acaaacaccg cctacatgga actgagcagc    360

ctgagaagcg aggacaccgc cgtgtactac tgtgccagag gcagacccgc catggattat    420

tggggacagg gcaccctggt caccgtttct agcggaggcg gaggatctgg tggcggagga    480

agtggcggag gcggttctga tatccagatg acacagagcc ccagcagcct gtctgccagc    540

gtgggagata gagtgaccat cacctgtaga gccagcgaga gcgtggacaa ctacggcatc    600

agcttcatga actggttcca gcagaagccc ggcaaggccc ctaagctgct gatctacgcc    660

gccagcaatc aaggcagcgg agtgcctagc agattttccg gctctggcag cggcaccgat    720

ttcaccctga caatctctag cctccagcct gacgacttcg ccacctacta ctgccagcag    780

agcaaagagg tgccctggac attcggccag ggcacaaagg tggaaatcaa gagcggagca    840

gcagctatcg aggtgatgta tcctccgccc tacctggata atgaaaagag taatggaact    900

atcattcatg taaaagggaa gcatctttgt ccttctcccc ttttccccgg tccgtctaaa    960

cctttctggg tgcttgtggt cgtgggtgga gtgcttgcgt gttactccct gctggtgacc   1020

gtcgccttca tcattttctg ggtcaggagc aaacgatctc gcctcctcca ttctgactat   1080

atgaacatga ctcctcgcag acccggacct acgcggaaac attaccaacc gtacgcgcct   1140

ccgagagact tcgccgcgta cagaagtagg gtcaagttta gcaggtcagc ggacgcacca   1200

gcttacaagc aaggccaaaa ccagctttat aacgaattga atttgggacg cagggaagaa   1260
```

```
tacgatgtgc tcgataaacg cagagggagg gacccggaaa tgggaggaaa gccaaggcgg   1320

aaaaacccac aggaggggtt gtacaacgag cttcaaaaag ataagatggc ggaagcatac   1380

tccgaaatag gaatgaaggg tgaacggagg aggggcaagg gccacgacgg cctgtaccag   1440

ggactctcaa ctgctacgaa ggatacttat gatgctcttc acatgcaagc tctgccgccg   1500

cgc                                                                 1503


<210> SEQ ID NO 159
<211> LENGTH: 504
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 159

Met Glu Thr Asp Thr Leu Leu Leu Trp Val Leu Leu Leu Trp Val Pro
1               5                   10                  15

Gly Ser Thr Gly Ala Gly Gly Ser Asp Tyr Lys Asp Asp Asp Asp Lys
            20                  25                  30

Gly Gly Ser Glu Val Gln Leu Val Gln Ser Gly Ala Glu Val Lys Lys
        35                  40                  45

Pro Gly Ser Ser Val Lys Val Ser Cys Lys Ala Ser Gly Tyr Thr Ile
    50                  55                  60

Thr Asp Ser Asn Ile His Trp Val Arg Gln Ala Pro Gly Gln Ser Leu
65                  70                  75                  80

Glu Trp Ile Gly Tyr Ile Tyr Pro Tyr Asn Gly Gly Thr Asp Tyr Asn
                85                  90                  95

Gln Lys Phe Lys Asn Arg Ala Thr Leu Thr Val Asp Asn Pro Thr Asn
            100                 105                 110

Thr Ala Tyr Met Glu Leu Ser Ser Leu Arg Ser Glu Asp Thr Ala Phe
        115                 120                 125

Tyr Tyr Cys Val Asn Gly Asn Pro Trp Leu Ala Tyr Trp Gly Gln Gly
    130                 135                 140

Thr Leu Val Thr Val Ser Ser Gly Gly Gly Gly Ser Gly Gly Gly Gly
145                 150                 155                 160

Ser Gly Gly Gly Gly Ser Asp Ile Gln Leu Thr Gln Ser Pro Ser Thr
                165                 170                 175

Leu Ser Ala Ser Val Gly Asp Arg Val Thr Ile Thr Cys Arg Ala Ser
            180                 185                 190

Glu Ser Leu Asp Asn Tyr Gly Ile Arg Phe Leu Thr Trp Phe Gln Gln
        195                 200                 205

Lys Pro Gly Lys Ala Pro Lys Leu Leu Met Tyr Ala Ala Ser Asn Gln
    210                 215                 220

Gly Ser Gly Val Pro Ser Arg Phe Ser Gly Ser Gly Ser Gly Thr Glu
225                 230                 235                 240

Phe Thr Leu Thr Ile Ser Ser Leu Gln Pro Asp Asp Phe Ala Thr Tyr
                245                 250                 255

Tyr Cys Gln Gln Thr Lys Glu Val Pro Trp Ser Phe Gly Gln Gly Thr
            260                 265                 270

Lys Val Glu Val Lys Arg Thr Ser Ser Gly Ala Ala Ala Ile Glu Val
        275                 280                 285

Met Tyr Pro Pro Pro Tyr Leu Asp Asn Glu Lys Ser Asn Gly Thr Ile
    290                 295                 300

Ile His Val Lys Gly Lys His Leu Cys Pro Ser Pro Leu Phe Pro Gly
```

-continued 305 310 315 320

Pro Ser Lys Pro Phe Trp Val Leu Val Val Val Gly Gly Val Leu Ala
325 330 335

Cys Tyr Ser Leu Leu Val Thr Val Ala Phe Ile Ile Phe Trp Val Arg
340 345 350

Ser Lys Arg Ser Arg Leu Leu His Ser Asp Tyr Met Asn Met Thr Pro
355 360 365

Arg Arg Pro Gly Pro Thr Arg Lys His Tyr Gln Pro Tyr Ala Pro Pro
370 375 380

Arg Asp Phe Ala Ala Tyr Arg Ser Arg Val Lys Phe Ser Arg Ser Ala
385 390 395 400

Asp Ala Pro Ala Tyr Lys Gln Gly Gln Asn Gln Leu Tyr Asn Glu Leu
405 410 415

Asn Leu Gly Arg Arg Glu Glu Tyr Asp Val Leu Asp Lys Arg Arg Gly
420 425 430

Arg Asp Pro Glu Met Gly Gly Lys Pro Arg Arg Lys Asn Pro Gln Glu
435 440 445

Gly Leu Tyr Asn Glu Leu Gln Lys Asp Lys Met Ala Glu Ala Tyr Ser
450 455 460

Glu Ile Gly Met Lys Gly Glu Arg Arg Arg Gly Lys Gly His Asp Gly
465 470 475 480

Leu Tyr Gln Gly Leu Ser Thr Ala Thr Lys Asp Thr Tyr Asp Ala Leu
485 490 495

His Met Gln Ala Leu Pro Pro Arg
500

<210> SEQ ID NO 160
<211> LENGTH: 1512
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 160
atggaaacgg atactctgct gctgtgggtc ctcttgcttt gggtacctgg gagtaccggc 60
gctggcgggt ccgattacaa ggacgatgac gacaaagggg gttctgaagt gcagctggtt 120
cagtctggcg ccgaagtgaa gaaacctggc agcagcgtga aggtgtcctg caaggccagc 180
ggctacacca tcaccgacag caacatccac tgggtccgac aggctccagg ccagtctctt 240
gagtggatcg gctacatcta cccctacaac ggcggcaccg actacaacca gaagttcaag 300
aaccgggcca cactgaccgt ggacaaccct accaataccg cctacatgga actgagcagc 360
ctgcggagcg aggacaccgc cttttactac tgcgtgaacg gcaacccctg gctggcctat 420
tggggacagg gaacactggt cacagtgtct agcggaggcg gaggatctgg tggcggagga 480
agtggcggag gcggttctga tattcagctg acacagagcc ccagcacact gtctgcctct 540
gtgggcgaca gagtgaccat cacctgtaga gccagcgaga gcctggacaa ctacggcatc 600
agatttctga cctggttcca gcagaagccc ggcaaggctc ctaagctgct gatgtacgcc 660
gccagcaatc aaggcagcgg agtgcctagc agattttccg gctctggcag cggcacagag 720
ttcaccctga caatctctag cctccagcct gacgacttcg ccacctacta ctgccagcag 780
accaaagagg tgccctggtc ctttggacag ggcaccaagg tggaagtgaa gcggactagc 840
tccggagcag cagctatcga ggtgatgtat cctccgccct acctggataa tgaaaagagt 900
aatgggacta tcattcatgt aaaagggaag catctttgtc cttctcccct tttccccggt 960
ccgtctaaac ctttctgggt gcttgtggtc gtgggtggag tgcttgcgtg ttactccctg 1020
ctggtgaccg tcgccttcat cattttctgg gtcaggagca aacgatctcg cctcctccat 1080
tctgactata tgaacatgac tcctcgcaga cccggaccta cgcggaaaca ttaccaaccg 1140
tacgcgcctc cgagagactt cgccgcgtac agaagtaggg tcaagtttag caggtcagcg 1200
gacgcaccag cttacaagca aggccaaaac cagctttata acgaattgaa tttgggacgc 1260
agggaagaat acgatgtgct cgataaacgc agagggaggg acccggaaat gggaggaaag 1320
ccaaggcgga aaaacccaca ggaggggttg tacaacgagc ttcaaaaaga taagatggcg 1380
gaagcatact ccgaaatagg aatgaagggt gaacggagga ggggcaaggg ccacgacggc 1440
ctgtaccagg gactctcaac tgctacgaag gatacttatg atgctcttca catgcaagct 1500
ctgccgccgc gc 1512

<210> SEQ ID NO 161

<400> SEQUENCE: 161

000

<210> SEQ ID NO 162
<211> LENGTH: 726
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 162

```
Met Ala Leu Pro Val Thr Ala Leu Leu Leu Pro Leu Ala Leu Leu Leu
1               5                   10                  15

His Ala Ala Arg Pro Gln Val Gln Leu Gln Glu Ser Gly Pro Gly Leu
            20                  25                  30

Val Lys Pro Ser Glu Thr Leu Ser Leu Thr Cys Val Val Ser Gly Gly
        35                  40                  45

Ser Ile Ser Ser Ser Asn Trp Trp Ser Trp Val Arg Gln Pro Pro Gly
    50                  55                  60

Lys Gly Leu Glu Trp Ile Gly Glu Ile Tyr His Ser Gly Ser Pro Asp
65                  70                  75                  80

Tyr Asn Pro Ser Leu Lys Ser Arg Val Thr Ile Ser Val Asp Lys Ser
                85                  90                  95

Arg Asn Gln Phe Ser Leu Lys Leu Ser Ser Val Thr Ala Ala Asp Thr
            100                 105                 110

Ala Val Tyr Tyr Cys Ala Lys Val Ser Thr Gly Gly Phe Phe Asp Tyr
        115                 120                 125

Trp Gly Gln Gly Thr Leu Val Thr Val Ser Ser Gly Gly Gly Gly Ser
    130                 135                 140

Gly Gly Gly Gly Ser Gly Gly Gly Gly Ser Glu Ile Glu Leu Thr Gln
145                 150                 155                 160

Ser Pro Ser Ser Leu Ser Ala Ser Val Gly Asp Arg Val Thr Ile Thr
                165                 170                 175

Cys Arg Ala Ser Gln Ser Ile Ser Ser Tyr Leu Asn Trp Tyr Gln Gln
            180                 185                 190

Lys Pro Gly Lys Ala Pro Lys Leu Leu Ile Tyr Ala Ala Ser Ser Leu
        195                 200                 205
```

-continued

Gln Ser Gly Val Pro Ser Arg Phe Ser Gly Ser Gly Ser Gly Thr Asp
    210                 215                 220

Phe Thr Leu Thr Ile Ser Ser Leu Gln Pro Glu Asp Phe Ala Thr Tyr
225                 230                 235                 240

Tyr Cys Gln Gln Ser Tyr Ser Thr Pro Pro Thr Phe Gly Pro Gly Thr
                245                 250                 255

Lys Val Glu Ile Lys Thr Thr Thr Pro Ala Pro Arg Pro Pro Thr Pro
            260                 265                 270

Ala Pro Thr Ile Ala Leu Gln Pro Leu Ser Leu Arg Pro Glu Ala Cys
        275                 280                 285

Arg Pro Ala Ala Gly Gly Ala Val His Thr Arg Gly Leu Asp Phe Ala
    290                 295                 300

Cys Asp Ile Tyr Ile Trp Ala Pro Leu Ala Gly Thr Cys Gly Val Leu
305                 310                 315                 320

Leu Leu Ser Leu Val Ile Thr Lys Arg Gly Arg Lys Lys Leu Leu Tyr
                325                 330                 335

Ile Phe Lys Gln Pro Phe Met Arg Pro Val Gln Thr Thr Gln Glu Glu
            340                 345                 350

Asp Gly Cys Ser Cys Arg Phe Pro Glu Glu Glu Glu Gly Gly Cys Glu
        355                 360                 365

Leu Arg Val Lys Phe Ser Arg Ser Ala Asp Ala Pro Ala Tyr Lys Gln
    370                 375                 380

Gly Gln Asn Gln Leu Tyr Asn Glu Leu Asn Leu Gly Arg Arg Glu Glu
385                 390                 395                 400

Tyr Asp Val Leu Asp Lys Arg Arg Gly Arg Asp Pro Glu Met Gly Gly
                405                 410                 415

Lys Pro Arg Arg Lys Asn Pro Gln Glu Gly Leu Tyr Asn Glu Leu Gln
            420                 425                 430

Lys Asp Lys Met Ala Glu Ala Tyr Ser Glu Ile Gly Met Lys Gly Glu
        435                 440                 445

Arg Arg Arg Gly Lys Gly His Asp Gly Leu Tyr Gln Gly Leu Ser Thr
    450                 455                 460

Ala Thr Lys Asp Thr Tyr Asp Ala Leu His Met Gln Ala Leu Pro Pro
465                 470                 475                 480

Arg Gly Ser Ser Gly Thr Gly Met Val Ser Lys Gly Glu Glu Leu Phe
                485                 490                 495

Thr Gly Val Val Pro Ile Leu Val Glu Leu Asp Gly Asp Val Asn Gly
            500                 505                 510

His Lys Phe Ser Val Ser Gly Glu Gly Glu Gly Asp Ala Thr Tyr Gly
        515                 520                 525

Lys Leu Thr Leu Lys Leu Ile Cys Thr Thr Gly Lys Leu Pro Val Pro
    530                 535                 540

Trp Pro Thr Leu Val Thr Thr Leu Gly Tyr Gly Leu Gln Cys Phe Ala
545                 550                 555                 560

Arg Tyr Pro Asp His Met Lys Gln His Asp Phe Phe Lys Ser Ala Met
                565                 570                 575

Pro Glu Gly Tyr Val Gln Glu Arg Thr Ile Phe Phe Lys Asp Asp Gly
            580                 585                 590

Asn Tyr Lys Thr Arg Ala Glu Val Lys Phe Glu Gly Asp Thr Leu Val
        595                 600                 605

Asn Arg Ile Glu Leu Lys Gly Ile Asp Phe Lys Glu Asp Gly Asn Ile
    610                 615                 620

Leu Gly His Lys Leu Glu Tyr Asn Tyr Asn Ser His Asn Val Tyr Ile

-continued

```
625                 630                 635                 640

Thr Ala Asp Lys Gln Lys Asn Gly Ile Lys Ala Asn Phe Lys Ile Arg
                645                 650                 655

His Asn Ile Glu Asp Gly Gly Val Gln Leu Ala Asp His Tyr Gln Gln
            660                 665                 670

Asn Thr Pro Ile Gly Asp Gly Pro Val Leu Leu Pro Asp Asn His Tyr
        675                 680                 685

Leu Ser Tyr Gln Ser Ala Leu Ser Lys Asp Pro Asn Glu Lys Arg Asp
    690                 695                 700

His Met Val Leu Leu Glu Phe Val Thr Ala Ala Gly Ile Thr Leu Gly
705                 710                 715                 720

Met Asp Glu Leu Tyr Lys
                725


<210> SEQ ID NO 163
<211> LENGTH: 2181
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 163

atggccttac cagtgaccgc cttgctcctg ccgctggcct tgctgctcca cgccgccagg     60

ccgcaggtgc agctgcagga gtcggggcca ggactggtga agccttcgga gaccctgtcc    120

ctcacctgcg ttgtctctgg tggctccatc agcagtagta actggtggag ctgggtccgc    180

cagcccccag ggaaggggct ggagtggatt ggggaaatct atcatagtgg gagccccgac    240

tacaacccgt ccctcaagag tcgagtcacc atatcagtag acaagtccag gaaccagttc    300

tccctgaagc tgagctctgt gaccgccgcg gacacggccg tgtattactg tgcaaaggtt    360

agtactggtg gtttctttga ctactggggg caaggtaccc tggtcaccgt ctcgagtggt    420

ggaggcggtt caggcggagg tggctctggc ggtggcggat cggaaattga gctcacccag    480

tctccatcct ccctgtctgc atctgtagga gacagagtca ccatcacttg ccgggcaagt    540

cagagcatta gcagctactt aaattggtat cagcagaaac cagggaaagc ccctaagctc    600

ctgatctatg ctgcatccag tttgcaaagt ggggtcccat caaggttcag tggcagtgga    660

tctgggacag atttcactct caccatcagc agtctgcaac ctgaagattt tgcaacttac    720

tactgtcaac agagttacag taccccctca acgttcggcc cagggaccaa ggtggagatc    780

aaaaccacga cgccggcgcc ccggcctccc accccgcac caacgatagc ccttcagccc    840

ttgagcctcc ggccagaagc atgccgcccg gcagccggag gtgcagtcca tacgcgcgga    900

ctggactttg catgtgacat ctacatatgg gcccccctcg ccggtacttg cggtgttttg    960

cttttgtcac tggtgattac gaagcgcggt cgaaaaaaac tcctctacat cttcaaacaa   1020

cctttcatgc ggcctgtcca aacaactcaa gaagaggacg ggtgttcatg ccgctttcca   1080

gaggaagagg aaggtggctg tgaacttagg gtcaagttta gcaggtcagc ggacgcacca   1140

gcttacaagc aaggccaaaa ccagctttat aacgaattga atttgggacg cagggaagaa   1200

tacgatgtgc tcgataaacg cagagggagg gacccggaaa tgggaggaaa gccaaggcgg   1260

aaaaacccac aggaggggtt gtacaacgag cttcaaaaag ataagatggc ggaagcatac   1320

tccgaaatag gaatgaaggg tgaacggagg aggggcaagg gccacgacgg cctgtaccag   1380

ggactctcaa ctgctacgaa ggatacttat gatgctcttc acatgcaagc tctgccgccg   1440
```

-continued

```
cgcggatcga gtggcaccgg tatggtgagc aagggcgagg agctgttcac cggggtggtg   1500

cccatcctgg tcgagctgga cggcgacgta aacggccaca agttcagcgt gtccggcgag   1560

ggcgagggcg atgccaccta cggcaagctg accctgaagc tgatctgcac caccggcaag   1620

ctgcccgtgc cctggcccac cctcgtgacc accctgggct acggcctcca gtgcttcgcc   1680

cgctaccccg accacatgaa gcagcacgac ttcttcaagt ccgccatgcc cgaaggctac   1740

gtccaggagc gcaccatctt cttcaaggac gacggcaact acaagacccg cgccgaggtg   1800

aagttcgagg gcgacaccct ggtgaaccgc atcgagctga agggcatcga cttcaaggag   1860

gacggcaaca tcctggggca caagctggag tacaactaca acagccacaa cgtctatatc   1920

accgccgaca agcagaagaa cggcatcaag gccaacttca agatccgcca caacatcgag   1980

gacggcggcg tgcagctcgc cgaccactac cagcagaaca cccccatcgg cgacggcccc   2040

gtgctgctgc ccgacaacca ctacctgagc taccagtccg ccctgagcaa agaccccaac   2100

gagaagcgcg atcacatggt cctgctggag ttcgtgaccg ccgccgggat cactctcggc   2160

atggacgagc tgtacaagta a                                              2181
```

<210> SEQ ID NO 164
<211> LENGTH: 726
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 164

```
Met Ala Leu Pro Val Thr Ala Leu Leu Leu Pro Leu Ala Leu Leu Leu
1               5                   10                  15

His Ala Ala Arg Pro Gln Val Gln Leu Gln Glu Ser Gly Pro Gly Leu
            20                  25                  30

Val Lys Pro Ser Glu Thr Leu Ser Leu Thr Cys Val Val Ser Gly Gly
        35                  40                  45

Ser Ile Ser Ser Ser Asn Trp Trp Ser Trp Val Arg Gln Pro Pro Gly
    50                  55                  60

Lys Gly Leu Glu Trp Ile Gly Glu Ile Tyr His Ser Gly Ser Pro Asn
65                  70                  75                  80

Tyr Asn Pro Ser Leu Lys Ser Arg Val Thr Ile Ser Val Asp Lys Ser
                85                  90                  95

Lys Asn Gln Phe Ser Leu Lys Leu Ser Ser Val Thr Ala Ala Asp Thr
            100                 105                 110

Ala Val Tyr Tyr Cys Ala Arg Ser Ser Ser Gly Gly Phe Phe Asp Tyr
        115                 120                 125

Trp Gly Gln Gly Thr Leu Val Thr Val Ser Ser Gly Gly Gly Gly Ser
    130                 135                 140

Gly Gly Gly Gly Ser Gly Gly Gly Gly Ser Glu Ile Glu Leu Thr Gln
145                 150                 155                 160

Ser Pro Ser Ser Leu Ser Ala Ser Val Gly Asp Arg Val Thr Ile Thr
                165                 170                 175

Cys Arg Ala Ser Gln Ser Ile Ser Ser Tyr Leu Asn Trp Tyr Gln Gln
            180                 185                 190

Lys Pro Gly Lys Ala Pro Lys Leu Leu Ile Tyr Ala Ala Ser Ser Leu
        195                 200                 205

Gln Ser Gly Val Pro Ser Arg Phe Ser Gly Ser Gly Ser Gly Thr Asp
    210                 215                 220
```

-continued

```
Phe Thr Leu Thr Ile Ser Ser Leu Gln Pro Glu Asp Phe Ala Thr Tyr
225                 230                 235                 240

Tyr Cys Gln Gln Ser Tyr Ser Thr Pro Pro Thr Phe Gly Gln Gly Thr
                245                 250                 255

Lys Val Glu Ile Lys Thr Thr Thr Pro Ala Pro Arg Pro Pro Thr Pro
            260                 265                 270

Ala Pro Thr Ile Ala Leu Gln Pro Leu Ser Leu Arg Pro Glu Ala Cys
        275                 280                 285

Arg Pro Ala Ala Gly Gly Ala Val His Thr Arg Gly Leu Asp Phe Ala
    290                 295                 300

Cys Asp Ile Tyr Ile Trp Ala Pro Leu Ala Gly Thr Cys Gly Val Leu
305                 310                 315                 320

Leu Leu Ser Leu Val Ile Thr Lys Arg Gly Arg Lys Lys Leu Leu Tyr
                325                 330                 335

Ile Phe Lys Gln Pro Phe Met Arg Pro Val Gln Thr Thr Gln Glu Glu
            340                 345                 350

Asp Gly Cys Ser Cys Arg Phe Pro Glu Glu Glu Glu Gly Gly Cys Glu
        355                 360                 365

Leu Arg Val Lys Phe Ser Arg Ser Ala Asp Ala Pro Ala Tyr Lys Gln
    370                 375                 380

Gly Gln Asn Gln Leu Tyr Asn Glu Leu Asn Leu Gly Arg Arg Glu Glu
385                 390                 395                 400

Tyr Asp Val Leu Asp Lys Arg Arg Gly Arg Asp Pro Glu Met Gly Gly
                405                 410                 415

Lys Pro Arg Arg Lys Asn Pro Gln Glu Gly Leu Tyr Asn Glu Leu Gln
            420                 425                 430

Lys Asp Lys Met Ala Glu Ala Tyr Ser Glu Ile Gly Met Lys Gly Glu
        435                 440                 445

Arg Arg Arg Gly Lys Gly His Asp Gly Leu Tyr Gln Gly Leu Ser Thr
    450                 455                 460

Ala Thr Lys Asp Thr Tyr Asp Ala Leu His Met Gln Ala Leu Pro Pro
465                 470                 475                 480

Arg Gly Ser Ser Gly Thr Gly Met Val Ser Lys Gly Glu Glu Leu Phe
                485                 490                 495

Thr Gly Val Val Pro Ile Leu Val Glu Leu Asp Gly Asp Val Asn Gly
            500                 505                 510

His Lys Phe Ser Val Ser Gly Glu Gly Glu Gly Asp Ala Thr Tyr Gly
        515                 520                 525

Lys Leu Thr Leu Lys Leu Ile Cys Thr Thr Gly Lys Leu Pro Val Pro
    530                 535                 540

Trp Pro Thr Leu Val Thr Thr Leu Gly Tyr Gly Leu Gln Cys Phe Ala
545                 550                 555                 560

Arg Tyr Pro Asp His Met Lys Gln His Asp Phe Phe Lys Ser Ala Met
                565                 570                 575

Pro Glu Gly Tyr Val Gln Glu Arg Thr Ile Phe Phe Lys Asp Asp Gly
            580                 585                 590

Asn Tyr Lys Thr Arg Ala Glu Val Lys Phe Glu Gly Asp Thr Leu Val
        595                 600                 605

Asn Arg Ile Glu Leu Lys Gly Ile Asp Phe Lys Glu Asp Gly Asn Ile
    610                 615                 620

Leu Gly His Lys Leu Glu Tyr Asn Tyr Asn Ser His Asn Val Tyr Ile
625                 630                 635                 640

Thr Ala Asp Lys Gln Lys Asn Gly Ile Lys Ala Asn Phe Lys Ile Arg
```

```
                645                 650                 655

His Asn Ile Glu Asp Gly Gly Val Gln Leu Ala Asp His Tyr Gln Gln
            660                 665                 670

Asn Thr Pro Ile Gly Asp Gly Pro Val Leu Leu Pro Asp Asn His Tyr
        675                 680                 685

Leu Ser Tyr Gln Ser Ala Leu Ser Lys Asp Pro Asn Glu Lys Arg Asp
    690                 695                 700

His Met Val Leu Leu Glu Phe Val Thr Ala Ala Gly Ile Thr Leu Gly
705                 710                 715                 720

Met Asp Glu Leu Tyr Lys
                725


<210> SEQ ID NO 165
<211> LENGTH: 2181
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 165

atggccttac cagtgaccgc cttgctcctg ccgctggcct tgctgctcca cgccgccagg     60

ccgcaggtgc agctgcagga gtcgggccca ggactggtga agccttcgga gaccctgtcc    120

ctcacctgcg ttgtctctgg tggctccatc agcagtagta actggtggag ctgggtccgc    180

cagcccccag ggaaggggct ggagtggatt ggggaaatct atcatagtgg gagccccaac    240

tacaacccgt ccctcaagag tcgagtcacc atatcagtag acaagtccaa gaaccagttc    300

tccctgaagc tgagctctgt gaccgccgcg gacacggccg tgtattactg tgcaaggtcg    360

tcttctggtg gtttctttga ctactggggc caaggtaccc tggtcaccgt ctcgagtggt    420

ggaggcggtt caggcggagg tggctctggc ggtggcggat cggaaattga gctcacccag    480

tctccatcct ccctgtctgc atctgtagga gacagagtca ccatcacttg ccgggcaagt    540

cagagcatta gcagctactt aaattggtat cagcagaaac cagggaaagc ccctaagctc    600

ctgatctatg ctgcatccag tttgcaaagt ggggtcccat caaggttcag tggcagtgga    660

tctgggacag atttcactct caccatcagc agtctgcaac ctgaagattt tgcaacttac    720

tactgtcaac agagttacag tacccctcca acgttcggcc aagggaccaa ggtggagatc    780

aaaaccacga cgccggcgcc ccggcctccc acccccgcac caacgatagc ccttcagccc    840

ttgagcctcc ggccagaagc atgccgcccg gcagccggag gtgcagtcca tacgcgcgga    900

ctggactttg catgtgacat ctacatatgg gcccccctcg ccggtacttg cggtgttttg    960

cttttgtcac tggtgattac gaagcgcggt cgaaaaaaac tcctctacat cttcaaacaa   1020

cctttcatgc ggcctgtcca aacaactcaa gaagaggacg ggtgttcatg ccgctttcca   1080

gaggaagagg aaggtggctg tgaacttagg gtcaagttta gcaggtcagc ggacgcacca   1140

gcttacaagc aaggccaaaa ccagctttat aacgaattga atttgggacg cagggaagaa   1200

tacgatgtgc tcgataaacg cagagggagg gacccggaaa tgggaggaaa gccaaggcgg   1260

aaaaacccac aggaggggtt gtacaacgag cttcaaaaag ataagatggc ggaagcatac   1320

tccgaaatag gaatgaaggg tgaacggagg aggggcaagg gccacgacgg cctgtaccag   1380

ggactctcaa ctgctacgaa ggatacttat gatgctcttc acatgcaagc tctgccgccg   1440

cgcggatcga gtggcaccgg tatggtgagc aagggcgagg agctgttcac cggggtggtg   1500

cccatcctgg tcgagctgga cggcgacgta aacggccaca agttcagcgt gtccggcgag   1560
```

```
ggcgagggcg atgccaccta cggcaagctg accctgaagc tgatctgcac caccggcaag   1620

ctgcccgtgc cctggcccac cctcgtgacc accctgggct acggcctcca gtgcttcgcc   1680

cgctaccccg accacatgaa gcagcacgac ttcttcaagt ccgccatgcc cgaaggctac   1740

gtccaggagc gcaccatctt cttcaaggac gacggcaact acaagacccg cgccgaggtg   1800

aagttcgagg gcgacaccct ggtgaaccgc atcgagctga agggcatcga cttcaaggag   1860

gacggcaaca tcctggggca caagctggag tacaactaca acagccacaa cgtctatatc   1920

accgccgaca agcagaagaa cggcatcaag gccaacttca agatccgcca caacatcgag   1980

gacggcggcg tgcagctcgc cgaccactac cagcagaaca cccccatcgg cgacggcccc   2040

gtgctgctgc ccgacaacca ctacctgagc taccagtccg ccctgagcaa agaccccaac   2100

gagaagcgcg atcacatggt cctgctggag ttcgtgaccg ccgccgggat cactctcggc   2160

atggacgagc tgtacaagta a                                              2181
```

<210> SEQ ID NO 166
<211> LENGTH: 726
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 166

```
Met Ala Leu Pro Val Thr Ala Leu Leu Leu Pro Leu Ala Leu Leu Leu
1               5                   10                  15

His Ala Ala Arg Pro Gln Val Gln Leu Gln Glu Ser Gly Pro Gly Leu
            20                  25                  30

Val Lys Pro Ser Glu Thr Leu Ser Leu Thr Cys Val Val Ser Gly Gly
        35                  40                  45

Ser Ile Ser Ser Ser Asn Trp Trp Ser Trp Val Arg Gln Pro Pro Gly
    50                  55                  60

Lys Gly Leu Glu Trp Ile Gly Glu Ile Tyr His Ser Gly Ser Pro Asn
65                  70                  75                  80

Tyr Asn Pro Ser Leu Lys Ser Arg Val Thr Ile Ser Val Asp Lys Ser
                85                  90                  95

Lys Asn Gln Phe Ser Leu Lys Leu Ser Ser Val Thr Ala Ala Asp Thr
            100                 105                 110

Ala Val Tyr Tyr Cys Ala Arg Gln Thr Thr Ala Gly Ser Phe Asp Tyr
        115                 120                 125

Trp Gly Gln Gly Thr Leu Val Thr Val Ser Ser Gly Gly Gly Gly Ser
    130                 135                 140

Gly Gly Gly Gly Ser Gly Gly Gly Gly Ser Glu Ile Glu Leu Thr Gln
145                 150                 155                 160

Ser Pro Ser Ser Leu Ser Ala Ser Val Gly Asp Arg Val Thr Ile Thr
                165                 170                 175

Cys Arg Ala Ser Gln Ser Ile Ser Ser Tyr Leu Asn Trp Tyr Gln Gln
            180                 185                 190

Lys Pro Gly Lys Ala Pro Lys Leu Leu Ile Tyr Ala Ala Ser Ser Leu
        195                 200                 205

Gln Ser Gly Val Pro Ser Arg Phe Ser Gly Ser Gly Ser Gly Thr Asp
    210                 215                 220

Phe Thr Leu Thr Ile Ser Ser Leu Gln Pro Glu Asp Phe Ala Thr Tyr
225                 230                 235                 240
```

-continued

```
Tyr Cys Gln Gln Ser Tyr Ser Thr Pro Pro Thr Phe Gly Gln Gly Thr
                245                 250                 255

Lys Val Glu Ile Lys Thr Thr Thr Pro Ala Pro Arg Pro Pro Thr Pro
            260                 265                 270

Ala Pro Thr Ile Ala Leu Gln Pro Leu Ser Leu Arg Pro Glu Ala Cys
        275                 280                 285

Arg Pro Ala Ala Gly Gly Ala Val His Thr Arg Gly Leu Asp Phe Ala
    290                 295                 300

Cys Asp Ile Tyr Ile Trp Ala Pro Leu Ala Gly Thr Cys Gly Val Leu
305                 310                 315                 320

Leu Leu Ser Leu Val Ile Thr Lys Arg Gly Arg Lys Lys Leu Leu Tyr
                325                 330                 335

Ile Phe Lys Gln Pro Phe Met Arg Pro Val Gln Thr Thr Gln Glu Glu
            340                 345                 350

Asp Gly Cys Ser Cys Arg Phe Pro Glu Glu Glu Glu Gly Gly Cys Glu
        355                 360                 365

Leu Arg Val Lys Phe Ser Arg Ser Ala Asp Ala Pro Ala Tyr Lys Gln
    370                 375                 380

Gly Gln Asn Gln Leu Tyr Asn Glu Leu Asn Leu Gly Arg Arg Glu Glu
385                 390                 395                 400

Tyr Asp Val Leu Asp Lys Arg Arg Gly Arg Asp Pro Glu Met Gly Gly
                405                 410                 415

Lys Pro Arg Arg Lys Asn Pro Gln Glu Gly Leu Tyr Asn Glu Leu Gln
            420                 425                 430

Lys Asp Lys Met Ala Glu Ala Tyr Ser Glu Ile Gly Met Lys Gly Glu
        435                 440                 445

Arg Arg Arg Gly Lys Gly His Asp Gly Leu Tyr Gln Gly Leu Ser Thr
    450                 455                 460

Ala Thr Lys Asp Thr Tyr Asp Ala Leu His Met Gln Ala Leu Pro Pro
465                 470                 475                 480

Arg Gly Ser Ser Gly Thr Gly Met Val Ser Lys Gly Glu Glu Leu Phe
                485                 490                 495

Thr Gly Val Val Pro Ile Leu Val Glu Leu Asp Gly Asp Val Asn Gly
            500                 505                 510

His Lys Phe Ser Val Ser Gly Glu Gly Glu Gly Asp Ala Thr Tyr Gly
        515                 520                 525

Lys Leu Thr Leu Lys Leu Ile Cys Thr Thr Gly Lys Leu Pro Val Pro
    530                 535                 540

Trp Pro Thr Leu Val Thr Thr Leu Gly Tyr Gly Leu Gln Cys Phe Ala
545                 550                 555                 560

Arg Tyr Pro Asp His Met Lys Gln His Asp Phe Phe Lys Ser Ala Met
                565                 570                 575

Pro Glu Gly Tyr Val Gln Glu Arg Thr Ile Phe Phe Lys Asp Asp Gly
            580                 585                 590

Asn Tyr Lys Thr Arg Ala Glu Val Lys Phe Glu Gly Asp Thr Leu Val
        595                 600                 605

Asn Arg Ile Glu Leu Lys Gly Ile Asp Phe Lys Glu Asp Gly Asn Ile
    610                 615                 620

Leu Gly His Lys Leu Glu Tyr Asn Tyr Asn Ser His Asn Val Tyr Ile
625                 630                 635                 640

Thr Ala Asp Lys Gln Lys Asn Gly Ile Lys Ala Asn Phe Lys Ile Arg
                645                 650                 655

His Asn Ile Glu Asp Gly Gly Val Gln Leu Ala Asp His Tyr Gln Gln
```

-continued

```
            660                 665                 670

Asn Thr Pro Ile Gly Asp Gly Pro Val Leu Leu Pro Asp Asn His Tyr
        675                 680                 685

Leu Ser Tyr Gln Ser Ala Leu Ser Lys Asp Pro Asn Glu Lys Arg Asp
    690                 695                 700

His Met Val Leu Leu Glu Phe Val Thr Ala Ala Gly Ile Thr Leu Gly
705                 710                 715                 720

Met Asp Glu Leu Tyr Lys
                725
```

<210> SEQ ID NO 167
<211> LENGTH: 2181
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 167

```
atggccttac cagtgaccgc cttgctcctg ccgctggcct tgctgctcca cgccgccagg     60

ccgcaggtgc agctgcagga gtcgggccca ggactggtga agccttcgga gaccctgtcc    120

ctcacctgcg ttgtctctgg tggctccatc agcagtagta actggtggag ctgggtccgc    180

cagcccccag ggaaggggct ggagtggatt ggggaaatct atcatagtgg gagccccaac    240

tacaacccgt ccctcaagag tcgagtcacc atatcagtag acaagtccaa gaaccagttc    300

tccctgaagc tgagctctgt gaccgccgcg gacacggccg tgtattactg tgcaaggcag    360

actactgctg ggtcctttga ctactggggc caaggtaccc tggtcaccgt ctcgagtggt    420

ggaggcggtt caggcggagg tggctctggc ggtggcggat cggaaattga gctcacccag    480

tctccatcct ccctgtctgc atctgtagga gacagagtca ccatcacttg ccgggcaagt    540

cagagcatta gcagctactt aaattggtat cagcagaaac cagggaaagc ccctaagctc    600

ctgatctatg ctgcatccag tttgcaaagt ggggtcccat caaggttcag tggcagtgga    660

tctgggacag atttcactct caccatcagc agtctgcaac ctgaagattt tgcaacttac    720

tactgtcaac agagttacag taccccctcca acgttcggcc aagggaccaa ggtggagatc    780

aaaaccacga cgccggcgcc ccggcctccc acccccgcac caacgatagc ccttcagccc    840

ttgagcctcc ggccagaagc atgccgcccg gcagccggag gtgcagtcca tacgcgcgga    900

ctggactttg catgtgacat ctacatatgg gcccccctcg ccggtacttg cggtgttttg    960

cttttgtcac tggtgattac gaagcgcggt cgaaaaaaac tcctctacat cttcaaacaa   1020

cctttcatgc ggcctgtcca aacaactcaa gaagaggacg ggtgttcatg ccgctttcca   1080

gaggaagagg aaggtggctg tgaacttagg gtcaagttta gcaggtcagc ggacgcacca   1140

gcttacaagc aaggccaaaa ccagctttat aacgaattga atttgggacg cagggaagaa   1200

tacgatgtgc tcgataaacg cagagggagg gacccggaaa tgggaggaaa gccaaggcgg   1260

aaaaacccac aggaggggtt gtacaacgag cttcaaaaag ataagatggc ggaagcatac   1320

tccgaaatag gaatgaaggg tgaacggagg aggggcaagg gccacgacgg cctgtaccag   1380

ggactctcaa ctgctacgaa ggatacttat gatgctcttc acatgcaagc tctgccgccg   1440

cgcggatcga gtggcaccgg tatggtgagc aagggcgagg agctgttcac cggggtggtg   1500

cccatcctgg tcgagctgga cggcgacgta aacggccaca agttcagcgt gtccggcgag   1560

ggcgagggcg atgccaccta cggcaagctg accctgaagc tgatctgcac caccggcaag   1620
```

```
ctgcccgtgc cctggcccac cctcgtgacc accctgggct acggcctcca gtgcttcgcc   1680

cgctaccccg accacatgaa gcagcacgac ttcttcaagt ccgccatgcc cgaaggctac   1740

gtccaggagc gcaccatctt cttcaaggac gacggcaact acaagacccg cgccgaggtg   1800

aagttcgagg gcgacaccct ggtgaaccgc atcgagctga agggcatcga cttcaaggag   1860

gacggcaaca tcctggggca caagctggag tacaactaca acagccacaa cgtctatatc   1920

accgccgaca agcagaagaa cggcatcaag gccaacttca agatccgcca caacatcgag   1980

gacggcggcg tgcagctcgc cgaccactac cagcagaaca cccccatcgg cgacggcccc   2040

gtgctgctgc ccgacaacca ctacctgagc taccagtccg ccctgagcaa agaccccaac   2100

gagaagcgcg atcacatggt cctgctggag ttcgtgaccg ccgccgggat cactctcggc   2160

atggacgagc tgtacaagta a                                             2181


<210> SEQ ID NO 168
<211> LENGTH: 728
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 168

Met Ala Leu Pro Val Thr Ala Leu Leu Leu Pro Leu Ala Leu Leu Leu
1               5                   10                  15

His Ala Ala Arg Pro Gln Val Gln Leu Gln Glu Ser Gly Pro Gly Leu
            20                  25                  30

Val Lys Pro Ser Glu Thr Leu Ser Leu Thr Cys Val Val Ser Gly Gly
        35                  40                  45

Ser Ile Ser Ser Ser Asn Trp Trp Ser Trp Val Arg Gln Pro Pro Gly
    50                  55                  60

Lys Gly Leu Glu Trp Ile Gly Glu Ile Tyr His Ser Gly Ser Pro Asp
65                  70                  75                  80

Tyr Asn Pro Ser Leu Lys Ser Arg Val Thr Ile Ser Val Asp Lys Ser
                85                  90                  95

Arg Asn Gln Phe Ser Leu Lys Leu Ser Ser Val Thr Ala Ala Asp Thr
            100                 105                 110

Ala Val Tyr Tyr Cys Ala Lys Val Ser Thr Gly Gly Phe Phe Asp Tyr
        115                 120                 125

Trp Gly Gln Gly Thr Leu Val Thr Val Ser Ser Gly Gly Gly Gly Ser
    130                 135                 140

Gly Gly Gly Gly Ser Gly Gly Gly Gly Ser Glu Ile Glu Leu Thr Gln
145                 150                 155                 160

Ser Pro Ser Ser Leu Ser Ala Ser Val Gly Asp Arg Val Thr Ile Thr
                165                 170                 175

Cys Arg Ala Ser Gln Ser Ile Ser Ser Tyr Leu Asn Trp Tyr Gln Gln
            180                 185                 190

Lys Pro Gly Lys Ala Pro Lys Leu Leu Ile Tyr Ala Ala Ser Ser Leu
        195                 200                 205

Gln Ser Gly Val Pro Ser Arg Phe Ser Gly Ser Gly Ser Gly Thr Asp
    210                 215                 220

Phe Thr Leu Thr Ile Ser Ser Leu Gln Pro Glu Asp Phe Ala Thr Tyr
225                 230                 235                 240

Tyr Cys Gln Gln Ser Tyr Ser Thr Pro Pro Thr Phe Gly Pro Gly Thr
                245                 250                 255
```

```
Lys Val Glu Ile Lys Ala Ala Ala Ile Glu Val Met Tyr Pro Pro Pro
            260                 265                 270

Tyr Leu Asp Asn Glu Lys Ser Asn Gly Thr Ile Ile His Val Lys Gly
        275                 280                 285

Lys His Leu Cys Pro Ser Pro Leu Phe Pro Gly Pro Ser Lys Pro Phe
    290                 295                 300

Trp Val Leu Val Val Val Gly Gly Val Leu Ala Cys Tyr Ser Leu Leu
305                 310                 315                 320

Val Thr Val Ala Phe Ile Ile Phe Trp Val Arg Ser Lys Arg Ser Arg
                325                 330                 335

Leu Leu His Ser Asp Tyr Met Asn Met Thr Pro Arg Arg Pro Gly Pro
            340                 345                 350

Thr Arg Lys His Tyr Gln Pro Tyr Ala Pro Pro Arg Asp Phe Ala Ala
        355                 360                 365

Tyr Arg Ser Arg Val Lys Phe Ser Arg Ser Ala Asp Ala Pro Ala Tyr
    370                 375                 380

Lys Gln Gly Gln Asn Gln Leu Tyr Asn Glu Leu Asn Leu Gly Arg Arg
385                 390                 395                 400

Glu Glu Tyr Asp Val Leu Asp Lys Arg Arg Gly Arg Asp Pro Glu Met
                405                 410                 415

Gly Gly Lys Pro Arg Arg Lys Asn Pro Gln Glu Gly Leu Tyr Asn Glu
            420                 425                 430

Leu Gln Lys Asp Lys Met Ala Glu Ala Tyr Ser Glu Ile Gly Met Lys
        435                 440                 445

Gly Glu Arg Arg Arg Gly Lys Gly His Asp Gly Leu Tyr Gln Gly Leu
    450                 455                 460

Ser Thr Ala Thr Lys Asp Thr Tyr Asp Ala Leu His Met Gln Ala Leu
465                 470                 475                 480

Pro Pro Arg Gly Ser Ser Gly Thr Gly Met Val Ser Lys Gly Glu Glu
                485                 490                 495

Leu Phe Thr Gly Val Val Pro Ile Leu Val Glu Leu Asp Gly Asp Val
            500                 505                 510

Asn Gly His Lys Phe Ser Val Ser Gly Glu Gly Glu Gly Asp Ala Thr
        515                 520                 525

Tyr Gly Lys Leu Thr Leu Lys Leu Ile Cys Thr Thr Gly Lys Leu Pro
    530                 535                 540

Val Pro Trp Pro Thr Leu Val Thr Thr Leu Gly Tyr Gly Leu Gln Cys
545                 550                 555                 560

Phe Ala Arg Tyr Pro Asp His Met Lys Gln His Asp Phe Phe Lys Ser
                565                 570                 575

Ala Met Pro Glu Gly Tyr Val Gln Glu Arg Thr Ile Phe Phe Lys Asp
            580                 585                 590

Asp Gly Asn Tyr Lys Thr Arg Ala Glu Val Lys Phe Glu Gly Asp Thr
        595                 600                 605

Leu Val Asn Arg Ile Glu Leu Lys Gly Ile Asp Phe Lys Glu Asp Gly
    610                 615                 620

Asn Ile Leu Gly His Lys Leu Glu Tyr Asn Tyr Asn Ser His Asn Val
625                 630                 635                 640

Tyr Ile Thr Ala Asp Lys Gln Lys Asn Gly Ile Lys Ala Asn Phe Lys
                645                 650                 655

Ile Arg His Asn Ile Glu Asp Gly Gly Val Gln Leu Ala Asp His Tyr
            660                 665                 670

Gln Gln Asn Thr Pro Ile Gly Asp Gly Pro Val Leu Leu Pro Asp Asn
```

675 680 685

His Tyr Leu Ser Tyr Gln Ser Ala Leu Ser Lys Asp Pro Asn Glu Lys
690 695 700

Arg Asp His Met Val Leu Leu Glu Phe Val Thr Ala Ala Gly Ile Thr
705 710 715 720

Leu Gly Met Asp Glu Leu Tyr Lys
725

<210> SEQ ID NO 169
<211> LENGTH: 2187
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 169
atggccttac cagtgaccgc cttgctcctg ccgctggcct tgctgctcca cgccgccagg 60
ccgcaggtgc agctgcagga gtcggggcca ggactggtga agccttcgga gaccctgtcc 120
ctcacctgcg ttgtctctgg tggctccatc agcagtagta actggtggag ctgggtccgc 180
cagcccccag ggaaggggct ggagtggatt ggggaaatct atcatagtgg gagccccgac 240
tacaacccgt ccctcaagag tcgagtcacc atatcagtag acaagtccag gaaccagttc 300
tccctgaagc tgagctctgt gaccgccgcg gacacggccg tgtattactg tgcaaaggtt 360
agtactggtg gtttctttga ctactggggg caaggtaccc tggtcaccgt ctcgagtggt 420
ggaggcggtt caggcggagg tggctctggc ggtggcggat cggaaattga gctcacccag 480
tctccatcct ccctgtctgc atctgtagga gacagagtca ccatcacttg ccgggcaagt 540
cagagcatta gcagctactt aaattggtat cagcagaaac cagggaaagc ccctaagctc 600
ctgatctatg ctgcatccag tttgcaaagt ggggtcccat caaggttcag tggcagtgga 660
tctgggacag atttcactct caccatcagc agtctgcaac ctgaagattt tgcaacttac 720
tactgtcaac agagttacag taccccctcca acgttcggcc cagggaccaa ggtggagatc 780
aaagcagcag ctatcgaggt gatgtatcct ccgccctacc tggataatga aaagagtaat 840
gggactatca ttcatgtaaa agggaagcat ctttgtcctt ctcccctttt ccccggtccg 900
tctaaacctt tctgggtgct tgtggtcgtg ggtggagtgc ttgcgtgtta ctccctgctg 960
gtgaccgtcg ccttcatcat tttctgggtc aggagcaaac gatctcgcct cctccattct 1020
gactatatga acatgactcc tcgcagaccc ggacctacgc ggaaacatta ccaaccgtac 1080
gcgcctccga gagacttcgc cgcgtacaga agtagggtca agtttagcag gtcagcggac 1140
gcaccagctt acaagcaagg ccaaaaccag ctttataacg aattgaattt gggacgcagg 1200
gaagaatacg atgtgctcga taaacgcaga gggagggacc cggaaatggg aggaaagcca 1260
aggcggaaaa acccacagga ggggttgtac aacgagcttc aaaaagataa gatggcggaa 1320
gcatactccg aaataggaat gaagggtgaa cggaggaggg gcaagggcca cgacggcctg 1380
taccagggac tctcaactgc tacgaaggat acttatgatg ctcttcacat gcaagctctg 1440
ccgccgcgcg gatcgagtgg caccggtatg gtgagcaagg gcgaggagct gttcaccggg 1500
gtggtgccca tcctggtcga gctggacggc gacgtaaacg gccacaagtt cagcgtgtcc 1560
ggcgagggcg agggcgatgc cacctacggc aagctgaccc tgaagctgat ctgcaccacc 1620
ggcaagctgc ccgtgccctg gcccaccctc gtgaccaccc tgggctacgg cctccagtgc 1680
ttcgcccgct accccgacca catgaagcag cacgacttct tcaagtccgc catgcccgaa 1740

```
ggctacgtcc aggagcgcac catcttcttc aaggacgacg gcaactacaa gacccgcgcc   1800

gaggtgaagt tcgagggcga caccctggtg aaccgcatcg agctgaaggg catcgacttc   1860

aaggaggacg gcaacatcct ggggcacaag ctggagtaca actacaacag ccacaacgtc   1920

tatatcaccg ccgacaagca gaagaacggc atcaaggcca acttcaagat ccgccacaac   1980

atcgaggacg gcggcgtgca gctcgccgac cactaccagc agaacacccc catcggcgac   2040

ggccccgtgc tgctgcccga caaccactac ctgagctacc agtccgccct gagcaaagac   2100

cccaacgaga agcgcgatca catggtcctg ctggagttcg tgaccgccgc cgggatcact   2160

ctcggcatgg acgagctgta caagtaa                                       2187


<210> SEQ ID NO 170
<211> LENGTH: 728
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 170

Met Ala Leu Pro Val Thr Ala Leu Leu Leu Pro Leu Ala Leu Leu Leu
1               5                   10                  15

His Ala Ala Arg Pro Gln Val Gln Leu Gln Glu Ser Gly Pro Gly Leu
            20                  25                  30

Val Lys Pro Ser Glu Thr Leu Ser Leu Thr Cys Val Val Ser Gly Gly
        35                  40                  45

Ser Ile Ser Ser Ser Asn Trp Trp Ser Trp Val Arg Gln Pro Pro Gly
    50                  55                  60

Lys Gly Leu Glu Trp Ile Gly Glu Ile Tyr His Ser Gly Ser Pro Asn
65                  70                  75                  80

Tyr Asn Pro Ser Leu Lys Ser Arg Val Thr Ile Ser Val Asp Lys Ser
                85                  90                  95

Lys Asn Gln Phe Ser Leu Lys Leu Ser Ser Val Thr Ala Ala Asp Thr
            100                 105                 110

Ala Val Tyr Tyr Cys Ala Arg Ser Ser Ser Gly Gly Phe Phe Asp Tyr
        115                 120                 125

Trp Gly Gln Gly Thr Leu Val Thr Val Ser Ser Gly Gly Gly Gly Ser
    130                 135                 140

Gly Gly Gly Gly Ser Gly Gly Gly Gly Ser Glu Ile Glu Leu Thr Gln
145                 150                 155                 160

Ser Pro Ser Ser Leu Ser Ala Ser Val Gly Asp Arg Val Thr Ile Thr
                165                 170                 175

Cys Arg Ala Ser Gln Ser Ile Ser Ser Tyr Leu Asn Trp Tyr Gln Gln
            180                 185                 190

Lys Pro Gly Lys Ala Pro Lys Leu Leu Ile Tyr Ala Ala Ser Ser Leu
        195                 200                 205

Gln Ser Gly Val Pro Ser Arg Phe Ser Gly Ser Gly Ser Gly Thr Asp
    210                 215                 220

Phe Thr Leu Thr Ile Ser Ser Leu Gln Pro Glu Asp Phe Ala Thr Tyr
225                 230                 235                 240

Tyr Cys Gln Gln Ser Tyr Ser Thr Pro Pro Thr Phe Gly Gln Gly Thr
                245                 250                 255

Lys Val Glu Ile Lys Ala Ala Ala Ile Glu Val Met Tyr Pro Pro Pro
            260                 265                 270
```

-continued

```
Tyr Leu Asp Asn Glu Lys Ser Asn Gly Thr Ile Ile His Val Lys Gly
        275                 280                 285

Lys His Leu Cys Pro Ser Pro Leu Phe Pro Gly Pro Ser Lys Pro Phe
    290                 295                 300

Trp Val Leu Val Val Val Gly Gly Val Leu Ala Cys Tyr Ser Leu Leu
305                 310                 315                 320

Val Thr Val Ala Phe Ile Ile Phe Trp Val Arg Ser Lys Arg Ser Arg
                325                 330                 335

Leu Leu His Ser Asp Tyr Met Asn Met Thr Pro Arg Arg Pro Gly Pro
            340                 345                 350

Thr Arg Lys His Tyr Gln Pro Tyr Ala Pro Pro Arg Asp Phe Ala Ala
        355                 360                 365

Tyr Arg Ser Arg Val Lys Phe Ser Arg Ser Ala Asp Ala Pro Ala Tyr
    370                 375                 380

Lys Gln Gly Gln Asn Gln Leu Tyr Asn Glu Leu Asn Leu Gly Arg Arg
385                 390                 395                 400

Glu Glu Tyr Asp Val Leu Asp Lys Arg Arg Gly Arg Asp Pro Glu Met
                405                 410                 415

Gly Gly Lys Pro Arg Arg Lys Asn Pro Gln Glu Gly Leu Tyr Asn Glu
            420                 425                 430

Leu Gln Lys Asp Lys Met Ala Glu Ala Tyr Ser Glu Ile Gly Met Lys
        435                 440                 445

Gly Glu Arg Arg Arg Gly Lys Gly His Asp Gly Leu Tyr Gln Gly Leu
    450                 455                 460

Ser Thr Ala Thr Lys Asp Thr Tyr Asp Ala Leu His Met Gln Ala Leu
465                 470                 475                 480

Pro Pro Arg Gly Ser Ser Gly Thr Gly Met Val Ser Lys Gly Glu Glu
                485                 490                 495

Leu Phe Thr Gly Val Val Pro Ile Leu Val Glu Leu Asp Gly Asp Val
            500                 505                 510

Asn Gly His Lys Phe Ser Val Ser Gly Glu Gly Glu Gly Asp Ala Thr
        515                 520                 525

Tyr Gly Lys Leu Thr Leu Lys Leu Ile Cys Thr Thr Gly Lys Leu Pro
    530                 535                 540

Val Pro Trp Pro Thr Leu Val Thr Thr Leu Gly Tyr Gly Leu Gln Cys
545                 550                 555                 560

Phe Ala Arg Tyr Pro Asp His Met Lys Gln His Asp Phe Phe Lys Ser
                565                 570                 575

Ala Met Pro Glu Gly Tyr Val Gln Glu Arg Thr Ile Phe Phe Lys Asp
            580                 585                 590

Asp Gly Asn Tyr Lys Thr Arg Ala Glu Val Lys Phe Glu Gly Asp Thr
        595                 600                 605

Leu Val Asn Arg Ile Glu Leu Lys Gly Ile Asp Phe Lys Glu Asp Gly
    610                 615                 620

Asn Ile Leu Gly His Lys Leu Glu Tyr Asn Tyr Asn Ser His Asn Val
625                 630                 635                 640

Tyr Ile Thr Ala Asp Lys Gln Lys Asn Gly Ile Lys Ala Asn Phe Lys
                645                 650                 655

Ile Arg His Asn Ile Glu Asp Gly Gly Val Gln Leu Ala Asp His Tyr
            660                 665                 670

Gln Gln Asn Thr Pro Ile Gly Asp Gly Pro Val Leu Leu Pro Asp Asn
        675                 680                 685

His Tyr Leu Ser Tyr Gln Ser Ala Leu Ser Lys Asp Pro Asn Glu Lys
```

690 695 700

Arg Asp His Met Val Leu Leu Glu Phe Val Thr Ala Ala Gly Ile Thr
705 710 715 720

Leu Gly Met Asp Glu Leu Tyr Lys
725

<210> SEQ ID NO 171
<211> LENGTH: 2187
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 171
atggccttac cagtgaccgc cttgctcctg ccgctggcct tgctgctcca cgccgccagg 60
ccgcaggtgc agctgcagga gtcgggccca ggactggtga agccttcgga gaccctgtcc 120
ctcacctgcg ttgtctctgg tggctccatc agcagtagta actggtggag ctgggtccgc 180
cagcccccag ggaaggggct ggagtggatt ggggaaatct atcatagtgg gagccccaac 240
tacaacccgt ccctcaagag tcgagtcacc atatcagtag acaagtccaa gaaccagttc 300
tccctgaagc tgagctctgt gaccgccgcg gacacggccg tgtattactg tgcaaggtcg 360
tcttctggtg gtttctttga ctactggggc caaggtaccc tggtcaccgt ctcgagtggt 420
ggaggcggtt caggcggagg tggctctggc ggtggcggat cggaaattga gctcacccag 480
tctccatcct ccctgtctgc atctgtagga gacagagtca ccatcacttg ccgggcaagt 540
cagagcatta gcagctactt aaattggtat cagcagaaac cagggaaagc ccctaagctc 600
ctgatctatg ctgcatccag tttgcaaagt ggggtcccat caaggttcag tggcagtgga 660
tctgggacag atttcactct caccatcagc agtctgcaac ctgaagattt tgcaacttac 720
tactgtcaac agagttacag taccccctcca acgttcggcc aagggaccaa ggtggagatc 780
aaagcagcag ctatcgaggt gatgtatcct ccgccctacc tggataatga aaagagtaat 840
gggactatca ttcatgtaaa agggaagcat ctttgtcctt ctcccctttt ccccggtccg 900
tctaaacctt tctgggtgct tgtggtcgtg ggtggagtgc ttgcgtgtta ctccctgctg 960
gtgaccgtcg ccttcatcat tttctgggtc aggagcaaac gatctcgcct cctccattct 1020
gactatatga acatgactcc tcgcagaccc ggacctacgc ggaaacatta ccaaccgtac 1080
gcgcctccga gagacttcgc cgcgtacaga agtagggtca agtttagcag gtcagcggac 1140
gcaccagctt acaagcaagg ccaaaaccag ctttataacg aattgaattt gggacgcagg 1200
gaagaatacg atgtgctcga taaacgcaga gggagggacc cggaaatggg aggaaagcca 1260
aggcggaaaa acccacagga ggggttgtac aacgagcttc aaaaagataa gatggcggaa 1320
gcatactccg aaataggaat gaagggtgaa cggaggaggg gcaagggcca cgacggcctg 1380
taccagggac tctcaactgc tacgaaggat acttatgatg ctcttcacat gcaagctctg 1440
ccgccgcgcg gatcgagtgg caccggtatg gtgagcaagg gcgaggagct gttcaccggg 1500
gtggtgccca tcctggtcga gctggacggc gacgtaaacg gccacaagtt cagcgtgtcc 1560
ggcgagggcg agggcgatgc cacctacggc aagctgaccc tgaagctgat ctgcaccacc 1620
ggcaagctgc ccgtgccctg gcccaccctc gtgaccaccc tgggctacgg cctccagtgc 1680
ttcgcccgct accccgacca catgaagcag cacgacttct tcaagtccgc catgcccgaa 1740
ggctacgtcc aggagcgcac catcttcttc aaggacgacg gcaactacaa gacccgcgcc 1800

-continued gaggtgaagt tcgagggcga caccctggtg aaccgcatcg agctgaaggg catcgacttc 1860
aaggaggacg gcaacatcct ggggcacaag ctggagtaca actacaacag ccacaacgtc 1920
tatatcaccg ccgacaagca gaagaacggc atcaaggcca acttcaagat ccgccacaac 1980
atcgaggacg gcggcgtgca gctcgccgac cactaccagc agaacacccc catcggcgac 2040
ggccccgtgc tgctgcccga caaccactac ctgagctacc agtccgccct gagcaaagac 2100
cccaacgaga agcgcgatca catggtcctg ctggagttcg tgaccgccgc cgggatcact 2160
ctcggcatgg acgagctgta caagtaa 2187

<210> SEQ ID NO 172
<211> LENGTH: 728
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 172

Met Ala Leu Pro Val Thr Ala Leu Leu Leu Pro Leu Ala Leu Leu Leu
1 5 10 15

His Ala Ala Arg Pro Gln Val Gln Leu Gln Glu Ser Gly Pro Gly Leu
20 25 30

Val Lys Pro Ser Glu Thr Leu Ser Leu Thr Cys Val Val Ser Gly Gly
35 40 45

Ser Ile Ser Ser Ser Asn Trp Trp Ser Trp Val Arg Gln Pro Pro Gly
50 55 60

Lys Gly Leu Glu Trp Ile Gly Glu Ile Tyr His Ser Gly Ser Pro Asn
65 70 75 80

Tyr Asn Pro Ser Leu Lys Ser Arg Val Thr Ile Ser Val Asp Lys Ser
85 90 95

Lys Asn Gln Phe Ser Leu Lys Leu Ser Ser Val Thr Ala Ala Asp Thr
100 105 110

Ala Val Tyr Tyr Cys Ala Arg Gln Thr Thr Ala Gly Ser Phe Asp Tyr
115 120 125

Trp Gly Gln Gly Thr Leu Val Thr Val Ser Ser Gly Gly Gly Gly Ser
130 135 140

Gly Gly Gly Gly Ser Gly Gly Gly Gly Ser Glu Ile Glu Leu Thr Gln
145 150 155 160

Ser Pro Ser Ser Leu Ser Ala Ser Val Gly Asp Arg Val Thr Ile Thr
165 170 175

Cys Arg Ala Ser Gln Ser Ile Ser Ser Tyr Leu Asn Trp Tyr Gln Gln
180 185 190

Lys Pro Gly Lys Ala Pro Lys Leu Leu Ile Tyr Ala Ala Ser Ser Leu
195 200 205

Gln Ser Gly Val Pro Ser Arg Phe Ser Gly Ser Gly Ser Gly Thr Asp
210 215 220

Phe Thr Leu Thr Ile Ser Ser Leu Gln Pro Glu Asp Phe Ala Thr Tyr
225 230 235 240

Tyr Cys Gln Gln Ser Tyr Ser Thr Pro Pro Thr Phe Gly Gln Gly Thr
245 250 255

Lys Val Glu Ile Lys Ala Ala Ala Ile Glu Val Met Tyr Pro Pro Pro
260 265 270

Tyr Leu Asp Asn Glu Lys Ser Asn Gly Thr Ile Ile His Val Lys Gly
275 280 285

-continued

```
Lys His Leu Cys Pro Ser Pro Leu Phe Pro Gly Pro Ser Lys Pro Phe
    290                 295                 300

Trp Val Leu Val Val Val Gly Gly Val Leu Ala Cys Tyr Ser Leu Leu
305                 310                 315                 320

Val Thr Val Ala Phe Ile Ile Phe Trp Val Arg Ser Lys Arg Ser Arg
                325                 330                 335

Leu Leu His Ser Asp Tyr Met Asn Met Thr Pro Arg Arg Pro Gly Pro
                340                 345                 350

Thr Arg Lys His Tyr Gln Pro Tyr Ala Pro Pro Arg Asp Phe Ala Ala
        355                 360                 365

Tyr Arg Ser Arg Val Lys Phe Ser Arg Ser Ala Asp Ala Pro Ala Tyr
    370                 375                 380

Lys Gln Gly Gln Asn Gln Leu Tyr Asn Glu Leu Asn Leu Gly Arg Arg
385                 390                 395                 400

Glu Glu Tyr Asp Val Leu Asp Lys Arg Arg Gly Arg Asp Pro Glu Met
                405                 410                 415

Gly Gly Lys Pro Arg Arg Lys Asn Pro Gln Glu Gly Leu Tyr Asn Glu
                420                 425                 430

Leu Gln Lys Asp Lys Met Ala Glu Ala Tyr Ser Glu Ile Gly Met Lys
        435                 440                 445

Gly Glu Arg Arg Arg Gly Lys Gly His Asp Gly Leu Tyr Gln Gly Leu
    450                 455                 460

Ser Thr Ala Thr Lys Asp Thr Tyr Asp Ala Leu His Met Gln Ala Leu
465                 470                 475                 480

Pro Pro Arg Gly Ser Ser Gly Thr Gly Met Val Ser Lys Gly Glu Glu
                485                 490                 495

Leu Phe Thr Gly Val Val Pro Ile Leu Val Glu Leu Asp Gly Asp Val
            500                 505                 510

Asn Gly His Lys Phe Ser Val Ser Gly Glu Gly Glu Gly Asp Ala Thr
        515                 520                 525

Tyr Gly Lys Leu Thr Leu Lys Leu Ile Cys Thr Thr Gly Lys Leu Pro
    530                 535                 540

Val Pro Trp Pro Thr Leu Val Thr Thr Leu Gly Tyr Gly Leu Gln Cys
545                 550                 555                 560

Phe Ala Arg Tyr Pro Asp His Met Lys Gln His Asp Phe Phe Lys Ser
                565                 570                 575

Ala Met Pro Glu Gly Tyr Val Gln Glu Arg Thr Ile Phe Phe Lys Asp
            580                 585                 590

Asp Gly Asn Tyr Lys Thr Arg Ala Glu Val Lys Phe Glu Gly Asp Thr
        595                 600                 605

Leu Val Asn Arg Ile Glu Leu Lys Gly Ile Asp Phe Lys Glu Asp Gly
    610                 615                 620

Asn Ile Leu Gly His Lys Leu Glu Tyr Asn Tyr Asn Ser His Asn Val
625                 630                 635                 640

Tyr Ile Thr Ala Asp Lys Gln Lys Asn Gly Ile Lys Ala Asn Phe Lys
                645                 650                 655

Ile Arg His Asn Ile Glu Asp Gly Gly Val Gln Leu Ala Asp His Tyr
            660                 665                 670

Gln Gln Asn Thr Pro Ile Gly Asp Gly Pro Val Leu Leu Pro Asp Asn
        675                 680                 685

His Tyr Leu Ser Tyr Gln Ser Ala Leu Ser Lys Asp Pro Asn Glu Lys
    690                 695                 700

Arg Asp His Met Val Leu Leu Glu Phe Val Thr Ala Ala Gly Ile Thr
```

705 710 715 720

Leu Gly Met Asp Glu Leu Tyr Lys
725

<210> SEQ ID NO 173
<211> LENGTH: 2187
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 173
atggccttac cagtgaccgc cttgctcctg ccgctggcct tgctgctcca cgccgccagg 60
ccgcaggtgc agctgcagga gtcgggccca ggactggtga agccttcgga gaccctgtcc 120
ctcacctgcg ttgtctctgg tggctccatc agcagtagta actggtggag ctgggtccgc 180
cagcccccag ggaaggggct ggagtggatt ggggaaatct atcatagtgg gagccccaac 240
tacaacccgt ccctcaagag tcgagtcacc atatcagtag acaagtccaa gaaccagttc 300
tccctgaagc tgagctctgt gaccgccgcg gacacggccg tgtattactg tgcaaggcag 360
actactgctg ggtcctttga ctactggggc caaggtaccc tggtcaccgt ctcgagtggt 420
ggaggcggtt caggcggagg tggctctggc ggtggcggat cggaaattga gctcacccag 480
tctccatcct ccctgtctgc atctgtagga gacagagtca ccatcacttg ccgggcaagt 540
cagagcatta gcagctactt aaattggtat cagcagaaac cagggaaagc ccctaagctc 600
ctgatctatg ctgcatccag tttgcaaagt ggggtcccat caaggttcag tggcagtgga 660
tctgggacag atttcactct caccatcagc agtctgcaac ctgaagattt tgcaacttac 720
tactgtcaac agagttacag taccccctcca acgttcggcc aagggaccaa ggtggagatc 780
aaagcagcag ctatcgaggt gatgtatcct ccgccctacc tggataatga aaagagtaat 840
gggactatca ttcatgtaaa agggaagcat ctttgtcctt ctccccttttt ccccggtccg 900 tctaaacctt tctgggtgct tgtggtcgtg ggtggagtgc ttgcgtgtta ctccctgctg 960
gtgaccgtcg ccttcatcat tttctgggtc aggagcaaac gatctcgcct cctccattct 1020
gactatatga acatgactcc tcgcagaccc ggacctacgc ggaaacatta ccaaccgtac 1080
gcgcctccga gagacttcgc cgcgtacaga agtagggtca agtttagcag gtcagcggac 1140
gcaccagctt acaagcaagg ccaaaaccag ctttataacg aattgaattt gggacgcagg 1200
gaagaatacg atgtgctcga taaacgcaga gggagggacc cggaaatggg aggaaagcca 1260
aggcggaaaa acccacagga ggggttgtac aacgagcttc aaaaagataa gatggcggaa 1320
gcatactccg aaataggaat gaagggtgaa cggaggaggg gcaagggcca cgacggcctg 1380
taccagggac tctcaactgc tacgaaggat acttatgatg ctcttcacat gcaagctctg 1440
ccgccgcgcg gatcgagtgg caccggtatg gtgagcaagg gcgaggagct gttcaccggg 1500
gtggtgccca tcctggtcga gctggacggc gacgtaaacg gccacaagtt cagcgtgtcc 1560
ggcgagggcg agggcgatgc cacctacggc aagctgaccc tgaagctgat ctgcaccacc 1620
ggcaagctgc ccgtgccctg gcccaccctc gtgaccaccc tgggctacgg cctccagtgc 1680
ttcgcccgct accccgacca catgaagcag cacgacttct tcaagtccgc catgcccgaa 1740
ggctacgtcc aggagcgcac catcttcttc aaggacgacg gcaactacaa gacccgcgcc 1800
gaggtgaagt tcgagggcga caccctggtg aaccgcatcg agctgaaggg catcgacttc 1860
aaggaggacg gcaacatcct ggggcacaag ctggagtaca actacaacag ccacaacgtc 1920
tatatcaccg ccgacaagca gaagaacggc atcaaggcca acttcaagat ccgccacaac 1980
atcgaggacg gcggcgtgca gctcgccgac cactaccagc agaacacccc catcggcgac 2040
ggccccgtgc tgctgcccga caaccactac ctgagctacc agtccgccct gagcaaagac 2100
cccaacgaga agcgcgatca catggtcctg ctggagttcg tgaccgccgc cgggatcact 2160
ctcggcatgg acgagctgta caagtaa 2187

<210> SEQ ID NO 174
<211> LENGTH: 497
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 174

Met Glu Thr Asp Thr Leu Leu Leu Trp Val Leu Leu Leu Trp Val Pro
1 5 10 15

Gly Ser Thr Gly Ala Gly Gly Ser Asp Tyr Lys Asp Asp Asp Asp Lys
20 25 30

Gly Gly Ser Gln Val Gln Leu Gln Glu Ser Gly Pro Gly Leu Val Lys
35 40 45

Pro Ser Glu Thr Leu Ser Leu Thr Cys Val Val Ser Gly Gly Ser Ile
50 55 60

Ser Ser Ser Asn Trp Trp Ser Trp Val Arg Gln Pro Pro Gly Lys Gly
65 70 75 80

Leu Glu Trp Ile Gly Glu Ile Tyr His Ser Gly Ser Pro Asp Tyr Asn
85 90 95

Pro Ser Leu Lys Ser Arg Val Thr Ile Ser Val Asp Lys Ser Arg Asn
100 105 110

Gln Phe Ser Leu Lys Leu Ser Ser Val Thr Ala Ala Asp Thr Ala Val
115 120 125

Tyr Tyr Cys Ala Lys Val Ser Thr Gly Gly Phe Phe Asp Tyr Trp Gly
130 135 140

Gln Gly Thr Leu Val Thr Val Ser Ser Gly Gly Gly Gly Ser Gly Gly
145 150 155 160

Gly Gly Ser Gly Gly Gly Gly Ser Glu Ile Glu Leu Thr Gln Ser Pro
165 170 175

Ser Ser Leu Ser Ala Ser Val Gly Asp Arg Val Thr Ile Thr Cys Arg
180 185 190

Ala Ser Gln Ser Ile Ser Ser Tyr Leu Asn Trp Tyr Gln Gln Lys Pro
195 200 205

Gly Lys Ala Pro Lys Leu Leu Ile Tyr Ala Ala Ser Ser Leu Gln Ser
210 215 220

Gly Val Pro Ser Arg Phe Ser Gly Ser Gly Ser Gly Thr Asp Phe Thr
225 230 235 240

Leu Thr Ile Ser Ser Leu Gln Pro Glu Asp Phe Ala Thr Tyr Tyr Cys
245 250 255

Gln Gln Ser Tyr Ser Thr Pro Pro Thr Phe Gly Pro Gly Thr Lys Val
260 265 270

Glu Ile Lys Ala Ala Ala Ile Glu Val Met Tyr Pro Pro Pro Tyr Leu
275 280 285

Asp Asn Glu Lys Ser Asn Gly Thr Ile Ile His Val Lys Gly Lys His
290 295 300

```
Leu Cys Pro Ser Pro Leu Phe Pro Gly Pro Ser Lys Pro Phe Trp Val
305                 310                 315                 320

Leu Val Val Val Gly Gly Val Leu Ala Cys Tyr Ser Leu Leu Val Thr
                325                 330                 335

Val Ala Phe Ile Ile Phe Trp Val Arg Ser Lys Arg Ser Arg Leu Leu
            340                 345                 350

His Ser Asp Tyr Met Asn Met Thr Pro Arg Arg Pro Gly Pro Thr Arg
        355                 360                 365

Lys His Tyr Gln Pro Tyr Ala Pro Pro Arg Asp Phe Ala Ala Tyr Arg
    370                 375                 380

Ser Arg Val Lys Phe Ser Arg Ser Ala Asp Ala Pro Ala Tyr Lys Gln
385                 390                 395                 400

Gly Gln Asn Gln Leu Tyr Asn Glu Leu Asn Leu Gly Arg Arg Glu Glu
                405                 410                 415

Tyr Asp Val Leu Asp Lys Arg Arg Gly Arg Asp Pro Glu Met Gly Gly
            420                 425                 430

Lys Pro Arg Arg Lys Asn Pro Gln Glu Gly Leu Tyr Asn Glu Leu Gln
        435                 440                 445

Lys Asp Lys Met Ala Glu Ala Tyr Ser Glu Ile Gly Met Lys Gly Glu
    450                 455                 460

Arg Arg Arg Gly Lys Gly His Asp Gly Leu Tyr Gln Gly Leu Ser Thr
465                 470                 475                 480

Ala Thr Lys Asp Thr Tyr Asp Ala Leu His Met Gln Ala Leu Pro Pro
                485                 490                 495

Arg


<210> SEQ ID NO 175
<211> LENGTH: 1491
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 175

atggaaacgg atactctgct gctgtgggtc ctcttgcttt gggtacctgg gagtaccggc      60

gctggcgggt ccgattacaa ggacgatgac gacaaagggg gttctcaggt gcagctgcag     120

gagtcggggc caggactggt gaagccttcg gagaccctgt ccctcacctg cgttgtctct     180

ggtggctcca tcagcagtag taactggtgg agctgggtcc gccagccccc agggaagggg     240

ctggagtgga ttggggaaat ctatcatagt gggagccccg actacaaccc gtccctcaag     300

agtcgagtca ccatatcagt agacaagtcc aggaaccagt tctccctgaa gctgagctct     360

gtgaccgccg cggacacggc cgtgtattac tgtgcaaagg ttagtactgg tggtttcttt     420

gactactggg ggcaaggtac cctggtcacc gtctcgagtg gtggaggcgg ttcaggcgga     480

ggtggctctg gcggtggcgg atcggaaatt gagctcaccc agtctccatc ctccctgtct     540

gcatctgtag gagacagagt caccatcact tgccgggcaa gtcagagcat tagcagctac     600

ttaaattggt atcagcagaa accagggaaa gcccctaagc tcctgatcta tgctgcatcc     660

agtttgcaaa gtggggtccc atcaaggttc agtggcagtg gatctgggac agatttcact     720

ctcaccatca gcagtctgca acctgaagat tttgcaactt actactgtca acagagttac     780

agtacccctc caacgttcgg cccagggacc aaggtggaga tcaaagcagc agctatcgag     840

gtgatgtatc ctccgcccta cctggataat gaaaagagta atgggactat cattcatgta     900
```

```
aaagggaagc atctttgtcc ttctcccctt ttccccggtc cgtctaaacc tttctgggtg    960

cttgtggtcg tgggtggagt gcttgcgtgt tactccctgc tggtgaccgt cgccttcatc   1020

attttctggg tcaggagcaa acgatctcgc ctcctccatt ctgactatat gaacatgact   1080

cctcgcagac ccggacctac gcggaaacat taccaaccgt acgcgcctcc gagagacttc   1140

gccgcgtaca gaagtagggt caagtttagc aggtcagcgg acgcaccagc ttacaagcaa   1200

ggccaaaacc agctttataa cgaattgaat ttgggacgca gggaagaata cgatgtgctc   1260

gataaacgca gagggaggga cccggaaatg ggaggaaagc caaggcggaa aaacccacag   1320

gaggggttgt acaacgagct tcaaaaagat aagatggcgg aagcatactc cgaaatagga   1380

atgaagggtg aacggaggag gggcaagggc cacgacggcc tgtaccaggg actctcaact   1440

gctacgaagg atacttatga tgctcttcac atgcaagctc tgccgccgcg c            1491
```

<210> SEQ ID NO 176
<211> LENGTH: 497
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 176

```
Met Glu Thr Asp Thr Leu Leu Leu Trp Val Leu Leu Leu Trp Val Pro
1               5                   10                  15

Gly Ser Thr Gly Ala Gly Gly Ser Asp Tyr Lys Asp Asp Asp Asp Lys
            20                  25                  30

Gly Gly Ser Gln Val Gln Leu Gln Glu Ser Gly Pro Gly Leu Val Lys
        35                  40                  45

Pro Ser Glu Thr Leu Ser Leu Thr Cys Val Val Ser Gly Gly Ser Ile
    50                  55                  60

Ser Ser Ser Asn Trp Trp Ser Trp Val Arg Gln Pro Pro Gly Lys Gly
65                  70                  75                  80

Leu Glu Trp Ile Gly Glu Ile Tyr His Ser Gly Ser Pro Asn Tyr Asn
                85                  90                  95

Pro Ser Leu Lys Ser Arg Val Thr Ile Ser Val Asp Lys Ser Lys Asn
            100                 105                 110

Gln Phe Ser Leu Lys Leu Ser Ser Val Thr Ala Ala Asp Thr Ala Val
        115                 120                 125

Tyr Tyr Cys Ala Arg Ser Ser Ser Gly Gly Phe Phe Asp Tyr Trp Gly
    130                 135                 140

Gln Gly Thr Leu Val Thr Val Ser Ser Gly Gly Gly Gly Ser Gly Gly
145                 150                 155                 160

Gly Gly Ser Gly Gly Gly Gly Ser Glu Ile Glu Leu Thr Gln Ser Pro
                165                 170                 175

Ser Ser Leu Ser Ala Ser Val Gly Asp Arg Val Thr Ile Thr Cys Arg
            180                 185                 190

Ala Ser Gln Ser Ile Ser Ser Tyr Leu Asn Trp Tyr Gln Gln Lys Pro
        195                 200                 205

Gly Lys Ala Pro Lys Leu Leu Ile Tyr Ala Ala Ser Ser Leu Gln Ser
    210                 215                 220

Gly Val Pro Ser Arg Phe Ser Gly Ser Gly Ser Gly Thr Asp Phe Thr
225                 230                 235                 240

Leu Thr Ile Ser Ser Leu Gln Pro Glu Asp Phe Ala Thr Tyr Tyr Cys
                245                 250                 255
```

Gln Gln Ser Tyr Ser Thr Pro Pro Thr Phe Gly Gln Gly Thr Lys Val
260 265 270

Glu Ile Lys Ala Ala Ala Ile Glu Val Met Tyr Pro Pro Pro Tyr Leu
275 280 285

Asp Asn Glu Lys Ser Asn Gly Thr Ile Ile His Val Lys Gly Lys His
290 295 300

Leu Cys Pro Ser Pro Leu Phe Pro Gly Pro Ser Lys Pro Phe Trp Val
305 310 315 320

Leu Val Val Val Gly Gly Val Leu Ala Cys Tyr Ser Leu Leu Val Thr
325 330 335

Val Ala Phe Ile Ile Phe Trp Val Arg Ser Lys Arg Ser Arg Leu Leu
340 345 350

His Ser Asp Tyr Met Asn Met Thr Pro Arg Arg Pro Gly Pro Thr Arg
355 360 365

Lys His Tyr Gln Pro Tyr Ala Pro Pro Arg Asp Phe Ala Ala Tyr Arg
370 375 380

Ser Arg Val Lys Phe Ser Arg Ser Ala Asp Ala Pro Ala Tyr Lys Gln
385 390 395 400

Gly Gln Asn Gln Leu Tyr Asn Glu Leu Asn Leu Gly Arg Arg Glu Glu
405 410 415

Tyr Asp Val Leu Asp Lys Arg Arg Gly Arg Asp Pro Glu Met Gly Gly
420 425 430

Lys Pro Arg Arg Lys Asn Pro Gln Glu Gly Leu Tyr Asn Glu Leu Gln
435 440 445

Lys Asp Lys Met Ala Glu Ala Tyr Ser Glu Ile Gly Met Lys Gly Glu
450 455 460

Arg Arg Arg Gly Lys Gly His Asp Gly Leu Tyr Gln Gly Leu Ser Thr
465 470 475 480

Ala Thr Lys Asp Thr Tyr Asp Ala Leu His Met Gln Ala Leu Pro Pro
485 490 495

Arg

<210> SEQ ID NO 177
<211> LENGTH: 1491
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 177
atggaaacgg atactctgct gctgtgggtc ctcttgcttt gggtacctgg gagtaccggc 60
gctggcgggt ccgattacaa ggacgatgac gacaaagggg gttctcaggt gcagctgcag 120
gagtcgggcc caggactggt gaagccttcg gagaccctgt ccctcacctg cgttgtctct 180
ggtggctcca tcagcagtag taactggtgg agctgggtcc gccagccccc agggaagggg 240
ctggagtgga ttggggaaat ctatcatagt gggagcccca actacaaccc gtccctcaag 300
agtcgagtca ccatatcagt agacaagtcc aagaaccagt tctccctgaa gctgagctct 360
gtgaccgccg cggacacggc cgtgtattac tgtgcaaggt cgtcttctgg tggtttcttt 420
gactactggg gccaaggtac cctggtcacc gtctcgagtg gtggaggcgg ttcaggcgga 480
ggtggctctg gcggtggcgg atcggaaatt gagctcaccc agtctccatc ctccctgtct 540
gcatctgtag gagacagagt caccatcact tgccgggcaa gtcagagcat tagcagctac 600
ttaaattggt atcagcagaa accagggaaa gcccctaagc tcctgatcta tgctgcatcc 660
agtttgcaaa gtggggtccc atcaaggttc agtggcagtg gatctgggac agatttcact 720
ctcaccatca gcagtctgca acctgaagat tttgcaactt actactgtca acagagttac 780
agtacccctc caacgttcgg ccaagggacc aaggtggaga tcaaagcagc agctatcgag 840
gtgatgtatc ctccgcccta cctggataat gaaaagagta atgggactat cattcatgta 900
aaagggaagc atctttgtcc ttctcccctt ttccccggtc cgtctaaacc tttctgggtg 960
cttgtggtcg tgggtggagt gcttgcgtgt tactccctgc tggtgaccgt cgccttcatc 1020
attttctggg tcaggagcaa acgatctcgc ctcctccatt ctgactatat gaacatgact 1080
cctcgcagac ccggacctac gcggaaacat taccaaccgt acgcgcctcc gagagacttc 1140
gccgcgtaca gaagtagggt caagtttagc aggtcagcgg acgcaccagc ttacaagcaa 1200
ggccaaaacc agctttataa cgaattgaat ttgggacgca gggaagaata cgatgtgctc 1260
gataaacgca gagggaggga cccggaaatg ggaggaaagc caaggcggaa aaacccacag 1320
gaggggttgt acaacgagct tcaaaaagat aagatggcgg aagcatactc cgaaatagga 1380
atgaagggtg aacggaggag gggcaagggc cacgacggcc tgtaccaggg actctcaact 1440
gctacgaagg atacttatga tgctcttcac atgcaagctc tgccgccgcg c 1491

<210> SEQ ID NO 178
<211> LENGTH: 497
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 178

Met Glu Thr Asp Thr Leu Leu Leu Trp Val Leu Leu Leu Trp Val Pro
1 5 10 15

Gly Ser Thr Gly Ala Gly Gly Ser Asp Tyr Lys Asp Asp Asp Asp Lys
20 25 30

Gly Gly Ser Gln Val Gln Leu Gln Glu Ser Gly Pro Gly Leu Val Lys
35 40 45

Pro Ser Glu Thr Leu Ser Leu Thr Cys Val Val Ser Gly Gly Ser Ile
50 55 60

Ser Ser Ser Asn Trp Trp Ser Trp Val Arg Gln Pro Pro Gly Lys Gly
65 70 75 80

Leu Glu Trp Ile Gly Glu Ile Tyr His Ser Gly Ser Pro Asn Tyr Asn
85 90 95

Pro Ser Leu Lys Ser Arg Val Thr Ile Ser Val Asp Lys Ser Lys Asn
100 105 110

Gln Phe Ser Leu Lys Leu Ser Ser Val Thr Ala Ala Asp Thr Ala Val
115 120 125

Tyr Tyr Cys Ala Arg Gln Thr Thr Ala Gly Ser Phe Asp Tyr Trp Gly
130 135 140

Gln Gly Thr Leu Val Thr Val Ser Ser Gly Gly Gly Gly Ser Gly Gly
145 150 155 160

Gly Gly Ser Gly Gly Gly Gly Ser Glu Ile Glu Leu Thr Gln Ser Pro
165 170 175

Ser Ser Leu Ser Ala Ser Val Gly Asp Arg Val Thr Ile Thr Cys Arg
180 185 190

Ala Ser Gln Ser Ile Ser Ser Tyr Leu Asn Trp Tyr Gln Gln Lys Pro
195 200 205

-continued

```
Gly Lys Ala Pro Lys Leu Leu Ile Tyr Ala Ala Ser Ser Leu Gln Ser
    210                 215                 220

Gly Val Pro Ser Arg Phe Ser Gly Ser Gly Ser Gly Thr Asp Phe Thr
225                 230                 235                 240

Leu Thr Ile Ser Ser Leu Gln Pro Glu Asp Phe Ala Thr Tyr Tyr Cys
                245                 250                 255

Gln Gln Ser Tyr Ser Thr Pro Pro Thr Phe Gly Gln Gly Thr Lys Val
            260                 265                 270

Glu Ile Lys Ala Ala Ala Ile Glu Val Met Tyr Pro Pro Pro Tyr Leu
        275                 280                 285

Asp Asn Glu Lys Ser Asn Gly Thr Ile Ile His Val Lys Gly Lys His
    290                 295                 300

Leu Cys Pro Ser Pro Leu Phe Pro Gly Pro Ser Lys Pro Phe Trp Val
305                 310                 315                 320

Leu Val Val Val Gly Gly Val Leu Ala Cys Tyr Ser Leu Leu Val Thr
                325                 330                 335

Val Ala Phe Ile Ile Phe Trp Val Arg Ser Lys Arg Ser Arg Leu Leu
            340                 345                 350

His Ser Asp Tyr Met Asn Met Thr Pro Arg Arg Pro Gly Pro Thr Arg
        355                 360                 365

Lys His Tyr Gln Pro Tyr Ala Pro Pro Arg Asp Phe Ala Ala Tyr Arg
    370                 375                 380

Ser Arg Val Lys Phe Ser Arg Ser Ala Asp Ala Pro Ala Tyr Lys Gln
385                 390                 395                 400

Gly Gln Asn Gln Leu Tyr Asn Glu Leu Asn Leu Gly Arg Arg Glu Glu
                405                 410                 415

Tyr Asp Val Leu Asp Lys Arg Arg Gly Arg Asp Pro Glu Met Gly Gly
            420                 425                 430

Lys Pro Arg Arg Lys Asn Pro Gln Glu Gly Leu Tyr Asn Glu Leu Gln
        435                 440                 445

Lys Asp Lys Met Ala Glu Ala Tyr Ser Glu Ile Gly Met Lys Gly Glu
    450                 455                 460

Arg Arg Arg Gly Lys Gly His Asp Gly Leu Tyr Gln Gly Leu Ser Thr
465                 470                 475                 480

Ala Thr Lys Asp Thr Tyr Asp Ala Leu His Met Gln Ala Leu Pro Pro
                485                 490                 495

Arg
```

<210> SEQ ID NO 179
<211> LENGTH: 1491
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 179

```
atggaaacgg atactctgct gctgtgggtc ctcttgcttt gggtacctgg gagtaccggc     60

gctggcgggt ccgattacaa ggacgatgac gacaaagggg gttctcaggt gcagctgcag    120

gagtcgggcc caggactggt gaagccttcg gagaccctgt ccctcacctg cgttgtctct    180

ggtggctcca tcagcagtag taactggtgg agctgggtcc gccagccccc agggaagggg    240

ctggagtgga ttggggaaat ctatcatagt gggagcccca actacaaccc gtccctcaag    300

agtcgagtca ccatatcagt agacaagtcc aagaaccagt tctccctgaa gctgagctct    360
```

-continued

```
gtgaccgccg cggacacggc cgtgtattac tgtgcaaggc agactactgc tgggtccttt    420

gactactggg gccaaggtac cctggtcacc gtctcgagtg gtggaggcgg ttcaggcgga    480

ggtggctctg gcggtggcgg atcggaaatt gagctcaccc agtctccatc ctccctgtct    540

gcatctgtag gagacagagt caccatcact tgccgggcaa gtcagagcat tagcagctac    600

ttaaattggt atcagcagaa accagggaaa gcccctaagc tcctgatcta tgctgcatcc    660

agtttgcaaa gtggggtccc atcaaggttc agtggcagtg gatctgggac agatttcact    720

ctcaccatca gcagtctgca acctgaagat tttgcaactt actactgtca acagagttac    780

agtacccctc caacgttcgg ccaagggacc aaggtggaga tcaaagcagc agctatcgag    840

gtgatgtatc ctccgcccta cctggataat gaaaagagta atgggactat cattcatgta    900

aaagggaagc atctttgtcc ttctcccctt ttccccggtc cgtctaaacc tttctgggtg    960

cttgtggtcg tgggtggagt gcttgcgtgt tactccctgc tggtgaccgt cgccttcatc   1020

attttctggg tcaggagcaa acgatctcgc ctcctccatt ctgactatat gaacatgact   1080

cctcgcagac ccggacctac gcggaaacat taccaaccgt acgcgcctcc gagagacttc   1140

gccgcgtaca gaagtagggt caagtttagc aggtcagcgg acgcaccagc ttacaagcaa   1200

ggccaaaacc agctttataa cgaattgaat ttgggacgca gggaagaata cgatgtgctc   1260

gataaacgca gagggaggga cccggaaatg ggaggaaagc caaggcggaa aaacccacag   1320

gaggggttgt acaacgagct tcaaaaagat aagatggcgg aagcatactc cgaaatagga   1380

atgaagggtg aacggaggag gggcaagggc cacgacggcc tgtaccaggg actctcaact   1440

gctacgaagg atacttatga tgctcttcac atgcaagctc tgccgccgcg c            1491
```

<210> SEQ ID NO 180
<211> LENGTH: 818
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 180

```
Met Ala Leu Pro Val Thr Ala Leu Leu Leu Pro Leu Ala Leu Leu Leu
1               5                   10                  15

His Ala Ala Arg Pro Asp Val Val Met Thr Gln Ser Pro Leu Ser Leu
            20                  25                  30

Pro Val Thr Pro Gly Glu Pro Ala Ser Ile Ser Cys Arg Ser Ser Gln
        35                  40                  45

Ser Leu Leu His Ser Asn Gly Tyr Asn Tyr Leu Asp Trp Tyr Leu Gln
    50                  55                  60

Lys Pro Gly Gln Ser Pro Gln Leu Leu Ile Tyr Leu Gly Ser Asn Arg
65                  70                  75                  80

Ala Ser Gly Val Pro Asp Arg Phe Ser Gly Ser Gly Ser Gly Thr Asp
                85                  90                  95

Phe Thr Leu Lys Ile Ser Arg Val Glu Ala Glu Asp Val Gly Val Tyr
            100                 105                 110

Tyr Cys Met Gln Ser Leu Gln Thr Pro Phe Thr Phe Gly Pro Gly Thr
        115                 120                 125

Lys Val Asp Ile Lys Gly Gly Gly Gly Ser Gly Gly Gly Gly Ser Gly
    130                 135                 140

Gly Gly Gly Ser Glu Val Gln Leu Val Gln Ser Gly Ala Glu Val Lys
145                 150                 155                 160
```

-continued

Lys Pro Gly Ala Ser Val Lys Val Ser Cys Lys Ala Ser Gly Tyr Thr
165 170 175

Phe Thr Ser Tyr Tyr Met His Trp Ala Arg Gln Ala Pro Gly Gln Gly
180 185 190

Leu Glu Trp Met Gly Ile Ile Asn Pro Ser Gly Gly Ser Thr Ser Tyr
195 200 205

Ala Gln Lys Phe Gln Gly Arg Val Thr Met Thr Arg Asp Thr Ser Thr
210 215 220

Ser Thr Val Tyr Met Glu Leu Ser Ser Leu Arg Ser Glu Asp Thr Ala
225 230 235 240

Val Tyr Tyr Cys Ala Arg Val Val Ala Ala Ala Val Ala Asp Tyr Trp
245 250 255

Gly Gln Gly Thr Leu Val Thr Val Ser Ser Ala Cys Pro Thr Gly Leu
260 265 270

Tyr Thr His Ser Gly Glu Cys Cys Lys Ala Cys Asn Leu Gly Glu Gly
275 280 285

Val Ala Gln Pro Cys Gly Ala Asn Gln Thr Val Cys Glu Pro Cys Leu
290 295 300

Asp Ser Val Thr Phe Ser Asp Val Val Ser Ala Thr Glu Pro Cys Lys
305 310 315 320

Pro Cys Thr Glu Cys Val Gly Leu Gln Ser Met Ser Ala Pro Cys Val
325 330 335

Glu Ala Asp Asp Ala Val Cys Arg Cys Ala Tyr Gly Tyr Tyr Gln Asp
340 345 350

Glu Thr Thr Gly Arg Cys Glu Ala Cys Arg Val Cys Glu Ala Gly Ser
355 360 365

Gly Leu Val Phe Ser Cys Gln Asp Lys Gln Asn Thr Val Cys Glu Glu
370 375 380

Cys Pro Asp Gly Thr Tyr Ser Asp Glu Ala Asp Ala Glu Cys Ile Tyr
385 390 395 400

Ile Trp Ala Pro Leu Ala Gly Thr Cys Gly Val Leu Leu Leu Ser Leu
405 410 415

Val Ile Thr Lys Arg Gly Arg Lys Lys Leu Leu Tyr Ile Phe Lys Gln
420 425 430

Pro Phe Met Arg Pro Val Gln Thr Thr Gln Glu Glu Asp Gly Cys Ser
435 440 445

Cys Arg Phe Pro Glu Glu Glu Glu Gly Gly Cys Glu Leu Arg Val Lys
450 455 460

Phe Ser Arg Ser Ala Asp Ala Pro Ala Tyr Lys Gln Gly Gln Asn Gln
465 470 475 480

Leu Tyr Asn Glu Leu Asn Leu Gly Arg Arg Glu Glu Tyr Asp Val Leu
485 490 495

Asp Lys Arg Arg Gly Arg Asp Pro Glu Met Gly Gly Lys Pro Arg Arg
500 505 510

Lys Asn Pro Gln Glu Gly Leu Tyr Asn Glu Leu Gln Lys Asp Lys Met
515 520 525

Ala Glu Ala Tyr Ser Glu Ile Gly Met Lys Gly Glu Arg Arg Arg Gly
530 535 540

Lys Gly His Asp Gly Leu Tyr Gln Gly Leu Ser Thr Ala Thr Lys Asp
545 550 555 560

Thr Tyr Asp Ala Leu His Met Gln Ala Leu Pro Pro Arg Gly Ser Ser
565 570 575

Gly Thr Gly Met Val Ser Lys Gly Glu Glu Leu Phe Thr Gly Val Val

```
            580                 585                 590

Pro Ile Leu Val Glu Leu Asp Gly Asp Val Asn Gly His Lys Phe Ser
        595                 600                 605

Val Ser Gly Glu Gly Glu Gly Asp Ala Thr Tyr Gly Lys Leu Thr Leu
    610                 615                 620

Lys Leu Ile Cys Thr Thr Gly Lys Leu Pro Val Pro Trp Pro Thr Leu
625                 630                 635                 640

Val Thr Thr Leu Gly Tyr Gly Leu Gln Cys Phe Ala Arg Tyr Pro Asp
                645                 650                 655

His Met Lys Gln His Asp Phe Phe Lys Ser Ala Met Pro Glu Gly Tyr
            660                 665                 670

Val Gln Glu Arg Thr Ile Phe Phe Lys Asp Asp Gly Asn Tyr Lys Thr
        675                 680                 685

Arg Ala Glu Val Lys Phe Glu Gly Asp Thr Leu Val Asn Arg Ile Glu
    690                 695                 700

Leu Lys Gly Ile Asp Phe Lys Glu Asp Gly Asn Ile Leu Gly His Lys
705                 710                 715                 720

Leu Glu Tyr Asn Tyr Asn Ser His Asn Val Tyr Ile Thr Ala Asp Lys
                725                 730                 735

Gln Lys Asn Gly Ile Lys Ala Asn Phe Lys Ile Arg His Asn Ile Glu
            740                 745                 750

Asp Gly Gly Val Gln Leu Ala Asp His Tyr Gln Gln Asn Thr Pro Ile
        755                 760                 765

Gly Asp Gly Pro Val Leu Leu Pro Asp Asn His Tyr Leu Ser Tyr Gln
    770                 775                 780

Ser Ala Leu Ser Lys Asp Pro Asn Glu Lys Arg Asp His Met Val Leu
785                 790                 795                 800

Leu Glu Phe Val Thr Ala Ala Gly Ile Thr Leu Gly Met Asp Glu Leu
                805                 810                 815

Tyr Lys
```

<210> SEQ ID NO 181
<211> LENGTH: 2454
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 181

```
atggccttac cagtgaccgc cttgctcctg ccgctggcct tgctgctcca cgccgccagg     60

ccggacgtag ttatgacaca gtctccactg tcattgccag taacaccagg tgagcccgcc    120

tccatctcat gtagatcctc ccaatctctc cttcattcaa acgggtataa ttatctcgac    180

tggtatttgc agaaaccggg ccagagccct caactgctca tctatttggg gagcaaccgg    240

gcctctggtg tccctgatag attctccggg agtggatcag gtacggattt tacactgaag    300

atcagcaggg tggaagcaga agatgttggt gtgtattact gtatgcaatc actccagacc    360

ccgtttacct ttgggcctgg aacaaaggta gatattaaag gcggaggggg atcagggggt    420

ggggggtcag gtggcggtgg aagtgaagtg caacttgttc agagcggggc agaagttaag    480

aagccaggcg cttccgtcaa ggtgagttgc aaggcaagtg gatacacctt tacgagttat    540

tatatgcact gggcacggca ggcccctggt cagggcctcg aatggatggg gattataaat    600

ccttctggcg ggtcaaccag ctacgcacaa aaatttcaag gtcgggtgac aatgacgcgc    660
```

gacacgtcaa cgagtacagt gtatatggaa ttgtctagcc tgaggtccga ggatactgct 720
gtctattatt gtgctcgcgt ggtcgctgct gctgtggcag actactgggg tcagggtaca 780
cttgtgacgg taagcagcgc ctgcccgacc gggctctaca ctcatagcgg ggaatgttgt 840
aaggcatgta acttgggtga gggcgtcgca cagccctgcg gagctaacca aacagtgtgc 900
gaaccctgcc tcgatagtgt gacgttctct gatgttgtat cagctacaga gccttgcaaa 960
ccatgtactg agtgcgttgg acttcagtca atgagcgctc catgtgtgga ggcagatgat 1020
gcggtctgtc gatgtgctta cggatactac caagacgaga caacagggcg gtgcgaggcc 1080
tgtagagttt gtgaggcggg ctccgggctg gtgttttcat gtcaagacaa gcaaaatacg 1140
gtctgtgaag agtgccctga tggcacctac tcagacgaag cagatgcaga atgcatctac 1200
atatgggccc ccctcgccgg tacttgcggt gttttgcttt tgtcactggt gattacgaag 1260
cgcggtcgaa aaaaactcct ctacatcttc aaacaacctt tcatgcggcc tgtccaaaca 1320
actcaagaag aggacgggtg ttcatgccgc tttccagagg aagaggaagg tggctgtgaa 1380
cttagggtca agtttagcag gtcagcggac gcaccagctt acaagcaagg ccaaaaccag 1440
ctttataacg aattgaattt gggacgcagg gaagaatacg atgtgctcga taaacgcaga 1500
gggagggacc cggaaatggg aggaaagcca aggcggaaaa acccacagga ggggttgtac 1560
aacgagcttc aaaaagataa gatggcggaa gcatactccg aaataggaat gaagggtgaa 1620
cggaggaggg gcaagggcca cgacggcctg taccagggac tctcaactgc tacgaaggat 1680
acttatgatg ctcttcacat gcaagctctg ccgccgcgcg gatcgagtgg caccggtatg 1740
gtgagcaagg gcgaggagct gttcaccggg gtggtgccca tcctggtcga gctggacggc 1800
gacgtaaacg gccacaagtt cagcgtgtcc ggcgagggcg agggcgatgc cacctacggc 1860
aagctgaccc tgaagctgat ctgcaccacc ggcaagctgc ccgtgccctg gcccaccctc 1920
gtgaccaccc tgggctacgg cctccagtgc ttcgcccgct accccgacca catgaagcag 1980
cacgacttct tcaagtccgc catgcccgaa ggctacgtcc aggagcgcac catcttcttc 2040
aaggacgacg gcaactacaa gacccgcgcc gaggtgaagt tcgagggcga caccctggtg 2100
aaccgcatcg agctgaaggg catcgacttc aaggaggacg gcaacatcct ggggcacaag 2160
ctggagtaca actacaacag ccacaacgtc tatatcaccg ccgacaagca gaagaacggc 2220
atcaaggcca acttcaagat ccgccacaac atcgaggacg gcggcgtgca gctcgccgac 2280
cactaccagc agaacacccc catcggcgac ggccccgtgc tgctgcccga caaccactac 2340
ctgagctacc agtccgccct gagcaaagac cccaacgaga agcgcgatca catggtcctg 2400
ctggagttcg tgaccgccgc cgggatcact ctcggcatgg acgagctgta caag 2454

<210> SEQ ID NO 182
<211> LENGTH: 720
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 182

Met Ala Leu Pro Val Thr Ala Leu Leu Leu Pro Leu Ala Leu Leu Leu
1               5                   10                  15

His Ala Ala Arg Pro Asp Val Val Met Thr Gln Ser Pro Leu Ser Leu
            20                  25                  30

Pro Val Thr Pro Gly Glu Pro Ala Ser Ile Ser Cys Arg Ser Ser Gln
        35                  40                  45

```
Ser Leu Leu His Ser Asn Gly Tyr Asn Tyr Leu Asp Trp Tyr Leu Gln
    50                  55                  60

Lys Pro Gly Gln Ser Pro Gln Leu Leu Ile Tyr Leu Gly Ser Asn Arg
65                  70                  75                  80

Ala Ser Gly Val Pro Asp Arg Phe Ser Gly Ser Gly Ser Gly Thr Asp
                85                  90                  95

Phe Thr Leu Lys Ile Ser Arg Val Glu Ala Glu Asp Val Gly Val Tyr
            100                 105                 110

Tyr Cys Met Gln Ser Leu Gln Thr Pro Phe Thr Phe Gly Pro Gly Thr
        115                 120                 125

Lys Val Asp Ile Lys Gly Gly Gly Gly Ser Gly Gly Gly Gly Ser Gly
    130                 135                 140

Gly Gly Gly Ser Glu Val Gln Leu Val Gln Ser Gly Ala Glu Val Lys
145                 150                 155                 160

Lys Pro Gly Ala Ser Val Lys Val Ser Cys Lys Ala Ser Gly Tyr Thr
                165                 170                 175

Phe Thr Ser Tyr Tyr Met His Trp Ala Arg Gln Ala Pro Gly Gln Gly
            180                 185                 190

Leu Glu Trp Met Gly Ile Ile Asn Pro Ser Gly Gly Ser Thr Ser Tyr
        195                 200                 205

Ala Gln Lys Phe Gln Gly Arg Val Thr Met Thr Arg Asp Thr Ser Thr
    210                 215                 220

Ser Thr Val Tyr Met Glu Leu Ser Ser Leu Arg Ser Glu Asp Thr Ala
225                 230                 235                 240

Val Tyr Tyr Cys Ala Arg Val Val Ala Ala Ala Val Ala Asp Tyr Trp
                245                 250                 255

Gly Gln Gly Thr Leu Val Thr Val Ser Ser Ala Cys Pro Thr Gly Leu
            260                 265                 270

Tyr Thr His Ser Gly Glu Cys Cys Lys Ala Cys Asn Leu Gly Glu Gly
        275                 280                 285

Val Ala Gln Pro Cys Gly Ala Asn Gln Thr Val Cys Ile Tyr Ile Trp
    290                 295                 300

Ala Pro Leu Ala Gly Thr Cys Gly Val Leu Leu Leu Ser Leu Val Ile
305                 310                 315                 320

Thr Lys Arg Gly Arg Lys Lys Leu Leu Tyr Ile Phe Lys Gln Pro Phe
                325                 330                 335

Met Arg Pro Val Gln Thr Thr Gln Glu Glu Asp Gly Cys Ser Cys Arg
            340                 345                 350

Phe Pro Glu Glu Glu Glu Gly Gly Cys Glu Leu Arg Val Lys Phe Ser
        355                 360                 365

Arg Ser Ala Asp Ala Pro Ala Tyr Lys Gln Gly Gln Asn Gln Leu Tyr
    370                 375                 380

Asn Glu Leu Asn Leu Gly Arg Arg Glu Glu Tyr Asp Val Leu Asp Lys
385                 390                 395                 400

Arg Arg Gly Arg Asp Pro Glu Met Gly Gly Lys Pro Arg Arg Lys Asn
                405                 410                 415

Pro Gln Glu Gly Leu Tyr Asn Glu Leu Gln Lys Asp Lys Met Ala Glu
            420                 425                 430

Ala Tyr Ser Glu Ile Gly Met Lys Gly Glu Arg Arg Arg Gly Lys Gly
        435                 440                 445

His Asp Gly Leu Tyr Gln Gly Leu Ser Thr Ala Thr Lys Asp Thr Tyr
    450                 455                 460
```

```
Asp Ala Leu His Met Gln Ala Leu Pro Pro Arg Gly Ser Ser Gly Thr
465                 470                 475                 480

Gly Met Val Ser Lys Gly Glu Glu Leu Phe Thr Gly Val Val Pro Ile
                485                 490                 495

Leu Val Glu Leu Asp Gly Asp Val Asn Gly His Lys Phe Ser Val Ser
            500                 505                 510

Gly Glu Gly Glu Gly Asp Ala Thr Tyr Gly Lys Leu Thr Leu Lys Leu
        515                 520                 525

Ile Cys Thr Thr Gly Lys Leu Pro Val Pro Trp Pro Thr Leu Val Thr
    530                 535                 540

Thr Leu Gly Tyr Gly Leu Gln Cys Phe Ala Arg Tyr Pro Asp His Met
545                 550                 555                 560

Lys Gln His Asp Phe Phe Lys Ser Ala Met Pro Glu Gly Tyr Val Gln
                565                 570                 575

Glu Arg Thr Ile Phe Phe Lys Asp Asp Gly Asn Tyr Lys Thr Arg Ala
            580                 585                 590

Glu Val Lys Phe Glu Gly Asp Thr Leu Val Asn Arg Ile Glu Leu Lys
        595                 600                 605

Gly Ile Asp Phe Lys Glu Asp Gly Asn Ile Leu Gly His Lys Leu Glu
    610                 615                 620

Tyr Asn Tyr Asn Ser His Asn Val Tyr Ile Thr Ala Asp Lys Gln Lys
625                 630                 635                 640

Asn Gly Ile Lys Ala Asn Phe Lys Ile Arg His Asn Ile Glu Asp Gly
                645                 650                 655

Gly Val Gln Leu Ala Asp His Tyr Gln Gln Asn Thr Pro Ile Gly Asp
            660                 665                 670

Gly Pro Val Leu Leu Pro Asp Asn His Tyr Leu Ser Tyr Gln Ser Ala
        675                 680                 685

Leu Ser Lys Asp Pro Asn Glu Lys Arg Asp His Met Val Leu Leu Glu
    690                 695                 700

Phe Val Thr Ala Ala Gly Ile Thr Leu Gly Met Asp Glu Leu Tyr Lys
705                 710                 715                 720
```

<210> SEQ ID NO 183
<211> LENGTH: 2160
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 183

```
atggccttac cagtgaccgc cttgctcctg ccgctggcct tgctgctcca cgccgccagg      60

ccggacgtag ttatgacaca gtctccactg tcattgccag taacaccagg tgagcccgcc     120

tccatctcat gtagatcctc ccaatctctc cttcattcaa acgggtataa ttatctcgac     180

tggtatttgc agaaaccggg ccagagccct caactgctca tctatttggg gagcaaccgg     240

gcctctggtg tccctgatag attctccggg agtggatcag gtacggattt tacactgaag     300

atcagcaggg tggaagcaga agatgttggt gtgtattact gtatgcaatc actccagacc     360

ccgtttacct ttgggcctgg aacaaaggta gatattaaag gcggaggggg atcagggggt     420

ggggggtcag gtggcggtgg aagtgaagtg caacttgttc agagcggggc agaagttaag     480

aagccaggcg cttccgtcaa ggtgagttgc aaggcaagtg gatacacctt tacgagttat     540

tatatgcact gggcacggca ggcccctggt cagggcctcg aatggatggg gattataaat     600
```

ccttctggcg ggtcaaccag ctacgcacaa aaatttcaag gtcgggtgac aatgacgcgc 660
gacacgtcaa cgagtacagt gtatatggaa ttgtctagcc tgaggtccga ggatactgct 720
gtctattatt gtgctcgcgt ggtcgctgct gctgtggcag actactgggg tcagggtaca 780
cttgtgacgg taagcagcgc ctgccctaca ggactctaca cgcatagcgg tgagtgttgt 840
aaagcatgca acctcgggga aggtgtagcc cagccatgcg ggctaacca aaccgtttgc 900 atctacatat gggcccccct cgccggtact tgcggtgttt tgcttttgtc actggtgatt 960
acgaagcgcg gtcgaaaaaa actcctctac atcttcaaac aacctttcat gcggcctgtc 1020
caaacaactc aagaagagga cgggtgttca tgccgctttc cagaggaaga ggaaggtggc 1080
tgtgaactta gggtcaagtt tagcaggtca gcggacgcac cagcttacaa gcaaggccaa 1140
aaccagcttt ataacgaatt gaatttggga cgcagggaag aatacgatgt gctcgataaa 1200
cgcagaggga gggacccgga aatgggagga aagccaaggc ggaaaaaccc acaggagggg 1260
ttgtacaacg agcttcaaaa agataagatg gcggaagcat actccgaaat aggaatgaag 1320
ggtgaacgga ggaggggcaa gggccacgac ggcctgtacc agggactctc aactgctacg 1380
aaggatactt atgatgctct tcacatgcaa gctctgccgc cgcgcggatc gagtggcacc 1440
ggtatggtga gcaagggcga ggagctgttc accggggtgg tgcccatcct ggtcgagctg 1500
gacggcgacg taaacggcca caagttcagc gtgtccggcg agggcgaggg cgatgccacc 1560
tacggcaagc tgaccctgaa gctgatctgc accaccggca agctgcccgt gccctggccc 1620
accctcgtga ccaccctggg ctacggcctc cagtgcttcg cccgctaccc cgaccacatg 1680
aagcagcacg acttcttcaa gtccgccatg cccgaaggct acgtccagga gcgcaccatc 1740
ttcttcaagg acgacggcaa ctacaagacc cgcgccgagg tgaagttcga gggcgacacc 1800
ctggtgaacc gcatcgagct gaagggcatc gacttcaagg aggacggcaa catcctgggg 1860
cacaagctgg agtacaacta caacagccac aacgtctata tcaccgccga caagcagaag 1920
aacggcatca aggccaactt caagatccgc cacaacatcg aggacggcgg cgtgcagctc 1980
gccgaccact accagcagaa cacccccatc ggcgacggcc ccgtgctgct gcccgacaac 2040
cactacctga gctaccagtc cgccctgagc aaagacccca acgagaagcg cgatcacatg 2100
gtcctgctgg agttcgtgac cgccgccggg atcactctcg gcatggacga gctgtacaag 2160

<210> SEQ ID NO 184
<211> LENGTH: 706
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 184

Met Ala Leu Pro Val Thr Ala Leu Leu Leu Pro Leu Ala Leu Leu Leu
1               5                   10                  15

His Ala Ala Arg Pro Asp Val Val Met Thr Gln Ser Pro Leu Ser Leu
            20                  25                  30

Pro Val Thr Pro Gly Glu Pro Ala Ser Ile Ser Cys Arg Ser Ser Gln
        35                  40                  45

Ser Leu Leu His Ser Asn Gly Tyr Asn Tyr Leu Asp Trp Tyr Leu Gln
    50                  55                  60

Lys Pro Gly Gln Ser Pro Gln Leu Leu Ile Tyr Leu Gly Ser Asn Arg
65                  70                  75                  80

Ala Ser Gly Val Pro Asp Arg Phe Ser Gly Ser Gly Ser Gly Thr Asp

-continued

```
                85                  90                  95

Phe Thr Leu Lys Ile Ser Arg Val Glu Ala Glu Asp Val Gly Val Tyr
            100                 105                 110

Tyr Cys Met Gln Ser Leu Gln Thr Pro Phe Thr Phe Gly Pro Gly Thr
        115                 120                 125

Lys Val Asp Ile Lys Gly Gly Gly Gly Ser Gly Gly Gly Gly Ser Gly
    130                 135                 140

Gly Gly Gly Ser Glu Val Gln Leu Val Gln Ser Gly Ala Glu Val Lys
145                 150                 155                 160

Lys Pro Gly Ala Ser Val Lys Val Ser Cys Lys Ala Ser Gly Tyr Thr
                165                 170                 175

Phe Thr Ser Tyr Tyr Met His Trp Ala Arg Gln Ala Pro Gly Gln Gly
            180                 185                 190

Leu Glu Trp Met Gly Ile Ile Asn Pro Ser Gly Gly Ser Thr Ser Tyr
        195                 200                 205

Ala Gln Lys Phe Gln Gly Arg Val Thr Met Thr Arg Asp Thr Ser Thr
    210                 215                 220

Ser Thr Val Tyr Met Glu Leu Ser Ser Leu Arg Ser Glu Asp Thr Ala
225                 230                 235                 240

Val Tyr Tyr Cys Ala Arg Val Val Ala Ala Ala Val Ala Asp Tyr Trp
                245                 250                 255

Gly Gln Gly Thr Leu Val Thr Val Ser Ser Ala Val Gly Gln Asp Thr
            260                 265                 270

Gln Glu Val Ile Val Val Pro His Ser Leu Pro Phe Lys Val Ile Tyr
        275                 280                 285

Ile Trp Ala Pro Leu Ala Gly Thr Cys Gly Val Leu Leu Leu Ser Leu
    290                 295                 300

Val Ile Thr Lys Arg Gly Arg Lys Lys Leu Leu Tyr Ile Phe Lys Gln
305                 310                 315                 320

Pro Phe Met Arg Pro Val Gln Thr Thr Gln Glu Glu Asp Gly Cys Ser
                325                 330                 335

Cys Arg Phe Pro Glu Glu Glu Glu Gly Gly Cys Glu Leu Arg Val Lys
            340                 345                 350

Phe Ser Arg Ser Ala Asp Ala Pro Ala Tyr Lys Gln Gly Gln Asn Gln
        355                 360                 365

Leu Tyr Asn Glu Leu Asn Leu Gly Arg Arg Glu Glu Tyr Asp Val Leu
    370                 375                 380

Asp Lys Arg Arg Gly Arg Asp Pro Glu Met Gly Gly Lys Pro Arg Arg
385                 390                 395                 400

Lys Asn Pro Gln Glu Gly Leu Tyr Asn Glu Leu Gln Lys Asp Lys Met
                405                 410                 415

Ala Glu Ala Tyr Ser Glu Ile Gly Met Lys Gly Glu Arg Arg Arg Gly
            420                 425                 430

Lys Gly His Asp Gly Leu Tyr Gln Gly Leu Ser Thr Ala Thr Lys Asp
        435                 440                 445

Thr Tyr Asp Ala Leu His Met Gln Ala Leu Pro Pro Arg Gly Ser Ser
    450                 455                 460

Gly Thr Gly Met Val Ser Lys Gly Glu Glu Leu Phe Thr Gly Val Val
465                 470                 475                 480

Pro Ile Leu Val Glu Leu Asp Gly Asp Val Asn Gly His Lys Phe Ser
                485                 490                 495

Val Ser Gly Glu Gly Glu Gly Asp Ala Thr Tyr Gly Lys Leu Thr Leu
            500                 505                 510
```

```
Lys Leu Ile Cys Thr Thr Gly Lys Leu Pro Val Pro Trp Pro Thr Leu
        515                 520                 525

Val Thr Thr Leu Gly Tyr Gly Leu Gln Cys Phe Ala Arg Tyr Pro Asp
    530                 535                 540

His Met Lys Gln His Asp Phe Phe Lys Ser Ala Met Pro Glu Gly Tyr
545                 550                 555                 560

Val Gln Glu Arg Thr Ile Phe Phe Lys Asp Asp Gly Asn Tyr Lys Thr
                565                 570                 575

Arg Ala Glu Val Lys Phe Glu Gly Asp Thr Leu Val Asn Arg Ile Glu
            580                 585                 590

Leu Lys Gly Ile Asp Phe Lys Glu Asp Gly Asn Ile Leu Gly His Lys
        595                 600                 605

Leu Glu Tyr Asn Tyr Asn Ser His Asn Val Tyr Ile Thr Ala Asp Lys
    610                 615                 620

Gln Lys Asn Gly Ile Lys Ala Asn Phe Lys Ile Arg His Asn Ile Glu
625                 630                 635                 640

Asp Gly Gly Val Gln Leu Ala Asp His Tyr Gln Gln Asn Thr Pro Ile
                645                 650                 655

Gly Asp Gly Pro Val Leu Leu Pro Asp Asn His Tyr Leu Ser Tyr Gln
            660                 665                 670

Ser Ala Leu Ser Lys Asp Pro Asn Glu Lys Arg Asp His Met Val Leu
        675                 680                 685

Leu Glu Phe Val Thr Ala Ala Gly Ile Thr Leu Gly Met Asp Glu Leu
    690                 695                 700

Tyr Lys
705
```

<210> SEQ ID NO 185
<211> LENGTH: 2118
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 185

```
atggccttac cagtgaccgc cttgctcctg ccgctggcct tgctgctcca cgccgccagg      60

ccggacgtag ttatgacaca gtctccactg tcattgccag taacaccagg tgagcccgcc     120

tccatctcat gtagatcctc ccaatctctc cttcattcaa acgggtataa ttatctcgac     180

tggtatttgc agaaaccggg ccagagccct caactgctca tctatttggg gagcaaccgg     240

gcctctggtg tccctgatag attctccggg agtggatcag gtacggattt tacactgaag     300

atcagcaggg tggaagcaga agatgttggt gtgtattact gtatgcaatc actccagacc     360

ccgtttacct ttgggcctgg aacaaaggta gatattaaag gcggaggggg atcagggggt     420

ggggggtcag gtggcggtgg aagtgaagtg caacttgttc agagcggggc agaagttaag     480

aagccaggcg cttccgtcaa ggtgagttgc aaggcaagtg gatacacctt tacgagttat     540

tatatgcact gggcacggca ggcccctggt cagggcctcg aatggatggg gattataaat     600

ccttctggcg ggtcaaccag ctacgcacaa aaatttcaag gtcgggtgac aatgacgcgc     660

gacacgtcaa cgagtacagt gtatatggaa ttgtctagcc tgaggtccga ggatactgct     720

gtctattatt gtgctcgcgt ggtcgctgct gctgtggcag actactgggg tcagggtaca     780

cttgtgacgg taagcagcgc tgtgggccag gacacgcagg aggtcatcgt ggtgccacac     840
```

```
tccttgccct ttaaggtgat ctacatatgg gcccccctcg ccggtacttg cggtgttttg    900

cttttgtcac tggtgattac gaagcgcggt cgaaaaaaac tcctctacat cttcaaacaa    960

cctttcatgc ggcctgtcca aacaactcaa gaagaggacg ggtgttcatg ccgctttcca   1020

gaggaagagg aaggtggctg tgaacttagg gtcaagttta gcaggtcagc ggacgcacca   1080

gcttacaagc aaggccaaaa ccagctttat aacgaattga atttgggacg cagggaagaa   1140

tacgatgtgc tcgataaacg cagagggagg gacccggaaa tgggaggaaa gccaaggcgg   1200

aaaaacccac aggaggggtt gtacaacgag cttcaaaaag ataagatggc ggaagcatac   1260

tccgaaatag gaatgaaggg tgaacggagg aggggcaagg gccacgacgg cctgtaccag   1320

ggactctcaa ctgctacgaa ggatacttat gatgctcttc acatgcaagc tctgccgccg   1380

cgcggatcga gtggcaccgg tatggtgagc aagggcgagg agctgttcac cggggtggtg   1440

cccatcctgg tcgagctgga cggcgacgta aacggccaca agttcagcgt gtccggcgag   1500

ggcgagggcg atgccaccta cggcaagctg accctgaagc tgatctgcac caccggcaag   1560

ctgcccgtgc cctggcccac cctcgtgacc accctgggct acggcctcca gtgcttcgcc   1620

cgctaccccg accacatgaa gcagcacgac ttcttcaagt ccgccatgcc cgaaggctac   1680

gtccaggagc gcaccatctt cttcaaggac gacggcaact acaagacccg cgccgaggtg   1740

aagttcgagg gcgacaccct ggtgaaccgc atcgagctga agggcatcga cttcaaggag   1800

gacggcaaca tcctggggca caagctggag tacaactaca acagccacaa cgtctatatc   1860

accgccgaca agcagaagaa cggcatcaag gccaacttca agatccgcca caacatcgag   1920

gacggcggcg tgcagctcgc cgaccactac cagcagaaca cccccatcgg cgacggcccc   1980

gtgctgctgc ccgacaacca ctacctgagc taccagtccg ccctgagcaa agaccccaac   2040

gagaagcgcg atcacatggt cctgctggag ttcgtgaccg ccgccgggat cactctcggc   2100

atggacgagc tgtacaag                                                 2118
```

<210> SEQ ID NO 186
<211> LENGTH: 698
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 186

```
Met Ala Leu Pro Val Thr Ala Leu Leu Leu Pro Leu Ala Leu Leu Leu
1               5                   10                  15

His Ala Ala Arg Pro Asp Val Val Met Thr Gln Ser Pro Leu Ser Leu
            20                  25                  30

Pro Val Thr Pro Gly Glu Pro Ala Ser Ile Ser Cys Arg Ser Ser Gln
        35                  40                  45

Ser Leu Leu His Ser Asn Gly Tyr Asn Tyr Leu Asp Trp Tyr Leu Gln
    50                  55                  60

Lys Pro Gly Gln Ser Pro Gln Leu Leu Ile Tyr Leu Gly Ser Asn Arg
65                  70                  75                  80

Ala Ser Gly Val Pro Asp Arg Phe Ser Gly Ser Gly Ser Gly Thr Asp
                85                  90                  95

Phe Thr Leu Lys Ile Ser Arg Val Glu Ala Glu Asp Val Gly Val Tyr
            100                 105                 110

Tyr Cys Met Gln Ser Leu Gln Thr Pro Phe Thr Phe Gly Pro Gly Thr
        115                 120                 125
```

-continued

Lys Val Asp Ile Lys Gly Gly Gly Gly Ser Gly Gly Gly Gly Ser Gly
    130                 135                 140

Gly Gly Gly Ser Glu Val Gln Leu Val Gln Ser Gly Ala Glu Val Lys
145                 150                 155                 160

Lys Pro Gly Ala Ser Val Lys Val Ser Cys Lys Ala Ser Gly Tyr Thr
                165                 170                 175

Phe Thr Ser Tyr Tyr Met His Trp Ala Arg Gln Ala Pro Gly Gln Gly
            180                 185                 190

Leu Glu Trp Met Gly Ile Ile Asn Pro Ser Gly Gly Ser Thr Ser Tyr
        195                 200                 205

Ala Gln Lys Phe Gln Gly Arg Val Thr Met Thr Arg Asp Thr Ser Thr
    210                 215                 220

Ser Thr Val Tyr Met Glu Leu Ser Ser Leu Arg Ser Glu Asp Thr Ala
225                 230                 235                 240

Val Tyr Tyr Cys Ala Arg Val Val Ala Ala Ala Val Ala Asp Tyr Trp
                245                 250                 255

Gly Gln Gly Thr Leu Val Thr Val Ser Ser Glu Ser Lys Tyr Gly Pro
            260                 265                 270

Pro Cys Pro Ser Cys Pro Ile Tyr Ile Trp Ala Pro Leu Ala Gly Thr
        275                 280                 285

Cys Gly Val Leu Leu Leu Ser Leu Val Ile Thr Lys Arg Gly Arg Lys
    290                 295                 300

Lys Leu Leu Tyr Ile Phe Lys Gln Pro Phe Met Arg Pro Val Gln Thr
305                 310                 315                 320

Thr Gln Glu Glu Asp Gly Cys Ser Cys Arg Phe Pro Glu Glu Glu Glu
                325                 330                 335

Gly Gly Cys Glu Leu Arg Val Lys Phe Ser Arg Ser Ala Asp Ala Pro
            340                 345                 350

Ala Tyr Lys Gln Gly Gln Asn Gln Leu Tyr Asn Glu Leu Asn Leu Gly
        355                 360                 365

Arg Arg Glu Glu Tyr Asp Val Leu Asp Lys Arg Arg Gly Arg Asp Pro
    370                 375                 380

Glu Met Gly Gly Lys Pro Arg Arg Lys Asn Pro Gln Glu Gly Leu Tyr
385                 390                 395                 400

Asn Glu Leu Gln Lys Asp Lys Met Ala Glu Ala Tyr Ser Glu Ile Gly
                405                 410                 415

Met Lys Gly Glu Arg Arg Arg Gly Lys Gly His Asp Gly Leu Tyr Gln
            420                 425                 430

Gly Leu Ser Thr Ala Thr Lys Asp Thr Tyr Asp Ala Leu His Met Gln
        435                 440                 445

Ala Leu Pro Pro Arg Gly Ser Ser Gly Thr Gly Met Val Ser Lys Gly
    450                 455                 460

Glu Glu Leu Phe Thr Gly Val Val Pro Ile Leu Val Glu Leu Asp Gly
465                 470                 475                 480

Asp Val Asn Gly His Lys Phe Ser Val Ser Gly Glu Gly Glu Gly Asp
                485                 490                 495

Ala Thr Tyr Gly Lys Leu Thr Leu Lys Leu Ile Cys Thr Thr Gly Lys
            500                 505                 510

Leu Pro Val Pro Trp Pro Thr Leu Val Thr Thr Leu Gly Tyr Gly Leu
        515                 520                 525

Gln Cys Phe Ala Arg Tyr Pro Asp His Met Lys Gln His Asp Phe Phe
    530                 535                 540

Lys Ser Ala Met Pro Glu Gly Tyr Val Gln Glu Arg Thr Ile Phe Phe

-continued 545 550 555 560

Lys Asp Asp Gly Asn Tyr Lys Thr Arg Ala Glu Val Lys Phe Glu Gly
565 570 575

Asp Thr Leu Val Asn Arg Ile Glu Leu Lys Gly Ile Asp Phe Lys Glu
580 585 590

Asp Gly Asn Ile Leu Gly His Lys Leu Glu Tyr Asn Tyr Asn Ser His
595 600 605

Asn Val Tyr Ile Thr Ala Asp Lys Gln Lys Asn Gly Ile Lys Ala Asn
610 615 620

Phe Lys Ile Arg His Asn Ile Glu Asp Gly Gly Val Gln Leu Ala Asp
625 630 635 640

His Tyr Gln Gln Asn Thr Pro Ile Gly Asp Gly Pro Val Leu Leu Pro
645 650 655

Asp Asn His Tyr Leu Ser Tyr Gln Ser Ala Leu Ser Lys Asp Pro Asn
660 665 670

Glu Lys Arg Asp His Met Val Leu Leu Glu Phe Val Thr Ala Ala Gly
675 680 685

Ile Thr Leu Gly Met Asp Glu Leu Tyr Lys
690 695

<210> SEQ ID NO 187
<211> LENGTH: 2094
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 187
atggccttac cagtgaccgc cttgctcctg ccgctggcct tgctgctcca cgccgccagg 60
ccggacgtag ttatgacaca gtctccactg tcattgccag taacaccagg tgagcccgcc 120
tccatctcat gtagatcctc ccaatctctc cttcattcaa acgggtataa ttatctcgac 180
tggtatttgc agaaaccggg ccagagccct caactgctca tctatttggg gagcaaccgg 240
gcctctggtg tccctgatag attctccggg agtggatcag gtacggattt tacactgaag 300
atcagcaggg tggaagcaga agatgttggt gtgtattact gtatgcaatc actccagacc 360
ccgtttacct ttgggcctgg aacaaaggta gatattaaag gcggaggggg atcagggggt 420
ggggggtcag gtggcggtgg aagtgaagtg caacttgttc agagcggggc agaagttaag 480
aagccaggcg cttccgtcaa ggtgagttgc aaggcaagtg gatacacctt tacgagttat 540
tatatgcact gggcacggca ggcccctggt cagggcctcg aatggatggg gattataaat 600
ccttctggcg ggtcaaccag ctacgcacaa aaatttcaag gtcgggtgac aatgacgcgc 660
gacacgtcaa cgagtacagt gtatatggaa ttgtctagcc tgaggtccga ggatactgct 720
gtctattatt gtgctcgcgt ggtcgctgct gctgtggcag actactgggg tcagggtaca 780
cttgtgacgg taagcagcga aagcaagtac ggtccacctt gccctagctg tccgatctac 840
atatgggccc ccctcgccgg tacttgcggt gttttgcttt tgtcactggt gattacgaag 900
cgcggtcgaa aaaaactcct ctacatcttc aaacaacctt tcatgcggcc tgtccaaaca 960
actcaagaag aggacgggtg ttcatgccgc tttccagagg aagaggaagg tggctgtgaa 1020
cttagggtca agtttagcag gtcagcggac gcaccagctt acaagcaagg ccaaaaccag 1080
ctttataacg aattgaattt gggacgcagg gaagaatacg atgtgctcga taaacgcaga 1140
gggagggacc cggaaatggg aggaaagcca aggcggaaaa acccacagga ggggttgtac 1200

```
aacgagcttc aaaaagataa gatggcggaa gcatactccg aaataggaat gaagggtgaa   1260

cggaggaggg gcaagggcca cgacggcctg taccagggac tctcaactgc tacgaaggat   1320

acttatgatg ctcttcacat gcaagctctg ccgccgcgcg gatcgagtgg caccggtatg   1380

gtgagcaagg gcgaggagct gttcaccggg gtggtgccca tcctggtcga gctggacggc   1440

gacgtaaacg gccacaagtt cagcgtgtcc ggcgagggcg agggcgatgc cacctacggc   1500

aagctgaccc tgaagctgat ctgcaccacc ggcaagctgc ccgtgccctg gcccaccctc   1560

gtgaccaccc tgggctacgg cctccagtgc ttcgcccgct accccgacca catgaagcag   1620

cacgacttct tcaagtccgc catgcccgaa ggctacgtcc aggagcgcac catcttcttc   1680

aaggacgacg gcaactacaa gacccgcgcc gaggtgaagt tcgagggcga caccctggtg   1740

aaccgcatcg agctgaaggg catcgacttc aaggaggacg gcaacatcct ggggcacaag   1800

ctggagtaca actacaacag ccacaacgtc tatatcaccg ccgacaagca gaagaacggc   1860

atcaaggcca acttcaagat ccgccacaac atcgaggacg gcggcgtgca gctcgccgac   1920

cactaccagc agaacacccc catcggcgac ggccccgtgc tgctgcccga caaccactac   1980

ctgagctacc agtccgccct gagcaaagac cccaacgaga agcgcgatca catggtcctg   2040

ctggagttcg tgaccgccgc cgggatcact ctcggcatgg acgagctgta caag         2094
```

<210> SEQ ID NO 188
<211> LENGTH: 698
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 188

```
Met Ala Leu Pro Val Thr Ala Leu Leu Leu Pro Leu Ala Leu Leu Leu
1               5                   10                  15

His Ala Ala Arg Pro Asp Val Val Met Thr Gln Ser Pro Leu Ser Leu
            20                  25                  30

Pro Val Thr Pro Gly Glu Pro Ala Ser Ile Ser Cys Arg Ser Ser Gln
        35                  40                  45

Ser Leu Leu His Ser Asn Gly Tyr Asn Tyr Leu Asp Trp Tyr Leu Gln
    50                  55                  60

Lys Pro Gly Gln Ser Pro Gln Leu Leu Ile Tyr Leu Gly Ser Asn Arg
65                  70                  75                  80

Ala Ser Gly Val Pro Asp Arg Phe Ser Gly Ser Gly Ser Gly Thr Asp
                85                  90                  95

Phe Thr Leu Lys Ile Ser Arg Val Glu Ala Glu Asp Val Gly Val Tyr
            100                 105                 110

Tyr Cys Met Gln Ser Leu Gln Thr Pro Phe Thr Phe Gly Pro Gly Thr
        115                 120                 125

Lys Val Asp Ile Lys Gly Gly Gly Gly Ser Gly Gly Gly Gly Ser Gly
    130                 135                 140

Gly Gly Gly Ser Glu Val Gln Leu Val Gln Ser Gly Ala Glu Val Lys
145                 150                 155                 160

Lys Pro Gly Ala Ser Val Lys Val Ser Cys Lys Ala Ser Gly Tyr Thr
                165                 170                 175

Phe Thr Ser Tyr Tyr Met His Trp Ala Arg Gln Ala Pro Gly Gln Gly
            180                 185                 190

Leu Glu Trp Met Gly Ile Ile Asn Pro Ser Gly Gly Ser Thr Ser Tyr
```

-continued

```
        195                 200                 205

Ala Gln Lys Phe Gln Gly Arg Val Thr Met Thr Arg Asp Thr Ser Thr
    210                 215                 220

Ser Thr Val Tyr Met Glu Leu Ser Ser Leu Arg Ser Glu Asp Thr Ala
225                 230                 235                 240

Val Tyr Tyr Cys Ala Arg Val Val Ala Ala Ala Val Ala Asp Tyr Trp
                245                 250                 255

Gly Gln Gly Thr Leu Val Thr Val Ser Ser Glu Ser Lys Tyr Gly Pro
            260                 265                 270

Pro Ala Pro Ser Ala Pro Ile Tyr Ile Trp Ala Pro Leu Ala Gly Thr
        275                 280                 285

Cys Gly Val Leu Leu Leu Ser Leu Val Ile Thr Lys Arg Gly Arg Lys
    290                 295                 300

Lys Leu Leu Tyr Ile Phe Lys Gln Pro Phe Met Arg Pro Val Gln Thr
305                 310                 315                 320

Thr Gln Glu Glu Asp Gly Cys Ser Cys Arg Phe Pro Glu Glu Glu Glu
                325                 330                 335

Gly Gly Cys Glu Leu Arg Val Lys Phe Ser Arg Ser Ala Asp Ala Pro
            340                 345                 350

Ala Tyr Lys Gln Gly Gln Asn Gln Leu Tyr Asn Glu Leu Asn Leu Gly
        355                 360                 365

Arg Arg Glu Glu Tyr Asp Val Leu Asp Lys Arg Arg Gly Arg Asp Pro
    370                 375                 380

Glu Met Gly Gly Lys Pro Arg Arg Lys Asn Pro Gln Glu Gly Leu Tyr
385                 390                 395                 400

Asn Glu Leu Gln Lys Asp Lys Met Ala Glu Ala Tyr Ser Glu Ile Gly
                405                 410                 415

Met Lys Gly Glu Arg Arg Arg Gly Lys Gly His Asp Gly Leu Tyr Gln
            420                 425                 430

Gly Leu Ser Thr Ala Thr Lys Asp Thr Tyr Asp Ala Leu His Met Gln
        435                 440                 445

Ala Leu Pro Pro Arg Gly Ser Ser Gly Thr Gly Met Val Ser Lys Gly
    450                 455                 460

Glu Glu Leu Phe Thr Gly Val Val Pro Ile Leu Val Glu Leu Asp Gly
465                 470                 475                 480

Asp Val Asn Gly His Lys Phe Ser Val Ser Gly Glu Gly Glu Gly Asp
                485                 490                 495

Ala Thr Tyr Gly Lys Leu Thr Leu Lys Leu Ile Cys Thr Thr Gly Lys
            500                 505                 510

Leu Pro Val Pro Trp Pro Thr Leu Val Thr Thr Leu Gly Tyr Gly Leu
        515                 520                 525

Gln Cys Phe Ala Arg Tyr Pro Asp His Met Lys Gln His Asp Phe Phe
    530                 535                 540

Lys Ser Ala Met Pro Glu Gly Tyr Val Gln Glu Arg Thr Ile Phe Phe
545                 550                 555                 560

Lys Asp Asp Gly Asn Tyr Lys Thr Arg Ala Glu Val Lys Phe Glu Gly
                565                 570                 575

Asp Thr Leu Val Asn Arg Ile Glu Leu Lys Gly Ile Asp Phe Lys Glu
            580                 585                 590

Asp Gly Asn Ile Leu Gly His Lys Leu Glu Tyr Asn Tyr Asn Ser His
        595                 600                 605

Asn Val Tyr Ile Thr Ala Asp Lys Gln Lys Asn Gly Ile Lys Ala Asn
    610                 615                 620
```

```
Phe Lys Ile Arg His Asn Ile Glu Asp Gly Gly Val Gln Leu Ala Asp
625                 630                 635                 640

His Tyr Gln Gln Asn Thr Pro Ile Gly Asp Gly Pro Val Leu Leu Pro
                645                 650                 655

Asp Asn His Tyr Leu Ser Tyr Gln Ser Ala Leu Ser Lys Asp Pro Asn
            660                 665                 670

Glu Lys Arg Asp His Met Val Leu Leu Glu Phe Val Thr Ala Ala Gly
        675                 680                 685

Ile Thr Leu Gly Met Asp Glu Leu Tyr Lys
    690                 695


<210> SEQ ID NO 189
<211> LENGTH: 2094
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 189

atggccttac cagtgaccgc cttgctcctg ccgctggcct tgctgctcca cgccgccagg     60

ccggacgtag ttatgacaca gtctccactg tcattgccag taacaccagg tgagcccgcc    120

tccatctcat gtagatcctc ccaatctctc cttcattcaa acgggtataa ttatctcgac    180

tggtatttgc agaaaccggg ccagagccct caactgctca tctatttggg gagcaaccgg    240

gcctctggtg tccctgatag attctccggg agtggatcag gtacggattt tacactgaag    300

atcagcaggg tggaagcaga agatgttggt gtgtattact gtatgcaatc actccagacc    360

ccgtttacct ttgggcctgg aacaaaggta gatattaaag gcggaggggg atcagggggt    420

gggggtcag gtggcggtgg aagtgaagtg caacttgttc agagcggggc agaagttaag    480

aagccaggcg cttccgtcaa ggtgagttgc aaggcaagtg gatacacctt tacgagttat    540

tatatgcact gggcacggca ggcccctggt cagggcctcg aatggatggg gattataaat    600

ccttctggcg ggtcaaccag ctacgcacaa aaatttcaag gtcgggtgac aatgacgcgc    660

gacacgtcaa cgagtacagt gtatatggaa ttgtctagcc tgaggtccga ggatactgct    720

gtctattatt gtgctcgcgt ggtcgctgct gctgtggcag actactgggg tcagggtaca    780

cttgtgacgg taagcagcga atccaagtac ggcccccag cgcctagtgc cccaatctac    840

atatgggccc ccctcgccgg tacttgcggt gttttgcttt tgtcactggt gattacgaag    900

cgcggtcgaa aaaaactcct ctacatcttc aaacaacctt tcatgcggcc tgtccaaaca    960

actcaagaag aggacgggtg ttcatgccgc tttccagagg aagaggaagg tggctgtgaa   1020

cttagggtca agtttagcag gtcagcggac gcaccagctt acaagcaagg ccaaaaccag   1080

ctttataacg aattgaattt gggacgcagg gaagaatacg atgtgctcga taaacgcaga   1140

gggagggacc cggaaatggg aggaaagcca aggcggaaaa acccacagga ggggttgtac   1200

aacgagcttc aaaaagataa gatggcggaa gcatactccg aaataggaat gaagggtgaa   1260

cggaggaggg gcaagggcca cgacggcctg taccagggac tctcaactgc tacgaaggat   1320

acttatgatg ctcttcacat gcaagctctg ccgccgcgcg gatcgagtgg caccggtatg   1380

gtgagcaagg gcgaggagct gttcaccggg gtggtgccca tcctggtcga gctggacggc   1440

gacgtaaacg gccacaagtt cagcgtgtcc ggcgagggcg agggcgatgc cacctacggc   1500

aagctgaccc tgaagctgat ctgcaccacc ggcaagctgc ccgtgccctg gcccaccctc   1560
```

gtgaccaccc tgggctacgg cctccagtgc ttcgcccgct accccgacca catgaagcag 1620
cacgacttct tcaagtccgc catgcccgaa ggctacgtcc aggagcgcac catcttcttc 1680
aaggacgacg gcaactacaa gacccgcgcc gaggtgaagt tcgagggcga caccctggtg 1740
aaccgcatcg agctgaaggg catcgacttc aaggaggacg gcaacatcct ggggcacaag 1800
ctggagtaca actacaacag ccacaacgtc tatatcaccg ccgacaagca gaagaacggc 1860
atcaaggcca acttcaagat ccgccacaac atcgaggacg gcggcgtgca gctcgccgac 1920
cactaccagc agaacacccc catcggcgac ggccccgtgc tgctgcccga caaccactac 1980
ctgagctacc agtccgccct gagcaaagac cccaacgaga agcgcgatca catggtcctg 2040
ctggagttcg tgaccgccgc cgggatcact ctcggcatgg acgagctgta caag 2094

<210> SEQ ID NO 190
<211> LENGTH: 698
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 190

Met Ala Leu Pro Val Thr Ala Leu Leu Leu Pro Leu Ala Leu Leu Leu
1 5 10 15

His Ala Ala Arg Pro Asp Val Val Met Thr Gln Ser Pro Leu Ser Leu
20 25 30

Pro Val Thr Pro Gly Glu Pro Ala Ser Ile Ser Cys Arg Ser Ser Gln
35 40 45

Ser Leu Leu His Ser Asn Gly Tyr Asn Tyr Leu Asp Trp Tyr Leu Gln
50 55 60

Lys Pro Gly Gln Ser Pro Gln Leu Leu Ile Tyr Leu Gly Ser Asn Arg
65 70 75 80

Ala Ser Gly Val Pro Asp Arg Phe Ser Gly Ser Gly Ser Gly Thr Asp
85 90 95

Phe Thr Leu Lys Ile Ser Arg Val Glu Ala Glu Asp Val Gly Val Tyr
100 105 110

Tyr Cys Met Gln Ser Leu Gln Thr Pro Phe Thr Phe Gly Pro Gly Thr
115 120 125

Lys Val Asp Ile Lys Gly Gly Gly Gly Ser Gly Gly Gly Gly Ser Gly
130 135 140

Gly Gly Gly Ser Glu Val Gln Leu Val Gln Ser Gly Ala Glu Val Lys
145 150 155 160

Lys Pro Gly Ala Ser Val Lys Val Ser Cys Lys Ala Ser Gly Tyr Thr
165 170 175

Phe Thr Ser Tyr Tyr Met His Trp Ala Arg Gln Ala Pro Gly Gln Gly
180 185 190

Leu Glu Trp Met Gly Ile Ile Asn Pro Ser Gly Gly Ser Thr Ser Tyr
195 200 205

Ala Gln Lys Phe Gln Gly Arg Val Thr Met Thr Arg Asp Thr Ser Thr
210 215 220

Ser Thr Val Tyr Met Glu Leu Ser Ser Leu Arg Ser Glu Asp Thr Ala
225 230 235 240

Val Tyr Tyr Cys Ala Arg Val Val Ala Ala Ala Val Ala Asp Tyr Trp
245 250 255

Gly Gln Gly Thr Leu Val Thr Val Ser Ser Glu Ser Lys Tyr Gly Pro
260 265 270

```
Pro Cys Pro Pro Cys Pro Ile Tyr Ile Trp Ala Pro Leu Ala Gly Thr
        275                 280                 285

Cys Gly Val Leu Leu Leu Ser Leu Val Ile Thr Lys Arg Gly Arg Lys
    290                 295                 300

Lys Leu Leu Tyr Ile Phe Lys Gln Pro Phe Met Arg Pro Val Gln Thr
305                 310                 315                 320

Thr Gln Glu Glu Asp Gly Cys Ser Cys Arg Phe Pro Glu Glu Glu Glu
                325                 330                 335

Gly Gly Cys Glu Leu Arg Val Lys Phe Ser Arg Ser Ala Asp Ala Pro
            340                 345                 350

Ala Tyr Lys Gln Gly Gln Asn Gln Leu Tyr Asn Glu Leu Asn Leu Gly
        355                 360                 365

Arg Arg Glu Glu Tyr Asp Val Leu Asp Lys Arg Arg Gly Arg Asp Pro
    370                 375                 380

Glu Met Gly Gly Lys Pro Arg Arg Lys Asn Pro Gln Glu Gly Leu Tyr
385                 390                 395                 400

Asn Glu Leu Gln Lys Asp Lys Met Ala Glu Ala Tyr Ser Glu Ile Gly
                405                 410                 415

Met Lys Gly Glu Arg Arg Arg Gly Lys Gly His Asp Gly Leu Tyr Gln
            420                 425                 430

Gly Leu Ser Thr Ala Thr Lys Asp Thr Tyr Asp Ala Leu His Met Gln
        435                 440                 445

Ala Leu Pro Pro Arg Gly Ser Ser Gly Thr Gly Met Val Ser Lys Gly
    450                 455                 460

Glu Glu Leu Phe Thr Gly Val Val Pro Ile Leu Val Glu Leu Asp Gly
465                 470                 475                 480

Asp Val Asn Gly His Lys Phe Ser Val Ser Gly Glu Gly Glu Gly Asp
                485                 490                 495

Ala Thr Tyr Gly Lys Leu Thr Leu Lys Leu Ile Cys Thr Thr Gly Lys
            500                 505                 510

Leu Pro Val Pro Trp Pro Thr Leu Val Thr Thr Leu Gly Tyr Gly Leu
        515                 520                 525

Gln Cys Phe Ala Arg Tyr Pro Asp His Met Lys Gln His Asp Phe Phe
    530                 535                 540

Lys Ser Ala Met Pro Glu Gly Tyr Val Gln Glu Arg Thr Ile Phe Phe
545                 550                 555                 560

Lys Asp Asp Gly Asn Tyr Lys Thr Arg Ala Glu Val Lys Phe Glu Gly
                565                 570                 575

Asp Thr Leu Val Asn Arg Ile Glu Leu Lys Gly Ile Asp Phe Lys Glu
            580                 585                 590

Asp Gly Asn Ile Leu Gly His Lys Leu Glu Tyr Asn Tyr Asn Ser His
        595                 600                 605

Asn Val Tyr Ile Thr Ala Asp Lys Gln Lys Asn Gly Ile Lys Ala Asn
    610                 615                 620

Phe Lys Ile Arg His Asn Ile Glu Asp Gly Gly Val Gln Leu Ala Asp
625                 630                 635                 640

His Tyr Gln Gln Asn Thr Pro Ile Gly Asp Gly Pro Val Leu Leu Pro
                645                 650                 655

Asp Asn His Tyr Leu Ser Tyr Gln Ser Ala Leu Ser Lys Asp Pro Asn
            660                 665                 670

Glu Lys Arg Asp His Met Val Leu Leu Glu Phe Val Thr Ala Ala Gly
        675                 680                 685
```

-continued

```
Ile Thr Leu Gly Met Asp Glu Leu Tyr Lys
    690                 695


<210> SEQ ID NO 191
<211> LENGTH: 2094
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 191

atggccttac cagtgaccgc cttgctcctg ccgctggcct tgctgctcca cgccgccagg     60

ccggacgtag ttatgacaca gtctccactg tcattgccag taacaccagg tgagcccgcc    120

tccatctcat gtagatcctc ccaatctctc cttcattcaa acgggtataa ttatctcgac    180

tggtatttgc agaaaccggg ccagagccct caactgctca tctatttggg gagcaaccgg    240

gcctctggtg tccctgatag attctccggg agtggatcag gtacggattt tacactgaag    300

atcagcaggg tggaagcaga agatgttggt gtgtattact gtatgcaatc actccagacc    360

ccgtttacct ttgggcctgg aacaaaggta gatattaaag gcggaggggg atcagggggt    420

ggggggtcag gtggcggtgg aagtgaagtg caacttgttc agagcggggc agaagttaag    480

aagccaggcg cttccgtcaa ggtgagttgc aaggcaagtg gatacacctt tacgagttat    540

tatatgcact gggcacggca ggcccctggt cagggcctcg aatggatggg gattataaat    600

ccttctggcg ggtcaaccag ctacgcacaa aaatttcaag gtcgggtgac aatgacgcgc    660

gacacgtcaa cgagtacagt gtatatggaa ttgtctagcc tgaggtccga ggatactgct    720

gtctattatt gtgctcgcgt ggtcgctgct gctgtggcag actactgggg tcagggtaca    780

cttgtgacgg taagcagcga atctaaatat ggcccgccat gcccgccttg cccaatctac    840

atatgggccc ccctcgccgg tacttgcggt gttttgcttt tgtcactggt gattacgaag    900

cgcggtcgaa aaaaactcct ctacatcttc aaacaacctt tcatgcggcc tgtccaaaca    960

actcaagaag aggacgggtg ttcatgccgc tttccagagg aagaggaagg tggctgtgaa   1020

cttagggtca agtttagcag gtcagcggac gcaccagctt acaagcaagg ccaaaaccag   1080

ctttataacg aattgaattt gggacgcagg gaagaatacg atgtgctcga taaacgcaga   1140

gggagggacc cggaaatggg aggaaagcca aggcggaaaa acccacagga ggggttgtac   1200

aacgagcttc aaaaagataa gatggcggaa gcatactccg aaataggaat gaagggtgaa   1260

cggaggaggg gcaagggcca cgacggcctg taccagggac tctcaactgc tacgaaggat   1320

acttatgatg ctcttcacat gcaagctctg ccgccgcgcg gatcgagtgg caccggtatg   1380

gtgagcaagg gcgaggagct gttcaccggg gtggtgccca tcctggtcga gctggacggc   1440

gacgtaaacg gccacaagtt cagcgtgtcc ggcgagggcg agggcgatgc cacctacggc   1500

aagctgaccc tgaagctgat ctgcaccacc ggcaagctgc ccgtgccctg gcccaccctc   1560

gtgaccaccc tgggctacgg cctccagtgc ttcgcccgct accccgacca catgaagcag   1620

cacgacttct tcaagtccgc catgcccgaa ggctacgtcc aggagcgcac catcttcttc   1680

aaggacgacg gcaactacaa gacccgcgcc gaggtgaagt tcgagggcga caccctggtg   1740

aaccgcatcg agctgaaggg catcgacttc aaggaggacg gcaacatcct ggggcacaag   1800

ctggagtaca actacaacag ccacaacgtc tatatcaccg ccgacaagca gaagaacggc   1860

atcaaggcca acttcaagat ccgccacaac atcgaggacg gcggcgtgca gctcgccgac   1920

cactaccagc agaacacccc catcggcgac ggccccgtgc tgctgcccga caaccactac   1980
```

ctgagctacc agtccgccct gagcaaagac cccaacgaga agcgcgatca catggtcctg 2040
ctggagttcg tgaccgccgc cgggatcact ctcggcatgg acgagctgta caag 2094

<210> SEQ ID NO 192
<211> LENGTH: 698
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 192

Met Ala Leu Pro Val Thr Ala Leu Leu Leu Pro Leu Ala Leu Leu Leu
1 5 10 15

His Ala Ala Arg Pro Asp Val Val Met Thr Gln Ser Pro Leu Ser Leu
20 25 30

Pro Val Thr Pro Gly Glu Pro Ala Ser Ile Ser Cys Arg Ser Ser Gln
35 40 45

Ser Leu Leu His Ser Asn Gly Tyr Asn Tyr Leu Asp Trp Tyr Leu Gln
50 55 60

Lys Pro Gly Gln Ser Pro Gln Leu Leu Ile Tyr Leu Gly Ser Asn Arg
65 70 75 80

Ala Ser Gly Val Pro Asp Arg Phe Ser Gly Ser Gly Ser Gly Thr Asp
85 90 95

Phe Thr Leu Lys Ile Ser Arg Val Glu Ala Glu Asp Val Gly Val Tyr
100 105 110

Tyr Cys Met Gln Ser Leu Gln Thr Pro Phe Thr Phe Gly Pro Gly Thr
115 120 125

Lys Val Asp Ile Lys Gly Gly Gly Gly Ser Gly Gly Gly Gly Ser Gly
130 135 140

Gly Gly Gly Ser Glu Val Gln Leu Val Gln Ser Gly Ala Glu Val Lys
145 150 155 160

Lys Pro Gly Ala Ser Val Lys Val Ser Cys Lys Ala Ser Gly Tyr Thr
165 170 175

Phe Thr Ser Tyr Tyr Met His Trp Ala Arg Gln Ala Pro Gly Gln Gly
180 185 190

Leu Glu Trp Met Gly Ile Ile Asn Pro Ser Gly Gly Ser Thr Ser Tyr
195 200 205

Ala Gln Lys Phe Gln Gly Arg Val Thr Met Thr Arg Asp Thr Ser Thr
210 215 220

Ser Thr Val Tyr Met Glu Leu Ser Ser Leu Arg Ser Glu Asp Thr Ala
225 230 235 240

Val Tyr Tyr Cys Ala Arg Val Val Ala Ala Ala Val Ala Asp Tyr Trp
245 250 255

Gly Gln Gly Thr Leu Val Thr Val Ser Ser Glu Pro Lys Ser Cys Asp
260 265 270

Lys Thr His Thr Cys Pro Ile Tyr Ile Trp Ala Pro Leu Ala Gly Thr
275 280 285

Cys Gly Val Leu Leu Leu Ser Leu Val Ile Thr Lys Arg Gly Arg Lys
290 295 300

Lys Leu Leu Tyr Ile Phe Lys Gln Pro Phe Met Arg Pro Val Gln Thr
305 310 315 320

Thr Gln Glu Glu Asp Gly Cys Ser Cys Arg Phe Pro Glu Glu Glu Glu
325 330 335

```
Gly Gly Cys Glu Leu Arg Val Lys Phe Ser Arg Ser Ala Asp Ala Pro
            340                 345                 350

Ala Tyr Lys Gln Gly Gln Asn Gln Leu Tyr Asn Glu Leu Asn Leu Gly
        355                 360                 365

Arg Arg Glu Glu Tyr Asp Val Leu Asp Lys Arg Arg Gly Arg Asp Pro
    370                 375                 380

Glu Met Gly Gly Lys Pro Arg Arg Lys Asn Pro Gln Glu Gly Leu Tyr
385                 390                 395                 400

Asn Glu Leu Gln Lys Asp Lys Met Ala Glu Ala Tyr Ser Glu Ile Gly
                405                 410                 415

Met Lys Gly Glu Arg Arg Arg Gly Lys Gly His Asp Gly Leu Tyr Gln
            420                 425                 430

Gly Leu Ser Thr Ala Thr Lys Asp Thr Tyr Asp Ala Leu His Met Gln
        435                 440                 445

Ala Leu Pro Pro Arg Gly Ser Ser Gly Thr Gly Met Val Ser Lys Gly
    450                 455                 460

Glu Glu Leu Phe Thr Gly Val Val Pro Ile Leu Val Glu Leu Asp Gly
465                 470                 475                 480

Asp Val Asn Gly His Lys Phe Ser Val Ser Gly Glu Gly Glu Gly Asp
                485                 490                 495

Ala Thr Tyr Gly Lys Leu Thr Leu Lys Leu Ile Cys Thr Thr Gly Lys
            500                 505                 510

Leu Pro Val Pro Trp Pro Thr Leu Val Thr Thr Leu Gly Tyr Gly Leu
        515                 520                 525

Gln Cys Phe Ala Arg Tyr Pro Asp His Met Lys Gln His Asp Phe Phe
    530                 535                 540

Lys Ser Ala Met Pro Glu Gly Tyr Val Gln Glu Arg Thr Ile Phe Phe
545                 550                 555                 560

Lys Asp Asp Gly Asn Tyr Lys Thr Arg Ala Glu Val Lys Phe Glu Gly
                565                 570                 575

Asp Thr Leu Val Asn Arg Ile Glu Leu Lys Gly Ile Asp Phe Lys Glu
            580                 585                 590

Asp Gly Asn Ile Leu Gly His Lys Leu Glu Tyr Asn Tyr Asn Ser His
        595                 600                 605

Asn Val Tyr Ile Thr Ala Asp Lys Gln Lys Asn Gly Ile Lys Ala Asn
    610                 615                 620

Phe Lys Ile Arg His Asn Ile Glu Asp Gly Gly Val Gln Leu Ala Asp
625                 630                 635                 640

His Tyr Gln Gln Asn Thr Pro Ile Gly Asp Gly Pro Val Leu Leu Pro
                645                 650                 655

Asp Asn His Tyr Leu Ser Tyr Gln Ser Ala Leu Ser Lys Asp Pro Asn
            660                 665                 670

Glu Lys Arg Asp His Met Val Leu Leu Glu Phe Val Thr Ala Ala Gly
        675                 680                 685

Ile Thr Leu Gly Met Asp Glu Leu Tyr Lys
    690                 695
```

<210> SEQ ID NO 193
<211> LENGTH: 2094
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 193

```
atggccttac cagtgaccgc cttgctcctg ccgctggcct tgctgctcca cgccgccagg      60
ccggacgtag ttatgacaca gtctccactg tcattgccag taacaccagg tgagcccgcc     120
tccatctcat gtagatcctc ccaatctctc cttcattcaa acgggtataa ttatctcgac     180
tggtatttgc agaaaccggg ccagagccct caactgctca tctatttggg gagcaaccgg     240
gcctctggtg tccctgatag attctccggg agtggatcag gtacggattt tacactgaag     300
atcagcaggg tggaagcaga agatgttggt gtgtattact gtatgcaatc actccagacc     360
ccgtttacct ttgggcctgg aacaaaggta gatattaaag gcggaggggg atcagggggt     420
ggggggtcag gtggcggtgg aagtgaagtg caacttgttc agagcggggc agaagttaag     480
aagccaggcg cttccgtcaa ggtgagttgc aaggcaagtg gatacacctt tacgagttat     540
tatatgcact gggcacggca ggcccctggt cagggcctcg aatggatggg gattataaat     600
ccttctggcg ggtcaaccag ctacgcacaa aaatttcaag gtcgggtgac aatgacgcgc     660
gacacgtcaa cgagtacagt gtatatggaa ttgtctagcc tgaggtccga ggatactgct     720
gtctattatt gtgctcgcgt ggtcgctgct gctgtggcag actactgggg tcagggtaca     780
cttgtgacgg taagcagcga accgaagtct tgtgataaaa ctcatacgtg cccgatctac     840
atatgggccc ccctcgccgg tacttgcggt gttttgcttt tgtcactggt gattacgaag     900
cgcggtcgaa aaaaactcct ctacatcttc aaacaacctt tcatgcggcc tgtccaaaca     960
actcaagaag aggacgggtg ttcatgccgc tttccagagg aagaggaagg tggctgtgaa    1020
cttagggtca agtttagcag gtcagcggac gcaccagctt acaagcaagg ccaaaaccag    1080
ctttataacg aattgaattt gggacgcagg gaagaatacg atgtgctcga taaacgcaga    1140
gggagggacc cggaaatggg aggaaagcca aggcggaaaa acccacagga ggggttgtac    1200
aacgagcttc aaaaagataa gatggcggaa gcatactccg aaataggaat gaagggtgaa    1260
cggaggaggg gcaagggcca cgacggcctg taccagggac tctcaactgc tacgaaggat    1320
acttatgatg ctcttcacat gcaagctctg ccgccgcgcg gatcgagtgg caccggtatg    1380
gtgagcaagg gcgaggagct gttcaccggg gtggtgccca tcctggtcga gctggacggc    1440
gacgtaaacg gccacaagtt cagcgtgtcc ggcgagggcg agggcgatgc cacctacggc    1500
aagctgaccc tgaagctgat ctgcaccacc ggcaagctgc ccgtgccctg gcccaccctc    1560
gtgaccaccc tgggctacgg cctccagtgc ttcgcccgct accccgacca catgaagcag    1620
cacgacttct tcaagtccgc catgcccgaa ggctacgtcc aggagcgcac catcttcttc    1680
aaggacgacg gcaactacaa gacccgcgcc gaggtgaagt tcgagggcga caccctggtg    1740
aaccgcatcg agctgaaggg catcgacttc aaggaggacg gcaacatcct ggggcacaag    1800
ctggagtaca actacaacag ccacaacgtc tatatcaccg ccgacaagca gaagaacggc    1860
atcaaggcca acttcaagat ccgccacaac atcgaggacg gcggcgtgca gctcgccgac    1920
cactaccagc agaacacccc catcggcgac ggccccgtgc tgctgcccga caaccactac    1980
ctgagctacc agtccgccct gagcaaagac cccaacgaga agcgcgatca catggtcctg    2040
ctggagttcg tgaccgccgc cgggatcact ctcggcatgg acgagctgta caag          2094
```

<210> SEQ ID NO 194
<211> LENGTH: 1282
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 194

```
Met Ala Leu Pro Val Thr Ala Leu Leu Leu Pro Leu Ala Leu Leu Leu
1               5                   10                  15

His Ala Ala Arg Pro Ala Gly Gly Ser Asp Tyr Lys Asp Asp Asp Asp
            20                  25                  30

Lys Gly Gly Gly Gly Ser Gly Gly Gly Gly Gln Val Gln Leu Val Gln
        35                  40                  45

Ser Gly Ala Glu Val Lys Lys Pro Gly Ser Ser Val Lys Val Ser Cys
    50                  55                  60

Lys Ala Ser Gly Tyr Thr Phe Thr Asp Tyr Asn Met His Trp Val Arg
65                  70                  75                  80

Gln Ala Pro Gly Gln Gly Leu Glu Trp Ile Gly Tyr Ile Tyr Pro Tyr
                85                  90                  95

Asn Gly Gly Thr Gly Tyr Asn Gln Lys Phe Lys Ser Lys Ala Thr Ile
            100                 105                 110

Thr Ala Asp Glu Ser Thr Asn Thr Ala Tyr Met Glu Leu Ser Ser Leu
        115                 120                 125

Arg Ser Glu Asp Thr Ala Val Tyr Tyr Cys Ala Arg Gly Arg Pro Ala
    130                 135                 140

Met Asp Tyr Trp Gly Gln Gly Thr Leu Val Thr Val Ser Ser Gly Gly
145                 150                 155                 160

Gly Gly Ser Gly Gly Gly Gly Ser Gly Gly Gly Gly Ser Asp Ile Gln
                165                 170                 175

Met Thr Gln Ser Pro Ser Ser Leu Ser Ala Ser Val Gly Asp Arg Val
            180                 185                 190

Thr Ile Thr Cys Arg Ala Ser Glu Ser Val Asp Asn Tyr Gly Ile Ser
        195                 200                 205

Phe Met Asn Trp Phe Gln Gln Lys Pro Gly Lys Ala Pro Lys Leu Leu
    210                 215                 220

Ile Tyr Ala Ala Ser Asn Gln Gly Ser Gly Val Pro Ser Arg Phe Ser
225                 230                 235                 240

Gly Ser Gly Ser Gly Thr Asp Phe Thr Leu Thr Ile Ser Ser Leu Gln
                245                 250                 255

Pro Asp Asp Phe Ala Thr Tyr Tyr Cys Gln Gln Ser Lys Glu Val Pro
            260                 265                 270

Trp Thr Phe Gly Gln Gly Thr Lys Val Glu Ile Lys Ser Gly Ala Ala
        275                 280                 285

Ala Ile Glu Val Met Tyr Pro Pro Pro Tyr Leu Asp Asn Glu Lys Ser
    290                 295                 300

Asn Gly Thr Ile Ile His Val Lys Gly Lys His Leu Cys Pro Ser Pro
305                 310                 315                 320

Leu Phe Pro Gly Pro Ser Lys Pro Phe Trp Val Leu Val Val Val Gly
                325                 330                 335

Gly Val Leu Ala Cys Tyr Ser Leu Leu Val Thr Val Ala Phe Ile Ile
            340                 345                 350

Phe Trp Val Arg Ser Lys Arg Ser Arg Leu Leu His Ser Asp Tyr Met
        355                 360                 365

Asn Met Thr Pro Arg Arg Pro Gly Pro Thr Arg Lys His Tyr Gln Pro
    370                 375                 380

Tyr Ala Pro Pro Arg Asp Phe Ala Ala Tyr Arg Ser Arg Val Lys Phe
385                 390                 395                 400

Ser Arg Ser Ala Asp Ala Pro Ala Tyr Lys Gln Gly Gln Asn Gln Leu
```

```
                405                 410                 415

Tyr Asn Glu Leu Asn Leu Gly Arg Arg Glu Glu Tyr Asp Val Leu Asp
            420                 425                 430

Lys Arg Arg Gly Arg Asp Pro Glu Met Gly Gly Lys Pro Arg Arg Lys
        435                 440                 445

Asn Pro Gln Glu Gly Leu Tyr Asn Glu Leu Gln Lys Asp Lys Met Ala
    450                 455                 460

Glu Ala Tyr Ser Glu Ile Gly Met Lys Gly Glu Arg Arg Arg Gly Lys
465                 470                 475                 480

Gly His Asp Gly Leu Tyr Gln Gly Leu Ser Thr Ala Thr Lys Asp Thr
                485                 490                 495

Tyr Asp Ala Leu His Met Gln Ala Leu Pro Pro Arg Gly Ser Gly Glu
            500                 505                 510

Gly Arg Gly Ser Leu Leu Thr Cys Gly Asp Val Glu Glu Asn Pro Gly
        515                 520                 525

Pro Gly Ser Gly Gln Cys Thr Asn Tyr Ala Leu Leu Lys Leu Ala Gly
    530                 535                 540

Asp Val Glu Ser Asn Pro Gly Pro Met Ala Leu Pro Val Thr Ala Leu
545                 550                 555                 560

Leu Leu Pro Leu Ala Leu Leu Leu His Ala Ala Arg Pro Glu Val Gln
                565                 570                 575

Leu Val Gln Ser Gly Ala Glu Val Lys Lys Pro Gly Ser Ser Val Lys
            580                 585                 590

Val Ser Cys Lys Ala Ser Gly Gly Thr Phe Ser Ser Tyr Ala Ile Ser
        595                 600                 605

Trp Val Arg Gln Ala Pro Gly Gln Gly Leu Glu Trp Met Gly Gly Ile
    610                 615                 620

Ile Pro Ile Phe Gly Thr Ala Asn Tyr Ala Gln Lys Phe Gln Gly Arg
625                 630                 635                 640

Val Thr Ile Thr Ala Asp Lys Ser Thr Ser Thr Ala Tyr Met Glu Leu
                645                 650                 655

Ser Ser Leu Arg Ser Glu Asp Thr Ala Val Tyr Tyr Cys Ala Thr Phe
            660                 665                 670

Ala Leu Phe Gly Phe Arg Glu Gln Ala Phe Asp Ile Trp Gly Gln Gly
        675                 680                 685

Thr Thr Val Thr Val Ser Ser Gly Gly Gly Gly Ser Gly Gly Gly Gly
    690                 695                 700

Ser Gly Gly Gly Gly Ser Asp Ile Gln Met Thr Gln Ser Pro Ser Ser
705                 710                 715                 720

Leu Ser Ala Ser Val Gly Asp Arg Val Thr Ile Thr Cys Arg Ala Ser
                725                 730                 735

Gln Ser Ile Ser Ser Tyr Leu Asn Trp Tyr Gln Gln Lys Pro Gly Lys
            740                 745                 750

Ala Pro Lys Leu Leu Ile Tyr Ala Ala Ser Ser Leu Gln Ser Gly Val
        755                 760                 765

Pro Ser Arg Phe Ser Gly Ser Gly Ser Gly Thr Asp Phe Thr Leu Thr
    770                 775                 780

Ile Ser Ser Leu Gln Pro Glu Asp Leu Ala Thr Tyr Tyr Cys Gln Gln
785                 790                 795                 800

Ser Tyr Ser Thr Pro Phe Thr Phe Gly Pro Gly Thr Lys Val Asp Ile
                805                 810                 815

Lys Thr Thr Thr Pro Ala Pro Arg Pro Pro Thr Pro Ala Pro Thr Ile
            820                 825                 830
```

```
Ala Leu Gln Pro Leu Ser Leu Arg Pro Glu Ala Cys Arg Pro Ala Ala
        835                 840                 845

Gly Gly Ala Val His Thr Arg Gly Leu Asp Phe Ala Cys Asp Ile Tyr
    850                 855                 860

Ile Trp Ala Pro Leu Ala Gly Thr Cys Gly Val Leu Leu Leu Ser Leu
865                 870                 875                 880

Val Ile Thr Lys Arg Gly Arg Lys Lys Leu Leu Tyr Ile Phe Lys Gln
                885                 890                 895

Pro Phe Met Arg Pro Val Gln Thr Thr Gln Glu Glu Asp Gly Cys Ser
            900                 905                 910

Cys Arg Phe Pro Glu Glu Glu Glu Gly Gly Cys Glu Leu Arg Val Lys
        915                 920                 925

Phe Ser Arg Ser Ala Asp Ala Pro Ala Tyr Lys Gln Gly Gln Asn Gln
    930                 935                 940

Leu Tyr Asn Glu Leu Asn Leu Gly Arg Arg Glu Glu Tyr Asp Val Leu
945                 950                 955                 960

Asp Lys Arg Arg Gly Arg Asp Pro Glu Met Gly Gly Lys Pro Arg Arg
                965                 970                 975

Lys Asn Pro Gln Glu Gly Leu Tyr Asn Glu Leu Gln Lys Asp Lys Met
            980                 985                 990

Ala Glu Ala Tyr Ser Glu Ile Gly  Met Lys Gly Glu Arg  Arg Arg Gly
        995                 1000                1005

Lys Gly  His Asp Gly Leu Tyr  Gln Gly Leu Ser Thr  Ala Thr Lys
    1010                1015                1020

Asp Thr  Tyr Asp Ala Leu His  Met Gln Ala Leu Pro  Pro Arg Gly
    1025                1030                1035

Ser Ser  Gly Thr Gly Met Val  Ser Lys Gly Glu Glu  Leu Phe Thr
    1040                1045                1050

Gly Val  Val Pro Ile Leu Val  Glu Leu Asp Gly Asp  Val Asn Gly
    1055                1060                1065

His Lys  Phe Ser Val Ser Gly  Glu Gly Glu Gly Asp  Ala Thr Tyr
    1070                1075                1080

Gly Lys  Leu Thr Leu Lys Leu  Ile Cys Thr Thr Gly  Lys Leu Pro
    1085                1090                1095

Val Pro  Trp Pro Thr Leu Val  Thr Thr Leu Gly Tyr  Gly Leu Gln
    1100                1105                1110

Cys Phe  Ala Arg Tyr Pro Asp  His Met Lys Gln His  Asp Phe Phe
    1115                1120                1125

Lys Ser  Ala Met Pro Glu Gly  Tyr Val Gln Glu Arg  Thr Ile Phe
    1130                1135                1140

Phe Lys  Asp Asp Gly Asn Tyr  Lys Thr Arg Ala Glu  Val Lys Phe
    1145                1150                1155

Glu Gly  Asp Thr Leu Val Asn  Arg Ile Glu Leu Lys  Gly Ile Asp
    1160                1165                1170

Phe Lys  Glu Asp Gly Asn Ile  Leu Gly His Lys Leu  Glu Tyr Asn
    1175                1180                1185

Tyr Asn  Ser His Asn Val Tyr  Ile Thr Ala Asp Lys  Gln Lys Asn
    1190                1195                1200

Gly Ile  Lys Ala Asn Phe Lys  Ile Arg His Asn Ile  Glu Asp Gly
    1205                1210                1215

Gly Val  Gln Leu Ala Asp His  Tyr Gln Gln Asn Thr  Pro Ile Gly
    1220                1225                1230
```

```
Asp Gly  Pro Val Leu Leu Pro  Asp Asn His Tyr Leu  Ser Tyr Gln
    1235                 1240                 1245

Ser Ala  Leu Ser Lys Asp Pro  Asn Glu Lys Arg Asp  His Met Val
    1250                 1255                 1260

Leu Leu  Glu Phe Val Thr Ala  Ala Gly Ile Thr Leu  Gly Met Asp
    1265                 1270                 1275

Glu Leu  Tyr Lys
    1280
```

<210> SEQ ID NO 195
<211> LENGTH: 3849
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 195

```
atggctctgc ctgtgacagc tctgctgctg cctctggctc tgcttctgca tgctgctaga     60
cctgccggcg gaagcgacta caaggacgac gatgacaaag gcggcggagg atctggtggc    120
ggaggacagg ttcagctggt tcagtctggc gccgaagtga agaaacctgg cagcagcgtg    180
aaggtgtcct gcaaggccag cggctacacc tttaccgact acaacatgca ctgggtccga    240
caggcccctg gacaaggact tgagtggatc ggctacatct acccctacaa tggcggcacc    300
ggctacaacc agaagttcaa gagcaaggcc accatcaccg ccgacgagag cacaaacacc    360
gcctacatgg aactgagcag cctgagaagc gaggacaccg ccgtgtacta ctgcgctaga    420
ggcagacccg ccatggatta ttggggccag ggaaccctgg tcaccgtttc tagcggaggc    480
ggaggtagtg gtggtggcgg tagtggcgga ggtggaagcg atatccagat gacacagagc    540
cccagcagcc tgtctgccag cgtgggagat agagtgacca tcacctgtag agccagcgag    600
agcgtggaca actacggcat cagcttcatg aactggttcc agcagaagcc cggcaaggcc    660
cctaagctgc tgatctacgc cgccagcaat caaggcagcg gagtgcctag cagattttcc    720
ggctctggca gcggcaccga tttcaccctg accatcagta gcctgcagcc tgacgacttc    780
gccacctact actgccagca gagcaaagag gtgccctgga catttggaca gggcaccaag    840
gtggaaatca agagcggagc cgccgctatc gaagtgatgt accctcctcc ttacctggac    900
aacgagaagt ccaacggcac catcatccac gtgaagggca agcacctgtg tccttctcca    960
ctgttccccg gacctagcaa gcctttctgg gtgctcgttg ttgttggcgg cgtgctggcc   1020
tgttactctc tgctggttac cgtggccttc atcatctttt gggtccgaag caagcggagc   1080
agactgctgc actccgacta catgaacatg acccctagac ggcccggacc aaccagaaag   1140
cactaccagc cttacgctcc tcctagagat ttcgccgcct accggtccag agtgaagttc   1200
agcagatccg ccgatgctcc cgcctataag cagggccaga atcagctgta caacgagctg   1260
aatctggggc gcagagaaga gtacgacgtg ctggataagc ggagaggcag agatcctgag   1320
atgggcggca agcccagacg gaagaatcct caagagggcc tgtataatga gctgcagaaa   1380
gacaagatgg ccgaggccta cagcgagatc ggaatgaagg gcgaacgcag aagaggcaag   1440
ggccacgatg gactgtatca gggcctgagc accgccacaa aggacaccta tgatgccctg   1500
cacatgcagg ccctgcctcc aagaggttct ggcgagggac gcgggagtct actgacgtgt   1560
ggagacgtgg aggaaaaccc tggacctggc tctggccagt gcaccaatta tgccctgctg   1620
aaactggccg gcgacgtgga atctaaccca ggacctatgg cactgcccgt cactgcactg   1680
```

-continued

```
ctgcttccgc tcgcacttct gctgcatgcc gcaagaccag aagtgcagct cgtccagtca   1740

ggggctgaag tgaaaaagcc aggctcctcc gtgaaagtgt cttgtaaagc ctccggcggc   1800

accttcagca gctacgccat ttcttgggtt cgacaagctc caggccaggg cctcgaatgg   1860

atgggaggaa tcatccccat cttcggcacc gccaactacg cccagaaatt ccagggacgc   1920

gtgacaatca cagccgacaa gtctaccagc acagcttata tggaactgtc tagcctgcgc   1980

tccgaggata cagctgtgta ctattgtgcc acattcgccc tgttcggctt cagagagcag   2040

gccttcgata tctggggcca aggcaccaca gtgacagtgt cctctggcgg tggtggatct   2100

ggcggaggcg gttctggcgg cggtggcagt gatattcaaa tgacccagtc tccatccagc   2160

ctgagcgcct ctgttggcga cagagtgaca attacatgcc gggccagcca gagcatcagc   2220

tcctacctga attggtatca gcagaaacca ggcaaagctc ccaaactcct gatctatgct   2280

gcctccagcc tgcagagtgg cgtgccctct agattttctg gaagcggctc cggcaccgac   2340

tttacactca ccataagctc cctgcagcca gaagatctgg ccacatatta ctgtcagcag   2400

tcctacagca cccctttcac attcggccca ggcacaaaag tggacattaa gaccaccaca   2460

ccagctcctc ggcctccaac tcctgctcct acaattgctc tgcagcccct gtctctgagg   2520

cccgaagctt gtagacctgc tgctggcgga gccgtgcata caagaggact ggatttcgcc   2580

tgcgacatct acatctgggc tcctctggcc ggaacatgcg gagtgttgct gctgagcctg   2640

gtcatcacca agcggggcag aaagaagctg ctgtacatct tcaagcagcc cttcatgcgg   2700

cccgtgcaga ccacacaaga ggaagatggc tgctcctgca gattccccga ggaagaagaa   2760

ggcggctgcg agctgcgcgt gaagttttct agaagcgctg acgcccctgc ctacaaacag   2820

ggacaaaacc agctctacaa tgaactgaac ctcggcagac gcgaggaata tgatgtgctg   2880

gacaaaagac gcggcaggga ccctgaaatg ggagggaagc ctcggcggaa aaacccacaa   2940

gaaggactgt ataacgaact ccaaaaggat aagatggcag aagcctattc cgagattggc   3000

atgaagggcg agcgtcggag aggaaaagga cacgacggcc tctaccaggg cctgtctaca   3060

gccaccaagg atacttacga cgcactccat atgcaggctc tcccacctag aggctctagc   3120

ggcactggca tggtgtccaa gggcgaagaa ctgttcacag gcgtggtgcc catcctggtg   3180

gaactggacg gggatgtgaa cggccacaag tttagcgtta gcggcgaagg cgaaggggat   3240

gccacatacg gaaagctgac actgaaactg atctgcacca ccggcaagct gcctgtgcca   3300

tggcctacac tggttaccac actcggctac ggcctgcagt gcttcgccag atatcccgac   3360

catatgaagc agcacgactt cttcaagagc gccatgcctg agggctacgt gcaagagaga   3420

accatcttct tcaaagacga cggcaactac aagacccggg cagaagtgaa gtttgagggc   3480

gacaccctcg tgaaccggat cgagctgaag ggcatcgact tcaaagagga tggaaacatc   3540

ctgggccaca agctcgagta caactacaac agccacaacg tgtacattac cgccgacaag   3600

cagaagaacg gcatcaaggc caacttcaag atccggcaca acatcgagga tggcggggtg   3660

cagctggccg atcattacca gcagaatacc cctatcggcg acggccctgt tctgctgccc   3720

gataatcact acctgagcta ccagagcgcc ctgagcaagg accccaatga gaagagggac   3780

cacatggtgc tgctggaatt cgtgacagcc gccggaatca ccctcggcat ggacgaactg   3840

tacaagtga                                                           3849
```

<210> SEQ ID NO 196
<211> LENGTH: 1282
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 196

Met Ala Leu Pro Val Thr Ala Leu Leu Leu Pro Leu Ala Leu Leu Leu
1 5 10 15

His Ala Ala Arg Pro Ala Gly Gly Ser Asp Tyr Lys Asp Asp Asp Asp
20 25 30

Lys Gly Gly Gly Gly Ser Gly Gly Gly Gly Gln Val Gln Leu Val Gln
35 40 45

Ser Gly Ala Glu Val Lys Lys Pro Gly Ser Ser Val Lys Val Ser Cys
50 55 60

Lys Ala Ser Gly Tyr Thr Phe Thr Asp Tyr Asn Met His Trp Val Arg
65 70 75 80

Gln Ala Pro Gly Gln Gly Leu Glu Trp Ile Gly Tyr Ile Tyr Pro Tyr
85 90 95

Asn Gly Gly Thr Gly Tyr Asn Gln Lys Phe Lys Ser Lys Ala Thr Ile
100 105 110

Thr Ala Asp Glu Ser Thr Asn Thr Ala Tyr Met Glu Leu Ser Ser Leu
115 120 125

Arg Ser Glu Asp Thr Ala Val Tyr Tyr Cys Ala Arg Gly Arg Pro Ala
130 135 140

Met Asp Tyr Trp Gly Gln Gly Thr Leu Val Thr Val Ser Ser Gly Gly
145 150 155 160

Gly Gly Ser Gly Gly Gly Gly Ser Gly Gly Gly Gly Ser Asp Ile Gln
165 170 175

Met Thr Gln Ser Pro Ser Ser Leu Ser Ala Ser Val Gly Asp Arg Val
180 185 190

Thr Ile Thr Cys Arg Ala Ser Glu Ser Val Asp Asn Tyr Gly Ile Ser
195 200 205

Phe Met Asn Trp Phe Gln Gln Lys Pro Gly Lys Ala Pro Lys Leu Leu
210 215 220

Ile Tyr Ala Ala Ser Asn Gln Gly Ser Gly Val Pro Ser Arg Phe Ser
225 230 235 240

Gly Ser Gly Ser Gly Thr Asp Phe Thr Leu Thr Ile Ser Ser Leu Gln
245 250 255

Pro Asp Asp Phe Ala Thr Tyr Tyr Cys Gln Gln Ser Lys Glu Val Pro
260 265 270

Trp Thr Phe Gly Gln Gly Thr Lys Val Glu Ile Lys Ser Gly Ala Ala
275 280 285

Ala Ile Glu Val Met Tyr Pro Pro Pro Tyr Leu Asp Asn Glu Lys Ser
290 295 300

Asn Gly Thr Ile Ile His Val Lys Gly Lys His Leu Cys Pro Ser Pro
305 310 315 320

Leu Phe Pro Gly Pro Ser Lys Pro Phe Trp Val Leu Val Val Val Gly
325 330 335

Gly Val Leu Ala Cys Tyr Ser Leu Leu Val Thr Val Ala Phe Ile Ile
340 345 350

Phe Trp Val Arg Ser Lys Arg Ser Arg Leu Leu His Ser Asp Tyr Met
355 360 365

Asn Met Thr Pro Arg Arg Pro Gly Pro Thr Arg Lys His Tyr Gln Pro
370 375 380

Tyr Ala Pro Pro Arg Asp Phe Ala Ala Tyr Arg Ser Arg Val Lys Phe 385 390 395 400

Ser Arg Ser Ala Asp Ala Pro Ala Tyr Lys Gln Gly Gln Asn Gln Leu
405 410 415

Tyr Asn Glu Leu Asn Leu Gly Arg Arg Glu Glu Tyr Asp Val Leu Asp
420 425 430

Lys Arg Arg Gly Arg Asp Pro Glu Met Gly Gly Lys Pro Arg Arg Lys
435 440 445

Asn Pro Gln Glu Gly Leu Tyr Asn Glu Leu Gln Lys Asp Lys Met Ala
450 455 460

Glu Ala Tyr Ser Glu Ile Gly Met Lys Gly Glu Arg Arg Arg Gly Lys
465 470 475 480

Gly His Asp Gly Leu Tyr Gln Gly Leu Ser Thr Ala Thr Lys Asp Thr
485 490 495

Tyr Asp Ala Leu His Met Gln Ala Leu Pro Pro Arg Gly Ser Gly Gln
500 505 510

Cys Thr Asn Tyr Ala Leu Leu Lys Leu Ala Gly Asp Val Glu Ser Asn
515 520 525

Pro Gly Pro Gly Ser Gly Glu Gly Arg Gly Ser Leu Leu Thr Cys Gly
530 535 540

Asp Val Glu Glu Asn Pro Gly Pro Met Ala Leu Pro Val Thr Ala Leu
545 550 555 560

Leu Leu Pro Leu Ala Leu Leu Leu His Ala Ala Arg Pro Glu Val Gln
565 570 575

Leu Val Gln Ser Gly Ala Glu Val Lys Lys Pro Gly Ser Ser Val Lys
580 585 590

Val Ser Cys Lys Ala Ser Gly Gly Thr Phe Ser Ser Tyr Ala Ile Ser
595 600 605

Trp Val Arg Gln Ala Pro Gly Gln Gly Leu Glu Trp Met Gly Gly Ile
610 615 620

Ile Pro Ile Phe Gly Thr Ala Asn Tyr Ala Gln Lys Phe Gln Gly Arg
625 630 635 640

Val Thr Ile Thr Ala Asp Lys Ser Thr Ser Thr Ala Tyr Met Glu Leu
645 650 655

Ser Ser Leu Arg Ser Glu Asp Thr Ala Val Tyr Tyr Cys Ala Thr Phe
660 665 670

Ala Leu Phe Gly Phe Arg Glu Gln Ala Phe Asp Ile Trp Gly Gln Gly
675 680 685

Thr Thr Val Thr Val Ser Ser Gly Gly Gly Gly Ser Gly Gly Gly Gly
690 695 700

Ser Gly Gly Gly Gly Ser Asp Ile Gln Met Thr Gln Ser Pro Ser Ser
705 710 715 720

Leu Ser Ala Ser Val Gly Asp Arg Val Thr Ile Thr Cys Arg Ala Ser
725 730 735

Gln Ser Ile Ser Ser Tyr Leu Asn Trp Tyr Gln Gln Lys Pro Gly Lys
740 745 750

Ala Pro Lys Leu Leu Ile Tyr Ala Ala Ser Ser Leu Gln Ser Gly Val
755 760 765

Pro Ser Arg Phe Ser Gly Ser Gly Ser Gly Thr Asp Phe Thr Leu Thr
770 775 780

Ile Ser Ser Leu Gln Pro Glu Asp Leu Ala Thr Tyr Tyr Cys Gln Gln
785 790 795 800

Ser Tyr Ser Thr Pro Phe Thr Phe Gly Pro Gly Thr Lys Val Asp Ile
805 810 815

-continued

Lys Thr Thr Thr Pro Ala Pro Arg Pro Pro Thr Pro Ala Pro Thr Ile
820 825 830

Ala Leu Gln Pro Leu Ser Leu Arg Pro Glu Ala Cys Arg Pro Ala Ala
835 840 845

Gly Gly Ala Val His Thr Arg Gly Leu Asp Phe Ala Cys Asp Ile Tyr
850 855 860

Ile Trp Ala Pro Leu Ala Gly Thr Cys Gly Val Leu Leu Leu Ser Leu
865 870 875 880

Val Ile Thr Lys Arg Gly Arg Lys Lys Leu Leu Tyr Ile Phe Lys Gln
885 890 895

Pro Phe Met Arg Pro Val Gln Thr Thr Gln Glu Glu Asp Gly Cys Ser
900 905 910

Cys Arg Phe Pro Glu Glu Glu Glu Gly Gly Cys Glu Leu Arg Val Lys
915 920 925

Phe Ser Arg Ser Ala Asp Ala Pro Ala Tyr Lys Gln Gly Gln Asn Gln
930 935 940

Leu Tyr Asn Glu Leu Asn Leu Gly Arg Arg Glu Glu Tyr Asp Val Leu
945 950 955 960

Asp Lys Arg Arg Gly Arg Asp Pro Glu Met Gly Gly Lys Pro Arg Arg
965 970 975

Lys Asn Pro Gln Glu Gly Leu Tyr Asn Glu Leu Gln Lys Asp Lys Met
980 985 990

Ala Glu Ala Tyr Ser Glu Ile Gly Met Lys Gly Glu Arg Arg Arg Gly
995 1000 1005

Lys Gly His Asp Gly Leu Tyr Gln Gly Leu Ser Thr Ala Thr Lys
1010 1015 1020

Asp Thr Tyr Asp Ala Leu His Met Gln Ala Leu Pro Pro Arg Gly
1025 1030 1035

Ser Ser Gly Thr Gly Met Val Ser Lys Gly Glu Glu Leu Phe Thr
1040 1045 1050

Gly Val Val Pro Ile Leu Val Glu Leu Asp Gly Asp Val Asn Gly
1055 1060 1065

His Lys Phe Ser Val Ser Gly Glu Gly Glu Gly Asp Ala Thr Tyr
1070 1075 1080

Gly Lys Leu Thr Leu Lys Leu Ile Cys Thr Thr Gly Lys Leu Pro
1085 1090 1095

Val Pro Trp Pro Thr Leu Val Thr Thr Leu Gly Tyr Gly Leu Gln
1100 1105 1110

Cys Phe Ala Arg Tyr Pro Asp His Met Lys Gln His Asp Phe Phe
1115 1120 1125

Lys Ser Ala Met Pro Glu Gly Tyr Val Gln Glu Arg Thr Ile Phe
1130 1135 1140

Phe Lys Asp Asp Gly Asn Tyr Lys Thr Arg Ala Glu Val Lys Phe
1145 1150 1155

Glu Gly Asp Thr Leu Val Asn Arg Ile Glu Leu Lys Gly Ile Asp
1160 1165 1170

Phe Lys Glu Asp Gly Asn Ile Leu Gly His Lys Leu Glu Tyr Asn
1175 1180 1185

Tyr Asn Ser His Asn Val Tyr Ile Thr Ala Asp Lys Gln Lys Asn
1190 1195 1200

Gly Ile Lys Ala Asn Phe Lys Ile Arg His Asn Ile Glu Asp Gly
1205 1210 1215

```
Gly Val  Gln Leu Ala Asp His  Tyr Gln Gln Asn Thr  Pro Ile Gly
    1220                 1225                 1230

Asp Gly  Pro Val Leu Leu Pro  Asp Asn His Tyr Leu  Ser Tyr Gln
    1235                 1240                 1245

Ser Ala  Leu Ser Lys Asp Pro  Asn Glu Lys Arg Asp  His Met Val
    1250                 1255                 1260

Leu Leu  Glu Phe Val Thr Ala  Ala Gly Ile Thr Leu  Gly Met Asp
    1265                 1270                 1275

Glu Leu  Tyr Lys
    1280


<210> SEQ ID NO 197
<211> LENGTH: 3849
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 197

atggctctgc ctgtgacagc tctgctgctg cctctggctc tgcttctgca tgctgctaga     60

cctgccggcg gaagcgacta caaggacgac gatgacaaag gcggcggagg atctggtggc    120

ggaggacagg ttcagctggt tcagtctggc gccgaagtga agaaacctgg cagcagcgtg    180

aaggtgtcct gcaaggccag cggctacacc tttaccgact acaacatgca ctgggtccga    240

caggcccctg gacaaggact tgagtggatc ggctacatct acccctacaa tggcggcacc    300

ggctacaacc agaagttcaa gagcaaggcc accatcaccg ccgacgagag cacaaacacc    360

gcctacatgg aactgagcag cctgagaagc gaggacaccg ccgtgtacta ctgcgctaga    420

ggcagacccg ccatggatta ttggggccag ggaaccctgg tcaccgtttc tagcggaggc    480

ggaggtagtg gtggtggcgg tagtggcgga ggtggaagcg atatccagat gacacagagc    540

cccagcagcc tgtctgccag cgtgggagat agagtgacca tcacctgtag agccagcgag    600

agcgtggaca actacggcat cagcttcatg aactggttcc agcagaagcc cggcaaggcc    660

cctaagctgc tgatctacgc cgccagcaat caaggcagcg gagtgcctag cagattttcc    720

ggctctggca gcggcaccga tttcaccctg accatcagta gcctgcagcc tgacgacttc    780

gccacctact actgccagca gagcaaagag gtgccctgga catttggaca gggcaccaag    840

gtggaaatca agagcggagc cgccgctatc gaagtgatgt accctcctcc ttacctggac    900

aacgagaagt ccaacggcac catcatccac gtgaagggca agcacctgtg tccttctcca    960

ctgttccccg gacctagcaa gcctttctgg gtgctcgttg ttgttggcgg cgtgctggcc   1020

tgttactctc tgctggttac cgtggccttc atcatctttt gggtccgaag caagcggagc   1080

agactgctgc actccgacta catgaacatg acccctagac ggcccggacc aaccagaaag   1140

cactaccagc cttacgctcc tcctagagat ttcgccgcct accggtccag agtgaagttc   1200

agcagatccg ccgatgctcc cgcctataag cagggccaga atcagctgta caacgagctg   1260

aatctggggc gcagagaaga gtacgacgtg ctggataagc ggagaggcag agatcctgag   1320

atgggcggca agcccagacg gaagaatcct caagagggcc tgtataatga gctgcagaaa   1380

gacaagatgg ccgaggccta cagcgagatc ggaatgaagg gcgaacgcag aagaggcaag   1440

ggccacgatg gactgtatca gggcctgagc accgccacaa aggacaccta tgatgccctg   1500

cacatgcagg cccttccacc tagaggtagc ggccagtgta ccaactacgc cctgctgaaa   1560

ctggccggcg acgtggaatc taatcctgga cctggatctg gcgagggacg cgggagtcta   1620
```

```
ctgacgtgtg gagacgtgga ggaaaaccct ggacctatgg cactgccagt cactgccctg   1680
ctgcttccac ttgcactgtt gctgcacgcc gctagaccag aagtgcagct cgttcaaagc   1740
ggagctgaag tgaaaaagcc cggctcctcc gtgaaagtgt cttgtaaagc ctccggcggc   1800
accttcagca gctacgccat ttcttgggtt cgacaagctc caggccaggg cctcgaatgg   1860
atgggaggaa tcatccccat cttcggcacc gccaattacg cccagaaatt ccagggacgc   1920
gtgacaatca cagccgacaa gtctaccagc acagcttata tggaactgtc tagcctgcgc   1980
tccgaggata cagctgtgta ctattgtgcc acattcgccc tgttcggctt cagagagcag   2040
gccttcgata tctggggcca aggcaccaca gtgacagtgt cctctggcgg tggtggttca   2100
ggtggcggtg gctctggcgg aggcggttct gatattcaga tgacccagtc tccatccagc   2160
ctgagcgcct ctgttggcga cagagtgaca attacatgcc gggccagcca gagcatcagc   2220
tcctacctga attggtatca gcagaaacca ggcaaagctc ccaaactcct gatctatgct   2280
gcctccagcc tgcagagtgg cgtgccctct agattttctg gaagcggctc cggcaccgac   2340
tttacactca ccataagctc cctgcagcca gaagatctgg ccacatatta ctgtcagcag   2400
tcctacagca ccccttttcac attcggccca ggcacaaaag tggacattaa gaccaccaca   2460
ccagctcctc ggcctccaac tcctgctcct acaattgctc tgcagcccct gtctctgagg   2520
cccgaagctt gtagacctgc tgctggcgga gccgtgcata caagaggact ggatttcgcc   2580
tgcgacatct acatctgggc tcctctggcc ggaacatgcg gagtgttgct gctgagcctg   2640
gtcatcacca agcggggcag aaagaagctg ctgtacatct tcaagcagcc cttcatgcgg   2700
cccgtgcaga ccacacaaga ggaagatggc tgctcctgca gattccccga ggaagaagaa   2760
ggcggctgcg aactgcgcgt gaagttctct agaagcgctg acgcccctgc ctacaaacag   2820
ggacaaaacc agctctacaa tgaactgaac ctcggcagac gcgaggaata tgatgtgctg   2880
gacaaaagac gcggcaggga ccctgaaatg ggagggaagc ctcggcggaa aaacccacaa   2940
gaaggactgt ataacgaact ccaaaaggat aagatggcag aagcctattc cgagattggc   3000
atgaagggcg agcgtcggag aggaaaagga cacgacggcc tctaccaggg cctgtctaca   3060
gccaccaagg atacttacga cgcactccat atgcaggctc tgccaccacg aggcagctct   3120
ggaactggca tggtgtccaa gggcgaagaa ctgttcacag gcgtggtgcc catcctggtt   3180
gaactggatg gcgacgtgaa cggccacaag tttagcgtta gcggagaagg cgaaggcgac   3240
gccacatacg gaaagctgac actgaaactg atctgcacca ccggcaagct gcctgtgcca   3300
tggcctacac tggttaccac actcggctac ggcctgcagt gcttcgccag atatcccgac   3360
catatgaagc agcacgactt cttcaagagc gccatgcctg agggctacgt gcaagagaga   3420
accatcttct tcaaagacga cggcaactac aagacccggg cagaagtgaa gtttgagggc   3480
gacaccctcg tgaaccggat cgagctgaag ggcatcgact tcaaagagga tggaaacatc   3540
ctgggccaca agctcgagta caactacaac agccacaacg tgtacattac cgccgacaag   3600
cagaagaacg gcatcaaggc caacttcaag atccggcaca acatcgagga tggcggggtg   3660
cagctggccg atcattacca gcagaatacc cctatcggcg acggccctgt tctgctgccc   3720
gataatcact acctgagcta ccagagcgcc ctgagcaagg accccaatga gaagagggac   3780
cacatggtgc tgctggaatt cgtgacagcc gccggaatca ccctcggcat ggacgagctg   3840
tataagtga                                                           3849
```

<210> SEQ ID NO 198

<211> LENGTH: 1263
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 198

Met Ala Leu Pro Val Thr Ala Leu Leu Leu Pro Leu Ala Leu Leu Leu
1 5 10 15

His Ala Ala Arg Pro Ala Gly Gly Ser Asp Tyr Lys Asp Asp Asp Asp
20 25 30

Lys Gly Gly Gly Gly Ser Gly Gly Gly Gly Gln Val Gln Leu Val Gln
35 40 45

Ser Gly Ala Glu Val Lys Lys Pro Gly Ser Ser Val Lys Val Ser Cys
50 55 60

Lys Ala Ser Gly Tyr Thr Phe Thr Asp Tyr Asn Met His Trp Val Arg
65 70 75 80

Gln Ala Pro Gly Gln Gly Leu Glu Trp Ile Gly Tyr Ile Tyr Pro Tyr
85 90 95

Asn Gly Gly Thr Gly Tyr Asn Gln Lys Phe Lys Ser Lys Ala Thr Ile
100 105 110

Thr Ala Asp Glu Ser Thr Asn Thr Ala Tyr Met Glu Leu Ser Ser Leu
115 120 125

Arg Ser Glu Asp Thr Ala Val Tyr Tyr Cys Ala Arg Gly Arg Pro Ala
130 135 140

Met Asp Tyr Trp Gly Gln Gly Thr Leu Val Thr Val Ser Ser Gly Gly
145 150 155 160

Gly Gly Ser Gly Gly Gly Gly Ser Gly Gly Gly Gly Ser Asp Ile Gln
165 170 175

Met Thr Gln Ser Pro Ser Ser Leu Ser Ala Ser Val Gly Asp Arg Val
180 185 190

Thr Ile Thr Cys Arg Ala Ser Glu Ser Val Asp Asn Tyr Gly Ile Ser
195 200 205

Phe Met Asn Trp Phe Gln Gln Lys Pro Gly Lys Ala Pro Lys Leu Leu
210 215 220

Ile Tyr Ala Ala Ser Asn Gln Gly Ser Gly Val Pro Ser Arg Phe Ser
225 230 235 240

Gly Ser Gly Ser Gly Thr Asp Phe Thr Leu Thr Ile Ser Ser Leu Gln
245 250 255

Pro Asp Asp Phe Ala Thr Tyr Tyr Cys Gln Gln Ser Lys Glu Val Pro
260 265 270

Trp Thr Phe Gly Gln Gly Thr Lys Val Glu Ile Lys Ser Gly Ala Ala
275 280 285

Ala Ile Glu Val Met Tyr Pro Pro Pro Tyr Leu Asp Asn Glu Lys Ser
290 295 300

Asn Gly Thr Ile Ile His Val Lys Gly Lys His Leu Cys Pro Ser Pro
305 310 315 320

Leu Phe Pro Gly Pro Ser Lys Pro Phe Trp Val Leu Val Val Val Gly
325 330 335

Gly Val Leu Ala Cys Tyr Ser Leu Leu Val Thr Val Ala Phe Ile Ile
340 345 350

Phe Trp Val Arg Ser Lys Arg Ser Arg Leu Leu His Ser Asp Tyr Met
355 360 365

Asn Met Thr Pro Arg Arg Pro Gly Pro Thr Arg Lys His Tyr Gln Pro

-continued 370 375 380

Tyr Ala Pro Pro Arg Asp Phe Ala Ala Tyr Arg Ser Arg Val Lys Phe
385 390 395 400

Ser Arg Ser Ala Asp Ala Pro Ala Tyr Lys Gln Gly Gln Asn Gln Leu
405 410 415

Tyr Asn Glu Leu Asn Leu Gly Arg Arg Glu Glu Tyr Asp Val Leu Asp
420 425 430

Lys Arg Arg Gly Arg Asp Pro Glu Met Gly Gly Lys Pro Arg Arg Lys
435 440 445

Asn Pro Gln Glu Gly Leu Tyr Asn Glu Leu Gln Lys Asp Lys Met Ala
450 455 460

Glu Ala Tyr Ser Glu Ile Gly Met Lys Gly Glu Arg Arg Arg Gly Lys
465 470 475 480

Gly His Asp Gly Leu Tyr Gln Gly Leu Ser Thr Ala Thr Lys Asp Thr
485 490 495

Tyr Asp Ala Leu His Met Gln Ala Leu Pro Pro Arg Arg Arg Lys Arg
500 505 510

Gly Ser Gly Glu Gly Arg Gly Ser Leu Leu Thr Cys Gly Asp Val Glu
515 520 525

Glu Asn Pro Gly Pro Met Ala Leu Pro Val Thr Ala Leu Leu Leu Pro
530 535 540

Leu Ala Leu Leu Leu His Ala Ala Arg Pro Glu Val Gln Leu Val Gln
545 550 555 560

Ser Gly Ala Glu Val Lys Lys Pro Gly Ser Ser Val Lys Val Ser Cys
565 570 575

Lys Ala Ser Gly Gly Thr Phe Ser Ser Tyr Ala Ile Ser Trp Val Arg
580 585 590

Gln Ala Pro Gly Gln Gly Leu Glu Trp Met Gly Gly Ile Ile Pro Ile
595 600 605

Phe Gly Thr Ala Asn Tyr Ala Gln Lys Phe Gln Gly Arg Val Thr Ile
610 615 620

Thr Ala Asp Lys Ser Thr Ser Thr Ala Tyr Met Glu Leu Ser Ser Leu
625 630 635 640

Arg Ser Glu Asp Thr Ala Val Tyr Tyr Cys Ala Thr Phe Ala Leu Phe
645 650 655

Gly Phe Arg Glu Gln Ala Phe Asp Ile Trp Gly Gln Gly Thr Thr Val
660 665 670

Thr Val Ser Ser Gly Gly Gly Gly Ser Gly Gly Gly Gly Ser Gly Gly
675 680 685

Gly Gly Ser Asp Ile Gln Met Thr Gln Ser Pro Ser Ser Leu Ser Ala
690 695 700

Ser Val Gly Asp Arg Val Thr Ile Thr Cys Arg Ala Ser Gln Ser Ile
705 710 715 720

Ser Ser Tyr Leu Asn Trp Tyr Gln Gln Lys Pro Gly Lys Ala Pro Lys
725 730 735

Leu Leu Ile Tyr Ala Ala Ser Ser Leu Gln Ser Gly Val Pro Ser Arg
740 745 750

Phe Ser Gly Ser Gly Ser Gly Thr Asp Phe Thr Leu Thr Ile Ser Ser
755 760 765

Leu Gln Pro Glu Asp Leu Ala Thr Tyr Tyr Cys Gln Gln Ser Tyr Ser
770 775 780

Thr Pro Phe Thr Phe Gly Pro Gly Thr Lys Val Asp Ile Lys Thr Thr
785 790 795 800

-continued

```
Thr Pro Ala Pro Arg Pro Pro Thr Pro Ala Pro Thr Ile Ala Leu Gln
                805                 810                 815

Pro Leu Ser Leu Arg Pro Glu Ala Cys Arg Pro Ala Ala Gly Gly Ala
            820                 825                 830

Val His Thr Arg Gly Leu Asp Phe Ala Cys Asp Ile Tyr Ile Trp Ala
        835                 840                 845

Pro Leu Ala Gly Thr Cys Gly Val Leu Leu Leu Ser Leu Val Ile Thr
    850                 855                 860

Lys Arg Gly Arg Lys Lys Leu Leu Tyr Ile Phe Lys Gln Pro Phe Met
865                 870                 875                 880

Arg Pro Val Gln Thr Thr Gln Glu Glu Asp Gly Cys Ser Cys Arg Phe
                885                 890                 895

Pro Glu Glu Glu Glu Gly Gly Cys Glu Leu Arg Val Lys Phe Ser Arg
            900                 905                 910

Ser Ala Asp Ala Pro Ala Tyr Lys Gln Gly Gln Asn Gln Leu Tyr Asn
        915                 920                 925

Glu Leu Asn Leu Gly Arg Arg Glu Glu Tyr Asp Val Leu Asp Lys Arg
    930                 935                 940

Arg Gly Arg Asp Pro Glu Met Gly Gly Lys Pro Arg Arg Lys Asn Pro
945                 950                 955                 960

Gln Glu Gly Leu Tyr Asn Glu Leu Gln Lys Asp Lys Met Ala Glu Ala
                965                 970                 975

Tyr Ser Glu Ile Gly Met Lys Gly Glu Arg Arg Arg Gly Lys Gly His
            980                 985                 990

Asp Gly Leu Tyr Gln Gly Leu Ser  Thr Ala Thr Lys Asp  Thr Tyr Asp
        995                 1000                1005

Ala Leu  His Met Gln Ala Leu  Pro Pro Arg Gly Ser  Ser Gly Thr
    1010                1015                1020

Gly Met  Val Ser Lys Gly Glu  Glu Leu Phe Thr Gly  Val Val Pro
    1025                1030                1035

Ile Leu  Val Glu Leu Asp Gly  Asp Val Asn Gly His  Lys Phe Ser
    1040                1045                1050

Val Ser  Gly Glu Gly Glu Gly  Asp Ala Thr Tyr Gly  Lys Leu Thr
    1055                1060                1065

Leu Lys  Leu Ile Cys Thr Thr  Gly Lys Leu Pro Val  Pro Trp Pro
    1070                1075                1080

Thr Leu  Val Thr Thr Leu Gly  Tyr Gly Leu Gln Cys  Phe Ala Arg
    1085                1090                1095

Tyr Pro  Asp His Met Lys Gln  His Asp Phe Phe Lys  Ser Ala Met
    1100                1105                1110

Pro Glu  Gly Tyr Val Gln Glu  Arg Thr Ile Phe Phe  Lys Asp Asp
    1115                1120                1125

Gly Asn  Tyr Lys Thr Arg Ala  Glu Val Lys Phe Glu  Gly Asp Thr
    1130                1135                1140

Leu Val  Asn Arg Ile Glu Leu  Lys Gly Ile Asp Phe  Lys Glu Asp
    1145                1150                1155

Gly Asn  Ile Leu Gly His Lys  Leu Glu Tyr Asn Tyr  Asn Ser His
    1160                1165                1170

Asn Val  Tyr Ile Thr Ala Asp  Lys Gln Lys Asn Gly  Ile Lys Ala
    1175                1180                1185

Asn Phe  Lys Ile Arg His Asn  Ile Glu Asp Gly Gly  Val Gln Leu
    1190                1195                1200
```

Ala Asp His Tyr Gln Gln Asn Thr Pro Ile Gly Asp Gly Pro Val
    1205                1210                1215

Leu Leu Pro Asp Asn His Tyr Leu Ser Tyr Gln Ser Ala Leu Ser
    1220                1225                1230

Lys Asp Pro Asn Glu Lys Arg Asp His Met Val Leu Leu Glu Phe
    1235                1240                1245

Val Thr Ala Ala Gly Ile Thr Leu Gly Met Asp Glu Leu Tyr Lys
    1250                1255                1260

<210> SEQ ID NO 199
<211> LENGTH: 3792
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 199
atggccttac cagtgaccgc cttgctcctg ccgctggcct tgctgctcca cgccgccagg 60
ccggctggcg ggtccgatta caaggacgat gacgacaaag gtggcggagg aagcggggga 120
ggcggccagg ttcagctggt tcagtctggc gccgaagtga agaaacctgg cagcagcgtg 180
aaggtgtcct gcaaggccag cggctacacc tttaccgact acaacatgca ctgggtccga 240
caggcccctg gacaaggact tgagtggatc ggctacatct acccctacaa tggcggcacc 300
ggctacaacc agaagttcaa gagcaaggcc accatcaccg ccgacgagag cacaaacacc 360
gcctacatgg aactgagcag cctgagaagc gaggacaccg ccgtgtacta ctgtgccaga 420
ggcagacccg ccatggatta ttggggacag ggcaccctgg tcaccgtttc tagcggaggc 480
ggaggatctg gtggcggagg aagtggcgga ggcggttctg atatccagat gacacagagc 540
cccagcagcc tgtctgccag cgtgggagat agagtgacca tcacctgtag agccagcgag 600
agcgtggaca actacggcat cagcttcatg aactggttcc agcagaagcc cggcaaggcc 660
cctaagctgc tgatctacgc cgccagcaat caaggcagcg gagtgcctag cagattttcc 720
ggctctggca gcggcaccga tttcaccctg acaatctcta gcctccagcc tgacgacttc 780
gccacctact actgccagca gagcaaagag gtgccctgga cattcggcca gggcacaaag 840
gtggaaatca agagcggagc agcagctatc gaggtgatgt atcctccgcc ctacctggat 900
aatgaaaaga gtaatgggac tatcattcat gtaaaaggga agcatctttg tccttctccc 960
cttttccccg gtccgtctaa acctttctgg gtgcttgtgg tcgtgggtgg agtgcttgcg 1020
tgttactccc tgctggtgac cgtcgccttc atcattttct gggtcaggag caaacgatct 1080
cgcctcctcc attctgacta tatgaacatg actcctcgca gacccggacc tacgcggaaa 1140
cattaccaac cgtacgcgcc tccgagagac ttcgccgcgt acagaagtag ggtcaagttt 1200
agcaggtcag cggacgcacc agcttacaag caaggccaaa accagcttta taacgaattg 1260
aatttgggac gcagggaaga atacgatgtg ctcgataaac gcagagggag ggacccggaa 1320
atgggaggaa agccaaggcg gaaaaaccca caggaggggt tgtacaacga gcttcaaaaa 1380
gataagatgg cggaagcata ctccgaaata ggaatgaagg gtgaacggag gaggggcaag 1440
ggccacgacg gcctgtacca gggactctca actgctacga aggatactta tgatgctctt 1500
cacatgcaag ctctgccgcc gcgccgcagg aaaagaggaa gcggcgaagg tcgaggctct 1560
ttgctcacat gcggcgatgt ggaagaaaat ccgggcccaa tggcgctccc ggtgacagca 1620
cttctcttgc ctcttgccct gctgttgcat gccgcgcgcc cagaggttca actggtacaa 1680
agcggagccg aggtaaagaa accagggagt agcgtcaaag tgtcctgcaa agcctcaggc 1740
ggcacattca gtagctatgc tatttcatgg gtacgccaag caccaggaca ggggctggag 1800
tggatgggcg ggattatccc catcttcggt acggcaaact atgcacaaaa gttccaggga 1860
cgagtcacca tcacggctga taagtccacc tccaccgcct atatggagct gagttccctt 1920
cggagcgagg atactgctgt gtattattgt gccacgttcg cactgttcgg ttttcgggag 1980
caggcgtttg atatttgggg acaaggcaca acggtcacgg tcagttcagg cggagggga 2040 tcaggggtg gggggtcagg tggcggtgga agtgacattc agatgaccca gagtccctct 2100
tcattgagtg cgagcgtcgg tgatcgggtt acgataacct gtagggcctc ccaaagtata 2160
tcatcatatt tgaactggta ccaacagaaa cctgggaaag cgccgaagct ccttatctat 2220
gctgccagct ctttgcaaag cggtgtgccc tcacggttct ccggtagtgg gtccgggacc 2280
gacttcactt tgaccatcag cagccttcag ccagaggatc ttgccactta ttactgccag 2340
caatcttata gcacaccgtt tacattcggt ccaggcacaa aggtagacat taagaccacg 2400
acgccggcgc cccggcctcc caccccgca ccaacgatag cccttcagcc cttgagcctc 2460
cggccagaag catgccgccc ggcagccgga ggtgcagtcc atacgcgcgg actggacttt 2520
gcatgtgaca tctacatatg ggccccctc gccggtactt gcggtgtttt gcttttgtca 2580
ctggtgatta cgaagcgcgg tcgaaaaaaa ctcctctaca tcttcaaaca acctttcatg 2640
cggcctgtcc aaacaactca agaagaggac gggtgttcat gccgctttcc agaggaagag 2700
gaaggtggct gtgaacttag ggtcaagttt agcaggtcag cggacgcacc agcttacaag 2760
caaggccaaa accagcttta taacgaattg aatttgggac gcagggaaga atacgatgtg 2820
ctcgataaac gcagagggag ggacccggaa atgggaggaa agccaaggcg gaaaaaccca 2880
caggaggggt tgtacaacga gcttcaaaaa gataagatgg cggaagcata ctccgaaata 2940
ggaatgaagg gtgaacggag gaggggcaag ggccacgacg gcctgtacca gggactctca 3000
actgctacga aggatactta tgatgctctt cacatgcaag ctctgccgcc gcgcggatcg 3060
agtggcaccg gtatggtgag caagggcgag gagctgttca ccggggtggt gcccatcctg 3120
gtcgagctgg acggcgacgt aaacggccac aagttcagcg tgtccggcga gggcgagggc 3180
gatgccacct acggcaagct gaccctgaag ctgatctgca ccaccggcaa gctgcccgtg 3240
ccctggccca ccctcgtgac caccctgggc tacggcctcc agtgcttcgc ccgctacccc 3300
gaccacatga agcagcacga cttcttcaag tccgccatgc ccgaaggcta cgtccaggag 3360
cgcaccatct tcttcaagga cgacggcaac tacaagaccc gcgccgaggt gaagttcgag 3420
ggcgacaccc tggtgaaccg catcgagctg aagggcatcg acttcaagga ggacggcaac 3480
atcctggggc acaagctgga gtacaactac aacagccaca acgtctatat caccgccgac 3540
aagcagaaga acggcatcaa ggccaacttc aagatccgcc acaacatcga ggacggcggc 3600
gtgcagctcg ccgaccacta ccagcagaac acccccatcg gcgacggccc cgtgctgctg 3660
cccgacaacc actacctgag ctaccagtcc gccctgagca aagaccccaa cgagaagcgc 3720
gatcacatgg tcctgctgga gttcgtgacc gccgccggga tcactctcgg catggacgag 3780
ctgtacaagt aa 3792

<210> SEQ ID NO 200
<211> LENGTH: 1263
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 200

Met Ala Leu Pro Val Thr Ala Leu Leu Leu Pro Leu Ala Leu Leu Leu
1 5 10 15

His Ala Ala Arg Pro Ala Gly Gly Ser Asp Tyr Lys Asp Asp Asp Asp
20 25 30

Lys Gly Gly Gly Gly Ser Gly Gly Gly Gly Gln Val Gln Leu Val Gln
35 40 45

Ser Gly Ala Glu Val Lys Lys Pro Gly Ser Ser Val Lys Val Ser Cys
50 55 60

Lys Ala Ser Gly Tyr Thr Phe Thr Asp Tyr Asn Met His Trp Val Arg
65 70 75 80

Gln Ala Pro Gly Gln Gly Leu Glu Trp Ile Gly Tyr Ile Tyr Pro Tyr
85 90 95

Asn Gly Gly Thr Gly Tyr Asn Gln Lys Phe Lys Ser Lys Ala Thr Ile
100 105 110

Thr Ala Asp Glu Ser Thr Asn Thr Ala Tyr Met Glu Leu Ser Ser Leu
115 120 125

Arg Ser Glu Asp Thr Ala Val Tyr Tyr Cys Ala Arg Gly Arg Pro Ala
130 135 140

Met Asp Tyr Trp Gly Gln Gly Thr Leu Val Thr Val Ser Ser Gly Gly
145 150 155 160

Gly Gly Ser Gly Gly Gly Gly Ser Gly Gly Gly Gly Ser Asp Ile Gln
165 170 175

Met Thr Gln Ser Pro Ser Ser Leu Ser Ala Ser Val Gly Asp Arg Val
180 185 190

Thr Ile Thr Cys Arg Ala Ser Glu Ser Val Asp Asn Tyr Gly Ile Ser
195 200 205

Phe Met Asn Trp Phe Gln Gln Lys Pro Gly Lys Ala Pro Lys Leu Leu
210 215 220

Ile Tyr Ala Ala Ser Asn Gln Gly Ser Gly Val Pro Ser Arg Phe Ser
225 230 235 240

Gly Ser Gly Ser Gly Thr Asp Phe Thr Leu Thr Ile Ser Ser Leu Gln
245 250 255

Pro Asp Asp Phe Ala Thr Tyr Tyr Cys Gln Gln Ser Lys Glu Val Pro
260 265 270

Trp Thr Phe Gly Gln Gly Thr Lys Val Glu Ile Lys Ser Gly Ala Ala
275 280 285

Ala Ile Glu Val Met Tyr Pro Pro Pro Tyr Leu Asp Asn Glu Lys Ser
290 295 300

Asn Gly Thr Ile Ile His Val Lys Gly Lys His Leu Cys Pro Ser Pro
305 310 315 320

Leu Phe Pro Gly Pro Ser Lys Pro Phe Trp Val Leu Val Val Val Gly
325 330 335

Gly Val Leu Ala Cys Tyr Ser Leu Leu Val Thr Val Ala Phe Ile Ile
340 345 350

Phe Trp Val Arg Ser Lys Arg Ser Arg Leu Leu His Ser Asp Tyr Met
355 360 365

Asn Met Thr Pro Arg Arg Pro Gly Pro Thr Arg Lys His Tyr Gln Pro
370 375 380

Tyr Ala Pro Pro Arg Asp Phe Ala Ala Tyr Arg Ser Arg Val Lys Phe
385 390 395 400

-continued

Ser Arg Ser Ala Asp Ala Pro Ala Tyr Lys Gln Gly Gln Asn Gln Leu
405 410 415

Tyr Asn Glu Leu Asn Leu Gly Arg Arg Glu Glu Tyr Asp Val Leu Asp
420 425 430

Lys Arg Arg Gly Arg Asp Pro Glu Met Gly Gly Lys Pro Arg Arg Lys
435 440 445

Asn Pro Gln Glu Gly Leu Tyr Asn Glu Leu Gln Lys Asp Lys Met Ala
450 455 460

Glu Ala Tyr Ser Glu Ile Gly Met Lys Gly Glu Arg Arg Arg Gly Lys
465 470 475 480

Gly His Asp Gly Leu Tyr Gln Gly Leu Ser Thr Ala Thr Lys Asp Thr
485 490 495

Tyr Asp Ala Leu His Met Gln Ala Leu Pro Pro Arg Arg Arg Lys Arg
500 505 510

Gly Ser Gly Glu Gly Arg Gly Ser Leu Leu Thr Cys Gly Asp Val Glu
515 520 525

Glu Asn Pro Gly Pro Met Ala Leu Pro Val Thr Ala Leu Leu Leu Pro
530 535 540

Leu Ala Leu Leu Leu His Ala Ala Arg Pro Glu Val Gln Leu Val Gln
545 550 555 560

Ser Gly Ala Glu Val Lys Lys Pro Gly Ser Ser Val Lys Val Ser Cys
565 570 575

Lys Ala Ser Gly Gly Thr Phe Ser Ser Tyr Ala Ile Ser Trp Val Arg
580 585 590

Gln Ala Pro Gly Gln Gly Leu Glu Trp Met Gly Gly Ile Ile Pro Ile
595 600 605

Phe Gly Thr Ala Asn Tyr Ala Gln Lys Phe Gln Gly Arg Val Thr Ile
610 615 620

Thr Ala Asp Lys Ser Thr Ser Thr Ala Tyr Met Glu Leu Ser Ser Leu
625 630 635 640

Arg Ser Glu Asp Thr Ala Val Tyr Tyr Cys Ala Thr Phe Ala Leu Phe
645 650 655

Gly Phe Arg Glu Gln Ala Phe Asp Ile Trp Gly Gln Gly Thr Thr Val
660 665 670

Thr Val Ser Ser Gly Gly Gly Gly Ser Gly Gly Gly Gly Ser Gly Gly
675 680 685

Gly Gly Ser Asp Ile Gln Met Thr Gln Ser Pro Ser Ser Leu Ser Ala
690 695 700

Ser Val Gly Asp Arg Val Thr Ile Thr Cys Arg Ala Ser Gln Ser Ile
705 710 715 720

Ser Ser Tyr Leu Asn Trp Tyr Gln Gln Lys Pro Gly Lys Ala Pro Lys
725 730 735

Leu Leu Ile Tyr Ala Ala Ser Ser Leu Gln Ser Gly Val Pro Ser Arg
740 745 750

Phe Ser Gly Ser Gly Ser Gly Thr Asp Phe Thr Leu Thr Ile Ser Ser
755 760 765

Leu Gln Pro Glu Asp Leu Ala Thr Tyr Tyr Cys Gln Gln Ser Tyr Ser
770 775 780

Thr Pro Phe Thr Phe Gly Pro Gly Thr Lys Val Asp Ile Lys Thr Thr
785 790 795 800

Thr Pro Ala Pro Arg Pro Pro Thr Pro Ala Pro Thr Ile Ala Leu Gln
805 810 815

Pro Leu Ser Leu Arg Pro Glu Ala Cys Arg Pro Ala Ala Gly Gly Ala

```
            820                 825                 830

Val His Thr Arg Gly Leu Asp Phe Ala Cys Asp Ile Tyr Ile Trp Ala
        835                 840                 845

Pro Leu Ala Gly Thr Cys Gly Val Leu Leu Leu Ser Leu Val Ile Thr
    850                 855                 860

Lys Arg Gly Arg Lys Lys Leu Leu Tyr Ile Phe Lys Gln Pro Phe Met
865                 870                 875                 880

Arg Pro Val Gln Thr Thr Gln Glu Glu Asp Gly Cys Ser Cys Arg Phe
                885                 890                 895

Pro Glu Glu Glu Glu Gly Gly Cys Glu Leu Arg Val Lys Phe Ser Arg
            900                 905                 910

Ser Ala Asp Ala Pro Ala Tyr Lys Gln Gly Gln Asn Gln Leu Tyr Asn
        915                 920                 925

Glu Leu Asn Leu Gly Arg Arg Glu Glu Tyr Asp Val Leu Asp Lys Arg
    930                 935                 940

Arg Gly Arg Asp Pro Glu Met Gly Gly Lys Pro Arg Arg Lys Asn Pro
945                 950                 955                 960

Gln Glu Gly Leu Tyr Asn Glu Leu Gln Lys Asp Lys Met Ala Glu Ala
                965                 970                 975

Tyr Ser Glu Ile Gly Met Lys Gly Glu Arg Arg Arg Gly Lys Gly His
            980                 985                 990

Asp Gly Leu Tyr Gln Gly Leu Ser  Thr Ala Thr Lys Asp  Thr Tyr Asp
        995                 1000                1005

Ala Leu  His Met Gln Ala Leu  Pro Pro Arg Gly Ser  Ser Gly Thr
    1010                 1015                 1020

Gly Met  Val Ser Lys Gly Glu  Glu Leu Phe Thr Gly  Val Val Pro
    1025                 1030                 1035

Ile Leu  Val Glu Leu Asp Gly  Asp Val Asn Gly His  Lys Phe Ser
    1040                 1045                 1050

Val Ser  Gly Glu Gly Glu Gly  Asp Ala Thr Tyr Gly  Lys Leu Thr
    1055                 1060                 1065

Leu Lys  Leu Ile Cys Thr Thr  Gly Lys Leu Pro Val  Pro Trp Pro
    1070                 1075                 1080

Thr Leu  Val Thr Thr Leu Gly  Tyr Gly Leu Gln Cys  Phe Ala Arg
    1085                 1090                 1095

Tyr Pro  Asp His Met Lys Gln  His Asp Phe Phe Lys  Ser Ala Met
    1100                 1105                 1110

Pro Glu  Gly Tyr Val Gln Glu  Arg Thr Ile Phe Phe  Lys Asp Asp
    1115                 1120                 1125

Gly Asn  Tyr Lys Thr Arg Ala  Glu Val Lys Phe Glu  Gly Asp Thr
    1130                 1135                 1140

Leu Val  Asn Arg Ile Glu Leu  Lys Gly Ile Asp Phe  Lys Glu Asp
    1145                 1150                 1155

Gly Asn  Ile Leu Gly His Lys  Leu Glu Tyr Asn Tyr  Asn Ser His
    1160                 1165                 1170

Asn Val  Tyr Ile Thr Ala Asp  Lys Gln Lys Asn Gly  Ile Lys Ala
    1175                 1180                 1185

Asn Phe  Lys Ile Arg His Asn  Ile Glu Asp Gly Gly  Val Gln Leu
    1190                 1195                 1200

Ala Asp  His Tyr Gln Gln Asn  Thr Pro Ile Gly Asp  Gly Pro Val
    1205                 1210                 1215

Leu Leu  Pro Asp Asn His Tyr  Leu Ser Tyr Gln Ser  Ala Leu Ser
    1220                 1225                 1230
```

```
Lys Asp  Pro Asn Glu Lys Arg  Asp His Met Val Leu  Leu Glu Phe
    1235                1240                1245

Val Thr  Ala Ala Gly Ile Thr  Leu Gly Met Asp Glu  Leu Tyr Lys
    1250                1255                1260


<210> SEQ ID NO 201
<211> LENGTH: 3792
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 201

atggctctgc ctgtgacagc tctgctgctg cctctggctc tgcttctgca tgctgctaga     60

cctgccggcg gaagcgacta caaggacgac gatgacaaag gcggcggagg atctggtggc    120

ggaggacagg ttcagctggt tcagtctggc gccgaagtga agaaacctgg cagcagcgtg    180

aaggtgtcct gcaaggccag cggctacacc tttaccgact acaacatgca ctgggtccga    240

caggcccctg gacaaggact tgagtggatc ggctacatct acccctacaa tggcggcacc    300

ggctacaacc agaagttcaa gagcaaggcc accatcaccg ccgacgagag cacaaacacc    360

gcctacatgg aactgagcag cctgagaagc gaggacaccg ccgtgtacta ctgcgctaga    420

ggcagacccg ccatggatta ttggggccag ggaaccctgg tcaccgtttc tagcggaggc    480

ggaggtagtg gtggtggcgg tagtggcgga ggtggaagcg atatccagat gacacagagc    540

cccagcagcc tgtctgccag cgtgggagat agagtgacca tcacctgtag agccagcgag    600

agcgtggaca actacggcat cagcttcatg aactggttcc agcagaagcc cggcaaggcc    660

cctaagctgc tgatctacgc cgccagcaat caaggcagcg gagtgcctag cagattttcc    720

ggctctggca gcggcaccga tttcaccctg accatcagta gcctgcagcc tgacgacttc    780

gccacctact actgccagca gagcaaagag gtgccctgga catttggaca gggcaccaag    840

gtggaaatca agagcggagc cgccgctatc gaagtgatgt accctcctcc ttacctggac    900

aacgagaagt ccaacggcac catcatccac gtgaagggca agcacctgtg tccttctcca    960

ctgttccccg gacctagcaa gcctttctgg gtgctcgttg ttgttggcgg cgtgctggcc   1020

tgttactctc tgctggttac cgtggccttc atcatctttt gggtccgaag caagcggagc   1080

agactgctgc actccgacta catgaacatg acccctagac ggcccggacc aaccagaaag   1140

cactaccagc cttacgctcc tcctagagat ttcgccgcct accggtccag agtgaagttc   1200

agcagatccg ccgatgctcc cgcctataag cagggccaga atcagctgta caacgagctg   1260

aatctggggc gcagagaaga gtacgacgtg ctggataagc ggagaggcag agatcctgag   1320

atgggcggca agcccagacg gaagaatcct caagagggcc tgtataatga gctgcagaaa   1380

gacaagatgg ccgaggccta cagcgagatc ggaatgaagg gcgaacgcag aagaggcaag   1440

ggccacgatg gactgtatca gggcctgagc accgccacaa aggacaccta tgatgccctg   1500

cacatgcagg ccctgccacc tcggagaaga aaaagaggct ctggcgaagg cagaggctcc   1560

ctgcttacat gtggcgacgt ggaagagaac cctggaccta tggcactgcc agtcactgcc   1620

ctgctgcttc cacttgcact gttgctgcac gccgctagac cagaagtgca gctcgttcaa   1680

agcggagctg aagtgaaaaa gcccggctcc tccgtgaaag tgtcttgtaa agcctccggc   1740

ggcaccttca gcagctacgc catttcttgg gttcgacaag ctccaggcca gggcctcgaa   1800

tggatgggag gaatcatccc catcttcggc accgccaact acgcccagaa attccaggga   1860
```

-continued cgcgtgacaa tcacagccga caagtctacc agcacagctt atatggaact gtctagcctg 1920
cgctccgagg atacagctgt gtactattgt gccacattcg ccctgttcgg cttcagagag 1980
caggccttcg atatctgggg ccaaggcacc acagtgacag tgtcctctgg cggtggtgga 2040
tctggcggag gcggttctgg cggcggtggc agtgatattc aaatgaccca gtctccatcc 2100
agcctgagcg cctctgttgg cgacagagtg acaattacat gccgggccag ccagagcatc 2160
agctcctacc tgaattggta tcagcagaaa ccaggcaaag ctcccaaact cctgatctat 2220
gctgcctcca gcctgcagag tggcgtgccc tctagatttt ctggaagcgg ctccggcacc 2280
gactttacac tcaccataag ctccctgcag ccagaagatc tggccacata ttactgtcag 2340
cagtcctaca gcaccccttt cacattcggc ccaggcacaa aagtggacat taagaccacc 2400
acaccagctc ctcggcctcc aactcctgct cctacaattg ctctgcagcc cctgtctctg 2460
aggcccgaag cttgtagacc tgctgctggc ggagccgtgc atacaagagg actggatttc 2520
gcctgcgaca tctacatctg ggctcctctg gccggaacat gcggagtgtt gctgctgagc 2580
ctggtcatca ccaagcgggg cagaaagaag ctgctgtaca tcttcaagca gcccttcatg 2640
cggcccgtgc agaccacaca agaggaagat ggctgctcct gcagattccc cgaggaagaa 2700
gaaggcggct gcgaactgcg cgtgaagttc tctagaagcg ctgacgcccc tgcctacaaa 2760
cagggacaaa accagctcta caatgaactg aacctcggca gacgcgagga atatgatgtg 2820
ctggacaaaa gacgcggcag ggaccctgaa atgggaggga agcctagaag aaagaaccca 2880
caagaaggcc tttacaacga actgcaaaag gataagatgg cagaagctta ctccgagatt 2940
ggcatgaagg gcgagcgtcg gagaggaaaa ggacacgacg gcctctacca gggcctgtct 3000
acagccacca aggatactta cgacgcactc catatgcagg ctctcccacc aagaggcagc 3060
tctggcactg gcatggtgtc caagggcgaa gaactgttca caggcgtggt gcccatcctg 3120
gtggaactgg acggggatgt gaacggccac aagtttagcg ttagcggaga aggcgaaggc 3180
gacgccacat acggaaagct gacactgaaa ctgatctgca ccaccggcaa gctgcctgtg 3240
ccatggccta cactggttac cacactcggc tacggcctgc agtgcttcgc tagatacccc 3300
gaccatatga agcagcacga cttcttcaag agcgccatgc ctgagggcta cgtgcaagag 3360
agaaccatct tcttcaaaga cgacggcaac tacaagaccc gggcagaagt gaagtttgag 3420
ggcgacaccc tcgtgaaccg gatcgagctg aagggcatcg acttcaaaga ggatggaaac 3480
atcctgggcc acaagctcga gtacaactac aacagccaca acgtgtacat taccgccgac 3540
aagcagaaga acggcatcaa ggccaacttc aagatccggc acaacatcga ggatggcggg 3600
gtgcagctgg ccgatcatta ccagcagaat acccctatcg gcgacggccc tgttctgctg 3660
cccgataatc actacctgag ctaccagagc gccctgagca aggaccccaa tgagaagagg 3720
gaccacatgg tgctgctgga attcgtgaca gccgccggaa tcaccctcgg catggacgag 3780
ctgtataagt ga 3792

<210> SEQ ID NO 202
<211> LENGTH: 973
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 202

Met Ala Leu Pro Val Thr Ala Leu Leu Leu Pro Leu Ala Leu Leu Leu

-continued

```
1               5                   10                  15

His Ala Ala Arg Pro Asp Val Val Met Thr Gln Ser Pro Leu Ser Leu
            20                  25                  30

Pro Val Thr Pro Gly Glu Pro Ala Ser Ile Ser Cys Arg Ser Ser Gln
        35                  40                  45

Ser Leu Leu His Ser Asn Gly Tyr Asn Tyr Leu Asp Trp Tyr Leu Gln
    50                  55                  60

Lys Pro Gly Gln Ser Pro Gln Leu Leu Ile Tyr Leu Gly Ser Asn Arg
65                  70                  75                  80

Ala Ser Gly Val Pro Asp Arg Phe Ser Gly Ser Gly Ser Gly Thr Asp
                85                  90                  95

Phe Thr Leu Lys Ile Ser Arg Val Glu Ala Glu Asp Val Gly Val Tyr
            100                 105                 110

Tyr Cys Met Gln Ser Leu Gln Thr Pro Phe Thr Phe Gly Pro Gly Thr
        115                 120                 125

Lys Val Asp Ile Lys Gly Gly Gly Gly Ser Glu Val Gln Leu Val Gln
    130                 135                 140

Ser Gly Ala Glu Val Lys Lys Pro Gly Ser Ser Val Lys Val Ser Cys
145                 150                 155                 160

Lys Ala Ser Gly Gly Thr Phe Ser Ser Tyr Ala Ile Ser Trp Val Arg
                165                 170                 175

Gln Ala Pro Gly Gln Gly Leu Glu Trp Met Gly Gly Ile Ile Pro Ile
            180                 185                 190

Phe Gly Thr Ala Asn Tyr Ala Gln Lys Phe Gln Gly Arg Val Thr Ile
        195                 200                 205

Thr Ala Asp Lys Ser Thr Ser Thr Ala Tyr Met Glu Leu Ser Ser Leu
    210                 215                 220

Arg Ser Glu Asp Thr Ala Val Tyr Tyr Cys Ala Thr Phe Ala Leu Phe
225                 230                 235                 240

Gly Phe Arg Glu Gln Ala Phe Asp Ile Trp Gly Gln Gly Thr Thr Val
                245                 250                 255

Thr Val Ser Ser Gly Ser Thr Ser Gly Ser Gly Lys Pro Gly Ser Gly
            260                 265                 270

Glu Gly Ser Thr Lys Gly Asp Ile Gln Met Thr Gln Ser Pro Ser Ser
        275                 280                 285

Leu Ser Ala Ser Val Gly Asp Arg Val Thr Ile Thr Cys Arg Ala Ser
    290                 295                 300

Gln Ser Ile Ser Ser Tyr Leu Asn Trp Tyr Gln Gln Lys Pro Gly Lys
305                 310                 315                 320

Ala Pro Lys Leu Leu Ile Tyr Ala Ala Ser Ser Leu Gln Ser Gly Val
                325                 330                 335

Pro Ser Arg Phe Ser Gly Ser Gly Ser Gly Thr Asp Phe Thr Leu Thr
            340                 345                 350

Ile Ser Ser Leu Gln Pro Glu Asp Leu Ala Thr Tyr Tyr Cys Gln Gln
        355                 360                 365

Ser Tyr Ser Thr Pro Phe Thr Phe Gly Pro Gly Thr Lys Val Asp Ile
    370                 375                 380

Lys Gly Gly Gly Gly Ser Glu Val Gln Leu Val Gln Ser Gly Ala Glu
385                 390                 395                 400

Val Lys Lys Pro Gly Ala Ser Val Lys Val Ser Cys Lys Ala Ser Gly
                405                 410                 415

Tyr Thr Phe Thr Ser Tyr Tyr Met His Trp Ala Arg Gln Ala Pro Gly
            420                 425                 430
```

-continued

```
Gln Gly Leu Glu Trp Met Gly Ile Ile Asn Pro Ser Gly Gly Ser Thr
        435                 440                 445

Ser Tyr Ala Gln Lys Phe Gln Gly Arg Val Thr Met Thr Arg Asp Thr
    450                 455                 460

Ser Thr Ser Thr Val Tyr Met Glu Leu Ser Ser Leu Arg Ser Glu Asp
465                 470                 475                 480

Thr Ala Val Tyr Tyr Cys Ala Arg Val Val Ala Ala Ala Val Ala Asp
                485                 490                 495

Tyr Trp Gly Gln Gly Thr Leu Val Thr Val Ser Ser Thr Thr Thr Pro
            500                 505                 510

Ala Pro Arg Pro Pro Thr Pro Ala Pro Thr Ile Ala Leu Gln Pro Leu
        515                 520                 525

Ser Leu Arg Pro Glu Ala Cys Arg Pro Ala Ala Gly Gly Ala Val His
    530                 535                 540

Thr Arg Gly Leu Asp Phe Ala Cys Asp Ile Tyr Ile Trp Ala Pro Leu
545                 550                 555                 560

Ala Gly Thr Cys Gly Val Leu Leu Leu Ser Leu Val Ile Thr Lys Arg
                565                 570                 575

Gly Arg Lys Lys Leu Leu Tyr Ile Phe Lys Gln Pro Phe Met Arg Pro
            580                 585                 590

Val Gln Thr Thr Gln Glu Glu Asp Gly Cys Ser Cys Arg Phe Pro Glu
        595                 600                 605

Glu Glu Glu Gly Gly Cys Glu Leu Arg Val Lys Phe Ser Arg Ser Ala
    610                 615                 620

Asp Ala Pro Ala Tyr Lys Gln Gly Gln Asn Gln Leu Tyr Asn Glu Leu
625                 630                 635                 640

Asn Leu Gly Arg Arg Glu Glu Tyr Asp Val Leu Asp Lys Arg Arg Gly
                645                 650                 655

Arg Asp Pro Glu Met Gly Gly Lys Pro Arg Arg Lys Asn Pro Gln Glu
            660                 665                 670

Gly Leu Tyr Asn Glu Leu Gln Lys Asp Lys Met Ala Glu Ala Tyr Ser
        675                 680                 685

Glu Ile Gly Met Lys Gly Glu Arg Arg Arg Gly Lys Gly His Asp Gly
    690                 695                 700

Leu Tyr Gln Gly Leu Ser Thr Ala Thr Lys Asp Thr Tyr Asp Ala Leu
705                 710                 715                 720

His Met Gln Ala Leu Pro Pro Arg Gly Ser Ser Gly Thr Gly Met Val
                725                 730                 735

Ser Lys Gly Glu Glu Leu Phe Thr Gly Val Val Pro Ile Leu Val Glu
            740                 745                 750

Leu Asp Gly Asp Val Asn Gly His Lys Phe Ser Val Ser Gly Glu Gly
        755                 760                 765

Glu Gly Asp Ala Thr Tyr Gly Lys Leu Thr Leu Lys Leu Ile Cys Thr
    770                 775                 780

Thr Gly Lys Leu Pro Val Pro Trp Pro Thr Leu Val Thr Thr Leu Gly
785                 790                 795                 800

Tyr Gly Leu Gln Cys Phe Ala Arg Tyr Pro Asp His Met Lys Gln His
                805                 810                 815

Asp Phe Phe Lys Ser Ala Met Pro Glu Gly Tyr Val Gln Glu Arg Thr
            820                 825                 830

Ile Phe Phe Lys Asp Asp Gly Asn Tyr Lys Thr Arg Ala Glu Val Lys
        835                 840                 845
```

```
Phe Glu Gly Asp Thr Leu Val Asn Arg Ile Glu Leu Lys Gly Ile Asp
    850                 855                 860

Phe Lys Glu Asp Gly Asn Ile Leu Gly His Lys Leu Glu Tyr Asn Tyr
865                 870                 875                 880

Asn Ser His Asn Val Tyr Ile Thr Ala Asp Lys Gln Lys Asn Gly Ile
                885                 890                 895

Lys Ala Asn Phe Lys Ile Arg His Asn Ile Glu Asp Gly Gly Val Gln
            900                 905                 910

Leu Ala Asp His Tyr Gln Gln Asn Thr Pro Ile Gly Asp Gly Pro Val
        915                 920                 925

Leu Leu Pro Asp Asn His Tyr Leu Ser Tyr Gln Ser Ala Leu Ser Lys
    930                 935                 940

Asp Pro Asn Glu Lys Arg Asp His Met Val Leu Leu Glu Phe Val Thr
945                 950                 955                 960

Ala Ala Gly Ile Thr Leu Gly Met Asp Glu Leu Tyr Lys
                965                 970
```

<210> SEQ ID NO 203
<211> LENGTH: 2922
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 203

```
atggctctgc ctgttacagc tctgctgctg cctctggctc tgcttctgca tgccgccaga     60

cctgacgtgg tcatgacaca gtctccactg agcctgcctg tgacacctgg cgaacctgcc    120

agcatcagct gtagaagcag ccagagcctg ctgcacagca acggctacaa ctacctggac    180

tggtatctgc agaagcccgg ccagtctcct cagctgctga tctacctggg ctccaataga    240

gccagcggcg tgcccgatag attttctggc agcggcagcg gaaccgactt caccctgaag    300

atctccagag tggaagccga ggacgtgggc gtgtactact gtatgcagtc cctgcagacc    360

cctttcacct tcggacctgg caccaaggtg gacatcaaag gcggcggagg atctgaggtg    420

cagctggttc aatctggcgc cgaagtgaag aaacccggca gctctgtgaa ggtgtcctgc    480

aaagctagcg gcggcacctt tagcagctac gccatctctt gggtccgaca ggctcctgga    540

caaggcctgg aatggatggg cggcatcatc cctatcttcg gcaccgccaa ttacgcccag    600

aaattccagg gcagagtgac catcaccgcc gacaagagca caagcaccgc ctacatggaa    660

ctgagcagcc tgagaagcga ggacaccgcc gtgtactatt gcgccacatt cgccctgttc    720

ggcttcagag agcaggcctt cgatatctgg ggccagggca caaccgtgac agtgtctagc    780

ggcagcacaa gcggctctgg caaacctgga tctggcgagg gaagcaccaa gggcgatatc    840

cagatgacac agagccccag cagcctgtct gcctctgtgg gagacagagt gacaattacc    900

tgccgggcca gccagtccat cagctcctac ctgaattggt atcagcaaaa acctggcaag    960

gcccctaagc tgctcatcta tgccgctagc agtctgcaga gcggagtgcc ctcaagattc   1020

agcggatctg gatccggcac cgatttcaca ctgaccataa gctcactgca gcccgaggac   1080

ctggccacct actattgtca gcagtcctac agcaccccgt tcacatttgg cccaggcaca   1140

aaagtcgata tcaaaggtgg tggcggcagc gaagtccagc tggtgcaaag cggagctgaa   1200

gtgaaaaagc caggcgccag cgtgaaagtg tcttgcaagg cctccggcta cacattcacc   1260

agctactaca tgcactgggc cagacaggca ccaggacagg gacttgagtg gatgggcatc   1320
```

-continued

```
atcaatcctt ccggcggctc cacaagctac gcccaaaagt ttcaaggccg cgtgaccatg   1380

accagagaca ccagcacctc caccgtgtat atggaactgt ctagcctgcg ctccgaggat   1440

acagccgtct actactgtgc cagagtggtg gctgctgccg tggccgatta ttggggacag   1500

ggaacactgg tcaccgtgtc cagcacaaca acccctgctc ctagacctcc tacaccagct   1560

ccaaccattg ctctgcagcc cctgtctctg aggccagagg cttgtagacc tgctgctggc   1620

ggagccgtgc atacaagagg actggatttc gcctgcgaca tctacatctg ggcccctctg   1680

gctggaacat gtggcgtgtt gctgctgagc ctggtcatca ccaagcgggg cagaaagaag   1740

ctgctgtaca tcttcaagca gcccttcatg cggcccgtgc agaccacaca agaggaagat   1800

ggctgctcct gcagattccc cgaggaagaa gaaggcggct gcgaactgag agtgaagttc   1860

agcagaagcg ccgacgctcc cgcctataag cagggacaga accagctcta caacgagctg   1920

aacctgggga gaagagaaga gtacgacgtg ctggataagc ggagaggcag agatcctgag   1980

atgggcggaa agcccagacg gaagaatcct caagagggcc tgtacaatga gctgcagaaa   2040

gacaagatgg ccgaggccta cagcgagatc ggaatgaagg gcgagcgcag aagaggcaag   2100

ggacacgatg gactgtacca gggcctgagc accgccacca aggataccta tgatgccctg   2160

cacatgcagg ccctgcctcc aagaggatct agcggaacag gcatggtgtc caaaggcgag   2220

gaactgttca caggcgtggt gcccattctg gtggaactgg atggcgacgt gaacggccac   2280

aagtttagcg ttagcggaga aggcgaaggc gacgccacat acggaaagct gaccctgaag   2340

ctgatctgca ccaccggcaa actgcctgtg ccttggccta cactcgtgac cacactcggc   2400

tatggcctgc agtgcttcgc cagatatccc gaccatatga agcagcacga cttcttcaag   2460

agcgccatgc ctgagggcta cgtgcaagag cggaccatct tctttaagga cgacggcaac   2520

tacaagaccc gggcagaagt gaagtttgag ggcgacaccc tggtcaaccg gatcgagctg   2580

aagggcatcg acttcaaaga ggacggcaac atcctgggcc acaagctcga gtacaactac   2640

aacagccaca acgtgtacat cacggccgat aagcagaaga acggcatcaa ggccaacttc   2700

aagatccgcc acaacatcga ggatggcggc gttcagctgg ccgatcacta ccagcagaat   2760

acccctatcg gcgacggacc tgtgctgctc cccgataatc actacctgag ctaccagagc   2820

gccctgagca aggaccccaa cgagaagagg gatcacatgg tgctgctgga attcgtgacc   2880

gctgccggca tcaccctcgg catggatgaa ctgtacaagt ga                      2922
```

<210> SEQ ID NO 204
<211> LENGTH: 1000
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 204

```
Met Ala Leu Pro Val Thr Ala Leu Leu Leu Pro Leu Ala Leu Leu Leu
1               5                   10                  15

His Ala Ala Arg Pro Glu Val Gln Leu Val Gln Ser Gly Ala Glu Val
            20                  25                  30

Lys Lys Pro Gly Ser Ser Val Lys Val Ser Cys Lys Ala Ser Gly Gly
        35                  40                  45

Thr Phe Ser Ser Tyr Ala Ile Ser Trp Val Arg Gln Ala Pro Gly Gln
    50                  55                  60

Gly Leu Glu Trp Met Gly Gly Ile Ile Pro Ile Phe Gly Thr Ala Asn
65                  70                  75                  80
```

```
Tyr Ala Gln Lys Phe Gln Gly Arg Val Thr Ile Thr Ala Asp Lys Ser
                85                  90                  95

Thr Ser Thr Ala Tyr Met Glu Leu Ser Ser Leu Arg Ser Glu Asp Thr
            100                 105                 110

Ala Val Tyr Tyr Cys Ala Thr Phe Ala Leu Phe Gly Phe Arg Glu Gln
        115                 120                 125

Ala Phe Asp Ile Trp Gly Gln Gly Thr Thr Val Thr Val Ser Ser Gly
    130                 135                 140

Gly Gly Gly Ser Gly Gly Gly Gly Ser Gly Gly Gly Gly Ser Asp Ile
145                 150                 155                 160

Gln Met Thr Gln Ser Pro Ser Ser Leu Ser Ala Ser Val Gly Asp Arg
                165                 170                 175

Val Thr Ile Thr Cys Arg Ala Ser Gln Ser Ile Ser Ser Tyr Leu Asn
            180                 185                 190

Trp Tyr Gln Gln Lys Pro Gly Lys Ala Pro Lys Leu Leu Ile Tyr Ala
        195                 200                 205

Ala Ser Ser Leu Gln Ser Gly Val Pro Ser Arg Phe Ser Gly Ser Gly
    210                 215                 220

Ser Gly Thr Asp Phe Thr Leu Thr Ile Ser Ser Leu Gln Pro Glu Asp
225                 230                 235                 240

Leu Ala Thr Tyr Tyr Cys Gln Gln Ser Tyr Ser Thr Pro Phe Thr Phe
                245                 250                 255

Gly Pro Gly Thr Lys Val Asp Ile Lys Gly Gly Gly Gly Ser Gly Gly
            260                 265                 270

Gly Gly Ser Gly Gly Gly Gly Ser Gly Gly Gly Gly Ser Gly Gly Gly
        275                 280                 285

Gly Ser Asp Val Val Met Thr Gln Ser Pro Leu Ser Leu Pro Val Thr
    290                 295                 300

Pro Gly Glu Pro Ala Ser Ile Ser Cys Arg Ser Ser Gln Ser Leu Leu
305                 310                 315                 320

His Ser Asn Gly Tyr Asn Tyr Leu Asp Trp Tyr Leu Gln Lys Pro Gly
                325                 330                 335

Gln Ser Pro Gln Leu Leu Ile Tyr Leu Gly Ser Asn Arg Ala Ser Gly
            340                 345                 350

Val Pro Asp Arg Phe Ser Gly Ser Gly Ser Gly Thr Asp Phe Thr Leu
        355                 360                 365

Lys Ile Ser Arg Val Glu Ala Glu Asp Val Gly Val Tyr Tyr Cys Met
    370                 375                 380

Gln Ser Leu Gln Thr Pro Phe Thr Phe Gly Pro Gly Thr Lys Val Asp
385                 390                 395                 400

Ile Lys Gly Gly Gly Gly Ser Gly Gly Gly Gly Ser Gly Gly Gly Gly
                405                 410                 415

Ser Glu Val Gln Leu Val Gln Ser Gly Ala Glu Val Lys Lys Pro Gly
            420                 425                 430

Ala Ser Val Lys Val Ser Cys Lys Ala Ser Gly Tyr Thr Phe Thr Ser
        435                 440                 445

Tyr Tyr Met His Trp Ala Arg Gln Ala Pro Gly Gln Gly Leu Glu Trp
    450                 455                 460

Met Gly Ile Ile Asn Pro Ser Gly Gly Ser Thr Ser Tyr Ala Gln Lys
465                 470                 475                 480

Phe Gln Gly Arg Val Thr Met Thr Arg Asp Thr Ser Thr Ser Thr Val
                485                 490                 495
```

-continued

```
Tyr Met Glu Leu Ser Ser Leu Arg Ser Glu Asp Thr Ala Val Tyr Tyr
            500                 505                 510

Cys Ala Arg Val Val Ala Ala Ala Val Ala Asp Tyr Trp Gly Gln Gly
        515                 520                 525

Thr Leu Val Thr Val Ser Ser Thr Thr Thr Pro Ala Pro Arg Pro Pro
    530                 535                 540

Thr Pro Ala Pro Thr Ile Ala Leu Gln Pro Leu Ser Leu Arg Pro Glu
545                 550                 555                 560

Ala Cys Arg Pro Ala Ala Gly Gly Ala Val His Thr Arg Gly Leu Asp
                565                 570                 575

Phe Ala Cys Asp Ile Tyr Ile Trp Ala Pro Leu Ala Gly Thr Cys Gly
            580                 585                 590

Val Leu Leu Leu Ser Leu Val Ile Thr Lys Arg Gly Arg Lys Lys Leu
        595                 600                 605

Leu Tyr Ile Phe Lys Gln Pro Phe Met Arg Pro Val Gln Thr Thr Gln
    610                 615                 620

Glu Glu Asp Gly Cys Ser Cys Arg Phe Pro Glu Glu Glu Glu Gly Gly
625                 630                 635                 640

Cys Glu Leu Arg Val Lys Phe Ser Arg Ser Ala Asp Ala Pro Ala Tyr
                645                 650                 655

Lys Gln Gly Gln Asn Gln Leu Tyr Asn Glu Leu Asn Leu Gly Arg Arg
            660                 665                 670

Glu Glu Tyr Asp Val Leu Asp Lys Arg Arg Gly Arg Asp Pro Glu Met
        675                 680                 685

Gly Gly Lys Pro Arg Arg Lys Asn Pro Gln Glu Gly Leu Tyr Asn Glu
    690                 695                 700

Leu Gln Lys Asp Lys Met Ala Glu Ala Tyr Ser Glu Ile Gly Met Lys
705                 710                 715                 720

Gly Glu Arg Arg Arg Gly Lys Gly His Asp Gly Leu Tyr Gln Gly Leu
                725                 730                 735

Ser Thr Ala Thr Lys Asp Thr Tyr Asp Ala Leu His Met Gln Ala Leu
            740                 745                 750

Pro Pro Arg Gly Ser Ser Gly Thr Gly Met Val Ser Lys Gly Glu Glu
        755                 760                 765

Leu Phe Thr Gly Val Val Pro Ile Leu Val Glu Leu Asp Gly Asp Val
    770                 775                 780

Asn Gly His Lys Phe Ser Val Ser Gly Glu Gly Glu Gly Asp Ala Thr
785                 790                 795                 800

Tyr Gly Lys Leu Thr Leu Lys Leu Ile Cys Thr Thr Gly Lys Leu Pro
                805                 810                 815

Val Pro Trp Pro Thr Leu Val Thr Thr Leu Gly Tyr Gly Leu Gln Cys
            820                 825                 830

Phe Ala Arg Tyr Pro Asp His Met Lys Gln His Asp Phe Phe Lys Ser
        835                 840                 845

Ala Met Pro Glu Gly Tyr Val Gln Glu Arg Thr Ile Phe Phe Lys Asp
    850                 855                 860

Asp Gly Asn Tyr Lys Thr Arg Ala Glu Val Lys Phe Glu Gly Asp Thr
865                 870                 875                 880

Leu Val Asn Arg Ile Glu Leu Lys Gly Ile Asp Phe Lys Glu Asp Gly
                885                 890                 895

Asn Ile Leu Gly His Lys Leu Glu Tyr Asn Tyr Asn Ser His Asn Val
            900                 905                 910

Tyr Ile Thr Ala Asp Lys Gln Lys Asn Gly Ile Lys Ala Asn Phe Lys
```

```
        915                 920                 925

Ile Arg His Asn Ile Glu Asp Gly Gly Val Gln Leu Ala Asp His Tyr
    930                 935                 940

Gln Gln Asn Thr Pro Ile Gly Asp Gly Pro Val Leu Leu Pro Asp Asn
945                 950                 955                 960

His Tyr Leu Ser Tyr Gln Ser Ala Leu Ser Lys Asp Pro Asn Glu Lys
                965                 970                 975

Arg Asp His Met Val Leu Leu Glu Phe Val Thr Ala Ala Gly Ile Thr
            980                 985                 990

Leu Gly Met Asp Glu Leu Tyr Lys
        995                 1000


<210> SEQ ID NO 205
<211> LENGTH: 3003
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 205

atggctctgc ctgttacagc tctgctgctg cctctggctc tgcttctgca tgccgctaga     60

cctgaagtgc agctggttca gtctggcgcc gaagtgaaga aacctggcag cagcgtgaag    120

gtgtcctgca aagcttctgg cggcaccttc agcagctacg ccatctcttg ggttcgacag    180

gcccctggac aaggcctgga atggatggga ggcatcatcc ccatcttcgg caccgccaat    240

tacgcccaga aattccaggg cagagtgacc atcaccgccg acaagagcac aagcaccgcc    300

tacatggaac tgagcagcct gagaagcgag gacaccgccg tgtactactg cgccacattt    360

gccctgttcg gcttcagaga gcaggccttc gatatctggg gccagggcac aaccgtgacc    420

gtttctagcg gaggcggagg atctggtggc ggaggaagtg gcggaggcgg ttctgatatc    480

cagatgacac agagccccag cagcctgtct gcctctgtgg gagacagagt gacaattacc    540

tgccgggcca gccagagcat cagctcctac ctgaactggt atcagcagaa gcccggcaag    600

gcccctaagc tgctgatcta tgctgcctcc agtctgcaga gcggcgtgcc atctagattt    660

tctggcagcg gctccggcac cgacttcacc ctgacaatat ctagcctgca gccagaggac    720

ctggccacct actactgtca gcagtcctac agcacccctt tcaccttcgg acctggcacc    780

aaggtggaca tcaaaggtgg tggtggcagt ggtggcggtg gctcaggtgg cggcggatca    840

ggcggtggtg gttctggcgg cggtggatct gatgtggtta tgacccagtc tcctctgagc    900

ctgcctgtga cacctggcga acctgccagc atctcctgta gaagcagcca gtctctgctg    960

cacagcaacg gctacaacta cctggattgg tatctccaga aaccaggaca gtcccctcag   1020

ctcctcatct acctgggcag caatagagcc tctggcgtgc ccgatagatt cagcggctct   1080

ggaagcggca cagatttcac actgaagatc tccagagtgg aagccgagga cgtgggcgtg   1140

tactattgca tgcagagcct gcagacccca ttcacatttg gcccaggcac aaaagtcgat   1200

atcaaaggcg gcggaggttc cggcggtggc ggaagcggag gtggtggctc tgaagttcag   1260

ctcgtgcaaa gcggagctga agtgaaaaag ccaggcgcct ccgtgaaagt gtcttgtaaa   1320

gccagcggct acacctttac cagctactac atgcactggg ccagacaggc accaggccag   1380

ggacttgagt ggatgggcat catcaatcct agcggcggca gcacaagcta cgcccaaaag   1440

tttcaaggcc gcgtgaccat gaccagagac accagcacct ccaccgtgta tatggaactg   1500

tcctctctgc ggagcgaaga tacagccgtg tattattgtg ccagagtggt ggccgctgcc   1560
```

gtggccgatt attggggaca gggaacactg gtcaccgtgt ccagcacaac aacccctgct 1620
cctagacctc ctacaccagc tccaaccatt gctctgcagc ccctgtctct gaggccagag 1680
gcctgtagac ctgctgctgg cggagctgtg catacaagag gcctggattt cgcctgcgac 1740
atctacatct gggctcctct ggccggaaca tgcggagtgt tgctgctgag cctggtcatc 1800
accaagcggg gcagaaagaa gctgctgtac atcttcaagc agcccttcat gcggcccgtg 1860
cagaccacac aagaggaaga tggctgctcc tgcagattcc ccgaggaaga agaaggcggc 1920
tgcgaactga gagtgaagtt tagcagaagc gccgacgctc ccgcctataa gcagggacag 1980
aatcagctgt acaatgagct gaacctgggg cgcagagaag agtacgacgt gctggataag 2040
cggagaggca gagatcctga gatgggcggc aagcccagac ggaagaatcc tcaagagggc 2100
ctgtataacg agctgcagaa agacaagatg gccgaggcct acagcgagat cggaatgaag 2160
ggcgaacgca gaagaggcaa gggccacgat ggactgtatc agggcctgtc cacagccacc 2220
aaggacacct atgatgccct gcacatgcag gccctgcctc caagaggatc ttctggcaca 2280
ggcatggtgt ccaagggcga agaactgttc acaggcgtgg tgcccatcct ggtggaactg 2340
gacggggatg tgaacggcca caagtttagc gttagcggcg aaggcgaagg ggatgccaca 2400
tacggaaagc tgaccctgaa gctgatctgc accaccggca aactgccagt gccttggcct 2460
acactcgtga ccacactcgg ctatggcctg cagtgcttcg ccagatatcc cgaccatatg 2520
aagcagcacg acttcttcaa gagcgccatg cctgagggct acgtgcaaga gagaaccatc 2580
ttctttaagg acgacggcaa ctacaagacc cgggcagaag tgaagttcga gggcgacacc 2640
ctggtcaacc ggatcgagct gaagggcatc gacttcaaag aggacggcaa catcctgggc 2700
cacaagctcg agtacaacta caacagccac aacgtgtaca tcacggccga taagcagaag 2760
aacggcatca aggccaactt caagatccgg cacaacatcg aggatggcgg cgttcagctg 2820
gccgatcact accagcagaa tacccctatc ggcgacggac ctgtcctgct gcctgacaat 2880
cactacctga gctaccagag cgccctgagc aaggacccca acgagaagag ggatcacatg 2940
gtgctgctgg aattcgtgac cgccgctggc atcaccctcg gcatggatga gctgtataag 3000
tga 3003

<210> SEQ ID NO 206
<211> LENGTH: 45
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 206

Thr Thr Thr Pro Ala Pro Arg Pro Pro Thr Pro Ala Pro Thr Ile Ala
1 5 10 15

Leu Gln Pro Leu Ser Leu Arg Pro Glu Ala Cys Arg Pro Ala Ala Gly
20 25 30

Gly Ala Val His Thr Arg Gly Leu Asp Phe Ala Cys Asp
35 40 45

<210> SEQ ID NO 207
<211> LENGTH: 66
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 207

Ala Leu Ser Asn Ser Ile Met Tyr Phe Ser His Phe Val Pro Val Phe
1               5                   10                  15

Leu Pro Ala Lys Pro Thr Thr Thr Pro Ala Pro Arg Pro Pro Thr Pro
            20                  25                  30

Ala Pro Thr Ile Ala Ser Gln Pro Leu Ser Leu Arg Pro Glu Ala Cys
        35                  40                  45

Arg Pro Ala Ala Gly Gly Ala Val His Thr Arg Gly Leu Asp Phe Ala
    50                  55                  60

Cys Asp
65

<210> SEQ ID NO 208
<211> LENGTH: 55
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 208

Phe Val Pro Val Phe Leu Pro Ala Lys Pro Thr Thr Thr Pro Ala Pro
1               5                   10                  15

Arg Pro Pro Thr Pro Ala Pro Thr Ile Ala Leu Gln Pro Leu Ser Leu
            20                  25                  30

Arg Pro Glu Ala Cys Arg Pro Ala Ala Gly Gly Ala Val His Thr Arg
        35                  40                  45

Gly Leu Asp Phe Ala Cys Asp
    50                  55

<210> SEQ ID NO 209
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 209

Ile Tyr Ile Trp Ala Pro Leu Ala Gly Thr Cys Gly Val Leu Leu Leu
1               5                   10                  15

Ser Leu Val Ile Thr
            20

<210> SEQ ID NO 210
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 210

Ile Tyr Ile Trp Ala Pro Leu Ala Gly Thr Cys Gly Val Leu Leu Leu
1               5                   10                  15

Ser Leu Val Ile Thr Leu Tyr Cys Asn His Arg
            20                  25

<210> SEQ ID NO 211
<211> LENGTH: 28
<212> TYPE: PRT

<213> ORGANISM: Artificial Sequence
<220> FEATURE:
<223> OTHER INFORMATION: Description of Artificial Sequence: Synthetic
peptide

<400> SEQUENCE: 211

Ile Tyr Ile Trp Ala Pro Leu Ala Gly Thr Cys Gly Val Leu Leu Leu
1 5 10 15

Ser Leu Val Ile Thr Leu Tyr Cys Asn His Arg Asn
20 25

<210> SEQ ID NO 212
<211> LENGTH: 730
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 212

Met Leu Leu Leu Val Thr Ser Leu Leu Leu Cys Glu Leu Pro His Pro
1 5 10 15

Ala Phe Leu Leu Ile Pro Gln Val Gln Leu Val Gln Ser Gly Ala Glu
20 25 30

Val Lys Lys Pro Gly Ser Ser Val Lys Val Ser Cys Lys Ala Ser Gly
35 40 45

Tyr Thr Phe Thr Asp Tyr Asn Met His Trp Val Arg Gln Ala Pro Gly
50 55 60

Gln Gly Leu Glu Trp Ile Gly Tyr Ile Tyr Pro Tyr Asn Gly Gly Thr
65 70 75 80

Gly Tyr Asn Gln Lys Phe Lys Ser Lys Ala Thr Ile Thr Ala Asp Glu
85 90 95

Ser Thr Asn Thr Ala Tyr Met Glu Leu Ser Ser Leu Arg Ser Glu Asp
100 105 110

Thr Ala Val Tyr Tyr Cys Ala Arg Gly Arg Pro Ala Met Asp Tyr Trp
115 120 125

Gly Gln Gly Thr Leu Val Thr Val Ser Ser Gly Gly Gly Gly Ser Gly
130 135 140

Gly Gly Gly Ser Gly Gly Gly Gly Ser Asp Ile Gln Met Thr Gln Ser
145 150 155 160

Pro Ser Ser Leu Ser Ala Ser Val Gly Asp Arg Val Thr Ile Thr Cys
165 170 175

Arg Ala Ser Glu Ser Val Asp Asn Tyr Gly Ile Ser Phe Met Asn Trp
180 185 190

Phe Gln Gln Lys Pro Gly Lys Ala Pro Lys Leu Leu Ile Tyr Ala Ala
195 200 205

Ser Asn Gln Gly Ser Gly Val Pro Ser Arg Phe Ser Gly Ser Gly Ser
210 215 220

Gly Thr Asp Phe Thr Leu Thr Ile Ser Ser Leu Gln Pro Asp Asp Phe
225 230 235 240

Ala Thr Tyr Tyr Cys Gln Gln Ser Lys Glu Val Pro Trp Thr Phe Gly
245 250 255

Gln Gly Thr Lys Val Glu Ile Lys Ser Gly Thr Thr Thr Pro Ala Pro
260 265 270

Arg Pro Pro Thr Pro Ala Pro Thr Ile Ala Leu Gln Pro Leu Ser Leu
275 280 285

Arg Pro Glu Ala Cys Arg Pro Ala Ala Gly Gly Ala Val His Thr Arg

-continued

```
    290                 295                 300

Gly Leu Asp Phe Ala Cys Asp Ile Tyr Ile Trp Ala Pro Leu Ala Gly
305                 310                 315                 320

Thr Cys Gly Val Leu Leu Leu Ser Leu Val Ile Thr Arg Ser Lys Arg
                325                 330                 335

Ser Arg Leu Leu His Ser Asp Tyr Met Asn Met Thr Pro Arg Arg Pro
            340                 345                 350

Gly Pro Thr Arg Lys His Tyr Gln Pro Tyr Ala Pro Pro Arg Asp Phe
        355                 360                 365

Ala Ala Tyr Arg Ser Arg Val Lys Phe Ser Arg Ser Ala Asp Ala Pro
    370                 375                 380

Ala Tyr Lys Gln Gly Gln Asn Gln Leu Tyr Asn Glu Leu Asn Leu Gly
385                 390                 395                 400

Arg Arg Glu Glu Tyr Asp Val Leu Asp Lys Arg Arg Gly Arg Asp Pro
                405                 410                 415

Glu Met Gly Gly Lys Pro Arg Arg Lys Asn Pro Gln Glu Gly Leu Tyr
            420                 425                 430

Asn Glu Leu Gln Lys Asp Lys Met Ala Glu Ala Tyr Ser Glu Ile Gly
        435                 440                 445

Met Lys Gly Glu Arg Arg Arg Gly Lys Gly His Asp Gly Leu Tyr Gln
    450                 455                 460

Gly Leu Ser Thr Ala Thr Lys Asp Thr Tyr Asp Ala Leu His Met Gln
465                 470                 475                 480

Ala Leu Pro Pro Arg Gly Ser Ser Gly Thr Gly Met Val Ser Lys Gly
                485                 490                 495

Glu Glu Leu Phe Thr Gly Val Val Pro Ile Leu Val Glu Leu Asp Gly
            500                 505                 510

Asp Val Asn Gly His Lys Phe Ser Val Ser Gly Glu Gly Glu Gly Asp
        515                 520                 525

Ala Thr Tyr Gly Lys Leu Thr Leu Lys Leu Ile Cys Thr Thr Gly Lys
    530                 535                 540

Leu Pro Val Pro Trp Pro Thr Leu Val Thr Thr Leu Gly Tyr Gly Leu
545                 550                 555                 560

Gln Cys Phe Ala Arg Tyr Pro Asp His Met Lys Gln His Asp Phe Phe
                565                 570                 575

Lys Ser Ala Met Pro Glu Gly Tyr Val Gln Glu Arg Thr Ile Phe Phe
            580                 585                 590

Lys Asp Asp Gly Asn Tyr Lys Thr Arg Ala Glu Val Lys Phe Glu Gly
        595                 600                 605

Asp Thr Leu Val Asn Arg Ile Glu Leu Lys Gly Ile Asp Phe Lys Glu
    610                 615                 620

Asp Gly Asn Ile Leu Gly His Lys Leu Glu Tyr Asn Tyr Asn Ser His
625                 630                 635                 640

Asn Val Tyr Ile Thr Ala Asp Lys Gln Lys Asn Gly Ile Lys Ala Asn
                645                 650                 655

Phe Lys Ile Arg His Asn Ile Glu Asp Gly Gly Val Gln Leu Ala Asp
            660                 665                 670

His Tyr Gln Gln Asn Thr Pro Ile Gly Asp Gly Pro Val Leu Leu Pro
        675                 680                 685

Asp Asn His Tyr Leu Ser Tyr Gln Ser Ala Leu Ser Lys Asp Pro Asn
    690                 695                 700

Glu Lys Arg Asp His Met Val Leu Leu Glu Phe Val Thr Ala Ala Gly
705                 710                 715                 720
```

Ile Thr Leu Gly Met Asp Glu Leu Tyr Lys
725 730

<210> SEQ ID NO 213
<211> LENGTH: 2193
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 213
atgctccttc tcgtgacctc tttgcttctt tgtgaactcc cacacccagc attcctcttg 60
atcccccaag tacaactcgt ccaatccggg gcagaggtca agaagcccgg gagttcagtc 120
aaagtctcat gtaaagcgtc tggatatact ttcactgatt ataatatgca ttgggtgaga 180
caagcacccg gccaggggct ggaatggatt gggtatattt atccatataa cggtggaaca 240
gggtataatc agaaattcaa atctaaagct actattacag cggatgaaag tacgaataca 300
gcttatatgg agttgtcctc actcaggtcc gaagatacag cagtatatta ttgcgctagg 360
ggtcggcctg caatggacta ctggggccaa ggtactctcg tgactgtgtc aagtggcggt 420
ggcggcagcg gcggcggcgg ctccggtggt ggtggaagtg acattcaaat gacgcaatcc 480
ccatctagtc tcagcgcttc cgttggggac cgcgtaacaa ttacttgcag ggcatcagaa 540
tccgttgata attatgggat ttcctttatg aattggtttc aacaaaagcc ggggaaagca 600
ccaaaactcc tcatttatgc agcttccaac caggggtcag ggtcccgtc ccgtttcagc 660 ggttcaggga gtggtacaga ctttacgctt acaatttcca gtctccaacc cgatgatttt 720
gcaacatatt attgtcaaca atccaaggaa gttccttgga cgtttgggca aggtaccaaa 780
gttgagataa aatctggaac aacaacccct gcaccacggc cccctacccc cgcaccaacc 840
attgcactcc aacccttgtc cttgcgcccc gaggcctgca ggcccgccgc cggtggtgca 900
gttcacacta ggggcttgga ctttgcttgt gatatatata tatgggctcc actcgcaggg 960
acttgcggag tccttttgct gtcacttgtg attacacgaa gtaaaagatc tcggcttttg 1020
cattcagatt atatgaatat gactccacgc aggcctgggc ccacacgaaa acattatcaa 1080
ccgtatgcac ccccacgcga ctttgctgct tataggagcc gggtcaaatt ttcccggagc 1140
gcagacgccc cagcttacaa acaaggtcaa aatcaacttt ataatgaact caatttgggc 1200
cggcgggaag aatatgatgt ccttgataaa agacgtgggc gcgacccgga aatgggcggg 1260
aaaccacgtc gcaagaaccc gcaggaaggt ttgtacaacg aactccaaaa ggataaaatg 1320
gctgaagctt attccgaaat agggatgaaa ggtgaacggc gccgcggtaa aggccatgac 1380
ggcttgtatc aaggtcttag tacagcaaca aaagacacat acgacgctct ccatatgcaa 1440
gcactcccac cgcgcggatc gagtggcacc ggtatggttt ctaaaggaga ggagctcttt 1500
actggtgtcg tccctatatt ggtcgagctc gatggcgacg ttaatggtca taaattcagt 1560
gtgtcaggag agggagaagg cgacgctacg tatggcaaat tgacattgaa gttgatatgt 1620
acaacgggta aactcccagt tccctggccg acgctcgtaa caacgctggg ttatggactt 1680
caatgttttg ctcgttaccc tgatcacatg aaacaacatg atttctttaa atctgctatg 1740
cccgaagggt atgtccagga acggactatc ttcttcaaag atgatggaaa ttataaaact 1800
cgcgcagagg tgaaattcga aggggatact cttgtgaatc gaattgaact taaaggtatt 1860
gatttcaagg aagatgggaa catactcggg cataaacttg aatataatta taacagccat 1920

```
aatgtttaca tcaccgcaga taaacagaag aatggaatta aagcgaattt taaaattcgc   1980

cataatattg aagacggcgg ggtgcaactc gctgatcact atcaacaaaa cactccaatt   2040

ggagatggtc cggtcctgct cccggacaac cattatcttt cttatcaatc cgctctctcc   2100

aaagatccta atgaaaagcg ggaccatatg gtcttgcttg agtttgtcac tgcagccggg   2160

ataactctgg ggatggatga actctacaaa taa                                2193


<210> SEQ ID NO 214
<211> LENGTH: 533
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 214

Met Leu Leu Leu Val Thr Ser Leu Leu Leu Cys Glu Leu Pro His Pro
1               5                   10                  15

Ala Phe Leu Leu Ile Pro Ala Gly Gly Ser Asp Tyr Lys Asp Asp Asp
            20                  25                  30

Asp Lys Gly Gly Gly Gly Ser Gly Gly Gly Gly Gln Val Gln Leu Val
        35                  40                  45

Gln Ser Gly Ala Glu Val Lys Lys Pro Gly Ser Ser Val Lys Val Ser
    50                  55                  60

Cys Lys Ala Ser Gly Tyr Thr Phe Thr Asp Tyr Asn Met His Trp Val
65                  70                  75                  80

Arg Gln Ala Pro Gly Gln Gly Leu Glu Trp Ile Gly Tyr Ile Tyr Pro
                85                  90                  95

Tyr Asn Gly Gly Thr Gly Tyr Asn Gln Lys Phe Lys Ser Lys Ala Thr
            100                 105                 110

Ile Thr Ala Asp Glu Ser Thr Asn Thr Ala Tyr Met Glu Leu Ser Ser
        115                 120                 125

Leu Arg Ser Glu Asp Thr Ala Val Tyr Tyr Cys Ala Arg Gly Arg Pro
    130                 135                 140

Ala Met Asp Tyr Trp Gly Gln Gly Thr Leu Val Thr Val Ser Ser Gly
145                 150                 155                 160

Gly Gly Gly Ser Gly Gly Gly Gly Ser Gly Gly Gly Gly Ser Asp Ile
                165                 170                 175

Gln Met Thr Gln Ser Pro Ser Ser Leu Ser Ala Ser Val Gly Asp Arg
            180                 185                 190

Val Thr Ile Thr Cys Arg Ala Ser Glu Ser Val Asp Asn Tyr Gly Ile
        195                 200                 205

Ser Phe Met Asn Trp Phe Gln Gln Lys Pro Gly Lys Ala Pro Lys Leu
    210                 215                 220

Leu Ile Tyr Ala Ala Ser Asn Gln Gly Ser Gly Val Pro Ser Arg Phe
225                 230                 235                 240

Ser Gly Ser Gly Ser Gly Thr Asp Phe Thr Leu Thr Ile Ser Ser Leu
                245                 250                 255

Gln Pro Asp Asp Phe Ala Thr Tyr Tyr Cys Gln Gln Ser Lys Glu Val
            260                 265                 270

Pro Trp Thr Phe Gly Gln Gly Thr Lys Val Glu Ile Lys Ser Gly Ala
        275                 280                 285

Leu Ser Asn Ser Ile Met Tyr Phe Ser His Phe Val Pro Val Phe Leu
    290                 295                 300

Pro Ala Lys Pro Thr Thr Thr Pro Ala Pro Arg Pro Pro Thr Pro Ala
```

```
305                 310                 315                 320

Pro Thr Ile Ala Ser Gln Pro Leu Ser Leu Arg Pro Glu Ala Cys Arg
                325                 330                 335

Pro Ala Ala Gly Gly Ala Val His Thr Arg Gly Leu Asp Phe Ala Cys
            340                 345                 350

Asp Ile Tyr Ile Trp Ala Pro Leu Ala Gly Thr Cys Gly Val Leu Leu
        355                 360                 365

Leu Ser Leu Val Ile Thr Leu Tyr Cys Asn His Arg Arg Ser Lys Arg
    370                 375                 380

Ser Arg Leu Leu His Ser Asp Tyr Met Asn Met Thr Pro Arg Arg Pro
385                 390                 395                 400

Gly Pro Thr Arg Lys His Tyr Gln Pro Tyr Ala Pro Pro Arg Asp Phe
                405                 410                 415

Ala Ala Tyr Arg Ser Arg Val Lys Phe Ser Arg Ser Ala Asp Ala Pro
            420                 425                 430

Ala Tyr Lys Gln Gly Gln Asn Gln Leu Tyr Asn Glu Leu Asn Leu Gly
        435                 440                 445

Arg Arg Glu Glu Tyr Asp Val Leu Asp Lys Arg Arg Gly Arg Asp Pro
    450                 455                 460

Glu Met Gly Gly Lys Pro Arg Arg Lys Asn Pro Gln Glu Gly Leu Tyr
465                 470                 475                 480

Asn Glu Leu Gln Lys Asp Lys Met Ala Glu Ala Tyr Ser Glu Ile Gly
                485                 490                 495

Met Lys Gly Glu Arg Arg Arg Gly Lys Gly His Asp Gly Leu Tyr Gln
            500                 505                 510

Gly Leu Ser Thr Ala Thr Lys Asp Thr Tyr Asp Ala Leu His Met Gln
        515                 520                 525

Ala Leu Pro Pro Arg
    530
```

<210> SEQ ID NO 215
<211> LENGTH: 1599
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 215

```
atgttgctgc tggttacctc tctcctcttg tgtgagcttc cgcaccctgc ctttctcctg     60

ataccggctg gcggatctga ctacaaggac gacgatgaca aaggcggcgg cgggtccgga    120

ggaggtggac aggtccagct cgtacagtct ggtgcagaag tgaagaaacc cggttcatca    180

gttaaggttt cttgcaaagc cagtggctac acatttaccg actacaacat gcactgggtc    240

agacaggccc ccggccaagg cttggagtgg atcgggtaca tataccctta caatggcggt    300

actggataca accagaaatt caagagcaag gccacgatta ccgcggatga gagcacaaac    360

acagcctata tggaactgtc atctttgcga agcgaggaca ccgccgttta ttattgtgcc    420

agaggacgtc ccgcgatgga ttattggggt caggggacac tcgtcacagt gagcagcggc    480

ggcggtggca gtggcggagg aggctcaggc ggcggcggat ctgatattca aatgacccaa    540

tcaccatctt ccctttctgc tagtgtggga gatagggtga ctatcacatg tagagctagc    600

gaatccgtag acaactacgg catcagcttc atgaactggt tccagcaaaa gcctggcaag    660

gccccaaagt tgctcattta cgcggccagc aatcaaggca gtggtgtgcc cagcagattt    720
```

-continued

```
tccggatcag gcagcggaac cgatttcacc ttgaccattt cttctctgca gcctgacgac    780

tttgccacgt actactgcca acagtctaaa gaggttcctt ggacttttgg gcagggaaca    840

aaagtcgaaa taaagtccgg cgccttgagc aactctatca tgtactttag ccacttcgtg    900

ccggtgtttc ttcctgccaa gcctacaact acaccagccc caagaccccc aactccagcg    960

ccaacaatcg cgtcccagcc cttgtctctg agaccagaag cctgtagacc cgctgcaggc   1020

ggagccgttc atactcgggg actggatttc gcatgcgaca tttacatctg ggccccactg   1080

gctggcacgt gtggggtcct gcttctgtct ctggtaatca ccctttattg caaccacagg   1140

agatccaaga ggagccgcct gttgcactca gactacatga acatgacacc taggcggcca   1200

ggtcctactc gaaaacacta tcaaccttac gctccccctc gggatttcgc ggcttaccga   1260

agcagagtga aattcagcag atccgctgat gcaccggctt ataagcaggg ccaaaatcaa   1320

ctgtacaacg agctgaatct ggggagacgg gaagagtacg acgtcctgga caagcgcagg   1380

ggaagagacc ctgagatggg cgggaagcca cgtaggaaga acccacaaga gggcctgtat   1440

aatgagctgc agaaagacaa gatggcagag gcttacagtg agattggaat gaagggtgaa   1500

aggcggcggg gaaagggcca tgacggcctc tatcagggac tgtccacagc aactaaggac   1560

acctatgatg cactccacat gcaggccctg cccccgaga                          1599
```

```
<210> SEQ ID NO 216
<211> LENGTH: 511
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 216

Met Ala Leu Pro Val Thr Ala Leu Leu Leu Pro Leu Ala Leu Leu Leu
1               5                   10                  15

His Ala Ala Arg Pro Ala Gly Gly Ser Asp Tyr Lys Asp Asp Asp Asp
            20                  25                  30

Lys Gly Gly Gly Gly Ser Gly Gly Gly Gly Gln Val Gln Leu Val Gln
        35                  40                  45

Ser Gly Ala Glu Val Lys Lys Pro Gly Ser Ser Val Lys Val Ser Cys
    50                  55                  60

Lys Ala Ser Gly Tyr Thr Phe Thr Asp Tyr Asn Met His Trp Val Arg
65                  70                  75                  80

Gln Ala Pro Gly Gln Gly Leu Glu Trp Ile Gly Tyr Ile Tyr Pro Tyr
                85                  90                  95

Asn Gly Gly Thr Gly Tyr Asn Gln Lys Phe Lys Ser Lys Ala Thr Ile
            100                 105                 110

Thr Ala Asp Glu Ser Thr Asn Thr Ala Tyr Met Glu Leu Ser Ser Leu
        115                 120                 125

Arg Ser Glu Asp Thr Ala Val Tyr Tyr Cys Ala Arg Gly Arg Pro Ala
    130                 135                 140

Met Asp Tyr Trp Gly Gln Gly Thr Leu Val Thr Val Ser Ser Gly Gly
145                 150                 155                 160

Gly Gly Ser Gly Gly Gly Gly Ser Gly Gly Gly Gly Ser Asp Ile Gln
                165                 170                 175

Met Thr Gln Ser Pro Ser Ser Leu Ser Ala Ser Val Gly Asp Arg Val
            180                 185                 190

Thr Ile Thr Cys Arg Ala Ser Glu Ser Val Asp Asn Tyr Gly Ile Ser
        195                 200                 205
```

```
Phe Met Asn Trp Phe Gln Gln Lys Pro Gly Lys Ala Pro Lys Leu Leu
    210                 215                 220

Ile Tyr Ala Ala Ser Asn Gln Gly Ser Gly Val Pro Ser Arg Phe Ser
225                 230                 235                 240

Gly Ser Gly Ser Gly Thr Asp Phe Thr Leu Thr Ile Ser Ser Leu Gln
                245                 250                 255

Pro Asp Asp Phe Ala Thr Tyr Tyr Cys Gln Gln Ser Lys Glu Val Pro
            260                 265                 270

Trp Thr Phe Gly Gln Gly Thr Lys Val Glu Ile Lys Ser Gly Thr Thr
        275                 280                 285

Thr Pro Ala Pro Arg Pro Pro Thr Pro Ala Pro Thr Ile Ala Ser Gln
    290                 295                 300

Pro Leu Ser Leu Arg Pro Glu Ala Cys Arg Pro Ala Ala Gly Gly Ala
305                 310                 315                 320

Val His Thr Arg Gly Leu Asp Phe Ala Cys Asp Ile Tyr Ile Trp Ala
                325                 330                 335

Pro Leu Ala Gly Thr Cys Gly Val Leu Leu Leu Ser Leu Val Ile Thr
            340                 345                 350

Leu Tyr Cys Asn His Arg Arg Ser Lys Arg Ser Arg Leu Leu His Ser
        355                 360                 365

Asp Tyr Met Asn Met Thr Pro Arg Arg Pro Gly Pro Thr Arg Lys His
    370                 375                 380

Tyr Gln Pro Tyr Ala Pro Pro Arg Asp Phe Ala Ala Tyr Arg Ser Arg
385                 390                 395                 400

Val Lys Phe Ser Arg Ser Ala Asp Ala Pro Ala Tyr Lys Gln Gly Gln
                405                 410                 415

Asn Gln Leu Tyr Asn Glu Leu Asn Leu Gly Arg Arg Glu Glu Tyr Asp
            420                 425                 430

Val Leu Asp Lys Arg Arg Gly Arg Asp Pro Glu Met Gly Gly Lys Pro
        435                 440                 445

Arg Arg Lys Asn Pro Gln Glu Gly Leu Tyr Asn Glu Leu Gln Lys Asp
    450                 455                 460

Lys Met Ala Glu Ala Tyr Ser Glu Ile Gly Met Lys Gly Glu Arg Arg
465                 470                 475                 480

Arg Gly Lys Gly His Asp Gly Leu Tyr Gln Gly Leu Ser Thr Ala Thr
                485                 490                 495

Lys Asp Thr Tyr Asp Ala Leu His Met Gln Ala Leu Pro Pro Arg
            500                 505                 510
```

<210> SEQ ID NO 217
<211> LENGTH: 1533
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 217

```
atggccctgc ccgtcaccgc attgttgctc cccctcgcgt tgctgctcca cgccgcgcgt     60

cccgctggtg gctctgatta taaagatgat gacgataaag gggggggcgg tagcggcggt    120

ggtggtcaag tccaactcgt gcaaagcggt gctgaggtca agaagcccgg atcaagtgta    180

aaagtaagct gtaaagcttc cgggtataca ttcactgatt ataatatgca ttgggtgcgt    240

caagctcccg ggcagggtct cgaatggatt gggtatatat atccttataa cggcgggaca    300
```

-continued

```
gggtataatc agaaatttaa atctaaagca acaataacgg cggatgaatc taccaatact    360
gcttatatgg agctttcctc tctccgcagt gaagatactg ctgtctatta ttgtgcacgg    420
ggacgccctg caatggacta ctggggacaa ggcacacttg tgacagtcag ctctggtggt    480
ggtggatccg gcggaggagg ctcaggtggt ggcgggagtg acattcaaat gactcaaagt    540
ccttcctctc ttagcgcaag tgtcggtgac cgcgtcacaa ttacgtgccg ggcaagtgaa    600
tcagtcgata attatggtat ttcatttatg aattggtttc aacaaaagcc cggaaaagct    660
ccaaaactgt tgatatatgc agcttcaaac cagggaagtg gcgtcccctc acgcttctct    720
ggaagcgggt ctggtactga ctttactctc acaatttcct ctctccaacc cgatgatttt    780
gcaacgtatt attgtcaaca atccaaggaa gtaccttgga ccttcggcca agggacaaaa    840
gttgagatta aatccgggac aacaaccccc gctccgcgcc cacccacacc agcaccaaca    900
attgcatccc aaccattgag tctcagaccc gaggcatgcc gaccagccgc aggcggtgca    960
gttcacactc gcggtctcga ctttgcgtgt gatatatata tttgggcacc cctcgccggc   1020
acctgcggtg ttcttttgct ctccctcgtg attactcttt attgtaatca tcgtagaagt   1080
aaaaggtccc gtttgcttca ttctgattat atgaatatga ctccaaggcg ccctggcccc   1140
acacggaaac attatcaacc atatgcccca ccccgggact ttgctgcata tagaagccgc   1200
gtcaaatttt cacggtcagc agacgcacct gcttacaaac aaggacaaaa ccaattgtat   1260
aatgaactta acctcggaag gcgcgaggaa tatgatgtct tggataaaag gcgcgggcgg   1320
gatcccgaaa tgggcgggaa acctcggcgc aagaatcccc aggaaggtct ttacaacgaa   1380
ctccaaaagg ataaaatggc agaagcttat tcagaaattg ggatgaaagg ggagcggcgc   1440
cgaggcaaag ggcatgatgg tctctaccaa ggactttcca ccgctacaaa agatacatac   1500
gacgcattgc atatgcaagc tttgccaccc cgt                                1533
```

<210> SEQ ID NO 218
<211> LENGTH: 25
<212> TYPE: PRT
<213> ORGANISM: Artificial Sequence
<220> FEATURE:
<223> OTHER INFORMATION: Description of Artificial Sequence: Synthetic peptide

<400> SEQUENCE: 218

```
Gly Gly Gly Gly Ser Gly Gly Gly Gly Ser Gly Gly Gly Gly Ser Gly
1               5                   10                  15

Gly Gly Gly Ser Gly Gly Gly Gly Ser
            20                  25
```

<210> SEQ ID NO 219
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 219

```
Gly Gly Gly Gly Ser Gly Gly Gly Gly Ser Gly Gly Gly Gly Ser
1               5                   10                  15
```

<210> SEQ ID NO 220
<211> LENGTH: 45
<212> TYPE: DNA
<213> ORGANISM: Artificial Sequence
<220> FEATURE:

<223> OTHER INFORMATION: Description of Artificial Sequence: Synthetic oligonucleotide

<400> SEQUENCE: 220
gaagccgcgg caaaagaggc agcagcaaaa gaggcagcag ccaaa 45

<210> SEQ ID NO 221
<211> LENGTH: 75
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 221
ggtggtggtg gcagtggtgg cggtggctca ggtggcggcg gatcaggcgg tggtggttct 60
ggcggcggtg gatct 75

<210> SEQ ID NO 222

<400> SEQUENCE: 222

000

<210> SEQ ID NO 223
<211> LENGTH: 45
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 223
ggcggcggag gttccggcgg tggcggaagc ggaggtggtg gctct 45

<210> SEQ ID NO 224
<211> LENGTH: 4
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: See specification as filed for detailed description of substitutions and preferred embodiments

<400> SEQUENCE: 224

Gly Gly Gly Ser
1

<210> SEQ ID NO 225
<211> LENGTH: 20
<212> TYPE: PRT
<213> ORGANISM: Artificial Sequence
<220> FEATURE:
<223> OTHER INFORMATION: Description of Artificial Sequence: Synthetic peptide

<400> SEQUENCE: 225

Gly Gly Gly Gly Ser Gly Gly Gly Gly Ser Gly Gly Gly Gly Ser Gly
1 5 10 15

Gly Gly Gly Ser
20

<210> SEQ ID NO 226
<211> LENGTH: 15

-continued

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 226

Gly Gly Gly Gly Ser Gly Gly Gly Gly Ser Gly Gly Gly Gly Ser
1               5                   10                  15


<210> SEQ ID NO 227
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(30)
<223> OTHER INFORMATION: This sequence may encompass 1-6 "Gly Gly Gly
      Gly Ser" repeating units

<400> SEQUENCE: 227

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser
            20                  25                  30


<210> SEQ ID NO 228
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Any amino acid
<220> FEATURE:
<221> NAME/KEY: MOD_RES
<222> LOCATION: (11)..(11)
<223> OTHER INFORMATION: Any amino acid

<400> SEQUENCE: 228

Gly Gly Cys Lys Xaa Ser Gly Gly Cys Lys Xaa Ser
1               5                   10


<210> SEQ ID NO 229
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 229

Gly Gly Gly Ser
1
```

CHIMERIC RECEPTORS AND METHODS OF USE THEREOF

CROSS REFERENCE TO RELATED APPLICATIONS

This application is a continuation of International Application No. PCT/US20/30640, filed Apr. 30, 2020, which claims the benefit of U.S. Provisional Application No. 62/841,128, filed Apr. 30, 2019; U.S. Provisional Application No. 62/854,151, filed May 29, 2019; and U.S. Provisional Application No. 62/893,106, filed Aug. 28, 2019; each of which are hereby incorporated in its entirety by reference.

SEQUENCE LISTING

The instant application contains a Sequence Listing which has been submitted via EFS-Web and is hereby incorporated by reference in its entirety. Said ASCII copy, created on May 28, 2020, is named STB-016WO_SL.txt, and is 363,903 bytes in size.

BACKGROUND

Chimeric antigen receptor (CAR) based adoptive cell therapies used to redirect the specificity and function of immunoresponsive cells, such as T cells, have shown efficacy in patients with lymphoid malignancies (Pule et al., *Nat. Med.* (14):1264-1270 (2008); Maude et al., N *Engl J Med.* (371):1507-17 (2014); Brentjens et al., *Sci Transl Med.* (5):177ra38 (2013)). CAR T cells have been shown to induce complete remission in patients with CD19-expressing malignancies for whom chemotherapies have led to drug resistance and tumor progression. The success of CD19 CAR therapy provides optimism for treating other hematological malignancies, such as acute myeloid leukemia (AML). Acute myeloid leukemia is the most common acute leukemia in adults. AML is a cancer of the myeloid line of blood cells and is characterized by the rapid growth of abnormal cells that build up in the bone marrow and blood and interfere with normal blood cells. Sometimes, AML can spread to the brain, skin, or gums. The standard chemotherapy treatments for AML have not changed substantially over the past 40 years (Pulte et al., 2008), and overall survival remains very poor.

One challenge to developing CAR therapy for AML is the lack of suitable targets. The ability to identify appropriate CAR targets is important to effectively targeting and treating the tumor without damaging normal cells that express the same target antigen. Thus, there remains a need for CAR-T cell-based AML therapies that target AML cells without targeting normal cells or tissues.

SUMMARY

In one aspect, provided herein are isolated immunoresponsive cells comprising: (a) a first chimeric receptor comprising an extracellular antigen-binding domain that binds to a first antigen, and (b) a second chimeric receptor comprising an extracellular antigen-binding domain that binds to a second antigen, wherein each antigen is selected from FLT3, CD33, CLEC12A, MS4A3, VSTM1, LAT2, MLC1, CD131, GAPT, PRAM1, SLC22A16, SLC17A9, SPNS3, ADGRE2, IL3RA, CD117, CD93, IL1RAP, CD244, CCR1, LILRB2, PIEZO1, CD38, EMB, MYADM, LILRA2, CD300LF, and CD70, and wherein the first antigen is different from the second antigen.

In some embodiments, the first antigen is FLT3 and the extracellular antigen-binding domain of the first chimeric receptor comprises a heavy chain variable domain (VH) and a light chain variable domain (VL) selected from (a) a VH comprising the amino acid sequence of SEQ ID NO: 3 or a sequence at least 90% identical thereto and a VL comprising the amino acid sequence of SEQ. ID NO: 4 or a sequence at least 90% identical thereto; (b) a VH comprising the amino acid sequence of SEQ ID NO: 1 or a sequence at least 90% identical thereto and a VL comprising the amino acid sequence of SEQ. ID NO: 2 or a sequence at least 90% identical thereto; (c) a VH comprising the amino acid sequence of SEQ ID NO: 5 or a sequence at least 90% identical thereto and a VL comprising the amino acid sequence of SEQ. ID NO: 6 or a sequence at least 90% identical thereto; (d) a VH comprising the amino acid sequence of SEQ ID NO: 7 or a sequence at least 90% identical thereto and a VL comprising the amino acid sequence of SEQ. ID NO: 8 or a sequence at least 90% identical thereto; (e) a VH comprising the amino acid sequence of SEQ ID NO: 9 or a sequence at least 90% identical thereto and a VL comprising the amino acid sequence of SEQ. ID NO: 10 or a sequence at least 90% identical thereto; (f) a VH comprising the amino acid sequence of SEQ ID NO: 11 or a sequence at least 90% identical thereto and a VL comprising the amino acid sequence of SEQ. ID NO: 12 or a sequence at least 90% identical thereto; (g) a VH comprising the amino acid sequence of SEQ ID NO: 13 or a sequence at least 90% identical thereto and a VL comprising the amino acid sequence of SEQ. ID NO: 14 or a sequence at least 90% identical thereto; and (h) a VH comprising the amino acid sequence of SEQ ID NO: 15 or a sequence at least 90% identical thereto and a VL comprising the amino acid sequence of SEQ. ID NO: 16 or a sequence at least 90% identical thereto.

In some embodiments, the second antigen is CD33 and the extracellular antigen-binding domain of the second chimeric receptor comprises a heavy chain variable domain (VH) and a light chain variable domain (VL) selected from: (a) a VH comprising the amino acid sequence of SEQ ID NO: 17 or a sequence at least 90% identical thereto and a VL comprising the amino acid sequence of SEQ. ID NO: 18 or a sequence at least 90% identical thereto, and (b) a VH comprising the amino acid sequence of SEQ ID NO: 19 or a sequence at least 90% identical thereto and a VL comprising the amino acid sequence of SEQ. ID NO: 20 or a sequence at least 90% identical thereto; or the second antigen is CLEC12A and comprises a heavy chain variable domain (VH) and a light chain variable domain (VL) selected from: (a) a VH comprising the amino acid sequence of SEQ ID NO: 21 or a sequence at least 90% identical thereto and a VL comprising the amino acid sequence of SEQ. ID NO: 22 or a sequence at least 90% identical thereto, (b) a VH comprising the amino acid sequence of SEQ ID NO: 23 or a sequence at least 90% identical thereto and a VL comprising the amino acid sequence of SEQ. ID NO: 24 or a sequence at least 90% identical thereto, and (c) a VH comprising the amino acid sequence of SEQ ID NO: 25 or a sequence at least 90% identical thereto and a VL comprising the amino acid sequence of SEQ. ID NO: 26 or a sequence at least 90% identical thereto.

In some embodiments, the first antigen is CLEC12A and the extracellular antigen-binding domain of the first chimeric receptor comprises a heavy chain variable domain (VH) and a light chain variable domain (VL) selected from: (a) a VH comprising the amino acid sequence of SEQ ID NO: 21 or a sequence at least 90% identical thereto and a VL comprising the amino acid sequence of SEQ. ID NO: 22 or a sequence at least 90% identical thereto; (b) a VH comprising the amino acid sequence of SEQ ID NO: 23 or a sequence at least 90% identical thereto and a VL comprising the amino acid sequence of SEQ. ID NO: 24 or a sequence at least 90% identical thereto; and (c) a VH comprising the amino acid sequence of SEQ ID NO: 25 or a sequence at least 90% identical thereto and a VL comprising the amino acid sequence of SEQ. ID NO: 26 or a sequence at least 90% identical thereto, optionally wherein the second antigen is CD33 and the extracellular antigen-binding domain of the second chimeric receptor comprises a heavy chain variable domain (VH) and a light chain variable domain (VL) selected from: (a) a VH comprising the amino acid sequence of SEQ ID NO: 17 or a sequence at least 90% identical thereto and a VL comprising the amino acid sequence of SEQ. ID NO: 18 or a sequence at least 90% identical thereto; and (b) a VH comprising the amino acid sequence of SEQ ID NO: 19 or a sequence at least 90% identical thereto and a VL comprising the amino acid sequence of SEQ. ID NO: 20 or a sequence at least 90% identical thereto.

In some embodiments, binding of the first chimeric receptor to the first antigen is capable of activating the immunoresponsive cell and/or binding of the second chimeric receptor to the second antigen is capable of stimulating the immunoresponsive cell; and/or the immunoresponsive cell exhibits a greater degree of cytolytic activity against target cells that are positive for both the first antigen and the second antigen as compared to cytolytic activity against target cells that are positive for only the first antigen or the second antigen; and/or the first chimeric receptor binds to the first antigen with a binding affinity that is lower than the binding affinity of the second chimeric receptor for the second antigen; and/or the first chimeric receptor binds to the first antigen with a low binding avidity.

In some embodiments, the first chimeric receptor is a first CAR and the second chimeric receptor is a second CAR and each CAR comprises: a CD3zeta-chain intracellular signaling domain, optionally wherein each CAR further comprises one or more additional intracellular signaling domains, and the one or more additional intracellular signaling domains are selected from a CD97 intracellular signaling domain, a CD11a-CD18 intracellular signaling domain, a CD2 intracellular signaling domain, an ICOS intracellular signaling domain, a CD27 intracellular signaling domain, a CD154 intracellular signaling domain, a CD8 intracellular signaling domain, an OX40 intracellular signaling domain, a 4-1BB intracellular signaling domain, a CD28 intracellular signaling domain, a ZAP40 intracellular signaling domain, a CD30 intracellular signaling domain, a GITR intracellular signaling domain, an HVEM intracellular signaling domain, a DAP10 intracellular signaling domain, a DAP12 intracellular signaling domain, a MyD88 intracellular signaling domain, and a 2B4 intracellular signaling domain; and/or a transmembrane domain, and the transmembrane domain is selected from a CD8 transmembrane domain, a CD28 transmembrane domain a CD3zeta-chain transmembrane domain, a CD4 transmembrane domain, a 4-1BB transmembrane domain, an OX40 transmembrane domain, an ICOS transmembrane domain, a CTLA-4 transmembrane domain, a PD-1 transmembrane domain, a LAG-3 transmembrane domain, a 2B4 transmembrane domain, and a BTLA transmembrane domain; and/or a spacer region between the antigen-binding domain and the transmembrane domain, and the spacer region has an amino acid sequence selected from SEQ ID NOs: 55-64.

In some embodiments, the cell further comprises an inhibitory chimeric receptor comprising an antigen-binding domain, optionally wherein the inhibitory chimeric receptor inhibits one or more activities of the cell.

In some embodiments, the inhibitory chimeric receptor binds an antigen that is expressed on a non-tumor cell, optionally wherein the antigen that is expressed on a non-tumor cell is derived from a tissue selected from brain, neuronal tissue, endocrine, bone, bone marrow, immune system, endothelial tissue, muscle, lung, liver, gallbladder, pancreas, gastrointestinal tract, kidney, urinary bladder, male reproductive organs, female reproductive organs, adipose, soft tissue, and skin.

In some embodiments, the inhibitory chimeric receptor binds an antigen selected from EMCN, JAM2, MS4A15, C4BPA, TRPM1, SCTR, SLC2A2, KCNQ2, PERP, WLS, FFAR2, PTPRB, NCKAP1, MPZL2, PLSCR4, TMEM47, ADGRL4, MET, BACE2, ATP8B1, LIFR, ART4, CALCRL, CNTNAP3, PCDH9, IL18R1, SLC8A3, CDH26, TMEM163, ABCA13, CACHD1, CYYR1, ABCB1, ADGRG6, ATP9A, CALN1, CDCP1, IL12RB2, SLC16A14, TMEM136, and TMEM200A.

In some embodiments, the inhibitory chimeric receptor comprises an antigen binding domain comprising a single chain variable fragment (scFv), and the scFv is derived from an anti-EMCN antibody.

In some embodiments, the antigen-binding domain of the first chimeric receptor, the antigen-binding domain of the second chimeric receptor, and/or the antigen-binding domain of the inhibitory chimeric receptor comprises one or more single chain variable fragments (scFvs), wherein each of the one or more scFvs comprises a heavy chain variable domain (VH) and a light chain variable domain (VL), optionally wherein the VH and VL are separated by a peptide linker, and optionally wherein the peptide linker comprises the amino acid sequence of SEQ ID NO: 27.

In some embodiments, each of the one or more scFvs comprises the structure VH-L-VL or VL-L-VH, wherein VH is the heavy chain variable domain, L is the peptide linker, and VL is the light chain variable domain.

In some embodiments, each of the one or more scFvs binds to a distinct epitope on the same antigen.

In some embodiments, each of the one or more scFvs is separated by a peptide linker, optionally wherein the peptide linker comprises the amino acid sequence of GGGGSGGGGSGGGGS (SEQ ID NO: 27) or EAAAKEAAAKEAAAKEAAAK (SEQ ID NO: 74).

In some embodiments, the cell is a T cell, a Natural Killer (NK) cell, a cytotoxic T lymphocyte (CTL), a regulatory T cell, a Natural Killer T (NKT) cell, a myeloid cell, a macrophage, a human embryonic stem cell (ESC), an ESC-derived cell, a pluripotent stem cell, and induced pluripotent stem cell (iPSC), and an iPSC-derived cell, optionally wherein the immunoresponsive cell is allogeneic.

In another aspect, provided herein are pharmaceutical compositions comprising an effective amount of the isolated immunoresponsive cell of any embodiment herein and a pharmaceutically acceptable carrier, pharmaceutically acceptable excipient, or a combination thereof.

In another aspect, provided herein are methods of providing an anti-tumor immunity in a subject, the method comprising administering to a subject in need thereof a therapeutically effective dose of any of the isolated immunoresponsive cells of any embodiment herein or the pharmaceutical composition of any embodiment herein.

In another aspect, provided herein are methods of treating or preventing a myeloid disorder in a subject, comprising administering to the subject an effective amount of the isolated immunoresponsive cell of any embodiment herein or the pharmaceutical composition of any embodiment herein, optionally wherein the myeloid disorder is myelodysplastic syndromes, myeloproliferative neoplasms, chronic myelomonocytic leukemia, acute myeloid leukemia (AML), acute myeloblastic leukemia, acute promyelocytic leukemia, acute myelomonocytic leukemia, chronic myelocytic leukemia, and polycythemia vera.

In another aspect, provided herein are kits for treating and/or preventing a myeloid disorder, comprising the isolated immunoresponsive cell of any embodiment herein or the pharmaceutical composition of any embodiment herein, optionally wherein the kit further comprises written instructions for using the cell for treating and/or preventing a myeloid disorder in a subject.

In one aspect, provided herein are chimeric receptors comprising an extracellular antigen-binding domain that binds to an antigen selected from the group consisting of MS4A3, VSTM1, LAT2, MLC1, CD131, GAPT, PRAM1, SLC22A16, SLC17A9, and SPNS3.

In some embodiments, the antigen is MS4A3. In some embodiments, the antigen is VSTM1. In some embodiments, wherein the antigen is LAT2. In some embodiments, the antigen is MLC1. In some embodiments, the antigen is CD131. In some embodiments, the antigen is GAPT. In some embodiments, the antigen is PRAM1. In some embodiments, the antigen is SLC22A16. In some embodiments, the antigen is SLC17A9. In some embodiments, the antigen is SPNS3.

In some embodiments, the chimeric receptor is a chimeric T cell receptor or a chimeric antigen receptor (CAR). In some embodiments, the chimeric receptor is a CAR.

In some embodiments, the CAR comprises one or more intracellular signaling domains, and the one or more intracellular signaling domains are selected from the group consisting of a CD3zeta-chain intracellular signaling domain, a CD97 intracellular signaling domain, a CD11a-CD18 intracellular signaling domain, a CD2 intracellular signaling domain, an ICOS intracellular signaling domain, a CD27 intracellular signaling domain, a CD154 intracellular signaling domain, a CD8 intracellular signaling domain, an OX40 intracellular signaling domain, a 4-1BB intracellular signaling domain, a CD28 intracellular signaling domain, a ZAP40 intracellular signaling domain, a CD30 intracellular signaling domain, a GITR intracellular signaling domain, an HVEM intracellular signaling domain, a DAP10 intracellular signaling domain, a DAP12 intracellular signaling domain, and a MyD88 intracellular signaling domain.

In some embodiments, the CAR comprises a transmembrane domain, and the transmembrane domain is selected from the group consisting of a CD8 transmembrane domain, a CD28 transmembrane domain a CD3zeta-chain transmembrane domain, a CD4 transmembrane domain, a 4-1BB transmembrane domain, an OX40 transmembrane domain, an ICOS transmembrane domain, a CTLA-4 transmembrane domain, a PD-1 transmembrane domain, a LAG-3 transmembrane domain, a 2B4 transmembrane domain, and a BTLA transmembrane domain.

In some embodiments, the CAR comprises a spacer region between the antigen-binding domain and the transmembrane domain, and the spacer region has an amino acid sequence selected from the group consisting of SEQ ID NOs: 55-64.

In some embodiments, the antigen-binding domain comprises an antibody, an antigen-binding fragment of an antibody, a F(ab) fragment, a F(ab') fragment, a single chain variable fragment (scFv), or a single-domain antibody (sdAb). In some embodiments, the antigen-binding domain comprises a single chain variable fragment (scFv). In some embodiments, the scFv comprises a heavy chain variable domain (VH) and a light chain variable domain (VL). In some embodiments, the VH and VL are separated by a peptide linker. In some embodiments, the peptide linker comprises the amino acid sequence of SEQ ID NO: 27. In some embodiments, the scFv comprises the structure VH-L-VL or VL-L-VH, wherein VH is the heavy chain variable domain, L is the peptide linker, and VL is the light chain variable domain.

In another aspect, provided herein are isolated cells comprising the chimeric receptor of any one of the embodiments.

In some embodiments, the chimeric receptor is recombinantly expressed. In some embodiments, the chimeric receptor is expressed from a vector or a selected locus from the genome of the cell.

In some embodiments, the cell selected from the group consisting of a T cell, a Natural Killer (NK) cell, a cytotoxic T lymphocyte (CTL), a regulatory T cell, a Natural Killer T (NKT) cell, a myeloid cell, a macrophage, a human embryonic stem cell (ESC), an ESC-derived cell, a pluripotent stem cell, and induced pluripotent stem cell (iPSC), and an iPSC-derived cell.

In some embodiments, the cell is autologous. In some embodiments, the cell is allogeneic.

In another aspect, provided herein are isolated cells comprising (a) a first chimeric receptor comprising an extracellular antigen-binding domain that binds to a first antigen, and (b) a second chimeric receptor comprising an extracellular antigen-binding domain that binds to a second antigen, wherein each antigen is selected from the group consisting of the antigens listed in Table 1 or the first and second antigens are selected from the group consisting of the antigen pairs listed in Table 3, and wherein the first antigen is different from the second.

In another aspect, provided herein are isolated cells comprising (a) a first chimeric receptor comprising an extracellular antigen-binding domain that binds to a first antigen, and (b) a second chimeric receptor comprising an extracellular antigen-binding domain that binds to a second antigen, wherein each antigen is selected from the group consisting of MS4A3, VSTM1, LAT2, MLC1, CD131, GAPT, PRAM1, SLC22A16, SLC17A9, SPNS3, FLT3, CD33, CLEC12A, ADGRE2, IL3RA, CD117, CD93, IL1RAP, CD244, CCR1, LILRB2, PIEZO1, CD38, EMB, MYADM, LILRA2, CD300LF, and CD70, and wherein the first antigen is different from the second.

In some embodiments, the first antigen is MS4A3 and the second antigen is selected from the group consisting of VSTM1, LAT2, MLC1, CD131, GAPT, PRAM1, SLC22A16, SLC17A9, SPNS3, FLT3, CD33, CLEC12A, ADGRE2, IL3RA, CD117, CD93, IL1RAP, CD244, CCR1, LILRB2, PIEZO1, CD38, EMB, MYADM, LILRA2, CD300LF, and CD70.

In some embodiments, the first antigen is VSTM1 and the second antigen is selected from the group consisting of MS4A3, LAT2, MLC1, CD131, GAPT, PRAM1, SLC22A16, SLC17A9, SPNS3, FLT3, CD33, CLEC12A, ADGRE2, IL3RA, CD117, CD93, IL1RAP, CD244, CCR1, LILRB2, PIEZO1, CD38, EMB, MYADM, LILRA2, CD300LF, and CD70.

In some embodiments, the first antigen is LAT2 and the second antigen is selected from the group consisting of MS4A3, VSTM1, MLC1, CD131, GAPT, PRAM1, SLC22A16, SLC17A9, SPNS3, FLT3, CD33, CLEC12A, ADGRE2, IL3RA, CD117, CD93, IL1RAP, CD244, CCR1, LILRB2, PIEZO1, CD38, EMB, MYADM, LILRA2, CD300LF, and CD70.

In some embodiments, the first antigen is MLC1 and the second antigen is selected from the group consisting of MS4A3, VSTM1, LAT2, CD131, GAPT, PRAM1, SLC22A16, SLC17A9, SPNS3, FLT3, CD33, CLEC12A, ADGRE2, IL3RA, CD117, CD93, IL1RAP, CD244, CCR1, LILRB2, PIEZO1, CD38, EMB, MYADM, LILRA2, CD300LF, and CD70.

In some embodiments, the first antigen is CD131 and the second antigen is selected from the group consisting of MS4A3, VSTM1, LAT2, MLC1, GAPT, PRAM1, SLC22A16, SLC17A9, SPNS3, FLT3, CD33, CLEC12A, ADGRE2, IL3RA, CD117, CD93, IL1RAP, CD244, CCR1, LILRB2, PIEZO1, CD38, EMB, MYADM, LILRA2, CD300LF, and CD70.

In some embodiments, the first antigen is GAPT and the second antigen is selected from the group consisting of MS4A3, VSTM1, LAT2, MLC1, CD131, PRAM1, SLC22A16, SLC17A9, SPNS3, FLT3, CD33, CLEC12A, ADGRE2, IL3RA, CD117, CD93, IL1RAP, CD244, CCR1, LILRB2, PIEZO1, CD38, EMB, MYADM, LILRA2, CD300LF, and CD70.

In some embodiments, the first antigen is PRAM1 and the second antigen is selected from the group consisting of MS4A3, VSTM1, LAT2, MLC1, CD131, GAPT, SLC22A16, SLC17A9, SPNS3, FLT3, CD33, CLEC12A, ADGRE2, IL3RA, CD117, CD93, IL1RAP, CD244, CCR1, LILRB2, PIEZO1, CD38, EMB, MYADM, LILRA2, CD300LF, and CD70.

In some embodiments, the first antigen is SLC22A16 and the second antigen is selected from the group consisting of MS4A3, VSTM1, LAT2, MLC1, CD131, GAPT, PRAM1, SLC17A9, SPNS3, FLT3, CD33, CLEC12A, ADGRE2, IL3RA, CD117, CD93, IL1RAP, CD244, CCR1, LILRB2, PIEZO1, CD38, EMB, MYADM, LILRA2, CD300LF, and CD70.

In some embodiments, the first antigen is SLC17A9 and the second antigen is selected from the group consisting of MS4A3, VSTM1, LAT2, MLC1, CD131, GAPT, PRAM1, SLC22A16, SPNS3, FLT3, CD33, CLEC12A, ADGRE2, IL3RA, CD117, CD93, IL1RAP, CD244, CCR1, LILRB2, PIEZO1, CD38, EMB, MYADM, LILRA2, CD300LF, and CD70.

In some embodiments, the first antigen is SPNS3 and the second antigen is selected from the group consisting of MS4A3, VSTM1, LAT2, MLC1, CD131, GAPT, PRAM1, SLC22A16, SLC17A9, FLT3, CD33, CLEC12A, ADGRE2, IL3RA, CD117, CD93, IL1RAP, CD244, CCR1, LILRB2, PIEZO1, CD38, EMB, MYADM, LILRA2, CD300LF, and CD70.

In some embodiments, the first antigen is FLT3. In some embodiments, the antigen-binding domain that binds to the first antigen comprises a heavy chain variable domain (VH) and a light chain variable domain (VL) selected from the group consisting of: (a) a VH comprising the amino acid sequence of SEQ ID NO: 1 or a sequence at least 90% identical thereto and a VL comprising the amino acid sequence of SEQ. ID NO: 2 or a sequence at least 90% identical thereto; (b) a VH comprising the amino acid sequence of SEQ ID NO: 3 or a sequence at least 90% identical thereto and a VL comprising the amino acid sequence of SEQ. ID NO: 4 or a sequence at least 90% identical thereto; (c) a VH comprising the amino acid sequence of SEQ ID NO: 5 or a sequence at least 90% identical thereto and a VL comprising the amino acid sequence of SEQ. ID NO: 6 or a sequence at least 90% identical thereto; (d) a VH comprising the amino acid sequence of SEQ ID NO: 7 or a sequence at least 90% identical thereto and a VL comprising the amino acid sequence of SEQ. ID NO: 8 or a sequence at least 90% identical thereto; (e) a VH comprising the amino acid sequence of SEQ ID NO: 9 or a sequence at least 90% identical thereto and a VL comprising the amino acid sequence of SEQ. ID NO: 10 or a sequence at least 90% identical thereto; (f) a VH comprising the amino acid sequence of SEQ ID NO: 11 or a sequence at least 90% identical thereto and a VL comprising the amino acid sequence of SEQ. ID NO: 12 or a sequence at least 90% identical thereto; (g) a VH comprising the amino acid sequence of SEQ ID NO: 13 or a sequence at least 90% identical thereto and a VL comprising the amino acid sequence of SEQ. ID NO: 14 or a sequence at least 90% identical thereto; and (h) a VH comprising the amino acid sequence of SEQ ID NO: 15 or a sequence at least 90% identical thereto and a VL comprising the amino acid sequence of SEQ. ID NO: 16 or a sequence at least 90% identical thereto. In some embodiments, the antigen-binding domain that binds to the first antigen comprises a heavy chain variable domain (VH) comprising the amino acid sequence of SEQ ID NO: 1 or a sequence at least 90% identical thereto and a light chain variable domain (VL) comprising the amino acid sequence of SEQ. ID NO: 2 or a sequence at least 90% identical thereto. In some embodiments, the antigen-binding domain that binds to the first antigen comprises a heavy chain variable domain (VH) comprising the amino acid sequence of SEQ ID NO: 3 or a sequence at least 90% identical thereto and a light chain variable domain (VL) comprising the amino acid sequence of SEQ. ID NO: 4 or a sequence at least 90% identical thereto. In some embodiments, the antigen-binding domain that binds to the first antigen comprises a heavy chain variable domain (VH) comprising the amino acid sequence of SEQ ID NO: 5 or a sequence at least 90% identical thereto and a light chain variable domain (VL) comprising the amino acid sequence of SEQ. ID NO: 6 or a sequence at least 90% identical thereto. In some embodiments, the antigen-binding domain that binds to the first antigen comprises a heavy chain variable domain (VH) comprising the amino acid sequence of SEQ ID NO: 7 or a sequence at least 90% identical thereto and a light chain variable domain (VL) comprising the amino acid sequence of SEQ. ID NO: 8 or a sequence at least 90% identical thereto. In some embodiments, the antigen-binding domain that binds to the first antigen comprises a heavy chain variable domain (VH) comprising the amino acid sequence of SEQ ID NO: 9 or a sequence at least 90% identical thereto and a light chain variable domain (VL) comprising the amino acid sequence of SEQ. ID NO: 10 or a sequence at least 90% identical thereto. In some embodiments, the antigen-binding domain that binds to the first antigen comprises a heavy chain variable domain (VH) comprising the amino acid sequence of SEQ ID NO: 11 or a sequence at least 90% identical thereto and a light chain variable domain (VL) comprising the amino acid sequence of SEQ. ID NO: 12 or a sequence at least 90% identical thereto. In some embodiments, the antigen-binding domain that binds to the first antigen comprises a heavy chain variable domain (VH) comprising the amino acid sequence of SEQ ID NO: 13 or a sequence at least 90% identical thereto and a light chain variable domain (VL) comprising the amino acid sequence of SEQ. ID NO: 14 or a sequence at least 90% identical thereto. In some embodiments, the antigen-binding domain that binds to the first antigen comprises a heavy chain variable domain (VH) comprising the amino acid sequence of SEQ ID NO: 15 or a sequence at least 90% identical thereto and a light chain variable domain (VL) comprising the amino acid sequence of SEQ. ID NO: 16 or a sequence at least 90% identical thereto. In some embodiments that may be combined with any of the preceding embodiments, the second antigen is CD33. In some embodiments that may be combined with any of the preceding embodiments, the antigen-binding domain that binds to the second antigen comprises a heavy chain variable domain (VH) and a light chain variable domain (VL) selected from the group consisting of: (a) a VH comprising the amino acid sequence of SEQ ID NO: 17 or a sequence at least 90% identical thereto and a VL comprising the amino acid sequence of SEQ. ID NO: 18 or a sequence at least 90% identical thereto; and (b) a VH comprising the amino acid sequence of SEQ ID NO: 19 or a sequence at least 90% identical thereto and a VL comprising the amino acid sequence of SEQ. ID NO: 20 or a sequence at least 90% identical thereto. In some embodiments that may be combined with any of the preceding embodiments, the antigen-binding domain that binds to the second antigen comprises a heavy chain variable domain (VH) comprising the amino acid sequence of SEQ ID NO: 17 or a sequence at least 90% identical thereto and a light chain variable domain (VL) comprising the amino acid sequence of SEQ. ID NO: 18 or a sequence at least 90% identical thereto. In some embodiments that may be combined with any of the preceding embodiments, the antigen-binding domain that binds to the second antigen comprises a heavy chain variable domain (VH) comprising the amino acid sequence of SEQ ID NO: 19 or a sequence at least 90% identical thereto and a light chain variable domain (VL) comprising the amino acid sequence of SEQ. ID NO: 20 or a sequence at least 90% identical thereto. In some embodiments that may be combined with any of the preceding embodiments, the second antigen is CLECL12A. In some embodiments that may be combined with any of the preceding embodiments, the antigen-binding domain that binds to the second antigen comprises a heavy chain variable domain (VH) and a light chain variable domain (VL) selected from the group consisting of: (a) a VH comprising the amino acid sequence of SEQ ID NO: 21 or a sequence at least 90% identical thereto and a VL comprising the amino acid sequence of SEQ. ID NO: 22 or a sequence at least 90% identical thereto; (b) a VH comprising the amino acid sequence of SEQ ID NO: 23 or a sequence at least 90% identical thereto and a VL comprising the amino acid sequence of SEQ. ID NO: 24 or a sequence at least 90% identical thereto; and (c) a VH comprising the amino acid sequence of SEQ ID NO: 25 or a sequence at least 90% identical thereto and a VL comprising the amino acid sequence of SEQ. ID NO: 26 or a sequence at least 90% identical thereto. In some embodiments that may be combined with any of the preceding embodiments, the antigen-binding domain that binds to the second antigen comprises a heavy chain variable domain (VH) comprising the amino acid sequence of SEQ ID NO: 21 or a sequence at least 90% identical thereto and a light chain variable domain (VL) comprising the amino acid sequence of SEQ. ID NO: 22 or a sequence at least 90% identical thereto. some embodiments that may be combined with any of the preceding embodiments, the antigen-binding domain that binds to the second antigen comprises a heavy chain variable domain (VH) comprising the amino acid sequence of SEQ ID NO: 23 or a sequence at least 90% identical thereto and a light chain variable domain (VL) comprising the amino acid sequence of SEQ. ID NO: 24 or a sequence at least 90% identical thereto. some embodiments that may be combined with any of the preceding embodiments, the antigen-binding domain that binds to the second antigen comprises a heavy chain variable domain (VH) comprising the amino acid sequence of SEQ ID NO: 25 or a sequence at least 90% identical thereto and a light chain variable domain (VL) comprising the amino acid sequence of SEQ. ID NO: 26 or a sequence at least 90% identical thereto.

In some embodiments, the first antigen is CLECL12A. In some embodiments, the antigen-binding domain that binds to the first antigen comprises a heavy chain variable domain (VH) and a light chain variable domain (VL) selected from the group consisting of: (a) a VH comprising the amino acid sequence of SEQ ID NO: 21 or a sequence at least 90% identical thereto and a VL comprising the amino acid sequence of SEQ. ID NO: 22 or a sequence at least 90% identical thereto; (b) a VH comprising the amino acid sequence of SEQ ID NO: 23 or a sequence at least 90% identical thereto and a VL comprising the amino acid sequence of SEQ. ID NO: 24 or a sequence at least 90% identical thereto; and (c) a VH comprising the amino acid sequence of SEQ ID NO: 25 or a sequence at least 90% identical thereto and a VL comprising the amino acid sequence of SEQ. ID NO: 26 or a sequence at least 90% identical thereto. In some embodiments, the antigen-binding domain that binds to the first antigen comprises a heavy chain variable domain (VH) comprising the amino acid sequence of SEQ ID NO: 21 or a sequence at least 90% identical thereto and a light chain variable domain (VL) comprising the amino acid sequence of SEQ. ID NO: 22 or a sequence at least 90% identical thereto. In some embodiments, the antigen-binding domain that binds to the first antigen comprises a heavy chain variable domain (VH) comprising the amino acid sequence of SEQ ID NO: 23 or a sequence at least 90% identical thereto and a light chain variable domain (VL) comprising the amino acid sequence of SEQ. ID NO: 24 or a sequence at least 90% identical thereto. In some embodiments, the antigen-binding domain that binds to the first antigen comprises a heavy chain variable domain (VH) comprising the amino acid sequence of SEQ ID NO: 25 or a sequence at least 90% identical thereto and a light chain variable domain (VL) comprising the amino acid sequence of SEQ. ID NO: 26 or a sequence at least 90% identical thereto. In some embodiments that may be combined with any of the preceding embodiments, the second antigen is CD33. In some embodiments that may be combined with any of the preceding embodiments, the antigen-binding domain that binds to the second antigen comprises a heavy chain variable domain (VH) and a light chain variable domain (VL) selected from the group consisting of: (a) a VH comprising the amino acid sequence of SEQ ID NO: 17 or a sequence at least 90% identical thereto and a VL comprising the amino acid sequence of SEQ. ID NO: 18 or a sequence at least 90% identical thereto; and (b) a VH comprising the amino acid sequence of SEQ ID NO: 19 or a sequence at least 90% identical thereto and a VL comprising the amino acid sequence of SEQ. ID NO: 20 or a sequence at least 90% identical thereto. In some embodiments that may be combined with any of the preceding embodiments, the antigen-binding domain that binds to the second antigen comprises a heavy chain variable domain (VH) comprising the amino acid sequence of SEQ ID NO: 17 or a sequence at least 90% identical thereto and a light chain variable domain (VL) comprising the amino acid sequence of SEQ. ID NO: 18 or a sequence at least 90% identical thereto. In some embodiments that may be combined with any of the preceding embodiments, the antigen-binding domain that binds to the second antigen comprises a heavy chain variable domain (VH) comprising the amino acid sequence of SEQ ID NO: 19 or a sequence at least 90% identical thereto and a light chain variable domain (VL) comprising the amino acid sequence of SEQ. ID NO: 20 or a sequence at least 90% identical thereto.

In some embodiments, the cell is an immunoresponsive cell. In some embodiments, binding of the first chimeric receptor to the first antigen is capable of activating the immunoresponsive cell. In some embodiments, binding of the second chimeric receptor to the second antigen is capable of stimulating the immunoresponsive cell.

In some embodiments, binding of the first chimeric receptor to the first antigen and binding of the second chimeric receptor to the second antigen are required for activating the immunoresponsive cell.

In some embodiments, the immunoresponsive cell exhibits a greater degree of cytolytic activity against cells that are positive for both the first antigen and the second antigen as compared to against cells that are singly positive for the first antigen.

In some embodiments, binding of the first chimeric receptor to the first antigen or binding of the second chimeric receptor to the second antigen is capable of activating the immunoresponsive cell.

In some embodiments, the first chimeric receptor binds to the first antigen with a low binding affinity. In some embodiments, the first chimeric receptor binds to the first antigen with a binding affinity that is lower than the binding affinity with which the second chimeric receptor binds to the second antigen. In some embodiments, the first chimeric receptor binds to the first antigen with a low binding avidity.

In some embodiments, the first chimeric receptor and/or the second chimeric receptor is a chimeric T cell receptor or a chimeric antigen receptor (CAR). In some embodiments, the first chimeric receptor and/or the second chimeric receptor is a CAR. In some embodiments, the first chimeric receptor is a first CAR and the second chimeric receptor is a second CAR.

In some embodiments, the CAR comprises one or more intracellular signaling domains, and the one or more intracellular signaling domains are selected from the group consisting of a CD3zeta-chain intracellular signaling domain, a CD97 intracellular signaling domain, a CD11a-CD18 intracellular signaling domain, a CD2 intracellular signaling domain, an ICOS intracellular signaling domain, a CD27 intracellular signaling domain, a CD154 intracellular signaling domain, a CD8 intracellular signaling domain, an OX40 intracellular signaling domain, a 4-1BB intracellular signaling domain, a CD28 intracellular signaling domain, a ZAP40 intracellular signaling domain, a CD30 intracellular signaling domain, a GITR intracellular signaling domain, an HVEM intracellular signaling domain, a DAP10 intracellular signaling domain, a DAP12 intracellular signaling domain, and a MyD88 intracellular signaling domain.

In some embodiments, the one or more intracellular signaling domains of the first CAR are different from the one or more intracellular signaling domains of the second CAR.

In some embodiments, the first CAR and the second CAR each comprise a CD3zeta-chain intracellular signaling domain.

In some embodiments, the first CAR and the second CAR each further comprises an additional intracellular signaling domain selected from the group consisting of a CD97 intracellular signaling domain, a CD11a-CD18 intracellular signaling domain, a CD2 intracellular signaling domain, an ICOS intracellular signaling domain, a CD27 intracellular signaling domain, a CD154 intracellular signaling domain, a CD8 intracellular signaling domain, an OX40 intracellular signaling domain, a 4-1BB intracellular signaling domain, a CD28 intracellular signaling domain, a ZAP40 intracellular signaling domain, a CD30 intracellular signaling domain, a GITR intracellular signaling domain, an HVEM intracellular signaling domain, a DAP10 intracellular signaling domain, a DAP12 intracellular signaling domain, and a MyD88 intracellular signaling domain.

In some embodiments, the additional intracellular signaling domain of the first CAR is different from the additional intracellular signaling domain of the second CAR.

In some embodiments, each CAR comprises a transmembrane domain, and the transmembrane domain is selected from the group consisting of a CD8 transmembrane domain, a CD28 transmembrane domain a CD3zeta-chain transmembrane domain, a CD4 transmembrane domain, a 4-1BB transmembrane domain, an OX40 transmembrane domain, an ICOS transmembrane domain, a CTLA-4 transmembrane domain, a PD-1 transmembrane domain, a LAG-3 transmembrane domain, a 2B4 transmembrane domain, and a BTLA transmembrane domain.

In some embodiments, the transmembrane domain of the first CAR is different from the transmembrane domain of the second CAR.

In some embodiments, each CAR comprises a spacer region between the antigen-binding domain and the transmembrane domain, and the spacer region has an amino acid sequence selected from the group consisting of SEQ ID NOs: 55-64.

In some embodiments, the antigen-binding domain of the first chimeric receptor and/or the second chimeric receptor comprises an antibody, an antigen-binding fragment of an antibody, a F(ab) fragment, a F(ab') fragment, a single chain variable fragment (scFv), or a single-domain antibody (sdAb). In some embodiments, the antigen-binding domain comprises a single chain variable fragment (scFv). In some embodiments, the scFv comprises a heavy chain variable domain (VH) and a light chain variable domain (VL). In some embodiments, the VH and VL are separated by a peptide linker. In some embodiments, the peptide linker comprises the amino acid sequence of SEQ ID NO: 27. In some embodiments, the scFv comprises the structure VH-L-VL or VL-L-VH, wherein VH is the heavy chain variable domain, L is the peptide linker, and VL is the light chain variable domain.

In some embodiments, the first chimeric receptor is recombinantly expressed.

In some embodiments, the first chimeric receptor is expressed from a vector, or a selected locus from the genome of the cell.

In some embodiments, the second chimeric receptor is recombinantly expressed.

In some embodiments, the second chimeric receptor is expressed from a vector, or a selected locus from the genome of the cell.

In some embodiments, the cell further comprises an inhibitory chimeric receptor comprising an antigen-binding domain.

In some embodiments, the inhibitory chimeric receptor inhibits one or more activities of the cell.

In some embodiments, the inhibitory chimeric receptor binds an antigen that is not expressed on a tumor cell.

In some embodiments, the inhibitory chimeric receptor binds an antigen that is expressed on a non-tumor cell.

In some embodiments, the inhibitory chimeric receptor binds an antigen that is expressed on a non-tumor cell derived from a tissue selected from the group consisting of brain, neuronal tissue, endocrine, bone, bone marrow, immune system, muscle, lung, liver, gallbladder, pancreas, gastrointestinal tract, kidney, urinary bladder, male reproductive organs, female reproductive organs, adipose, soft tissue, and skin.

In some embodiments, the tumor cell is an acute myeloid leukemia (AML) cell.

In some embodiments, the inhibitory chimeric receptor comprises an enzymatic inhibitory domain.

In some embodiments, the enzymatic inhibitory domain inhibits immune receptor activation when proximal to an immune receptor.

In some embodiments, the enzymatic inhibitory domain comprises an enzyme catalytic domain.

In some embodiments, the enzyme catalytic domain is derived from an enzyme selected from the group consisting of CSK, SHP-1, PTEN, CD45, CD148, PTP-MEG1, PTP-PEST, c-CBL, CBL-b, PTPN22, LAR, PTPH1, SHIP-1, and RasGAP.

In some embodiments, the inhibitory chimeric receptor further comprises one or more intracellular inhibitory co-signaling domains.

In some embodiments, the one or more intracellular inhibitory co-signaling domains are selected from the group consisting of PD-1, CTLA4, TIGIT, LAIR1, GRB-2, Dok-1, Dok-2, SLAP, LAG3, HAVR, BTLA, GITR, and PD-L1.

In some embodiments, the inhibitory chimeric receptor binds an antigen selected from the group consisting of EMCN, JAM2, MS4A15, C4BPA, TRPM1, SCTR, SLC2A2, KCNQ2, PERP, WLS, and FFAR2.

In some embodiments, the cell is selected from the group consisting of a T cell, a Natural Killer (NK) cell, a cytotoxic T lymphocyte (CTL), a regulatory T cell, a Natural Killer T (NKT) cell, a myeloid cell, a macrophage, a human embryonic stem cell (ESC), an ESC-derived cell, a pluripotent stem cell, and induced pluripotent stem cell (iPSC), and an iPSC-derived cell.

In some embodiments, the cell is autologous.

In some embodiments, the cell is allogeneic.

In another aspect, provided herein are chimeric receptors comprising two or more antigen-binding domains, wherein each antigen-binding domain binds to an antigen selected from the group consisting of the antigens listed in Table 1 or the two or more antigen-bonding domains bind to an antigen pair selected from the group consisting of the antigen pairs listed in Table 3, wherein each antigen-binding domain binds to a different antigen.

In another aspect, provided herein are chimeric receptors comprising two or more antigen-binding domains, wherein each antigen-binding domain binds to an antigen selected from the group consisting of MS4A3, VSTM1, LAT2, MLC1, CD131, GAPT, PRAM1, SLC22A16, SLC17A9, SPNS3, FLT3, CD33, CLEC12A, ADGRE2, IL3RA, CD117, CD93, IL1RAP, CD244, CCR1, LILRB2, PIEZO1, CD38, EMB, MYADM, LILRA2, CD300LF, and CD70, wherein each antigen-binding domain binds to a different antigen.

In some embodiments, one antigen-binding domain binds MS4A3 and a second antigen-binding domain binds to an antigen selected from the group consisting of VSTM1, LAT2, MLC1, CD131, GAPT, PRAM1, SLC22A16, SLC17A9, SPNS3, FLT3, CD33, CLEC12A, ADGRE2, IL3RA, CD117, CD93, IL1RAP, CD244, CCR1, LILRB2, PIEZO1, CD38, EMB, MYADM, LILRA2, CD300LF, and CD70.

In some embodiments, one antigen-binding domain binds VSTM1 and a second antigen-binding domain binds to an antigen selected from the group consisting of MS4A3, LAT2, MLC1, CD131, GAPT, PRAM1, SLC22A16, SLC17A9, SPNS3, FLT3, CD33, CLEC12A, ADGRE2, IL3RA, CD117, CD93, IL1RAP, CD244, CCR1, LILRB2, PIEZO1, CD38, EMB, MYADM, LILRA2, CD300LF, and CD70.

In some embodiments, one antigen-binding domain binds LAT2 and a second antigen-binding domain binds to an antigen selected from the group consisting of MS4A3, VSTM1, MLC1, CD131, GAPT, PRAM1, SLC22A16, SLC17A9, SPNS3, FLT3, CD33, CLEC12A, ADGRE2, IL3RA, CD117, CD93, IL1RAP, CD244, CCR1, LILRB2, PIEZO1, CD38, EMB, MYADM, LILRA2, CD300LF, and CD70.

In some embodiments, one antigen-binding domain binds MLC1 and a second antigen-binding domain binds to an antigen selected from the group consisting of MS4A3, VSTM1, LAT2, CD131, GAPT, PRAM1, SLC22A16, SLC17A9, SPNS3, FLT3, CD33, CLEC12A, ADGRE2, IL3RA, CD117, CD93, IL1RAP, CD244, CCR1, LILRB2, PIEZO1, CD38, EMB, MYADM, LILRA2, CD300LF, and CD70.

In some embodiments, one antigen-binding domain binds CD131 and a second antigen-binding domain binds to an antigen selected from the group consisting of MS4A3, VSTM1, LAT2, MLC1, GAPT, PRAM1, SLC22A16, SLC17A9, SPNS3, FLT3, CD33, CLEC12A, ADGRE2, IL3RA, CD117, CD93, IL1RAP, CD244, CCR1, LILRB2, PIEZO1, CD38, EMB, MYADM, LILRA2, CD300LF, and CD70.

In some embodiments, one antigen-binding domain binds GAPT and a second antigen-binding domain binds to an antigen selected from the group consisting of MS4A3, VSTM1, LAT2, MLC1, CD131, PRAM1, SLC22A16, SLC17A9, SPNS3, FLT3, CD33, CLEC12A, ADGRE2, IL3RA, CD117, CD93, IL1RAP, CD244, CCR1, LILRB2, PIEZO1, CD38, EMB, MYADM, LILRA2, CD300LF, and CD70.

In some embodiments, one antigen-binding domain binds PRAM1 and a second antigen-binding domain binds to an antigen selected from the group consisting of MS4A3, VSTM1, LAT2, MLC1, CD131, GAPT, SLC22A16, SLC17A9, SPNS3, FLT3, CD33, CLEC12A, ADGRE2, IL3RA, CD117, CD93, IL1RAP, CD244, CCR1, LILRB2, PIEZO1, CD38, EMB, MYADM, LILRA2, CD300LF, and CD70.

In some embodiments, one antigen-binding domain binds SLC22A16 and a second antigen-binding domain binds to an antigen selected from the group consisting of MS4A3, VSTM1, LAT2, MLC1, CD131, GAPT, PRAM1, SLC17A9, SPNS3, FLT3, CD33, CLEC12A, ADGRE2, IL3RA, CD117, CD93, IL1RAP, CD244, CCR1, LILRB2, PIEZO1, CD38, EMB, MYADM, LILRA2, CD300LF, and CD70.

In some embodiments, one antigen-binding domain binds SLC17A9 and a second antigen-binding domain binds to an antigen selected from the group consisting of MS4A3, VSTM1, LAT2, MLC1, CD131, GAPT, PRAM1, SLC22A16, SPNS3, FLT3, CD33, CLEC12A, ADGRE2, IL3RA, CD117, CD93, IL1RAP, CD244, CCR1, LILRB2, PIEZO1, CD38, EMB, MYADM, LILRA2, CD300LF, and CD70.

In some embodiments, one antigen-binding domain binds SPNS3 and a second antigen-binding domain binds to an antigen selected from the group consisting of MS4A3, VSTM1, LAT2, MLC1, CD131, GAPT, PRAM1, SLC22A16, SLC17A9, FLT3, CD33, CLEC12A, ADGRE2, IL3RA, CD117, CD93, IL1RAP, CD244, CCR1, LILRB2, PIEZO1, CD38, EMB, MYADM, LILRA2, CD300LF, and CD70.

In some embodiments, one antigen binding domain binds FLT3. In some embodiments, the antigen-binding domain that binds FLT3 comprises a heavy chain variable domain (VH) and a light chain variable domain (VL) selected from the group consisting of: (a) a VH comprising the amino acid sequence of SEQ ID NO: 1 or a sequence at least 90% identical thereto and a VL comprising the amino acid sequence of SEQ. ID NO: 2 or a sequence at least 90% identical thereto; (b) a VH comprising the amino acid sequence of SEQ ID NO: 3 or a sequence at least 90% identical thereto and a VL comprising the amino acid sequence of SEQ. ID NO: 4 or a sequence at least 90% identical thereto; (c) a VH comprising the amino acid sequence of SEQ ID NO: 5 or a sequence at least 90% identical thereto and a VL comprising the amino acid sequence of SEQ. ID NO: 6 or a sequence at least 90% identical thereto; (d) a VH comprising the amino acid sequence of SEQ ID NO: 7 or a sequence at least 90% identical thereto and a VL comprising the amino acid sequence of SEQ. ID NO: 8 or a sequence at least 90% identical thereto; (e) a VH comprising the amino acid sequence of SEQ ID NO: 9 or a sequence at least 90% identical thereto and a VL comprising the amino acid sequence of SEQ. ID NO: 10 or a sequence at least 90% identical thereto; (f) a VH comprising the amino acid sequence of SEQ ID NO: 11 or a sequence at least 90% identical thereto and a VL comprising the amino acid sequence of SEQ. ID NO: 12 or a sequence at least 90% identical thereto; (g) a VH comprising the amino acid sequence of SEQ ID NO: 13 or a sequence at least 90% identical thereto and a VL comprising the amino acid sequence of SEQ. ID NO: 14 or a sequence at least 90% identical thereto; and (h) a VH comprising the amino acid sequence of SEQ ID NO: 15 or a sequence at least 90% identical thereto and a VL comprising the amino acid sequence of SEQ. ID NO: 16 or a sequence at least 90% identical thereto. In some embodiments, the antigen-binding domain that binds FLT3 comprises a heavy chain variable domain (VH) comprising the amino acid sequence of SEQ ID NO: 1 or a sequence at least 90% identical thereto and a light chain variable domain (VL) comprising the amino acid sequence of SEQ. ID NO: 2 or a sequence at least 90% identical thereto. In some embodiments, the antigen-binding domain that binds FLT3 comprises a heavy chain variable domain (VH) comprising the amino acid sequence of SEQ ID NO: 3 or a sequence at least 90% identical thereto and a light chain variable domain (VL) comprising the amino acid sequence of SEQ. ID NO: 4 or a sequence at least 90% identical thereto. In some embodiments, the antigen-binding domain that binds FLT3 comprises a heavy chain variable domain (VH) comprising the amino acid sequence of SEQ ID NO: 5 or a sequence at least 90% identical thereto and a light chain variable domain (VL) comprising the amino acid sequence of SEQ. ID NO: 6 or a sequence at least 90% identical thereto. In some embodiments, the antigen-binding domain that binds FLT3 comprises a heavy chain variable domain (VH) comprising the amino acid sequence of SEQ ID NO: 7 or a sequence at least 90% identical thereto and a light chain variable domain (VL) comprising the amino acid sequence of SEQ. ID NO: 8 or a sequence at least 90% identical thereto. In some embodiments, the antigen-binding domain that binds FLT3 comprises a heavy chain variable domain (VH) comprising the amino acid sequence of SEQ ID NO: 9 or a sequence at least 90% identical thereto and a light chain variable domain (VL) comprising the amino acid sequence of SEQ. ID NO: 10 or a sequence at least 90% identical thereto. In some embodiments, the antigen-binding domain that binds FLT3 comprises a heavy chain variable domain (VH) comprising the amino acid sequence of SEQ ID NO: 11 or a sequence at least 90% identical thereto and a light chain variable domain (VL) comprising the amino acid sequence of SEQ. ID NO: 12 or a sequence at least 90% identical thereto. In some embodiments, the antigen-binding domain that binds FLT3 comprises a heavy chain variable domain (VH) comprising the amino acid sequence of SEQ ID NO: 13 or a sequence at least 90% identical thereto and a light chain variable domain (VL) comprising the amino acid sequence of SEQ. ID NO: 14 or a sequence at least 90% identical thereto. In some embodiments, the antigen-binding domain that binds FLT3 comprises a heavy chain variable domain (VH) comprising the amino acid sequence of SEQ ID NO: 15 or a sequence at least 90% identical thereto and a light chain variable domain (VL) comprising the amino acid sequence of SEQ. ID NO: 16 or a sequence at least 90% identical thereto. In some embodiments that may be combined with any of the preceding embodiments, a second antigen-binding domain binds CD33. In some embodiments that may be combined with any of the preceding embodiments, the second antigen-binding domain that binds CD33 comprises a heavy chain variable domain (VH) and a light chain variable domain (VL) selected from the group consisting of: (a) a VH comprising the amino acid sequence of SEQ ID NO: 17 or a sequence at least 90% identical thereto and a VL comprising the amino acid sequence of SEQ. ID NO: 18 or a sequence at least 90% identical thereto; and (b) a VH comprising the amino acid sequence of SEQ ID NO: 19 or a sequence at least 90% identical thereto and a VL comprising the amino acid sequence of SEQ. ID NO: 20 or a sequence at least 90% identical thereto. In some embodiments that may be combined with any of the preceding embodiments, the second antigen-binding domain that binds CD33 comprises a heavy chain variable domain (VH) comprising the amino acid sequence of SEQ ID NO: 17 or a sequence at least 90% identical thereto and a light chain variable domain (VL) comprising the amino acid sequence of SEQ. ID NO: 18 or a sequence at least 90% identical thereto. In some embodiments that may be combined with any of the preceding embodiments, the second antigen-binding domain that binds CD33 comprises a heavy chain variable domain (VH) comprising the amino acid sequence of SEQ ID NO: 19 or a sequence at least 90% identical thereto and a light chain variable domain (VL) comprising the amino acid sequence of SEQ. ID NO: 20 or a sequence at least 90% identical thereto. In some embodiments that may be combined with any of the preceding embodiments, a second antigen-binding domain binds CLEC12A. In some embodiments that may be combined with any of the preceding embodiments, the second antigen-binding domain that binds CLECL12A comprises a heavy chain variable domain (VH) and a light chain variable domain (VL) selected from the group consisting of: (a) a VH comprising the amino acid sequence of SEQ ID NO: 21 or a sequence at least 90% identical thereto and a VL comprising the amino acid sequence of SEQ. ID NO: 22 or a sequence at least 90% identical thereto; (b) a VH comprising the amino acid sequence of SEQ ID NO: 23 or a sequence at least 90% identical thereto and a VL comprising the amino acid sequence of SEQ. ID NO: 24 or a sequence at least 90% identical thereto; and (c) a VH comprising the amino acid sequence of SEQ ID NO: 25 or a sequence at least 90% identical thereto and a VL comprising the amino acid sequence of SEQ. ID NO: 26 or a sequence at least 90% identical thereto. In some embodiments that may be combined with any of the preceding embodiments, the second antigen-binding domain that binds CLECL12A comprises a heavy chain variable domain (VH) comprising the amino acid sequence of SEQ ID NO: 21 or a sequence at least 90% identical thereto and a light chain variable domain (VL) comprising the amino acid sequence of SEQ. ID NO: 22 or a sequence at least 90% identical thereto. some embodiments that may be combined with any of the preceding embodiments, the second antigen-binding domain that binds CLECL12A comprises a heavy chain variable domain (VH) comprising the amino acid sequence of SEQ ID NO: 23 or a sequence at least 90% identical thereto and a light chain variable domain (VL) comprising the amino acid sequence of SEQ. ID NO: 24 or a sequence at least 90% identical thereto. some embodiments that may be combined with any of the preceding embodiments, the second antigen-binding domain that binds CLECL12A comprises a heavy chain variable domain (VH) comprising the amino acid sequence of SEQ ID NO: 25 or a sequence at least 90% identical thereto and a light chain variable domain (VL) comprising the amino acid sequence of SEQ. ID NO: 26 or a sequence at least 90% identical thereto.

In some embodiments, one antigen binding domain binds CLEC12A. In some embodiments, the antigen-binding domain that binds CLEC12A comprises a heavy chain variable domain (VH) and a light chain variable domain (VL) selected from the group consisting of: (a) a VH comprising the amino acid sequence of SEQ ID NO: 21 or a sequence at least 90% identical thereto and a VL comprising the amino acid sequence of SEQ. ID NO: 22 or a sequence at least 90% identical thereto; (b) a VH comprising the amino acid sequence of SEQ ID NO: 23 or a sequence at least 90% identical thereto and a VL comprising the amino acid sequence of SEQ. ID NO: 24 or a sequence at least 90% identical thereto; and (c) a VH comprising the amino acid sequence of SEQ ID NO: 25 or a sequence at least 90% identical thereto and a VL comprising the amino acid sequence of SEQ. ID NO: 26 or a sequence at least 90% identical thereto. In some embodiments, the antigen-binding domain that binds CLEC12A comprises a heavy chain variable domain (VH) comprising the amino acid sequence of SEQ ID NO: 21 or a sequence at least 90% identical thereto and a light chain variable domain (VL) comprising the amino acid sequence of SEQ. ID NO: 22 or a sequence at least 90% identical thereto. In some embodiments, the antigen-binding domain that binds CLEC12A comprises a heavy chain variable domain (VH) comprising the amino acid sequence of SEQ ID NO: 23 or a sequence at least 90% identical thereto and a light chain variable domain (VL) comprising the amino acid sequence of SEQ. ID NO: 24 or a sequence at least 90% identical thereto. In some embodiments, the antigen-binding domain that binds CLEC12A comprises a heavy chain variable domain (VH) comprising the amino acid sequence of SEQ ID NO: 25 or a sequence at least 90% identical thereto and a light chain variable domain (VL) comprising the amino acid sequence of SEQ. ID NO: 26 or a sequence at least 90% identical thereto. In some embodiments that may be combined with any of the preceding embodiments, a second antigen-binding domain binds CD33. In some embodiments that may be combined with any of the preceding embodiments, the second antigen-binding domain that binds CD33 comprises a heavy chain variable domain (VH) and a light chain variable domain (VL) selected from the group consisting of: (a) a VH comprising the amino acid sequence of SEQ ID NO: 17 or a sequence at least 90% identical thereto and a VL comprising the amino acid sequence of SEQ. ID NO: 18 or a sequence at least 90% identical thereto; and (b) a VH comprising the amino acid sequence of SEQ ID NO: 19 or a sequence at least 90% identical thereto and a VL comprising the amino acid sequence of SEQ. ID NO: 20 or a sequence at least 90% identical thereto. In some embodiments that may be combined with any of the preceding embodiments, the second antigen-binding domain that binds CD33 comprises a heavy chain variable domain (VH) comprising the amino acid sequence of SEQ ID NO: 17 or a sequence at least 90% identical thereto and a light chain variable domain (VL) comprising the amino acid sequence of SEQ. ID NO: 18 or a sequence at least 90% identical thereto. In some embodiments that may be combined with any of the preceding embodiments, the second antigen-binding domain that binds CD33 comprises a heavy chain variable domain (VH) comprising the amino acid sequence of SEQ ID NO: 19 or a sequence at least 90% identical thereto and a light chain variable domain (VL) comprising the amino acid sequence of SEQ. ID NO: 20 or a sequence at least 90% identical thereto.

In some embodiments, the chimeric receptor is a chimeric T cell receptor or a chimeric antigen receptor (CAR).

In some embodiments, the chimeric receptor is a CAR.

In some embodiments, the CAR is a bispecific CAR.

In some embodiments, the CAR comprises one or more intracellular signaling domains, and the one or more intracellular signaling domains are selected from the group consisting of a CD3-zeta chain intracellular signaling domain, a CD97 intracellular signaling domain, a CD11a-CD18 intracellular signaling domain, a CD2 intracellular signaling domain, an ICOS intracellular signaling domain, a CD27 intracellular signaling domain, a CD154 intracellular signaling domain, a CD8 intracellular signaling domain, an OX40 intracellular signaling domain, a 4-1BB intracellular signaling domain, a CD28 intracellular signaling domain, a ZAP40 intracellular signaling domain, a CD30 intracellular signaling domain, a GITR intracellular signaling domain, an HVEM intracellular signaling domain, a DAP10 intracellular signaling domain, a DAP12 intracellular signaling domain, and a MyD88 intracellular signaling domain.

In some embodiments, the CAR comprises a transmembrane domain, and the transmembrane domain is selected from the group consisting of a CD8 transmembrane domain, a CD28 transmembrane domain a CD3zeta-chain transmembrane domain, a CD4 transmembrane domain, a 4-1BB transmembrane domain, an OX40 transmembrane domain, an ICOS transmembrane domain, a CTLA-4 transmembrane domain, a PD-1 transmembrane domain, a LAG-3 transmembrane domain, a 2B4 transmembrane domain, and a BTLA transmembrane domain.

In some embodiments, the CAR comprises a spacer region between the antigen-binding domain and the transmembrane domain, and the spacer region has an amino acid sequence selected from the group consisting of SEQ ID NOs: 55-64.

In some embodiments, each antigen-binding domain comprises an antibody, an antigen-binding fragment of an antibody, a F(ab) fragment, a F(ab') fragment, a single chain variable fragment (scFv), or a single-domain antibody (sdAb). In some embodiments, the antigen-binding domain comprises a single chain variable fragment (scFv). In some embodiments, the scFv comprises a heavy chain variable domain (VH) and a light chain variable domain (VL). In some embodiments, the VH and VL are separated by a peptide linker. In some embodiments, the peptide linker comprises the amino acid sequence of SEQ ID NO: 27. In some embodiments, the scFv comprises the structure VH-L-VL or VL-L-VH, wherein VH is the heavy chain variable domain, L is the peptide linker, and VL is the light chain variable domain.

In another aspect, provided herein are isolated cells comprising the chimeric receptor of any one of the embodiments.

In some embodiments, the cell further comprises an additional chimeric receptor comprising an antigen-binding domain.

In some embodiments, the additional chimeric receptor binds to an antigen selected from the group consisting of MS4A3, VSTM1, LAT2, MLC1, CD131, GAPT, PRAM1, SLC22A16, SLC17A9, SPNS3, FLT3, CD33, CLEC12A, ADGRE2, IL3RA, CD117, CD93, IL1RAP, CD244, CCR1, LILRB2, PIEZO1, CD38, EMB, MYADM, LILRA2, CD300LF, and CD70.

In some embodiments, each of the two chimeric receptors binds to different antigens.

In some embodiments, the cell is an immunoresponsive cell.

In some embodiments, binding of the chimeric receptor to either of the two antigens is capable of activating the immunoresponsive cell.

In some embodiments, binding of the additional chimeric receptor to its cognate antigen is capable of stimulating the immunoresponsive cell.

In some embodiments, binding of the chimeric receptor to either of the two antigens and binding of the additional chimeric receptor to its cognate antigen are required for activating the immunoresponsive cell.

In some embodiments, the immunoresponsive cell exhibits a greater degree of cytolytic activity against cells that are positive for either of the two antigens bound by the chimeric receptor and positive for the antigen bound by the additional chimeric receptor, as compared to against cells that are only positive for a single antigen.

In some embodiments, the additional chimeric receptor is a chimeric T cell receptor or a chimeric antigen receptor (CAR).

In some embodiments, the additional chimeric receptor is a CAR.

In some embodiments, the chimeric receptor is a first CAR and the additional chimeric receptor is a second CAR.

In some embodiments, the second CAR comprises one or more intracellular signaling domains, and the one or more intracellular signaling domains are selected from the group consisting of a CD3zeta-chain intracellular signaling domain, a CD97 intracellular signaling domain, a CD11a-CD18 intracellular signaling domain, a CD2 intracellular signaling domain, an ICOS intracellular signaling domain, a CD27 intracellular signaling domain, a CD154 intracellular signaling domain, a CD8 intracellular signaling domain, an OX40 intracellular signaling domain, a 4-1BB intracellular signaling domain, a CD28 intracellular signaling domain, a ZAP40 intracellular signaling domain, a CD30 intracellular signaling domain, a GITR intracellular signaling domain, an HVEM intracellular signaling domain, a DAP10 intracellular signaling domain, a DAP12 intracellular signaling domain, and a MyD88 intracellular signaling domain.

In some embodiments, the one or more intracellular signaling domains of the first CAR are different from the one or more intracellular signaling domains of the second CAR.

In some embodiments, the first CAR and the second CAR each comprise a CD3zeta-chain intracellular signaling domain.

In some embodiments, the first CAR and the second CAR each further comprises an additional intracellular signaling domain selected from the group consisting of a CD97 intracellular signaling domain, a CD11a-CD18 intracellular signaling domain, a CD2 intracellular signaling domain, an ICOS intracellular signaling domain, a CD27 intracellular signaling domain, a CD154 intracellular signaling domain, a CD8 intracellular signaling domain, an OX40 intracellular signaling domain, a 4-1BB intracellular signaling domain, a CD28 intracellular signaling domain, a ZAP40 intracellular signaling domain, a CD30 intracellular signaling domain, a GITR intracellular signaling domain, an HVEM intracellular signaling domain, a DAP10 intracellular signaling domain, a DAP12 intracellular signaling domain, and a MyD88 intracellular signaling domain.

In some embodiments, the additional intracellular signaling domain of the first CAR is different from the additional intracellular signaling domain of the second CAR.

In some embodiments, the second CAR comprises a transmembrane domain, and the transmembrane domain is selected from the group consisting of a CD8 transmembrane domain, a CD28 transmembrane domain a CD3zeta-chain transmembrane domain, a CD4 transmembrane domain, a 4-1BB transmembrane domain, an OX40 transmembrane domain, an ICOS transmembrane domain, a CTLA-4 transmembrane domain, a PD-1 transmembrane domain, a LAG-3 transmembrane domain, a 2B4 transmembrane domain, and a BTLA transmembrane domain.

In some embodiments, the transmembrane domain of the first CAR is different from the transmembrane domain of the second CAR.

In some embodiments, the second CAR comprises a spacer region between the antigen-binding domain and the transmembrane domain, and the spacer region has an amino acid sequence selected from the group consisting of SEQ ID NOs: 55-64.

In some embodiments, the cell further comprises an inhibitory chimeric receptor comprising an antigen-binding domain.

In some embodiments, the additional chimeric receptor is an inhibitory chimeric receptor comprising an antigen-binding domain.

In some embodiments, the inhibitory chimeric receptor inhibits one or more activities of the cell.

In some embodiments, the inhibitory chimeric receptor binds an antigen that is not expressed on a tumor cell.

In some embodiments, the inhibitory chimeric receptor binds an antigen that is expressed on a non-tumor cell.

In some embodiments, the inhibitory chimeric receptor binds an antigen that is expressed on a non-tumor cell derived from a tissue selected from the group consisting of brain, neuronal tissue, endocrine, bone, bone marrow, immune system, muscle, lung, liver, gallbladder, pancreas, gastrointestinal tract, kidney, urinary bladder, male reproductive organs, female reproductive organs, adipose, soft tissue, and skin.

In some embodiments, the tumor cell is an acute myeloid leukemia (AML) cell.

In some embodiments, the inhibitory chimeric receptor comprises an enzymatic inhibitory domain.

In some embodiments, the enzymatic inhibitory domain inhibits immune receptor activation when proximal to an immune receptor.

In some embodiments, wherein the enzymatic inhibitory domain comprises an enzyme catalytic domain.

In some embodiments, the enzyme catalytic domain is derived from an enzyme selected from the group consisting of CSK, SHP-1, PTEN, CD45, CD148, PTP-MEG1, PTP-PEST, c-CBL, CBL-b, PTPN22, LAR, PTPH1, SHIP-1, and RasGAP.

In some embodiments, the inhibitory chimeric receptor further comprises one or more intracellular inhibitory co-signaling domains.

In some embodiments, the one or more intracellular inhibitory co-signaling domains are selected from the group consisting of PD-1, CTLA4, TIGIT, LAIR1, GRB-2, Dok-1, Dok-2, SLAP, LAG3, HAVR, BTLA, GITR, and PD-L1.

In some embodiments, in the inhibitory chimeric receptor binds an antigen selected from the group consisting of EMCN, JAM2, MS4A15, C4BPA, TRPM1, SCTR, SLC2A2, KCNQ2, PERP, WLS, and FFAR2.

In some embodiments, the antigen-binding domain of the additional chimeric receptor and/or inhibitory chimeric receptor comprises an antibody, an antigen-binding fragment of an antibody, a F(ab) fragment, a F(ab') fragment, a single chain variable fragment (scFv), or a single-domain antibody (sdAb). In some embodiments, the antigen-binding domain comprises a single chain variable fragment (scFv). In some embodiments, the scFv comprises a heavy chain variable domain (VH) and a light chain variable domain (VL). In some embodiments, the VH and VL are separated by a peptide linker. In some embodiments, the peptide linker comprises the amino acid sequence of SEQ ID NO: 27. In some embodiments, the scFv comprises the structure VH-L-VL or VL-L-VH, wherein VH is the heavy chain variable domain, L is the peptide linker, and VL is the light chain variable domain.

In some embodiments, each chimeric receptor is recombinantly expressed.

In some embodiments, each chimeric receptor is expressed from a vector or a selected locus from the genome of the cell.

In some embodiments, the cell selected from the group consisting of a T cell, a Natural Killer (NK) cell, a cytotoxic T lymphocyte (CTL), a regulatory T cell, a Natural Killer T (NKT) cell, a myeloid cell, a macrophage, a human embryonic stem cell (ESC), an ESC-derived cell, a pluripotent stem cell, and induced pluripotent stem cell (iPSC), and an iPSC-derived cell.

In some embodiments, the cell is autologous.

In some embodiments, the cell is allogeneic.

In another aspect, provided herein are chimeric inhibitory receptors comprising an extracellular antigen-binding domain that binds to an antigen selected from the group consisting of EMCN, JAM2, MS4A15, C4BPA, TRPM1, SCTR, SLC2A2, KCNQ2, PERP, WLS, and FFAR2.

In some embodiments, the antigen is EMCN.

In some embodiments, the antigen is JAM2.

In some embodiments, the antigen is MS4A15.

In some embodiments, the antigen is C4BPA.

In some embodiments, the antigen is TRPM1.

In some embodiments, the antigen is SCTR.

In some embodiments, the antigen is SLC2A2.

In some embodiments, the antigen is KCNQ2.

In some embodiments, the antigen is PERP.

In some embodiments, when expressed on a cell the inhibitory chimeric receptor inhibits one or more activities of the cell.

In some embodiments, the antigen that is not expressed on a tumor cell.

In some embodiments, the antigen is expressed on a non-tumor cell.

In some embodiments, the antigen is expressed on a non-tumor cell derived from a tissue selected from the group consisting of brain, neuronal tissue, endocrine, bone, bone marrow, immune system, muscle, lung, liver, gallbladder, pancreas, gastrointestinal tract, kidney, urinary bladder, male reproductive organs, female reproductive organs, adipose, soft tissue, and skin.

In some embodiments, the inhibitory chimeric receptor comprises an enzymatic inhibitory domain.

In some embodiments, the enzymatic inhibitory domain inhibits immune receptor activation when proximal to an immune receptor.

In some embodiments, the enzymatic inhibitory domain comprises an enzyme catalytic domain.

In some embodiments, the enzyme catalytic domain is derived from an enzyme selected from the group consisting of CSK, SHP-1, PTEN, CD45, CD148, PTP-MEG1, PTP-PEST, c-CBL, CBL-b, PTPN22, LAR, PTPH1, SHIP-1, and RasGAP.

In some embodiments, the inhibitory chimeric receptor further comprises one or more intracellular inhibitory co-signaling domains.

In some embodiments, the one or more intracellular inhibitory co-signaling domains are selected from the group consisting of PD-1, CTLA4, TIGIT, LAIR1, GRB-2, Dok-1, Dok-2, SLAP, LAG3, HAVR, BTLA, GITR, and PD-L1.

In some embodiments, the antigen-binding domain comprises an antibody, an antigen-binding fragment of an antibody, a F(ab) fragment, a F(ab') fragment, a single chain variable fragment (scFv), or a single-domain antibody (sdAb). In some embodiments, the antigen-binding domain comprises a single chain variable fragment (scFv). In some embodiments, the scFv comprises a heavy chain variable domain (VH) and a light chain variable domain (VL). In some embodiments, the VH and VL are separated by a peptide linker. In some embodiments, the peptide linker comprises the amino acid sequence of SEQ ID NO: 27. In some embodiments, the scFv comprises the structure VH-L-VL or VL-L-VH, wherein VH is the heavy chain variable domain, L is the peptide linker, and VL is the light chain variable domain.

In another aspect, provided herein are isolated cells comprising the chimeric inhibitory receptor of any one of the embodiments.

In some embodiments, the chimeric inhibitory receptor is recombinantly expressed.

In some embodiments, the chimeric inhibitory receptor is expressed from a vector or a selected locus from the genome of the cell.

In some embodiments, the cell further comprises a chimeric receptor comprising an extracellular antigen-binding domain that binds to an antigen selected from the group consisting of MS4A3, VSTM1, LAT2, MLC1, CD131, GAPT, PRAM1, SLC22A16, SLC17A9, SPNS3, FLT3, CD33, CLEC12A, ADGRE2, IL3RA, CD117, CD93, IL1RAP, CD244, CCR1, LILRB2, PIEZO1, CD38, EMB, MYADM, LILRA2, CD300LF, and CD70.

In another aspect, provided herein are isolated cells comprising (a) a chimeric inhibitory receptor comprising an extracellular antigen-binding domain that binds to a first antigen, wherein the first antigen is selected from the group consisting of EMCN, JAM2, MS4A15, C4BPA, TRPM1, SCTR, SLC2A2, KCNQ2, PERP, WLS, and FFAR2, and (b) a chimeric receptor comprising one or more extracellular antigen-binding domains, wherein each antigen-binding domain binds to an antigen selected from the group consisting of the antigens listed in Table 1.

In another aspect, provided herein are isolated cells comprising (a) a chimeric inhibitory receptor comprising an extracellular antigen-binding domain that binds to a first antigen, wherein the first antigen is selected from the group consisting of EMCN, JAM2, MS4A15, C4BPA, TRPM1, SCTR, SLC2A2, KCNQ2, PERP, WLS, and FFAR2, and (b) a chimeric receptor comprising one or more extracellular antigen-binding domains, wherein each antigen-bind domain binds to an antigen selected from the group consisting of MS4A3, VSTM1, LAT2, MLC1, CD131, GAPT, PRAM1, SLC22A16, SLC17A9, SPNS3, FLT3, CD33, CLEC12A, ADGRE2, IL3RA, CD117, CD93, IL1RAP, CD244, CCR1, LILRB2, PIEZO1, CD38, EMB, MYADM, LILRA2, CD300LF, and CD70.

In some embodiments, the chimeric receptor is a chimeric T cell receptor or a chimeric antigen receptor (CAR).

In some embodiments, the chimeric receptor is a CAR.

In some embodiments, the CAR comprises one or more intracellular signaling domains, and the one or more intracellular signaling domains are selected from the group consisting of a CD3zeta-chain intracellular signaling domain, a CD97 intracellular signaling domain, a CD11a-CD18 intracellular signaling domain, a CD2 intracellular signaling domain, an ICOS intracellular signaling domain, a CD27 intracellular signaling domain, a CD154 intracellular signaling domain, a CD8 intracellular signaling domain, an OX40 intracellular signaling domain, a 4-1BB intracellular signaling domain, a CD28 intracellular signaling domain, a ZAP40 intracellular signaling domain, a CD30 intracellular signaling domain, a GITR intracellular signaling domain, an HVEM intracellular signaling domain, a DAP10 intracellular signaling domain, a DAP12 intracellular signaling domain, and a MyD88 intracellular signaling domain.

In some embodiments, the CAR comprises a transmembrane domain, and the transmembrane domain is selected from the group consisting of a CD8 transmembrane domain, a CD28 transmembrane domain a CD3zeta-chain transmembrane domain, a CD4 transmembrane domain, a 4-1BB transmembrane domain, an OX40 transmembrane domain, an ICOS transmembrane domain, a CTLA-4 transmembrane domain, a PD-1 transmembrane domain, a LAG-3 transmembrane domain, a 2B4 transmembrane domain, and a BTLA transmembrane domain.

In some embodiments, the CAR comprises a spacer region between the antigen-binding domain and the transmembrane domain, and the spacer region has an amino acid sequence selected from the group consisting of SEQ ID NOs: 55-64.

In some embodiments, the antigen-binding domain of the chimeric inhibitory receptor and/or the chimeric receptor comprises an antibody, an antigen-binding fragment of an antibody, a F(ab) fragment, a F(ab') fragment, a single chain variable fragment (scFv), or a single-domain antibody (sdAb). In some embodiments, the antigen-binding domain comprises a single chain variable fragment (scFv). In some embodiments, the scFv comprises a heavy chain variable domain (VH) and a light chain variable domain (VL). In some embodiments, the VH and VL are separated by a peptide linker. In some embodiments, the peptide linker comprises the amino acid sequence of SEQ ID NO: 27. In some embodiments, the scFv comprises the structure VH-L-VL or VL-L-VH, wherein VH is the heavy chain variable domain, L is the peptide linker, and VL is the light chain variable domain.

In some embodiments, the cell is an immunoresponsive cell.

In some embodiments, binding of the chimeric inhibitory receptor to the first antigen is capable of inhibiting the immunoresponsive cell.

In some embodiments, binding of the chimeric receptor to the second antigen is capable of activating the immunoresponsive cell.

In some embodiments, the chimeric receptor binds to the second antigen with a low binding affinity.

In some embodiments, the chimeric receptor binds to the second antigen with a binding affinity that is lower than the binding affinity with which the chimeric inhibitory receptor binds to the first antigen.

In some embodiments, the chimeric receptor binds to the first antigen with a low binding avidity.

In some embodiments, the chimeric receptor is recombinantly expressed.

In some embodiments, the chimeric receptor is expressed from a vector or a selected locus from the genome of the cell.

In some embodiments, the cell selected from the group consisting of a T cell, a Natural Killer (NK) cell, a cytotoxic T lymphocyte (CTL), a regulatory T cell, a Natural Killer T (NKT) cell, a myeloid cell, a macrophage, a human embryonic stem cell (ESC), an ESC-derived cell, a pluripotent stem cell, and induced pluripotent stem cell (iPSC), and an iPSC-derived cell.

In some embodiments, the cell is autologous.

In some embodiments, the cell is allogeneic.

In another aspect, provided herein are isolated nucleic acids encoding the chimeric receptor of any one of the embodiments.

In another aspect, provided herein are isolated nucleic acids encoding the chimeric receptor of any one the embodiments.

In another aspect, provided herein are isolated nucleic acid encoding the chimeric inhibitory receptor of any one the embodiments.

In another aspect, provided herein are vectors comprising the nucleic acid of the embodiments.

In some embodiments, the vector further comprises the nucleic acid of the embodiments.

In another aspect, provided herein vectors comprising the nucleic acid of the embodiments.

In another aspect, provided herein are genetically modified cells comprising the nucleic acid of the embodiments.

In some embodiments, the cell further comprises the nucleic acid of the embodiments.

In another aspect, provided herein are genetically modified cells comprising the nucleic acid of the embodiments.

In another aspect, provided herein are genetically engineered cells comprising the vector of any one of the embodiments In another aspect, provided herein are methods of reducing tumor burden in a subject, comprising administering to the subject an effective amount of the isolated cell of any one of the embodiments.

In some embodiments, the method reduces the number of tumor cells.

In some embodiments, the method reduces tumor size.

In some embodiments, the method eradicates the tumor in the subject.

In another aspect, provided herein are methods of treating or preventing a myeloid disorder in a subject, comprising administering to the subject an effective amount of the isolated cell of any one of the embodiments.

In some embodiments, the myeloid disorder is myelodysplastic syndromes, myeloproliferative neoplasms, chronic myelomonocytic leukemia, acute myeloid leukemia (AML), acute myeloblastic leukemia, acute promyelocytic leukemia, acute myelomonocytic leukemia, chronic myelocytic leukemia, and polycythemia vera.

In some embodiments, the myeloid disorder is acute myeloid leukemia (AML).

In some embodiments, the method reduces or eradicates the tumor burden in the subject.

In another aspect, provided herein are pharmaceutical compositions comprising an effective amount of the isolated cell of any one of the embodiments and a pharmaceutically acceptable excipient.

In some embodiment, the pharmaceutical composition is for treating and/or preventing a myeloid disorder.

In another aspect, provided herein are kits for treating and/or preventing a myeloid disorder, comprising an isolated cell of any one of the embodiments.

In some embodiments, the kit further comprises written instructions for using the cell for treating and/or preventing a myeloid disorder in a subject.

In another aspect, provided herein are kits for treating and/or preventing a myeloid disorder, comprising the isolated nucleic acid of any one of the embodiments.

In some embodiments, the kit further comprises written instructions for using the nucleic acid for producing one or more antigen-specific cells for treating and/or preventing a myeloid disorder in a subject.

In another aspect, provided herein are kits for treating and/or preventing a myeloid disorder, comprising a vector of any one of the embodiments.

In some embodiments, the kit further comprises written instructions for using the vector for producing one or more antigen-specific cells for treating and/or preventing a myeloid disorder in a subject.

In another aspect, provided herein are methods of treating and/or preventing a myeloid disorder, comprising administering an effective amount of at least one antibody that binds to an antigen, wherein the antigen is selected from the group consisting of MS4A3, VSTM1, LAT2, MLC1, CD131, GAPT, PRAM1, SLC22A16, SLC17A9, and SPNS3.

In some embodiments, the myeloid disorder is selected from the group consisting of myelodysplastic syndromes, myeloproliferative neoplasms, chronic myelomonocytic leukemia, or acute myeloid leukemia (AML), acute myeloblastic leukemia, acute promyelocytic leukemia, acute myelomonocytic leukemia, chronic myelocytic leukemia, and polycythemia vera.

In some embodiments, the myeloid disorder is acute myeloid leukemia (AML).

In some embodiments, the method reduces or eradicates the tumor burden in the subject.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

These and other features, aspects, and advantages of the present disclosure will become better understood with regard to the following description, and accompanying drawings.

FIG. 42A shows the flow cytometry histogram plots showing expression of CD33 protein expression (x-axis) in the AML cell lines MOLM-13, MV4-1, and THP-1. FIG. 42B shows that the CD33 CAR T cells killed MOML-13, MV-11, and THP-1 human leukemia cells. FIG. 42C shows a dose dependent CD33 CAR T cell killing of MOLM-13 AML cells with both CD33 CAR T cells.

FIG. 47 provides schematics of CLEC12A CARs synthesized.

DETAILED DESCRIPTION

Figure 1:
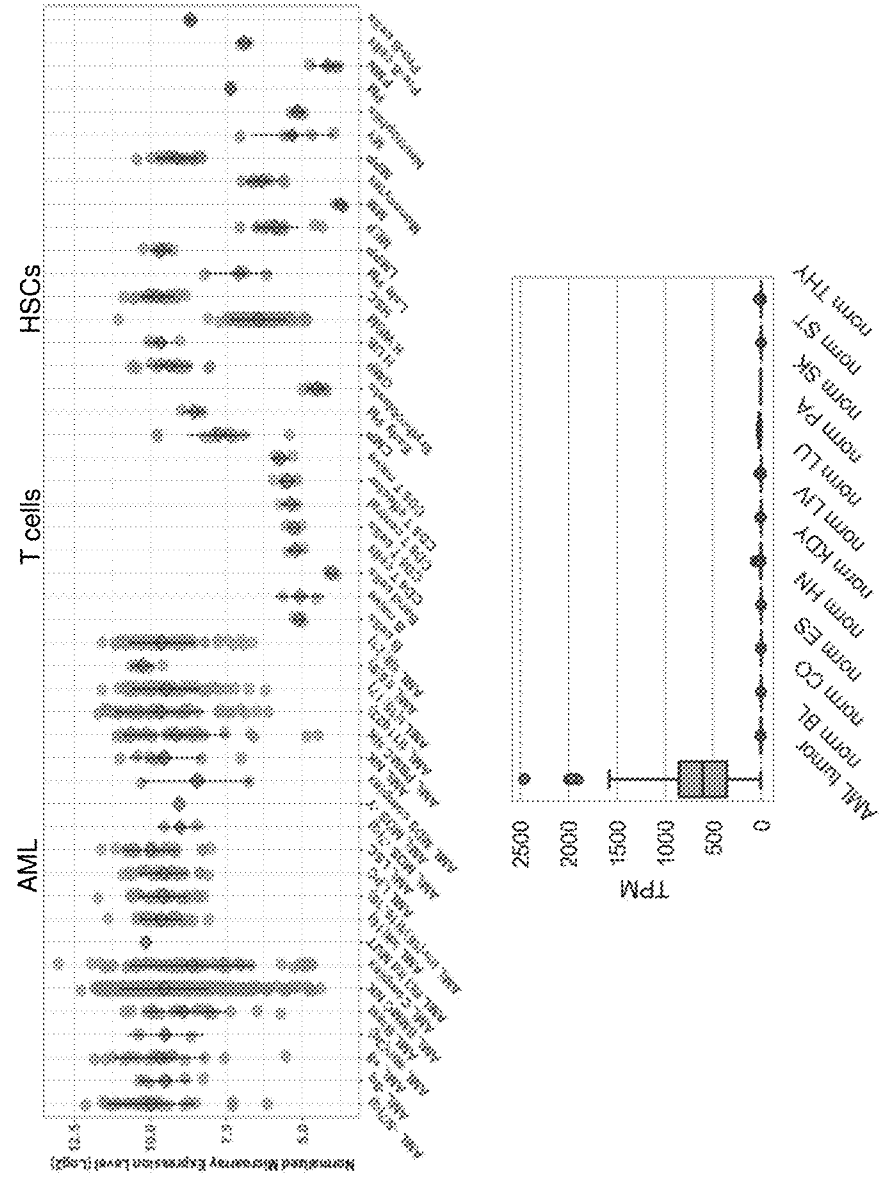
FIG. 1 provides microarray and RNA-Seq data for FLT3 expression in the indicated tissues or cell types.
Figure 2:
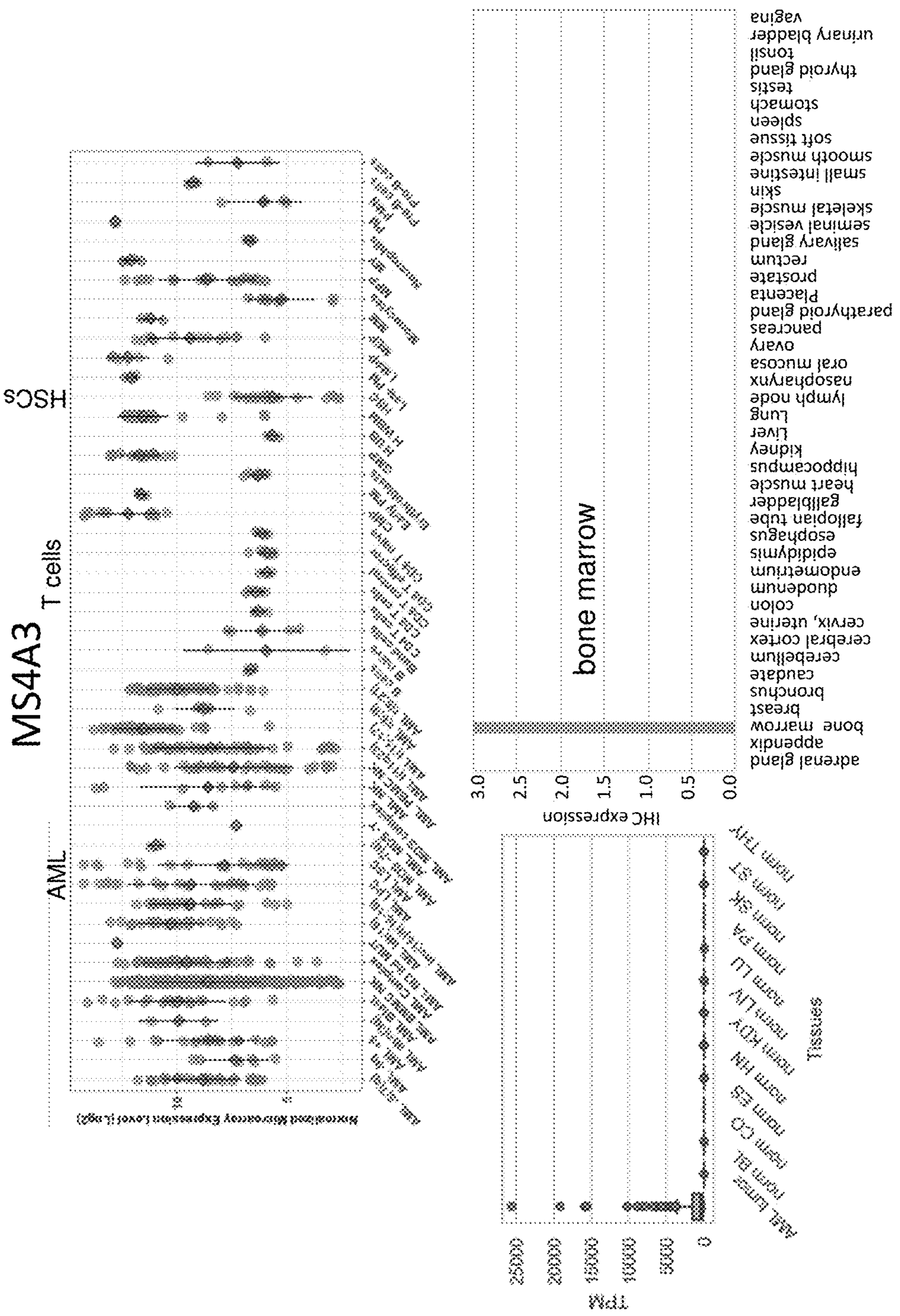
FIG. 2 provides microarray and RNA-Seq data for MS4A3 expression in the indicated tissues or cell types.
Figure 3:
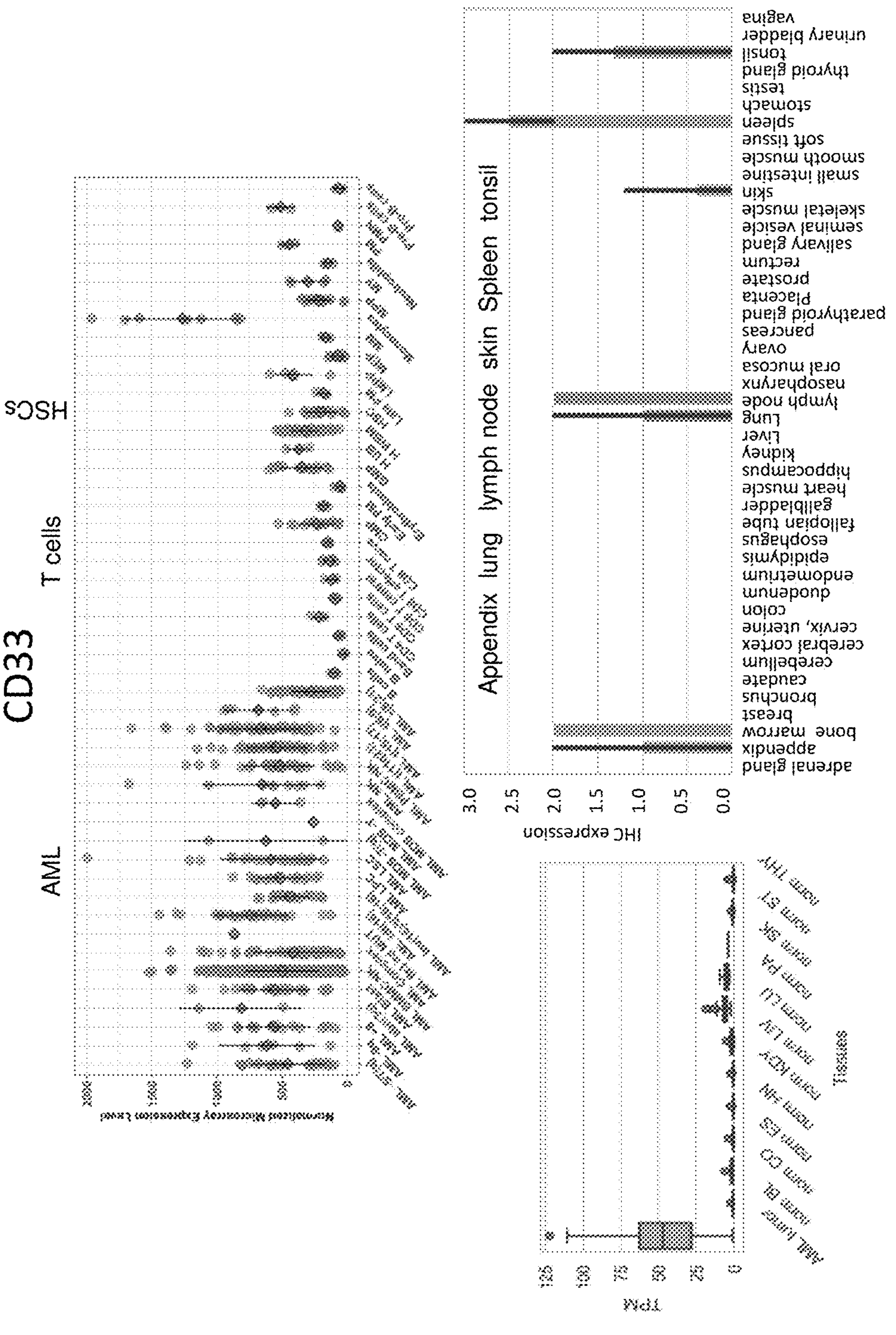
FIG. 3 provides microarray and RNA-Seq data for CD33 expression in the indicated tissues or cell types.
Figure 4:
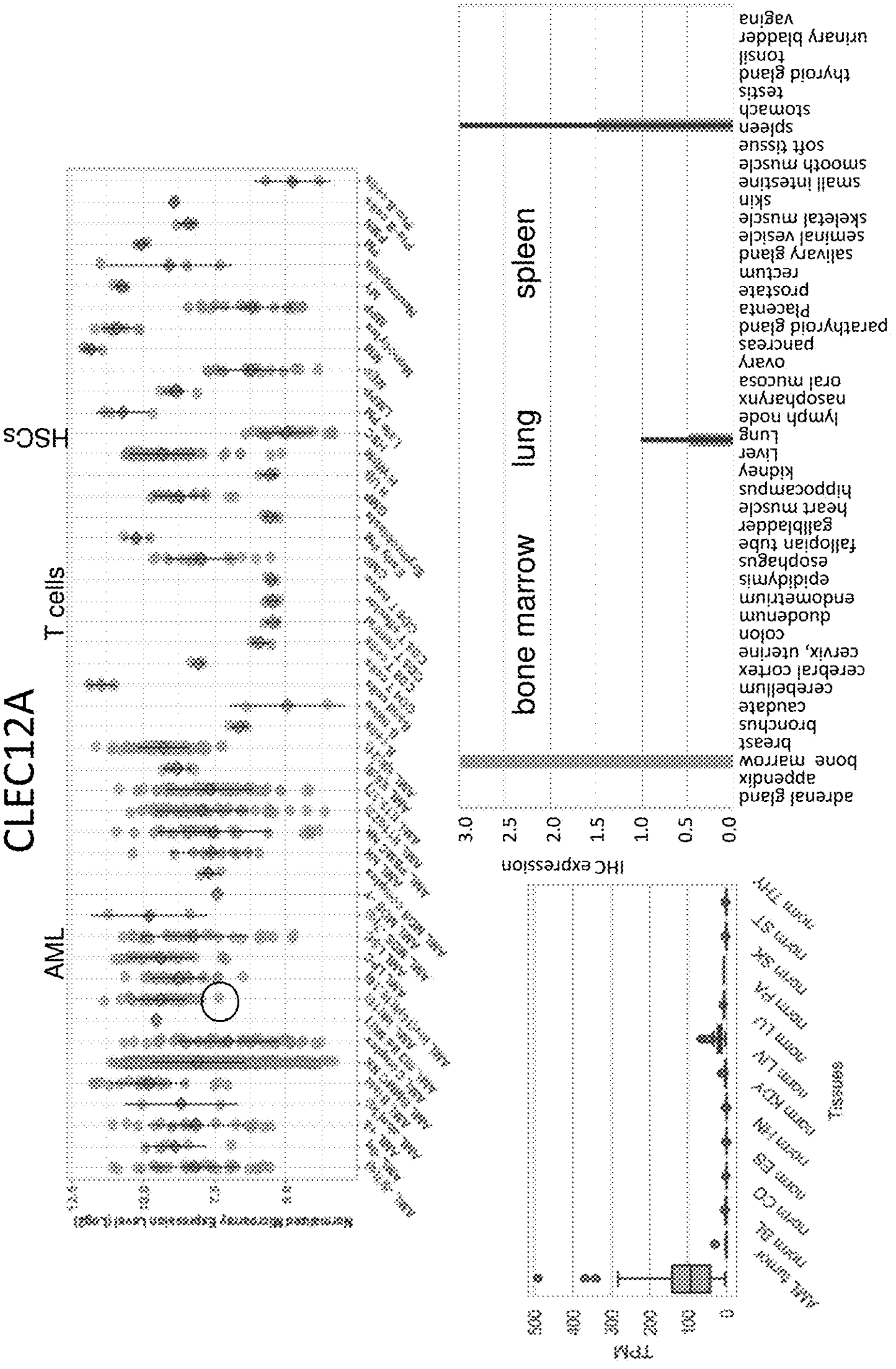
FIG. 4 provides microarray and RNA-Seq data for CLEC12A expression in the indicated tissues or cell types.
Figure 5:
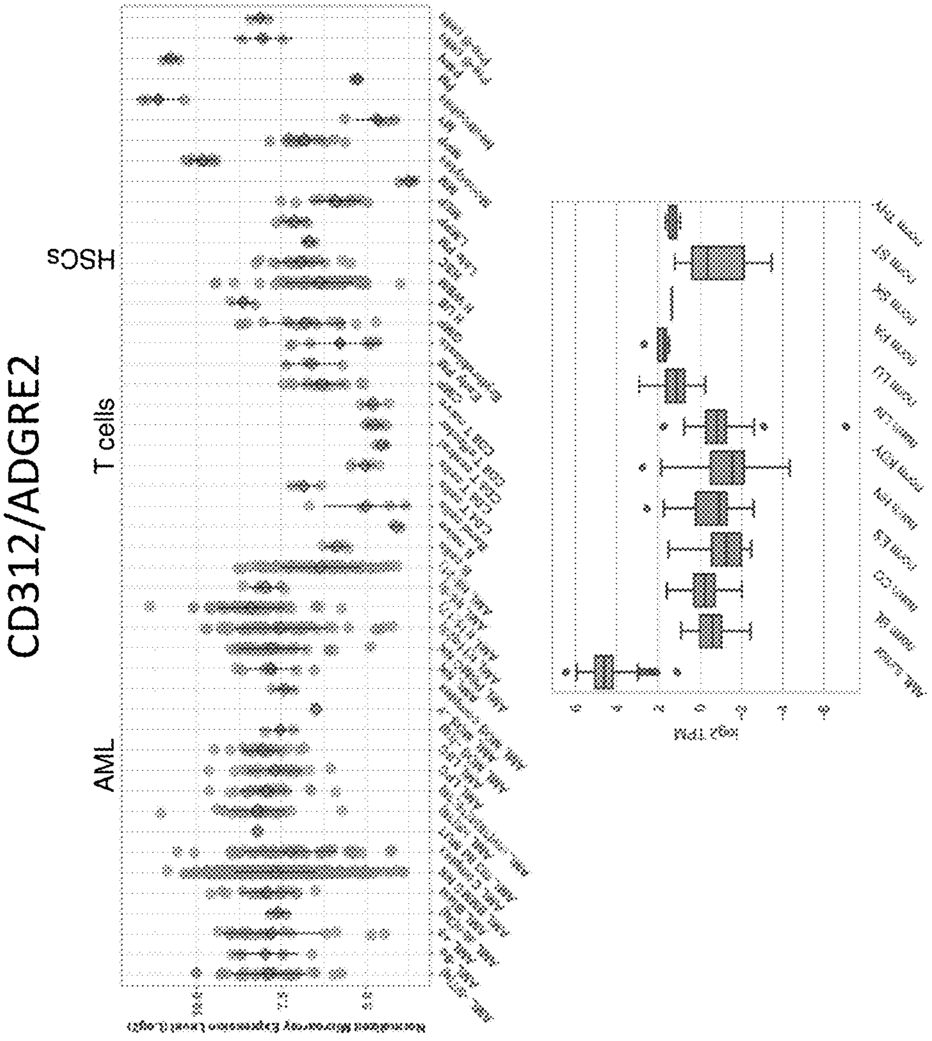
FIG. 5 provides microarray and RNA-Seq data for CD312/ADGRE2 expression in the indicated tissues or cell types.
Figure 6:
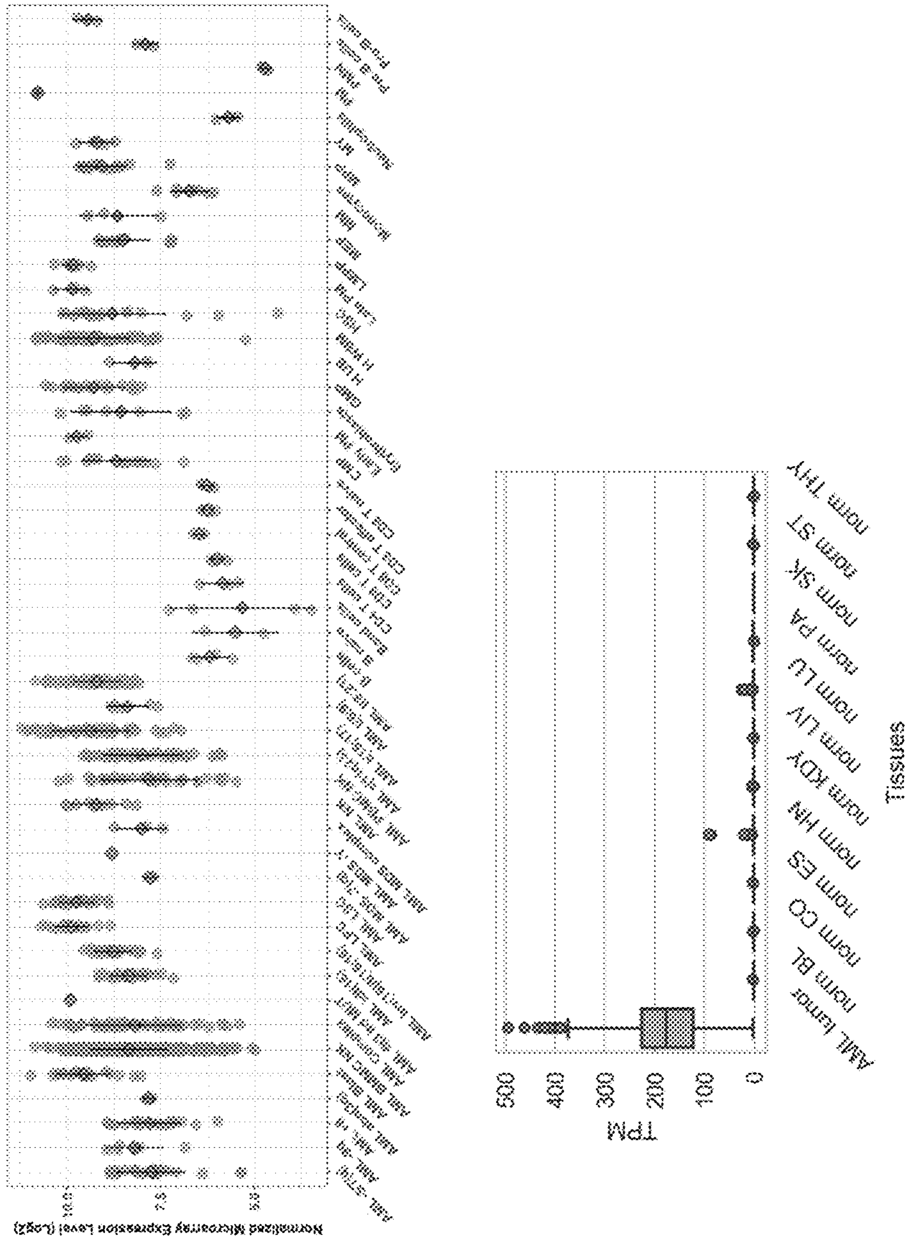
FIG. 6 provides microarray and RNA-Seq data for SLC22A16 expression in the indicated tissues or cell types.
Figure 7:
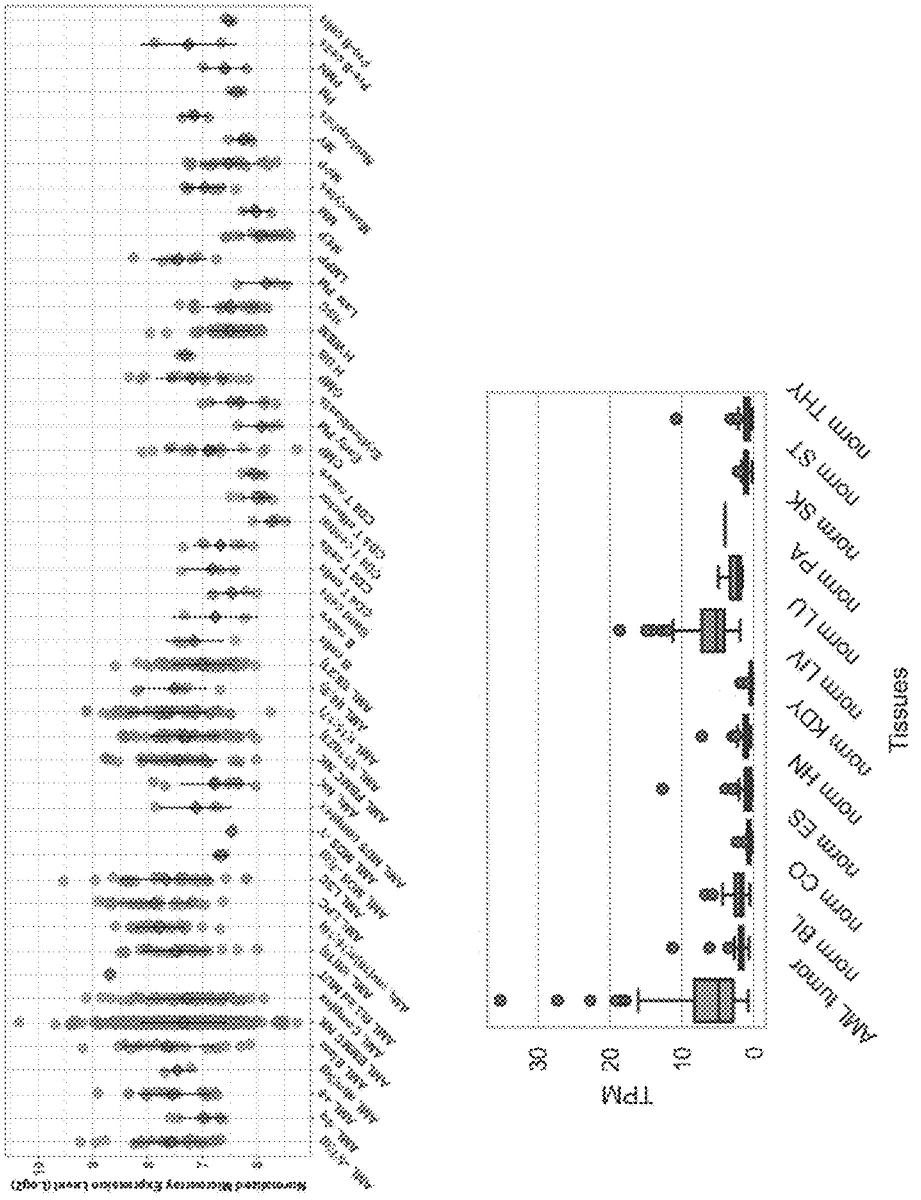
FIG. 7 provides microarray and RNA-Seq data for CD123/ILR3RA expression in the indicated tissues or cell types.
Figure 8:
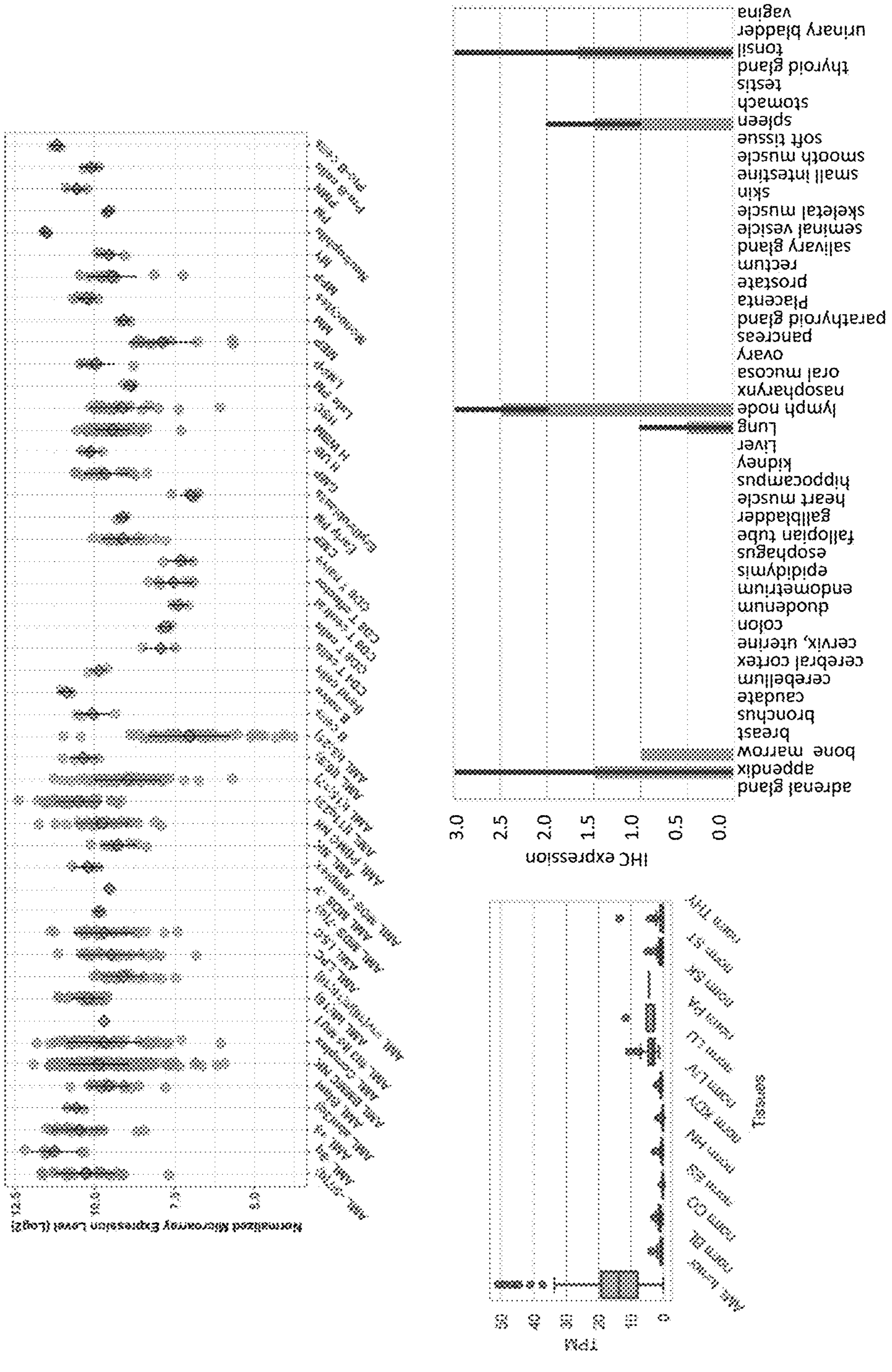
FIG. 8 provides microarray and RNA-Seq data for LAT2 expression in the indicated tissues or cell types.
Figure 9:
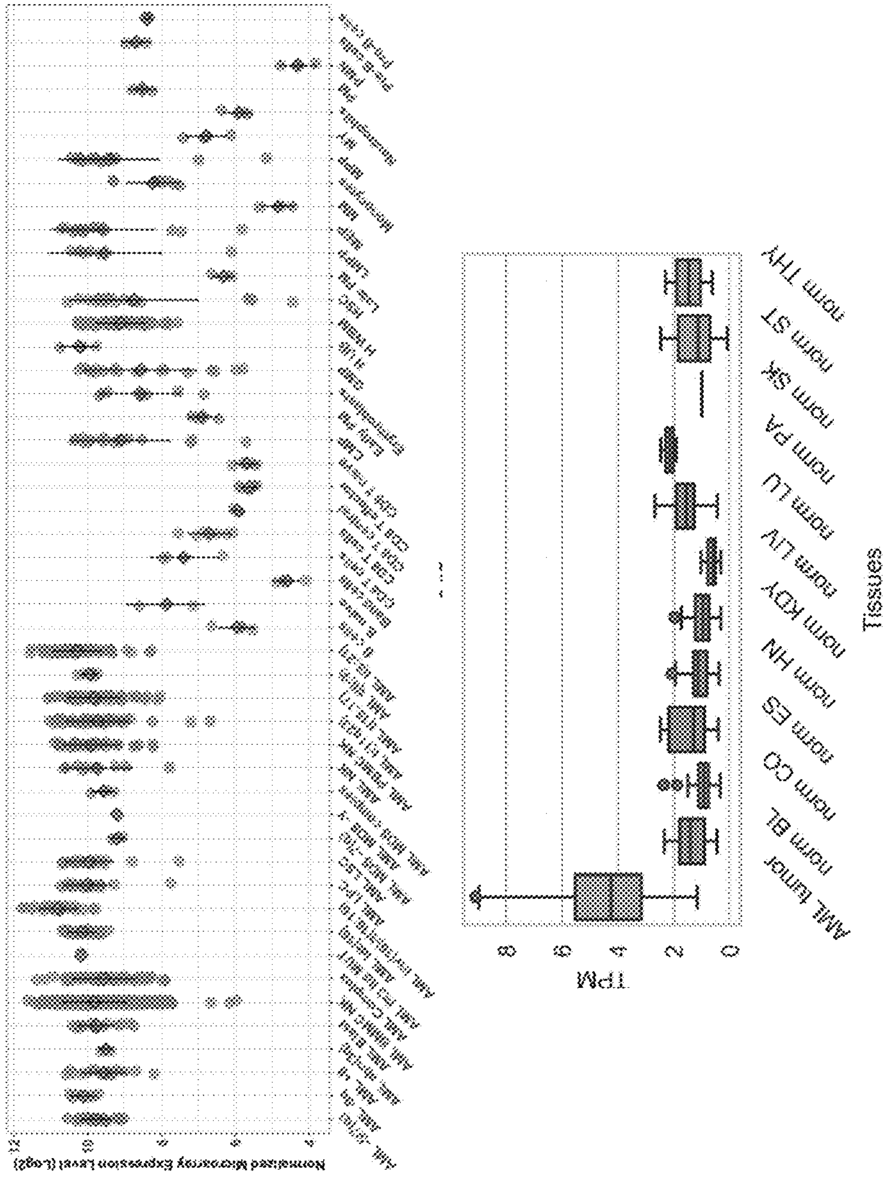
FIG. 9 provides microarray and RNA-Seq data for PIEZO1/FAM38A expression in the indicated tissues or cell types.
Figure 10:
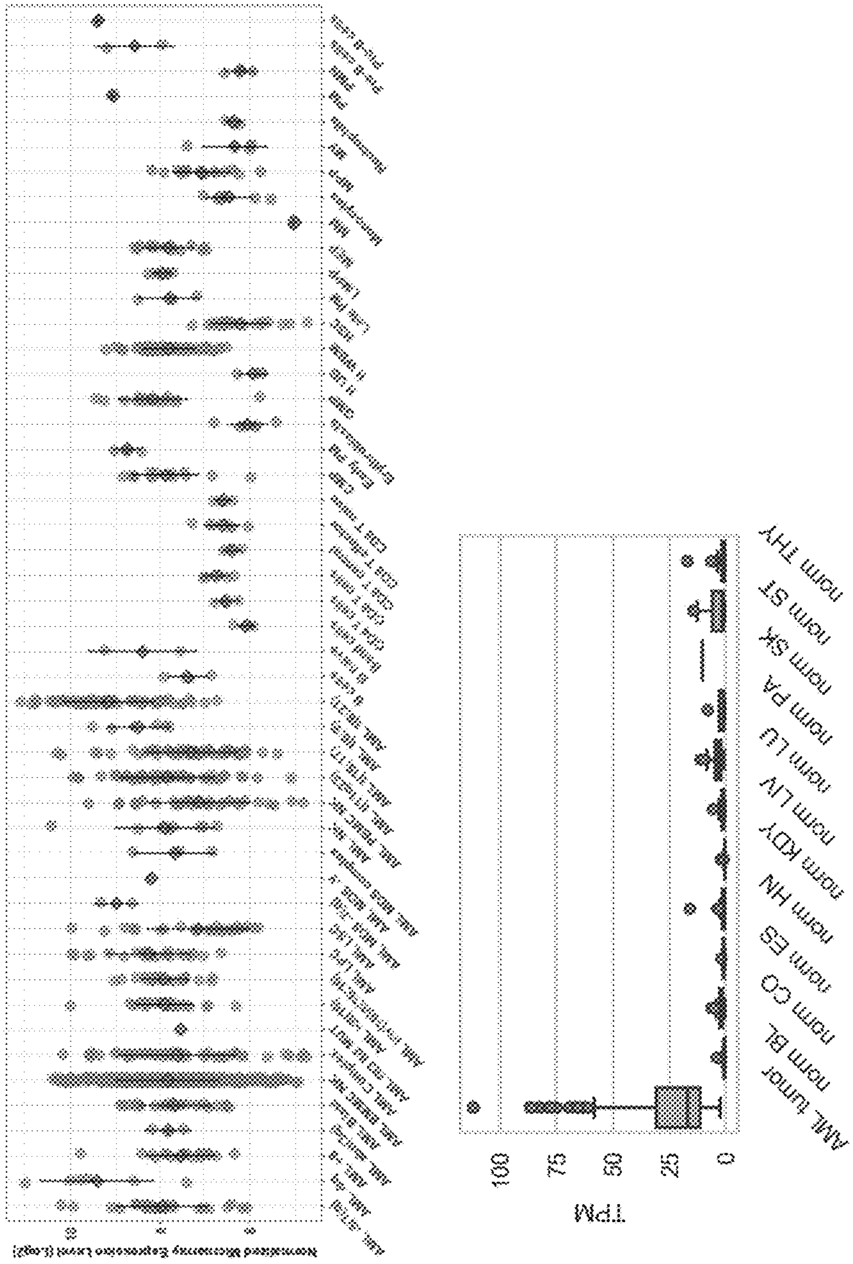
FIG. 10 provides microarray and RNA-Seq data for CD38 expression in the indicated tissues or cell types.
Figure 11:
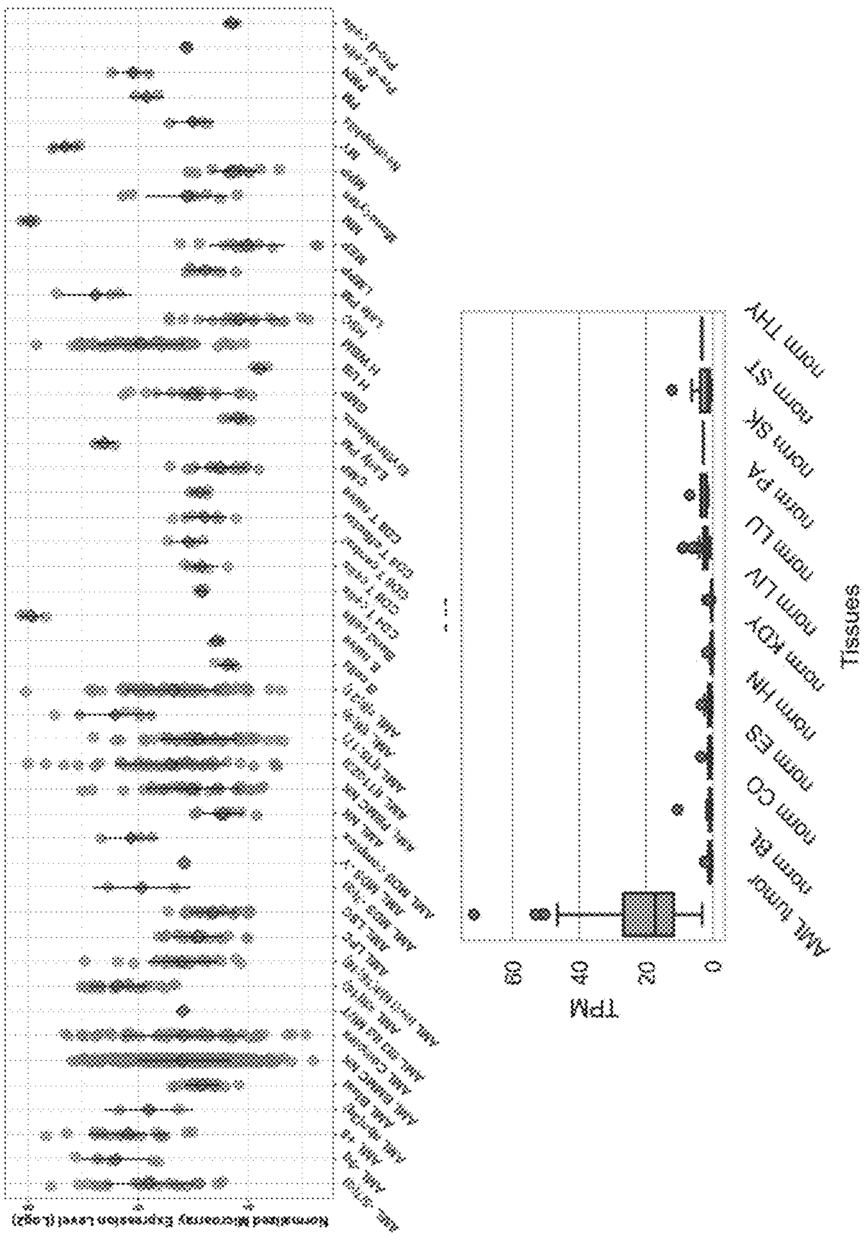
FIG. 11 provides microarray and RNA-Seq data for EMB expression in the indicated tissues or cell types.
Figure 12:
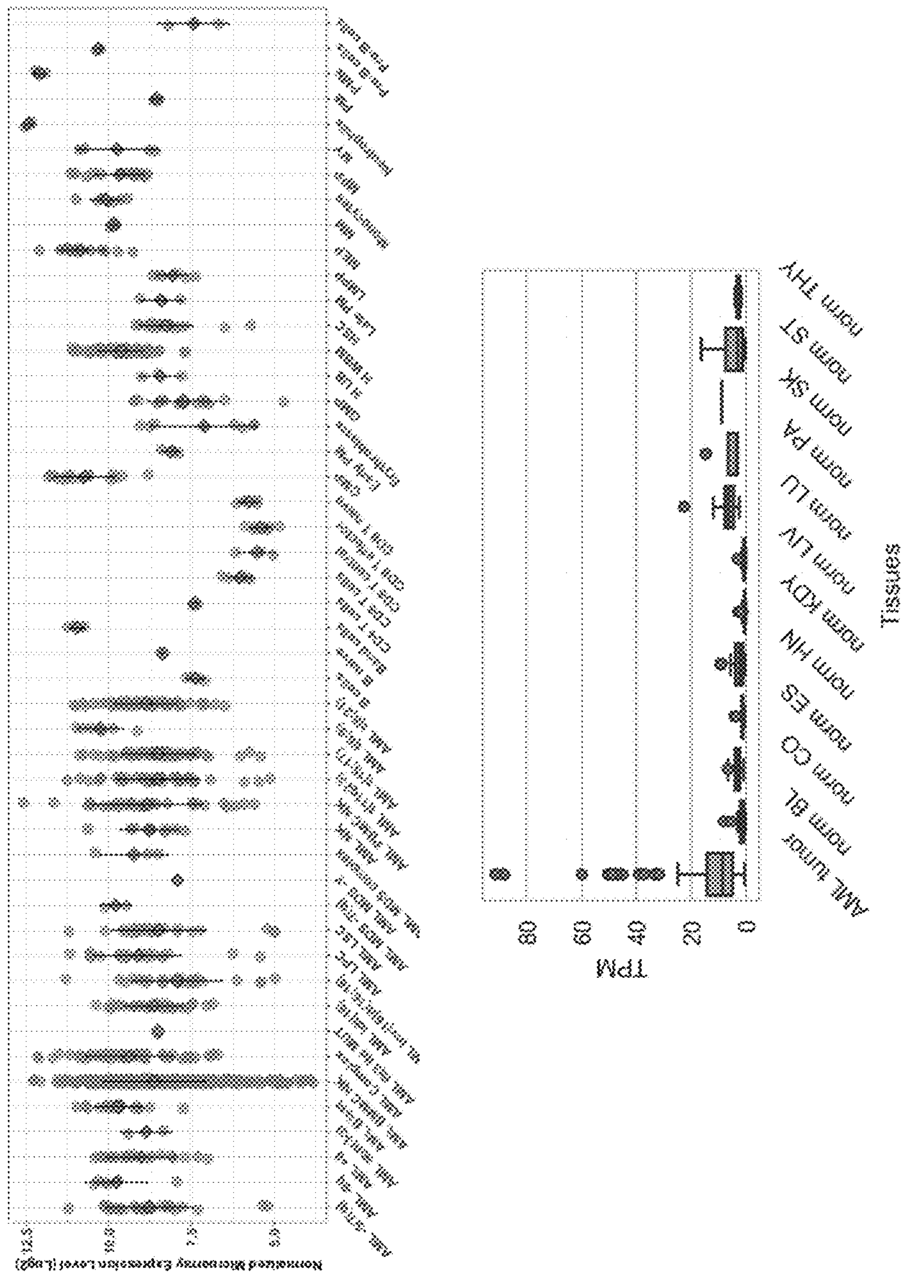
FIG. 12 provides microarray and RNA-Seq data for CD131/CSF2RB expression in the indicated tissues or cell types.
Figure 13:
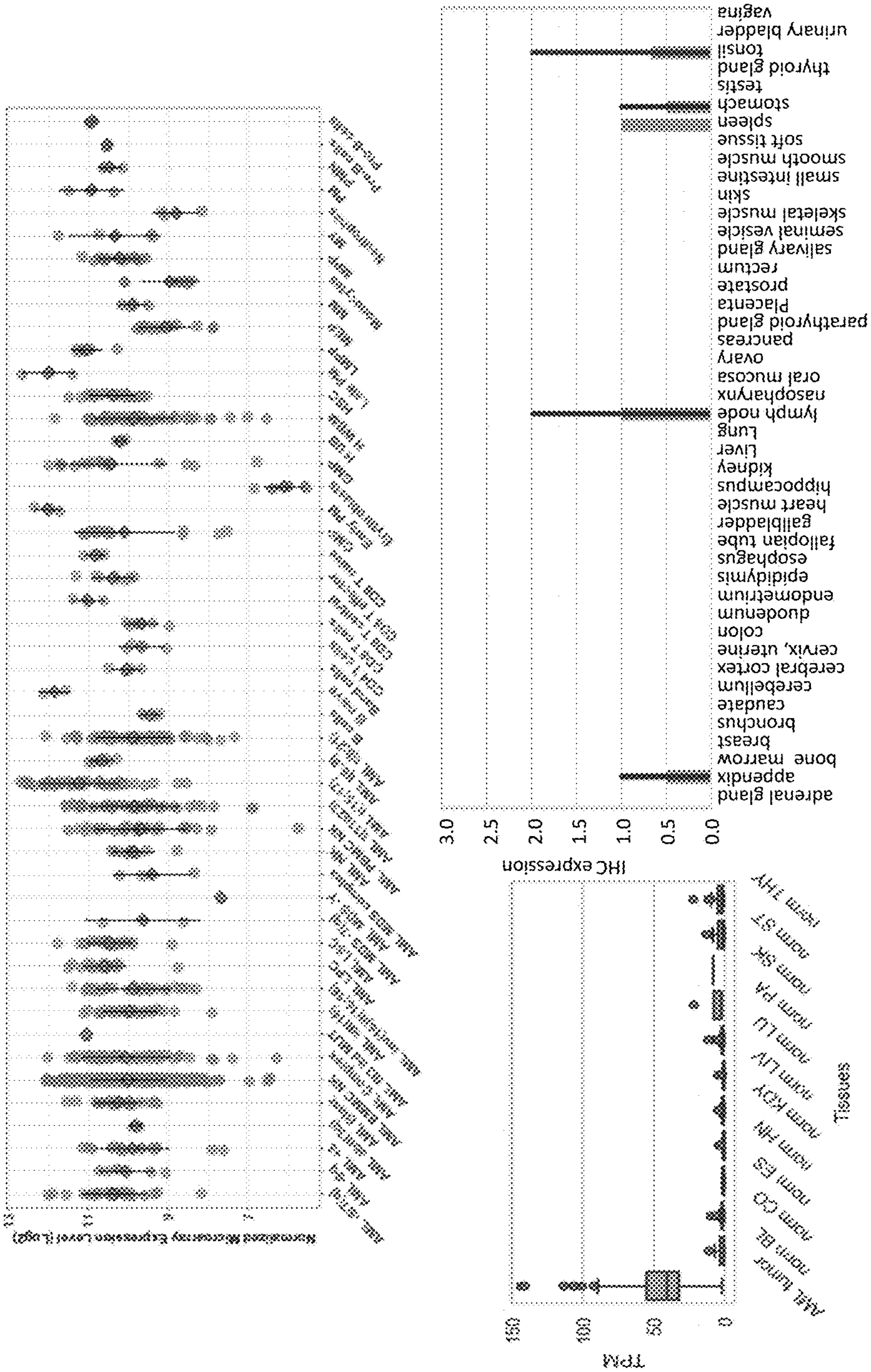
FIG. 13 provides microarray and RNA-Seq data for P2RY8 expression in the indicated tissues or cell types.
Figure 14:
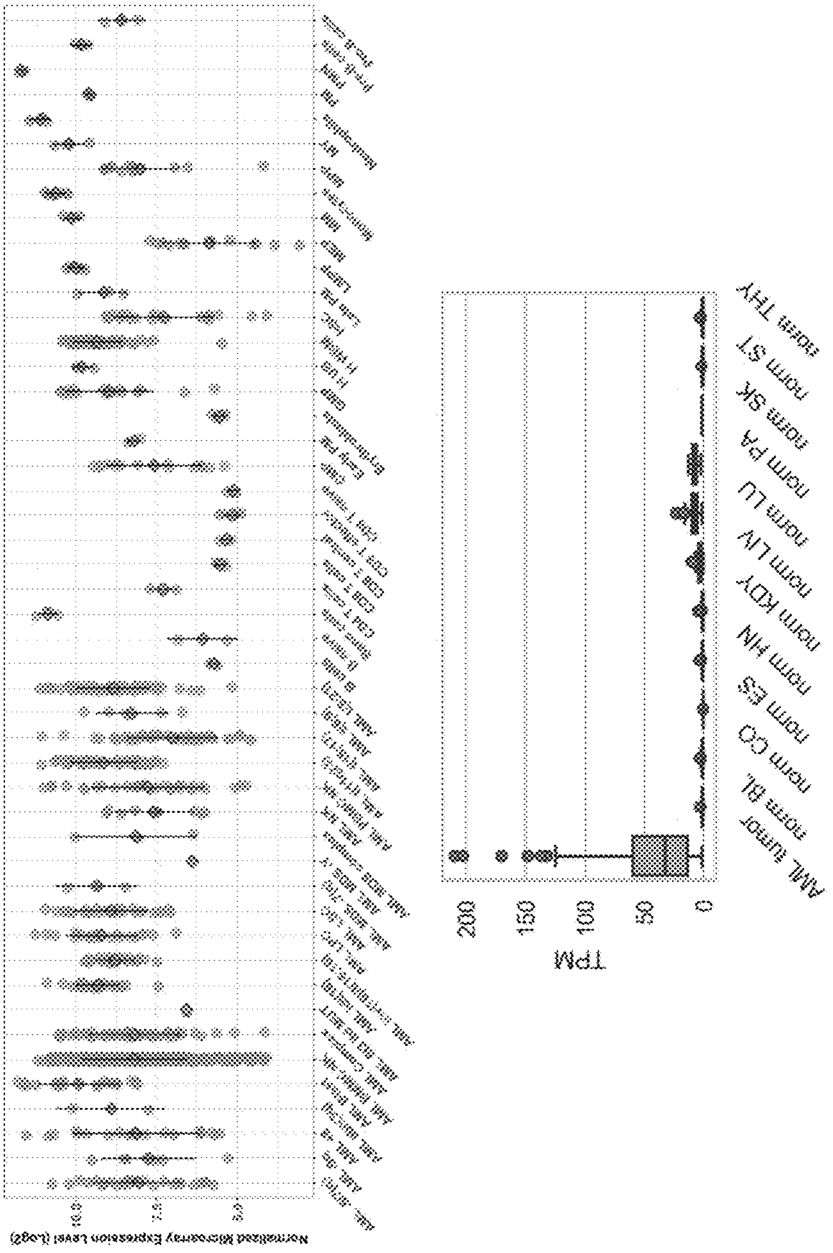
FIG. 14 provides microarray and RNA-Seq data for LILRA2/CD85H expression in the indicated tissues or cell types.
Figure 15:
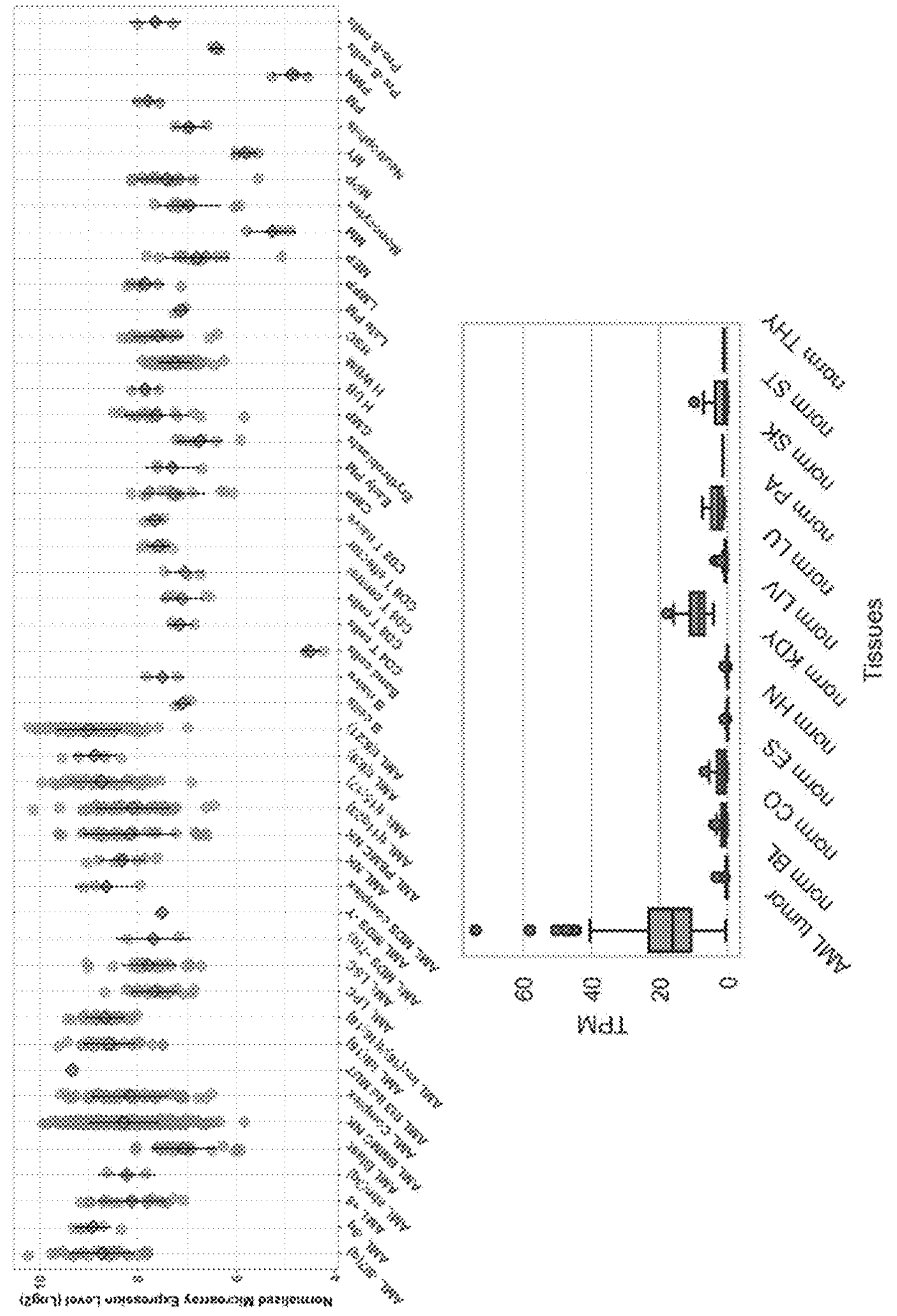
FIG. 15 provides microarray and RNA-Seq data for SLC17A9 expression in the indicated tissues or cell types.
Figure 16:
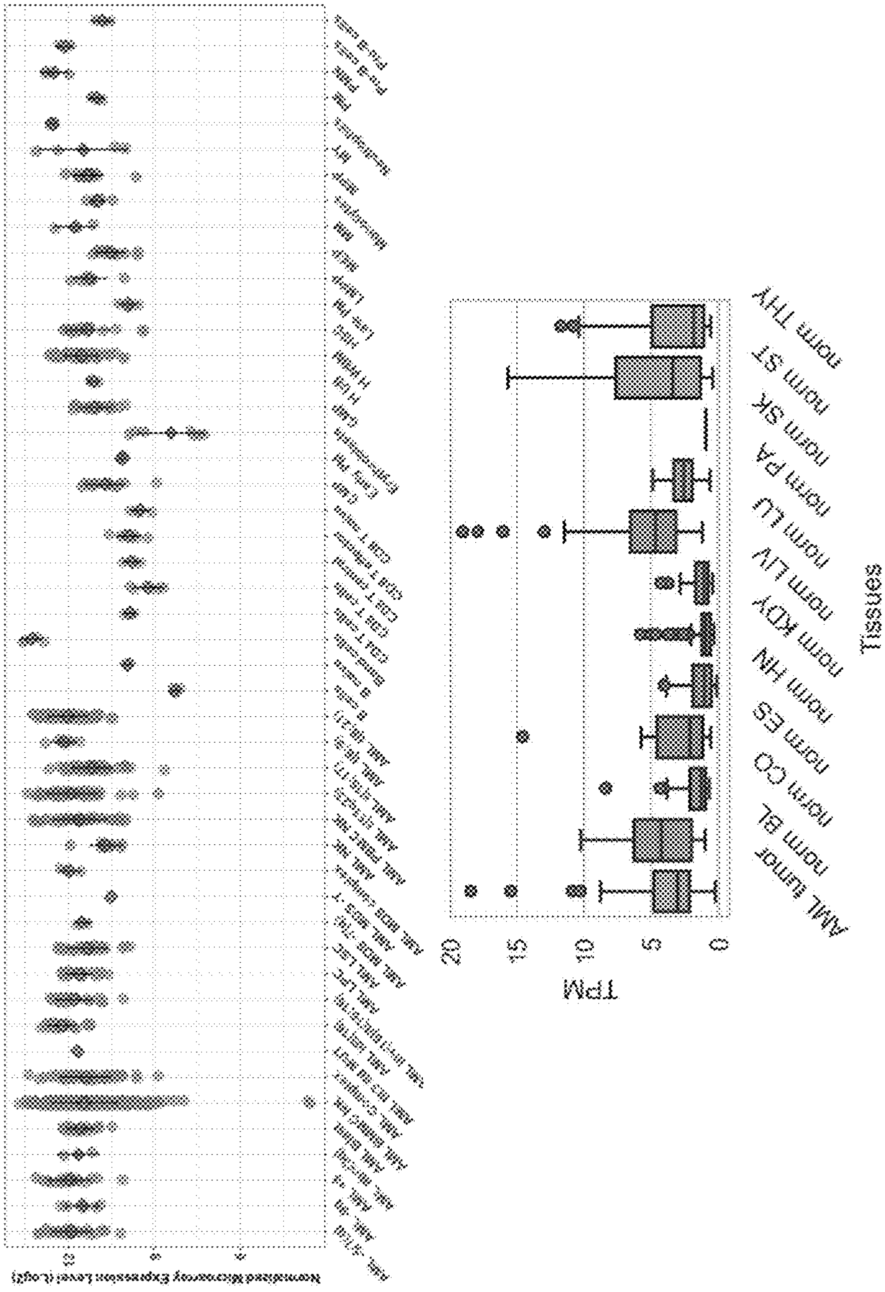
FIG. 16 provides microarray and RNA-Seq data for MYADM expression in the indicated tissues or cell types.
Figure 17:
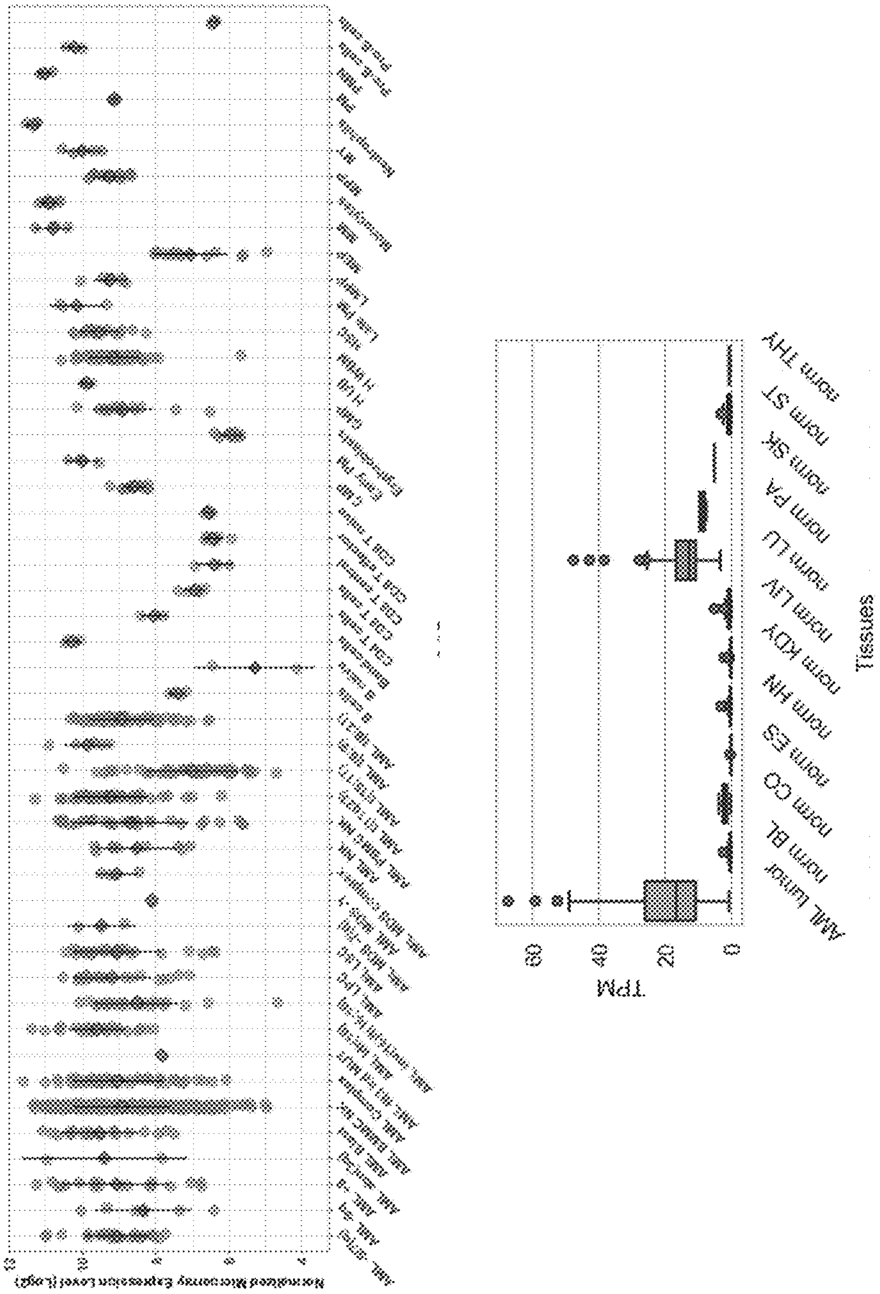
FIG. 17 provides microarray and RNA-Seq data for CD300LF expression in the indicated tissues or cell types.
Figure 18:
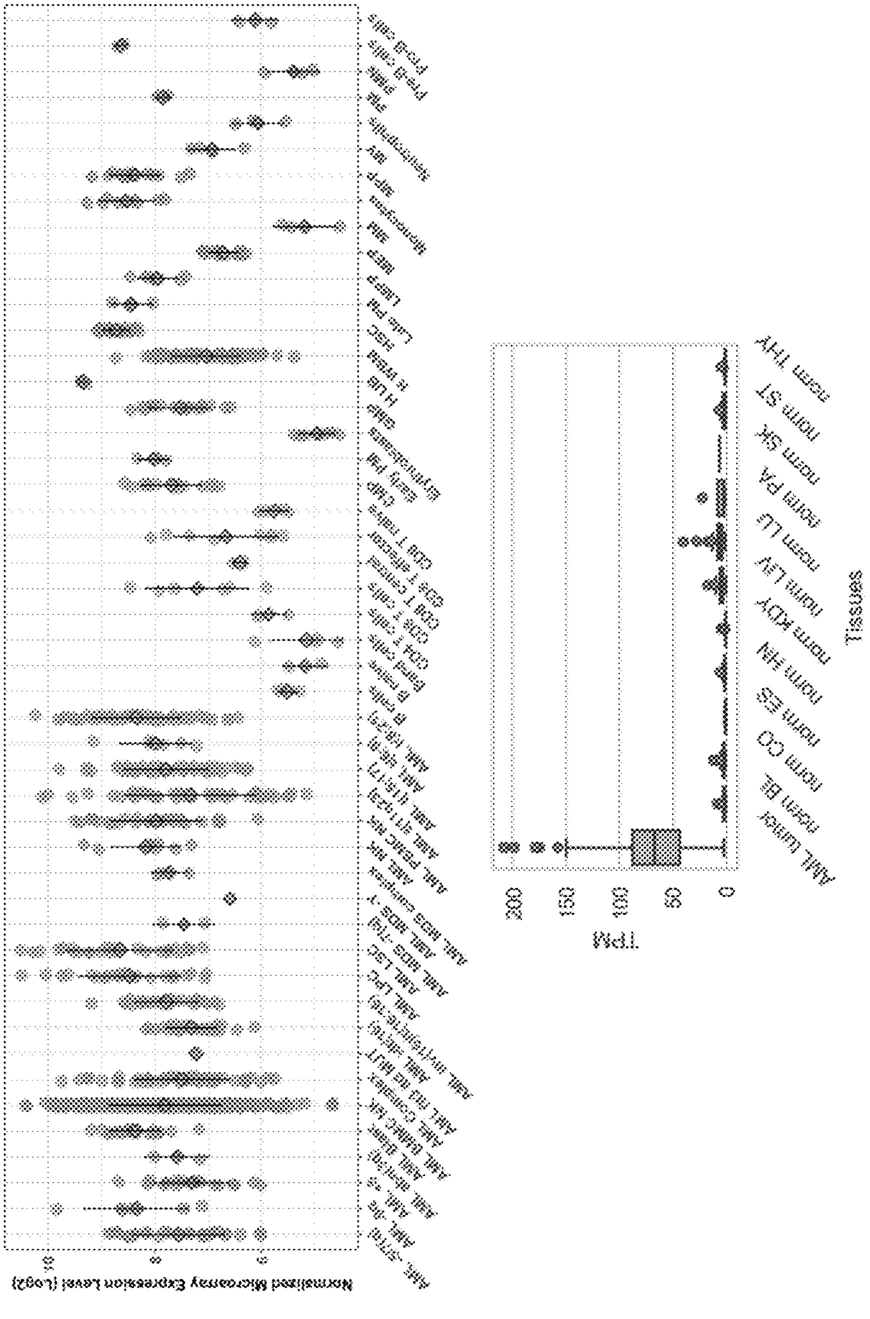
FIG. 18 provides microarray and RNA-Seq data for CD244/SLAMF4 expression in the indicated tissues or cell types.
Figure 19:
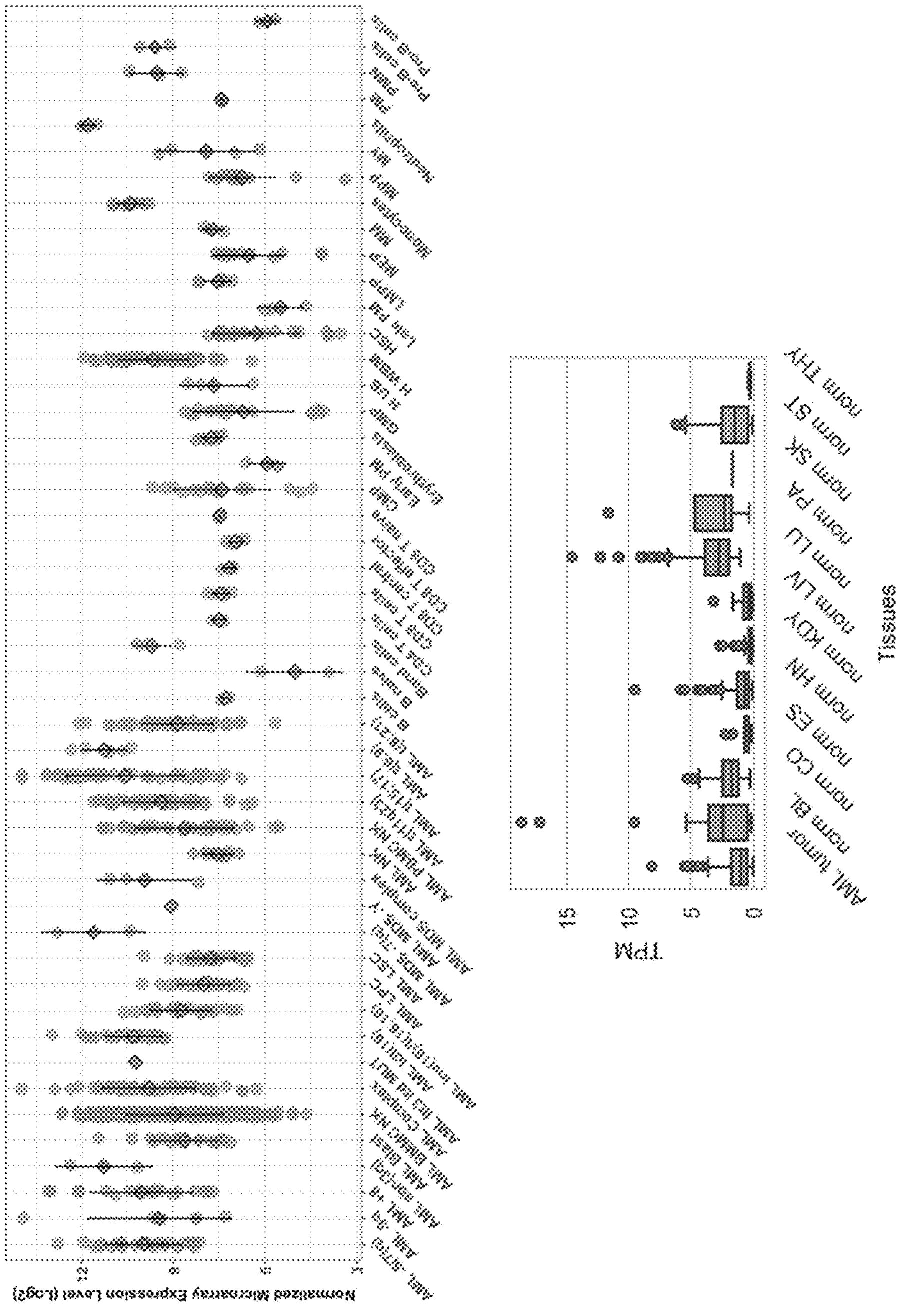
FIG. 19 provides microarray and RNA-Seq data for PLAUR expression in the indicated tissues or cell types.
Figure 20:
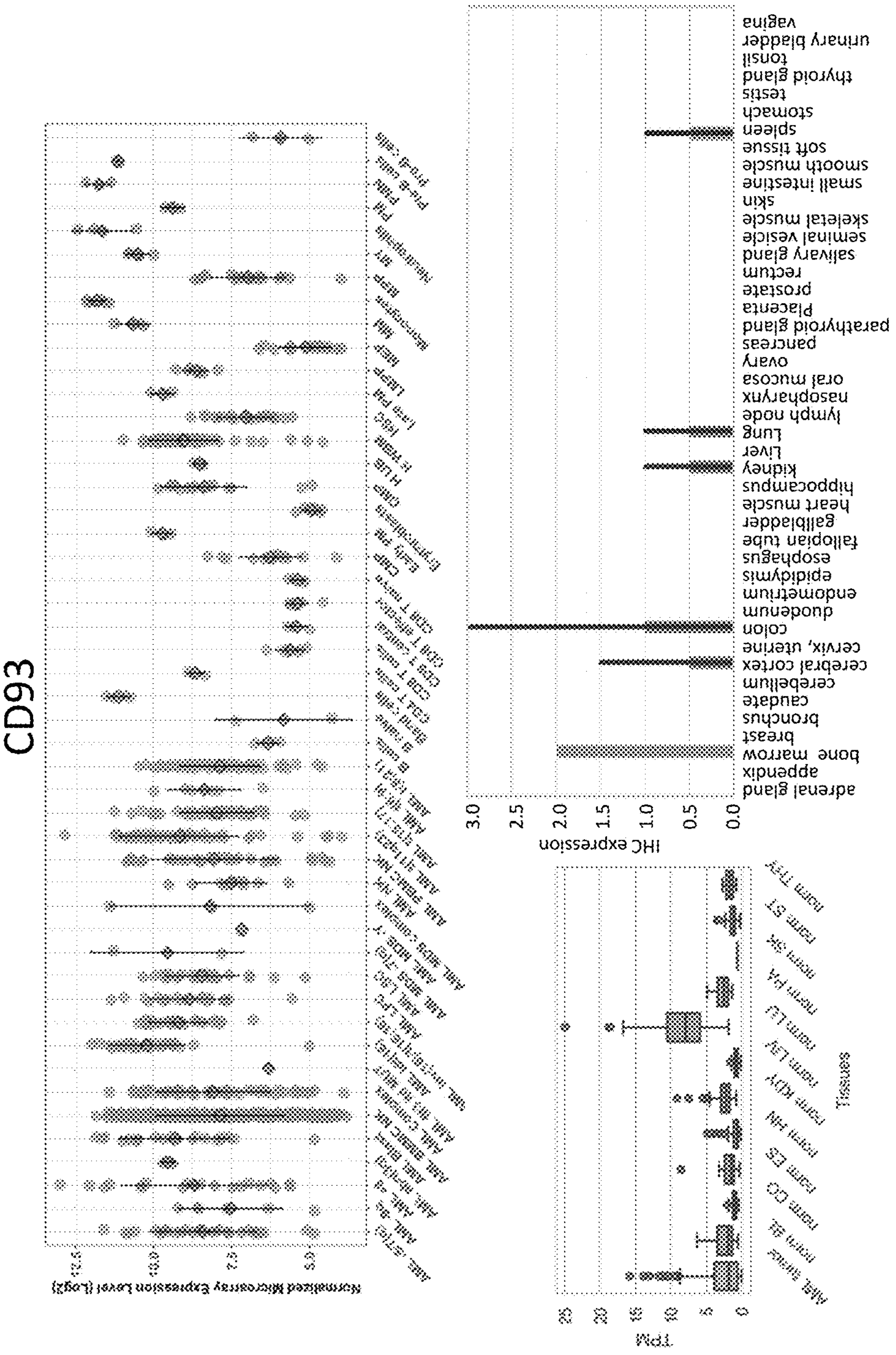
FIG. 20 provides microarray and RNA-Seq data for CD93 expression in the indicated tissues or cell types.
Figure 21:
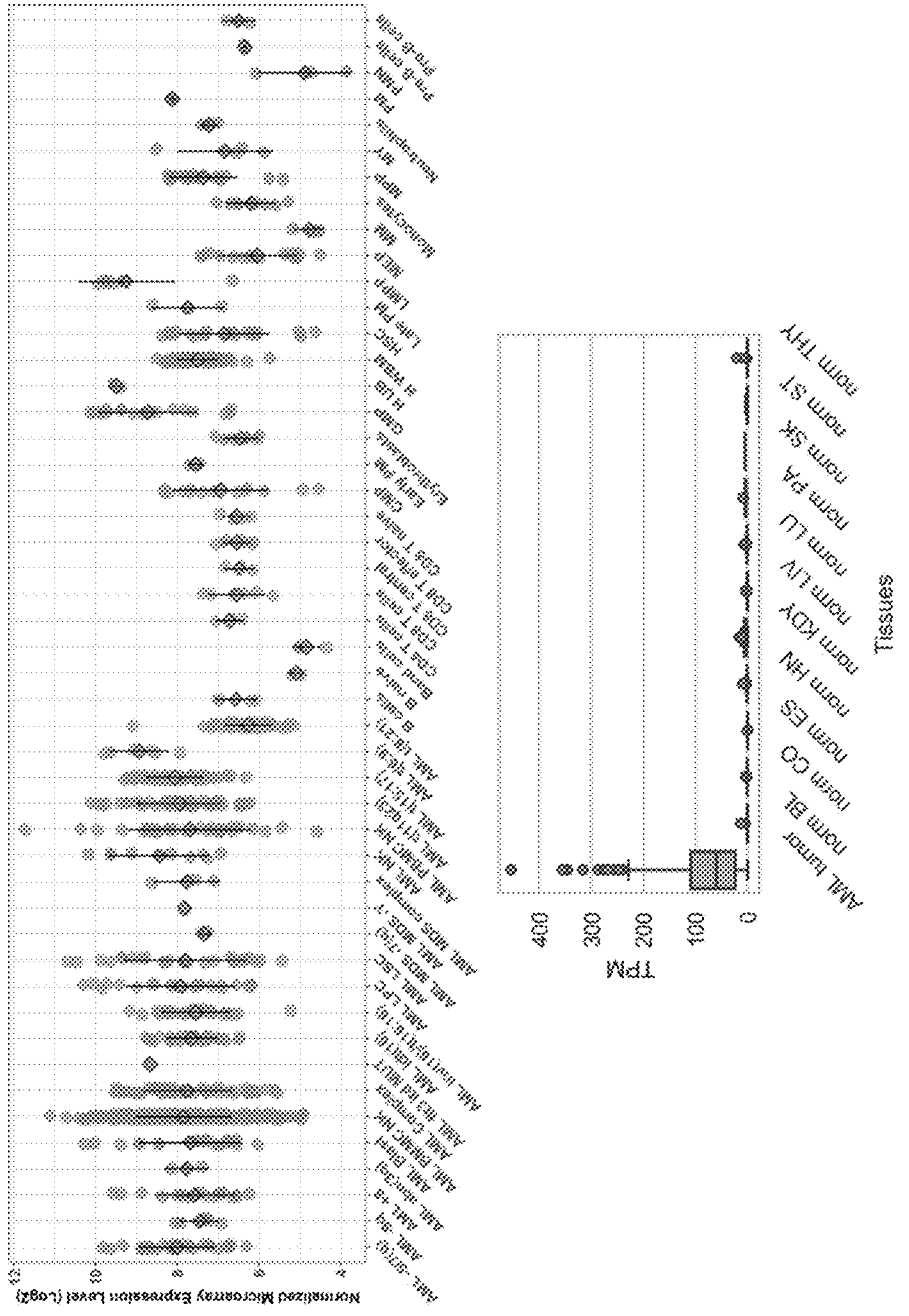
FIG. 21 provides microarray and RNA-Seq data for SPNS3 expression in the indicated tissues or cell types.
Figure 22:
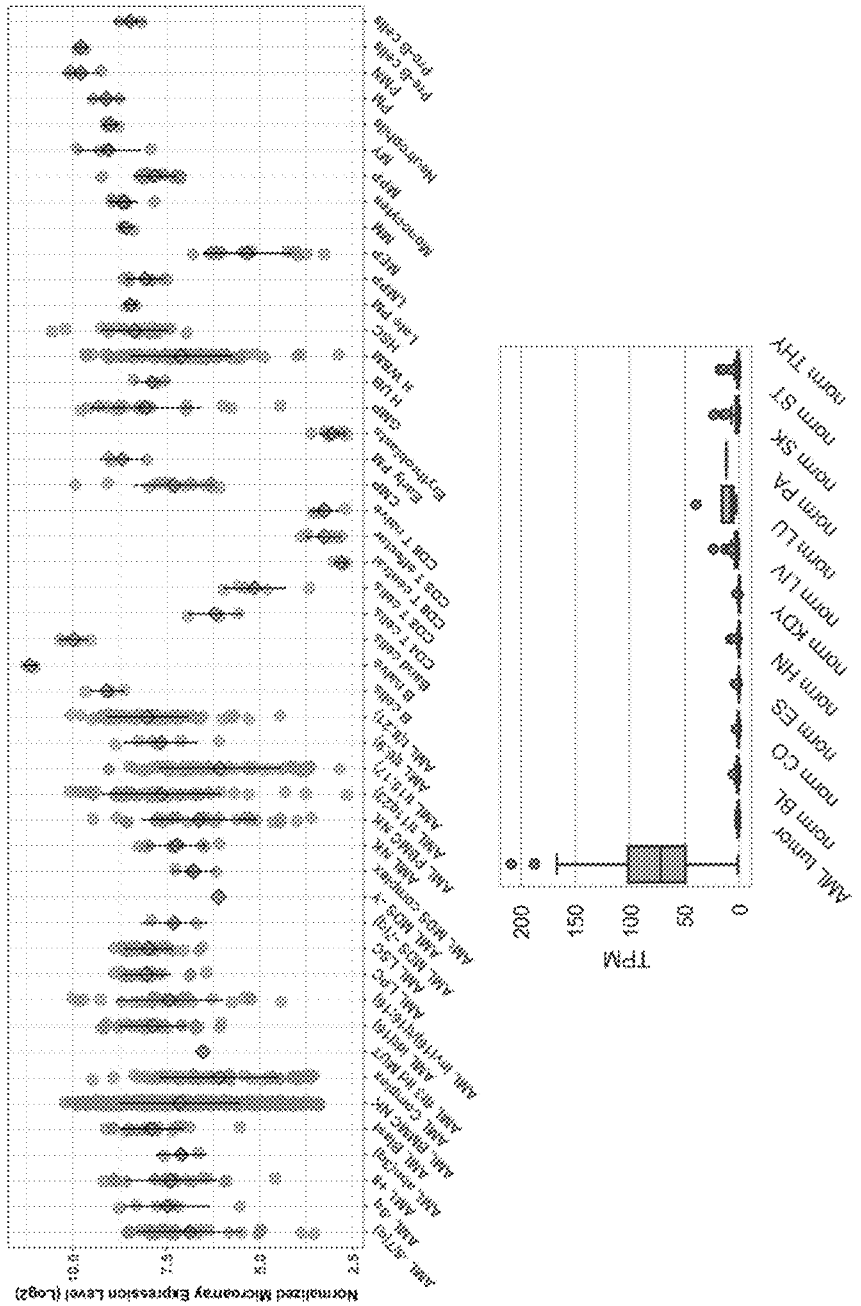
FIG. 22 provides microarray and RNA-Seq data for GAPT expression in the indicated tissues or cell types.
Figure 23:
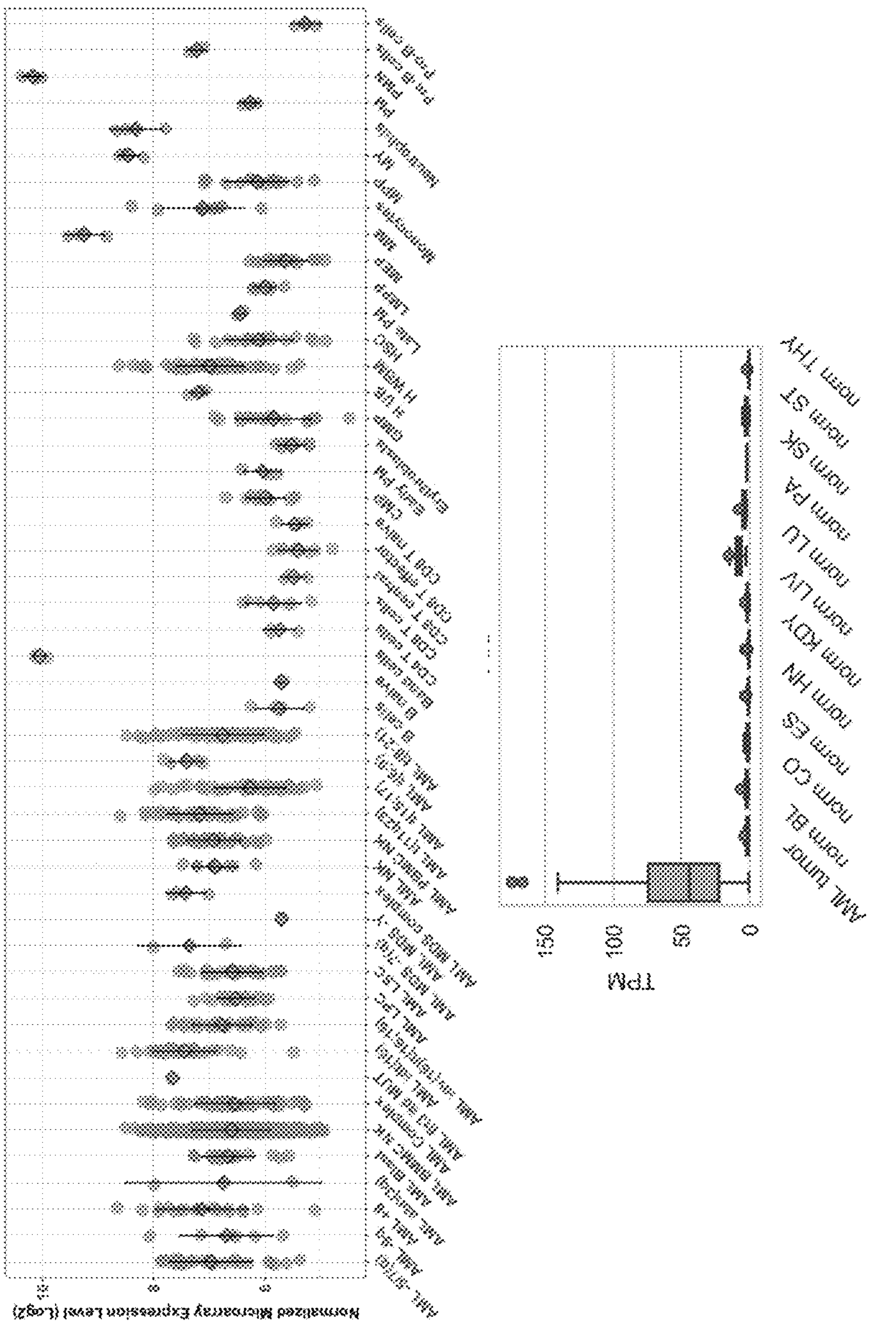
FIG. 23 provides microarray and RNA-Seq data for RASGRP4 expression in the indicated tissues or cell types.
Figure 24:
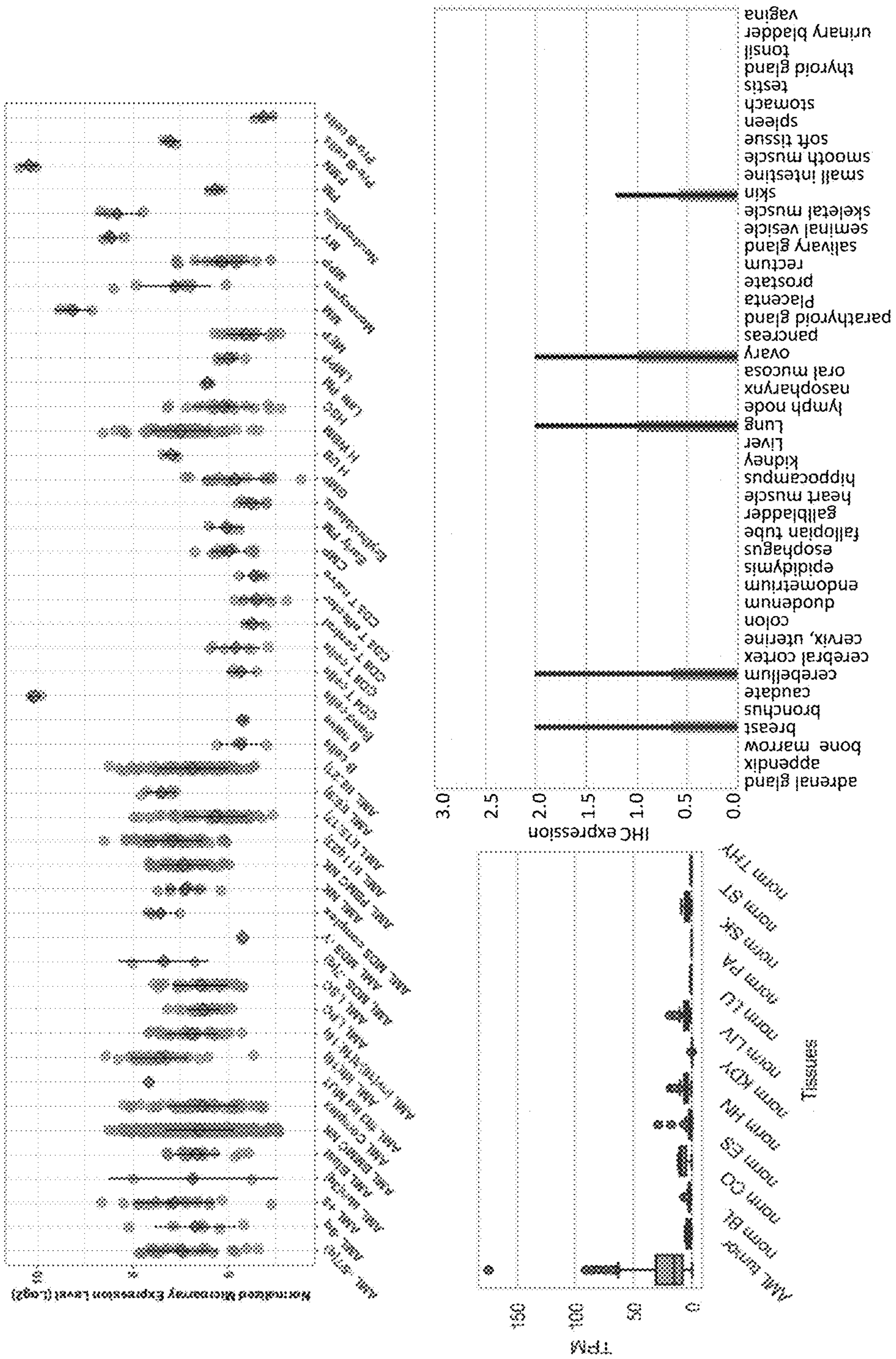
FIG. 24 provides microarray and RNA-Seq data for CD117/c-Kit expression in the indicated tissues or cell types.
Figure 25:
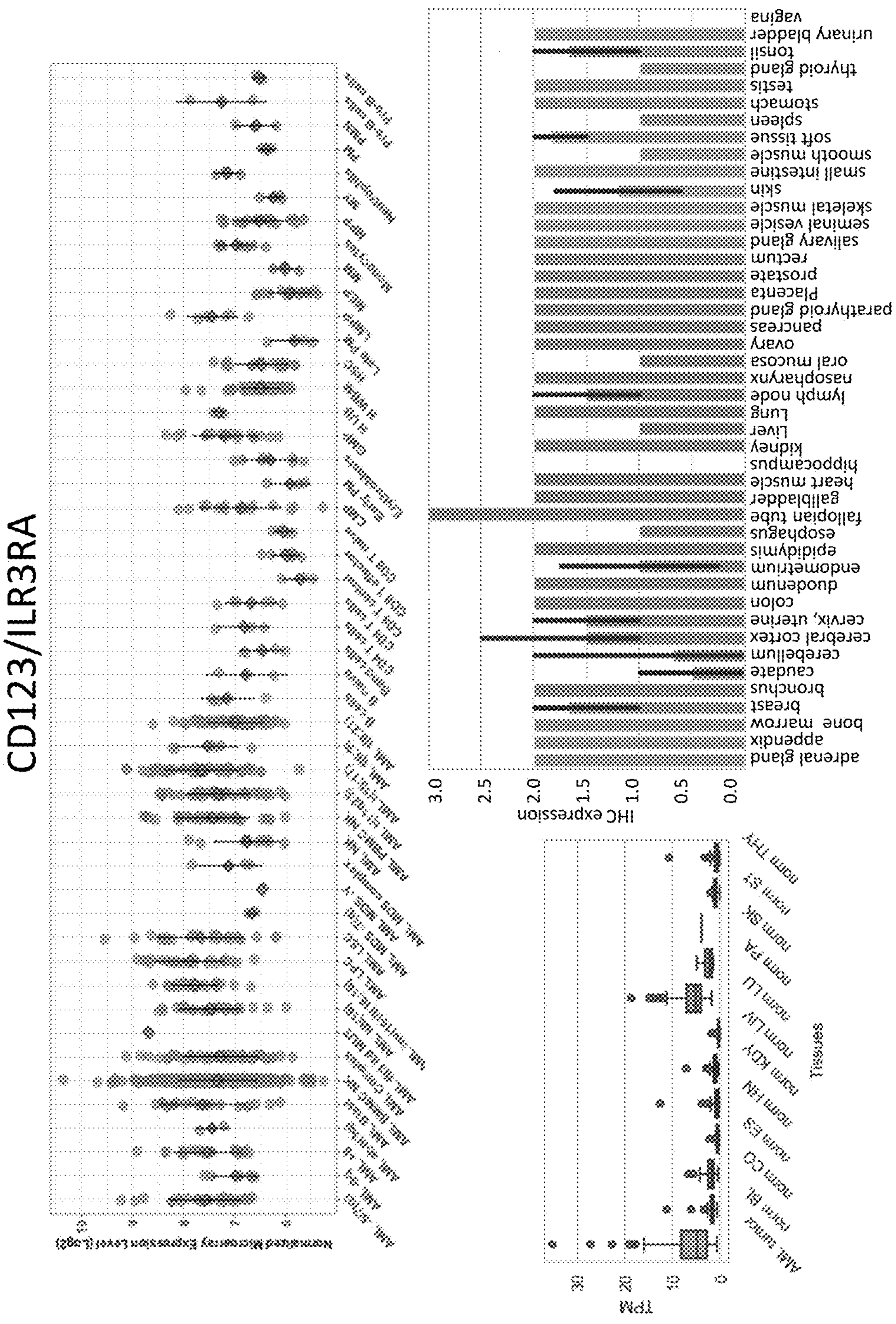
FIG. 25 provides microarray and RNA-Seq data for CD123/ILR3RA expression in the indicated tissues or cell types.
Figure 26:
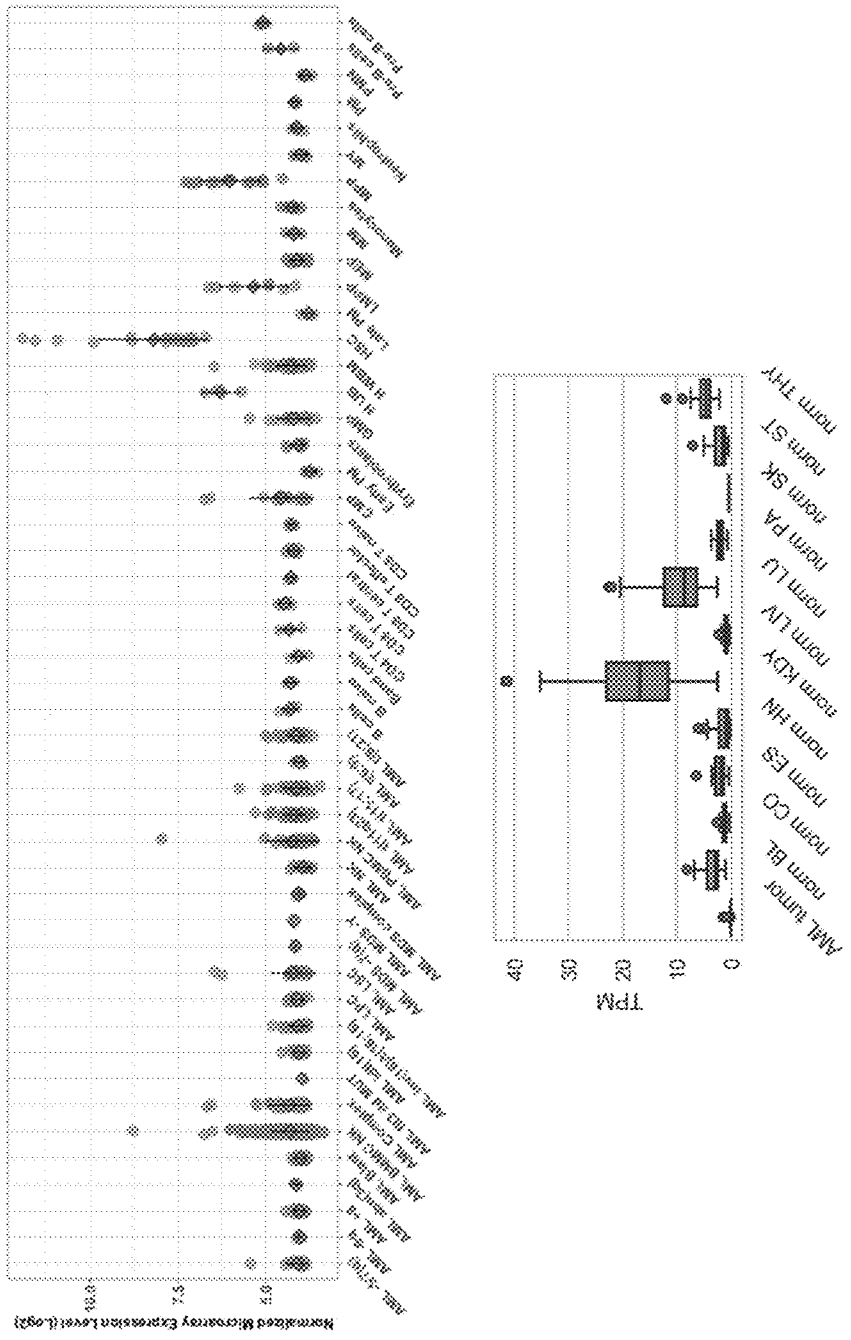
FIG. 26 provides microarray and RNA-Seq data for EMCN (endomucin) expression in the indicated tissues or cell types.
Figure 27:
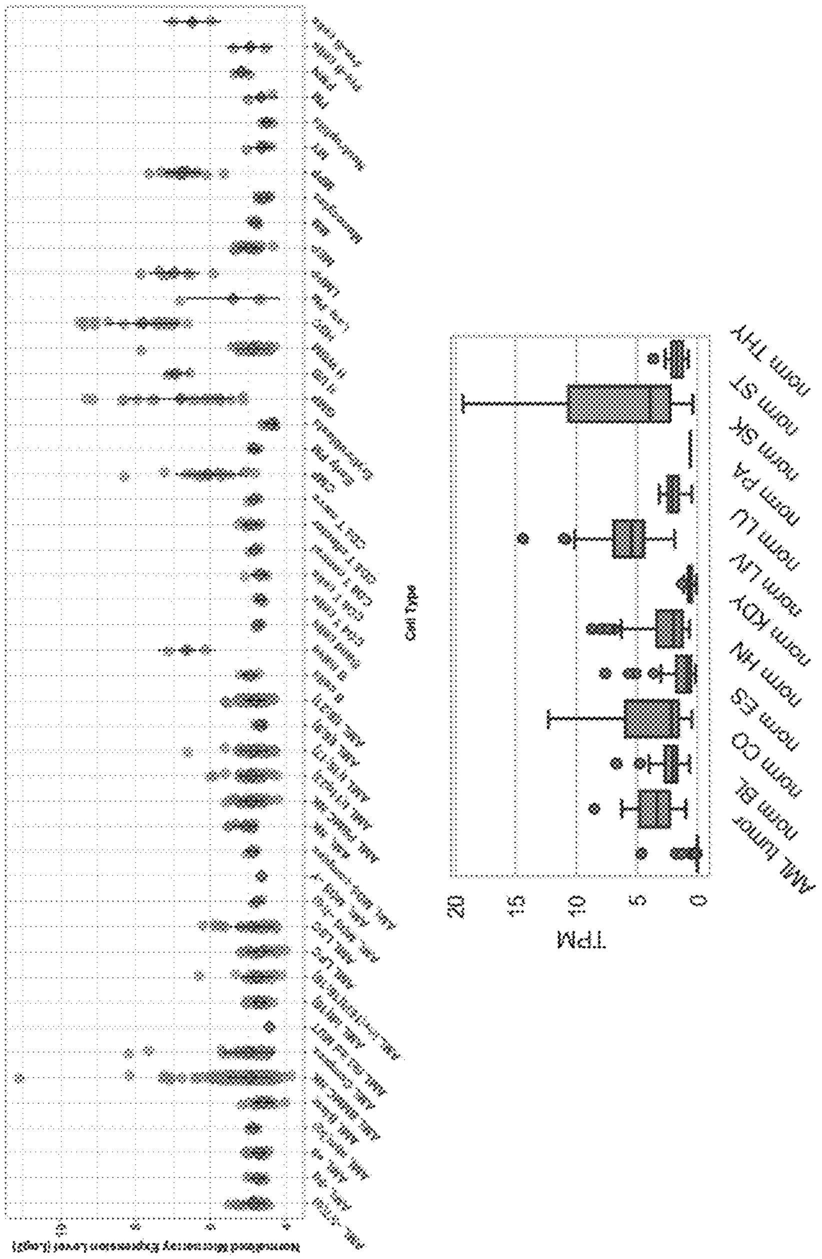
FIG. 27 provides microarray and RNA-Seq data for JAM2 expression in the indicated tissues or cell types.
Figure 28:
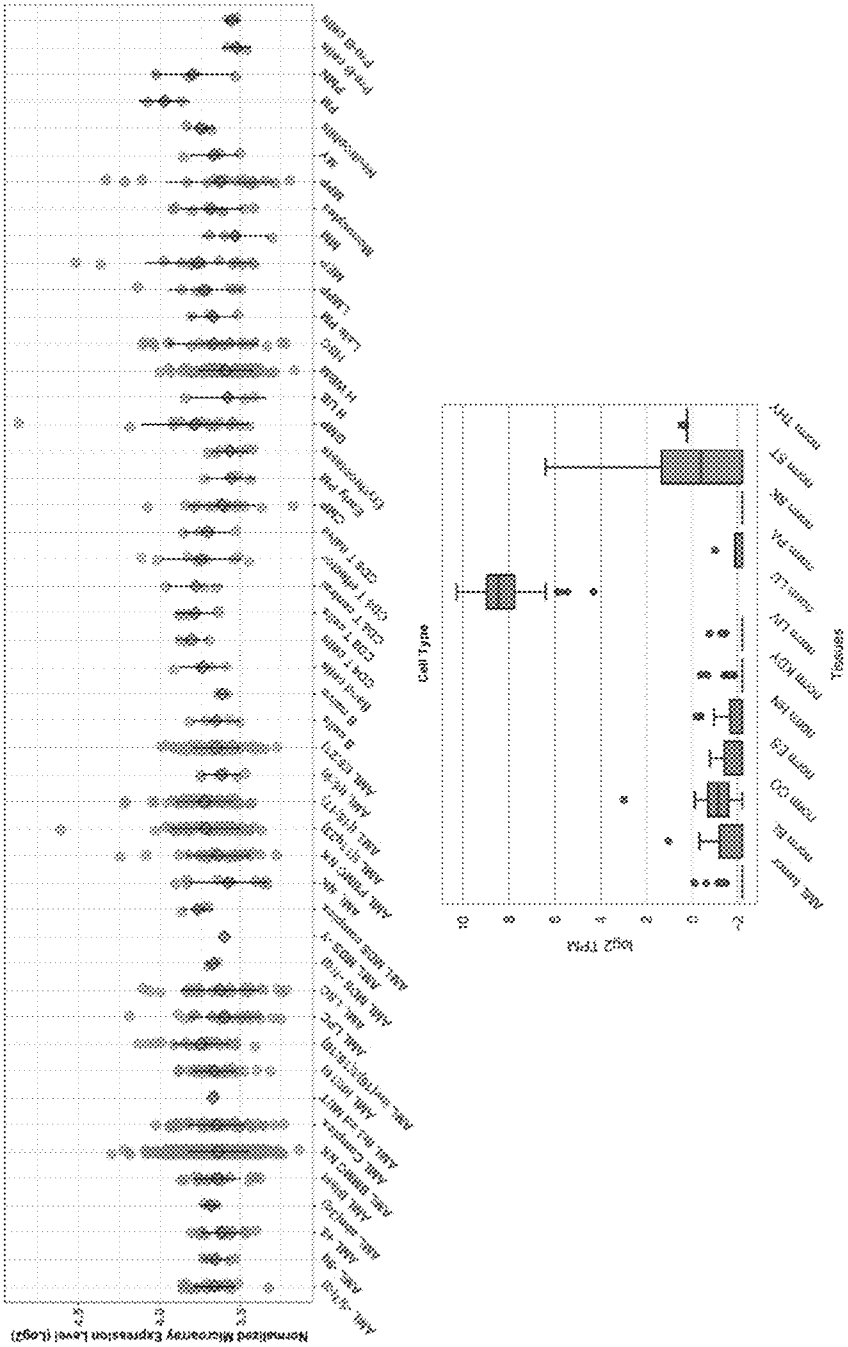
FIG. 28 provides microarray and RNA-Seq data for MS4A15 expression in the indicated tissues or cell types.
Figure 29:
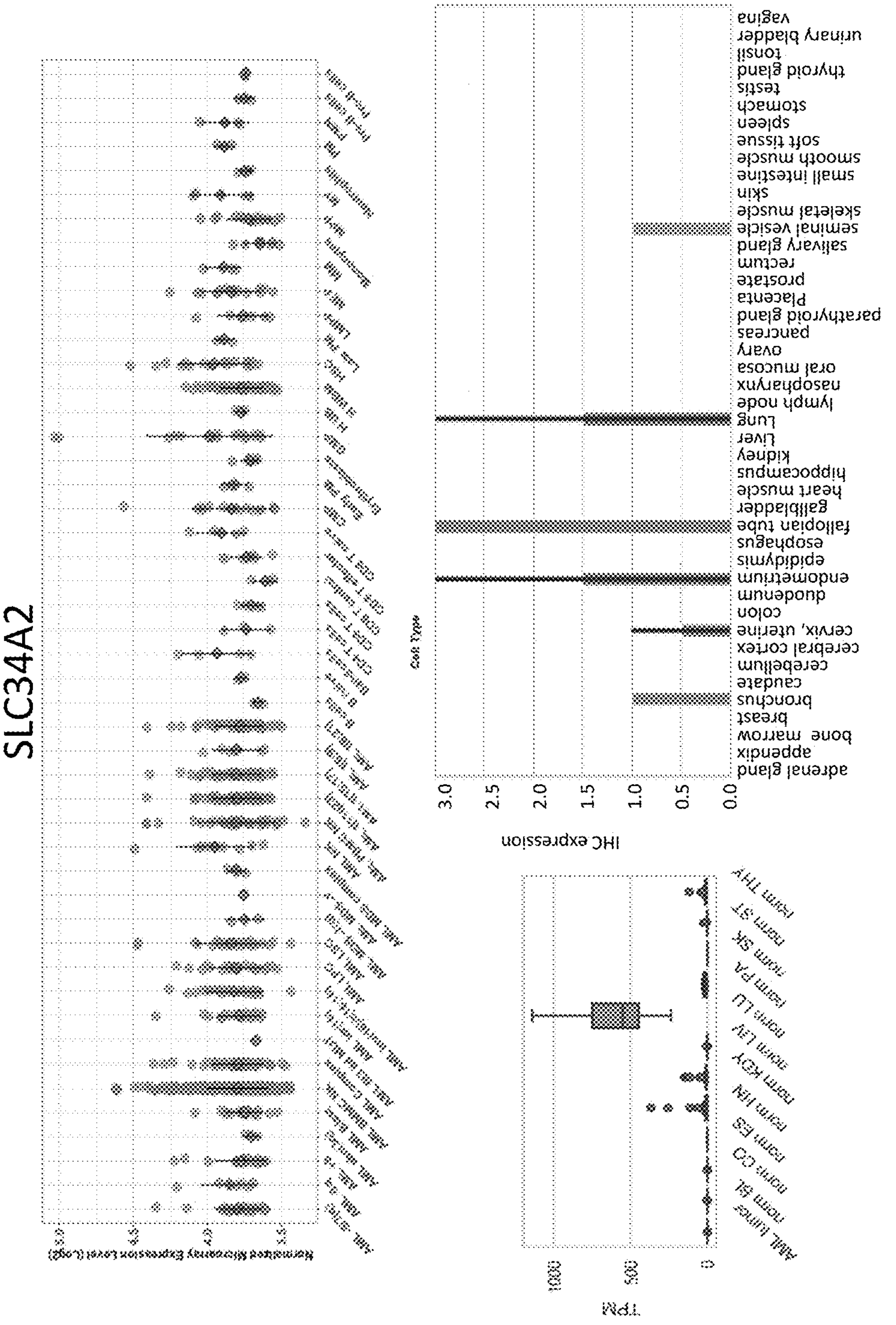
FIG. 29 provides microarray and RNA-Seq data for SLC34A2 expression in the indicated tissues or cell types.
Figure 30:
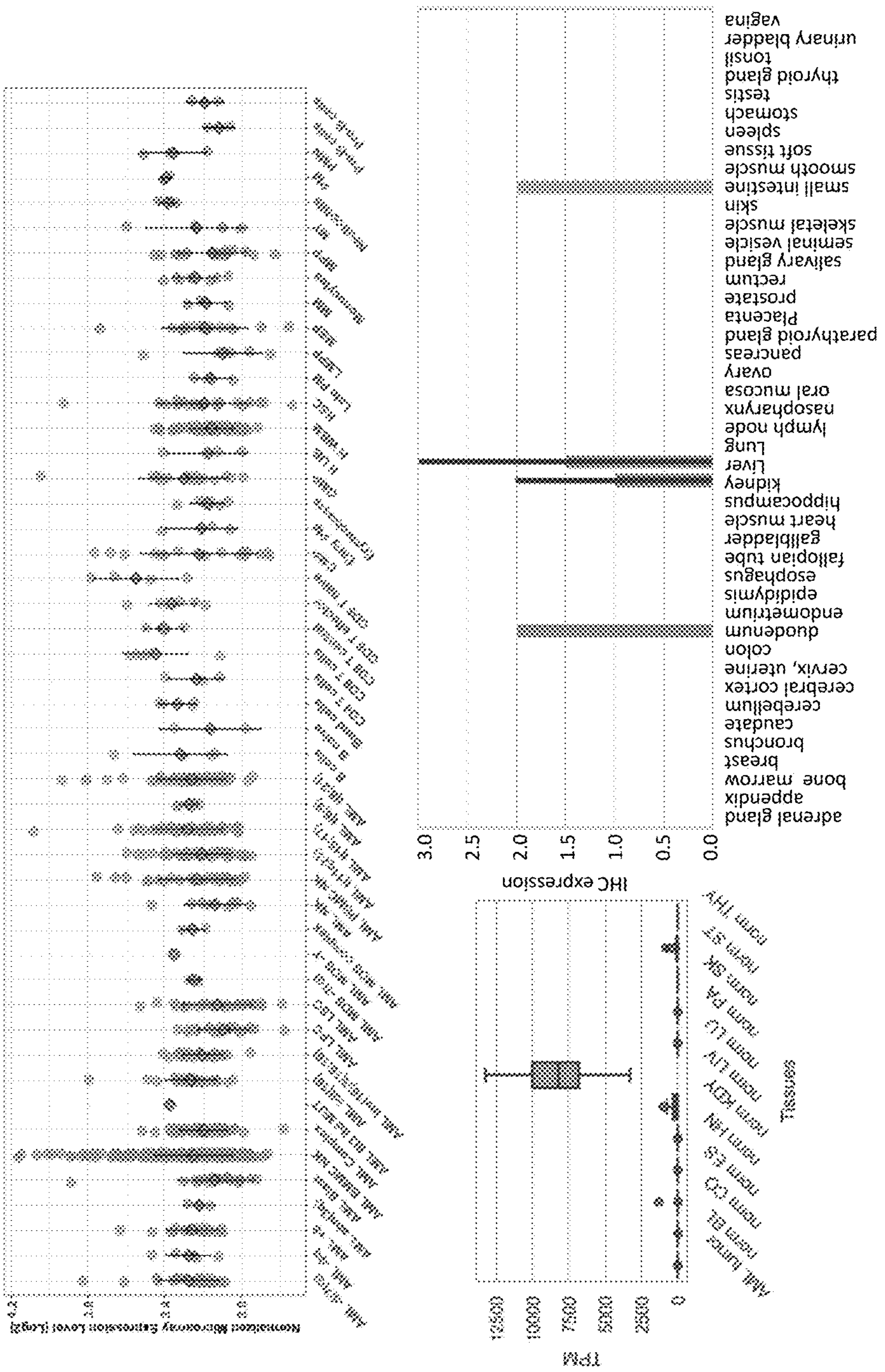
FIG. 30 provides microarray and RNA-Seq data for SLC2A2 expression in the indicated tissues or cell types.
Figure 31:
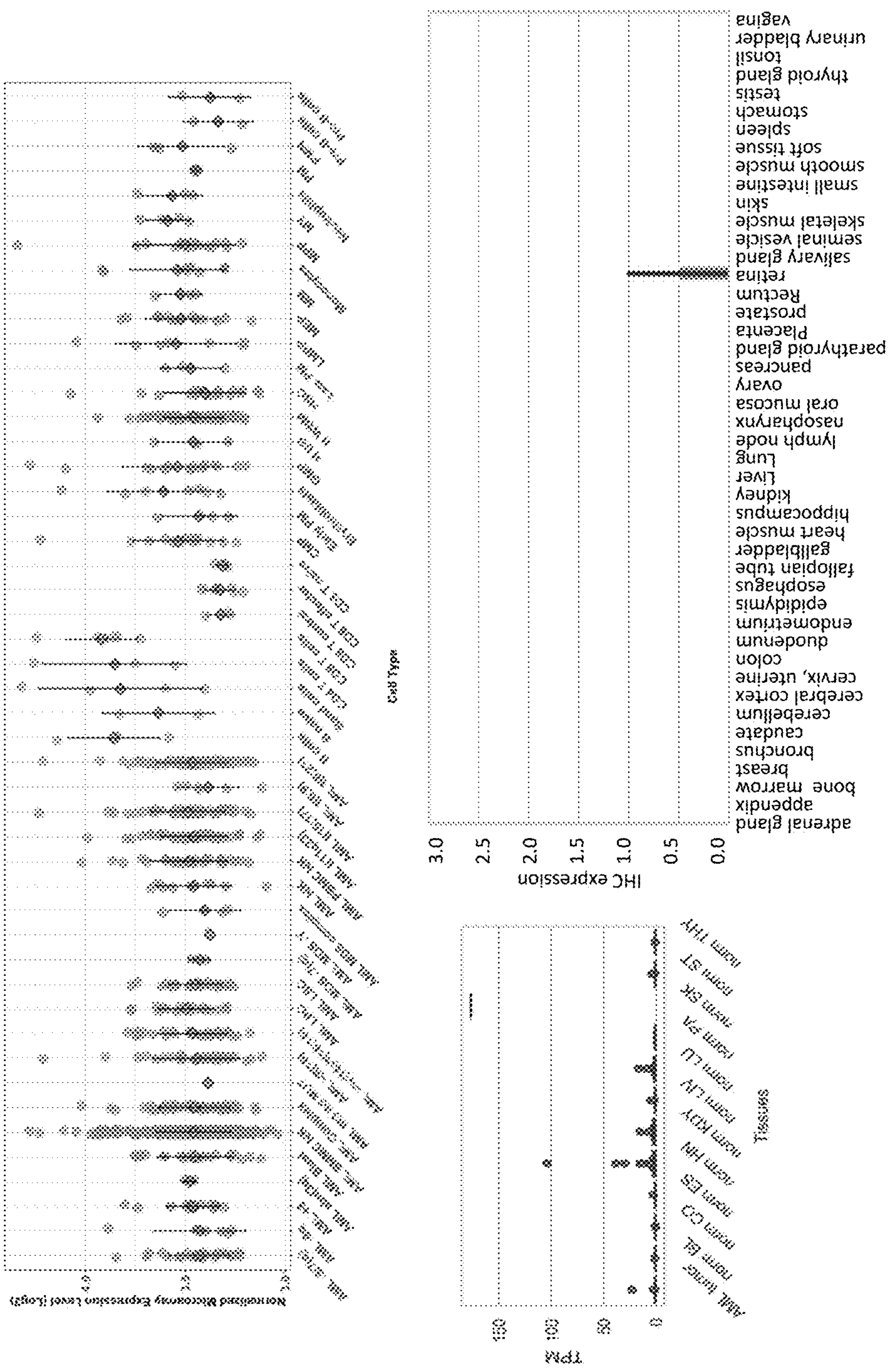
FIG. 31 provides microarray and RNA-Seq data for TRPM1 expression in the indicated tissues or cell types.
Figure 32:
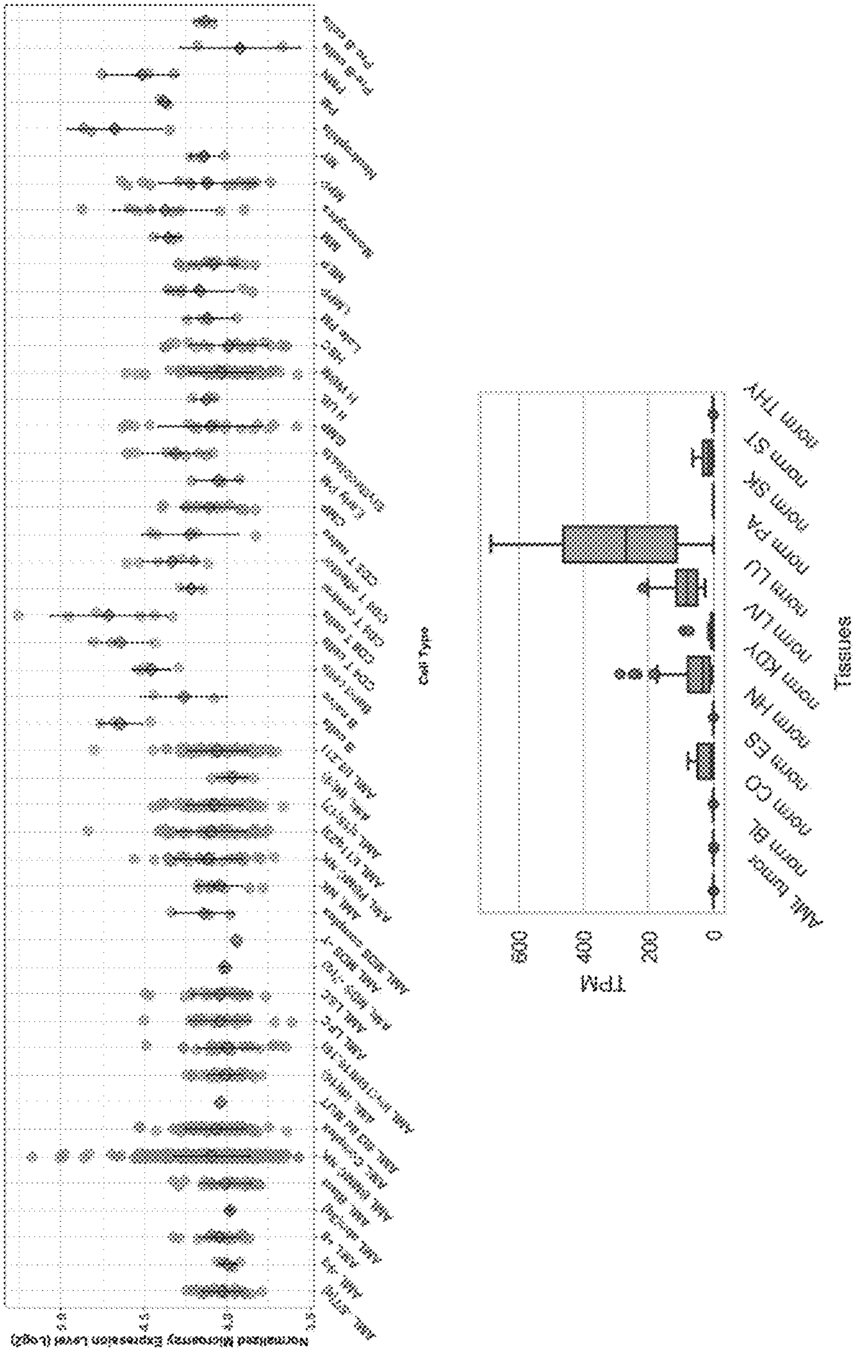
FIG. 32 provides microarray and RNA-Seq data for SCTR expression in the indicated tissues or cell types.
Figure 33:
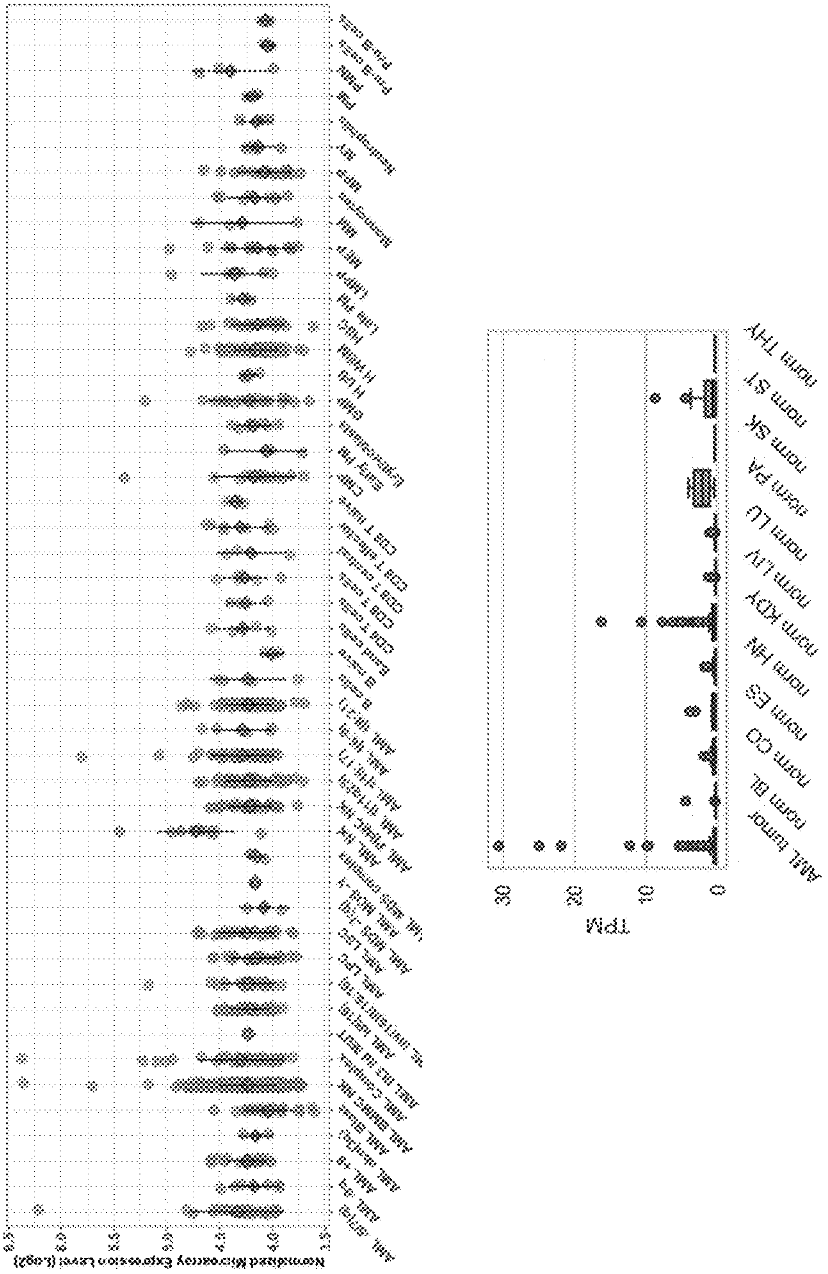
FIG. 33 provides microarray and RNA-Seq data for KCNQ2 expression in the indicated tissues or cell types.
Figure 34:
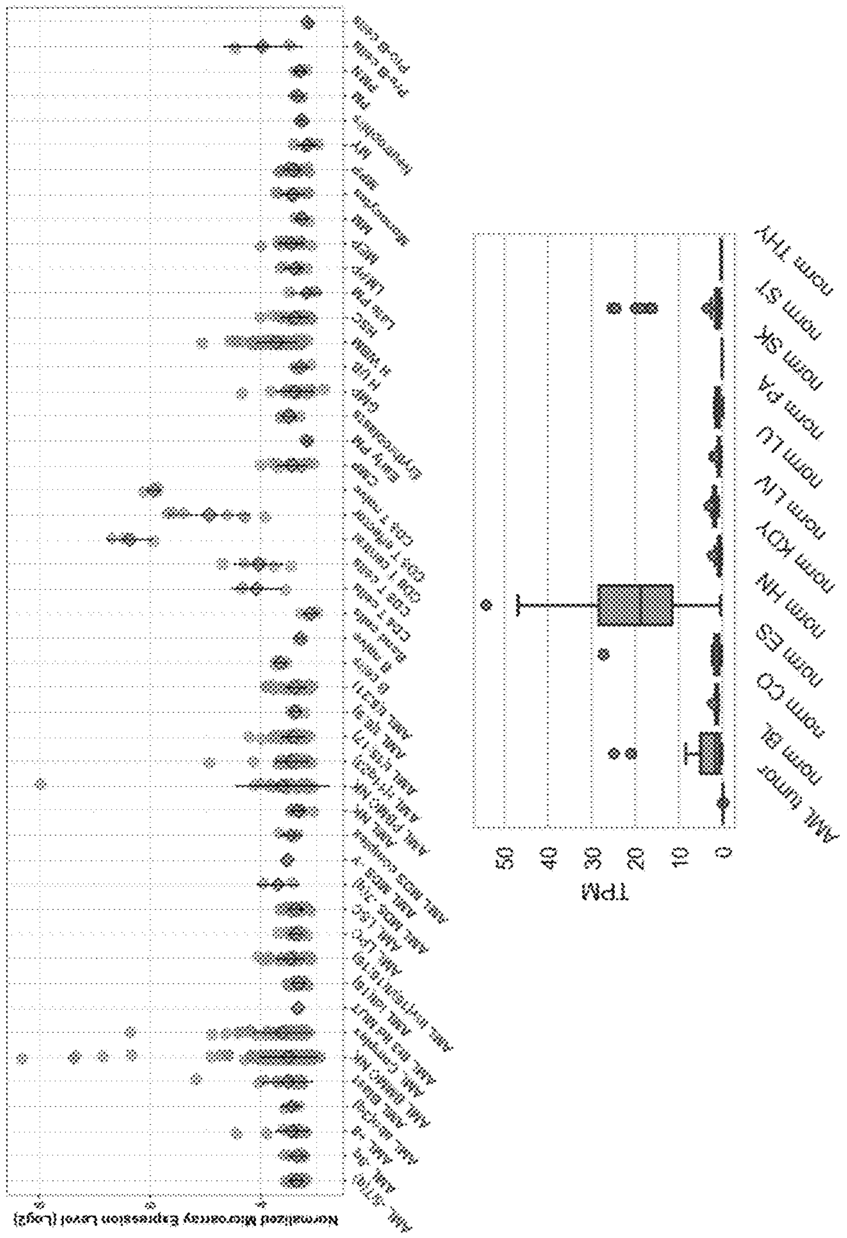
FIG. 34 provides microarray and RNA-Seq data for PERP expression in the indicated tissues or cell types.

The practice of the present disclosure will employ, unless otherwise indicated, conventional methods of molecular biology, chemistry, biochemistry, virology, and immunology, within the skill of the art. Such techniques are explained fully in the literature. See, e.g., Hepatitis C Viruses: Genomes and Molecular Biology (S. L. Tan ed., Taylor & Francis, 2006); Fundamental Virology, 3rd Edition, vol. I & II (B. N. Fields and D. M. Knipe, eds.); Handbook of Experimental Immunology, Vols. I-IV (D. M. Weir and C. C. Blackwell eds., Blackwell Scientific Publications); A. L. Lehninger, Biochemistry (Worth Publishers, Inc., current addition); Sambrook, et al., Molecular Cloning: A Laboratory Manual (3rd Edition, 2001); Methods In Enzymology (S. Colowick and N. Kaplan eds., Academic Press, Inc.).

Definitions

Unless otherwise defined, all terms of art, notations and other scientific terminology used herein are intended to have the meanings commonly understood by those of skill in the art. In some cases, terms with commonly understood meanings are defined herein for clarity and/or for ready reference, and the inclusion of such definitions herein should not necessarily be construed to represent a difference over what is generally understood in the art. The techniques and procedures described or referenced herein are generally well understood and commonly employed using conventional methodologies by those skilled in the art, such as, for example, the widely utilized molecular cloning methodologies described in Sambrook et al., *Molecular Cloning: A Laboratory Manual* 4th ed. (2012) Cold Spring Harbor Laboratory Press, Cold Spring Harbor, N.Y. As appropriate, procedures involving the use of commercially available kits and reagents are generally carried out in accordance with manufacturer-defined protocols and conditions unless otherwise noted.

As used herein, the singular forms "a," "an," and "the" include the plural referents unless the context clearly indicates otherwise. The terms "include," "such as," and the like are intended to convey inclusion without limitation, unless otherwise specifically indicated.

As used herein, the term "comprising" also specifically includes embodiments "consisting of" and "consisting essentially of" the recited elements, unless specifically indicated otherwise.

The term "about" indicates and encompasses an indicated value and a range above and below that value. In certain embodiments, the term "about" indicates the designated value ±10%, ±5%, or ±1%. In certain embodiments, where applicable, the term "about" indicates the designated value(s) ±one standard deviation of that value(s).

As used herein, the term "activating an immunoresponsive cell" refers to the induction of signal transduction or changes in protein expression in the cell that results in the initiation of an immune response. For example, when CD3 chains cluster in response to ligand binding and immunoreceptor tyrosine-based inhibition motifs (ITAMs) a signal transduction cascade is produced. In certain embodiments, when an endogenous TCR or an exogenous CAR binds antigen, a formation of an immunological synapse occurs that includes clustering of many molecules near the bound receptor (e.g. CD4 or CD8, CD3γ/δ/ε/ζ, etc.). This clustering of membrane bound signaling molecules allows for ITAM motifs contained within the CD3 chains to become phosphorylated. This phosphorylation in turn initiates a T cell activation pathway ultimately activating transcription factors, such as NF-κB and AP-1. These transcription factors induce global gene expression of the T cell to increase IL-2 production for proliferation and expression of master regulator T cell proteins in order to initiate a T cell mediated immune response.

As used herein, the term "stimulates an immunoresponsive cell" refers to a signal that results in a robust and sustained immune response. In various embodiments, this occurs after immune cell (e.g., T-cell) activation or concomitantly mediated through receptors including, but not limited to, CD28, CD137 (4-1BB), OX40, CD40 and ICOS. Without being bound to a particular theory, receiving multiple stimulatory signals is important to mount a robust and long-term T cell mediated immune response. Without receiving these stimulatory signals, T cells quickly become inhibited and unresponsive to antigen. While the effects of these co-stimulatory signals vary and remain partially understood, they generally result in increasing gene expression in order to generate long lived, proliferative, and anti-apoptotic T cells that robustly respond to antigen for complete and sustained eradication.

As used herein, the term "chimeric antigen receptor" or alternatively a "CAR" refers to a recombinant polypeptide construct comprising at least an extracellular antigen-binding domain, a transmembrane domain and a cytoplasmic signaling domain (also referred to herein as "an intracellular signaling domain") comprising a functional signaling domain derived from a stimulatory molecule as defined below. In some embodiments, the domains in the CAR polypeptide construct are in the same polypeptide chain, e.g., comprise a chimeric fusion protein. In some embodiments, the domains in the CAR polypeptide construct are not contiguous with each other, e.g., are in different polypeptide chains, e.g., as provided in an RCAR as described herein. In one aspect, the stimulatory molecule is the zeta chain associated with the T cell receptor complex. In one aspect, the cytoplasmic signaling domain comprises a primary signaling domain (e.g., a primary signaling domain of CD3-zeta). In one aspect, the cytoplasmic signaling domain further comprises one or more functional signaling domains derived from at least one costimulatory molecule as defined below. In one aspect, the costimulatory molecule is chosen from 4-1BB (i.e., CD 137), CD27, ICOS, and/or CD28. In one aspect, the CAR. comprises a chimeric fusion protein comprising an extracellular antigen-binding domain, a transmembrane domain and an intracellular signaling domain comprising a functional signaling domain derived from a stimulatory molecule. In one aspect, the CAR comprises a chimeric fusion protein comprising an extracellular antigen-binding domain, a transmembrane domain and an intracellular signaling domain comprising a functional signaling domain derived from a co-stimulatory molecule and a functional signaling domain derived from a stimulatory molecule. In one aspect, the CAR comprises a chimeric fusion protein comprising an extracellular antigen-binding domain, a transmembrane domain and an intracellular signaling domain comprising two functional signaling domains derived from one or more co-stimulatory molecule(s) and a functional signaling domain derived from a stimulatory molecule. In one aspect, the CAR comprises a chimeric fusion protein comprising an extracellular antigen-binding domain, a transmembrane domain and an intracellular signaling domain comprising at least two functional signaling domains derived from one or more co-stimulatory molecule(s) and a functional signaling domain derived from a stimulator}' molecule. In one aspect the CAR comprises an optional leader sequence at the amino-terminus (N-ter) of the CAR fusion protein. In one aspect, the CAR further comprises a leader sequence at the N-terminus of the extracellular antigen-binding domain, wherein the leader sequence is optionally cleaved from the antigen recognition domain (e.g., an scFv) during cellular processing and localization of the CAR to the cellular membrane.

As used herein, the term "intracellular signaling domain" refers to the functional portion of a protein which acts by transmitting information within the cell to regulate cellular activity via defined signaling pathways by generating second messengers or functioning as effectors by responding to such messengers. In some embodiments, the signaling domain of a chimeric receptor of the present disclosure is derived from a stimulatory molecule or co-stimulatory molecule described herein, or is a synthesized or engineered signaling domain.

The term "antibody," as used herein, refers to a protein, or polypeptide sequence derived from an immunoglobulin molecule which specifically binds with an antigen. Antibodies can be polyclonal or monoclonal, multiple or single chain, or intact immunoglobulins, and may be derived from natural sources or from recombinant sources. Antibodies can be tetramers of immunoglobulin molecules.

As used herein, the term "antibody fragment" refers to at least one portion of an intact antibody, or recombinant variants thereof, and refers to the antigen-binding domain, e.g., an antigenic determining variable region of an intact antibody, that is sufficient to confer recognition and specific binding of the antibody fragment to a target, such as an antigen. Examples of antibody fragments include, but are not limited to, Fab, Fab', $F(ab')_2$, and Fv fragments, scFv antibody fragments, linear antibodies, single domain antibodies such as sdAb (either VL or VH), camelid VHH domains, and multi-specific antibodies formed from antibody fragments such as a bivalent fragment comprising two Fab fragments linked by a disulfide bridge at the hinge region, and an isolated CDR or other epitope binding fragments of an antibody. An antigen binding fragment can also be incorporated into single domain antibodies, maxibodies, minibodies, nanobodies, intrabodies, diabodies, triabodies, tetrabodies, v-NAR and bis-scFv (see, e.g., Hollinger and Hudson, Nature Biotechnology 23: 1126-1 136, 2005). Antigen binding fragments can also be grafted into scaffolds based on polypeptides such as a fibronectin type III (Fn3)(see U.S. Pat. No. 6,703,199, which describes fibronectin polypeptide minibodies).

As used herein, the term "single-chain variable fragment" or "scFv" refers to a fusion protein comprising at least one antibody fragment comprising a variable region of a light chain and at least one antibody fragment comprising a variable region of a heavy chain, wherein the light and heavy chain variable regions are contiguously linked via a short flexible polypeptide linker, and capable of being expressed as a single chain poly peptide, and wherein the scFv retains the specificity of the intact antibody from which it is derived. Unless specified, as used herein an scFv may have the VL and VH variable regions in either order, e.g., with respect to the N-terminal and C-terminal ends of the polypeptide, the scFv may comprise VL-linker-VH or may comprise VH-linker-VL.

The term "complementarity determining region" or "CDR," as used herein, refers to the sequences of ammo acids within antibody variable regions which confer antigen specificity and binding affinity. For example, in general, there are three CDRs in each heavy chain variable region (e.g., HCDR1, HCDR2, and HCDR3) and three CDRs in each light chain variable region (LCDR1, LCDR2, and LCDR3). The precise ammo acid sequence boundaries of a given CDR can be determined using any of a number of well-known schemes, including those described by Kabat et al. (1991), "Sequences of Proteins of Immunological Interest," 5th Ed. Public Health Service, National Institutes of Health, Bethesda, Md. ("Kabat" numbering scheme), Al-Lazikani et al, (1997) JMB 273,927-948 ("Chothia" numbering scheme), or a combination thereof. Under the Kabat numbering scheme, in some embodiments, the CDR amino acid residues in the heavy chain variable domain (VH) are numbered 31-35 (HCDR1), 50-65 (HCDR2), and 95-102 (HCDR3); and the CDR amino acid residues in the light chain variable domain (VL) are numbered 24-34 (LCDR1), 50-56 (LCDR2), and 89-97 (LCDR3). Under the Chothia numbering scheme, in some embodiments, the CDR amino acids in the VH are numbered 26-32 (HCDR1), 52-56 (HCDR2), and 95-102 (HCDR3); and the CDR amino acid residues in the VL are numbered 26-32 (LCDR1), 50-52 (LCDR2), and 91-96 (LCDR3). In a combined Kabat and Chothia numbering scheme, in some embodiments, the CDRs correspond to the amino acid residues that are part of a Kabat CDR, a Chothia CDR, or both. For instance, in some embodiments, the CDRs correspond to amino acid residues 26-35 (HCDR1), 50-65 (HCDR2), and 95-102 (HCDR3) in a VH, e.g., a mammalian VH, e.g., a human VH; and ammo acid residues 24-34 (LCDR1), 50-56 (LCDR2), and 89-97 (LCDR3) in a VL, e.g., a mammalian VL, e.g., a human VL.

The portion of the chimeric receptor of the present disclosure comprising an antibody or antibody fragment thereof may exist in a variety of forms where the antigen-binding domain is expressed as part of a contiguous polypeptide chain including, for example, scFv antibody fragments, linear antibodies, single domain antibodies such as sdAb (either VL or VH), camelid VHH domains, a humanized antibody, a bispecific antibody, an antibody conjugate (Harlow et al., 1999, In: Using Antibodies: A Laboratory Manual, Cold Spring Harbor Laboratory Press, NY; Harlow et al, 1989, In: Antibodies: A Laboratory Manual, Cold Spring Harbor, N.Y.; Houston et al, 1988, Proc. Natl. Acad. Sci. USA 85:5879-5883; Bird et al, 1988, Science 242:423-426). In one aspect, the antigen-binding domain of a chimeric receptor of the present disclosure comprises an antibody fragment. In a further aspect, the chimeric receptor comprises an antibody fragment that comprises an scFv.

As used herein, the term "antibody heavy chain" refers to the larger of the two types of polypeptide chains present in antibody molecules in their naturally occurring conformations, and which normally determines the class to which the antibody belongs.

As used herein, the term "antibody light chain" refers to the smaller of the two types of polypeptide chains present in antibody molecules in their naturally occurring conformations. Kappa (κ) and lambda (λ) light chains refer to the two major antibody light chain isotypes.

As used herein, the term "recombinant antibody" refers to an antibody which is generated using recombinant DNA technology, such as, for example, an antibody expressed by a bacteriophage or yeast expression system. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using recombinant DNA or amino acid sequence technology which is available and well known in the art.

As used herein, the term "antigen" or "Ag" refers to a molecule that provokes an immune response. This immune response may involve either antibody production, or the activation of specific immunologically-competent cells, or both. The skilled artisan will understand that any macromolecule, including virtually all proteins or peptides, can serve as an antigen.

As used herein, the term "anti-tumor effect" or "anti-tumor activity" refers to a biological effect which can be manifested by various means, including but not limited to, e.g., a decrease in tumor volume, a decrease in the number of tumor cells, a decrease in the number of metastases, an increase in life expectancy, decrease in tumor cell proliferation, decrease in tumor ceil survival, or amelioration of various physiological symptoms associated with the cancerous condition. An "anti-tumor effect" can also be manifested by the ability of the peptides, polynucleotides, cells and antibodies of the present disclosure in prevention of the occurrence of tumor in the first place.

As used herein, the term "autologous" refers to any material derived from the same individual to whom it is later to be re-introduced into the individual.

As used herein, the term "allogeneic" refers to any material derived from a different animal of the same species as the individual to whom the material is introduced. Two or more individuals are said to be allogeneic to one another when the genes at one or more loci are not identical. In some embodiments, allogeneic material from individuals of the same species may be sufficiently unlike genetically to interact antigenically.

As used herein, the term "affinity" refers to a measure of binding strength. Without being bound to theory, affinity depends on the closeness of stereochemical fit between antibody combining sites and antigen determinants, on the size of the area of contact between them, and on the distribution of charged and hydrophobic groups. Affinity also includes the term "avidity," which refers to the strength of the antigen-antibody bond after formation of reversible complexes. Methods for calculating the affinity of an antibody for an antigen are known in the art, including use of binding experiments to calculate affinity. Antibody activity in functional assays (e.g., flow cytometry assay) is also reflective of antibody affinity. Antibodies and affinities can be phenotypically characterized and compared using functional assays (e.g., flow cytometry assay).

As used herein, the term "immunosuppressive activity" refers to the induction of signal transduction or changes in protein expression in a cell, such as an activated immunoresponsive cell, that results in a decrease in an immune response. Non-limiting examples of polypeptides known to suppress or decrease an immune response via their binding include CD47, PD-1, CTLA-4, and their corresponding ligands, including SIRPa, PD-L1, PD-L2, B7-1, and B7-2. Such polypeptides may be present in the tumor microenvironment and can inhibit immune responses to neoplastic cells. In various embodiments, inhibiting, blocking, or otherwise antagonizing the interaction of immunosuppressive polypeptides and/or their ligands may enhance the immune response of the immunoresponsive cell.

As used herein, the term "enzymatic inhibitory domain" refers to a protein domain that inhibits an intracellular signal transduction cascade, for example a native T cell activation cascade. In some embodiments, the enzymatic inhibitory domain of a chimeric inhibitory receptor of the present disclosure comprises at least a portion of an extracellular domain, a transmembrane domain, and/or an intracellular domain. In some embodiments, the enzymatic inhibitory domain comprises at least a portion of an enzyme. In some embodiments, the enzyme is selected from CSK, SHP-1, PTEN, CD45, CD148, PTP-MEG1, PTP-PEST, c-CBL, CBL-b, PTPN22, LAR, PTPH1, SHIP-1, and RasGAP (see e.g., Stanford et al., Regulation of TCR signaling by tyrosine phosphatases: from immune homeostasis to autoimmunity, Immunology, 2012 September; 137(1): 1-19). In some embodiments, the portion of the enzyme comprises an enzyme domain(s), an enzyme fragment(s), or a mutant(s) thereof In some embodiments, the portion of the enzyme is a catalytic domain of the enzyme. In some embodiments, the enzyme domain(s), enzyme fragment(s), or mutants(s) thereof are selected to maximize efficacy and minimize basal inhibition.

As used herein, the term "immunostimulatory activity" refers to induction of signal transduction or changes in protein expression in a cell, such as an activated immunoresponsive cell, that results in an increase in an immune response. Immunostimulatory activity may include pro-inflammatory activity. Non-limiting examples of polypeptides known to stimulate or increase an immune response via their binding include CD28, OX-40, 4-1BB, and their corresponding ligands, including B7-1, B7-2, OX-40L, and 4-1BBL. Such polypeptides may be present in the tumor microenvironment and can activate immune responses to neoplastic cells. In various embodiments, promoting, stimulating, or otherwise agonizing pro-inflammatory polypeptides and/or their ligands may enhance the immune response of the immunoresponsive cell.

Isolated nucleic acid molecules of the present disclosure include any nucleic acid molecule that encodes a polypeptide of the present disclosure, or fragment thereof. Such nucleic acid molecules need not be 100% homologous or identical with an endogenous nucleic acid sequence, but will typically exhibit substantial identity. Nucleic acids having "substantial identity" or "substantial homology" to an endogenous sequence are typically capable of hybridizing with at least one strand of a double-stranded nucleic acid molecule. As used herein, "hybridize" refers to pairing to form a double-stranded molecule between complementary polynucleotide sequences (e.g., a gene described herein), or portions thereof, under various conditions of stringency. For example, stringent salt concentration may be less than about 750 mM NaCl and 75 mM trisodium citrate, less than about 500 mM NaCl and 50 mM trisodium citrate, or less than about 250 mM NaCl and 25 mM trisodium citrate. Low stringency hybridization can be obtained in the absence of organic solvent, e.g., formamide, while high stringency hybridization can be obtained in the presence of at least about 35% formamide or at least about 50% formamide. Stringent temperature conditions will ordinarily include temperatures of at least about 30° C., at least about 37° C., or at least about 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency may be accomplished by combining these various conditions as needed.

By "substantially identical" or "substantially homologous" is meant a polypeptide or nucleic acid molecule exhibiting at least about 50% homologous or identical to a reference amino acid sequence (for example, any one of the amino acid sequences described herein) or nucleic acid sequence (for example, any one of the nucleic acid sequences described herein). Preferably, such a sequence is at least about 60%, about 80%, about 85%, about 90%, about 95%, about 99%, or about 100% homologous or identical at the amino acid level or nucleic acid to the sequence used for comparison. Sequence identity is typically measured using sequence analysis software (for example, Sequence Analysis Software Package of the Genetics Computer Group, University of Wisconsin Biotechnology Center, 1710 University Avenue, Madison, Wis. 53705, BLAST, BESTFIT, GAP, or PILEUP/PRETTYBOX programs). Such software matches identical or similar sequences by assigning degrees of homology to various substitutions, deletions, and/or other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine. In an exemplary approach to determining the degree of identity, a BLAST program may be used, with a probability score between e-3 and e-100 indicating a closely related sequence.

As used herein, the term "encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (e.g., rRNA, tRNA and mRNA) or a defined sequence of amino acids and the biological properties resulting therefrom. Thus, a gene, cDNA, or RNA, encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA. Unless otherwise specified, a "nucleotide sequence encoding an amino acid sequence" includes all nucleotide sequences that are degenerate versions of each other and that encode the same amino acid sequence. The phrase nucleotide sequence that encodes a protein or an RNA may also include introns to the extent that the nucleotide sequence encoding the protein may in some version contain an intron(s).

As used herein, the term "ligand" refers to a molecule that binds to a receptor. In particular, the ligand binds a receptor on another cell, allowing for cell-to-cell recognition and/or interaction.

The terms "effective amount" and "therapeutically effective amount" are used interchangeably herein, and refer to an amount of a compound, formulation, material, or composition, as described herein effective to achieve a particular biological result. In some embodiments, an "effective amount" or a "therapeutically effective amount" is an amount sufficient to arrest, ameliorate, or inhibit the continued proliferation, growth, or metastasis of a disease or disorder of interest, e.g., a myeloid disorder.

As used herein, the term "immunoresponsive cell" refers to a cell that functions in an immune response (e.g., an immune effector response) or a progenitor, or progeny thereof. Examples of immune effector cells include, without limitation, alpha/beta T cells, gamma/delta T cells, B cells, natural killer (NK) cells, natural killer T (NKT) cells, mast cells, and myeloid-derived phagocytes.

As used herein, the term "immune effector response" or "immune effector function" refers to a function or response, e.g., of an immunoresponsive cell, that enhances or promotes an immune attack of a target cell. For example, an immune effector function or response may refer to a property of a T cell or NK cell that promotes killing or the inhibition of growth or proliferation, of a target cell. In the case of a T cell, primary stimulation and co-stimulation are examples of immune effector function or response.

As used herein, the term "flexible polypeptide linker" or "linker" refers to a peptide linker that consists of amino acids such as glycine and/or serine residues used alone or in combination, to link variable heavy and variable light chain regions together. In one embodiment, the flexible polypeptide linker is a Gly/Ser linker and comprises the amino acid sequence $(Gly\text{-}Gly\text{-}Gly\text{-}Ser)_n$, where n is a positive integer equal to or greater than 1 (SEQ ID NO: 224). For example, n-1, n-2, n-3, n-4, n-5 and n-6, n-7, n-8, n-9 and n-10. In some embodiments, the flexible polypeptide linkers include, but are not limited to, $(Gly_4Ser)_4$ (SEQ ID NO: 225) or $(Gly_4Ser)_3$ (SEQ ID NO: 226). In other embodiments, the linkers include multiple repeats of $(Gly_2Ser)$, (GlySer) or $(Gly_3Ser)$ (SEQ ID NO: 229). Also included within the scope of the present disclosure are linkers described, for example, in WO2012/138475.

As used herein, the term "specifically binds" refers to a polypeptide, or fragment thereof, that recognizes and binds a biological molecule of interest (e.g., a polypeptide), but which does not substantially recognize and bind other molecules in a sample, for example, a biological sample, which naturally includes a polypeptide of the present disclosure. In certain embodiments, "specifically binds" refers to binding of, for example, an antibody to an epitope or antigen or antigenic determinant in such a manner that binding can be displaced or competed with a second preparation of identical or similar epitope, antigen or antigenic determinant.

As used herein, the terms "treat", "treatment" and "treating" refer to the reduction or amelioration of the progression, severity and/or duration of a proliferative disorder, or the amelioration of one or more symptoms (preferably, one or more discernible symptoms) of a proliferative disorder resulting from the administration of one or more therapies (e.g., one or more therapeutic agents such as a CAR of the present disclosure). In some embodiments, the terms "treat," "treatment", and "treating" refer to the amelioration of at least one measurable physical parameter of a proliferative disorder, such as growth of a tumor, not necessarily discernible by the patient. In other embodiments, the terms "treat", "treatment", and "treating" refer to the inhibition of the progression of a proliferative disorder, either physically by, e.g., stabilization of a discernible symptom, physiologically by, e.g., stabilization of a physical parameter, or both. In some embodiments the terms "treat", "treatment", and "treating" refer to the reduction or stabilization of tumor size or cancerous cell count.

As used herein, the term "subject" is intended to include living organisms in which an immune response can be elicited (e.g., mammals, human).

Other aspects of the present disclosure are described in the following sections and are within the ambit of the claimed invention.

Other Interpretational Conventions

Ranges recited herein are understood to be shorthand for all of the values within the range, inclusive of the recited endpoints. For example, a range of 1 to 50 is understood to include any number, combination of numbers, or sub-range from 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50

Unless otherwise indicated, reference to a compound that has one or more stereocenters intends each stereoisomer, and all combinations of stereoisomers, thereof.

Myeloid Antigens

Certain aspects of the present disclosure relate to chimeric receptors and cells, such as immunoresponsive cells, that have been genetically modified to express one or more of such chimeric receptors that bind to an antigen of interest, and to methods of using such receptors and cells to treat and/or prevent myeloid malignancies, such as AML, and other pathologies where an antigen-specific immune response is desired. Malignant cells have developed a series of mechanisms to protect themselves from immune recognition and elimination. The present disclosure provides immunogenicity within the tumor microenvironment for treating such malignant cells.

Certain aspects of the present disclosure related to chimeric receptors that specifically bind one or more antigens expressed on a myeloid cell useful for treating myeloid malignancies, and to immunoresponsive cells genetically modified to express such chimeric receptors. Myeloid malignancies are clonal diseases caused by dysfunction of hematopoietic stem cells or progenitor cells, resulting from genetic and epigenetic alterations that disrupt key processes such as cell proliferation and differentiation. Myeloid malignancies can be chronic or acute. Chronic diseases include myeloproliferative neoplasms (MPN), myelodysplastic syndromes (MDS) and chronic myelomonocytic leukemia (CMML). Acute diseases include acute myeloid leukemia (AML).

AML is characterized by the rapid growth of abnormal leukocytes which accumulate in the bone marrow and disrupt the production of normal blood cells. Symptoms of AML include fatigue, shortness of breath, increased susceptibility of infection, and easy bruising and bleeding. The majority of AML cases occur de novo, but some cases can be secondary to a chronic disease. There are eight different subtypes of AML that are based on the type of cell from which the leukemia is originated and how mature the cells are. The AML subtypes include myeloblastic-undifferentiated (M0), myeloblastic-minimal maturation (M1), myeloblastic-full maturation (M2), promyeloctic (M3), myelomonocytic (M4), monocytic (M5), erythroleukemia (M6), and megakaryocyte (M7).

In certain embodiments, the present disclosure relates to AML antigens and combinations of AML antigen that are suitable for use in chimeric receptors (e.g., chimeric TCRs or CARs) to increase efficacy and reduce off-tumor toxicity in the treatment of AML.

Table 1 provides AML antigens suitable for use in chimeric receptors described in the methods and compositions presented herein.

TABLE 1

AML Antigens

| Antigen | UniProt Accession No. | Name | Short Description |
|---|---|---|---|
| FLT3 | P36888 | Fms Related Tyrosine Kinase 3 | A receptor tyrosine kinase that regulates hematopoiesis and involved in apoptosis, proliferation, and differentiation of hematopoietic cells in bone marrow. |
| MS4A3/CD20L | Q96HJ5 | Membrane Spanning 4-Domains A3 | A member of the membrane-spanning 4A gene family, which display unique expression patterns among meatopoietic cells and nonlymphoid tissues. This protein likely plays a role in signal transduction and may function as a subunit associate with other receptor complexes. |
| CD33 | P20138 | CD33 Molecule | A putative adhesion molecule of myelomonocytic-derived cells, and may act as an inhibitory receptor |
| CLEC12A/CD371 | Q5QGZ9 | C-Type Lectin Domain Family 12 Member A | A cell surface receptor negative regulator of granulocyte and monocyte function, and modulates signaling cascades and tyrosine phosphorylation of target MAP kinases. |
| ADGRE2/EMR2 | Q9UHX3 | Adhesion G Protein-Coupled Receptor E2 | A transmembrane receptor that promotes cell-cell adhesion through interaction with chondroitin sulfate chains. |
| SLC22A16 | Q86VW1 | Solute Carrier Family 22 Member 16 | A carnitine transporter that is partially sodium-ion dependent. |
| CD123/IL3RA | P26951 | Interleukin 3 Receptor Subunit Alpha | The ligand specific alpha subunit of a heterodimeric cytokine receptor for interleukin 3. |
| MLC1 | Q15049 | Megalencephalic Leukoencephalopathy With Subcortical Cysts 1 | Unknown gene product, but has homology to other proteins suggest it to be an integral membrane transporter. |
| SPNS3 | Q6ZMD2 | Sphingolipid Transporter 3 (Putative) | A sphingolipid transporter. |
| GAPT | Q8N292 | GRB2 Binding Adaptor Protein, Transmembrane | A transmembrane protein that has been shown to negatively regulate B-cell proliferation. |
| LAT2 | Q9GZY6 | Linker For Activation Of T Cells Family Member 2 | Involved in receptor mediated signaling in mast cells, B cells, and myeloid cells through recruitment of GRB2 (Growth Factor Receptor Bound Protein 2) |
| PIEZO1 | Q92508 | Piezo Type Mechanosensitive Ion Channel Component 1 | Subunit of a mechanosensitive ion channel that links mechanical forces to biological signals. |

TABLE 1-continued

AML Antigens

| Antigen | UniProt Accession No. | Name | Short Description |
|---|---|---|---|
| CD38 | P28907 | CD38 Molecule | A transmembrane glycoprotein that synthesizes and hydrolyzes cyclic ADP-ribose, which is an intracellular calcium ion mobilizing messenger. |
| EMB | Q6PCB8 | Embigin | A transmembrane glycoprotein that is a member of the immunoglobulin superfamily. May be involved in cell growth and development |
| CD131/CSF2RB | P32927 | Colony Stimulating Factor 2 Receptor Beta Common Subunit | The common beta chain of the high affinity receptor for IL3, IL5, and CSF. |
| LILRA2/CD85H | Q8N149 | Leukocyte Immunoglobulin Like Receptor A2 | A receptor that inhibits dendritic cell differentiation and antigen presentation and suppresses innate immune response. Predominantly expressed on monocytes and B cells. |
| SLC17A9 | Q9BYT1 | Solute Carrier Family 17 Member 9 | Transmembrane protein that is involved in transport of small molecules, participating in vesicular uptake, storage, and secretion of ATP. |
| MYADM | Q96S97 | Myeloid Associated Differentiation Marker | Hematopoietic-associate marker gene expressed in multipotent progenitor cells and up-regulated during myeloid differentiation. |
| CD300LF | Q8TDQ1 | CD300 Molecule Like Family Member F | A cell surface glycoprotein that is involved in regulation of immune response. Acts as inhibitory receptor for myeloid cells and mast cells. |
| CD244 | Q9BZW8 | CD244 Molecule | A cell surface receptor expressed on NK cells and some T cells, and mediates non-MHC restricted killing. Ligand is CD48 |
| CD93 | Q9NPY3 | CD93 Molecule | A cell surface glycoprotein and thought to be involved in intercellular adhesion and clearance of apoptotic cells. |
| CD117/CKIT | P10721 | KIT Proto-Oncogene Receptor Tyrosine Kinase | A tyrosine-protein kinase that acts as a cell-surface receptor for the cytokine KITLG/SCF and plays an essential role in regulation of cell survival and proliferation, hematopoiesis, stem cell maintenance, gametogenesis, mas cell development, migration and function, and in melanogenesis. |
| CMTM7 | Q96FZ5 | CKLF Like MARVEL Transmembrane Domain Containing 7 | A gene that belongs to the chemokine-like factor gene superfamily, and acts as a tumor suppressor and epidermal growth factor receptor during tumor pathogenesis. |
| CYBA | P13498 | Cytochrome B-245 Alpha Chain | Critical component of membrane-bound oxidase of phagocytes that generates superoxide. |
| HCK | P08631 | HCK Proto-Oncogene, Src Family Tyrosine Kinase | A tyrosine kinase that is primarily hemopoietic, particularly in cells of myeloid and B-lymphoid lineages. |
| ICAM3 | P32942 | Intercellular Adhesion Molecule 3 | An intercellular adhesion molecule that binds to leukocyte adhesion LFA-1 protein. This protein is constitutively and abundantly expressed on all leukocytes and may also be a potent signaling molecule. |
| LRRC37A2 | A6NM11 | Leucine Rich Repeat Containing 37 Member A2 | A protein that belongs to the LRRC37 gene family. Contains leucine-rich repeat motifs and predicted to mediate protein-ligand interactions. |
| ITGAM | P11215 | Integrin Subunit Alpha M | The integrin alpha M chain, and is implicated in various adhesive interaction of monocytes, macrophages, and granulocytes. |
| ITGB2 | P05107 | Integrin Subunit Beta 2 | An integrin beta chain that combines with multiple alpha chains to form multiple heterodimers. Involved in cell adhesion and cell-surface mediated signaling, and plays role in immune response. |
| LILRA1 | O75019 | Leukocyte Immunoglobulin Like Receptor A1 | This protein is an activating member of the leukocyte immunoglobulin-like receptor (LIR) family and may act as a receptor for class I MHC antigens. Predominantly expressed in B cells and contributes to the regulation of immune responses. |
| PRTN3 | P24158 | Proteinase 3 | Serine protease that degrades elastin, fibronectin, laminin, vitronectine, and collagen. May play a role in neutrophil transendothelial migration. |
| CARD9 | Q9H257 | Caspase Recruitment Domain Family Member 9 | An adapter protein that plays a role in innate immune response to a number of intracellular pathogens. CARD is a domain know play a regulatory role in cell apoptosis. |
| SIGLEC5 | O15389 | Sialic Acid Binding Ig Like Lectin 5 | A cell surface adhesion molecule that mediates sialic-acid dependent binding to cells. A member of CD33-related subset of siglecs and inhibits activation of several cells, including monocytes, macrophages, and neutrophils. |
| SELL | P14151 | Selectin L | A cell surface adhesion molecule required for binding and subsequent rolling of leukocytes on endothelial cells migrating into secondary lymphoid organs and inflammation sites. |

TABLE 1-continued

| AML Antigens | | | |
|---|---|---|---|
| Antigen | UniProt Accession No. | Name | Short Description |
| MLKL | Q8NB16 | Mixed Lineage Kinase Domain Like Pseudokinase | A pseudokinase that plays a role in TNF-induced necroptosis, a programmed cell death process. |
| INPP5D | Q92835 | Inositol Polyphosphate-5-Phosphatase D | A phosphatidylinositol phosphatase that acts overall as a negative regulator of myeloid cell proliferation and survival. |
| APBB1IP | Q7Z5R6 | Amyloid Beta Precursor Protein Binding Family B Member 1 | Appears to function in signal transduction from Ras activation to actin cytoskeletal remodeling. |
| ITGA4 | P13612 | Integrin Subunit Alpha 4 | Integrins are heterodimeric integral membrane proteins and functions in cell surface adhesion and signaling. This protein is the alpha 4 subunit which associates with a beta 1 or beta 7 subunit to form an integrin that may play a role in cell motility and migration. |
| C3AR1 | Q16581 | Complement C3a Receptor 1 | Receptor for chemotactic and inflammatory peptide anaphylatoxin C3a. This receptor stimulates chemotaxis, granule enzyme release and superoxide anion production. |
| ITGA5 | P08648 | Integrin Subunit Alpha 5 | Integrins are heterodimeric integral membrane proteins and functions in cell surface adhesion and signaling. This protein is the alpha 5 subunit which associates with a beta 1 subunit, and may play a role in tumor invasion. |
| FMNL1 | O95466 | Formin Like 1 | A formin-related protein, and is implicated in morphogenesis, cytokinesis, and cell polarity. May play a role in control of cell motility and survival of macrophages. |
| VSTM1 | Q6UX27 | V-set and transmembrane domain-containing protein 1 | VSTM1 is an inhibitory receptor encoded within the leukocyte receptor complex (LRC) on chromosome 19 that contains 2 immunoreceptor tyrosine-based inhibitory motifs (ITIMs). |
| PRAM1 | Q96QH2 | PML-RARA-regulated adapter molecule 1 | PRAM1 is similar to FYN binding protein (FYB/SLAP-130), which is an adaptor protein involved in T cell receptor mediated signaling. PRAM1 is expressed and regulated during normal myelopoiesis. |
| IL1RAP | Q9NPH3 | Interleukin-1 receptor accessory protein | IL1RAP induces synthesis of acute phase and proinflammatory proteins during infection, tissue damage, or stress, by forming a complex at the cell membrane with an interleukin 1 receptor and an accessory protein |
| CCR1/CD191 | P32246 | C-C chemokine receptor type 1 | CCR1 is a member of the beta chemokine receptor family, which belongs to G protein-coupled receptors. Chemokines and their receptors, which mediate signal transduction, are critical for the recruitment of effector immune cells to the site of inflammation. |
| LILRB2 | Q8N423 | Leukocyte immunoglobulin-like receptor subfamily B member 2 | LILRB2 is a member of the leukocyte immunoglobulin-like receptor (LIR) family that contains two or four extracellular immunoglobulin domains, a transmembrane domain, and two to four cytoplasmic immunoreceptor tyrosine-based inhibitory motifs (ITIMs). LILRB2 is expressed on immune cells where it binds to MHC class I molecules on antigen-presenting cells and transduces a negative signal that inhibits stimulation of an immune response. |
| CD70 | P32970 | CD70 Molecule | CD70 is a ligand for CD27 and is expressed on highly activated lymphocytes (e.g., T-cell and B-cell lymphomas). |

In some embodiments, the AML antigen is an FLT3 antigen. In some embodiments, the AML antigen is an MS4A3 antigen. In some embodiments, the AML antigen is a CD33 antigen. In some embodiments, the AML antigen is a CLEC12A antigen. In some embodiments, the AML antigen is a CD312/ADGRE2 antigen. In some embodiments, the AML antigen is an SLC22A16 antigen. In some embodiments, the AML antigen is a CD123/ILR3RA antigen. In some embodiments, the AML antigen is an LAT2 antigen. In some embodiments, the AML antigen is a PIEZO1/FAM38A antigen. In some embodiments, the AML antigen is a CD38 antigen. In some embodiments, the AML antigen is an EMB antigen. In some embodiments, the AML antigen is a CD131/CSF2RB antigen. In some embodiments, the AML antigen is a P2RY8 antigen. In some embodiments, the AML antigen is a LILRA2/CD85H antigen. In some embodiments, the AML antigen is an SLC17A9 antigen. In some embodiments, the AML antigen is an MYADM antigen. In some embodiments, the AML antigen is a CD300LF antigen. In some embodiments, the AML antigen is a CD244/SLAMF4 antigen. In some embodiments, the AML antigen is a PLAUR antigen. In some embodiments, the AML antigen is a CD93 antigen. In some embodiments, the AML antigen is an SPNS3 antigen. In some embodiments, the AML antigen is a GAPT antigen. In some embodiments, the AML antigen is a RASGRP4 antigen. In some embodiments, the AML antigen is a CD117/c-Kit antigen. In some embodiments, the AML antigen is a CD123/ILR3RA antigen. In some embodiments, the AML antigen is an SLC34A2 antigen. In some embodiments, the AML antigen is a VSTM1 antigen. In some embodiments, the AML antigen is an MLC1 antigen. In some embodiments, the AML antigen is a PRAM1 antigen. In some embodiments, the AML antigen is an HCK antigen.

In some embodiments, the AML antigen is an ICAM3 antigen. In some embodiments, the AML antigen is a LRRC37A2 antigen. In some embodiments, the AML antigen is an ITGAM antigen. In some embodiments, the AML antigen is an ITGB2 antigen. In some embodiments, the AML antigen is a LILRA1 antigen. In some embodiments, the AML antigen is a PRTN3 antigen. In some embodiments, AML antigen is a CARDS antigen. In some embodiments, the AML antigen is an SIGLEC5 antigen. In some embodiments, the AML antigen is a SELL antigen. In some embodiments, the AML antigen is a MLKL antigen. In some embodiments, the AML antigen is an INPP5D antigen. In some embodiments, the AML antigen is an APBB1IP antigen. In some embodiments, the AML antigen is an ITGA4 antigen. In some embodiments, the AML antigen is a C3AR1 antigen. In some embodiments, the AML antigen is an ITGA5 antigen. In some embodiments, the AML antigen is an FMNL1 antigen. In some embodiments, the AML antigen is an IL1RAP antigen. In some embodiments, the AML antigen is a CCR1/CD191 antigen. In some embodiments, the AML antigen is an LILRB2 antigen. In some embodiments, the AML antigen is a CD70 antigen.

Chimeric Receptors

Certain aspects of the present disclosure relate to chimeric receptors and nucleic acids that encode such chimeric receptors that bind to an antigen of interest.

Antibodies and Antigen-Binding Fragments

In some embodiments, chimeric receptors comprise one or more of the amino acid sequences listed in Table A1 or Table A2. Table A1 provides the variable domains of an antibody heavy chain or light chain. The CDRs were determined using the Kabat method and are underlined in Table A1 for each variable heavy chain or variable light chain and shown in Table A2. In some embodiments, nucleic acids encoding any of the chimeric receptors of the present disclosure comprise one or more of the nucleic acid sequences listed in Table B.

TABLE A1

| Amino Acid Sequence | SEQ ID NO: | Description |
|---|---|---|
| EVQLVQSGAEVKKPGASVKVSCKASGYTFTSYYMHWARQAPGQGLEWMGIINPSGGSTSYAQKFQGRVTMTRDTSTSTVYMELSSLRSEDTAVYYCARVVAAAVADYWGQGTLVTVSS | 1 | Heavy chain variable domain of anti-FLT3 antibody D4-3 |
| DVVMTQSPLSLPVTPGEPASISCRSSQSLLHSNGYNYLDWYLQKPGQSPQLLIYLGSNRASGVPDRFSGSGSGTDFTLKISRVEAEDVGVYYCMQSLQTPFTFGPGTKVDIK | 2 | Light chain variable domain of anti-FLT3 antibody D4-3 |
| EVQLVQSGAEVKKPGSSVKVSCKASGGTFSSYAISWVRQAPGQGLEWMGGIIPIFGTANYAQKFQGRVTITADKSTSTAYMELSSLRSEDTAVYYCATFALFGFREQAFDIWGQGTTVTVSS | 3 | Heavy chain variable domain of anti-FLT3 antibody NC7 |
| DIQMTQSPSSLSASVGDRVTITCRASQSISSYLNWYQQKPGKAPKLLIYAASSLQSGVPSRFSGSGSGTDFTLTISSLQPEDLATYYCQQSYSTPFTFGPGTKVDIK | 4 | Light chain variable domain of anti-FLT3 antibody NC7 |
| EVQLVQSGAEVKKPGASVKVSCKASGYTFTSYYMHWVRQAPGQGLEWMGIINPSGGSTSYAQKFQGRVTMTRDTSTSTVYMELSSLRSEDTAVYYCARGVGAHDAFDIWGQGTTVTVSS | 5 | Heavy chain variable domain of anti-FLT3 antibody EB10 |
| DVVMTQSPLSLPVTPGEPASISCRSSQSLLHSNGNNYLDWYLQKPGQSPQLLIYLGSNRASGVPDRFSGSGSDTDFTLQISRVEAEDVGVYYCMQGTHPAISFGQGTRLEIK | 6 | Light chain variable domain of anti-FLT3 antibody EB10 |
| QVQLQQPGAELVKPGASLKLSCKSSGYTFTSYWMHWVRQRPGHGLEWIGEIDPSDSYKDYNQKFKDKATLTVDRSSNTAYMHLSSLTSDDSAVYYCARAITTTPFDFWGQGTTLTVSS | 7 | Heavy chain variable domain of anti-FLT3 antibody 4G8 |
| DIVLTQSPATLSVTPGDSVSLSCRASQSISNNLHWYQQKSHESPRLLIKYASQSISGIPSRFSGSGSGTDFTLSINSVETEDFGVYFCQQSNTWPYTFGGGTKLEIKR | 8 | Light chain variable domain of anti-FLT3 antibody 4G8 |
| QVTLKESGPTLVKPTETLTLTCTLSGFSLNNARMGVSWIRQPPGKCLEWLAHIFSNDEKSYSTSLKNRLTISKDSSKTQVVLTMTNVDPVDTATYYCARIVGYGSGWYGFFDYWGQGTLVTVSS | 9 | Heavy chain variable domain of anti-FLT3 antibody FL_39 |
| DIQMTQSPSSLSASVGDRVTITCRASQGIRNDLGWYQQKPGKAPKRLIYAASTLQSGVPSRFSGSGSGTEFTLTISSLQPEDFATYYCLQHNSYPLTFGCGTKVEIK | 10 | Light chain variable domain of anti-FLT3 antibody FL_39 |
| QVTLKESGPVLVKPTETLTLTCTVSGFSLRNARMAVSWIRQPPGKTLEWLAHIFSNDEKSYSTSLKSRLTISKDTSKSQVVLTMTNMDPVDTATYYCARIVGYGSGWYGYFDYWGQGTLVTVSS | 11 | Heavy chain variable domain of anti-FLT3 antibody FL_16 |
| DIQMTQSPSSVSASVGDRVTITCRASQDIRYDLAWYQQKPGKAPKRLIYAASSLQSGVPSRFSGSGSGTEFTLTISSLQPEDFATYYCLQHNFYPLTFGGGTKVEIK | 12 | Light chain variable domain of anti-FLT3 antibody FL_16 |
| EVQLVESGGGLVQPGGSLRLSCAASGFTFSSYGMHWVRQAPGKGLEWVAVISYDGSNKYYADSVKGRFTISRDNSKNTLYLQMNSLRAEDTAVYYCANLAPWAAYWGQGTLVTVSS | 13 | Heavy chain variable domain of anti-FLT3 antibody m10006 |

TABLE A1-continued

| Amino Acid Sequence | SEQ ID NO: | Description |
|---|---|---|
| EIVLTQSPLSLPVTPGEPASISCRSSQSLLHSNGYNYLDWYLQKPG QSPQLLIYLGSNRASGVPDRFSGSGSGTDFTLKISRVEAEDVGVYY CMQALQTPHTFGQGTKLEIK | 14 | Light chain variable domain of anti-FLT3 antibody m10006 |
| QVQLKQSGPGLVQPSQSLSITCTVSGFSLTNYGLHWVRQSPGKGLE WLGVIWSGGSTDYNAAFISRLSISKDNSKSQVFFKMNSLQADDTAI YYCARKGGIYYANHYYAMDYWGQGTSVTVSS | 15 | Heavy chain variable domain of anti-FLT3 antibody BV10 |
| DIVMTQSPSSLSVSAGEKVTMSCKSSQSLLNSGNQKNYMAWYQQKP GQPPKLLIYGASTRESGVPDRFTGSGSGTDFTLTISSVQAEDLAVY YCQNDHSYPLTFGAGTKLELKR | 16 | Light chain variable domain of anti-FLT3 antibody BV10 |
| QVQLVQSGAEVKKPGSSVKVSCKASGYTFTDYNMHWVRQAPGQGLE WIGYIYPYNGGTGYNQKFKSKATITADESTNTAYMELSSLRSEDTA VYYCARGRPAMDYWGQGTLVTVSS | 17 | Heavy chain variable domain of anti-CD33 antibody lintuzumab |
| DIQMTQSPSSLSASVGDRVTITCRASESVDNYGISFMNWFQQKPGK APKLLIYAASNQGSGVPSRFSGSGSGTDFTLTISSLQPDDFATYYC QQSKEVPWTFGQGTKVEIK | 18 | Light chain variable domain of anti-CD33 antibody lintuzumab |
| EVQLVQSGAEVKKPGSSVKVSCKASGYTITDSNIHWVRQAPGQSLE WIGYIYPYNGGTDYNQKFKNRATLTVDNPTNTAYMELSSLRSEDTA FYYCVNGNPWLAYWGQGTLVTVSS | 19 | Heavy chain variable domain of anti-CD33 antibody gemtuzumab |
| DIQLTQSPSTLSASVGDRVTITCRASESLDNYGIRFLTWFQQKPGK APKLLMYAASNQGSGVPSRFSGSGSGTEFTLTISSLQPDDFATYYC QQTKEVPWSFGQGTKVEVKR | 20 | Light chain variable domain of anti-CD33 antibody gemtuzumab |
| QVQLQESGPGLVKPSETLSLTCVVSGGSISSSNWWSWVRQPPGKGL EWIGEIYHSGSPDYNPSLKSRVTISVDKSRNQFSLKLSSVTAADTA VYYCAKVSTGGFFDYWGQGTLVTVSS | 21 | Heavy chain variable domain of anti-CLEC12A antibody SC02-357 |
| EIELTQSPSSLSASVGDRVTITCRASQSISSYLNWYQQKPGKAPKL LIYAASSLQSGVPSRFSGSGSGTDFTLTISSLQPEDFATYYCQQSY STPPTFGPGTKVEIK | 22 | Light chain variable domain of anti-CLEC12A antibody SC02-357 |
| QVQLQESGPGLVKPSETLSLTCVVSGGSISSSNWWSWVRQPPGKGL EWIGEIYHSGSPNYNPSLKSRVTISVDKSKNQFSLKLSSVTAADTA VYYCARSSSGGFFDYWGQGTLVTVSS | 23 | Heavy chain variable domain of anti-CLEC12A antibody SC02-378 |
| EIELTQSPSSLSASVGDRVTITCRASQSISSYLNWYQQKPGKAPKL LIYAASSLQSGVPSRFSGSGSGTDFTLTISSLQPEDFATYYCQQSY STPPTFGQGTKVEIK | 24 | Light chain variable domain of anti-CLEC12A antibody SC02-378 |
| EIELTQSPSSLSASVGDRVTITCRASQSISSYLNWYQQKPGKAPKL LIYAASSLQSGVPSRFSGSGSGTDFTLTISSLQPEDFATYYCQQSY STPPTFGQGTKVEIK | 25 | Heavy chain variable domain of anti-CLEC12A antibody SC02-161 |
| QVQLQESGPGLVKPSETLSLTCVVSGGSISSSNWWSWVRQPPGKGL EWIGEIYHSGSPNYNPSLKSRVTISVDKSKNQFSLKLSSVTAADTA VYYCARQTTAGSFDYWGQGTLVTVSS | 26 | Light chain variable domain of anti-CLEC12A antibody SC02-161 |
| GGGGSGGGGSGGGGS | 27 | scFv linker 1 |
| EAAAKEAAAKEAAAKEAAAK | 74 | scFv linker 2 |
| GGGGSGGGGSGGGGSGGGGSGGGGS | 218 | scFv linker 3 |
| GGGGSGGGGSGGGGS | 219 | scFv linker 4 |

TABLE B

| Nucleic Acid Sequence | SEQ ID NO: | Description |
|---|---|---|
| GAAGTGCAACTTGTTCAGAGCGGGGCAGAAGTTAAGAAGCCAGGCGCTTCCGTCAAGGTGA GTTGCAAGGCAAGTGGATACACCTTTACGAGTTATTATATGCACTGGGCACGGCAGGCCCC TGGTCAGGGCCTCGAATGGATGGGGATTATAAATCCTTCTGGCGGGTCAACCAGCTACGCA CAAAAATTTCAAGGTCGGGTGACAATGACGCGCGACACGTCAACGAGTACAGTGTATATGG AATTGTCTAGCCTGAGGTCCGAGGATACTGCTGTCTATTATTGTGCTCGCGTGGTCGCTGC TGCTGTGGCAGACTACTGGGGTCAGGGTACACTTGTGACGGTAAGCAGC | 28 | Heavy chain variable domain of anti-FLT3 antibody D4-3 |

TABLE B-continued

| Nucleic Acid Sequence | SEQ ID NO: | Description |
|---|---|---|
| GACGTAGTTATGACACAGTCTCCACTGTCATTGCCAGTAACACCAGGTGAGCCCGCCTCCA<br>TCTCATGTAGATCCTCCCAATCTCTCCTTCATTCAAACGGGTATAATTATCTCGACTGGTA<br>TTTGCAGAAACCGGGCCAGAGCCCTCAACTGCTCATCTATTTGGGGAGCAACCGGGCCTCT<br>GGTGTCCCTGATAGATTCTCCGGGAGTGGATCAGGTACGGATTTTACACTGAAGATCAGCA<br>GGGTGGAAGCAGAAGATGTTGGTGTGTATTACTGTATGCAATCACTCCAGACCCCGTTTAC<br>CTTTGGGCCTGGAACAAAGGTAGATATTAAA | 29 | Light chain variable domain of anti-FLT3 antibody D4-3 |
| GAGGTTCAACTGGTACAAAGCGGAGCCGAGGTAAAGAAACCAGGGAGTAGCGTCAAAGTGT<br>CCTGCAAAGCCTCAGGCGGCACATTCAGTAGCTATGCTATTTCATGGGTACGCCAAGCACC<br>AGGACAGGGGCTGGAGTGGATGGGCGGGATTATCCCCATCTTCGGTACGGCAAACTATGCA<br>CAAAAGTTCCAGGGACGAGTCACCATCACGGCTGATAAGTCCACCTCCACCGCCTATATGG<br>AGCTGAGTTCCCTTCGGAGCGAGGATACTGCTGTGTATTATTGTGCCACGTTCGCACTGTT<br>CGGTTTTCGGGAGCAGGCGTTTGATATTTGGGGACAAGGCACAACGGTCACGGTCAGTTCA | 30 | Heavy chain variable domain of anti-FLT3 antibody NC7 |
| GACATTCAGATGACCCAGAGTCCCTCTTCATTGAGTGCGAGCGTCGGTGATCGGGTTACGA<br>TAACCTGTAGGGCCTCCCAAAGTATATCATCATATTTGAACTGGTACCAACAGAAACCTGG<br>GAAAGCGCCGAAGCTCCTTATCTATGCTGCCAGCTCTTTGCAAAGCGGTGTGCCCTCACGG<br>TTCTCCGGTAGTGGGTCCGGGACCGACTTCACTTTGACCATCAGCAGCCTTCAGCCAGAGG<br>ATCTTGCCACTTATTACTGCCAGCAATCTTATAGCACACCGTTTACATTCGGTCCAGGCAC<br>AAAGGTAGACATTAAG | 31 | Light chain variable domain of anti-FLT3 antibody NC7 |
| GAGGTACAGCTTGTGCAGAGTGGAGCAGAAGTTAAAAAACCCGGAGCTTCCGTGAAGGTAA<br>GCTGCAAGGCTTCAGGATATACATTTACTAGCTACTACATGCACTGGGTCCGCCAAGCTCC<br>GGGCCAAGGCCTTGAATGGATGGGCATCATAAATCCCAGTGGAGGCTCAACGAGCTATGCA<br>CAAAAGTTCCAAGGGCGCGTTACCATGACGCGCGACACCAGCACGTCCACCGTCTATATGG<br>AACTCTCAAGTTTGCGATCTGAAGATACGGCTGTCTACTATTGCGCACGAGGGGTCGGAGC<br>GCATGACGCCTTCGACATCTGGGGACAAGGGACTACAGTAACTGTGTCAAGC | 32 | Heavy chain variable domain of anti-FLT3 antibody EB10 |
| GATGTTGTTATGACACAGTCTCCCCTCTCTTTGCCTGTTACGCCTGGCGAGCCCGCCTCTA<br>TTTCTTGTCGATCTAGTCAGAGCCTGCTGCATTCTAATGGAAACAACTATTTGGACTGGTA<br>CTTGCAAAAGCCGGGTCAAAGTCCC | 33 | Light chain variable domain of anti-FLT3 antibody EB10 |
| CAAGTCCAACTTCAGCAGCCAGGCGCTGAGTTGGTTAAACCGGGCGCAAGCCTCAAACTTA<br>GTTGCAAGTCATCCGGATATACTTTCACGTCTTATTGGATGCATTGGGTACGACAAAGACC<br>TGGTCACGGCCTCGAATGGATTGGCGAAATCGACCCGTCAGACAGCTACAAGGATTACAAC<br>CAGAAATTCAAAGATAAGGCAACACTTACTGTGGATCGCTCAAGTAACACGGCTTACATGC<br>ACCTCTCTTCACTCACGTCTGACGACAGTGCGGTGTATTATTGCGCCCGCGCTATTACAAC<br>AACCCCTTTCGATTTCTGGGGCCAGGGTACTACGCTCACAGTCTCATCC | 34 | Heavy chain variable domain of anti-FLT3 antibody 4G8 |
| GATATCGTCCTCACCCAATCCCCGGCTACTTTGAGTGTAACACCAGGCGACAGCGTGTCAC<br>TGTCATGCCGAGCCTCCCAGTCAATCAGCAATAATCTGCATTGGTATCAACAGAAATCACA<br>CGAATCCCCCCGACTTTTGATAAAGTATGCGTCACAGTCCATATCAGGCATTCCCAGTAGG<br>TTTTCAGGCAGTGGTTCAGGTACTGACTTCACCCTCTCCATTAACTCTGTAGAAACAGAGG<br>ACTTTGGCGTCTACTTCTGTCAGCAATCCAACACCTGGCCTTATACATTCGGCGGCGGCAC<br>TAAGCTGGAAATTAAGAGA | 35 | Light chain variable domain of anti-FLT3 antibody 4G8 |
| CAAGTAACCCTTAAAGAGTCCGGCCCCACTTTGGTTAAACCTACTGAAACACTTACACTCA<br>CATGCACATTGTCCGGCTTTTCACTCAACAACGCAAGGATGGGTGTGTCCTGGATTCGCCA<br>GCCCCCTGGAAAATGTTTGGAATGGCTCGCTCATATATTTAGCAACGACGAGAAAAGTTAC<br>TCAACTTCACTCAAGAACCGCCTCACTATTAGCAAAGATTCCTCCAAAACCCAAGTAGTTC<br>TGACAATGACGAATGTAGACCCAGTCGATACTGCAACTTACTATTGCGCACGAATAGTCGG<br>TTACGGGAGTGGCTGGTATGGGTTTTTCGACTATTGGGGACAGGGCACTCTTGTAACAGTA<br>AGTAGC | 36 | Heavy chain variable domain of anti-FLT3 antibody FL39 |
| GACATCCAGATGACTCAATCTCCATCTAGCCTCTCAGCGTCTGTGGGCGATCGAGTCACCA<br>TCACCTGTAGGGCTTCCCAGGGTATAAGGAATGATTTGGGCTGGTACCAGCAAAAACCGGG<br>TAAGGCTCCGAAACGACTGATATACGCAGCTTCTACGTTGCAATCCGGGGTGCCATCCAGA<br>TTTAGTGGCAGCGGGAGCGGTACTGAGTTTACGCTGACTATCTCCTCACTTCAGCCAGAGG<br>ATTTCGCCACGTACTATTGTCTGCAACACAACTCCTATCCGCTGACCTTCGGGTGCGGGAC<br>AAAGGTGGAAATTAAA | 37 | Light chain variable domain of anti-FLT3 antibody FL39 |
| CAAGTGACCTTGAAGGAGTCAGGGCCAGTGTTGGTAAAACCTACTGAGACTCTCACGTTGA<br>CATGCACGGTATCAGGTTTCAGCCTGAGGAACGCTCGGATGGCCGTCAGTTGGATACGCCA<br>GCCGCCAGGCAAAACTCTTGAATGGTTGGCGCACATATTCAGTAACGACGAGAAATCTTAC<br>TCTACATCCCTTAAGTCTCGCCTCACCATTTCTAAAGACACATCCAAATCACAAGTGGTAC<br>TCACGATGACAAACATGGACCCTGTTGACACTGCTACATATTATTGTGCTAGGATAGTGGG<br>CTACGGTAGCGGATGGTACGGTTATTTTGATTACTGGGGACAAGGGACGCTTGTTACGGTG<br>TCCTCA | 38 | Heavy chain variable domain of anti-FLT3 antibody FL16 |
| GACATTCAGATGACCCAGTCTCCGTCCAGCGTTAGCGCAAGCGTGGGGGATAGAGTCACTA<br>TTACGTGTAGAGCCAGTCAAGATATACGGTACGATCTTGCTTGGTATCAGCAAAAACCGGG<br>AAAAGCCCCGAAGAGACTTATATATGCAGCTTCCTCCTTGCAAAGCGGGGTCCCATCCCGG<br>TTTAGTGGTAGTGGTTCCGGAACAGAGTTCACGCTGACTATTTCATCACTGCAACCCGAAG<br>ATTTTGCCACCTACTACTGCCTTCAACACAATTTCTATCCTCTTACCTTCGGCGGAGGTAC<br>TAAGGTAGAGATTAAG | 39 | Light chain variable domain of anti-FLT3 antibody FL16 |

TABLE B-continued

| Nucleic Acid Sequence | SEQ ID NO: | Description |
|---|---|---|
| GAAGTACAGTTGGTTGAGAGTGGTGGAGGACTCGTTCAACCTGGCGGTAGTTTGCGACTCA GCTGCGCGGCTTCCGGTTTCACCTTCTCATCCTATGGGATGCACTGGGTCAGACAAGCCCC TGGAAAGGGCCTCGAATGGGTTGCTGTGATTAGCTATGACGGCTCTAATAAATACTATGCA GATAGTGTAAAGGGGAGATTTACGATTTCTCGCGATAATAGCAAAAATACGCTGTACCTGC AAATGGAAACCAACAGCCTGCGAGCGGAAGATACGGCGGTTTATTACTGCGCGAATCTTGC CCCGTGGGCAGCATACTGGGGACAGGGGACGTTGGTGACGGTAAGCAGT | 40 | Heavy chain variable domain of anti-FLT3 antibody ml0006 |
| GAGATTGTGCTCACCCAGTCTCCACTCAGCCTTCCTGTAACGCCCGGTGAGCCTGCCTCTA TATCATGCCGAAGTTCCCAAAGCCTTCTGCACTCAAACGGCTATAACTACTTGGACTGGTA CCTCCAGAAGCCCGGCCAAAGTCCTCAACTGTTGATATACTGGGGTCCAACCGGGCATCA GGAGTACCTGATAGATTCTCAGGAAGTGGGTCAGGAACCGACTTCACGCTGAAAATTAGTC GCGTAGAGGCGGAAGATGTAGGTGTGTATTACTGTATGCAGGCGTTGCAAACACCGCACAC TTTTGGACAGGGAACCAAACTGGAAATAAAGACCAGTAGTGGT | 41 | Light chain variable domain of anti-FLT3 antibody ml0006 |
| CAGGTCCAACTGAAACAAAGCGGTCCCGGTCTTGTCCAGCCCTCCCAATCTCTCAGTATTA CTTGCACTGTGTCAGGTTTCAGCCTCACGAACTACGGTCTGCATTGGGTCCGCCAGTCTCC AGGAAAAGGCCTGGAGTGGCTCGGTGTTATCTGGAGTGGTGGAAGTACGGATTACAATGCT GCCTTTATCTCTCGGCTCAGTATCTCCAAAGATAACTCTAAGTCCCAAGTCTTTTTCAAAA TGAACTCTTTGCAGGCAGATGATACGGCCATATACTATTGCGCACGCAAGGGTGGGATCTA CTATGCAAACCACTATTACGCGATGGACTACTGGGGCCAAGGCACGAGTGTTACCGTGTCA AGC | 42 | Heavy chain variable domain of anti-FLT3 antibody BV10 |
| GACATAGTGATGACTCAGTCTCCGTCCTCTCTTTCCGTGAGTGCGGGCGAAAAGGTTACCA TGTCCTGCAAAAGTTCACAGTCACTTCTCAATTCTGGCAACCAAAAAAATTACATGGCATG GTATCAACAGAAACCAGGTCAGCCGCCAAAGCTCCTCATATATGGTGCATCAACGCGAGAG TCAGGCGTACCTGACAGGTTTACCGGATCTGGCAGCGGTACAGACTTTACTCTTACCATAT CAAGTGTGCAGGCAGAGGACTTGGCGGTATACTATTGTCAAAACGATCATAGTTACCCTCT TACATTTGGCGCGGGCACTAAACTGGAGCTGAAACGC | 43 | Light chain variable domain of anti-FLT3 antibody BV10 |
| CAGGTTCAGCTGGTTCAGTCTGGCGCCGAAGTGAAGAAACCTGGCAGCAGCGTGAAGGTGT CCTGCAAGGCCAGCGGCTACACCTTTACCGACTACAACATGCACTGGGTCCGACAGGCCCC TGGACAAGGACTTGAGTGGATCGGCTACATCTACCCCTACAATGGCGGCACCGGCTACAAC CAGAAGTTCAAGAGCAAGGCCACCATCACCGCCGACGAGAGCACAAACACCGCCTACATGG AACTGAGCAGCCTGAGAAGCGAGGACACCGCCGTGTACTACTGTGCCAGAGGCAGACCCGC CATGGATTATTGGGGACAGGGCACCCTGGTCACCGTTTCTAGC | 44 | Heavy chain variable domain of anti-CD33 antibody lintuzumab |
| GATATCCAGATGACACAGAGCCCCAGCAGCCTGTCTGCCAGCGTGGGAGATAGAGTGACCA TCACCTGTAGAGCCAGCGAGAGCGTGGACAACTACGGCATCAGCTTCATGAACTGGTTCCA GCAGAAGCCCGGCAAGGCCCCTAAGCTGCTGATCTACGCCGCCAGCAATCAAGGCAGCGGA GTGCCTAGCAGATTTTCCGGCTCTGGCAGCGGCACCGATTTCACCCTGACAATCTCTAGCC TCCAGCCTGACGACTTCGCCACCTACTACTGCCAGCAGAGCAAAGAGGTGCCCTGGACATT CGGCCAGGGCACAAAGGTGGAAATCAAG | 45 | Light chain variable domain of anti-CD33 antibody lintuzumab |
| GAAGTGCAGCTGGTTCAGTCTGGCGCCGAAGTGAAGAAACCTGGCAGCAGCGTGAAGGTGT CCTGCAAGGCCAGCGGCTACACCATCACCGACAGCAACATCCACTGGGTCCGACAGGCTCC AGGCCAGTCTCTTGAGTGGATCGGCTACATCTACCCCTACAACGGCGGCACCGACTACAAC CAGAAGTTCAAGAACCGGGCCACACTGACCGTGGACAACCCTACCAATACCGCCTACATGG AACTGAGCAGCCTGCGGAGCGAGGACACCGCCTTTTACTACTGCGTGAACGGCAACCCCTG GCTGGCCTATTGGGGACAGGGAACACTGGTCACAGTGTCTAGC | 46 | Heavy chain variable domain of anti-CD33 antibody gemtuzumab |
| GATATTCAGCTGACACAGAGCCCCAGCACACTGTCTGCCTCTGTGGGCGACAGAGTGACCA TCACCTGTAGAGCCAGCGAGAGCCTGGACAACTACGGCATCAGATTTCTGACCTGGTTCCA GCAGAAGCCCGGCAAGGCTCCTAAGCTGCTGATGTACGCCGCCAGCAATCAAGGCAGCGGA GTGCCTAGCAGATTTTCCGGCTCTGGCAGCGGCACAGAGTTCACCCTGACAATCTCTAGCC TCCAGCCTGACGACTTCGCCACCTACTACTGCCAGCAGACCAAAGAGGTGCCCTGGTCCTT TGGACAGGGCACCAAGGTGGAAGTGAAGCGG | 47 | Light chain variable domain of anti-CD33 antibody gemtuzumab |
| CAGGTGCAGCTGCAGGAGTCGGGGCCAGGACTGGTGAAGCCTTCGGAGACCCTGTCCCTCA CCTGCGTTGTCTCTGGTGGCTCCATCAGCAGTAGTAACTGGTGGAGCTGGGTCCGCCAGCC CCCAGGGAAGGGGCTGGAGTGGATTGGGGAAATCTATCATAGTGGGAGCCCCGACTACAAC CCGTCCCTCAAGAGTCGAGTCACCATATCAGTAGACAAGTCCAGGAACCAGTTCTCCCTGA AGCTGAGCTCTGTGACCGCCGCGGACACGGCCGTGTATTACTGTGCAAAGGTTAGTACTGG TGGTTTCTTTGACTACTGGGGCCAAGGTACCCTGGTCACCGTCTCGAGT | 48 | Heavy chain variable domain of anti-CLEC12A antibody SC02-357 |
| GAAATTGAGCTCACCCAGTCTCCATCCTCCCTGTCTGCATCTGTAGGAGACAGAGTCACCA TCACTTGCCGGGCAAGTCAGAGCATTAGCAGCTACTTAAATTGGTATCAGCAGAAACCAGG GAAAGCCCCTAAGCTCCTGATCTATGCTGCATCCAGTTTGCAAAGTGGGGTCCCATCAAGG TTCAGTGGCAGTGGATCTGGGACAGATTTCACTCTCACCATCAGCAGTCTGCAACCTGAAG ATTTTGCAACTTACTACTGTCAACAGAGTTACAGTACCCCTCCAACGTTCGGCCCAGGGAC CAAGGTGGAGATCAAA | 49 | Light chain variable domain of anti-CLEC12A antibody SC02-357 |

TABLE B-continued

| Nucleic Acid Sequence | SEQ ID NO: | Description |
|---|---|---|
| CAGGTGCAGCTGCAGGAGTCGGGCCCAGGACTGGTGAAGCCTTCGGAGACCCTGTCCCTCA CCTGCGTTGTCTCTGGTGGCTCCATCAGCAGTAGTAACTGGTGGAGCTGGGTCCGCCAGCC CCCAGGGAAGGGGCTGGAGTGGATTGGGGAAATCTATCATAGTGGGAGCCCCAACTACAAC CCGTCCCTCAAGAGTCGAGTCACCATATCAGTAGACAAGTCCAAGAACCAGTTCTCCCTGA AGCTGAGCTCTGTGACCGCCGCGGACACGGCCGTGTATTACTGTGCAAGGTCGTCTTCTGG TGGTTTCTTTGACTACTGGGGCCAAGGTACCCTGGTCACCGTCTCGAGT | 50 | Heavy chain variable domain of anti-CLEC12A antibody SC02-378 |
| GAAATTGAGCTCACCCAGTCTCCATCCTCCCTGTCTGCATCTGTAGGAGACAGAGTCACCA TCACTTGCCGGGCAAGTCAGAGCATTAGCAGCTACTTAAATTGGTATCAGCAGAAACCAGG GAAAGCCCCTAAGCTCCTGATCTATGCTGCATCCAGTTTGCAAAGTGGGGTCCCATCAAGG TTCAGTGGCAGTGGATCTGGGACAGATTTCACTCTCACCATCAGCAGTCTGCAACCTGAAG ATTTTGCAACTTACTACTGTCAACAGAGTTACAGTACCCCTCCAACGTTCGGCCAAGGGAC CAAGGTGGAGATCAAA | 51 | Light chain variable domain of anti-CLEC12A antibody SC02-378 |
| CAGGTGCAGCTGCAGGAGTCGGGCCCAGGACTGGTGAAGCCTTCGGAGACCCTGTCCCTCA CCTGCGTTGTCTCTGGTGGCTCCATCAGCAGTAGTAACTGGTGGAGCTGGGTCCGCCAGCC CCCAGGGAAGGGGCTGGAGTGGATTGGGGAAATCTATCATAGTGGGAGCCCCAACTACAAC CCGTCCCTCAAGAGTCGAGTCACCATATCAGTAGACAAGTCCAAGAACCAGTTCTCCCTGA AGCTGAGCTCTGTGACCGCCGCGGACACGGCCGTGTATTACTGTGCAAGGCAGACTACTGC TGGGTCCTTTGACTACTGGGGCCAAGGTACCCTGGTCACCGTCTCGAGT | 52 | Heavy chain variable domain of anti-CLEC12A antibody SC02-161 |
| GAAATTGAGCTCACCCAGTCTCCATCCTCCCTGTCTGCATCTGTAGGAGACAGAGTCACCA TCACTTGCCGGGCAAGTCAGAGCATTAGCAGCTACTTAAATTGGTATCAGCAGAAACCAGG GAAAGCCCCTAAGCTCCTGATCTATGCTGCATCCAGTTTGCAAAGTGGGGTCCCATCAAGG TTCAGTGGCAGTGGATCTGGGACAGATTTCACTCTCACCATCAGCAGTCTGCAACCTGAAG ATTTTGCAACTTACTACTGTCAACAGAGTTACAGTACCCCTCCAACGTTCGGCCAAGGGAC CAAGGTGGAGATCAAA | 53 | Light chain variable domain of anti-CLEC12A antibody SC02-161 |
| GGAGGCGGAGGATCTGGTGGCGGAGGAAGTGGCGGAGGCGGTTCT | 54 | scFv linker 1 |
| GAAGCCGCGGCAAAAGAGGCAGCAGCAAAAGAGGCAGCAGCCAAA | 220 | scFv linker 2 |
| GGTGGTGGTGGCAGTGGTGGCGGTGGCTCAGGTGGCGGCGGATCAGGCGGTGGTGGTTCTG GCGGCGGTGGATCT | 221 | scFv linker 3 |
| GGCGGCGGAGGTTCCGGCGGTGGCGGAAGCGGAGGTGGTGGCTCT | 223 | scFv linker 4 |

TABLE A2

| Ab | SEQ ID NO | CDR-H1 | SEQ ID NO | CDR-H2 | SEQ ID NO | CDR-H3 | SEQ ID NO | CDR-L1 | SEQ ID NO | CDR-L2 | SEQ ID NO | CDR-L3 |
|---|---|---|---|---|---|---|---|---|---|---|---|---|
| FLT3 antibody D4-3 | 75 | GYTFTSYYMH | 76 | IINPSGGSTSYAQKFQG | 77 | VVAAAVADY | 78 | RSSQSLLHSNGYNYLD | 79 | LGSNRA | 80 | MQSLQTPFT |
| FLT3 antibody NC7 | 81 | GGTFSSYAIS | 82 | GIIPIFGTANYAQKFQG | 83 | FALFGFREQAFDI | 84 | RASQSISSYLN | 85 | AASSLQS | 86 | QQSYSTPFT |
| FLT3 antibody EB10 | 87 | GYTFTSYYMH | 88 | IINPSGGSTSYAQKFQG | 89 | GVGAHDAFDI | 90 | RSSQSLLHSNGNNYLD | 91 | LGSNRA | 92 | MQGTHPAIS |
| FLT3 antibody 4G8 | 93 | SYWMH | 94 | EIDPSDSYKDYNQKFKD | 95 | AITTTPFDF | 96 | RASQSISNNLH | 97 | YASQSIS | 98 | QQSNTWPYT |
| FLT3 antibody FL 39 | 99 | NARMGVS | 100 | HIFSNDEKSYSTSLKN | 101 | IVGYGSGWYGFFDY | 102 | RASQGIRNDLG | 103 | AASTLQS | 104 | LQHNSYPLT |
| FLT3 antibody FL 16 | 105 | NARMAVS | 106 | HIFSNDEKSYSTSLKS | 107 | IVGYGSGWYGYFDY | 108 | RASQDIRYDLA | 109 | AASSLQS | 110 | LQHNFYPLT |
| FLT3 antibody m10006 | 111 | GFTFSSYG | 112 | ISYDGSNK | 113 | ANLAPWAAYW | 114 | QSLLHSNGYNY | 115 | LGS | 116 | MQALQTPHT |

TABLE A2-continued

| Ab | SEQ ID NO | CDR-H1 | SEQ ID NO | CDR-H2 | SEQ ID NO | CDR-H3 | SEQ ID NO | CDR-L1 | SEQ ID NO | CDR-L2 | SEQ ID NO | CDR-L3 |
|---|---|---|---|---|---|---|---|---|---|---|---|---|
| FLT3 antibody BV10 | 117 | NYGLH | 118 | VIWSGGSTDYNAAFIS | 119 | KGGIYYANHYYAMDY | 120 | KSSQSLLNSGNQKNYMA | 121 | GASTRES | 122 | QNDHSYPLT |
| CD33 antibody lintuzumab | 123 | DYNMH | 124 | YIYPYNGGTGYNQKFKSKA | 125 | GRPAMDYWGQ | 126 | RASESVDNYGISFMN | 127 | AASNQGS | 128 | QQSKEVPWT |
| CD33 antibody gemtuzumab | 129 | GYTITDSN | 130 | IYPYNGGT | 131 | VNGNPWLAY | 132 | ESLDNYGIRF | 133 | AAS | 134 | QQTKEVPWS |
| CLEC12A antibody SC02-357 | 135 | SSNWWS | 136 | EIYHSGSPDYNPSLKS | 137 | VSTGGFFDY | 138 | RASQSISSYLN | 139 | AASSLQS | 140 | QQSYSTPPT |
| CLEC12A antibody SC02-378 | 141 | SSNWWS | 142 | EIYHSGSPNYNPSLKS | 143 | SSSGGFFDY | 144 | RASQSISSYLN | 145 | AASSLQS | 146 | QQSYSTPPT |
| CLEC12A antibody SC02-161 | 147 | RASQSISSYLN | 148 | AASSLQ | 149 | QQSYSTPPT | 150 | SSNWWS | 151 | EIYHSGSPNYNPSLKS | 152 | QTTAGSFDY |

Certain aspects of the present disclosure relate to chimeric receptors (e.g., CAR or chimeric TCR) comprising an extracellular antigen-binding domain that bind to one or more antigens of the present disclosure. In some embodiments, the antigen-binding domain are derived from an antibody, or antigen-binding fragment thereof.

In some embodiments, the antigen binding domain comprises a VH comprising the amino acid sequence of SEQ ID NO: 1 or a sequence at least 90% identical thereto. In some embodiments, the antigen binding domain comprises a VL comprising the amino acid sequence of SEQ. ID NO: 2 or a sequence at least 90% identical thereto. In some embodiments, the antigen binding domain comprises a VH comprising the amino acid sequence of SEQ ID NO: 3 or a sequence at least 90% identical thereto. In some embodiments, the antigen binding domain comprises a VL comprising the amino acid sequence of SEQ. ID NO: 4 or a sequence at least 90% identical thereto. In some embodiments, the antigen binding domain comprises a VH comprising the amino acid sequence of SEQ ID NO: 5 or a sequence at least 90% identical thereto. In some embodiments, the antigen binding domain comprises a VL comprising the amino acid sequence of SEQ ID NO: 6 or a sequence at least 90% identical thereto. In some embodiments, the antigen binding domain comprises a VH comprising the amino acid sequence of SEQ ID NO: 7 or a sequence at least 90% identical thereto. In some embodiments, the antigen binding domain comprises a VL comprising the amino acid sequence of SEQ ID NO: 8 or a sequence at least 90% identical thereto. In some embodiments, the antigen binding domain comprises a VH comprising the amino acid sequence of SEQ ID NO: 9 or a sequence at least 90% identical thereto. In some embodiments, the antigen binding domain comprises a VL comprising the amino acid sequence of SEQ ID NO: 10 or a sequence at least 90% identical thereto. In some embodiments, the antigen binding domain comprises a VH comprising the amino acid sequence of SEQ ID NO: 11 or a sequence at least 90% identical thereto. In some embodiments, the antigen binding domain comprises a VL comprising the amino acid sequence of SEQ ID NO: 12 or a sequence at least 90% identical thereto. In some embodiments, the antigen binding domain comprises a VH comprising the amino acid sequence of SEQ ID NO: 13 or a sequence at least 90% identical thereto. In some embodiments, the antigen binding domain comprises a VL comprising the amino acid sequence of SEQ ID NO: 14 or a sequence at least 90% identical thereto. In some embodiments, the antigen binding domain comprises a VH comprising the amino acid sequence of SEQ ID NO: 15 or a sequence at least 90% identical thereto. In some embodiments, the antigen binding domain comprises a VL comprising the amino acid sequence of SEQ ID NO: 16 or a sequence at least 90% identical thereto. In some embodiments, the antigen binding domain comprises a VH comprising the amino acid sequence of SEQ ID NO: 17 or a sequence at least 90% identical thereto. In some embodiments, the antigen binding domain comprises a VL comprising the amino acid sequence of SEQ ID NO: 18 or a sequence at least 90% identical thereto. In some embodiments, the antigen binding domain comprises a VH comprising the amino acid sequence of SEQ ID NO: 19 or a sequence at least 90% identical thereto. In some embodiments, the antigen binding domain comprises a VL comprising the amino acid sequence of SEQ ID NO: 20 or a sequence at least 90% identical thereto. In some embodiments, the antigen binding domain comprises a VH comprising the amino acid sequence of SEQ ID NO: 21 or a sequence at least 90% identical thereto. In some embodiments, the antigen binding domain comprises a VL comprising the amino acid sequence of SEQ ID NO: 22 or a sequence at least 90% identical thereto. In some embodiments, the antigen binding domain comprises a VH comprising the amino acid sequence of SEQ ID NO: 23 or a sequence at least 90% identical thereto. In some embodiments, the antigen binding domain comprises a VL comprising the amino acid sequence of SEQ ID NO: 24 or a sequence at least 90% identical thereto. In some embodiments, the antigen binding domain comprises a VH comprising the amino acid sequence of SEQ ID NO: 25 or a sequence at least 90% identical thereto. In some embodiments, the antigen binding domain comprises a VL comprising the amino acid sequence of SEQ ID NO: 26 or a sequence at least 90% identical thereto.

In some embodiments, the antigen binding domain comprises a CDR-H1 sequence as shown in SEQ ID NO: 75, a CDR-H2 sequence as shown in SEQ ID NO: 76, and a CDR-H3 sequence as shown in SEQ ID NO: 77. In some embodiments, the antigen binding domain comprises a CDR-L1 sequence as shown in SEQ ID NO: 78, a CDR-L2 sequence as shown in SEQ ID NO: 79, and a CDR-L3 sequence as shown in SEQ ID NO: 80. In some embodiments, the antigen binding domain comprises a CDR-H1 sequence as shown in SEQ ID NO: 81, a CDR-H2 sequence as shown in SEQ ID NO: 82, and a CDR-H3 sequence as shown in SEQ ID NO: 83. In some embodiments, the antigen binding domain comprises a CDR-L1 sequence as shown in SEQ ID NO: 84, a CDR-L2 sequence as shown in SEQ ID NO: 85, and a CDR-L3 sequence as shown in SEQ ID NO: 86. In some embodiments, the antigen binding domain comprises a CDR-H1 sequence as shown in SEQ ID NO: 87, a CDR-H2 sequence as shown in SEQ ID NO: 88, and a CDR-H3 sequence as shown in SEQ ID NO: 89. In some embodiments, the antigen binding domain comprises a CDR-L1 sequence as shown in SEQ ID NO: 90, a CDR-L2 sequence as shown in SEQ ID NO: 91, and a CDR-L3 sequence as shown in SEQ ID NO: 92. In some embodiments, the antigen binding domain comprises a CDR-H1 sequence as shown in SEQ ID NO: 93, a CDR-H2 sequence as shown in SEQ ID NO: 94, and a CDR-H3 sequence as shown in SEQ ID NO: 95. In some embodiments, the antigen binding domain comprises a CDR-L1 sequence as shown in SEQ ID NO: 96, a CDR-L2 sequence as shown in SEQ ID NO: 97, and a CDR-L3 sequence as shown in SEQ ID NO: 98. In some embodiments, the antigen binding domain comprises a CDR-H1 sequence as shown in SEQ ID NO: 99, a CDR-H2 sequence as shown in SEQ ID NO: 100, and a CDR-H3 sequence as shown in SEQ ID NO: 101. In some embodiments, the antigen binding domain comprises a CDR-L1 sequence as shown in SEQ ID NO: 102, a CDR-L2 sequence as shown in SEQ ID NO: 103, and a CDR-L3 sequence as shown in SEQ ID NO: 104. In some embodiments, the antigen binding domain comprises a CDR-H1 sequence as shown in SEQ ID NO: 105, a CDR-H2 sequence as shown in SEQ ID NO: 106, and a CDR-H3 sequence as shown in SEQ ID NO: 107. In some embodiments, the antigen binding domain comprises a CDR-L1 sequence as shown in SEQ ID NO: 108, a CDR-L2 sequence as shown in SEQ ID NO: 109, and a CDR-L3 sequence as shown in SEQ ID NO: 110. In some embodiments, the antigen binding domain comprises a CDR-H1 sequence as shown in SEQ ID NO: 111, a CDR-H2 sequence as shown in SEQ ID NO: 112, and a CDR-H3 sequence as shown in SEQ ID NO: 113. In some embodiments, the antigen binding domain comprises a CDR-L1 sequence as shown in SEQ ID NO: 114, a CDR-L2 sequence as shown in SEQ ID NO: 115, and a CDR-L3 sequence as shown in SEQ ID NO: 116. In some embodiments, the antigen binding domain comprises a CDR-H1 sequence as shown in SEQ ID NO: 117, a CDR-H2 sequence as shown in SEQ ID NO: 118, and a CDR-H3 sequence as shown in SEQ ID NO: 119. In some embodiments, the antigen binding domain comprises a CDR-L1 sequence as shown in SEQ ID NO: 120, a CDR-L2 sequence as shown in SEQ ID NO: 121, and a CDR-L3 sequence as shown in SEQ ID NO: 122. In some embodiments, the antigen binding domain comprises a CDR-H1 sequence as shown in SEQ ID NO: 123, a CDR-H2 sequence as shown in SEQ ID NO: 124, and a CDR-H3 sequence as shown in SEQ ID NO: 125. In some embodiments, the antigen binding domain comprises a CDR-L1 sequence as shown in SEQ ID NO: 126, a CDR-L2 sequence as shown in SEQ ID NO: 127, and a CDR-L3 sequence as shown in SEQ ID NO: 128. In some embodiments, the antigen binding domain comprises a CDR-H1 sequence as shown in SEQ ID NO: 129, a CDR-H2 sequence as shown in SEQ ID NO: 130, and a CDR-H3 sequence as shown in SEQ ID NO: 131. In some embodiments, the antigen binding domain comprises a CDR-L1 sequence as shown in SEQ ID NO: 132, a CDR-L2 sequence as shown in SEQ ID NO: 133, and a CDR-L3 sequence as shown in SEQ ID NO: 134. In some embodiments, the antigen binding domain comprises a CDR-H1 sequence as shown in SEQ ID NO: 135, a CDR-H2 sequence as shown in SEQ ID NO: 136, and a CDR-H3 sequence as shown in SEQ ID NO: 137. In some embodiments, the antigen binding domain comprises a CDR-L1 sequence as shown in SEQ ID NO: 138, a CDR-L2 sequence as shown in SEQ ID NO: 139, and a CDR-L3 sequence as shown in SEQ ID NO: 140. In some embodiments, the antigen binding domain comprises a CDR-H1 sequence as shown in SEQ ID NO: 141, a CDR-H2 sequence as shown in SEQ ID NO: 142, and a CDR-H3 sequence as shown in SEQ ID NO: 143. In some embodiments, the antigen binding domain comprises a CDR-L1 sequence as shown in SEQ ID NO: 144, a CDR-L2 sequence as shown in SEQ ID NO: 145, and a CDR-L3 sequence as shown in SEQ ID NO: 146. In some embodiments, the antigen binding domain comprises a CDR-H1 sequence as shown in SEQ ID NO: 147, a CDR-H2 sequence as shown in SEQ ID NO: 148, and a CDR-H3 sequence as shown in SEQ ID NO: 149. In some embodiments, the antigen binding domain comprises a CDR-L1 sequence as shown in SEQ ID NO: 150, a CDR-L2 sequence as shown in SEQ ID NO: 151, and a CDR-L3 sequence as shown in SEQ ID NO: 152.

Suitable antibodies of the present disclosure include any antibody, whether natural or synthetic, full length or a fragment thereof, monoclonal or polyclonal, that binds sufficiently strongly and specifically to a myeloid (e.g., AML) antigen. In some embodiments, the antibody may have a $K_d$ of at most about at most $10^{-6}$ M, at most about $10^{-7}$ M, at most about $10^{-8}$ M, at most about $10^{-9}$ M, at most about $10^{-10}$ M, at most about $10^{-11}$ M, or at most about $10^{-12}$ M.

In some embodiments, antibodies and derivatives thereof that may be used include, without limitation, polyclonal antibodies, monoclonal antibodies, chimeric antibodies, human antibodies, humanized, antibodies primatized (CDR-grafted) antibodies, veneered antibodies, single-chain antibodies, phage-produced antibodies (e.g., from phage display libraries), and functional binding fragments of antibodies. For example, antibody fragments capable of binding to a myeloid (e.g., AML) antigen, or portions thereof, include, without limitation, Fv, Fab, Fab' and $F(ab')_2$ fragments. Such fragments can be produced by enzymatic cleavage or by recombinant techniques. For example, and not by way of limitation, papain or pepsin cleavage can generate Fab or $F(ab')_2$ fragments, respectively. Other proteases with the requisite substrate specificity can also be used to generate Fab or $F(ab')_2$ fragments. Antibodies can also be produced in a variety of truncated forms using antibody genes in which one or more stop codons have been introduced upstream of the natural stop site. For example, a chimeric gene encoding a $F(ab')_2$ heavy chain portion can be designed to include DNA sequences encoding the CH, domain and hinge region of the heavy chain.

Methods of raising an antibody targeting a specific antigen are generally known in the art. Synthetic and engineered antibodies are described in, e.g., U.S. Pat. No. 4,816,567, EP0125023B1, U.S. Pat. No. 4,816,397, EP0120694B1, WO 86/01533, EP0194276B1, U.S. Pat. No. 5,225,539, EP0239400B1, EP0451216B1, EP0519596A1 and U.S. Pat. No. 4,946,778.

In some embodiments, commercially available antibodies may be used for binding to a myeloid (e.g., AML) antigen. The CDRs of the commercially available antibodies are readily accessible by one skilled in the art using conventional sequencing technology. Further, one skilled in the art is able to construct nucleic acids encoding scFvs and chimeric receptors (e.g., CARs and TCRs) based on the CDRs of such commercially available antibodies.

In some embodiments, a chimeric receptor comprises an antigen-binding domain that specifically binds FLT3. In some embodiments, the FLT3-specific antigen-binding domain is derived from an anti-FLT3 antibody, such as the D4-3, NC7, or EB10 antibody described in U.S. Pat. No. 8,071,099. In some embodiments, the FLT3-specific antigen-binding domain is derived from an anti-FLT3 antibody, such as the 4G8 or BV10 antibody described in U.S. Pat. No. 9,023,996. In some embodiments, the FLT3-specific antigen-binding domain is derived from an anti-FLT3 antibody, such as the FL_16 or FL_39 antibody described in U.S. Patent Publication No. 2017/0037149, published Feb. 9, 2017. In some embodiments, the FLT3-specific antigen-binding domain is derived from an anti-FLT3 antibody, such as the ml0006 antibody described in International Patent Publication WO 2018/119279, published Jun. 28, 2018. The antigen-binding domain may be an scFv that comprises a light chain variable domain (VL) and a heavy chain variable domain (VH). In some embodiments, the chimeric receptor may have a multispecific antigen-binding domain. For example, the chimeric receptor may be specific for FLT3 and one or more additional antigens, such as CD33 and/or CLEC12A.

In some embodiments, a chimeric receptor comprises an antigen-binding domain that specifically binds CD33. In some embodiments, the CD33-specific antigen-binding domain is derived from an anti-CD33 antibody, such as lintuzumab described in U.S. Patent Publication No. 2018/0002397, published Jan. 4, 2018. In some embodiments, the CD33-specific antigen-binding domain is derived from an anti-CD33 antibody, such as gemtuzumab described in U.S. Pat. No. 5,739,116. The antigen-binding domain may be an scFv that comprises a light chain variable domain (VL) and a heavy chain variable domain (VH). In some embodiments, the chimeric receptor may have a multispecific antigen-binding domain. For example, the chimeric receptor may be specific for CD33 and one or more additional antigens, such as FLT3 and/or CLEC12A.

In some embodiments, a chimeric receptor comprises an antigen-binding domain that specifically binds CLEC12A. In some embodiments, the CLEC12A-specific antigen-binding domain is derived from an anti-CLEC12A antibody, such as the SC02-357, SC02-378, or SC02-161 antibody described in U.S. Pat. No. 7,741,443. The antigen-binding domain may be an scFv that comprises a light chain variable domain (VL) and a heavy chain variable domain (VH). In some embodiments, the chimeric receptor may have a multispecific antigen-binding domain. For example, the chimeric receptor may be specific for CLEC12A and one or more additional antigens, such as FLT3 and/or CD33.

T Cell Receptor (TCR)

Certain aspects of the present disclosure relate to chimeric receptors that specifically bind to an antigen expressed on myeloid cell, such as an AML cell. In some embodiments, the chimeric receptor is a chimeric T cell receptor (TCR). TCRs of the present disclosure are disulfide-linked heterodimeric proteins containing two variable chains expressed as part of a complex with the invariant CD3 chain molecules. TCRs are found on the surface of T cells, and are responsible for recognizing antigens as peptides bound to major histocompatibility complex (MHC) molecules. In certain embodiments, a TCR of the present disclosure comprises an alpha chain encoded by TRA and a beta chain encoded by TRB. In certain embodiments, a TCR comprises a gamma chain and a delta chain (encoded by TRG and TRD, respectively).

Each chain of a TCR is composed of two extracellular domains: a variable (V) region and a constant (C) region. The constant region is proximal to the cell membrane, followed by a transmembrane region and a short cytoplasmic tail. The variable region binds to the peptide/MHC complex. Each of the variable regions has three complementarity determining regions (CDRs).

In certain embodiments, a TCR can form a receptor complex with three dimeric signaling modules CD3δ/ε, CD3γ/ε, and CD247ζ/ζ or CD247ζ/η. When a TCR complex engages with its antigen and MHC (peptide/MHC), the T cell expressing the TCR complex is activated.

In some embodiments, a TCR of the present disclosure is a recombinant TCR. In certain embodiments, the TCR is a non-naturally occurring TCR. In certain embodiments, the TCR differs from a naturally occurring TCR by at least one amino acid residue. In some embodiments, the TCR differs from a naturally occurring TCR by at least 2 amino acid residues, at least 3 amino acid residues, at least 4 amino acid residues, at least 5 amino acid residues, at least 6 amino acid residues, at least 7 amino acid residues, at least 8 amino acid residues, at least 9 amino acid residues, at least 10 amino acid residues, at least 11 amino acid residues, at least 12 amino acid residues, at least 13 amino acid residues, at least 14 amino acid residues, at least 15 amino acid residues, at least 20 amino acid residues, at least 25 amino acid residues, at least 30 amino acid residues, at least 40 amino acid residues, at least 50 amino acid residues, at least 60 amino acid residues, at least 70 amino acid residues, at least 80 amino acid residues, at least 90 amino acid residues, at least 100 amino acid residues, or more amino acid residues. In certain embodiments, the TCR is modified from a naturally occurring TCR by at least one amino acid residue. In some embodiments, the TCR is modified from a naturally occurring TCR by at least 2 amino acid residues, at least 3 amino acid residues, at least 4 amino acid residues, at least 5 amino acid residues, at least 6 amino acid residues, at least 7 amino acid residues, at least 8 amino acid residues, at least 9 amino acid residues, at least 10 amino acid residues, at least 11 amino acid residues, at least 12 amino acid residues, at least 13 amino acid residues, at least 14 amino acid residues, at least 15 amino acid residues, at least 20 amino acid residues, at least 25 amino acid residues, at least 30 amino acid residues, at least 40 amino acid residues, at least 50 amino acid residues, at least 60 amino acid residues, at least 70 amino acid residues, at least 80 amino acid residues, at least 90 amino acid residues, at least 100 amino acid residues, or more amino acid residues.

Chimeric TCRs

In some embodiments, a TCR of the present disclosure comprises one or more antigen-binding domains that may be grafted to one or more constant domain of a TCR chain, for example a TCR alpha chain or TCR beta chain, to create a chimeric TCR that binds specifically to a target antigen of the present disclosure (e.g., an AML antigen). Without wishing to be bound by theory, it is believed that chimeric TCRs may signal through the TCR complex upon antigen binding. For example, an antibody or antibody fragment (e.g., scFv) can be grafted to the constant domain, e.g., at least a portion of the extracellular constant domain, the transmembrane domain and the cytoplasmic domain, of a TCR chain, such as the TCR alpha chain and/or the TCR beta chain. As another example, the CDRs of an antibody or antibody fragment may be grafted into a TCR alpha chain and/or beta chain to create a chimeric TCR that binds specifically to an antigen of the present disclosure (e.g., an AML antigen). Such chimeric TCRs may be produced by methods known in the art (e.g., Willemsen R A et al., Gene Therapy 2000; 7:1369-1377; Zhang T et al., Cancer Gene Ther 2004 11: 487-496; and Aggen et al., Gene Ther. 2012 April; 19(4): 365-74).

Chimeric Antigen Receptors (CARs)

Certain aspects of the present disclosure relate to chimeric receptors that specifically bind to an antigen expressed on myeloid cell, such as an AML cell. In some embodiments, the chimeric receptor is a chimeric antigen receptor (CAR).

In some embodiments, CARs are engineered receptors that graft or confer a specificity of interest onto an immune effector cell. In certain embodiments, CARs can be used to graft the specificity of an antibody onto an immunoresponsive cell, such as a T cell. In some embodiments, CARs of the present disclosure comprise an extracellular antigen-binding domain (e.g., an scFv) fused to a transmembrane domain, fused to one or more intracellular signaling domains.

In some embodiments, binding of the chimeric antigen receptor to its cognate ligand is sufficient to induce activation of the immunoresponsive cell. In some embodiments, binding of the chimeric antigen receptor to its cognate ligand is sufficient to induce stimulation of the immunoresponsive cell. In some embodiments, activation of an immunoresponsive cell results in killing of target cells. In some embodiments, activation of an immunoresponsive cell results in cytokine or chemokine expression and/or secretion by the immunoresponsive cell. In some embodiments, stimulation of an immunoresponsive cell results in cytokine or chemokine expression and/or secretion by the immunoresponsive cell. In some embodiments, stimulation of an immunoresponsive cell induces differentiation of the immunoresponsive cell. In some embodiments, stimulation of an immunoresponsive cell induces proliferation of the immunoresponsive cell.

A CAR of the present disclosure may be a first, second, or third generation CAR. "First generation" CARs comprise a single intracellular signaling domain, generally derived from a T cell receptor chain. "First generation" CARs generally have the intracellular signaling domain from the CD3-zeta (CD3ζ) chain, which is the primary transmitter of signals from endogenous TCRs. "First generation" CARs can provide de novo antigen recognition and cause activation of both $CD4^+$ and $CD8^+$ T cells through their CD3ζ chain signaling domain in a single fusion molecule, independent of HLA-mediated antigen presentation. "Second generation" CARs add a second intracellular signaling domain from one of various co-stimulatory molecules (e.g., CD28, 4-1BB, ICOS, OX40) to the cytoplasmic tail of the CAR to provide additional signals to the T cell. "Second generation" CARs provide both co-stimulation (e.g., CD28 or 4-1BB) and activation (CD3ζ). Preclinical studies have indicated that "Second Generation" CARs can improve the anti-tumor activity of immunoresponsive cell, such as a T cell. "Third generation" CARs have multiple intracellular co-stimulation signaling domains (e.g., CD28 and 4-1BB) and an intracellular activation signaling domain (CD3ζ).

In some embodiments, the extracellular antigen-binding domain of a CAR of the present disclosure binds to one or more antigens expressed on a myeloid cell, such as an AML cell, with a dissociation constant ($K_d$) of about $2\times10^{-7}$ M or less, about $1\times10^{-7}$ M or less, about $9\times10^{-8}$ M or less, about $1\times10^{-8}$ M or less, about $9\times10^{-9}$ M or less, about $5\times10^{-9}$ M or less, about $4\times10^{-9}$ M or less, about $3\times10^{-9}$ M or less, about $2\times10^{-9}$ M or less, or about $1\times10^{-9}$ M or less. In some embodiments, the $K_d$ ranges from about is about $2\times10^{-7}$ M to about $1\times10^{-9}$ M.

Binding of the extracellular antigen-binding domain of a CAR of the present disclosure can be determined by, for example, an enzyme-linked immunosorbent assay (ELISA), a radioimmunoassay (RIA), FACS analysis, a bioassay (e.g., growth inhibition), or a Western Blot assay. Each of these assays generally detect the presence of protein-antibody complexes of particular interest by employing a labeled reagent (e.g., an antibody or scFv) specific for the complex of interest. For example, the scFv can be radioactively labeled and used in an RIA assay. The radioactive isotope can be detected by such means as the use of a γ counter or a scintillation counter or by autoradiography. In certain embodiments, the extracellular antigen-binding domain of the CAR is labeled with a fluorescent marker. Non-limiting examples of fluorescent markers include green fluorescent protein (GFP), blue fluorescent protein (e.g., EBFP, EBFP2, Azurite, and mKalamal), cyan fluorescent protein (e.g., ECFP, Cerulean, and CyPet), and yellow fluorescent protein (e.g., YFP, Citrine, Venus, and YPet).

In some embodiments, CARs of the present disclosure comprise an extracellular antigen-binding domain that binds to one or more antigens expressed on a myeloid (e.g., an AML) cell, a transmembrane domain, and one or more intracellular signaling domains. In some embodiments, the extracellular antigen-binding domain comprises an scFv. In some embodiments, the extracellular antigen-binding domain comprises a Fab fragment, which may be cross-linked. In certain embodiments, the extracellular binding domain is a $F(ab)_2$ fragment.

Extracellular Antigen-Binding Domain

In some embodiments, the extracellular antigen-binding domain of a CAR of the present disclosure specifically binds to one or more antigens expressed on a myeloid cell, such as an AML cell. In certain embodiments, the extracellular antigen-binding domain binds to one or more antigens expressed on an AML cell (AML antigens). In some embodiments, the one or more AML antigens are human polypeptides.

Antigen-binding domains of the present disclosure can include any domain that binds to the antigen including, without limitation, a monoclonal antibody, a polyclonal antibody, a recombinant antibody, a bispecific antibody, a conjugated antibody, a human antibody, a humanized antibody, and a functional fragment thereof, including but not limited to a single-domain antibody (sdAb) such as a heavy chain variable domain (VH), a light chain variable domain (VL) and a variable domain (VHH) of camelid derived nanobody, and to an alternative scaffold known in the art to function as antigen-binding domain, such as a recombinant fibronectin domain, a T cell receptor (TCR), a recombinant TCR with enhanced affinity, or a fragment thereof, e.g., single chain TCR, and the like. In some instances, it is beneficial for the antigen-binding domain to be derived from the same species in which the CAR will ultimately be used in. For example, for use in humans, it may be beneficial for the antigen-binding domain of the CAR to comprise human or humanized residues for the antigen-binding domain of an antibody or antibody fragment.

In some embodiments, the extracellular antigen-binding domain comprises an antibody. In certain embodiments, the antibody is a human antibody. In certain embodiments, the antibody is a humanized antibody. In certain embodiments, the antibody is a chimeric antibody. In some embodiments, the extracellular antigen-binding domain comprises an antigen-binding fragment of an antibody.

In some embodiments, the extracellular antigen-binding domain comprises a F(ab) fragment. In certain embodiments, the extracellular antigen-binding domain comprises a F(ab') fragment.

In some embodiments, the extracellular antigen-binding domain comprises an scFv. In some embodiments, the extracellular antigen-binding domain comprises two single chain variable fragments (scFvs). In some embodiments, each of the two scFvs binds to a distinct epitope on the same antigen. In some embodiments, the extracellular antigen-binding domain comprises a first scFv and a second scFv. In some embodiments, the first scFv and the second scFv bind distinct epitopes on the same antigen. In certain embodiments, the scFv is a human scFv. In certain embodiments, the scFv is a humanized scFv. In certain embodiments, the scFv is a chimeric scFv. In certain embodiments, the scFv comprises a heavy chain variable domain (VH) and a light chain variable domain (VL). In certain embodiments, the VH and VL are separated by a peptide linker. In certain embodiments, the peptide linker comprises the amino acid sequence of SEQ ID NO: 27 or SEQ ID NO: 74. In certain embodiments, the peptide linker comprises the amino acid sequence of SEQ ID NO: 218 or 219. In certain embodiments, the peptide linker is encoded by a nucleic acid comprising the sequence of SEQ ID NO: 54, 220, 221, or 223. In certain embodiments, the scFv comprises the structure VH-L-VL or VL-L-VH, wherein VH is the heavy chain variable domain, L is the peptide linker, and VL is the light chain variable domain.

In some embodiments, each of the one or more scFvs comprises the structure VH-L-VL or VL-L-VH, wherein VH is the heavy chain variable domain, L is the peptide linker, and VL is the light chain variable domain. When there are two or more scFv linked together, each scFv can be linked to the next scFv with a peptide linked. In some embodiments, each of the one or more scFvs is separated by a peptide linker. In some embodiments, the peptide linker comprises the amino acid sequence of GGGGSGGGGSGGGGS (SEQ ID NO: 27) or EAAAKEAAAKEAAAKEAAAK (SEQ ID NO: 74).

In some embodiments, the cell comprises a first chimeric receptor and a second chimeric receptor. The antigen binding domain of the first chimeric receptor and the antigen binding domain of the second chimeric receptor can be an appropriate antigen biding domain described herein or known in the art. For example, the first or second antigen binding domain can be one or more antibodies, antigen-binding fragments of an antibody, F(ab) fragments, F(ab') fragments, single chain variable fragments (scFvs), or single-domain antibodies (sdAbs). In some embodiments, the antigen-binding domain of the first chimeric receptor and/or the second chimeric receptor comprises two single chain variable fragments (scFvs). In some embodiments, each of the two scFvs binds to a distinct epitope on the same antigen.

In some embodiments, the extracellular antigen-binding domain comprises a single-domain antibody (sdAb). In certain embodiments, the sdAb is a humanized sdAb. In certain embodiments, the sdAb is a chimeric sdAb.

In some embodiments, a CAR of the present disclosure may comprise two or more antigen-binding domains, three or more antigen-binding domains, four or more antigen-binding domains, five or more antigen-binding domains, six or more antigen-binding domains, seven or more antigen-binding domains, eight or more antigen-binding domains, nine or more antigen-binding domains, or ten or more antigen-binding domains. In some embodiments, each of the two or more antigen-binding domains binds the same antigen. In some embodiments, each of the two or more antigen-binding domains binds a different epitope of the same antigen. In some embodiments, each of the two or more antigen-binding domains binds a different antigen. In some embodiments, the two or more antigen-binding domains provide the CAR with logic gating, such as OR logic gating.

In some embodiments, the CAR comprises two antigen-binding domains. In some embodiments, the two antigen-binding domains are attached to one another via a flexible linker. In some embodiments, each of the two-antigen-binding domains may be independently selected from an antibody, an antigen-binding fragment of an antibody, an scFv, a sdAb, a recombinant fibronectin domain, a T cell receptor (TCR), a recombinant TCR with enhanced affinity, and a single chain TCR. In some embodiments, the CAR comprising two antigen-binding domains is a bispecific CAR or a tandem CAR (tanCAR).

In certain embodiments, the bispecific CAR or tanCAR comprises an antigen-binding domain comprising a bispecific antibody or antibody fragment (e.g., scFv). In some embodiments, within each antibody or antibody fragment (e.g., scFv) of a bispecific antibody molecule, the VH can be upstream or downstream of the VL. In some embodiments, the upstream antibody or antibody fragment (e.g., scFv) is arranged with its VH ($VH_1$) upstream of its VL ($VL_1$) and the downstream antibody or antibody fragment (e.g., scFv) is arranged with its VL ($VL_2$) upstream of its VH ($VH_2$), such that the overall bispecific antibody molecule has the arrangement $VH_1$-$VL_1$-$VL_2$-$VH_2$. In other embodiments, the upstream antibody or antibody fragment (e.g., scFv) is arranged with its VL ($VL_1$) upstream of its VH ($VH_1$) and the downstream antibody or antibody fragment (e.g., scFv) is arranged with its VH ($VH_2$) upstream of its VL ($VL_2$), such that the overall bispecific antibody molecule has the arrangement $VL_1$ $VH_1$-$VH_2$-$VL_2$. In some embodiments, a linker is disposed between the two antibodies or antibody fragments (e.g., scFvs), for example, between $VL_1$ and $VL_2$ if the construct is arranged as $VH_1$-$VL_1$-$VL_2$-$VH_2$, or between $VH_1$ and $VH_2$ if the construct is arranged as $VL_1$-$VH_1$-$VH_2$-$VL_2$. The linker may be a linker as described herein, e.g., a ($Gly_4$-Ser)n linker, wherein n is 1, 2, 3, 4, 5, or 6 (SEQ ID NO: 227). In general, the linker between the two scFvs should be long enough to avoid mispairing between the domains of the two scFvs. In some embodiments, a linker is disposed between the VL and VH of the first scFv. In some embodiments, a linker is disposed between the VL and VH of the second scFv. In constructs that have multiple linkers, any two or more of the linkers may be the same or different. Accordingly, in some embodiments, a bispecific CAR or tanCAR comprises VLs, VHs, and may further comprise one or more linkers in an arrangement as described herein.

In some embodiments, chimeric receptors comprise a bivalent CAR. In some embodiments, the bivalent CAR is an FLT3 bivalent CAR. In some embodiments, the bivalent FLT3 CAR comprises an NC7 scFv and a D4-3 scFv. In some embodiments, the bivalent CAR is a CD33 bivalent CAR. In some embodiments, the bivalent CAR is a CLEC12A bivalent CAR.

In some embodiments, the chimeric receptor comprises a bivalent chimeric antigen receptor. In some embodiments, the bivalent chimeric receptor comprises an FLT3 CAR and a CD33 CAR. In some embodiments, the bivalent chimeric receptor comprises an FLT3 CAR and a CLEC12A CAR. In some embodiments, the bivalent chimeric receptor comprises an CLEC12A CAR and a CD33 CAR. In some embodiments, the bivalent chimeric receptor comprises an EMCN CAR. In some embodiments, the bivalent chimeric receptor comprises a CAR with an antigen binding domain targeting any antigen provided in Table 1. In some embodiments, the bivalent chimeric receptor comprises a CAR with an antigen binding domain targeting any antigen provided in Table 2. In some embodiments, the bivalent chimeric receptor comprises a CAR with two or more antigen binding domains targeting any antigen pair provided in Table 3. In some embodiments, the bivalent chimeric antigen receptor comprises a CAR with any combination of two or more antigen binding domains as described herein.

In some embodiments, chimeric receptors comprise a bicistronic chimeric antigen receptor. In some embodiments, the bicistronic chimeric antigen receptor comprises an FLT3 CAR and a CD33 CAR. In some embodiments, the bicistronic chimeric antigen receptor comprises an FLT3 CAR and a CLEC12A CAR. In some embodiments, the bicistronic chimeric antigen receptor comprises an CLEC12A CAR and a CD33 CAR. In some embodiments, the bicistronic chimeric antigen receptor comprises an EMCN CAR. In some embodiments, the bicistronic chimeric antigen receptor comprises a CAR with an antigen binding domain targeting any antigen provided in Table 1. In some embodiments, the bicistronic chimeric antigen receptor comprises a CAR with an antigen binding domain targeting any antigen provided in Table 2. In some embodiments, the bicistronic chimeric antigen receptor comprises a CAR with two or more antigen binding domains targeting any antigen pair provided in Table 3. In some embodiments, the bicistronic chimeric antigen receptor comprises a CAR with any combination of two or more antigen binding domains as described herein.

Transmembrane Domain

In some embodiments, the transmembrane domain of a CAR of the present disclosure comprises a hydrophobic alpha helix that spans at least a portion of a cell membrane. It has been shown that different transmembrane domains can result in different receptor stability. After antigen recognition, receptors cluster and a signal is transmitted to the cell. In some embodiments, the transmembrane domain of a CAR of the present disclosure can comprise the transmembrane domain of a CD8 polypeptide, a CD28 polypeptide, a CD3-zeta polypeptide, a CD4 polypeptide, a 4-1BB polypeptide, an OX40 polypeptide, an ICOS polypeptide, a CTLA-4 polypeptide, a PD-1 polypeptide, a LAG-3 polypeptide, a 2B4 polypeptide, a BTLA polypeptide, a LIR-1 (LILRB1) polypeptide, or can be a synthetic peptide, or any combination thereof.

In some embodiments, the transmembrane domain is derived from a CD8 polypeptide. Any suitable CD8 polypeptide may be used. Exemplary CD8 polypeptides include, without limitation, NCBI Reference Nos. NP_001139345 and AAA92533.1. In some embodiments, the transmembrane domain is derived from a CD28 polypeptide. Any suitable CD28 polypeptide may be used. Exemplary CD28 polypeptides include, without limitation, NCBI Reference Nos. NP_006130.1 and NP_031668.3. In some embodiments, the transmembrane domain is derived from a CD3-zeta polypeptide. Any suitable CD3-zeta polypeptide may be used. Exemplary CD3-zeta polypeptides include, without limitation, NCBI Reference Nos. NP_932170.1 and NP_001106862.1. In some embodiments, the transmembrane domain is derived from a CD4 polypeptide. Any suitable CD4 polypeptide may be used. Exemplary CD4 polypeptides include, without limitation, NCBI Reference Nos. NP_000607.1 and NP_038516.1. In some embodiments, the transmembrane domain is derived from a 4-1BB polypeptide. Any suitable 4-1BB polypeptide may be used. Exemplary 4-1BB polypeptides include, without limitation, NCBI Reference Nos. NP_001552.2 and NP_001070977.1. In some embodiments, the transmembrane domain is derived from an OX40 polypeptide. Any suitable OX40 polypeptide may be used. Exemplary OX40 polypeptides include, without limitation, NCBI Reference Nos. NP_003318.1 and NP_035789.1. In some embodiments, the transmembrane domain is derived from an ICOS polypeptide. Any suitable ICOS polypeptide may be used. Exemplary ICOS polypeptides include, without limitation, NCBI Reference Nos. NP_036224 and NP_059508. In some embodiments, the transmembrane domain is derived from a CTLA-4 polypeptide. Any suitable CTLA-4 polypeptide may be used. Exemplary CTLA-4 polypeptides include, without limitation, NCBI Reference Nos. NP_005205.2 and NP_033973.2. In some embodiments, the transmembrane domain is derived from a PD-1 polypeptide. Any suitable PD-1 polypeptide may be used. Exemplary PD-1 polypeptides include, without limitation, NCBI Reference Nos. NP_005009 and NP_032824. In some embodiments, the transmembrane domain is derived from a LAG-3 polypeptide. Any suitable LAG-3 polypeptide may be used. Exemplary LAG-3 polypeptides include, without limitation, NCBI Reference Nos. NP_002277.4 and NP_032505.1. In some embodiments, the transmembrane domain is derived from a 2B4 polypeptide. Any suitable 2B4 polypeptide may be used. Exemplary 2B4 polypeptides include, without limitation, NCBI Reference Nos. NP_057466.1 and NP_061199.2. In some embodiments, the transmembrane domain is derived from a BTLA polypeptide. Any suitable BTLA polypeptide may be used. Exemplary BTLA polypeptides include, without limitation, NCBI Reference Nos. NP_861445.4 and NP_001032808.2. Any suitable LIR-1 (LILRB1) polypeptide may be used. Exemplary LIR-1 (LILRB1) polypeptides include, without limitation, NCBI Reference Nos. NP_001075106.2 and NP_001075107.2.

In some embodiments, the transmembrane domain comprises a polypeptide comprising an amino acid sequence that is at least 85%, at least 90%, at least 91%, at least 92%, at least 93%, at least 94%, at least 95%, at least 96%, at least 97%, at least 98%, at least 99%, or 100% homologous to the sequence of NCBI Reference No. NP_001139345, AAA92533.1, NP_006130.1, NP_031668.3, NP_932170.1, NP_001106862.1, NP_000607.1, NP_038516.1, NP_001552.2, NP_001070977.1, NP_003318.1, NP_035789.1, NP_036224, NP_059508, NP_005205.2, NP_033973.2, NP_005009, NP_032824, NP_002277.4, NP_032505.1, NP_057466.1, NP_061199.2, NP_861445.4, or NP_001032808.2, or fragments thereof. In some embodiments, the homology may be determined using standard software such as BLAST or FASTA. In some embodiments, the polypeptide may comprise one conservative amino acid substitution, up to two conservative amino acid substitutions, or up to three conservative amino acid substitutions. In some embodiments, the polypeptide can have an amino acid sequence that is a consecutive portion of NCBI Reference No. NP_001139345, AAA92533.1, NP_006130.1, NP_031668.3, NP_932170.1, NP_001106862.1, NP_000607.1, NP_038516.1, NP_001552.2, NP_001070977.1, NP_003318.1, NP_035789.1, NP_036224, NP_059508, NP_005205.2, NP_033973.2, NP_005009, NP_032824, NP_002277.4, NP_032505.1, NP_057466.1, NP_061199.2, NP_861445.4, or NP_001032808.2 that is at least 20, at least 30, at least 40, at least 50, at least 60, at least 70, at least 80, at least 90, at least 100, at least 110, at least 120, at least 130, at least 140, at least 150, at least 160, at least 170, at least 180, at least 190, at least 200, at least 210, at least 220, at least 230, or at least 240 amino acids in length.

Further examples of suitable polypeptides from which a transmembrane domain may be derived include, without limitation, the transmembrane region(s) of the alpha, beta or zeta chain of the T-cell receptor, CD27, CD3 epsilon, CD45, CD5, CD9, CD16, CD22, CD33, CD37, CD64, CD80, CD86, CD134, CD137, CD154, KIRDS2, CD2, CD27, LFA-1 (CD11a, CD18), GITR, CD40, BAFFR, HVEM (LIGHTR), SLAMF7, NKp80 (KLRF1), NKp44, NKp30, NKp46, CD160, CD19, IL2R beta, IL2R gamma, IL7Ra, ITGA1, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, TNFR2, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), SLAMF6 (NTB-A, Ly108), SLAM (SLAMF1, CD150, IPO-3), BLAME (SLAMF8), SELPLG (CD162), LTBR, PAG/Cbp, NKG2D, and NG2C.

In some embodiments, the transmembrane domain comprises the sequence shown in SEQ ID NO: 209. In some embodiments, the transmembrane domain comprises the sequence shown in SEQ ID NO: 210. In some embodiments, the transmembrane domain comprises the sequence shown in SEQ ID NO: 211.

Spacer Region

In some embodiments, a CAR of the present disclosure can also comprise a spacer region that links the extracellular antigen-binding domain to the transmembrane domain. The spacer region may be flexible enough to allow the antigen-binding domain to orient in different directions to facilitate antigen recognition. In some embodiments, the spacer region may be a hinge from a human protein. For example, the hinge may be a human Ig (immunoglobulin) hinge, including without limitation an IgG4 hinge, an IgG2 hinge, a CD8a hinge, or an IgD hinge. In some embodiments, the spacer region may comprise an IgG4 hinge, an IgG2 hinge, an IgD hinge, a CD28 hinge, a KIR2DS2 hinge, an LNGFR hinge, or a PDGFR-beta extracellular linker. In some embodiments, the spacer region is localized between the antigen-binding domain and the transmembrane domain. In some embodiments, a spacer region may comprise any of the amino acid sequences listed in Table C, or an amino acid sequence that is at least 90%, at least 91%, at least 92%, at least 93%, at least 94%, at least 95%, at least 96%, at least 97%, at least 98%, or at least 99% identical to any of the amino acid sequences listed in Table C. In some embodiments, nucleic acids encoding any of the spacer regions of the present disclosure may comprise any of the nucleic acid sequences listed in Table D, or a nucleic acid sequence that is at least 90%, at least 91%, at least 92%, at least 93%, at least 94%, at least 95%, at least 96%, at least 97%, at least 98%, or at least 99% identical to any of the nucleic acid sequences listed in Table D.

TABLE C

| Amino Acid Sequence | SEQ ID NO: | Description |
|---|---|---|
| AAAIEVMYPPPYLDNEKSNGTIIHVKGKHLCPSPLFPGPSKP | 55 | CD28 hinge |
| ESKYGPPCPSCP | 56 | IgG4 minimal hinge |
| ESKYGPPAPSAP | 57 | IgG4 minimal hinge, no disulfides |
| ESKYGPPCPPCP | 58 | IgG4 S228P minimal hinge, enhanced disulfide formation |
| EPKSCDKTHTCP | 59 | IgG1 minimal hinge |
| AAAFVPVFLPAKPTTTPAPRPPTPAPTIASQPLSLRPEACRPAAGGAVHTRGLDFACDIYIWAPLAGTCGVLLLSLVITLYCNHRN | 60 | Extended CD8a hinge |
| ACPTGLYTHSGECCKACNLGEGVAQPCGANQTVCEPCLDSVTFSDVVSATEPCKPCTECVGLQSMSAPCVEADDAVCRCAYGYYQDETTGRCEACRVCEAGSGLVFSCQDKQNTVCEECPDGTYSDEADAEC | 61 | LNGFR hinge |
| ACPTGLYTHSGECCKACNLGEGVAQPCGANQTVC | 62 | Truncated LNGFR hinge (TNFR-Cys1) |
| AVGQDTQEVIVVPHSLPFKV | 64 | PDGFR-beta extracellular linker |

TABLE D

| Nucleic Acid Sequence | SEQ ID NO: | Description |
|---|---|---|
| GCAGCAGCTATCGAGGTGATGTATCCTCCGCCCTACC TGGATAATGAAAAGAGTAATGGGACTATCATTCATGT AAAAGGGAAGCATCTTTGTCCTTCTCCCCTTTTCCCCG GTCCGTCTAAACCT | 65 | CD28 hinge |
| GAA AGC AAG TAC GGT CCA CCT TGC CCT AGC TGT CCG | 66 | IgG4 minimal hinge |
| GAA TCC AAG TAC GGC CCC CCA GCG CCT AGT GCC CCA | 67 | IgG4 minimal hinge, no disulfides |
| GAA TCT AAA TAT GGC CCG CCA TGC CCG CCT TGC CCA | 68 | IgG4 S228P minimal hinge, enhanced disulfide formation |
| GAA CCG AAG TCT TGT GAT AAA ACT CAT ACG TGC CCG | 69 | IgG1 minimal hinge |
| GCT GCT GCT TTC GTA CCC GTG TTC CTC CCT GCT AAG CCT ACG ACT ACC CCC GCA CCG AGA CCA CCC ACG CCA GCA CCC ACG ATTGCT AGC CAG CCC CTT AGT TTG CGA CCA GAA GCT TGT CGG CCT GCT GCT GGT GGC GCG GTA CAT ACC CGC GGC CTT GAT TTT GCTTGC GAT ATA TAT ATC TGG GCG CCT CTG GCC GGA ACA TGC GGG GTC CTC CTC CTT TCT CTG GTT ATT ACT CTC TAC TGT AAT CACAGG AAT | 70 | Extended CD8a hinge |
| GCC TGC CCG ACC GGG CTC TAC ACT CAT AGC GGG GAA TGT TGT AAG GCA TGT AAC TTG GGT GAG GGC GTC GCA CAG CCC TGC GGAGCT AAC CAA ACA GTG TGC GAA CCC TGC CTC GAT AGT GTG ACG TTC TCT GAT GTT GTA TCA GCT ACA GAG CCT TGC AAA CCA TGTACT GAG TGC GTT GGA CTT CAG TCA ATG AGC GCT CCA TGT GTG GAG GCA GAT GAT GCG GTC TGT CGA TGT GCT TAC GGA TAC TACCAA GAC GAG ACA ACA GGG CGG TGC GAG GCC TGT AGA GTT TGT GAG GCG GGC TCC GGG CTG GTG TTT TCA TGT CAA GAC AAG CAAAAT ACG GTC TGT GAA GAG TGC CCT GAT GGC ACC TAC TCA GAC GAA GCA GAT GCA GAA TGC | 71 | LNGFR hinge |
| GCC TGC CCT ACA GGA CTC TAC ACG CAT AGC GGT GAG TGT TGT AAA GCA TGC AAC CTC GGG GAA GGT GTA GCC CAG CCA TGC GGG GCT AAC CAA ACC GTT TGC | 72 | Truncated LNGFR hinge (TNFR-Cys1) |
| GCTGTGGGCCAGGACACGCAGGAGGTCATCGTGGTG CCACACTCCTTGCCCTTTAAGGTG | 73 | PDGFR-beta extracellular linker |

In some embodiments, the spacer region comprises the sequence shown in SEQ ID NO: 55. In some embodiments, the spacer region comprises the sequence shown in SEQ ID NO: 56. In some embodiments, the spacer region comprises the sequence shown in SEQ ID NO: 57. In some embodiments, the spacer region comprises the sequence shown in SEQ ID NO: 58. In some embodiments, the spacer region comprises the sequence shown in SEQ ID NO: 59. In some embodiments, the spacer region comprises the sequence shown in SEQ ID NO: 60. In some embodiments, the spacer region comprises the sequence shown in SEQ ID NO: 61. In some embodiments, the spacer region comprises the sequence shown in SEQ ID NO: 62. In some embodiments, the spacer region comprises the sequence shown in SEQ ID NO: 63. In some embodiments, the spacer region comprises the sequence shown in SEQ ID NO: 64. In some embodiments, the spacer region comprises the sequence shown in SEQ ID NO: 206. In some embodiments, the spacer region comprises the sequence shown in SEQ ID NO: 207. In some embodiments, the spacer region comprises the sequence shown in SEQ ID NO: 208.

In some embodiments, a CAR of the present disclosure may further include a short oligopeptide or polypeptide linker that is between 2 amino acid residues and 10 amino acid residues in length, and that may form the linkage between the transmembrane domain and the cytoplasmic region of the CAR. A non-limiting example of a suitable linker is a glycine-serine doublet. In some embodiments, the linker comprises the ammo acid sequence of GGCKJSGGCKJS (SEQ ID NO: 228).

Intracellular Signaling Domains

In some embodiments, a CAR of the present disclosure comprises one or more cytoplasmic domains or regions. The cytoplasmic domain or region of the CAR may include an intracellular signaling domain. An intracellular signaling domain is typically responsible for activation of one or more effector functions of an immune cell (e.g., a T cell or an NK cell) that has been engineered to express a CAR of the present disclosure. For example, an effector function of a T cell may be cytolytic activity or helper activity, such as the secretion of cytokines. Accordingly, in some embodiments the term "intracellular signaling domain" refers to the portion of a protein which transduces an effector function signal and directs the cell to perform a specialized function. While the entire intracellular signaling domain may be employed, in many instances it is not necessary to use the entire chain. In embodiments where a truncated portion of the intracellular signaling domain is used, such a truncated portion may be used in place of the corresponding intact chain as long as the truncated portion transduces the effector function signal.

Examples of suitable intracellular signaling domains that may be used in CARs of the present disclosure include, without limitation, cytoplasmic sequences of the T cell receptor (TCR) and co-receptors that act in concert to initiate signal transduction following antigen receptor engagement, as well as any derivative or variant of these sequences and any recombinant sequence that has the same functional capability.

Without wishing to be bound by theory, it is believed that signals generated through the TCR alone are insufficient for full activation of the T cell and that a secondary and/or costimulatory signal is thus also required for full activation. Accordingly, T cell activation may be mediated by two distinct classes of cytoplasmic signaling sequences, those that initiate antigen-dependent primary activation through the TCR (primary intracellular signaling domains) and those that act in an antigen-independent manner to provide a secondary or costimulatory signal (secondary cytoplasmic domain, e.g., a costimulatory domain).

In some embodiments, a primary signaling domain regulates primary activation of the TCR complex either in a stimulatory way, or in an inhibitory way. Primary intracellular signaling domains that act in a stimulatory manner may contain signaling motifs which are known as immunoreceptor tyrosine-based activation motifs (ITAMs). Examples of suitable ITAM-containing primary intracellular signaling domains that that may be used in the CARs of the present disclosure include, without limitation, those of CD3-zeta, FcR gamma, FcR beta, CD3 gamma, CD3 delta, CD3 epsilon, CD5, CD22, CD79a, CD79b, CD278 (also known as "ICOS"), FcεRI, DAP10, DAP12, and CD66d.

In some embodiments, a CAR of the present disclosure comprises an intracellular signaling domain, e.g., a primary signaling domain of CD3-zeta polypeptide. A CD3-zeta polypeptide of the present disclosure may have an amino acid sequence that is at least 85%, at least 90%, at least 91%, at least 92%, at least 93%, at least 94%, at least 95%, at least 96%, at least 97%, at least 98%, at least 99%, or 100% homologous to the sequence of NCBI Reference No. NP_932170 or NP_001106864.2, or fragments thereof. In some embodiments, the CD3-zeta polypeptide may comprise one conservative amino acid substitution, up to two conservative amino acid substitutions, or up to three conservative amino acid substitutions. In some embodiments, the polypeptide can have an amino acid sequence that is a consecutive portion of NCBI Reference No. NP_932170 or NP_001106864.2 that is at least 20, at least 30, at least 40, at least 50, at least 60, at least 70, at least 80, at least 90, at least 100, at least 110, at least 120, at least 130, at least 140, at least 150, or at least 160, at least 170, or at least 180 amino acids in length.

In other embodiments, a primary signaling domain comprises a modified ITAM domain, e.g., a mutated ITAM domain which has altered (e.g., increased or decreased) activity as compared to the native ITAM domain. In one embodiment, a primary signaling domain comprises a modified ITAM-containing primary intracellular signaling domain, e.g., an optimized and/or truncated ITAM-containing primary intracellular signaling domain. In one embodiment, a primary signaling domain comprises one, two, three, four or more ITAM motifs.

In some embodiments, the intracellular signaling domain of a CAR of the present disclosure can comprise the CD3-zeta signaling domain by itself or it can be combined with any other desired intracellular signaling domain(s) useful in the context of a CAR of the present disclosure. For example, the intracellular signaling domain of the CAR can comprise a CD3-zeta chain portion and a costimulatory signaling domain. The costimulatory signaling domain may refer to a portion of the CAR comprising the intracellular domain of a costimulatory molecule. A costimulatory molecule of the present disclosure is a cell surface molecule other than an antigen receptor or its ligands that may be required for an efficient response of lymphocytes to an antigen. Examples of suitable costimulatory molecules include, without limitation, CD97, CD2, ICOS, CD27, CD154, CD8, OX40, 4-1BB, CD28, ZAP40, CD30, GITR, HVEM, DAP10, DAP12, MyD88, 2B4, CD40, PD-1, lymphocyte function-associated antigen-1 (LFA-1), CD7, LIGHT, NKG2C, B7-H3, and a ligand that specifically binds with CD83, an MHC class I molecule, a TNF receptor protein, an Immunoglobulin-like protein, a cytokine receptor, an integrin, a signaling lymphocytic activation molecule (SLAM protein), an activating NK cell receptor, BTLA, a Toll ligand receptor, CDS, ICAM-1, (CD11a/CD18), BAFFR, KIRDS2, SLAMF7, NKp80 (KLRF1), NKp44, NKp30, NKp46, CD19, CD4, IL2R beta, IL2R gamma, IL7R alpha, ITGA4, VLA1, CD49a, ITGA4, IA4, CD49D, ITGA6, VLA-6, CD49f, ITGAD, CD11d, ITGAE, CD103, ITGAL, CD11a, ITGAM, CD11b, ITGAX, CD11c, ITGB1, CD29, ITGB2, CD18, ITGB7, NKG2D, TNFR2, TRANCE/RANKL, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, CD19a, and the like.

In some embodiments, the intracellular signaling sequences within the cytoplasmic portion of a CAR of the present disclosure may be linked to each other in a random or specified order. In some embodiments, a short oligopeptide or polypeptide linker, for example, between 2 amino acids and 10 amino acids (e.g., 2 amino acids, 3 amino acids, 4 amino acids, 5 amino acids, 6 amino acids, 7 amino acids, 8 amino acids, 9 amino acids, or 10 amino acids) in length may form the linkage between intracellular signaling sequences. In one embodiment, a glycine-serine doublet can be used as a suitable linker. In one embodiment, a single ammo acid, e.g., an alanine or a glycine, can be used as a suitable linker.

In some embodiments, the intracellular signaling domain comprises two or more costimulatory signaling domains, e.g., two costimulatory signaling domains, three costimulatory signaling domains, four costimulatory signaling domains, five costimulatory signaling domains, six costimulatory signaling domains, seven costimulatory signaling domains, eight costimulatory signaling domains, nine costimulatory signaling domains, 10 costimulatory signaling domains, or more costimulatory signaling domains. In one embodiment, the intracellular signaling domain comprises two costimulatory signaling domains. In some embodiments, the two or more costimulatory signaling domains are separated by a linker of the present disclosure. In one embodiment, the linker is a glycine residue. In another embodiment, the linker is an alanine residue.

In some embodiments, a cell of the present disclosure expresses a CAR that includes an antigen-binding domain that binds a target antigen of the present disclosure, a transmembrane domain of the present disclosure, a primary signaling domain, and one or more costimulatory signaling domains.

In some embodiments, a CAR comprises the amino acid sequence as shown in SEQ ID NO: 153 or a sequence at least 90% identical thereto. In some embodiments, a CAR comprises the amino acid sequence as shown in SEQ ID NO: 155 or a sequence at least 90% identical thereto. In some embodiments, a CAR comprises the amino acid sequence as shown in SEQ ID NO: 157 or a sequence at least 90% identical thereto. In some embodiments, a CAR comprises the amino acid sequence as shown in SEQ ID NO: 159 or a sequence at least 90% identical thereto. In some embodiments, a CAR comprises the amino acid sequence as shown in SEQ ID NO: 161 or a sequence at least 90% identical thereto. In some embodiments, a CAR comprises the amino acid sequence as shown in SEQ ID NO: 163 or a sequence at least 90% identical thereto. In some embodiments, a CAR comprises the amino acid sequence as shown in SEQ ID NO: 165 or a sequence at least 90% identical thereto. In some embodiments, a CAR comprises the amino acid sequence as shown in SEQ ID NO: 167 or a sequence at least 90% identical thereto. In some embodiments, a CAR comprises the amino acid sequence as shown in SEQ ID NO: 169 or a sequence at least 90% identical thereto. In some embodiments, a CAR comprises the amino acid sequence as shown in SEQ ID NO: 171 or a sequence at least 90% identical thereto. In some embodiments, a CAR comprises the amino acid sequence as shown in SEQ ID NO: 173 or a sequence at least 90% identical thereto. In some embodiments, a CAR comprises the amino acid sequence as shown in SEQ ID NO: 175 or a sequence at least 90% identical thereto. In some embodiments, a CAR comprises the amino acid sequence as shown in SEQ ID NO: 177 or a sequence at least 90% identical thereto. In some embodiments, a CAR comprises the amino acid sequence as shown in SEQ ID NO: 179 or a sequence at least 90% identical thereto. In some embodiments, a CAR comprises the amino acid sequence as shown in SEQ ID NO: 181 or a sequence at least 90% identical thereto. In some embodiments, a CAR comprises the amino acid sequence as shown in SEQ ID NO: 183 or a sequence at least 90% identical thereto. In some embodiments, a CAR comprises the amino acid sequence as shown in SEQ ID NO: 185 or a sequence at least 90% identical thereto. In some embodiments, a CAR comprises the amino acid sequence as shown in SEQ ID NO: 187 or a sequence at least 90% identical thereto. In some embodiments, a CAR comprises the amino acid sequence as shown in SEQ ID NO: 189 or a sequence at least 90% identical thereto. In some embodiments, a CAR comprises the amino acid sequence as shown in SEQ ID NO: 191 or a sequence at least 90% identical thereto. In some embodiments, a CAR comprises the amino acid sequence as shown in SEQ ID NO: 19 or a sequence at least 90% identical thereto 3. In some embodiments, a CAR comprises the amino acid sequence as shown in SEQ ID NO: 195 or a sequence at least 90% identical thereto. In some embodiments, a CAR comprises the amino acid sequence as shown in SEQ ID NO: 197 or a sequence at least 90% identical thereto. In some embodiments, a CAR comprises the amino acid sequence as shown in SEQ ID NO: 199 or a sequence at least 90% identical thereto. In some embodiments, a CAR comprises the amino acid sequence as shown in SEQ ID NO: 201 or a sequence at least 90% identical thereto. In some embodiments, a CAR comprises the amino acid sequence as shown in SEQ ID NO: 203 or a sequence at least 90% identical thereto. In some embodiments, a CAR comprises the amino acid sequence as shown in SEQ ID NO: 205 or a sequence at least 90% identical thereto. In some embodiments, a CAR comprises the amino acid sequence as shown in SEQ ID NO: 212 or a sequence at least 90% identical thereto. In some embodiments, a CAR comprises the amino acid sequence as shown in SEQ ID NO: 214 or a sequence at least 90% identical thereto. In some embodiments, a CAR comprises the amino acid sequence as shown in SEQ ID NO: 216 or a sequence at least 90% identical thereto.

In some embodiments, a CAR comprises the nucleotide sequence as shown in SEQ ID NO: 154 or a sequence at least 90% identical thereto. In some embodiments, a CAR comprises the nucleotide sequence as shown in SEQ ID NO: 156 or a sequence at least 90% identical thereto. In some embodiments, a CAR comprises the nucleotide sequence as shown in SEQ ID NO: 158 or a sequence at least 90% identical thereto. In some embodiments, a CAR comprises the nucleotide sequence as shown in SEQ ID NO: 160 or a sequence at least 90% identical thereto. In some embodiments, a CAR comprises the nucleotide sequence as shown in SEQ ID NO: 162 or a sequence at least 90% identical thereto. In some embodiments, a CAR comprises the nucleotide sequence as shown in SEQ ID NO: 164 or a sequence at least 90% identical thereto. In some embodiments, a CAR comprises the nucleotide sequence as shown in SEQ ID NO: 166 or a sequence at least 90% identical thereto. In some embodiments, a CAR comprises the nucleotide sequence as shown in SEQ ID NO: 168 or a sequence at least 90% identical thereto. In some embodiments, a CAR comprises the nucleotide sequence as shown in SEQ ID NO: 170 or a sequence at least 90% identical thereto. In some embodiments, a CAR comprises the nucleotide sequence as shown in SEQ ID NO: 172 or a sequence at least 90% identical thereto. In some embodiments, a CAR comprises the nucleotide sequence as shown in SEQ ID NO: 174 or a sequence at least 90% identical thereto. In some embodiments, a CAR comprises the nucleotide sequence as shown in SEQ ID NO: 176 or a sequence at least 90% identical thereto. In some embodiments, a CAR comprises the nucleotide sequence as shown in SEQ ID NO: 178 or a sequence at least 90% identical thereto. In some embodiments, a CAR comprises the nucleotide sequence as shown in SEQ ID NO: 180 or a sequence at least 90% identical thereto. In some embodiments, a CAR comprises the nucleotide sequence as shown in SEQ ID NO: 182 or a sequence at least 90% identical thereto. In some embodiments, a CAR comprises the nucleotide sequence as shown in SEQ ID NO: 184 or a sequence at least 90% identical thereto. In some embodiments, a CAR comprises the nucleotide sequence as shown in SEQ ID NO: 186 or a sequence at least 90% identical thereto. In some embodiments, a CAR comprises the nucleotide sequence as shown in SEQ ID NO: 188 or a sequence at least 90% identical thereto. In some embodiments, a CAR comprises the nucleotide sequence as shown in SEQ ID NO: 190 or a sequence at least 90% identical thereto. In some embodiments, a CAR comprises the nucleotide sequence as shown in SEQ ID NO: 192 or a sequence at least 90% identical thereto. In some embodiments, a CAR comprises the nucleotide sequence as shown in SEQ ID NO: 194 or a sequence at least 90% identical thereto. In some embodiments, a CAR comprises the nucleotide sequence as shown in SEQ ID NO: 196 or a sequence at least 90% identical thereto. In some embodiments, a CAR comprises the nucleotide sequence as shown in SEQ ID NO: 198 or a sequence at least 90% identical thereto. In some embodiments, a CAR comprises the nucleotide sequence as shown in SEQ ID NO: 200 or a sequence at least 90% identical thereto. In some embodiments, a CAR comprises the nucleotide sequence as shown in SEQ ID NO: 202 or a sequence at least 90% identical thereto. In some embodiments, a CAR comprises the nucleotide sequence as shown in SEQ ID NO: 204 or a sequence at least 90% identical thereto. In some embodiments, a CAR comprises the nucleotide sequence as shown in SEQ ID NO: 213 or a sequence at least 90% identical thereto. In some embodiments, a CAR comprises the nucleotide sequence as shown in SEQ ID NO: 215 or a sequence at least 90% identical thereto. In some embodiments, a CAR comprises the nucleotide sequence as shown in SEQ ID NO: 217 or a sequence at least 90% identical thereto.

Natural Killer Cell Receptor (NKR) CARs

In some embodiments, a CAR of the present disclosure comprises one or more components of a natural killer cell receptor (NKR), thereby forming an NKR-CAR. The NKR component may be a transmembrane domain, a hinge domain, or a cytoplasmic domain from any suitable natural killer cell receptor, including without limitation, a killer cell immunoglobulin-like receptor (KIR), such as KIR2DL1, KIR2DL2/L3, KIR2DL4, KIR2DL5A, KIR2DL5B, KIR2DS1, KIR2DS2, KIR2DS3, KIR2DS4, DIR2DS5, KIR3DL1/S1, KIR3DL2, KIR3DL3, KIR2DP1, and KIRS DPI; a natural cytotoxicity receptor (NCR), such as NKp30, NKp44, NKp46; a signaling lymphocyte activation molecule (SLAM) family of immune cell receptor, such as CD48, CD229, 2B4, CD84, NTB-A, CRACC, BLAME, and CD2F-10; an Fc receptor (FcR), such as CD16, and CD64; and an Ly49 receptor, such as LY49A and LY49C. In some embodiments, the NKR-CAR may interact with an adaptor molecule or intracellular signaling domain, such as DAP12. Exemplary configurations and sequences of CARs comprising NKR components are described in International Patent Publication WO2014/145252, published Sep. 18, 2014.

Chimeric Inhibitory Receptors

Certain aspects of the present disclosure relate to chimeric inhibitory receptors. Chimeric inhibitory receptors are useful, for example, as NOT logic gates for controlling cell activity, such as immune cell activity. In some embodiments, chimeric inhibitory receptors of the present disclosure specifically bind to one or more antigens that are expressed on normal cells but not on tumor cells.

In some embodiments, the chimeric inhibitory receptor comprises an antigen-binding domain, a transmembrane domain of the present disclosure (e.g., any suitable transmembrane domain used in conjunction with a chimeric receptor of the present disclosure), and an intracellular domain. In some embodiments, the chimeric inhibitory receptor may inhibit one or more activities of a cell, such as an immunoresponsive cell.

In some embodiments, the chimeric inhibitory receptor may comprise an enzymatic inhibitory domain. When the chimeric inhibitory receptor is located proximal to a receptor, such as an immune receptor in a cell membrane, binding of a cognate antigen to the antigen-binding domain activates the enzymatic inhibitory domain to inhibit activation of the receptor. As used herein, the term "enzymatic inhibitory domain" refers to a protein domain that inhibits an intracellular signal transduction cascade, for example a native T cell activation cascade. The disclosed chimeric inhibitory receptors thus can be engineered to contain appropriate antigen-binding domains that will reduce, for example, immune responses in the presence of the cognate antigen. Uses of chimeric inhibitory receptors of the present disclosure include, but are not limited to, reducing immune responses, controlling T cell activation, and controlling CAR-T responses.

In some embodiments, the enzymatic inhibitory domain of a chimeric inhibitory receptor of the present disclosure comprises at least a portion of an extracellular domain, a transmembrane domain, and/or an intracellular domain. In some embodiments, the enzymatic inhibitory domain comprises at least a portion of an enzyme. In some embodiments, the enzyme is selected from CSK, SHP-1, PTEN, CD45, CD148, PTP-MEG1, PTP-PEST, c-CBL, CBL-b, PTPN22, LAR, PTPH1, SHIP-1, and RasGAP (see e.g., Stanford et al., Regulation of TCR signaling by tyrosine phosphatases: from immune homeostasis to autoimmunity, Immunology, 2012 September; 137(1): 1-19). In some embodiments, the portion of the enzyme comprises an enzyme domain(s), an enzyme fragment(s), or a mutant(s) thereof. In some embodiments, the portion of the enzyme is a catalytic domain of the enzyme. In some embodiments, the enzyme domain(s), enzyme fragment(s), or mutants(s) thereof are selected to maximize efficacy and minimize basal inhibition.

In some embodiments, the enzymatic inhibitory domain comprises one or more modifications that modulate basal inhibition. Examples of modifications include, but are not limited to, truncation mutation(s), amino acid substitution(s), introduction of locations for post-translational modification (examples of which are known to those having skill in the art), and addition of new functional groups. In some embodiments, the enzyme domain(s), enzyme fragment(s), or mutants(s) thereof are selected to maximize efficacy and minimize basal inhibition. In some embodiments, the one or more modifications reduce basal inhibition. In other embodiments, the one or more modifications increase basal inhibition.

In some embodiments, the enzymatic inhibitory domain inhibits, for example, immune receptor activation upon recruitment of a chimeric inhibitory receptor of the present disclosure proximal to an immune receptor. In some embodiments, the immune receptor is a naturally-occurring immune receptor. In some embodiments, the immune receptor is a naturally-occurring antigen receptor. In some embodiments, the immune receptor is selected from a T cell receptor, a pattern recognition receptor (PRR), a NOD-like receptor (NLR), a Toll-like receptor (TLR), a killer activated receptor (KAR), a killer inhibitor receptor (KIR), a complement receptor, an Fc receptor, a B cell receptor, and a cytokine receptor. In some embodiments, the immune receptor is a T cell receptor. In some embodiments, the immune receptor is a chimeric immune receptor. In some embodiments, the chimeric immune receptor is a chimeric TCR or a CAR.

In some embodiments, a chimeric inhibitory receptor of the present disclosure may also comprise one or more intracellular inhibitory co-signaling domains. In some embodiments, the intracellular inhibitory co-signaling domains comprise an inhibitory domain. In some embodiments, the one or more intracellular inhibitory co-signaling domains comprise one or more ITIM-containing protein, or fragment(s) thereof. ITIMs are conserved amino acid sequences found in cytoplasmic tails of many inhibitory immune receptors. In some embodiments, the one or more ITIM-containing proteins, or fragments thereof, are selected from PD-1, CTLA4, TIGIT, and LAIR1. In some embodiments, the one or more intracellular inhibitory co-signaling domains comprise one or more non-ITIM scaffold proteins, or a fragment(s) thereof. In some embodiments, the one or more non-ITIM scaffold proteins, or fragments thereof, are selected from GRB-2, Dok-1, Dok-2, SLAP, LAG3, HAVR, BTLA, GITR, and PD-L1. Further examples suitable intracellular inhibitory co-signaling domains include, without limitation, PD-L1, TIM3, VISTA, CD160, 2B4, CD80, CD86, B7-H3 (CD276), B7-H4 (VTCN1), HVEM (TNFRSF14 or CD270), KIR, A2aR, MHC class I, MHC class II, GALS, adenosine, and TGF beta.

In some embodiments, the inhibitory chimeric receptor binds an antigen that is expressed on a non-tumor cell. Exemplary antigens for use in a chimeric inhibitory receptor are described in Table 2.

TABLE 2

| Antigen | UniProt Accession No. | Name | Short Description |
|---|---|---|---|
| EMCN | Q9ULC0 | Endomucin | A sialoglycoprotein that interferes with assembly of focal adhesion complexes and inhibits interaction between cells and extracellular matrix. |
| JAM2 | P57087 | Junctional Adhesion Molecule 2 | Localized at tight junctions, acts as an adhesive ligand for interacting with variety of immune cell types |
| MS4A15 | Q8N5U1 | Membrane-spanning 4-domains subfamily A member 15 | A four-transmembrane spanning protein, member of the CD20-like family. |
| C4BPA | P04003 | Complement Component 4 Binding Protein Alpha | Subunit of the C4b-binding protein that controls activation of the complement cascade via the classical complement activation pathway. |
| TRPM1 | Q7Z4N2 | Transient Receptor Potential Cation Channel Subfamily M Member 1 | Calcium permeable cation channel expressed in melanocytes and may play role in melanin synthesis. Essential for the depolarizing photoresponse. |
| SCTR | P47872 | Secretin Receptor | Binds secretin, which is most potent regulator of pancreatic bicarbonate, electrolyte and volume secretion |
| SLC2A2 | P11168 | Solute Carrier Family 2, facilitated glucose transporter member 2 | Glycoprotein of liver, intestine, and kidney, that mediates facilitated bidirectional transfer of glucose across plasma membrane |
| KCNQ2 | O43526 | Potassium Voltage-Gated Channel Subfamily Q Member 2 | Associates with KCNQ3 and forms a potassium channel. Important in regulation of neuronal excitability. |
| PERP | Q96FX8 | P53 Apoptosis Effector Related To PMP22 | Component of intercellular desmosome junctions, plays role in stratified epithelial integrity |
| WLS | Q5T9L3 | Wntless Wnt Ligand Secretion Mediator | Regulates Wnt protein sorting and secretion, plays key role in regulation of expression, subcellular localization, binding and organelle-specific association of Wnt proteins. |
| FFAR2 | O15552 | Free Fatty Acid Receptor 2 | G protein-coupled receptor activated by short chain fatty acids. |
| PTPRB | P23467 | Protein Tyrosine Phosphatase Receptor Type B | Member of the protein tyrosine phosphatase (PTP) family. The extracellular region of this PTP is composed of multiple fibronectin type_III repeats. |
| NCKAP1 | Q9Y2A7 | NCK Associated Protein 1 | Part of the WAVE complex that regulates lamellipodia formation. The WAVE complex regulates actin filament reorganization via its interaction with the Arp2/3 complex. |
| MPZL2 | O60487 | Myelin Protein Zero Like 2, Epithelial V-like antigen | Epithelial V-like antigen (EVA) is expressed in thymus epithelium and strongly downregulated by thymocyte developmental progression. |
| PLSCR4 | Q9NRQ2 | Phospholipid Scramblase 4 | May mediate accelerated ATP-independent bidirectional transbilayer migration of phospholipids upon binding calcium ions that results in a loss of phospholipid asymmetry in the plasma membrane. |
| TMEM47 | Q9BQJ4 | Transmembrane Protein 47 | Encodes a member of the PMP22/EMP/claudin protein family. The encoded protein is localized to the ER and the plasma membrane. |
| ADGRL4 | Q9HBW9 | Adhesion G Protein-Coupled Receptor L4 | Endothelial orphan receptor that acts as a key regulator of angiogenesis. |
| MET | P08581 | MET Proto-Oncogene, Receptor Tyrosine Kinase | Mesenchymal Epithelial Transition MET is a prototypical receptor tyrosine kinase. Its ligand is Hepatocyte Growth Factor (HGF). |
| BACE2 | Q9Y5Z0 | Beta-Secretase 2 | An integral membrane glycoprotein that functions as an aspartic protease. The encoded protein cleaves amyloid precursor protein into amyloid beta peptide |
| ATP8B1 | O43520 | ATPase Phospholipid Transporting 8B1 | A member of the P-type cation transport ATPase family, which belongs to the subfamily of aminophospholipid-transporting ATPases. |

TABLE 2-continued

| Antigen | UniProt Accession No. | Name | Short Description |
|---|---|---|---|
| LIFR | P42702 | LIF Receptor Subunit Alpha | a protein that belongs to the type I cytokine receptor family. This protein combines with a high-affinity converter subunit, gp130, to form a receptor complex that mediates the action of the leukemia inhibitory factor |
| ART4 | Q93070 | ADP-Ribosyltransferase 4 | A member of the ADP-ribosyltransferase gene family |
| CALCRL | Q16602 | Calcitonin Receptor Like Receptor | Receptor for calcitonin-gene-related peptide (CGRP) together with RAMP1 and receptor for adrenomedullin together with RAMP3 |
| CNTNAP3 | Q9BZ76 | Contactin Associated Protein Family Member 3 | NCP proteins mediate neuron-glial interactions in vertebrates and glial-glial contact in invertebrates. |
| PCDH9 | Q9HC56 | Protocadherin 9 | Mediates cell adhesion in neural tissues in the presence of calcium. |
| IL18R1 | Q13478 | Interleukin 18 Receptor 1 | Type I transmembrane protein and interleukin 18 (IL-18) cytokine receptor |
| SLC8A3 | P57103 | Solute Carrier Family 8 Member A3 | Multi-pass (11) transmembrane sodium/calcium exchanger integral membrane protein |
| CDH26 | Q8IXH8 | Cadherin 26 | Type I transmembrane protein involved in cell interactions, migration, and differentiation |
| TMEM163 | Q8TC26 | Transmembrane Protein 163 | Multi-pass (6) transmembrane protein that binds divalent cations |
| ABCA13 | Q86UQ4 | ATP Binding Cassette Subfamily A Member 13 | Member of ATP-binding cassette (ABC) gene subfamily A (ABCA). |
| CACHD1 | Q5VU97 | Cache Domain Containing 1 | Type I transmembrane voltage-dependent calcium channel |
| CYYR1 | Q96J86 | Cysteine And Tyrosine Rich 1 | Type I transmembrane protein |
| ABCB1 | P08183 | ATP Binding Cassette Subfamily B Member 1 | Multi-pass (14) ATP-binding transmembrane protein |
| ADGRG6 | Q86SQ4 | Adhesion G Protein-Coupled Receptor G6 | G-protein coupled receptor which is activated by type IV collagen. Couples to G(i)-proteins as well as G(s)-proteins |
| ATP9A | O75110 | ATPase Phospholipid Transporting 9A | Gene Ontology (GO) annotations related to this gene include nucleotide binding and cation-transporting ATPase activity. |
| CALNI | Q9BXU9 | Calneuron 1 | A protein with high similarity to the calcium-binding proteins of the calmodulin family. |
| CDCP1 | Q9H5V8 | CUB Domain Containing Protein 1 | A transmembrane protein which contains three extracellular CUB domains and acts as a substrate for Src family kinases. |
| IL12RB2 | Q99665 | Interleukin 12 Receptor Subunit Beta 2 | A type I transmembrane protein identified as a subunit of the interleukin 12 receptor complex. |
| SLC16A14 | Q7RTX9 | Solute Carrier Family 16 Member 14 | Proton-linked monocarboxylate transporter. May catalyze the transport of monocarboxylates across the plasma membrane. |
| TMEM136 | Q6ZRR5 | Transmembrane Protein 136 | Gene Ontology (GO) annotations related to this gene include integral component of membrane |
| TMEM200A | Q86VY9 | Transmembrane Protein 200A | Gene Ontology (GO) annotations related to this gene include integral component of membrane |

In some embodiments, the chimeric inhibitory receptor binds an EMCN antigen. In some embodiments, the chimeric inhibitory receptor binds an JAM2 antigen. In some embodiments, the chimeric inhibitory receptor binds an MS4A15 antigen. In some embodiments, the chimeric inhibitory receptor binds an C4BPA antigen. In some embodiments, the chimeric inhibitory receptor binds an TRPM1 antigen. In some embodiments, the chimeric inhibitory receptor binds an SCTR antigen. In some embodiments, the chimeric inhibitory receptor binds an SLC2A2 antigen. In some embodiments, the chimeric inhibitory receptor binds an KCNQ2 antigen. In some embodiments, the chimeric inhibitory receptor binds a PERP antigen. In some embodiments, the chimeric inhibitory receptor binds an WLS antigen. In some embodiments, the chimeric inhibitory receptor binds an FFAR2 antigen.

In some embodiments, the chimeric inhibitory receptor is a multispecific receptor comprising two or more antigen-binding domains, such that the chimeric inhibitory receptor can bind two or more antigens. Alternatively, a cell can be edited to express two or more chimeric inhibitory receptors that bind to different antigens.

In some embodiments, the chimeric inhibitory receptor binds a PTPRB antigen. In some embodiments, the chimeric inhibitory receptor binds an NCKAP1 antigen. In some embodiments, the chimeric inhibitory receptor binds an MPZL2 antigen. In some embodiments, the chimeric inhibitory receptor binds a PLSCR4 antigen. In some embodiments, the chimeric inhibitory receptor binds a TMEM47 antigen. In some embodiments, the chimeric inhibitory receptor binds an ADGRL4 antigen. In some embodiments, the chimeric inhibitory receptor binds an MET antigen. In some embodiments, the chimeric inhibitory receptor binds a BACE2 antigen. In some embodiments, the chimeric inhibitory receptor binds an ATP8B1 antigen. In some embodiments, the chimeric inhibitory receptor binds an LIFR antigen. In some embodiments, the chimeric inhibitory receptor binds an ART4 antigen. In some embodiments, the chimeric inhibitory receptor binds a CALCRL antigen. In some embodiments, the chimeric inhibitory receptor binds a CNTNAP3 antigen In some embodiments, the chimeric inhibitory receptor binds a PCDH9 antigen. In some embodiments, the chimeric inhibitory receptor binds an IL18R1 antigen. In some embodiments, the chimeric inhibitory receptor binds an SLC8A3 antigen. In some embodiments, the chimeric inhibitory receptor binds a CDH26 antigen. In some embodiments, the chimeric inhibitory receptor binds a TMEM163 antigen. In some embodiments, the chimeric inhibitory receptor binds an ABCA13 antigen. In some embodiments, the chimeric inhibitory receptor binds a CACHD1 antigen. In some embodiments, the chimeric inhibitory receptor binds a CYYR1 antigen. In some embodiments, the chimeric inhibitory receptor binds an ABCB1 antigen. In some embodiments, the chimeric inhibitory receptor binds an ADGRG6 antigen. In some embodiments, the chimeric inhibitory receptor binds an ATP9A antigen. In some embodiments, the chimeric inhibitory receptor binds a CALN1 antigen. In some embodiments, the chimeric inhibitory receptor binds a CALN1 antigen. In some embodiments, the chimeric inhibitory receptor binds a CDCP1 antigen. In some embodiments, the chimeric inhibitory receptor binds an IL12RB2 antigen. In some embodiments, the chimeric inhibitory receptor binds a SLC16A14 antigen. In some embodiments, the chimeric inhibitory receptor binds a TMEM136 antigen. In some embodiments, the chimeric inhibitory receptor binds a TMEM200A antigen.

Immunoresponsive Cells

Certain aspects of the present disclosure relate to a cell, such as an immunoresponsive cell, that has been genetically engineered to comprise one or more chimeric receptors of the present disclosure or one or more nucleic acids encoding such chimeric receptors, and to methods of using such cells for treating myeloid malignancies (e.g., AML).

In some embodiments, the cell is a mammalian cell. In some embodiments, the mammalian cell is a primary cell. In some embodiments, the mammalian cell is a cell line. In some embodiments, the mammalian cell a bone marrow cell, a blood cell, a skin cell, bone cell, a muscle cell, a neuronal cell, a fat cell, a liver cell, or a heart cell. In some embodiments, the cell is a stem cell. Exemplary stem cells include, without limitation embryonic stem cells (ESCs), induced pluripotent stem cells (iPSCs), adult stem cells, and tissue-specific stem cells, such as hematopoietic stem cells (blood stem cells), mesenchymal stem cells (MSC), neural stem cells, epithelial stem cells, or skin stem cells. In some embodiments, the cell is a cell that is derived or differentiated from a stem cell of the present disclosure. In some embodiments, the cell is an immune cell. Immune cells of the present disclosure may be isolated or differentiated from a stem cell of the present disclosure (e.g., from an ESC or iPSC). Exemplary immune cells include, without limitation, T cells (e.g., helper T cells, cytotoxic T cells, memory T cells, regulatory T cells, natural killer T cells, alpha beta T cells, and gamma delta T cells), B cells, natural killer (NK) cells, dendritic cells, myeloid cells, macrophages, and monocytes. In some embodiments, the cell is a neuronal cell. Neuronal cells of the present disclosure may be isolated or differentiated from a stem cell of the present disclosure (e.g., from an ESC or iPSC). Exemplary neuronal cells include, without limitation, neural progenitor cells, neurons (e.g., sensory neurons, motor neurons, cholinergic neurons, GABAergic neurons, glutamatergic neurons, dopaminergic neurons, or serotonergic neurons), astrocytes, oligodendrocytes, and microglia.

In some embodiments, the cell is an immunoresponsive cell. Immunoresponsive cells of the present disclosure may be isolated or differentiated from a stem cell of the present disclosure (e.g., from an ESC or iPSC). Exemplary immunoresponsive cells of the present disclosure include, without limitation, cells of the lymphoid lineage. The lymphoid lineage, comprising B cells, T cells, and natural killer (NK) cells, provides for the production of antibodies, regulation of the cellular immune system, detection of foreign agents in the blood, detection of cells foreign to the host, and the like. Examples of immunoresponsive cells of the lymphoid lineage include, without limitation, T cells, Natural Killer (NK) cells, embryonic stem cells, pluripotent stem cells, and induced pluripotent stem cells (e.g., those from which lymphoid cells may be derived or differentiated). T cells can be lymphocytes that mature in the thymus and are chiefly responsible for cell-mediated immunity. T cells are involved in the adaptive immune system. In some embodiments, T cells of the present disclosure can be any type of T cells, including, without limitation, T helper cells, cytotoxic T cells, memory T cells (including central memory T cells, stem-cell-like memory T cells (or stem-like memory T cells), and two types of effector memory T cells: e.g., $T_{EM}$ cells and $T_{EMRA}$ cells, regulatory T cells (also known as suppressor T cells), natural killer T cells, mucosal associated invariant T cells, and γδ T cells. Cytotoxic T cells (CTL or killer T cells) are a subset of T lymphocytes capable of inducing the death of infected somatic or tumor cells. A patient's own T cells may be genetically modified to target specific antigens through the introduction of one or more chimeric receptors, such as a chimeric TCRs or CARs.

Natural killer (NK) cells can be lymphocytes that are part of cell-mediated immunity and act during the innate immune response. NK cells do not require prior activation in order to perform their cytotoxic effect on target cells.

In some embodiments, an immunoresponsive cell of the present disclosure is a T cell. T cells of the present disclosure may be autologous, allogeneic, or derived in vitro from engineered progenitor or stem cells.

In some embodiments, an immunoresponsive cell of the present disclosure is a universal T cell with deficient TCR-αβ. Methods of developing universal T cells are described in the art, for example, in Valton et al., Molecular Therapy (2015); 23 9, 1507-1518, and Torikai et al., Blood 2012 119:5697-5705.

In some embodiments, an immunoresponsive cell of the present disclosure is an isolated immunoresponsive cell comprising one or more chimeric receptors of the present disclosure. In some embodiments, the immunoresponsive cell comprises one or more, two or more, three or more, four or more, five or more, six or more, seven or more, eight or more, nine or more, or ten or more chimeric receptors of the present disclosure.

In some embodiments, an immunoresponsive cell is a T cell. In some embodiments, an immunoresponsive cell is a Natural Killer (NK) cell.

Cells Expressing Multiple Chimeric Receptors

In some embodiments, a cell of the present disclosure (e.g., an immunoresponsive cell) comprises two or more chimeric receptors of the present disclosure. In some embodiments, the cell comprises two or more chimeric receptors, wherein one of the two or more chimeric receptors is a chimeric inhibitory receptor. In some embodiments, the cell comprises three or more chimeric receptors, wherein at least one of the three or more chimeric receptors is a chimeric inhibitory receptor. In some embodiments, the cell comprises four or more chimeric receptors, wherein at least one of the four or more chimeric receptors is a chimeric inhibitory receptor. In some embodiments, the cell comprises five or more chimeric receptors, wherein at least one of the five or more chimeric receptors is a chimeric inhibitory receptor.

In some embodiments, each of the two or more chimeric receptors comprise a different antigen-binding domain, e.g., that binds to the same antigen or to a different antigen. In some embodiments each antigen bound by the two or more chimeric receptors are expressed on the same myeloid cell type (e.g., same AML cell type). In one embodiment, the cell comprises a first chimeric receptor that targets a first antigen and includes an intracellular signaling domain having a costimulatory signaling domain but not a primary signaling domain, and a second chimeric receptor that targets a second, different, antigen and includes an intracellular signaling domain having a primary signaling domain but not a costimulatory signaling domain. Without wishing to be bound by theory, it is believed that placement of a costimulatory signaling domain (e.g., 4-1BB, CD28, or OX-40) onto the first chimeric receptor, and placement of a primary signaling domain (e.g., CD3-zeta chain) on the second chimeric receptor may limit chimeric receptor activity to cells where both targets are expressed. Accordingly, in some embodiments, a cell of the present disclosure (e.g., an immunoresponsive cell) includes: (a) a first chimeric receptor comprising an antigen-binding domain that binds a first antigen, a transmembrane domain, and a costimulatory signaling domain; and (b) a second chimeric receptor comprising an antigen-binding domain that binds a second antigen, a transmembrane domain, and a primary signaling domain. In some embodiments, a cell of the present disclosure (e.g., an immunoresponsive cell) includes: (a) a first chimeric receptor comprising an antigen-binding domain that binds a first antigen, a transmembrane domain, and a primary signaling domain; and (b) a second chimeric receptor comprising an antigen-binding domain that binds a second antigen, a transmembrane domain, and a costimulatory signaling domain. In some embodiments, a cell of the present disclosure (e.g., an immunoresponsive cell) includes: (a) a first chimeric receptor comprising an antigen-binding domain that binds a first antigen, a transmembrane domain, a primary signaling domain and a costimulatory domain; and (b) a second chimeric receptor comprising an antigen-binding domain that binds a second antigen, a transmembrane domain, a primary signaling domain and a costimulatory domain. In embodiments where both the first chimeric receptor and the second chimeric receptor each comprise a costimulatory signaling domain, the costimulatory signaling domain of the first chimeric receptor and the costimulatory signaling domain of the second chimeric receptor may be derived from the same protein, such as from 4-1BB, CD28, or OX40. Alternatively, the costimulatory signaling domain of the first chimeric receptor may be derived from a different protein than that of the costimulatory signaling domain of the second chimeric receptor.

In embodiments where a cell of the present disclosure (e.g., an immunoresponsive cell) expresses two or more distinct chimeric receptors, the antigen-binding domain of each of the different chimeric receptors may be designed such that the antigen-binding domains do not interact with one another. For example, a cell of the present disclosure (e.g., an immunoresponsive cell) expressing a first chimeric receptor and a second chimeric receptor may comprise a first chimeric receptor that comprises an antigen-binding domain that does not form an association with the antigen-binding domain of the second chimeric receptor. For example, the antigen-binding domain of the first chimeric receptor may comprise an antibody fragment, such as an scFv, while the antigen-binding domain of the second chimeric receptor may comprise a VHH.

Without wishing to be bound by theory, it is believed that in cells having a plurality of chimeric membrane embedded receptors that each comprise an antigen-binding domain, interactions between the antigen-binding domains of each of the receptors can be undesirable, because such interactions may inhibit the ability of one or more of the antigen-binding domains to bind their cognate antigens. Accordingly, in embodiments where cells of the present disclosure (e.g., immunoresponsive cells) express two or more chimeric receptors, the chimeric receptors comprise antigen-binding domains that minimize such inhibitory interactions. In one embodiment, the antigen-binding domain of one chimeric receptor comprises an scFv and the antigen-binding domain of the second chimeric receptor comprises a single VH domain, e.g., a camelid, shark, or lamprey single VH domain, or a single VH domain derived from a human or mouse sequence.

In some embodiments, when present on the surface of a cell, binding of the antigen-binding domain of the first chimeric receptor to its cognate antigen is not substantially reduced by the presence of the second chimeric receptor. In some embodiments, binding of the antigen-binding domain of the first chimeric receptor to its cognate antigen in the presence of the second chimeric receptor is 85%, 90%, 95%, 96%, 97%, 98%, or 99% of binding of the antigen-binding domain of the first chimeric receptor to its cognate antigen in the absence of the second chimeric receptor. In some embodiments, when present on the surface of a cell, the antigen-binding domains of the first chimeric receptor and the second chimeric receptor associate with one another less than if both were scFv antigen-binding domains. In some embodiments, the antigen-binding domains of the first chimeric receptor and the second chimeric receptor associate with one another 85%, 90%, 95%, 96%, 97%, 98%, or 99% less than if both were scFv antigen-binding domains.

In embodiments where a cell of the present disclosure (e.g., an immunoresponsive cell) comprises two or more distinct chimeric receptors of the present disclosure that bind to different antigens, the two or more chimeric receptor provide the cell with logic gating, such as OR logic gating, AND logic gating, NOT logic gating, or any combination of such logic gating. Accordingly, in certain embodiments, a cell of the present disclosure (e.g., an immunoresponsive cell) comprises two or more chimeric receptors, and binding of the first chimeric receptor to the first antigen is capable of activating the cell. In some embodiments, a cell of the present disclosure (e.g., an immunoresponsive cell) comprises two or more chimeric receptors, and binding of the second chimeric receptor to the second antigen is capable of stimulating the cell. In some embodiments, a cell of the present disclosure (e.g., an immunoresponsive cell) comprises two or more chimeric receptors, and binding of the first chimeric receptor to the first antigen and binding of the second chimeric receptor to the second antigen are required for activating the cell. In some embodiments, a cell of the present disclosure (e.g., an immunoresponsive cell) comprises two or more chimeric receptors, and binding of the first chimeric receptor to the first antigen and binding of the second chimeric receptor to the second antigen are required for simulating the cell. In some embodiments, a cell of the present disclosure (e.g., an immunoresponsive cell) comprises two or more chimeric receptors, and the cell exhibits a greater degree of cytolytic activity against cells that are positive for both the first antigen and the second antigen as compared to the cytolytic activity against cells that are positive for only the first antigen or only the second antigen. In some embodiments, a cell of the present disclosure (e.g., an immunoresponsive cell) comprises two or more chimeric receptors, and binding of the first chimeric receptor to the first antigen or binding of the second chimeric receptor to the second antigen is capable of activating the immunoresponsive cell.

In some embodiments, a cell of the present disclosure (e.g., an immunoresponsive cell) comprises a split chimeric receptor system, such as a split CAR system. Exemplary split chimeric receptor systems are described in WO2014/055442 and WO2014/055657. In some embodiments, a split chimeric receptor system comprises a cell expressing a first chimeric receptor having a first antigen-binding domain and a costimulatory domain (e.g., 4-1BB), as well as a second chimeric receptor having a second antigen-binding domain and an intracellular signaling domain (e.g., CD3-zeta). In such embodiments, when the cell encounters the first antigen, the costimulatory domain is activated, and the cell proliferates. Additionally, when the cell encounters the second antigen, the intracellular signaling domain is activated and cell-killing activity is induced. Accordingly, in some embodiments, a cell of the present disclosure (e.g., an immunoresponsive cell) is only fully activated in the presence of both antigens.

In certain embodiments, a cell of the present disclosure (e.g., an immunoresponsive cell) exhibits a greater degree of cytolytic activity against cells that are positive for both the first antigen and the second antigen as compared to against cells that are singly positive for the first antigen. In certain embodiments, the first chimeric receptor binds to a first antigen with a low binding affinity or a low binding avidity. In certain embodiments, the first chimeric receptor binds to the first antigen at an epitope of low accessibility. In certain embodiments, first chimeric receptor binds to the first antigen with a binding affinity that is lower compared to the binding affinity with which the second chimeric receptor binds to the second antigen. In some embodiments, the first chimeric receptor binds to the first antigen with a binding affinity that is at least 5-fold lower compared to the binding affinity with which the second chimeric receptor binds to the second antigen. In some embodiments, the first chimeric receptor binds to the first antigen with a binding affinity that is at least 10-fold, 20-fold, 30-fold, 40-fold, 50-fold, 60-fold, 70-fold, 80-fold, 90-fold, 100-fold, 200-fold, 5000-fold, 1000-fold, 5000-fold, or 10000-fold lower compared to the binding affinity with which the second chimeric receptor binds to the second antigen.

In some embodiments, pairing choices should favor redundant expression of the two target antigens in the tumor in order to minimize the risk of antigen escape. Accordingly, in some embodiments, a cell of the present disclosure (e.g., an immunoresponsive cell) comprises (i) a first chimeric receptor that binds to a first antigen and (ii) a second chimeric receptor that binds to a second antigen, wherein the combination of both chimeric receptors binding to their targets antigens produces a therapeutic effect. In embodiments, binding to only one target antigen does not achieve a therapeutic effect.

In some embodiments, the chimeric receptor binds an FLT3 antigen. In some embodiments, the chimeric receptor binds an MS4A3 antigen. In some embodiments, the chimeric receptor binds a CD33 antigen. In some embodiments, the chimeric receptor binds a CLEC12A antigen. In some embodiments, the chimeric receptor binds a CD312/ADGRE2 antigen. In some embodiments, the chimeric receptor binds an SLC22A16 antigen. In some embodiments, the chimeric receptor binds a CD123/ILR3RA antigen. In some embodiments, the chimeric receptor binds an LAT2 antigen. In some embodiments, the chimeric receptor binds a PIEZO1/FAM38A antigen. In some embodiments, the chimeric receptor binds a CD38 antigen. In some embodiments, the chimeric receptor binds an EMB antigen. In some embodiments, the chimeric receptor binds a CD131/CSF2RB antigen. In some embodiments, the chimeric receptor binds a P2RY8 antigen. In some embodiments, the chimeric receptor binds a LILRA2/CD85H antigen. In some embodiments, the chimeric receptor binds an SLC17A9 antigen. In some embodiments, the chimeric receptor binds an MYADM antigen. In some embodiments, the chimeric receptor binds a CD300LF antigen. In some embodiments, the chimeric receptor binds a CD244/SLAMF4 antigen. In some embodiments, the chimeric receptor binds a PLAUR antigen. In some embodiments, the chimeric receptor binds a CD93 antigen. In some embodiments, the chimeric receptor binds an SPNS3 antigen. In some embodiments, the chimeric receptor binds a GAPT antigen. In some embodiments, the chimeric receptor binds a RASGRP4 antigen. In some embodiments, the chimeric receptor binds a CD117/c-Kit antigen. In some embodiments, the chimeric receptor binds a CD123/ILR3RA antigen.

In some embodiments, the chimeric receptor binds a VSTM1 antigen. In some embodiments, the chimeric receptor binds an MLC1 antigen. In some embodiments, the chimeric receptor binds a PRAM1 antigen. In some embodiments, the chimeric receptor binds an HCK antigen. In some embodiments, the chimeric receptor binds an ICAM3 antigen. In some embodiments, the chimeric receptor binds an LRRC37A2 antigen. In some embodiments, the chimeric receptor binds an ITGAM antigen. In some embodiments, the chimeric receptor binds an ITGB2 antigen. In some embodiments, the chimeric receptor binds an LILRA1 antigen. In some embodiments, the chimeric receptor binds a PRTN3 antigen. In some embodiments, the chimeric receptor binds a CARDS antigen. In some embodiments, the chimeric receptor binds a SIGLEC5 antigen. In some embodiments, the chimeric receptor binds a SELL antigen. In some embodiments, the chimeric receptor binds an MLKL antigen. In some embodiments, the chimeric receptor binds an INPP5D antigen. In some embodiments, the chimeric receptor binds an APBB1IP antigen. In some embodiments, the chimeric receptor binds an ITGA4 antigen. In some embodiments, the chimeric receptor binds a C3AR1 antigen. In some embodiments, the chimeric receptor binds an ITGA5 antigen. In some embodiments, the chimeric receptor binds a FMNL1 antigen. In some embodiments, the chimeric receptor binds an IL1RAP antigen. In some embodiments, the chimeric receptor binds a CCR1/CD191 antigen. In some embodiments, the chimeric receptor binds an LILRB2 antigen. In some embodiments, the chimeric receptor binds a CD70 antigen. In some embodiments, the chimeric receptor is a multispecific receptor comprising two or more antigen-binding domains, such that the chimeric receptor can bind two or more antigens.

In some embodiments, an immunoresponsive cell may comprise one or more more tumor-targeting chimeric receptors and one or more inhibitory chimeric receptors that targets an antigen that is not expressed on the tumor. Combinations of tumor-targeting chimeric receptors and inhibitory chimeric receptors in the same immunoresponsive cell may be used to reduce on-target off-tumor toxicity. For instance, if a healthy cell expresses both an antigen that is recognized by a tumor-targeting chimeric receptor and an antigen that is recognized by an inhibitory chimeric receptor, an immunoresponsive cell expressing the tumor antigen may bind to the healthy cell. In such a case, the inhibitory chimeric antigen will also bind its cognate ligand on the healthy cell and the inhibitory function of the inhibitory chimeric receptor will reduce, decrease, prevent, or inhibit the activation of the immunoresponsive cell via the tumor-targeting chimeric receptor.

In some embodiments, the inhibitory chimeric receptor binds an EMCN (Endomucin) antigen. In some embodiments, the inhibitory chimeric receptor binds a JAM2 antigen. In some embodiments, the inhibitory chimeric receptor binds an MS4A15 antigen. In some embodiments, the inhibitory chimeric receptor binds an SLC34A2 antigen. In some embodiments, the inhibitory chimeric receptor binds an SLC2A2 antigen. In some embodiments, the c inhibitory himeric receptor binds a TRPM1 antigen. In some embodiments, the inhibitory chimeric receptor binds an SCTR antigen. In some embodiments, the inhibitory chimeric receptor binds a KCNQ2 antigen. In some embodiments, the inhibitory chimeric receptor binds a PERP antigen. In some embodiments, the inhibitory chimeric receptor binds a WLS antigen. In some embodiments, the inhibitory chimeric receptor binds a FFAR2 antigen. In some embodiments, the inhibitory chimeric receptor binds a PTPRB antigen. In some embodiments, the inhibitory chimeric receptor binds an NCKAP1 antigen. In some embodiments, the inhibitory chimeric receptor binds an MPZL2 antigen. In some embodiments, the inhibitory chimeric receptor binds a PLSCR4 antigen. In some embodiments, the inhibitory chimeric receptor binds a TMEM47 antigen. In some embodiments, the inhibitory chimeric receptor binds an ADGRL4 antigen. In some embodiments, the inhibitory chimeric receptor binds a MET antigen. In some embodiments, the inhibitory chimeric receptor binds a BACE2 antigen. In some embodiments, the inhibitory chimeric receptor binds a ATP8B1 antigen. In some embodiments, the inhibitory chimeric receptor binds an LIFR antigen. In some embodiments, the inhibitory chimeric receptor binds an ART4 antigen. In some embodiments, the inhibitory chimeric receptor binds a CALCRL antigen. In some embodiments, the inhibitory chimeric receptor binds a CNTNAP3 antigen. In some embodiments, the inhibitory chimeric receptor binds a PCDH9 antigen. In some embodiments, the inhibitory chimeric receptor binds an IL18R1 antigen. In some embodiments, the inhibitory chimeric receptor binds an SLC8A3 antigen. In some embodiments, the inhibitory chimeric receptor binds a CDH26 antigen. In some embodiments, the inhibitory chimeric receptor binds an SLC8A3 antigen. In some embodiments, the inhibitory chimeric receptor binds a TMEM163 antigen. In some embodiments, the inhibitory chimeric receptor binds an ABCA13 antigen. In some embodiments, the inhibitory chimeric receptor binds a CACHD1 antigen. In some embodiments, the inhibitory chimeric receptor binds a CYYR1 antigen. In some embodiments, the inhibitory chimeric receptor binds an ABCB1 antigen. In some embodiments, the inhibitory chimeric receptor binds an ADGRG6 antigen. In some embodiments, the inhibitory chimeric receptor binds an ATP9A antigen. In some embodiments, the inhibitory chimeric receptor binds a CALN1 antigen. In some embodiments, the inhibitory chimeric receptor binds a CDCP1 antigen. In some embodiments, the inhibitory chimeric receptor binds a IL12RB2 antigen. In some embodiments, the inhibitory chimeric receptor binds a SLC16A14 antigen. In some embodiments, the inhibitory chimeric receptor binds a TMEM136 antigen. In some embodiments, the inhibitory chimeric receptor binds a TMEM200A antigen.

Alternatively, a cell express two or more chimeric receptors that bind to different antigens. Exemplary pairs of antigens are shown in Table 3.

TABLE 3

| Antigen 1 | Antigen 2 | Antigen 1 | Antigen 2 |
|---|---|---|---|
| ITGA4 | SLC17A9 | CD244 | EMB |
| ITGA4 | LRRC37A2 | CD244 | MLKL |
| ITGA4 | EMB | CD244 | ADGRE2 |
| ITGA4 | MLKL | PRTN3 | SIGLEC5 |
| ITGA4 | MYADM | EMB | MLKL |
| ITGA4 | ADGRE2 | EMB | MYADM |
| ITGA5 | ITGAM | EMB | FLT3 |
| ITGA5 | LRRC37A2 | EMB | ADGRE2 |
| ITGA5 | PRTN3 | EMB | LILRA2 |
| ITGA5 | MLC1 | CARD9 | MLC1 |
| ITGA5 | ITGB2 | CARD9 | LAT2 |
| ITGA5 | LAT2 | CARD9 | SIGLEC5 |
| ITGA5 | MS4A3 | CARD9 | CD300LF |
| ITGA5 | PIEZO1 | CARD9 | INPP5D |
| ITGAM | LRRC37A2 | CARD9 | MS4A3 |
| ITGAM | PRTN3 | CARD9 | HCK |
| ITGAM | MLC1 | CARD9 | ICAM3 |
| ITGAM | LAT2 | CARD9 | CD38 |
| ITGAM | MS4A3 | CARD9 | CD33 |
| ITGAM | PIEZO1 | CARD9 | PIEZO1 |
| CSF2RB | SLC17A9 | CARD9 | FMNL1 |
| CSF2RB | LRRC37A2 | CARD9 | CLEC12A |
| CSF2RB | EMB | CARD9 | CD93 |
| CSF2RB | MLKL | MLC1 | SIGLEC5 |
| CSF2RB | ADGRE2 | MLC1 | MS4A3 |
| SLC17A9 | CMTM7 | MLC1 | PIEZO1 |
| SLC17A9 | LRRC37A2 | ITGB2 | MS4A3 |
| SLC17A9 | CD244 | ITGB2 | PIEZO1 |
| SLC17A9 | EMB | LAT2 | SIGLEC5 |
| SLC17A9 | MLKL | LAT2 | MS4A3 |
| SLC17A9 | MYADM | LAT2 | PIEZO1 |
| SLC17A9 | FLT3 | CD300LF | MS4A3 |
| SLC17A9 | ADGRE2 | CD300LF | PIEZO1 |
| SLC17A9 | LILRA2 | MLKL | MYADM |
| SLC17A9 | LILRA1 | MLKL | FLT3 |
| CYBA | LRRC37A2 | MLKL | ADGRE2 |
| CYBA | PRTN3 | MLKL | LILRA2 |
| CYBA | MLC1 | MLKL | LILRA1 |
| CYBA | LAT2 | INPP5D | MS4A3 |
| CYBA | MS4A3 | INPP5D | PIEZO1 |
| CYBA | ICAM3 | MYADM | FLT3 |
| CYBA | PIEZO1 | MS4A3 | PIEZO1 |
| CMTM7 | LRRC37A2 | HCK | PIEZO1 |
| CMTM7 | EMB | APBB1IP | C3AR1 |
| CMTM7 | MLKL | ICAM3 | PIEZO1 |
| CMTM7 | MYADM | CD38 | PIEZO1 |
| CMTM7 | ADGRE2 | CD38 | CD93 |
| CMTM7 | LILRA2 | CD33 | PIEZO1 |
| CMTM7 | LILRA1 | FLT3 | ADGRE2 |
| LRRC37A2 | CD244 | ADGRE2 | LILRA2 |
| LRRC37A2 | PRTN3 | ADGRE2 | LILRA1 |
| LRRC37A2 | EMB | LRRC37A2 | HCK |
| LRRC37A2 | CARD9 | LRRC37A2 | APBB1IP |
| LRRC37A2 | MLC1 | LRRC37A2 | ICAM3 |
| LRRC37A2 | ITGB2 | LRRC37A2 | CD33 |
| LRRC37A2 | LAT2 | LRRC37A2 | PIEZO1 |
| LRRC37A2 | SIGLEC5 | LRRC37A2 | FLT3 |

TABLE 3-continued

| Antigen 1 | Antigen 2 | Antigen 1 | Antigen 2 |
|---|---|---|---|
| LRRC37A2 | CD300LF | LRRC37A2 | ADGRE2 |
| LRRC37A2 | MLKL | LRRC37A2 | FMNL1 |
| LRRC37A2 | INPP5D | LRRC37A2 | CLEC12A |
| LRRC37A2 | MYADM | LRRC37A2 | LILRA2 |
| LRRC37A2 | MS4A3 | LRRC37A2 | LILRA1 |

In some embodiments, the two or more antigens are ITGA4 and SLC17A9. In some embodiments, the two or more antigens are ITGA4 and LRRC37A2. In some embodiments, the two or more antigens are ITGA4 and EMB. In some embodiments, the two or more antigens are ITGA4 and MLKL. In some embodiments, the two or more antigens are ITGA4 and MYADM. In some embodiments, the two or more antigens are ITGA4 and ADGRE2.

In some embodiments, the two or more antigens are ITGA5 and ITGAM. In some embodiments, the two or more antigens are ITGA5 and LRRC37A2. In some embodiments, the two or more antigens are ITGA5 and PRTN3. In some embodiments, the two or more antigens are ITGA5 and MLC1. In some embodiments, the two or more antigens are ITGA5 and ITGB2. some embodiments, the two or more antigens are ITGA5 and LAT2. In some embodiments, the two or more antigens are ITGA5 and MS4A3. In some embodiments, the two or more antigens are ITGA5 and PIEZO1.

In some embodiments, the two or more antigens are ITGAM and PIEZO1. In some embodiments, the two or more antigens are ITGAM and LRRC37A2. In some embodiments, the two or more antigens are ITGAM and PRTN3. In some embodiments, the two or more antigens are ITGAM and MLC1. In some embodiments, the two or more antigens are ITGAM and LAT2. In some embodiments, the two or more antigens are ITGAM and MS4A3.

In some embodiments, the two or more antigens are CSF2RB and SLC17A9. In some embodiments, the two or more antigens are CSF2RB and LRRC37A2. In some embodiments, the two or more antigens are CSF2RB and EMB. In some embodiments, the two or more antigens are CSF2RB and MLKL. In some embodiments, the two or more antigens are CSF2RB and ADGRE2.

In some embodiments, the two or more antigens are SLC17A9 and CMTM7. In some embodiments, the two or more antigens are SLC17A9 and LRRC37A2. In some embodiments, the two or more antigens are SLC17A9 and CD244. In some embodiments, the two or more antigens are SLC17A9 and EMB. In some embodiments, the two or more antigens are SLC17A9 and MLKL. In some embodiments, the two or more antigens are SLC17A9 and MYADM. In some embodiments, the two or more antigens are SLC17A9 and FLT3. In some embodiments, the two or more antigens are SLC17A9 and ADGRE2. In some embodiments, the two or more antigens are SLC17A9 and LILRA2. In some embodiments, the two or more antigens are SLC17A9 and LILRA1.

In some embodiments, the two or more antigens are CYBA and LRRC37A2. In some embodiments, the two or more antigens are CYBA and PRTN3. In some embodiments, the two or more antigens are CYBA and MLC1. In some embodiments, the two or more antigens are CYBA and LAT2. In some embodiments, the two or more antigens are CYBA and MS4A3. In some embodiments, the two or more antigens are CYBA and ICAM3. In some embodiments, the two or more antigens are CYBA and PIEZO1.

In some embodiments, the two or more antigens are CMTM7 and LRRC37A2. In some embodiments, the two or more antigens are CMTM7 and EMB. In some embodiments, the two or more antigens are CMTM7 and MLKL. In some embodiments, the two or more antigens are CMTM7 and MYADM. In some embodiments, the two or more antigens are CMTM7 and ADGRE2. In some embodiments, the two or more antigens are CMTM7 and LILRA2. In some embodiments, the two or more antigens are CMTM7 and LILRA1.

In some embodiments, the two or more antigens are LRRC37A2 and CD244. In some embodiments, the two or more antigens are LRRC37A2 and PRTN3. In some embodiments, the two or more antigens are LRRC37A2 and EMB. In some embodiments, the two or more antigens are LRRC37A2 and CARDS. In some embodiments, the two or more antigens are LRRC37A2 and MLC1. In some embodiments, the two or more antigens are LRRC37A2 and ITGB2. In some embodiments, the two or more antigens are LRRC37A2 and LAT2. In some embodiments, the two or more antigens are LRRC37A2 and SIGLEC5. In some embodiments, the two or more antigens are LRRC37A2 and CD300LF. In some embodiments, the two or more antigens are LRRC37A2 and MLKL. In some embodiments, the two or more antigens are LRRC37A2 and INPP5D. In some embodiments, the two or more antigens are LRRC37A2 and MYADM. In some embodiments, the two or more antigens are LRRC37A2 and MS4A3. In some embodiments, the two or more antigens are LRRC37A2 and HCK. In some embodiments, the two or more antigens are LRRC37A2 and APBB1IP. In some embodiments, the two or more antigens are LRRC37A2 and ICAM3. In some embodiments, the two or more antigens are LRRC37A2 and CD33. In some embodiments, the two or more antigens are LRRC37A2 and PIEZO1. In some embodiments, the two or more antigens are LRRC37A2 and FLT3. In some embodiments, the two or more antigens are LRRC37A2 and ADGRE2. In some embodiments, the two or more antigens are LRRC37A2 and FMNL1. In some embodiments, the two or more antigens are LRRC37A2 and CLEC12A. In some embodiments, the two or more antigens are LRRC37A2 and LILRA2. In some embodiments, the two or more antigens are LRRC37A2 and LILRA1. In some embodiments, the two or more antigens are LRRC37A2 and CD93. In some embodiments, the two or more antigens are LRRC37A2 and C3AR1.

In some embodiments, the two or more antigens are CD244 and EMB. In some embodiments, the two or more antigens are CD244 and MLKL. In some embodiments, the two or more antigens are CD244 and ADGRE2.

In some embodiments, the two or more antigens are PRTN3 and SIGLEC5.

In some embodiments, the two or more antigens are EMB and MLKL. In some embodiments, the two or more antigens are EMB and MYADM. In some embodiments, the two or more antigens are EMB and FLT3. In some embodiments, the two or more antigens are EMB and ADGRE2. In some embodiments, the two or more antigens are EMB and LILRA2.

In some embodiments, the two or more antigens are CARD9 and MLC1. In some embodiments, the two or more antigens are CARD9 and LAT2. In some embodiments, the two or more antigens are CARD9 and SIGLEC5. In some embodiments, the two or more antigens are CARD9 and CD300LF. In some embodiments, the two or more antigens are CARD9 and INPP5D. In some embodiments, the two or more antigens are CARD9 and MS4A3. In some embodiments, the two or more antigens are CARD9 and HCK. In some embodiments, the two or more antigens are CARD9 and ICAM3. In some embodiments, the two or more antigens are CARD9 and CD38. In some embodiments, the two or more antigens are CARD9 and CD33. In some embodiments, the two or more antigens are CARD9 and PIEZO1. In some embodiments, the two or more antigens are CARD9 and FMNL1. In some embodiments, the two or more antigens are CARD9 and CLEC12A. In some embodiments, the two or more antigens are CARD9 and CD93.

In some embodiments, the two or more antigens are MLC1 and SIGLEC5. In some embodiments, the two or more antigens are MLC1 and MS4A3. In some embodiments, the two or more antigens are MLC1 and PIEZO1.

In some embodiments, the two or more antigens are ITGB2 and PIEZO1. In some embodiments, the two or more antigens are ITGB2 and MS4A3.

In some embodiments, the two or more antigens are LAT2 and MS4A3. In some embodiments, the two or more antigens are LAT2 and SIGLEC5. In some embodiments, the two or more antigens are LAT2 and PIEZO1.

In some embodiments, the two or more antigens are CD300LF and PIEZO1. In some embodiments, the two or more antigens are CD300LF and MS4A3.

In some embodiments, the two or more antigens are MLKL and MYADM. In some embodiments, the two or more antigens are MLKL and FLT3. In some embodiments, the two or more antigens are MLKL and ADGRE2. In some embodiments, the two or more antigens are MLKL and LILRA2. In some embodiments, the two or more antigens are MLKL and LILRA1.

In some embodiments, the two or more antigens are INPP5D and PIEZO1. In some embodiments, the two or more antigens are INPP5D and MS4A3.

In some embodiments, the two or more antigens are MYADM and FLT3.

In some embodiments, the two or more antigens are MS4A3 and PIEZO1. In some embodiments, the two or more antigens are HCK and PIEZO1. In some embodiments, the two or more antigens are ICAM3 and PIEZO1. In some embodiments, the two or more antigens are CD38 and PIEZO1. In some embodiments, the two or more antigens are CD93 and CD38. In some embodiments, the two or more antigens are CD33 and PIEZO1.

In some embodiments, the two or more antigens are APBB1IP and C3AR1.

In some embodiments, the two or more antigens are FLT3 and ADGRE2. In some embodiments, the two or more antigens are ADGRE2 and LILRA2. In some embodiments, the two or more antigens are ADGRE2 and LILRA1.

In some embodiments, the two or more antigens are PIEZO1 and P2RY8.

In some embodiments, the two or more antigens are FLT3 and CD33. In some embodiments, a cell expresses two or more chimeric receptors of the present disclosure, wherein one chimeric receptor binds FLT3 and the second chimeric receptor binds CD33. In some embodiments, a chimeric receptor is a multispecific receptor comprising two or more antigen-binding domains, such that one antigen-binding domain binds FLT3 and a second antigen-binding domain binds CD33. In some embodiments, the chimeric antigen receptor and/or antigen-binding domain that binds FLT3 comprises a heavy chain variable domain (VH) and a light chain variable domain (VL) selected from: (a) a VH comprising the amino acid sequence of SEQ ID NO: 1 or a sequence at least 90% identical thereto and a VL comprising the amino acid sequence of SEQ. ID NO: 2 or a sequence at least 90% identical thereto; (b) a VH comprising the amino acid sequence of SEQ ID NO: 3 or a sequence at least 90% identical thereto and a VL comprising the amino acid sequence of SEQ. ID NO: 4 or a sequence at least 90% identical thereto; (c) a VH comprising the amino acid sequence of SEQ ID NO: 5 or a sequence at least 90% identical thereto and a VL comprising the amino acid sequence of SEQ. ID NO: 6 or a sequence at least 90% identical thereto; (d) a VH comprising the amino acid sequence of SEQ ID NO: 7 or a sequence at least 90% identical thereto and a VL comprising the amino acid sequence of SEQ. ID NO: 8 or a sequence at least 90% identical thereto; (e) a VH comprising the amino acid sequence of SEQ ID NO: 9 or a sequence at least 90% identical thereto and a VL comprising the amino acid sequence of SEQ. ID NO: 10 or a sequence at least 90% identical thereto; (f) a VH comprising the amino acid sequence of SEQ ID NO: 11 or a sequence at least 90% identical thereto and a VL comprising the amino acid sequence of SEQ. ID NO: 12 or a sequence at least 90% identical thereto; (g) a VH comprising the amino acid sequence of SEQ ID NO: 13 or a sequence at least 90% identical thereto and a VL comprising the amino acid sequence of SEQ. ID NO: 14 or a sequence at least 90% identical thereto; and (h) a VH comprising the amino acid sequence of SEQ ID NO: 15 or a sequence at least 90% identical thereto and a VL comprising the amino acid sequence of SEQ. ID NO: 16 or a sequence at least 90% identical thereto. In some embodiments, the chimeric antigen receptor and/or or antigen-binding domain that binds CD33 comprises a heavy chain variable domain (VH) and a light chain variable domain (VL) selected from: (a) a VH comprising the amino acid sequence of SEQ ID NO: 17 or a sequence at least 90% identical thereto and a VL comprising the amino acid sequence of SEQ. ID NO: 18 or a sequence at least 90% identical thereto; and (b) a VH comprising the amino acid sequence of SEQ ID NO: 19 or a sequence at least 90% identical thereto and a VL comprising the amino acid sequence of SEQ. ID NO: 20 or a sequence at least 90% identical thereto.

In some embodiments, the two or more antigens are FLT3 and CLEC12A. In some embodiments, a cell expresses two or more chimeric receptors of the present disclosure, wherein one chimeric receptor binds FLT3 and the second chimeric receptor binds CLEC12A. In some embodiments, a chimeric receptor is a multispecific receptor comprising two or more antigen-binding domains, such that one antigen-binding domain binds FLT3 and a second antigen-binding domain binds CLEC12A. In some embodiments, a chimeric receptor is a multispecific receptor comprising two or more antigen-binding domains, such that one antigen-binding domain binds FLT3 and a second antigen-binding domain binds CD33. In some embodiments, the chimeric antigen receptor and/or or antigen-binding domain that binds FLT3 comprises a heavy chain variable domain (VH) and a light chain variable domain (VL) selected from: (a) a VH comprising the amino acid sequence of SEQ ID NO: 1 or a sequence at least 90% identical thereto and a VL comprising the amino acid sequence of SEQ. ID NO: 2 or a sequence at least 90% identical thereto; (b) a VH comprising the amino acid sequence of SEQ ID NO: 3 or a sequence at least 90% identical thereto and a VL comprising the amino acid sequence of SEQ. ID NO: 4 or a sequence at least 90% identical thereto; (c) a VH comprising the amino acid sequence of SEQ ID NO: 5 or a sequence at least 90% identical thereto and a VL comprising the amino acid sequence of SEQ. ID NO: 6 or a sequence at least 90% identical thereto; (d) a VH comprising the amino acid sequence of SEQ ID NO: 7 or a sequence at least 90% identical thereto and a VL comprising the amino acid sequence of SEQ. ID NO: 8 or a sequence at least 90% identical thereto; (e) a VH comprising the amino acid sequence of SEQ ID NO: 9 or a sequence at least 90% identical thereto and a VL comprising the amino acid sequence of SEQ. ID NO: 10 or a sequence at least 90% identical thereto; (f) a VH comprising the amino acid sequence of SEQ ID NO: 11 or a sequence at least 90% identical thereto and a VL comprising the amino acid sequence of SEQ. ID NO: 12 or a sequence at least 90% identical thereto; (g) a VH comprising the amino acid sequence of SEQ ID NO: 13 or a sequence at least 90% identical thereto and a VL comprising the amino acid sequence of SEQ. ID NO: 14 or a sequence at least 90% identical thereto; and (h) a VH comprising the amino acid sequence of SEQ ID NO: 15 or a sequence at least 90% identical thereto and a VL comprising the amino acid sequence of SEQ. ID NO: 16 or a sequence at least 90% identical thereto. In some embodiments, the chimeric antigen receptor and/or or antigen-binding domain that binds CLEC12A comprises a heavy chain variable domain (VH) and a light chain variable domain (VL) selected from: (a) a VH comprising the amino acid sequence of SEQ ID NO: 21 or a sequence at least 90% identical thereto and a VL comprising the amino acid sequence of SEQ. ID NO: 22 or a sequence at least 90% identical thereto; (b) a VH comprising the amino acid sequence of SEQ ID NO: 23 or a sequence at least 90% identical thereto and a VL comprising the amino acid sequence of SEQ. ID NO: 24 or a sequence at least 90% identical thereto; and (c) a VH comprising the amino acid sequence of SEQ ID NO: 25 or a sequence at least 90% identical thereto and a VL comprising the amino acid sequence of SEQ. ID NO: 26 or a sequence at least 90% identical thereto.

In some embodiments, the two or more antigens are CLEC12A and CD33. In some embodiments, a cell expresses two or more chimeric receptors of the present disclosure, wherein one chimeric receptor binds CLEC12A and the second chimeric receptor binds CD33. In some embodiments, a chimeric receptor is a multispecific receptor comprising two or more antigen-binding domains, such that one antigen-binding domain binds CLEC12A and a second antigen-binding domain binds CD33. In some embodiments, the chimeric antigen receptor and/or or antigen-binding domain that binds CLEC12A comprises a heavy chain variable domain (VH) and a light chain variable domain (VL) selected from: (a) a VH comprising the amino acid sequence of SEQ ID NO: 21 or a sequence at least 90% identical thereto and a VL comprising the amino acid sequence of SEQ. ID NO: 22 or a sequence at least 90% identical thereto; (b) a VH comprising the amino acid sequence of SEQ ID NO: 23 or a sequence at least 90% identical thereto and a VL comprising the amino acid sequence of SEQ. ID NO: 24 or a sequence at least 90% identical thereto; and (c) a VH comprising the amino acid sequence of SEQ ID NO: 25 or a sequence at least 90% identical thereto and a VL comprising the amino acid sequence of SEQ. ID NO: 26 or a sequence at least 90% identical thereto. In some embodiments, the chimeric antigen receptor and/or or antigen-binding domain that binds CD33 comprises a heavy chain variable domain (VH) and a light chain variable domain (VL) selected from: (a) a VH comprising the amino acid sequence of SEQ ID NO: 17 or a sequence at least 90% identical thereto and a VL comprising the amino acid sequence of SEQ. ID NO: 18 or a sequence at least 90% identical thereto; and (b) a VH comprising the amino acid sequence of SEQ ID NO: 19 or a sequence at least 90% identical thereto and a VL comprising the amino acid sequence of SEQ. ID NO: 20 or a sequence at least 90% identical thereto.

In some embodiments, the immunoresponsive cell comprises a bicistronic chimeric antigen receptor. In some embodiments, the bicistronic chimeric antigen receptor comprises an FLT3 CAR and a CD33 CAR. In some embodiments, the bicistronic chimeric antigen receptor comprises an FLT3 CAR and a CLEC12A CAR. In some embodiments, the bicistronic chimeric antigen receptor comprises an CLEC12A CAR and a CD33 CAR. In some embodiments, the bicistronic chimeric antigen receptor comprises any pair of antigens provided in Table 3.

Chimeric Inhibitory Receptors

In some embodiments, a cell of the present disclosure (e.g., an immunoresponsive cell) comprises one or more chimeric inhibitory receptors of the present disclosure. In some embodiments, each of the one or more chimeric inhibitory receptors comprises an antigen-binding domain that binds an antigen expressed on normal cells but not on tumor cells, such as AML cells. In some embodiments, the one or more chimeric inhibitory receptors bind antigens that are expressed on a non-tumor cell derived from a tissue selected from the group consisting of brain, neuronal tissue, endocrine, bone, bone marrow, immune system, endothelial tissue, muscle, lung, liver, gallbladder, pancreas, gastrointestinal tract, kidney, urinary bladder, male reproductive organs, female reproductive organs, adipose, soft tissue, and skin.

In some embodiments, a chimeric inhibitory receptor may be used, for example, with one or more chimeric receptors (e.g., chimeric TCRs or CARs) expressed on a cell of the present disclosure (e.g., an immunoresponsive cell) as NOT logic gates to control, modulate, or otherwise inhibit one or more activities of the one or more chimeric receptors. In some embodiments, a chimeric receptor of the present disclosure may inhibit one or more activities of a cell of the present disclosure (e.g., an immunoresponsive cell). In some embodiments, the chimeric inhibitory receptor is combined with one or more chimeric receptors of the present disclosure to combine OR logic gating with NOT logic gating and/or AND logic gating with NOT logic gating.

In some embodiments, the chimeric inhibitory receptor binds one or more antigens selected from EMCN, JAM2, MS4A15, C4BPA, TRPM1, SCTR, SLC2A2, KCNQ2, PERP, WLS, FFAR2, PTPRB, NCKAP1, MPZL2, PLSCR4, TMEM47, ADGRL4, MET, BACE2, ATP8B1, LIFR, ART4, CALCRL, CNTNAP3, PCDH9, IL18R1, SLC8A3, CDH26, TMEM163, ABCA13, CACHD1, CYYR1, ABCB1, ADGRG6, ATP9A, CALN1, CDCP1, IL12RB2, SLC16A14, TMEM136, and TMEM200A.

In some embodiments, the chimeric receptor binds an FLT3 antigen and the chimeric inhibitory receptor binds an EMCN, a JAM2, an MS4A15, a C4BPA, a TRPM1, an SCTR, an SLC2A2, a KCNQ2, a PERP, a WLS, a FFAR, a PTPRB, a NCKAP1, an MPZL2, a PLSCR4, a TMEM47, an ADGRL4, a MET, a BACE2, an ATP8B1, a LIFR, an ART4, a CALCRL, a CNTNAP3, a PCDH9, an IL18R1, an SLC8A3, a CDH26, a TMEM163, an ABCA13, a CACHD1, a CYYR1, an ABCB1, an ADGRG6, an ATP9A, a CALN1, a CDCP1, an IL12RB2, an SLC16A14, a TMEM136, or a TMEM200A antigen.

In some embodiments, the chimeric receptor binds an MS4A3antigen and the chimeric inhibitory receptor binds an EMCN, a JAM2, an MS4A15, a C4BPA, a TRPM1, an SCTR, an SLC2A2, a KCNQ2, a PERP, a WLS, a FFAR, a PTPRB, a NCKAP1, an MPZL2, a PLSCR4, a TMEM47, an ADGRL4, a MET, a BACE2, an ATP8B1, a LIFR, an ART4, a CALCRL, a CNTNAP3, a PCDH9, an IL18R1, an SLC8A3, a CDH26, a TMEM163, an ABCA13, a CACHD1, a CYYR1, an ABCB1, an ADGRG6, an ATP9A, a CALN1, a CDCP1, an IL12RB2, an SLC16A14, a TMEM136, or a TMEM200A antigen.

In some embodiments, the chimeric receptor binds a CD33 antigen and the chimeric inhibitory receptor binds an EMCN, a JAM2, an MS4A15, a C4BPA, a TRPM1, an SCTR, an SLC2A2, a KCNQ2, a PERP, a WLS, a FFAR, a PTPRB, a NCKAP1, an MPZL2, a PLSCR4, a TMEM47, an ADGRL4, a MET, a BACE2, an ATP8B1, a LIFR, an ART4, a CALCRL, a CNTNAP3, a PCDH9, an IL18R1, an SLC8A3, a CDH26, a TMEM163, an ABCA13, a CACHD1, a CYYR1, an ABCB1, an ADGRG6, an ATP9A, a CALN1, a CDCP1, an IL12RB2, an SLC16A14, a TMEM136, or a TMEM200A antigen.

In some embodiments, the chimeric receptor binds a CLEC12A antigen and the chimeric inhibitory receptor binds an EMCN, a JAM2, an MS4A15, a C4BPA, a TRPM1, an SCTR, an SLC2A2, a KCNQ2, a PERP, a WLS, a FFAR, a PTPRB, a NCKAP1, an MPZL2, a PLSCR4, a TMEM47, an ADGRL4, a MET, a BACE2, an ATP8B1, a LIFR, an ART4, a CALCRL, a CNTNAP3, a PCDH9, an IL18R1, an SLC8A3, a CDH26, a TMEM163, an ABCA13, a CACHD1, a CYYR1, an ABCB1, an ADGRG6, an ATP9A, a CALN1, a CDCP1, an IL12RB2, an SLC16A14, a TMEM136, or a TMEM200A antigen.

In some embodiments, the chimeric receptor binds an ADGRE2 antigen and the chimeric inhibitory receptor binds an EMCN, a JAM2, an MS4A15, a C4BPA, a TRPM1, an SCTR, an SLC2A2, a KCNQ2, a PERP, a WLS, a FFAR, a PTPRB, a NCKAP1, an MPZL2, a PLSCR4, a TMEM47, an ADGRL4, a MET, a BACE2, an ATP8B1, a LIFR, an ART4, a CALCRL, a CNTNAP3, a PCDH9, an IL18R1, an SLC8A3, a CDH26, a TMEM163, an ABCA13, a CACHD1, a CYYR1, an ABCB1, an ADGRG6, an ATP9A, a CALN1, a CDCP1, an IL12RB2, an SLC16A14, a TMEM136, or a TMEM200A antigen.

In some embodiments, the chimeric receptor binds a SLC22A16 antigen and the chimeric inhibitory receptor binds an EMCN, a JAM2, an MS4A15, a C4BPA, a TRPM1, an SCTR, an SLC2A2, a KCNQ2, a PERP, a WLS, a FFAR, a PTPRB, a NCKAP1, an MPZL2, a PLSCR4, a TMEM47, an ADGRL4, a MET, a BACE2, an ATP8B1, a LIFR, an ART4, a CALCRL, a CNTNAP3, a PCDH9, an IL18R1, an SLC8A3, a CDH26, a TMEM163, an ABCA13, a CACHD1, a CYYR1, an ABCB1, an ADGRG6, an ATP9A, a CALN1, a CDCP1, an IL12RB2, an SLC16A14, a TMEM136, or a TMEM200A antigen.

In some embodiments, the chimeric receptor binds a CD123/IL3RA antigen and the chimeric inhibitory receptor binds an EMCN, a JAM2, an MS4A15, a C4BPA, a TRPM1, an SCTR, an SLC2A2, a KCNQ2, a PERP, a WLS, a FFAR, a PTPRB, a NCKAP1, an MPZL2, a PLSCR4, a TMEM47, an ADGRL4, a MET, a BACE2, an ATP8B1, a LIFR, an ART4, a CALCRL, a CNTNAP3, a PCDH9, an IL18R1, an SLC8A3, a CDH26, a TMEM163, an ABCA13, a CACHD1, a CYYR1, an ABCB1, an ADGRG6, an ATP9A, a CALN1, a CDCP1, an IL12RB2, an SLC16A14, a TMEM136, or a TMEM200A antigen.

In some embodiments, the chimeric receptor binds an MLC1 antigen and the chimeric inhibitory receptor an EMCN, a JAM2, an MS4A15, a C4BPA, a TRPM1, an SCTR, an SLC2A2, a KCNQ2, a PERP, a WLS, a FFAR, a PTPRB, a NCKAP1, an MPZL2, a PLSCR4, a TMEM47, an ADGRL4, a MET, a BACE2, an ATP8B1, a LIFR, an ART4, a CALCRL, a CNTNAP3, a PCDH9, an IL18R1, an SLC8A3, a CDH26, a TMEM163, an ABCA13, a CACHD1, a CYYR1, an ABCB1, an ADGRG6, an ATP9A, a CALN1, a CDCP1, an IL12RB2, an SLC16A14, a TMEM136, or a TMEM200A antigen.

In some embodiments, the chimeric receptor binds an SPNS3 antigen and the chimeric inhibitory receptor binds an EMCN, a JAM2, an MS4A15, a C4BPA, a TRPM1, an SCTR, an SLC2A2, a KCNQ2, a PERP, a WLS, a FFAR, a PTPRB, a NCKAP1, an MPZL2, a PLSCR4, a TMEM47, an ADGRL4, a MET, a BACE2, an ATP8B1, a LIFR, an ART4, a CALCRL, a CNTNAP3, a PCDH9, an IL18R1, an SLC8A3, a CDH26, a TMEM163, an ABCA13, a CACHD1, a CYYR1, an ABCB1, an ADGRG6, an ATP9A, a CALN1, a CDCP1, an IL12RB2, an SLC16A14, a TMEM136, or a TMEM200A antigen.

In some embodiments, the chimeric receptor binds a GAPT antigen and the chimeric inhibitory receptor binds an EMCN, a JAM2, an MS4A15, a C4BPA, a TRPM1, an SCTR, an SLC2A2, a KCNQ2, a PERP, a WLS, a FFAR, a PTPRB, a NCKAP1, an MPZL2, a PLSCR4, a TMEM47, an ADGRL4, a MET, a BACE2, an ATP8B1, a LIFR, an ART4, a CALCRL, a CNTNAP3, a PCDH9, an IL18R1, an SLC8A3, a CDH26, a TMEM163, an ABCA13, a CACHD1, a CYYR1, an ABCB1, an ADGRG6, an ATP9A, a CALN1, a CDCP1, an IL12RB2, an SLC16A14, a TMEM136, or a TMEM200A antigen.

In some embodiments, the chimeric receptor binds a LAT2 antigen and the chimeric inhibitory receptor binds an EMCN, a JAM2, an MS4A15, a C4BPA, a TRPM1, an SCTR, an SLC2A2, a KCNQ2, a PERP, a WLS, a FFAR, a PTPRB, a NCKAP1, an MPZL2, a PLSCR4, a TMEM47, an ADGRL4, a MET, a BACE2, an ATP8B1, a LIFR, an ART4, a CALCRL, a CNTNAP3, a PCDH9, an IL18R1, an SLC8A3, a CDH26, a TMEM163, an ABCA13, a CACHD1, a CYYR1, an ABCB1, an ADGRG6, an ATP9A, a CALN1, a CDCP1, an IL12RB2, an SLC16A14, a TMEM136, or a TMEM200A antigen.

In some embodiments, the chimeric receptor binds a PIEZO1 antigen and the chimeric inhibitory receptor binds an EMCN, a JAM2, an MS4A15, a C4BPA, a TRPM1, an SCTR, an SLC2A2, a KCNQ2, a PERP, a WLS, a FFAR, a PTPRB, a NCKAP1, an MPZL2, a PLSCR4, a TMEM47, an ADGRL4, a MET, a BACE2, an ATP8B1, a LIFR, an ART4, a CALCRL, a CNTNAP3, a PCDH9, an IL18R1, an SLC8A3, a CDH26, a TMEM163, an ABCA13, a CACHD1, a CYYR1, an ABCB1, an ADGRG6, an ATP9A, a CALN1, a CDCP1, an IL12RB2, an SLC16A14, a TMEM136, or a TMEM200A antigen.

In some embodiments, the chimeric receptor binds a CD38 antigen and the chimeric inhibitory receptor binds an EMCN, a JAM2, an MS4A15, a C4BPA, a TRPM1, an SCTR, an SLC2A2, a KCNQ2, a PERP, a WLS, a FFAR, a PTPRB, a NCKAP1, an MPZL2, a PLSCR4, a TMEM47, an ADGRL4, a MET, a BACE2, an ATP8B1, a LIFR, an ART4, a CALCRL, a CNTNAP3, a PCDH9, an IL18R1, an SLC8A3, a CDH26, a TMEM163, an ABCA13, a CACHD1, a CYYR1, an ABCB1, an ADGRG6, an ATP9A, a CALN1, a CDCP1, an IL12RB2, an SLC16A14, a TMEM136, or a TMEM200A antigen.

In some embodiments, the chimeric receptor binds an EMB antigen and the chimeric inhibitory receptor binds an EMCN, a JAM2, an MS4A15, a C4BPA, a TRPM1, an SCTR, an SLC2A2, a KCNQ2, a PERP, a WLS, a FFAR, a PTPRB, a NCKAP1, an MPZL2, a PLSCR4, a TMEM47, an ADGRL4, a MET, a BACE2, an ATP8B1, a LIFR, an ART4, a CALCRL, a CNTNAP3, a PCDH9, an IL18R1, an SLC8A3, a CDH26, a TMEM163, an ABCA13, a CACHD1, a CYYR1, an ABCB1, an ADGRG6, an ATP9A, a CALN1, a CDCP1, an IL12RB2, an SLC16A14, a TMEM136, or a TMEM200A antigen.

In some embodiments, the chimeric receptor binds a CD131/CSF2RB antigen and the chimeric inhibitory receptor binds an EMCN, a JAM2, an MS4A15, a C4BPA, a TRPM1, an SCTR, an SLC2A2, a KCNQ2, a PERP, a WLS, a FFAR, a PTPRB, a NCKAP1, an MPZL2, a PLSCR4, a TMEM47, an ADGRL4, a MET, a BACE2, an ATP8B1, a LIFR, an ART4, a CALCRL, a CNTNAP3, a PCDH9, an IL18R1, an SLC8A3, a CDH26, a TMEM163, an ABCA13, a CACHD1, a CYYR1, an ABCB1, an ADGRG6, an ATP9A, a CALN1, a CDCP1, an IL12RB2, an SLC16A14, a TMEM136, or a TMEM200A antigen.

In some embodiments, the chimeric receptor binds a LILRA2/CD85H antigen and the chimeric inhibitory receptor binds an EMCN, a JAM2, an MS4A15, a C4BPA, a TRPM1, an SCTR, an SLC2A2, a KCNQ2, a PERP, a WLS, a FFAR, a PTPRB, a NCKAP1, an MPZL2, a PLSCR4, a TMEM47, an ADGRL4, a MET, a BACE2, an ATP8B1, a LIFR, an ART4, a CALCRL, a CNTNAP3, a PCDH9, an IL18R1, an SLC8A3, a CDH26, a TMEM163, an ABCA13, a CACHD1, a CYYR1, an ABCB1, an ADGRG6, an ATP9A, a CALN1, a CDCP1, an IL12RB2, an SLC16A14, a TMEM136, or a TMEM200A antigen.

In some embodiments, the chimeric receptor binds a SLC17A9 antigen and the chimeric inhibitory receptor binds an EMCN, a JAM2, an MS4A15, a C4BPA, a TRPM1, an SCTR, an SLC2A2, a KCNQ2, a PERP, a WLS, a FFAR, a PTPRB, a NCKAP1, an MPZL2, a PLSCR4, a TMEM47, an ADGRL4, a MET, a BACE2, an ATP8B1, a LIFR, an ART4, a CALCRL, a CNTNAP3, a PCDH9, an IL18R1, an SLC8A3, a CDH26, a TMEM163, an ABCA13, a CACHD1, a CYYR1, an ABCB1, an ADGRG6, an ATP9A, a CALN1, a CDCP1, an IL12RB2, an SLC16A14, a TMEM136, or a TMEM200A antigen.

In some embodiments, the chimeric receptor binds a MYADM antigen and the chimeric inhibitory receptor binds an EMCN, a JAM2, an MS4A15, a C4BPA, a TRPM1, an SCTR, an SLC2A2, a KCNQ2, a PERP, a WLS, a FFAR, a PTPRB, a NCKAP1, an MPZL2, a PLSCR4, a TMEM47, an ADGRL4, a MET, a BACE2, an ATP8B1, a LIFR, an ART4, a CALCRL, a CNTNAP3, a PCDH9, an IL18R1, an SLC8A3, a CDH26, a TMEM163, an ABCA13, a CACHD1, a CYYR1, an ABCB1, an ADGRG6, an ATP9A, a CALN1, a CDCP1, an IL12RB2, an SLC16A14, a TMEM136, or a TMEM200A antigen.

In some embodiments, the chimeric receptor binds a CD300LF antigen and the chimeric inhibitory receptor binds an EMCN, a JAM2, an MS4A15, a C4BPA, a TRPM1, an SCTR, an SLC2A2, a KCNQ2, a PERP, a WLS, a FFAR, a PTPRB, a NCKAP1, an MPZL2, a PLSCR4, a TMEM47, an ADGRL4, a MET, a BACE2, an ATP8B1, a LIFR, an ART4, a CALCRL, a CNTNAP3, a PCDH9, an IL18R1, an SLC8A3, a CDH26, a TMEM163, an ABCA13, a CACHD1, a CYYR1, an ABCB1, an ADGRG6, an ATP9A, a CALN1, a CDCP1, an IL12RB2, an SLC16A14, a TMEM136, or a TMEM200A antigen.

In some embodiments, the chimeric receptor binds a CD244 antigen and the chimeric inhibitory receptor binds an EMCN, a JAM2, an MS4A15, a C4BPA, a TRPM1, an SCTR, an SLC2A2, a KCNQ2, a PERP, a WLS, a FFAR, a PTPRB, a NCKAP1, an MPZL2, a PLSCR4, a TMEM47, an ADGRL4, a MET, a BACE2, an ATP8B1, a LIFR, an ART4, a CALCRL, a CNTNAP3, a PCDH9, an IL18R1, an SLC8A3, a CDH26, a TMEM163, an ABCA13, a CACHD1, a CYYR1, an ABCB1, an ADGRG6, an ATP9A, a CALN1, a CDCP1, an IL12RB2, an SLC16A14, a TMEM136, or a TMEM200A antigen.

In some embodiments, the chimeric receptor binds a CD93 antigen. In some embodiments, the chimeric receptor binds a CD117/CKIT antigen and the chimeric inhibitory receptor binds an EMCN, a JAM2, an MS4A15, a C4BPA, a TRPM1, an SCTR, an SLC2A2, a KCNQ2, a PERP, a WLS, a FFAR, a PTPRB, a NCKAP1, an MPZL2, a PLSCR4, a TMEM47, an ADGRL4, a MET, a BACE2, an ATP8B1, a LIFR, an ART4, a CALCRL, a CNTNAP3, a PCDH9, an IL18R1, an SLC8A3, a CDH26, a TMEM163, an ABCA13, a CACHD1, a CYYR1, an ABCB1, an ADGRG6, an ATP9A, a CALN1, a CDCP1, an IL12RB2, an SLC16A14, a TMEM136, or a TMEM200A antigen.

In some embodiments, the chimeric receptor binds a CD117/c-KIT antigen and the chimeric inhibitory receptor binds an EMCN, a JAM2, an MS4A15, a C4BPA, a TRPM1, an SCTR, an SLC2A2, a KCNQ2, a PERP, a WLS, a FFAR, a PTPRB, a NCKAP1, an MPZL2, a PLSCR4, a TMEM47, an ADGRL4, a MET, a BACE2, an ATP8B1, a LIFR, an ART4, a CALCRL, a CNTNAP3, a PCDH9, an IL18R1, an SLC8A3, a CDH26, a TMEM163, an ABCA13, a CACHD1, a CYYR1, an ABCB1, an ADGRG6, an ATP9A, a CALN1, a CDCP1, an IL12RB2, an SLC16A14, a TMEM136, or a TMEM200A antigen.

In some embodiments, the chimeric receptor binds a CMTM7 antigen and the chimeric inhibitory receptor binds an EMCN, a JAM2, an MS4A15, a C4BPA, a TRPM1, an SCTR, an SLC2A2, a KCNQ2, a PERP, a WLS, a FFAR, a PTPRB, a NCKAP1, an MPZL2, a PLSCR4, a TMEM47, an ADGRL4, a MET, a BACE2, an ATP8B1, a LIFR, an ART4, a CALCRL, a CNTNAP3, a PCDH9, an IL18R1, an SLC8A3, a CDH26, a TMEM163, an ABCA13, a CACHD1, a CYYR1, an ABCB1, an ADGRG6, an ATP9A, a CALN1, a CDCP1, an IL12RB2, an SLC16A14, a TMEM136, or a TMEM200A antigen.

In some embodiments, the chimeric receptor binds a CYBA antigen and the chimeric inhibitory receptor binds an EMCN, a JAM2, an MS4A15, a C4BPA, a TRPM1, an SCTR, an SLC2A2, a KCNQ2, a PERP, a WLS, a FFAR, a PTPRB, a NCKAP1, an MPZL2, a PLSCR4, a TMEM47, an ADGRL4, a MET, a BACE2, an ATP8B1, a LIFR, an ART4, a CALCRL, a CNTNAP3, a PCDH9, an IL18R1, an SLC8A3, a CDH26, a TMEM163, an ABCA13, a CACHD1, a CYYR1, an ABCB1, an ADGRG6, an ATP9A, a CALN1, a CDCP1, an IL12RB2, an SLC16A14, a TMEM136, or a TMEM200A antigen.

In some embodiments, the chimeric receptor binds an HCK antigen and the chimeric inhibitory receptor binds an EMCN, a JAM2, an MS4A15, a C4BPA, a TRPM1, an SCTR, an SLC2A2, a KCNQ2, a PERP, a WLS, a FFAR, a PTPRB, a NCKAP1, an MPZL2, a PLSCR4, a TMEM47, an ADGRL4, a MET, a BACE2, an ATP8B1, a LIFR, an ART4, a CALCRL, a CNTNAP3, a PCDH9, an IL18R1, an SLC8A3, a CDH26, a TMEM163, an ABCA13, a CACHD1, a CYYR1, an ABCB1, an ADGRG6, an ATP9A, a CALN1, a CDCP1, an IL12RB2, an SLC16A14, a TMEM136, or a TMEM200A antigen.

In some embodiments, the chimeric receptor binds an ICAM3 antigen and the chimeric inhibitory receptor binds an EMCN, a JAM2, an MS4A15, a C4BPA, a TRPM1, an SCTR, an SLC2A2, a KCNQ2, a PERP, a WLS, a FFAR, a PTPRB, a NCKAP1, an MPZL2, a PLSCR4, a TMEM47, an ADGRL4, a MET, a BACE2, an ATP8B1, a LIFR, an ART4, a CALCRL, a CNTNAP3, a PCDH9, an IL18R1, an SLC8A3, a CDH26, a TMEM163, an ABCA13, a CACHD1, a CYYR1, an ABCB1, an ADGRG6, an ATP9A, a CALN1, a CDCP1, an IL12RB2, an SLC16A14, a TMEM136, or a TMEM200A antigen.

In some embodiments, the chimeric receptor binds a LRRC37A3 antigen and the chimeric inhibitory receptor binds an EMCN, a JAM2, an MS4A15, a C4BPA, a TRPM1, an SCTR, an SLC2A2, a KCNQ2, a PERP, a WLS, a FFAR, a PTPRB, a NCKAP1, an MPZL2, a PLSCR4, a TMEM47, an ADGRL4, a MET, a BACE2, an ATP8B1, a LIFR, an ART4, a CALCRL, a CNTNAP3, a PCDH9, an IL18R1, an SLC8A3, a CDH26, a TMEM163, an ABCA13, a CACHD1, a CYYR1, an ABCB1, an ADGRG6, an ATP9A, a CALN1, a CDCP1, an IL12RB2, an SLC16A14, a TMEM136, or a TMEM200A antigen.

In some embodiments, the chimeric receptor binds an ITGAM antigen and the chimeric inhibitory receptor binds an EMCN, a JAM2, an MS4A15, a C4BPA, a TRPM1, an SCTR, an SLC2A2, a KCNQ2, a PERP, a WLS, a FFAR, a PTPRB, a NCKAP1, an MPZL2, a PLSCR4, a TMEM47, an ADGRL4, a MET, a BACE2, an ATP8B1, a LIFR, an ART4, a CALCRL, a CNTNAP3, a PCDH9, an IL18R1, an SLC8A3, a CDH26, a TMEM163, an ABCA13, a CACHD1, a CYYR1, an ABCB1, an ADGRG6, an ATP9A, a CALN1, a CDCP1, an IL12RB2, an SLC16A14, a TMEM136, or a TMEM200A antigen.

In some embodiments, the chimeric receptor binds an ITGB2 antigen and the chimeric inhibitory receptor binds an EMCN, a JAM2, an MS4A15, a C4BPA, a TRPM1, an SCTR, an SLC2A2, a KCNQ2, a PERP, a WLS, a FFAR, a PTPRB, a NCKAP1, an MPZL2, a PLSCR4, a TMEM47, an ADGRL4, a MET, a BACE2, an ATP8B1, a LIFR, an ART4, a CALCRL, a CNTNAP3, a PCDH9, an IL18R1, an SLC8A3, a CDH26, a TMEM163, an ABCA13, a CACHD1, a CYYR1, an ABCB1, an ADGRG6, an ATP9A, a CALN1, a CDCP1, an IL12RB2, an SLC16A14, a TMEM136, or a TMEM200A antigen.

In some embodiments, the chimeric receptor binds a LILRA1 antigen and the chimeric inhibitory receptor binds an EMCN, a JAM2, an MS4A15, a C4BPA, a TRPM1, an SCTR, an SLC2A2, a KCNQ2, a PERP, a WLS, a FFAR, a PTPRB, a NCKAP1, an MPZL2, a PLSCR4, a TMEM47, an ADGRL4, a MET, a BACE2, an ATP8B1, a LIFR, an ART4, a CALCRL, a CNTNAP3, a PCDH9, an IL18R1, an SLC8A3, a CDH26, a TMEM163, an ABCA13, a CACHD1, a CYYR1, an ABCB1, an ADGRG6, an ATP9A, a CALN1, a CDCP1, an IL12RB2, an SLC16A14, a TMEM136, or a TMEM200A antigen.

In some embodiments, the chimeric receptor binds a PRTN3 antigen and the chimeric inhibitory receptor binds an EMCN, a JAM2, an MS4A15, a C4BPA, a TRPM1, an SCTR, an SLC2A2, a KCNQ2, a PERP, a WLS, a FFAR, a PTPRB, a NCKAP1, an MPZL2, a PLSCR4, a TMEM47, an ADGRL4, a MET, a BACE2, an ATP8B1, a LIFR, an ART4, a CALCRL, a CNTNAP3, a PCDH9, an IL18R1, an SLC8A3, a CDH26, a TMEM163, an ABCA13, a CACHD1, a CYYR1, an ABCB1, an ADGRG6, an ATP9A, a CALN1, a CDCP1, an IL12RB2, an SLC16A14, a TMEM136, or a TMEM200A antigen.

In some embodiments, the chimeric receptor binds a CARDS antigen and the chimeric inhibitory receptor binds an EMCN, a JAM2, an MS4A15, a C4BPA, a TRPM1, an SCTR, an SLC2A2, a KCNQ2, a PERP, a WLS, a FFAR, a PTPRB, a NCKAP1, an MPZL2, a PLSCR4, a TMEM47, an ADGRL4, a MET, a BACE2, an ATP8B1, a LIFR, an ART4, a CALCRL, a CNTNAP3, a PCDH9, an IL18R1, an SLC8A3, a CDH26, a TMEM163, an ABCA13, a CACHD1, a CYYR1, an ABCB1, an ADGRG6, an ATP9A, a CALN1, a CDCP1, an IL12RB2, an SLC16A14, a TMEM136, or a TMEM200A antigen.

In some embodiments, the chimeric receptor binds a SIGLEC5 antigen and the chimeric inhibitory receptor binds an EMCN, a JAM2, an MS4A15, a C4BPA, a TRPM1, an SCTR, an SLC2A2, a KCNQ2, a PERP, a WLS, a FFAR, a PTPRB, a NCKAP1, an MPZL2, a PLSCR4, a TMEM47, an ADGRL4, a MET, a BACE2, an ATP8B1, a LIFR, an ART4, a CALCRL, a CNTNAP3, a PCDH9, an IL18R1, an SLC8A3, a CDH26, a TMEM163, an ABCA13, a CACHD1, a CYYR1, an ABCB1, an ADGRG6, an ATP9A, a CALN1, a CDCP1, an IL12RB2, an SLC16A14, a TMEM136, or a TMEM200A antigen.

In some embodiments, the chimeric receptor binds a SELL antigen and the chimeric inhibitory receptor binds an EMCN, a JAM2, an MS4A15, a C4BPA, a TRPM1, an SCTR, an SLC2A2, a KCNQ2, a PERP, a WLS, a FFAR, a PTPRB, a NCKAP1, an MPZL2, a PLSCR4, a TMEM47, an ADGRL4, a MET, a BACE2, an ATP8B1, a LIFR, an ART4, a CALCRL, a CNTNAP3, a PCDH9, an IL18R1, an SLC8A3, a CDH26, a TMEM163, an ABCA13, a CACHD1, a CYYR1, an ABCB1, an ADGRG6, an ATP9A, a CALN1, a CDCP1, an IL12RB2, an SLC16A14, a TMEM136, or a TMEM200A antigen.

In some embodiments, the chimeric receptor binds a MLKL antigen and the chimeric inhibitory receptor binds an EMCN, a JAM2, an MS4A15, a C4BPA, a TRPM1, an SCTR, an SLC2A2, a KCNQ2, a PERP, a WLS, a FFAR, a PTPRB, a NCKAP1, an MPZL2, a PLSCR4, a TMEM47, an ADGRL4, a MET, a BACE2, an ATP8B1, a LIFR, an ART4, a CALCRL, a CNTNAP3, a PCDH9, an IL18R1, an SLC8A3, a CDH26, a TMEM163, an ABCA13, a CACHD1, a CYYR1, an ABCB1, an ADGRG6, an ATP9A, a CALN1, a CDCP1, an IL12RB2, an SLC16A14, a TMEM136, or a TMEM200A antigen.

In some embodiments, the chimeric receptor binds an INPP5D antigen and the chimeric inhibitory receptor binds an EMCN, a JAM2, an MS4A15, a C4BPA, a TRPM1, an SCTR, an SLC2A2, a KCNQ2, a PERP, a WLS, a FFAR, a PTPRB, a NCKAP1, an MPZL2, a PLSCR4, a TMEM47, an ADGRL4, a MET, a BACE2, an ATP8B1, a LIFR, an ART4, a CALCRL, a CNTNAP3, a PCDH9, an IL18R1, an SLC8A3, a CDH26, a TMEM163, an ABCA13, a CACHD1, a CYYR1, an ABCB1, an ADGRG6, an ATP9A, a CALN1, a CDCP1, an IL12RB2, an SLC16A14, a TMEM136, or a TMEM200A antigen.

In some embodiments, the chimeric receptor binds an APBB1IP antigen and the chimeric inhibitory receptor binds an EMCN, a JAM2, an MS4A15, a C4BPA, a TRPM1, an SCTR, an SLC2A2, a KCNQ2, a PERP, a WLS, a FFAR, a PTPRB, a NCKAP1, an MPZL2, a PLSCR4, a TMEM47, an ADGRL4, a MET, a BACE2, an ATP8B1, a LIFR, an ART4, a CALCRL, a CNTNAP3, a PCDH9, an IL18R1, an SLC8A3, a CDH26, a TMEM163, an ABCA13, a CACHD1, a CYYR1, an ABCB1, an ADGRG6, an ATP9A, a CALN1, a CDCP1, an IL12RB2, an SLC16A14, a TMEM136, or a TMEM200A antigen.

In some embodiments, the chimeric receptor binds an ITGA4 antigen and the chimeric inhibitory receptor binds an EMCN, a JAM2, an MS4A15, a C4BPA, a TRPM1, an SCTR, an SLC2A2, a KCNQ2, a PERP, a WLS, a FFAR, a PTPRB, a NCKAP1, an MPZL2, a PLSCR4, a TMEM47, an ADGRL4, a MET, a BACE2, an ATP8B1, a LIFR, an ART4, a CALCRL, a CNTNAP3, a PCDH9, an IL18R1, an SLC8A3, a CDH26, a TMEM163, an ABCA13, a CACHD1, a CYYR1, an ABCB1, an ADGRG6, an ATP9A, a CALN1, a CDCP1, an IL12RB2, an SLC16A14, a TMEM136, or a TMEM200A antigen.

In some embodiments, the chimeric receptor binds a C3AR1 antigen and the chimeric inhibitory receptor binds an EMCN, a JAM2, an MS4A15, a C4BPA, a TRPM1, an SCTR, an SLC2A2, a KCNQ2, a PERP, a WLS, a FFAR, a PTPRB, a NCKAP1, an MPZL2, a PLSCR4, a TMEM47, an ADGRL4, a MET, a BACE2, an ATP8B1, a LIFR, an ART4, a CALCRL, a CNTNAP3, a PCDH9, an IL18R1, an SLC8A3, a CDH26, a TMEM163, an ABCA13, a CACHD1, a CYYR1, an ABCB1, an ADGRG6, an ATP9A, a CALN1, a CDCP1, an IL12RB2, an SLC16A14, a TMEM136, or a TMEM200A antigen.

In some embodiments, the chimeric receptor binds an ITGA5 antigen and the chimeric inhibitory receptor binds an EMCN, a JAM2, an MS4A15, a C4BPA, a TRPM1, an SCTR, an SLC2A2, a KCNQ2, a PERP, a WLS, a FFAR, a PTPRB, a NCKAP1, an MPZL2, a PLSCR4, a TMEM47, an ADGRL4, a MET, a BACE2, an ATP8B1, a LIFR, an ART4, a CALCRL, a CNTNAP3, a PCDH9, an IL18R1, an SLC8A3, a CDH26, a TMEM163, an ABCA13, a CACHD1, a CYYR1, an ABCB1, an ADGRG6, an ATP9A, a CALN1, a CDCP1, an IL12RB2, an SLC16A14, a TMEM136, or a TMEM200A antigen.

In some embodiments, the chimeric receptor binds an FMNL1 antigen and the chimeric inhibitory receptor binds an EMCN, a JAM2, an MS4A15, a C4BPA, a TRPM1, an SCTR, an SLC2A2, a KCNQ2, a PERP, a WLS, a FFAR, a PTPRB, a NCKAP1, an MPZL2, a PLSCR4, a TMEM47, an ADGRL4, a MET, a BACE2, an ATP8B1, a LIFR, an ART4, a CALCRL, a CNTNAP3, a PCDH9, an IL18R1, an SLC8A3, a CDH26, a TMEM163, an ABCA13, a CACHD1, a CYYR1, an ABCB1, an ADGRG6, an ATP9A, a CALN1, a CDCP1, an IL12RB2, an SLC16A14, a TMEM136, or a TMEM200A antigen.

In some embodiments, the chimeric receptor binds a VSTM1 antigen and the chimeric inhibitory receptor binds an EMCN, a JAM2, an MS4A15, a C4BPA, a TRPM1, an SCTR, an SLC2A2, a KCNQ2, a PERP, a WLS, a FFAR, a PTPRB, a NCKAP1, an MPZL2, a PLSCR4, a TMEM47, an ADGRL4, a MET, a BACE2, an ATP8B1, a LIFR, an ART4, a CALCRL, a CNTNAP3, a PCDH9, an IL18R1, an SLC8A3, a CDH26, a TMEM163, an ABCA13, a CACHD1, a CYYR1, an ABCB1, an ADGRG6, an ATP9A, a CALN1, a CDCP1, an IL12RB2, an SLC16A14, a TMEM136, or a TMEM200A antigen.

In some embodiments, the chimeric receptor binds a PRAM1 antigen and the chimeric inhibitory receptor binds an EMCN, a JAM2, an MS4A15, a C4BPA, a TRPM1, an SCTR, an SLC2A2, a KCNQ2, a PERP, a WLS, a FFAR, a PTPRB, a NCKAP1, an MPZL2, a PLSCR4, a TMEM47, an ADGRL4, a MET, a BACE2, an ATP8B1, a LIFR, an ART4, a CALCRL, a CNTNAP3, a PCDH9, an IL18R1, an SLC8A3, a CDH26, a TMEM163, an ABCA13, a CACHD1, a CYYR1, an ABCB1, an ADGRG6, an ATP9A, a CALN1, a CDCP1, an IL12RB2, an SLC16A14, a TMEM136, or a TMEM200A antigen.

In some embodiments, the chimeric receptor binds an IL1RAP antigen and the chimeric inhibitory receptor binds an EMCN, a JAM2, an MS4A15, a C4BPA, a TRPM1, an SCTR, an SLC2A2, a KCNQ2, a PERP, a WLS, a FFAR, a PTPRB, a NCKAP1, an MPZL2, a PLSCR4, a TMEM47, an ADGRL4, a MET, a BACE2, an ATP8B1, a LIFR, an ART4, a CALCRL, a CNTNAP3, a PCDH9, an IL18R1, an SLC8A3, a CDH26, a TMEM163, an ABCA13, a CACHD1, a CYYR1, an ABCB1, an ADGRG6, an ATP9A, a CALN1, a CDCP1, an IL12RB2, an SLC16A14, a TMEM136, or a TMEM200A antigen.

In some embodiments, the chimeric receptor binds a CCR1/CD191 antigen and the chimeric inhibitory receptor binds an EMCN, a JAM2, an MS4A15, a C4BPA, a TRPM1, an SCTR, an SLC2A2, a KCNQ2, a PERP, a WLS, a FFAR, a PTPRB, a NCKAP1, an MPZL2, a PLSCR4, a TMEM47, an ADGRL4, a MET, a BACE2, an ATP8B1, a LIFR, an ART4, a CALCRL, a CNTNAP3, a PCDH9, an IL18R1, an SLC8A3, a CDH26, a TMEM163, an ABCA13, a CACHD1, a CYYR1, an ABCB1, an ADGRG6, an ATP9A, a CALN1, a CDCP1, an IL12RB2, an SLC16A14, a TMEM136, or a TMEM200A antigen.

In some embodiments, the chimeric receptor binds a LILRB2 antigen and the chimeric inhibitory receptor binds an EMCN, a JAM2, an MS4A15, a C4BPA, a TRPM1, an SCTR, an SLC2A2, a KCNQ2, a PERP, a WLS, a FFAR, a PTPRB, a NCKAP1, an MPZL2, a PLSCR4, a TMEM47, an ADGRL4, a MET, a BACE2, an ATP8B1, a LIFR, an ART4, a CALCRL, a CNTNAP3, a PCDH9, an IL18R1, an SLC8A3, a CDH26, a TMEM163, an ABCA13, a CACHD1, a CYYR1, an ABCB1, an ADGRG6, an ATP9A, a CALN1, a CDCP1, an IL12RB2, an SLC16A14, a TMEM136, or a TMEM200A antigen.

In some embodiments, the chimeric receptor binds a CD70 antigen and the chimeric inhibitory receptor binds an EMCN, a JAM2, an MS4A15, a C4BPA, a TRPM1, an SCTR, an SLC2A2, a KCNQ2, a PERP, a WLS, a FFAR, a PTPRB, a NCKAP1, an MPZL2, a PLSCR4, a TMEM47, an ADGRL4, a MET, a BACE2, an ATP8B1, a LIFR, an ART4, a CALCRL, a CNTNAP3, a PCDH9, an IL18R1, an SLC8A3, a CDH26, a TMEM163, an ABCA13, a CACHD1, a CYYR1, an ABCB1, an ADGRG6, an ATP9A, a CALN1, a CDCP1, an IL12RB2, an SLC16A14, a TMEM136, or a TMEM200A antigen.

In some embodiments, the chimeric inhibitory receptor binds an EMCN antigen and the chimeric receptor binds an FLT3 antigen. In some embodiments, the chimeric inhibitory receptor binds an EMCN antigen and the chimeric receptor binds an MLC1 antigen.

In some embodiments, the chimeric inhibitory receptor binds a JAM2 antigen and the chimeric receptor binds an FLT3 antigen. In some embodiments, the chimeric inhibitory receptors binds a JAM2 antigen and the chimeric receptor binds an MLC1 antigen.

In some embodiments, the chimeric inhibitory receptor binds an MS4A15 antigen and the chimeric receptor binds a CLEC12A antigen.

In some embodiments, the chimeric inhibitory receptor binds an SLC34A2 antigen and the chimeric receptor binds a CLEC12A antigen.

In some embodiments, the chimeric inhibitory receptor binds a C4BPA antigen and the chimeric receptor binds a CD33 antigen.

In some embodiments, the chimeric inhibitory receptor binds a TRPM1 antigen and the chimeric receptor binds a CD33 antigen.

In some embodiments, the chimeric inhibitory receptor binds an SCTR antigen and the chimeric receptor binds an SLC22A16 antigen.

In some embodiments, the chimeric inhibitory receptor binds an SLC2A2 antigen and the chimeric receptor binds an IL1RAP antigen.

In some embodiments, the chimeric inhibitory receptor binds a KCNQ2 antigen and the chimeric receptor binds a PIEZO1 antigen. In some embodiments, the chimeric inhibitory receptor binds a KCNQ2 antigen and the chimeric receptor binds an IL1RAP antigen.

In some embodiments, the chimeric inhibitory receptor binds a PERP antigen and the chimeric receptor binds a CD123 antigen. In some embodiments, the chimeric inhibitory receptor binds a PERP antigen and the chimeric receptor binds an IL3RA antigen.

In some embodiments, the chimeric inhibitory receptor binds a WLS antigen. In some embodiments, the chimeric inhibitory receptor binds a FFAR2 antigen. In some embodiments, the chimeric inhibitory receptor binds an NCKAP1 antigen. In some embodiments, the chimeric inhibitory receptor binds an MPZL2 antigen. In some embodiments, the chimeric inhibitory receptor binds a PLSCR4 antigen. In some embodiments, the chimeric inhibitory receptor binds a TMEM47 antigen. In some embodiments, the chimeric inhibitory receptor binds an ADGRL4 antigen. In some embodiments, the chimeric inhibitory receptor binds an MET antigen. In some embodiments, the chimeric inhibitory receptor binds a BACE2 antigen. In some embodiments, the chimeric inhibitory receptor binds an ATP8B1 antigen. In some embodiments, the chimeric inhibitory receptor binds an LIFR antigen. In some embodiments, the chimeric inhibitory receptor binds an ART4 antigen. In some embodiments, the chimeric inhibitory receptor binds a CALCRL antigen. In some embodiments, the chimeric inhibitory receptor binds a CNTNAP3 antigen. In some embodiments, the chimeric inhibitory receptor binds a PCDH9 antigen. In some embodiments, the chimeric inhibitory receptor binds an IL18R1 antigen. In some embodiments, the chimeric inhibitory receptor binds an SLC8A3 antigen. In some embodiments, the chimeric inhibitory receptor binds a CDH26 antigen. In some embodiments, the chimeric inhibitory receptor binds a TMEM163 antigen. In some embodiments, the chimeric inhibitory receptor binds a ABCA13 antigen. In some embodiments, the chimeric inhibitory receptor binds a CACHD1 antigen. In some embodiments, the chimeric inhibitory receptor binds a CYYR1 antigen. In some embodiments, the chimeric inhibitory receptor binds an ADGRG6 antigen. In some embodiments, the chimeric inhibitory receptor binds an ATP9A antigen. In some embodiments, the chimeric inhibitory receptor binds a CALN1 antigen. In some embodiments, the chimeric inhibitory receptor binds a CDCP1 antigen. In some embodiments, the chimeric inhibitory receptor binds an IL12RB2 antigen. In some embodiments, the chimeric inhibitory receptor binds an SLC16A14 antigen. In some embodiments, the chimeric inhibitory receptor binds a TMEM136 antigen. In some embodiments, the chimeric inhibitory receptor binds a TMEM200A antigen.

In some embodiments, the chimeric inhibitory receptor binds an EMCN, a JAM2, a MS4A15, a C4BPA, a TRPM1, an SCTR, an SLC2A2, a KCNQ2, a PERP, a WLS, a FFAR2, a PTPRB, an NCKAP1, an MPZL2, a PLSCR4, a TMEM47, an ADGRL4, an MET, a BACE2, an ATP8B1, a LIFR, an ART4, a CALCRL, a CNTNAP3, a PCDH9, an IL18R1, a SLC8A3, a CDH26, a TMEM163, an ABCA13, a CACHD1, a CYYR1, an ABCB1, an ADGRG6, an ATP9A, a CALN1, a CDCP1, an IL12RB2, an SLC16A14, a TMEM136, or a TMEM200A antigen and the chimeric receptor binds a MS4A3, VSTM1, LAT2, MLC1, CD131, GAPT, PRAM1, SLC22A16, SLC17A9, SPNS3, FLT3, CD33, CLEC12A, ADGRE2, IL3RA, CD117, CD93, IL1RAP, CD244, CCR1, LILRB2, PIEZO1, CD38, EMB, MYADM, LILRA2, CD300LF, or CD70 antigen.

In some embodiments, the chimeric inhibitory receptor binds an EMCN antigen and the chimeric receptor binds a MS4A3, VSTM1, LAT2, MLC1, CD131, GAPT, PRAM1, SLC22A16, SLC17A9, SPNS3, FLT3, CD33, CLEC12A, ADGRE2, IL3RA, CD117, CD93, IL1RAP, CD244, CCR1, LILRB2, PIEZO1, CD38, EMB, MYADM, LILRA2, CD300LF, or CD70 antigen.

In some embodiments, the chimeric inhibitory receptor binds a JAM2 antigen and the chimeric receptor binds a MS4A3, VSTM1, LAT2, MLC1, CD131, GAPT, PRAM1, SLC22A16, SLC17A9, SPNS3, FLT3, CD33, CLEC12A, ADGRE2, IL3RA, CD117, CD93, IL1RAP, CD244, CCR1, LILRB2, PIEZO1, CD38, EMB, MYADM, LILRA2, CD300LF, or CD70 antigen.

In some embodiments, the chimeric inhibitory receptor binds an MS4A15 antigen and the chimeric receptor binds a MS4A3, VSTM1, LAT2, MLC1, CD131, GAPT, PRAM1, SLC22A16, SLC17A9, SPNS3, FLT3, CD33, CLEC12A, ADGRE2, IL3RA, CD117, CD93, IL1RAP, CD244, CCR1, LILRB2, PIEZO1, CD38, EMB, MYADM, LILRA2, CD300LF, or CD70 antigen.

In some embodiments, the chimeric inhibitory receptor binds a C4BPA antigen and the chimeric receptor binds a MS4A3, VSTM1, LAT2, MLC1, CD131, GAPT, PRAM1, SLC22A16, SLC17A9, SPNS3, FLT3, CD33, CLEC12A, ADGRE2, IL3RA, CD117, CD93, IL1RAP, CD244, CCR1, LILRB2, PIEZO1, CD38, EMB, MYADM, LILRA2, CD300LF, or CD70 antigen.

In some embodiments, the chimeric inhibitory receptor binds an TRPM1 antigen and the chimeric receptor binds a MS4A3, VSTM1, LAT2, MLC1, CD131, GAPT, PRAM1, SLC22A16, SLC17A9, SPNS3, FLT3, CD33, CLEC12A, ADGRE2, IL3RA, CD117, CD93, IL1RAP, CD244, CCR1, LILRB2, PIEZO1, CD38, EMB, MYADM, LILRA2, CD300LF, or CD70 antigen.

In some embodiments, the chimeric inhibitory receptor binds an SCTR antigen and the chimeric receptor binds a MS4A3, VSTM1, LAT2, MLC1, CD131, GAPT, PRAM1, SLC22A16, SLC17A9, SPNS3, FLT3, CD33, CLEC12A, ADGRE2, IL3RA, CD117, CD93, IL1RAP, CD244, CCR1, LILRB2, PIEZO1, CD38, EMB, MYADM, LILRA2, CD300LF, or CD70 antigen.

In some embodiments, the chimeric inhibitory receptor binds an SLC2A2 antigen and the chimeric receptor binds a MS4A3, VSTM1, LAT2, MLC1, CD131, GAPT, PRAM1, SLC22A16, SLC17A9, SPNS3, FLT3, CD33, CLEC12A, ADGRE2, IL3RA, CD117, CD93, IL1RAP, CD244, CCR1, LILRB2, PIEZO1, CD38, EMB, MYADM, LILRA2, CD300LF, or CD70 antigen.

In some embodiments, the chimeric inhibitory receptor binds a KCNQ2 antigen and the chimeric receptor binds a MS4A3, VSTM1, LAT2, MLC1, CD131, GAPT, PRAM1, SLC22A16, SLC17A9, SPNS3, FLT3, CD33, CLEC12A, ADGRE2, IL3RA, CD117, CD93, IL1RAP, CD244, CCR1, LILRB2, PIEZO1, CD38, EMB, MYADM, LILRA2, CD300LF, or CD70 antigen.

In some embodiments, the chimeric inhibitory receptor binds a PERP antigen and the chimeric receptor binds a MS4A3, VSTM1, LAT2, MLC1, CD131, GAPT, PRAM1, SLC22A16, SLC17A9, SPNS3, FLT3, CD33, CLEC12A, ADGRE2, IL3RA, CD117, CD93, IL1RAP, CD244, CCR1, LILRB2, PIEZO1, CD38, EMB, MYADM, LILRA2, CD300LF, or CD70 antigen.

In some embodiments, the chimeric inhibitory receptor binds a WLS antigen and the chimeric receptor binds a MS4A3, VSTM1, LAT2, MLC1, CD131, GAPT, PRAM1, SLC22A16, SLC17A9, SPNS3, FLT3, CD33, CLEC12A, ADGRE2, IL3RA, CD117, CD93, IL1RAP, CD244, CCR1, LILRB2, PIEZO1, CD38, EMB, MYADM, LILRA2, CD300LF, or CD70 antigen.

In some embodiments, the chimeric inhibitory receptor binds a FFAR2 antigen and the chimeric receptor binds a MS4A3, VSTM1, LAT2, MLC1, CD131, GAPT, PRAM1, SLC22A16, SLC17A9, SPNS3, FLT3, CD33, CLEC12A, ADGRE2, IL3RA, CD117, CD93, IL1RAP, CD244, CCR1, LILRB2, PIEZO1, CD38, EMB, MYADM, LILRA2, CD300LF, or CD70 antigen.

In some embodiments, the chimeric inhibitory receptor binds a PTPRB antigen and the chimeric receptor binds a MS4A3, VSTM1, LAT2, MLC1, CD131, GAPT, PRAM1, SLC22A16, SLC17A9, SPNS3, FLT3, CD33, CLEC12A, ADGRE2, IL3RA, CD117, CD93, IL1RAP, CD244, CCR1, LILRB2, PIEZO1, CD38, EMB, MYADM, LILRA2, CD300LF, or CD70 antigen.

In some embodiments, the chimeric inhibitory receptor binds an NCKAP1 antigen and the chimeric receptor binds a MS4A3, VSTM1, LAT2, MLC1, CD131, GAPT, PRAM1, SLC22A16, SLC17A9, SPNS3, FLT3, CD33, CLEC12A, ADGRE2, IL3RA, CD117, CD93, IL1RAP, CD244, CCR1, LILRB2, PIEZO1, CD38, EMB, MYADM, LILRA2, CD300LF, or CD70 antigen.

In some embodiments, the chimeric inhibitory receptor binds an MPZL2 antigen and the chimeric receptor binds a MS4A3, VSTM1, LAT2, MLC1, CD131, GAPT, PRAM1, SLC22A16, SLC17A9, SPNS3, FLT3, CD33, CLEC12A, ADGRE2, IL3RA, CD117, CD93, IL1RAP, CD244, CCR1, LILRB2, PIEZO1, CD38, EMB, MYADM, LILRA2, CD300LF, or CD70 antigen.

In some embodiments, the chimeric inhibitory receptor binds a PLSCR4 antigen and the chimeric receptor binds a MS4A3, VSTM1, LAT2, MLC1, CD131, GAPT, PRAM1, SLC22A16, SLC17A9, SPNS3, FLT3, CD33, CLEC12A, ADGRE2, IL3RA, CD117, CD93, IL1RAP, CD244, CCR1, LILRB2, PIEZO1, CD38, EMB, MYADM, LILRA2, CD300LF, or CD70 antigen.

In some embodiments, the chimeric inhibitory receptor binds a TMEM47 antigen and the chimeric receptor binds a MS4A3, VSTM1, LAT2, MLC1, CD131, GAPT, PRAM1, SLC22A16, SLC17A9, SPNS3, FLT3, CD33, CLEC12A, ADGRE2, IL3RA, CD117, CD93, IL1RAP, CD244, CCR1, LILRB2, PIEZO1, CD38, EMB, MYADM, LILRA2, CD300LF, or CD70 antigen.

In some embodiments, the chimeric inhibitory receptor binds an ADGRL4 antigen and the chimeric receptor binds a MS4A3, VSTM1, LAT2, MLC1, CD131, GAPT, PRAM1, SLC22A16, SLC17A9, SPNS3, FLT3, CD33, CLEC12A, ADGRE2, IL3RA, CD117, CD93, IL1RAP, CD244, CCR1, LILRB2, PIEZO1, CD38, EMB, MYADM, LILRA2, CD300LF, or CD70 antigen.

In some embodiments, the chimeric inhibitory receptor binds an MET antigen and the chimeric receptor binds a MS4A3, VSTM1, LAT2, MLC1, CD131, GAPT, PRAM1, SLC22A16, SLC17A9, SPNS3, FLT3, CD33, CLEC12A, ADGRE2, IL3RA, CD117, CD93, IL1RAP, CD244, CCR1, LILRB2, PIEZO1, CD38, EMB, MYADM, LILRA2, CD300LF, or CD70 antigen.

In some embodiments, the chimeric inhibitory receptor binds a BACE2 antigen and the chimeric receptor binds a MS4A3, VSTM1, LAT2, MLC1, CD131, GAPT, PRAM1, SLC22A16, SLC17A9, SPNS3, FLT3, CD33, CLEC12A, ADGRE2, IL3RA, CD117, CD93, IL1RAP, CD244, CCR1, LILRB2, PIEZO1, CD38, EMB, MYADM, LILRA2, CD300LF, or CD70 antigen.

In some embodiments, the chimeric inhibitory receptor binds a ATP8B1 antigen and the chimeric receptor binds a MS4A3, VSTM1, LAT2, MLC1, CD131, GAPT, PRAM1, SLC22A16, SLC17A9, SPNS3, FLT3, CD33, CLEC12A, ADGRE2, IL3RA, CD117, CD93, IL1RAP, CD244, CCR1, LILRB2, PIEZO1, CD38, EMB, MYADM, LILRA2, CD300LF, or CD70 antigen.

In some embodiments, the chimeric inhibitory receptor binds a LIFR antigen and the chimeric receptor binds a MS4A3, VSTM1, LAT2, MLC1, CD131, GAPT, PRAM1, SLC22A16, SLC17A9, SPNS3, FLT3, CD33, CLEC12A, ADGRE2, IL3RA, CD117, CD93, IL1RAP, CD244, CCR1, LILRB2, PIEZO1, CD38, EMB, MYADM, LILRA2, CD300LF, or CD70 antigen.

In some embodiments, the chimeric inhibitory receptor binds an ART4 antigen and the chimeric receptor binds a MS4A3, VSTM1, LAT2, MLC1, CD131, GAPT, PRAM1, SLC22A16, SLC17A9, SPNS3, FLT3, CD33, CLEC12A, ADGRE2, IL3RA, CD117, CD93, IL1RAP, CD244, CCR1, LILRB2, PIEZO1, CD38, EMB, MYADM, LILRA2, CD300LF, or CD70 antigen.

In some embodiments, the chimeric inhibitory receptor binds a CALCRL antigen and the chimeric receptor binds a MS4A3, VSTM1, LAT2, MLC1, CD131, GAPT, PRAM1, SLC22A16, SLC17A9, SPNS3, FLT3, CD33, CLEC12A, ADGRE2, IL3RA, CD117, CD93, IL1RAP, CD244, CCR1, LILRB2, PIEZO1, CD38, EMB, MYADM, LILRA2, CD300LF, or CD70 antigen.

In some embodiments, the chimeric inhibitory receptor binds a CNTNAP3 antigen and the chimeric receptor binds a MS4A3, VSTM1, LAT2, MLC1, CD131, GAPT, PRAM1, SLC22A16, SLC17A9, SPNS3, FLT3, CD33, CLEC12A, ADGRE2, IL3RA, CD117, CD93, IL1RAP, CD244, CCR1, LILRB2, PIEZO1, CD38, EMB, MYADM, LILRA2, CD300LF, or CD70 antigen.

In some embodiments, the chimeric inhibitory receptor binds a PCDH9 antigen and the chimeric receptor binds a MS4A3, VSTM1, LAT2, MLC1, CD131, GAPT, PRAM1, SLC22A16, SLC17A9, SPNS3, FLT3, CD33, CLEC12A, ADGRE2, IL3RA, CD117, CD93, IL1RAP, CD244, CCR1, LILRB2, PIEZO1, CD38, EMB, MYADM, LILRA2, CD300LF, or CD70 antigen.

In some embodiments, the chimeric inhibitory receptor binds an IL18R1 antigen and the chimeric receptor binds a MS4A3, VSTM1, LAT2, MLC1, CD131, GAPT, PRAM1, SLC22A16, SLC17A9, SPNS3, FLT3, CD33, CLEC12A, ADGRE2, IL3RA, CD117, CD93, IL1RAP, CD244, CCR1, LILRB2, PIEZO1, CD38, EMB, MYADM, LILRA2, CD300LF, or CD70 antigen.

In some embodiments, the chimeric inhibitory receptor binds an SLC8A3 antigen and the chimeric receptor binds a MS4A3, VSTM1, LAT2, MLC1, CD131, GAPT, PRAM1, SLC22A16, SLC17A9, SPNS3, FLT3, CD33, CLEC12A, ADGRE2, IL3RA, CD117, CD93, IL1RAP, CD244, CCR1, LILRB2, PIEZO1, CD38, EMB, MYADM, LILRA2, CD300LF, or CD70 antigen.

In some embodiments, the chimeric inhibitory receptor binds a CDH26 antigen and the chimeric receptor binds a MS4A3, VSTM1, LAT2, MLC1, CD131, GAPT, PRAM1, SLC22A16, SLC17A9, SPNS3, FLT3, CD33, CLEC12A, ADGRE2, IL3RA, CD117, CD93, IL1RAP, CD244, CCR1, LILRB2, PIEZO1, CD38, EMB, MYADM, LILRA2, CD300LF, or CD70 antigen.

In some embodiments, the chimeric inhibitory receptor binds a TMEM163 antigen and the chimeric receptor binds a MS4A3, VSTM1, LAT2, MLC1, CD131, GAPT, PRAM1, SLC22A16, SLC17A9, SPNS3, FLT3, CD33, CLEC12A, ADGRE2, IL3RA, CD117, CD93, IL1RAP, CD244, CCR1, LILRB2, PIEZO1, CD38, EMB, MYADM, LILRA2, CD300LF, or CD70 antigen.

In some embodiments, the chimeric inhibitory receptor binds an ABCA13 antigen and the chimeric receptor binds a MS4A3, VSTM1, LAT2, MLC1, CD131, GAPT, PRAM1, SLC22A16, SLC17A9, SPNS3, FLT3, CD33, CLEC12A, ADGRE2, IL3RA, CD117, CD93, IL1RAP, CD244, CCR1, LILRB2, PIEZO1, CD38, EMB, MYADM, LILRA2, CD300LF, or CD70 antigen.

In some embodiments, the chimeric inhibitory receptor binds a CACHD1 antigen and the chimeric receptor binds a MS4A3, VSTM1, LAT2, MLC1, CD131, GAPT, PRAM1, SLC22A16, SLC17A9, SPNS3, FLT3, CD33, CLEC12A, ADGRE2, IL3RA, CD117, CD93, IL1RAP, CD244, CCR1, LILRB2, PIEZO1, CD38, EMB, MYADM, LILRA2, CD300LF, or CD70 antigen.

In some embodiments, the chimeric inhibitory receptor binds a CYYR1 antigen and the chimeric receptor binds a MS4A3, VSTM1, LAT2, MLC1, CD131, GAPT, PRAM1, SLC22A16, SLC17A9, SPNS3, FLT3, CD33, CLEC12A, ADGRE2, IL3RA, CD117, CD93, IL1RAP, CD244, CCR1, LILRB2, PIEZO1, CD38, EMB, MYADM, LILRA2, CD300LF, or CD70 antigen.

In some embodiments, the chimeric inhibitory receptor binds an ABCB1 antigen and the chimeric receptor binds a MS4A3, VSTM1, LAT2, MLC1, CD131, GAPT, PRAM1, SLC22A16, SLC17A9, SPNS3, FLT3, CD33, CLEC12A, ADGRE2, IL3RA, CD117, CD93, IL1RAP, CD244, CCR1, LILRB2, PIEZO1, CD38, EMB, MYADM, LILRA2, CD300LF, or CD70 antigen.

In some embodiments, the chimeric inhibitory receptor binds an ADGRG6 antigen and the chimeric receptor binds a MS4A3, VSTM1, LAT2, MLC1, CD131, GAPT, PRAM1, SLC22A16, SLC17A9, SPNS3, FLT3, CD33, CLEC12A, ADGRE2, IL3RA, CD117, CD93, IL1RAP, CD244, CCR1, LILRB2, PIEZO1, CD38, EMB, MYADM, LILRA2, CD300LF, or CD70 antigen.

In some embodiments, the chimeric inhibitory receptor binds an ATP9A antigen and the chimeric receptor binds a MS4A3, VSTM1, LAT2, MLC1, CD131, GAPT, PRAM1, SLC22A16, SLC17A9, SPNS3, FLT3, CD33, CLEC12A, ADGRE2, IL3RA, CD117, CD93, IL1RAP, CD244, CCR1, LILRB2, PIEZO1, CD38, EMB, MYADM, LILRA2, CD300LF, or CD70 antigen.

In some embodiments, the chimeric inhibitory receptor binds a CALN1 antigen and the chimeric receptor binds a MS4A3, VSTM1, LAT2, MLC1, CD131, GAPT, PRAM1, SLC22A16, SLC17A9, SPNS3, FLT3, CD33, CLEC12A, ADGRE2, IL3RA, CD117, CD93, IL1RAP, CD244, CCR1, LILRB2, PIEZO1, CD38, EMB, MYADM, LILRA2, CD300LF, or CD70 antigen.

In some embodiments, the chimeric inhibitory receptor binds a CDCP1 antigen and the chimeric receptor binds a MS4A3, VSTM1, LAT2, MLC1, CD131, GAPT, PRAM1, SLC22A16, SLC17A9, SPNS3, FLT3, CD33, CLEC12A, ADGRE2, IL3RA, CD117, CD93, IL1RAP, CD244, CCR1, LILRB2, PIEZO1, CD38, EMB, MYADM, LILRA2, CD300LF, or CD70 antigen.

In some embodiments, the chimeric inhibitory receptor binds an IL12RB2 antigen and the chimeric receptor binds a MS4A3, VSTM1, LAT2, MLC1, CD131, GAPT, PRAM1, SLC22A16, SLC17A9, SPNS3, FLT3, CD33, CLEC12A, ADGRE2, IL3RA, CD117, CD93, IL1RAP, CD244, CCR1, LILRB2, PIEZO1, CD38, EMB, MYADM, LILRA2, CD300LF, or CD70 antigen.

In some embodiments, the chimeric inhibitory receptor binds an SLC16A14 antigen and the chimeric receptor binds a MS4A3, VSTM1, LAT2, MLC1, CD131, GAPT, PRAM1, SLC22A16, SLC17A9, SPNS3, FLT3, CD33, CLEC12A, ADGRE2, IL3RA, CD117, CD93, IL1RAP, CD244, CCR1, LILRB2, PIEZO1, CD38, EMB, MYADM, LILRA2, CD300LF, or CD70 antigen.

In some embodiments, the chimeric inhibitory receptor binds a TMEM136 antigen and the chimeric receptor binds a MS4A3, VSTM1, LAT2, MLC1, CD131, GAPT, PRAM1, SLC22A16, SLC17A9, SPNS3, FLT3, CD33, CLEC12A, ADGRE2, IL3RA, CD117, CD93, IL1RAP, CD244, CCR1, LILRB2, PIEZO1, CD38, EMB, MYADM, LILRA2, CD300LF, or CD70 antigen.

In some embodiments, the chimeric inhibitory receptor binds a TMEM200A antigen and the chimeric receptor binds a MS4A3, VSTM1, LAT2, MLC1, CD131, GAPT, PRAM1, SLC22A16, SLC17A9, SPNS3, FLT3, CD33, CLEC12A, ADGRE2, IL3RA, CD117, CD93, IL1RAP, CD244, CCR1, LILRB2, PIEZO1, CD38, EMB, MYADM, LILRA2, CD300LF, or CD70 antigen.

In some embodiments, the inhibitory chimeric receptor comprises an antigen binding domain derived from an anti-EMCN antibody. The EMCN antibody can be any suitable EMCN antibody known, including, but not limited to, the EMCN antibodies CBFYE-0213, V.7.C7.1, L4B1, L5F12, L10B5, L3F12, L6H3, L9H8, and L10F12, as described in Samulowitz J, et al, Am. J. Path., 30 Apr. 2002, 160(5):1669-1681, hereby incorporated by reference. EMCN antibodies are generally commercially available. For instance, CBFYE-0213 is a rat anti-human EMCN IgG and is available from Creative Biolabs (Cat. #CBMAB-E0461-FY) and V.7.C7.1 is a rat anti-EMCN IgG2a that cross-reacts with human and mouse EMCN and is available from Abcam (Cat. #ab106100).

In some embodiments, the EMCN antigen binding domain is an antibody selected from CBFYE-0213, V.7.C7.1, L6H10, L4B1, L5F12, L10B5, L3F12, L6H3, L9H8, L10F12, 18HCLC, or V.7.C7.

Antibodies that bind to CALN1, IL12RB2, CDH26, IL18R1, SLC8A3, ABCB1, ATP9A, CDCP1, EMCN, JAM2, PCDH9, TMEM200A, ADGRL4, ART4, BACE2, CALCRL, LIFR, MET, MPZL2, PTPRB, and WLS are generally known and commercially available from a variety of vendors. In some embodiments, the inhibitory chimeric receptor comprises an antigen binding domain derived from the anti-CALN1 antibodies 2G5, 2G2, or 3H3. In some embodiments, the inhibitory chimeric receptor an antigen binding domain selected from the anti-IL12RB2 antibodies 2H6, S16020B, 305719, 9H1, 11D102, or REA333. In some embodiments, the inhibitory chimeric receptor comprises an antigen binding domain selected from the anti-CDH26 antibodies 6C10 or CH-19. In some embodiments, the inhibitory chimeric receptor comprises an antigen binding domain selected from the anti-IL18R1 antibodies 70625.111, H44, REA947, REA1095, B-E43, 44G6, or 5. In some embodiments, the inhibitory chimeric receptor comprises an antigen binding domain selected from from the anti-SLC8A3 antibody C2C12. In some embodiments, the inhibitory chimeric receptor comprises an antigen binding domain selected from the anti-ABCB1 antibodies C219, 4E3.16, C494, JSB-1, REA495, UIC2, SN06-42, OTI1A7, OTI5B3, OTI2G6, OTI6H2, or OTI2C7. In some embodiments, the inhibitory chimeric receptor comprises an antigen binding domain of the anti-ATP9A antibody 3G2. In some embodiments, the inhibitory chimeric receptor comprises an antigen binding domain selected from the anti-CDCP1 antibodies CUB1, REA194, OTI2B2, OTI2C1, OTI2B8, OTI4G5, OTI5B3, CSTEM26, 309116, or 309121. In some embodiments, the inhibitory chimeric receptor comprises an antigen binding domain selected from the anti-JAM2 antibodies 988905, 988901, 988934, EPR2489(2), CBL560, C47B10-2A9S, C47B10-2B11S, C47B10-2B8S, 500A, J1, CBFYC-2851, MM0425-4L28-IgG1, 14L655, 156623, 156624, 1C2, 1G4, 4L28, CBLXJ-018, 2H5, or FQS3590(3). In some embodiments, the inhibitory chimeric receptor comprises an antigen binding domain selected from the anti-PCDH9 antibodies 7G3A2 or 7G3F7. In some embodiments, the inhibitory chimeric receptor comprises an antigen binding domain selected from the anti-TMEM200A antibodies 4-B3, CBYJT-3509, or CBYJT-3510. In some embodiments, the inhibitory chimeric receptor comprises an antigen binding domain selected from the anti-ADGRL4 antibody CL4164. In some embodiments, the inhibitory chimeric receptor comprises an antigen binding domain selected from the anti-ART4 antibody 8C11A12. In some embodiments, the inhibitory chimeric receptor comprises an antigen binding domain selected from the anti-BACE2 antibody 391017. In some embodiments, the inhibitory chimeric receptor comprises an antigen binding domain selected from the anti-CALCRL antibody 998820. In some embodiments, the inhibitory chimeric receptor comprises an antigen binding domain selected from the anti-LIFR antibodies 8E5E4D3, 32953. In some embodiments, the inhibitory chimeric receptor comprises an antigen binding domain selected from the anti-MPZL2 antibodies G9P3-1 or OTI2C7. In some embodiments, the inhibitory chimeric receptor comprises an antigen binding domain from the anti-PTPRB antibody 2-A2. In some embodiments, the inhibitory chimeric receptor comprises an antigen binding domain from the anti-WLS antibody YJ5.

Co-Stimulatory Ligands

In some embodiments, a cell of the present disclosure (e.g., an immunoresponsive cell) can further include one or more recombinant or exogenous co-stimulatory ligands. For example, the cell can be further transduced with one or more co-stimulatory ligands, such that the cell co-expresses or is induced to co-express one or more chimeric receptors of the present disclosure and one or more co-stimulatory ligands. Without wishing to be bound by theory, it is believed that the interaction between the one or more chimeric receptors and the one or more co-stimulatory ligands may provide a non-antigen-specific signal important for full activation of the cell. Examples of suitable co-stimulatory ligands include, without limitation, members of the tumor necrosis factor (TNF) superfamily, and immunoglobulin (Ig) superfamily ligands. TNF is a cytokine involved in systemic inflammation and stimulates the acute phase reaction. Its primary role is in the regulation of immune cells. Members of TNF superfamily share a number of common features. The majority of TNF superfamily members are synthesized as type II transmembrane proteins (extracellular C-terminus) containing a short cytoplasmic segment and a relatively long extracellular region. Examples of suitable TNF superfamily members include, without limitation, nerve growth factor (NGF), CD40L (CD40L)/CD 154, CD137L/4-1BBL, TNF-a, CD134L/OX40L/CD252, CD27L/CD70, Fas ligand (FasL), CD30L/CD153, tumor necrosis factor beta (TNFP)/lymphotoxin-alpha (LTa), lymphotoxin-beta (LTP), CD257/B cell-activating factor (B AFF)/Bly s/THANK/Tall-1, glucocorticoid-induced TNF Receptor ligand (GITRL), and TNF-related apoptosis-inducing ligand (TRAIL), LIGHT (TNFSF 14). The immunoglobulin (Ig) superfamily is a large group of cell surface and soluble proteins that are involved in the recognition, binding, or adhesion processes of cells. These proteins share structural features with immunoglobulins and possess an immunoglobulin domain (fold). Examples of suitable immunoglobulin superfamily ligands include, without limitation, CD80 and CD86, both ligands for CD28, PD-L1/(B7-H1) that ligands for PD-1. In certain embodiments, the one or more co-stimulatory ligands are selected from 4-1BBL, CD80, CD86, CD70, OX40L, CD48, TNFRSF14, PD-L1, and combinations thereof.

Chemokine Receptor

In some embodiments, a cell of the present disclosure (e.g., an immunoresponsive cell) comprises one or more chimeric receptors and may further include one or more chemokine receptors. For example, transgenic expression of chemokine receptor CCR2b or CXCR2 in cells, such as T cells, enhances trafficking to CCL2-secreting or CXCL1-secreting solid tumors (Craddock et al, J Immunother. 2010 October; 33(8):780-8 and Kershaw et al. Hum Gene Ther. 2002 Nov. 1; 13(16): 1971-80). Without wishing to be bound by theory, it is believed that chemokine receptors expressed on chimeric receptor-expressing cells of the present disclosure may recognize chemokines secreted by tumors and improve targeting of the cell to the tumor, which may facilitate the infiltration of the cell to the tumor and enhance the antitumor efficacy of the cell. Chemokine receptors of the present disclosure may include a naturally occurring chemokine receptor, a recombinant chemokine receptor, or a chemokine-binding fragment thereof. Examples of suitable chemokine receptors that may expressed on a cell of the present disclosure include, without limitation, a CXC chemokine receptor, such as CXCR1, CXCR2, CXCR3, CXCR4, CXCR5, CXCR6, or CXCR7; a CC chemokine receptor, such as CCR1, CCR2, CCR3, CCR4, CCR5, CCR6, CCR7, CCR8, CCR9, CCR10, or CCR11; a CX3C chemokine receptor, such as CX3CR1; an XC chemokine receptor, such as XCR1; and chemokine-binding fragments thereof. In some embodiments, the chemokine receptor to be expressed on the cell is chosen based on the chemokines secreted by the tumor.

Chimeric Receptor Regulation

Some embodiments of the present disclosure relate to regulating one or more chimeric receptor activities of chimeric receptor-expressing cells of the present disclosure. There are several ways chimeric receptor activities can be regulated. In some embodiments, a regulatable chimeric receptor, wherein one or more chimeric receptor activities can be controlled, may be desirable to optimize the safety and/or efficacy of the chimeric receptor therapy. For example, inducing apoptosis using a caspase fused to a dimerization domain (see, e.g., Di et al., N Engl. J. Med. 2011 Nov. 3; 365(18): 1673-1683) can be used as a safety switch in the chimeric receptor therapy. In some embodiments, a chimeric receptor-expressing cell of the present disclosure can also express an inducible Caspase-9 (iCaspase-9) that, upon administration of a dimerizer drug, such as rimiducid (IUPAC name: R1R)-3-(3,4-dimethoxyphenyl)-1-[3-[2-[2-[[2-[3-[(1R)-3-(3,4-dimethoxyphenyl)-1-[(2S)-1-[(2S)-2-(3,4,5-trimethoxyphenyl)butanoyl]piperidine-2-carbonyl]oxypropyl]phenoxy]acetyl]amino]ethylamino]-2-oxoethoxy]phenyl]propyl] (2S)-1-[(2S)-2-(3,4,5-trimethoxyphenyl)butanoyl]piperidine-2-carboxylate), induces activation of the Caspase-9 and results in apoptosis of the cells. In some embodiments, the iCaspase-9 contains a binding domain that comprises a chemical inducer of dimerization (CID) that mediates dimerization in the presence of the CID, which results in inducible and selective depletion of the chimeric receptor-expressing cells.

Alternatively, in some embodiments a chimeric receptor of the present disclosure may be regulated by utilizing a small molecule or an antibody that deactivates or otherwise inhibits chimeric receptor activity. For example, an antibody may delete the chimeric receptor-expressing cells by inducing antibody dependent cell-mediated cytotoxicity (ADCC). In some embodiments, a chimeric receptor-expressing cell of the present disclosure may further express an antigen that is recognized by a molecule that is capable of inducing cell death by ADCC or complement-induced cell death. For example, a chimeric receptor-expressing cell of the present disclosure may further express a receptor capable of being targeted by an antibody or antibody fragment. Examples of suitable receptors that may be targeted by an antibody or antibody fragment include, without limitation, EpCAM, VEGFR, integrins (e.g., αvβ3, α4, αI¾β3, α4β7, α5β1, αvβ3, αv), members of the TNF receptor superfamily (e.g., TRAIL-R1 and TRAIL-R2), PDGF receptor, interferon receptor, folate receptor, GPNMB, ICAM-1, HLA-DR, CEA, CA-125, MUC1, TAG-72, IL-6 receptor, 5T4, GD2, GD3, CD2, CD3, CD4, CD5, CD11, CD11a/LFA-1, CD15, CD18/ITGB2, CD19, CD20, CD22, CD23/IgE Receptor, CD25, CD28, CD30, CD33, CD38, CD40, CD41, CD44, CD51, CD52, CD62L, CD74, CD80, CD125, CD147/basigin, CD152/CTLA-4, CD154/CD40L, CD195/CCR5, CD319/SLAMF7, and EGFR, and truncated versions thereof.

In some embodiments, a chimeric receptor-expressing cell of the present disclosure may also express a truncated epidermal growth factor receptor (EGFR) that lacks signaling capacity but retains an epitope that is recognized by molecules capable of inducing ADCC (e.g., WO2011/056894).

In some embodiments, a chimeric receptor-expressing cell of the present disclosure further includes a highly expressing compact marker/suicide gene that combines target epitopes from both CD32 and CD20 antigens in the chimeric receptor-expressing cell, which binds an anti-CD20 antibody (e.g., rituximab) resulting in selective depletion of the chimeric receptor-expressing cell by ADCC. Other methods for depleting chimeric receptor-expressing cells of the present disclosure my include, without limitation, administration of a monoclonal anti-CD52 antibody that selectively binds and targets the chimeric receptor-expressing cell for destruction by inducing ADCC. In some embodiments, the chimeric receptor-expressing cell can be selectively targeted using a chimeric receptor ligand, such as an anti-idiotypic antibody. In some embodiments, the anti-idiotypic antibody can cause effector cell activity, such as ADCC or ADC activity. In some embodiments, the chimeric receptor ligand can be further coupled to an agent that induces cell killing, such as a toxin. In some embodiments, a chimeric receptor-expressing cell of the present disclosure may further express a target protein recognized by a cell depleting agent of the present disclosure. In some embodiments, the target protein is CD20 and the cell depleting agent is an anti-CD20 antibody. In such embodiments, the cell depleting agent is administered once it is desirable to reduce or eliminate the chimeric receptor-expressing cell. In some embodiments, the cell depleting agent is an anti-CD52 antibody.

In some embodiments, a regulated chimeric receptor comprises a set of polypeptides, in which the components of a chimeric receptor of the present disclosure are partitioned on separate polypeptides or members. For example, the set of polypeptides may include a dimerization switch that, when in the presence of a dimerization molecule, can couple the polypeptides to one another to form a functional chimeric receptor.

Chimeric Receptor-Encoding Nucleic Acid Constructs

Certain aspects of the present disclosure relate to nucleic acids (e.g., isolated nucleic acids) encoding one or more chimeric receptors of the present disclosure. In some embodiments, the nucleic acid is an RNA construct, such as a messenger RNA (mRNA) transcript or a modified RNA. In some embodiments, the nucleic acid is a DNA construct.

In some embodiments, a nucleic acid of the present disclosure encodes a chimeric receptor that comprises one or more antigen-binding domain, where each domain binds to a target antigen (e.g., an AML antigen), a transmembrane domain, and one or more intracellular signaling domains. In some embodiments, the nucleic acid encodes a chimeric receptor that comprises an antigen-binding domain, a transmembrane domain, a primary signaling domain (e.g., CD3-zeta domain), and one or more costimulatory signaling domains. In some embodiments, the nucleic acid further comprises a nucleotide sequence encoding a spacer region. In some embodiments, the antigen-binding domain is connected to the transmembrane domain by the spacer region. In some embodiments, the spacer region comprises a nucleic acid sequence selected from any of the nucleic acid sequences listed in Table D. In some embodiments, the nucleic acid further comprises a nucleotide sequence encoding a leader sequence.

The nucleic acids of the present disclosure may be obtained using any suitable recombinant methods known in the art, including, without limitation, by screening libraries from cells expressing the gene of interest, by deriving the gene of interest from a vector known to include the gene, or by isolating the gene of interest directly from cells and tissues containing the gene using standard techniques. Alternatively, the gene of interest may be produced synthetically.

In some embodiments, a nucleic acid of the present disclosure in comprised within a vector. In some embodiments, a nucleic acid of the present disclosure is expressed in a cell via transposons, a CRISPR/Cas9 system, a TALEN, or a zinc finger nuclease.

In some embodiments, expression of a nucleic acid encoding a chimeric receptor of the present disclosure may be achieved by operably linking the nucleic acid to a promoter and incorporating the construct into an expression vector. A suitable vector can replicate and integrate in eukaryotic cells. Typical cloning vectors contain transcription and translation terminators, initiation sequences, and promoters useful for regulating expression of the desired nucleic acid.

In some embodiments, expression constructs of the present disclosure may also be used for nucleic acid immunization and gene therapy, using standard gene delivery protocols (e.g., U.S. Pat. Nos. 5,399,346, 5,580,859, and 5,589,466). In some embodiments, a vector of the present disclosure is a gene therapy vector.

A nucleic acid of the present disclosure can be cloned into a number of types of vectors. For example, the nucleic acid can be cloned into a vector including, without limitation, a plasmid, a phagemid, a phage derivative, an animal virus, or a cosmid. In some embodiments, the vector may be an expression vector, a replication vector, a probe generation vector, or a sequencing vector.

In some embodiments, the plasmid vector comprises a transposon/transposase system to incorporate the nucleic acids of the present disclosure into the host cell genome.

Methods of expressing proteins in immune cells using a transposon and transposase plasmid system are generally described in Chicaybam L, Hum Gene Ther. 2019 April; 30(4):511-522. doi: 10.1089/hum.2018.218; and Ptáčková P, Cytotherapy. 2018 April; 20(4):507-520. doi: 10.1016/j.jcyt.2017.10.001, each of which are hereby incorporated by reference in their entirety. In some embodiments, the transposon system is the Sleeping Beauty transposon/transposase or the piggyBac transposon/transposase.

In some embodiments, an expression vector of the present disclosure may be provided to a cell in the form of a viral vector. Suitable viral vector systems are well known in the art. For example, viral vectors may be derived from retroviruses, adenoviruses, adeno-associated viruses, herpes viruses, and lentiviruses. In some embodiments, a vector of the present disclosure is a lentiviral vector. Lentiviral vectors are suitable for long-term gene transfer as such vectors allow long-term, stable integration of a transgene and its propagation in daughter cells. Lentiviral vectors are also advantageous over vectors derived from onco-retroviruses (e.g., murine leukemia viruses) in that lentiviral vectors can transduce non-proliferating cells. In some embodiments, a vector of the present disclosure is an adenoviral vector (A5/35). In some embodiments, a vector of the present disclosure contains an origin of replication functional in at least one organism, a promoter sequence, convenient restriction endonuclease sites, and one or more selectable markers (e.g., WO01/96584; WO01/29058; and U.S. Pat. No. 6,326,193). A number of viral based systems have been developed for gene transfer into mammalian cells. A selected gene can be inserted into a vector and packaged in retroviral particles using techniques known in the art. The recombinant virus can then be isolated and delivered to mammalian cells either in vivo or ex vivo. A number of retroviral systems are known in the art.

In some embodiments, vectors of the present disclosure include additional promoter elements, such as enhancers that regulate the frequency of transcriptional initiation. Enhancers are typically located in a region that is 30 bp to 110 bp upstream of the start site, although a number of promoters have been shown to contain functional elements downstream of the start site as well. The spacing between promoter elements may be flexible, so that promoter function is preserved when elements are inverted or moved relative to one another. For example, in the thymidine kinase (tk) promoter the spacing between promoter elements can be increased to 50 bp apart before activity begins to decline. Depending on the promoter, individual elements may function either cooperatively or independently to activate transcription. Exemplary promoters may include, without limitation, the SFFV gene promoter, the EFS gene promoter, the CMV IE gene promoter, the EF1a promoter, the ubiquitin C promoter, and the phosphoglycerokinase (PGK) promoter.

In some embodiments, a promoter that is capable of expressing a nucleic acid of the present disclosure in a mammalian cell, such as an immunoresponsive cell of the present disclosure, is the EF1a promoter. The native EF1a promoter drives expression of the alpha subunit of the elongation factor-1 complex, which is responsible for the enzymatic delivery of aminoacyl tRNAs to the ribosome. The EF1a promoter has been widely used in mammalian expression plasmids and has been shown to be effective in driving chimeric receptor expression from nucleic acids cloned into a lentiviral vector.

In some embodiments, a promoter that is capable of expressing a nucleic acid of the present disclosure in a mammalian cell, such as an immunoresponsive cell of the present disclosure, is a constitutive promoter. For example, a suitable constitutive promoter is the immediate early cytomegalovirus (CMV) promoter. The CMV promoter is a strong constitutive promoter that is capable of driving high levels of expression of any polynucleotide sequence operatively linked to the promoter. Other suitable constitutive promoters include, without limitation, a ubiquitin C (UbiC) promoter, a simian virus 40 (SV40) early promoter, a mouse mammary tumor virus (MMTV) promoter, a human immunodeficiency virus (HIV) long terminal repeat (LTR) promoter, a MoMuLV promoter, an avian leukemia virus promoter, an Epstein-Barr virus immediate early promoter, a Rous sarcoma virus promoter, an actin promoter, a myosin promoter, an elongation factor-la promoter, a hemoglobin promoter, and a creatine kinase promoter.

In some embodiments, a promoter that is capable of expressing a nucleic acid of the present disclosure in a mammalian cell, such as an immunoresponsive cell of the present disclosure, is an inducible promoter. Use of an inducible promoter may provide a molecular switch that is capable of inducing or repressing expression of a nucleic acid of the present disclosure when the promoter is operatively linked to the nucleic acid. Examples of inducible promoters include, without limitation, a metallothionine promoter, a glucocorticoid promoter, a progesterone promoter, and a tetracycline promoter.

In some embodiments, a vector of the present disclosure may further comprise a signal sequence to facilitate secretion, a polyadenylation signal and transcription terminator, an element allowing episomal replication, and/or elements allowing for selection.

In some embodiments, a vector of the present disclosure can further comprise a selectable marker gene and/or reporter gene to facilitate identification and selection of chimeric receptor-expressing cells from a population of cells that have been transduced with the vector. In some embodiments, the selectable marker may be encoded by a nucleic acid that is separate from the vector and used in a co-transfection procedure. Either selectable marker or reporter gene may be flanked with appropriate regulator sequences to allow expression in host cells. Examples of selectable markers include, without limitation, antibiotic-resistance genes, such as neo and the like.

In some embodiments, reporter genes may be used for identifying transduced cells and for evaluating the functionality of regulatory sequences. As disclosed herein, a reporter gene is a gene that is not present in or expressed by the recipient organism or tissue and that encodes a polypeptide whose expression results in an easily detectable property, such as enzymatic activity. Expression of the reporter gene can be assayed at a suitable time after the nucleic acid has been introduced into the recipient cells. Examples of reporter genes include, without limitation, genes encoding for luciferase, genes encoding for beta-galactosidase, genes encoding for chloramphenicol acetyl transferase, genes encoding for secreted alkaline phosphatase, and genes encoding for green fluorescent protein. Suitable expression systems are well known in the art and may be prepared using known techniques or obtained commercially. In some embodiments, a construct with a minimal 5' flanking region showing the highest level of expression of the reporter gene is identified as the promoter. Such promoter regions may be linked to a reporter gene and used to evaluate agents for the ability to modulate promoter-driven transcription.

In some embodiments, a vector comprising a nuclei acid sequence encoding a chimeric receptor of the present disclosure further comprises a second nucleic acid encoding a polypeptide that increases the activity of the chimeric receptor.

In embodiments where a chimeric receptor-expressing cell comprises two or more chimeric receptors, a single nucleic acid may encode the two or more chimeric receptors under a single regulatory control element (e.g., promoter) or under separate regulatory control elements for each chimeric receptor-encoding nucleotide sequence comprised in the nucleic acid. In some embodiments where a chimeric receptor-expressing cell comprises two or more chimeric receptors, each chimeric receptor may be encoded by separate nucleic acid. In some embodiments, each separate nucleic acid comprises its own control element (e.g., promoter). In some embodiments, a single nucleic acid encodes the two or more chimeric receptors and the chimeric receptor-encoding nucleotide sequences are in the same reading frame and are expressed as a single polypeptide chain. In such embodiments, the two or more chimeric receptors may be separated by one or more peptide cleavage sites, such as auto-cleavage sites or substrates for an intracellular protease. Suitable peptide cleavage sites may include, without limitation, a T2A peptide cleavage site, a P2A peptide cleavage site, an E2A peptide cleavage sire, and an F2A peptide cleavage site. In some embodiments, the two or more chimeric receptors comprise a T2A peptide cleavage site. In some embodiments, the two or more chimeric receptors comprise an E2A peptide cleavage site. In some embodiments, the two or more chimeric receptors comprise a T2A and an E2A peptide cleavage site.

Methods of introducing and expressing genes into a cell are well known in the art. For example, in some embodiments, an expression vector can be transferred into a host cell by physical, chemical, or biological means. Examples of physical means for introducing a nucleic acid into a host cell include, without limitation, calcium phosphate precipitation, lipofection, particle bombardment, microinjection, and electroporation. Examples of chemical means for introducing a nucleic acid into a host cell include, without limitation, colloidal dispersion systems, macromolecule complexes, nanocapsules, microspheres, beads, and lipid-based systems including oil-in-water emulsions, micelles, mixed micelles, and liposomes. Examples of biological means for introducing a nucleic acid into a host cell include, without limitation, the use of DNA and RNA vectors.

In some embodiments, liposomes may be used as a non-viral delivery system to introduce a nucleic acid or vector of the present disclosure into a host cell in vitro, ex vivo, or in vivo. In some embodiments, the nucleic acid may be associated with a lipid, for example by being encapsulated in the aqueous interior of a liposome, being interspersed within the lipid bilayer of a liposome, being attached to a liposome via a linking molecule that is associated with both the liposome and the nucleic acid, being entrapped in a liposome, being complexed with a liposome, being dispersed in a solution containing a lipid, being mixed with a lipid, being combined with a lipid, being contained as a suspension in a lipid, being contained or complexed with a micelle, or otherwise being associated with a lipid. As disclosed herein, lipid-associated nucleic acid or vector compositions are not limited to any particular structure in solution. In some embodiments, such compositions may be present in a bilayer structure, as micelles or with a "collapsed" structure. Such compositions may also be interspersed in a solution, forming aggregates that are not uniform in size or shape. As disclosed herein, lipids are fatty substances that may be naturally occurring or synthetic. In some embodiments, lipids can include the fatty droplets that naturally occur in the cytoplasm or the class of compounds that contain long-chain aliphatic hydrocarbons and their derivatives, such as fatty acids, alcohols, amines, amino alcohols, and aldehydes. Suitable lipids may be obtained from commercial sources and include, without limitation, dimyristyl phosphatidylcholine ("DMPC"), dicetylphosphate ("DCP"), cholesterol, and dimyristylphosphatidylglycerol ("DMPG"). Stock solutions of lipids in chloroform or chloroform/methanol can be stored at about −20° C. Chloroform is used as the solvent, as it is more readily evaporated than methanol. As used herein, a "liposome" may encompass a variety of single and multilamellar lipid vehicles formed by the generation of enclosed lipid bilayers or aggregates. In some embodiments, liposomes can be characterized as having vesicular structures with a phospholipid bilayer membrane and an inner aqueous medium. In some embodiments, multilamellar liposomes may have multiple lipid layers separated by aqueous medium. Multilamellar liposomes can form spontaneously when phospholipids are suspended in an excess of aqueous solution. In some embodiments, lipid components may undergo self-rearrangement before the formation of closed structures and can entrap water and dissolved solutes between the lipid bilayers. In some embodiments, the lipids may assume a micellar structure or merely exist as nonuniform aggregates of lipid molecules.

In some embodiments, a nucleic acid or vector of the present disclosure is introduced into a mammalian host cell, such as an immunoresponsive cell of the present disclosure. In some embodiments, the presence of a nucleic acid or vector of the present disclosure in a host cell may be confirmed by any suitable assay known in the art, including without limitation Southern blot assays, Northern blot assays, RT-PCR, PCR, ELISA assays, and Western blot assays.

In some embodiments, a nucleic acid or vector of the present disclosure is stably transduced into an immunoresponsive cell of the present disclosure. In some embodiments, cells that exhibit stable expression of the nucleic acid or vector express the encoded chimeric receptor for at least 1 week, at least 2 weeks, at least 3 weeks, at least 4 weeks, at least 5 weeks, at least 6 weeks, at least 7 weeks, at least 8 weeks, at least 3 months, at least 6 months, at least 9 months, or at least 12 months after transduction.

In embodiments where a chimeric receptor of the present disclosure is transiently expressed in a cell, a chimeric receptor-encoding nucleic acid or vector of the present disclosure is transfected into an immunoresponsive cell of the present disclosure. In some embodiments the immunoresponsive cell expresses the chimeric receptor for about 4 days, about 5 days, about 6 days, about 7 days, about 8 days, about 9 days, about 10 days, about 11 days, about 12 days, about 13 days, about 14 days, or about 15 days after transfection.

In some embodiments, the nucleic acid construct encodes a bicistronic chimeric antigen receptor. In some embodiments, the encoded bicistronic chimeric antigen receptor comprises an FLT3 CAR and a CD33 CAR. In some embodiments, the encoded bicistronic chimeric antigen receptor comprises an FLT3 CAR and a CLEC12A CAR. In some embodiments, the encoded bicistronic chimeric antigen receptor comprises an CLEC12A CAR and a CD33 CAR. In some embodiments, the encoded bicistronic chimeric antigen receptor comprises an EMCN CAR. In some embodiments, the encoded bicistronic chimeric antigen receptor comprises a CAR with an antigen binding domain targeting any antigen provided in Table 1. In some embodiments, the encoded bicistronic chimeric antigen receptor comprises a CAR with an antigen binding domain targeting any antigen provided in Table 2. In some embodiments, the encoded bicistronic chimeric antigen receptor comprises a CAR with two or more antigen binding domains targeting any antigen pair provided in Table 3.

In some embodiments, the nucleic acid construct encodes a bivalent chimeric antigen receptor. In some embodiments, the encoded bivalent chimeric antigen receptor comprises an FLT3 CAR and a CD33 CAR. In some embodiments, the encoded bivalent chimeric antigen receptor comprises an FLT3 CAR and a CLEC12A CAR. In some embodiments, the encoded bivalent chimeric antigen receptor comprises an CLEC12A CAR and a CD33 CAR. In some embodiments, the encoded bivalent chimeric antigen receptor comprises an EMCN CAR. In some embodiments, the encoded bivalent chimeric antigen receptor comprises a CAR with an antigen binding domain targeting any antigen provided in Table 1. In some embodiments, the encoded bivalent chimeric antigen receptor comprises a CAR with an antigen binding domain targeting any antigen provided in Table 2. In some embodiments, the encoded bivalent chimeric antigen receptor comprises a CAR with two or more antigen binding domains targeting any antigen pair provided in Table 3.

Pharmaceutical Compositions and Administration

Certain aspects of the present disclosure relate to compositions (e.g., pharmaceutical compositions) comprising one or more chimeric receptors of the present disclosure or immunoresponsive cells of the present disclosure that express such one or more chimeric receptors. In some embodiments, compositions comprising chimeric receptors or genetically modified immunoresponsive cells that express such chimeric receptors can be provided systemically or directly to a subject for the treatment of a proliferative disorder, such as a myeloid disorder. In certain embodiments, the composition is directly injected into an organ of interest (e.g., an organ affected by a disorder). Alternatively, the composition may be provided indirectly to the organ of interest, for example, by administration into the circulatory system (e.g., the tumor vasculature). Expansion and differentiation agents can be provided prior to, during, or after administration of the composition to increase production of T cells, NK cells, or CTL cells in vitro or in vivo.

Compositions comprising genetically modified cells of the present disclosure may be administered in any physiologically acceptable vehicle, for example intravascularly, although they may also be introduced into bone or other convenient sites where the genetically modified cells may find an appropriate site for regeneration and differentiation (e.g., thymus). In some embodiments, at least $1\times10^5$ cells may be administered, eventually reaching $1\times10^{10}$ or more cells. Compositions comprising genetically modified cells of the present disclosure can comprise a purified population of cells. Methods for determining the percentage of genetically modified cells in a population of cells are well known in the art and include, without limitation, fluorescence activated cell sorting (FACS). In some embodiments, the purity of genetically modified cells in a population of cells may be about 50%, about 55%, about 60%, or about 65%, about 70%, about 75%, about 80%, about 85%, about 90%, about 95%, about 97%, about 98%, about 99%, or more of the cells in the population of cells. Dosages can be readily adjusted by those skilled in the art (e.g., a decrease in purity may require an increase in dosage). The cells can be introduced by injection, catheter, or the like. In some embodiments, factors can also be included, for example, IL-2, IL-3, IL-6, IL-11, IL-7, IL-12, IL-15, IL-21, G-CSF, MCSF, GM-CSF, gamma-interferon, and erythropoietin.

In certain embodiments, the compositions are pharmaceutical compositions comprising genetically modified cells, such as immunoresponsive cells or their progenitors and a pharmaceutically acceptable carrier. Administration can be autologous or heterologous. For example, immunoresponsive cells, or progenitors can be obtained from one subject, and administered to the same subject or a different, compatible subject. In some embodiments, immunoresponsive cells of the present disclosure or their progeny may be derived from peripheral blood cells (e.g., in vivo, ex vivo, or in vitro derived) and may be administered via localized injection, including catheter administration, systemic injection, localized injection, intravenous injection, or parenteral administration. When administering a therapeutic composition of the present disclosure (e.g., a pharmaceutical composition containing a genetically modified cell of the present disclosure), it will generally be formulated in a unit dosage injectable form (solution, suspension, emulsion).

Formulations

Certain aspects of the present disclosure relate to formulations of compositions comprising chimeric receptors of the present disclosure or genetically modified cells (e.g., immunoresponsive cells of the present disclosure) expressing such chimeric receptors. In some embodiments, compositions of the present disclosure comprising genetically modified cells may be provided as sterile liquid preparations, including without limitation isotonic aqueous solutions, suspensions, emulsions, dispersions, and viscous compositions, which may be buffered to a selected pH. Liquid preparations are typically easier to prepare than gels, other viscous compositions, and solid compositions. Additionally, liquid compositions may be more convenient to administer, especially by injection. In some embodiments, viscous compositions can be formulated within the appropriate viscosity range to provide longer contact periods with specific tissues. Liquid or viscous compositions can comprise carriers, which can be a solvent or dispersing medium containing, for example, water, saline, phosphate buffered saline, polyol (e.g., glycerol, propylene glycol, liquid polyethylene glycol, etc.) and suitable mixtures thereof.

In some embodiments, sterile injectable solutions can be prepared by incorporating genetically modified cells of the present disclosure in a sufficient amount of the appropriate solvent with various amounts of any other ingredients, as desired. Such compositions may be in admixture with a suitable carrier, diluent, or excipient such as sterile water, physiological saline, glucose, dextrose, or the like. In some embodiments, the compositions can also be lyophilized. The compositions can contain auxiliary substances such as wetting, dispersing agents, pH buffering agents, and antimicrobials depending upon the route of administration and the preparation desired.

In some embodiments, compositions of the present disclosure may further include various additives that may enhance the stability and sterility of the compositions. Examples of such additives include, without limitation, antimicrobial preservatives, antioxidants, chelating agents, and buffers. In some embodiments, microbial contamination may be prevented by the inclusions of any of various antibacterial and antifungal agents, including without limitation parabens, chlorobutanol, phenol, sorbic acid, and the like. Prolonged absorption of an injectable pharmaceutical formulation of the present disclosure can be brought about by the use of suitable agents that delay absorption, such as aluminum monostearate and gelatin.

In some embodiments, compositions of the present disclosure can be isotonic, i.e., having the same osmotic pressure as blood and lacrimal fluid. In some embodiments, the desired isotonicity may be achieved using, for example, sodium chloride, dextrose, boric acid, sodium tartrate, propylene glycol, or other inorganic or organic solutes.

In some embodiments, the components of the formulations of the present disclosure are selected to be chemically inert and to not affect the viability or efficacy of the genetically modified cells of the present disclosure.

One consideration concerning the therapeutic use of the genetically modified cells of the present disclosure is the quantity of cells needed to achieve optimal efficacy. In some embodiments, the quantity of cells to be administered will vary for the subject being treated. In certain embodiments, the quantity of genetically modified cells that are administered to a subject in need thereof may range from $1\times10^4$ cells to $1\times10^{10}$ cells. In some embodiments, the precise quantity of cells that would be considered an effective dose may be based on factors individual to each subject, including their size, age, sex, weight, and condition of the particular subject. Dosages can be readily ascertained by those skilled in the art based on the present disclosure and the knowledge in the art.

Methods of Treatment

Certain aspects of the present disclosure relate to methods of using the chimeric receptors and genetically modified cells of the present disclosure (e.g., immunoresponsive cells) that express such chimeric receptors to treat subjects in need thereof. In some embodiments, the methods of the present disclosure are useful for treating cancer in a subject, such as a myeloid disorder. In some embodiments, the myeloid disorder is a myelodysplastic syndrome, a myeloproliferative neoplasm, a chronic myelomonocytic leukemia, acute myeloid leukemia (AML), acute myeloblastic leukemia, acute promyelocytic leukemia, acute myelomonocytic leukemia, chronic myelocytic leukemia, or polycythemia vera. In some embodiments, the myeloid disorder is AML. Other aspects of the present disclosure relate to use of the chimeric receptors and genetically modified cells of the present disclosure (e.g., immunoresponsive cells) that express such chimeric receptors in methods for treating a pathogen infection or other infectious disease in a subject, such as an immunocompromised human subject. In some embodiments, the methods of the present disclosure may comprise administering genetically modified cells of the present disclosure in an amount effective to achieve the desired effect, including without limitation palliation of an existing condition, prevention of a condition, treatment an existing condition, management of an existing condition, or prevention of recurrence or relapse of a condition. In some embodiments, the effective amount can be provided in one or a series of administrations of the genetically modified cells of the present disclosure (e.g., immunoresponsive cells). In some embodiments, an effective amount can be provided in a bolus or by continuous perfusion.

As disclosed herein, an "effective amount" or "therapeutically effective amount" is an amount sufficient to affect a beneficial or desired clinical result upon treatment. An effective amount can be administered to a subject in one or more doses. In terms of treatment, an effective amount is an amount that is sufficient to palliate, ameliorate, stabilize, reverse or slow the progression of the disease, or otherwise reduce the pathological consequences of the disease. The effective amount is generally determined by the physician on a case-by-case basis and is within the skill of one in the art. Several factors are typically taken into account when determining an appropriate dosage to achieve an effective amount. These factors include age, sex and weight of the subject, the condition being treated, the severity of the condition and the form and effective concentration of the immunoresponsive cells administered.

For adoptive immunotherapy using antigen-specific cells (e.g., immunoresponsive cells such as T cells), cell doses in the range of about $1\times10^6$ to $1\times10^{10}$ cells (e.g., about $1\times10^9$ cells) are typically infused. Upon administration of the cells into the subject and subsequent differentiation, immunoresponsive cells are induced that are specifically directed against the specific antigen. In some embodiments, induction of immunoresponsive cells can include, without limitation, inactivation of antigen-specific cells such as by deletion or anergy. Inactivation is particularly useful to establish or reestablish tolerance such as in autoimmune disorders. The genetically modified cells can be administered by any method known in the art including, but not limited to, intravenous, subcutaneous, intranodal, intratumoral, intrathecal, intrapleural, intraperitoneal and directly to the thymus.

Therapeutic Treatment

In some embodiments, the methods of the present disclosure increase an immune response in a subject in need thereof. In some embodiments, the methods of the present disclosure include methods for treating and/or preventing a myeloid disorder in a subject. In some embodiments, the subject is a human. In some embodiments, suitable human subjects for therapy may comprise two treatment groups that can be distinguished by clinical criteria. Subjects with "advanced disease" or "high tumor burden" are those who bear a clinically measurable tumor. A clinically measurable tumor is one that can be detected on the basis of tumor mass (e.g., based on percentage of leukemic cells, by palpation, CAT scan, sonogram, mammogram or X-ray; positive biochemical or histopathologic markers on their own are insufficient to identify this population). In some embodiments, a pharmaceutical composition of the present disclosure is administered to these subjects to elicit an anti-tumor response, with the objective of palliating their condition. In some embodiments, reduction in tumor mass occurs as a result of administration of the pharmaceutical composition, but any clinical improvement will constitute a benefit. In some embodiments, clinical improvement includes decreased risk or rate of progression or reduction in pathological consequences of the tumor. In some embodiments, a second group of suitable human subjects are "adjuvant group" subjects. These subjects are individuals who have had a history of a myeloid disorder, but have been responsive to another mode of therapy. The prior therapy may have included, without limitation, surgical resection, radiotherapy, and/or traditional chemotherapy. As a result, these individuals have no clinically measurable tumor. However, they are suspected of being at risk for progression of the disease, either near the original tumor site, or by metastases. In some embodiments, this group can be further subdivided into high-risk and low-risk individuals. The subdivision can be made on the basis of features observed before or after the initial treatment. These features are known in the clinical arts, and are suitably defined for each different myeloid disorder. Features typical of high-risk subgroups are those in which the tumor has invaded neighboring tissues, or who show involvement of lymph nodes.

In any and all aspects of increasing an immune response as described herein, any increase or decrease or alteration of an aspect of characteristic(s) or function(s) is as compared to a cell not contacted with an immunoresponsive cell as described herein.

Increasing an immune response can be both enhancing an immune response or inducing an immune response. For instance, increasing an immune response encompasses both the start or initiation of an immune response, or ramping up or amplifying an on-going or existing immune response. In some embodiments, the treatment induces an immune response. In some embodiments, the induced immune response is an adaptive immune response. In some embodiments, the induced immune response is an innate immune response. In some embodiments, the treatment enhances an immune response. In some embodiments, the enhanced immune response is an adaptive immune response. In some embodiments, the enhanced immune response is an innate immune response. In some embodiments, the treatment increases an immune response. In some embodiments, the increased immune response is an adaptive immune response. In some embodiments, the increased immune response is an innate immune response.

In some embodiments, a further group of subjects are those having a genetic predisposition to a myeloid disorder, but that have not yet evidenced clinical signs of the myeloid disorder. For example, women testing positive for a genetic mutation associated with AML, but still of childbearing age, may benefit from receiving one or more of the cells of the present disclosure (e.g., immunoresponsive cells) in treatment prophylactically to prevent the occurrence of AML until it is suitable to perform preventive surgery. In some embodiments, the subjects can have an advanced form of disease, in which case the treatment objective can include mitigation or reversal of disease progression, and/or amelioration of side effects. In some embodiments, the subjects may have a history of the condition, for which they have already been treated, in which case the therapeutic objective may typically include a decrease or delay in the risk of recurrence.

Combination Therapies

In some embodiments, genetically modified cells of the present disclosure (e.g., immunoresponsive ells) expressing one or more chimeric receptors of the present disclosure may be used in combination with other known agents and therapies. In some embodiments, a combination therapy of the present disclosure comprises a genetically modified cells of the present disclosure that can be administered in combination with one or more additional therapeutic agents. In some embodiments, the genetically modified cell and the one or more additional therapeutic agents can be administered simultaneously, in the same or in separate compositions, or sequentially. For sequential administration, the genetically modified can be administered first, and the one or more additional agents can be administered second, or the order of administration can be reversed. In some embodiments, the genetically modified cells are further modified to express one or more additional therapeutic agents.

In some embodiments, a genetically modified cell of the present disclosure may be used in a treatment regimen in combination with surgery, chemotherapy, radiation, immunosuppressive agents (e.g., cyclosporin, azathioprine, methotrexate, mycophenolate, and FK506), antibodies, or other immunoablative agents (e.g., CAMPATH or anti-CD3 antibodies), cytoxin, fludarabme, cyclosporin, FK506, rapamycin, mycophenolic acid, steroids, FR901228, cytokines, irradiation, and peptide vaccines.

In some embodiments, a genetically modified cell of the present disclosure may be used in combination with a lymphodepleting agent. Suitable lymphodepleting agents reduce or decrease lymphocytes, e.g., B cell lymphocytes and/or T cell lymphocytes, prior to immunotherapy. Examples of suitable lymphodepleting agents include, without limitation, fludarabine, cyclophosphamide, corticosteroids, alemtuzumab, total body irradiation (TBI), and any combination thereof.

In some embodiments, a genetically modified cell of the present disclosure may be used in combination with a chemotherapeutic agent. Suitable chemotherapeutic agents include, without limitation, an anthracycline (e.g., doxorubicin), a vinca alkaloid (e.g., vinblastine, vincristine, vindesine, vinorelbine), an alkylating agent (e.g., cyclophosphamide, decarbazine, melphalan, ifosfamide, temozolomide), an immune cell antibody (e.g., alemtuzamab, gemtuzumab, rituximab, tositumomab), an antimetabolite (e.g., folic acid antagonists, pyrimidine analogs, purine analogs and adenosine deaminase inhibitors, such as fludarabine), an mTOR inhibitor, a TNFR glucocorticoid induced TNFR related protein (GITR) agonist, a proteasome inhibitor (e.g., aclacinomycin A, gliotoxin or bortezomib), an immunomodulator such as thalidomide or a thalidomide derivative (e.g., lenalidomide).

Examples of general chemotherapeutic agents suitable for use in combination therapies include, without limitation, anastrozole (Arimidex®), bicalutamide (Casodex®), bleomycin sulfate (Blenoxane®), busulfan (Myleran®), busulfan injection (Busulfex®), capecitabine (Xeloda®), N4-pentoxycarbonyl-5-deoxy-5-fluorocytidine, carboplatin (Paraplatin®), carmustine (BiCNU®), chlorambucil (Leukeran®), cisplatin (Piatinol®), cladribine (Leustatin®), cyclophosphamide (Cytoxan® or Neosar®), cytarabine, cytosine arabinoside (Cytosar-U®), cytarabine liposome injection (DepoCyt®), dacarbazine (DTIC-Dome®), dactinomycin (Actinomycin D, Cosmegan), daunorubicin hydrochloride (Cerubidine®), daunorubicin citrate liposome injection (DaunoXome®), dexamethasone, docetaxel (Taxotere®), doxorubicin hydrochloride (Adriamycin®, Rubex®), etoposide (Vepesid®), fludarabine phosphate (Fludara®), 5-fluorouracil (Adrucil®, Efudex®), flutamide (Eulexin®), tezacitibine, Gemcitabine (difluorodeoxycitidine), hydroxyurea (Hydrea®), Idarubicin (Idaniycin®), ifosfamide (IFEX®), irinotecan (Camptosar®), L-asparaginase (ELSPAR®), leucovorin calcium, melphalan (Alkeran®), 6-mercaptopurine (Purinethol®), methotrexate (Folex®), mitoxantrone (Novantrone®), mylotarg, paclitaxel (Taxol®), phoenix (Yttrium90/MX-DTPA), pentostatin, polifeprosan 20 with carmustine implant (Gliadel®), tamoxifen citrate (Nolvadex®), teniposide (Vumon®), 6-thioguanine, thiotepa, tirapazamine (Tirazone®), topotecan hydrochloride for injection (Hycamptin®), vinblastine (Velban®), vincristine (Oncovin®), and vinorelbine (Navelbine®).

Examples of suitable alkylating agents include, without limitation, nitrogen mustards, ethylenimine derivatives, alkyl sulfonates, nitrosoureas and triazenes): uracil mustard (Aminouracil Mustard®, Chlorethaminacil®, Demethyldopan®, Desmethyldopan®, Haemanthamine®, Nordopan®, Uracil nitrogen Mustard®. Uracilmostaza®, Uramustin®, Uramustine®), chlormethine (Mustargen®), cyclophosphamide (Cytoxan®, Neosar®, Clafen®, Endoxan®, Procytox®, Rev Immune™), ifosfamide (Mitoxana®), melphalan (Alkeran®), Chlorambucil (Leukeran®), pipobroman (Amedel®, Vercyte®), triethylenemelamine (Hemel®, Hexalen®, Hexastat®), triethylenethiophosphoramine, Temozolomide (Temodar®), thiotepa (Thioplex®), busulfan (Busilvex®, Myleran®), carmustine (BiCNU®), lomustine (CeeNU®), streptozocin (Zanosar®), and Dacarbazine (DTIC-Dome®). Additional exemplary alkylating agents include, without limitation, Oxaliplatin (Eloxatin®); Temozolomide (Temodar® and Temodal®); Dactinomycin (also known as actinomycin-D, Cosmegen®); Melphalan (also known as L-PAM, L-sarcolysin, and phenylalanine mustard, Alkeran®); Altretamme (also known as hexamethylmelamine (HMM), Hexalen®); Carmustine (BiCNU®); Bendamustine (Treanda®); Busulfan (Busulfex® and Myleran®); Carboplatin (Paraplatin®); Lomustine (also known as CCNU, CeeNU®); Cisplatin (also known as CDDP, Platinol® and Platinol®-AQ); Chlorambucil (Leukeran®); Cyclophosphamide (Cytoxan® and Neosar®); Dacarbazine (also known as DTIC, DIC and imidazole carboxamide, DTIC-Dome®); Aitretamine (also known as hexamethylmelamine (HMM), Hexalen®); Ifosfamide (Ifex®); Prednumustine; Procarbazine (Matulane®); Mechlorethamine (also known as nitrogen mustard, mustine and mechloroethamine hydrochloride, Mustargen®); Streptozocin (Zanosar®); Thiotepa (also known as thiophosphoamide, TESPA and TSPA, Thioplex®); Cyclophosphamide (Endoxan®, Cytoxan®, Neosar®, Procytox®, Revimmune®); and Bendamustine HCl (Treanda®).

Examples of suitable mTOR inhibitors include, without limitation, temsirolimus, ridaforolimus (deferolimus), AP23573, MK8669, everolimus (Afimtor® or RADOO1), rapamycin (AY22989, Sirolmius®), and XL765.

Examples of suitable immunomodulators include, without limitation, afutuzumab, pegfilgrastim (Neulasta®), lenalidomide (CC-5013, Revlimid®), thalidomide (Thalomid®), actimid (CC4047), and IRX-2.

Examples of suitable anthracyclines include, without limitation, doxorubicin (Adriamycin® and Rubex®); bleomycin (Lenoxane®); daunorubicin (dauorubicin hydrochloride, daunomyem, and rubidomycin hydrochloride, Cerubidine®); daunorubicin liposomal (daunorubicin citrate liposome, DaunoXome®); mitoxantrone (DHAD, Novantrone®); epirubicin (Ellence™); idarubicin (Idamycin®, Idamycin PES®); mitomycin C (Mutamycin®); geldanamycin; herbimycin; ravidomycin; and desacet lravidomycin.

Examples of suitable vinca alkaloids include, without limitation, vinorelbine tartrate (Navelbine®), Vincristine (Oncovin®), and Vindesine (Eldisine®)); vinblastine (also known as vinblastine sulfate, vincaleukoblastine and VLB, Alkaban-AQ® and Velban®); and vinorelbine (Navelbme®).

Examples of suitable proteosome inhibitors include, without limitation, bortezomib (Velcade®); carfilzomib; marizomib (NPI-0052); ixazomib citrate (MLN-9708); delanzomib (CEP-18770); and ONX-0912.

In some embodiments, a genetically modified cell of the present disclosure is administered in combination with a CD20 inhibitor, e.g., an anti-CD20 antibody, or fragment thereof. Exemplary anti-CD20 antibodies include, without limitation, rituximab, ofatumumab, ocrelizumab, veltuzumab, obinutuzumab, TRU-015 (Trubion Pharmaceuticals), ocaratuzumab, and Prol31921.

In some embodiments, a genetically modified cell of the present disclosure is administered in combination with an oncolytic virus. In some embodiments, oncolytic viruses are capable of selectively replicating in and triggering the death of or slowing the growth of a cancer cell. In some cases, oncolytic viruses have no effect or a minimal effect on non-cancer cells. Suitable oncolytic viruses include, without limitation, an oncolytic adenovirus, oncolytic Herpes Simplex Viruses, oncolytic retrovirus, oncolytic parvovirus, oncolytic vaccinia virus, oncolytic Sinbis virus, oncolytic influenza virus, or oncolytic RNA virus (e.g., oncolytic reovirus, oncolytic Newcastle Disease Virus (NDV), oncolytic measles virus, or oncolytic vesicular stomatitis virus (VSV)). In some embodiments, the oncolytic virus is a recombinant oncolytic virus.

In some embodiments, a genetically modified cell of the present disclosure is administered to a subject in combination with a protein tyrosine phosphatase inhibitor, e.g., a SHP-I inhibitor or a SHP-2 inhibitor. In one embodiment, a genetically modified cell of the present disclosure can be used in combination with a kinase inhibitor. Examples of suitable kinase inhibitors include, without limitation, CDK4 inhibitors, CDK4/6 inhibitors, BTK inhibitors, phosphatidylinositol 3-kinase (PI3K) inhibitors, mTOR inhibitors, MNK inhibitors, and anaplastic lymphoma kinase (ALK) inhibitors.

In some embodiments, a genetically modified cell of the present disclosure is administered to a subject in combination with a modulator of myeloid-derived suppressor cells (MDSCs). MDSCs accumulate in the periphery and at the tumor site of many solid tumors. These cells suppress T cell responses, thereby hindering the efficacy of chimeric receptor-expressing cell therapy. Without being bound by theory, it is believed that administration of a MDSC modulator enhances the efficacy of a genetically modified cell of the present disclosure. Examples of suitable modulators of MDSCs include, without limitation, MCS110 and BLZ945.

In some embodiments, a genetically modified cell of the present disclosure is administered to a subject in combination with an agent that inhibits or reduces the activity of immunosuppressive plasma cells. Immunosuppressive plasma cells have been shown to impede T cell-dependent immunogenic chemotherapy, such as oxaliplatin (Shalapour et al., Nature 2015, 521:94-101). In one embodiment, immunosuppressive plasma cells can express one or more of IgA, interleukin (IL)-10, and PD-L1.

In some embodiments, a genetically modified cell of the present disclosure is administered to a subject in combination with an interleukin-15 (IL-15) polypeptide, an interleukin-15 receptor alpha (IL-I5Ra) polypeptide, or a combination of both an IL-15 polypeptide and an IL-15Ra polypeptide. In some embodiments, a genetically modified cell of the present disclosure is further modified to express an interleukin-15 (IL-15) polypeptide, an interleukin-15 receptor alpha (IL-I5Ra) polypeptide, or a combination of both an IL-15 polypeptide and an IL-15Ra polypeptide.

In some embodiments, a subject having a myeloid disorder (e.g., AML) is administered a genetically modified cell of the present disclosure in combination with an agent, e.g., cytotoxic or chemotherapy agent, a biologic therapy (e.g., antibody, e.g., monoclonal antibody, or cellular therapy), or an inhibitor (e.g., kinase inhibitor). In some embodiments, the subject is administered a genetically modified cell of the present disclosure in combination with a cytotoxic agent, e.g., CPX-351 (Celator Pharmaceuticals), cytarabme, daunorubicin, vosaroxin (Sunesis Pharmaceuticals), sapacitabine (Cyclacel Pharmaceuticals), idarubicin, or mitoxantrone. CPX-351 is a liposomal formulation comprising cytarabine and daunorubicin at a 5:1 molar ratio. In some embodiments, the subject is administered a chimeric receptor-expressing cell described herein in combination with a hypomethylating agent, e.g., a DNA methyltransferase inhibitor, e.g., azacytidine or decitabine. In some embodiments, the subject is administered a genetically modified cell of the present disclosure in combination with a biologic therapy, e.g., an antibody or cellular therapy, e.g., 225Ac-lintuzumab (Actimab-A; Actinium Pharmaceuticals), IPH2102 (Innate Pharma/Bristol Myers Squibb), SGN-CD33A (Seattle Genetics), or gemtuzumab ozogamicin (Mylotarg; Pfizer). In some embodiments, the subject is administered a genetically modified cell of the present disclosure in combination a FLT3 inhibitor, e.g., sorafenib (Bayer), midostaurin (Novartis), quizartinib (Daiichi Sankyo), crenoianib (Arog Pharmaceuticals), PLX3397 (Daiichi Sankyo), AKN-028 (Akinion Pharmaceuticals), or ASP2215 (Astelias). In some embodiments, the subject is administered a genetically modified cell of the present disclosure in combination with an isocitrate dehydrogenase (IDH) inhibitor, e.g., AG-221 (Celgene/Agios) or AG-120 (Agios/Celgene). In some embodiments, the subject is administered a genetically modified cell of the present disclosure in combination with a cell cycle regulator, e.g., inhibitor of polo-like kinase 1 (Plk1), e.g., volasertib (Boehringer Ingelheim); or an inhibitor of cyclin-dependent kinase 9 (Cdk9), e.g., alvocidib (Tolero Pharmaceuticals/Sanofi Aventis). In some embodiments, the subject is administered a genetically modified cell of the present disclosure in combination with a B cell receptor signaling network inhibitor, e.g., an inhibitor of B-cell lymphoma 2 (Bcl-2), e.g., venetoclax (Abbvie/Roche); or an inhibitor of Button's tyrosine kinase (Btk), e.g., ibrutinib (Pharmacyclics/Johnson & Johnson Janssen Pharmaceutical). In some embodiments, the subject is administered a genetically modified cell of the present disclosure in combination with an inhibitor of M1 aminopeptidase; an inhibitor of histone deacetylase (HDAC), e.g., pracinostat (MEI Pharma); a multi-kinase inhibitor, e.g., rigosertib (Onconova Therapeutics/Baxter/SymBio); or a peptidic CXCR4 inverse agonist, e.g., BL-8040 (BioLineRx).

In some embodiments, a subject can be administered an agent which enhances the activity or fitness of a genetically modified cell of the present disclosure. For example, the agent may inhibit a molecule that modulates or regulates, e.g., inhibits, T cell function. In some embodiments, the molecule that modulates or regulates T cell function is an inhibitory molecule. In some embodiments, inhibitory molecules, such as Programmed Death 1 (PD-1) can decrease the ability of the genetically modified cell to mount an immune effector response. Examples of suitable inhibitory molecules include, without limitation, PD-1, PD-L1, CTLA4, TIM3, CEACAM (e.g., CEACAM-1, CEACAM-3 and/or CEACAM-5), LAG3, VISTA, BTLA, TIGIT, LAIR1, CD 160, 2B4, CD80, CD86, B7-H3 (CD276), B7-H4 (VTCN1), HVEM (TNFRSF14 or CD270), KIR, A2aR, MHC class I, MHC class II, GALS, adenosine, and TGF beta. Inhibition of a molecule that modulates or regulates, e.g., inhibits, T cell function, e.g., by inhibition at the DNA, RNA or protein level, can optimize the performance of genetically modified cells of the present disclosure. In some embodiments, an agent, e.g., an inhibitory nucleic acid, e.g., an inhibitory nucleic acid, e.g., an inhibitory nucleic acid, e.g., a dsRNA, e.g., an siRNA or shRNA, a clustered regularly interspaced short palindromic repeats (CRISPR), a transcription-activator like effector nuclease (TALEN), or a zinc finger endonuclease (ZFN), can be used to inhibit expression of an inhibitory molecule in the genetically modified cell. In one embodiment, the inhibitor is an shRNA. In some embodiments, a genetically modified cell of the present disclosure may be further modified to express an inhibitory nucleic acid, e.g., an inhibitory nucleic acid, e.g., an inhibitory nucleic acid, e.g., a dsRNA, e.g., an siRNA or shRNA, a clustered regularly interspaced short palindromic repeats (CRISPR), a transcription-activator like effector nuclease (TALEN), or a zinc finger endonuclease (ZFN), can be used to inhibit expression of an inhibitory molecule in the genetically modified cell.

In one embodiment, the agent that modulates or regulates, e.g., inhibits, T-cell function is inhibited within a genetically modified cell of the present disclosure. In such embodiments, a dsRNA molecule that inhibits expression of a molecule that modulates or regulates, e.g., inhibits, T-cell function is linked to the nucleic acid that encodes a component, e.g., all of the components, of a chimeric receptor of the present disclosure. In one embodiment, a nucleic acid molecule that encodes a dsRNA molecule that inhibits expression of the molecule that modulates or regulates, e.g., inhibits, T-cell function is operably linked to a promoter, e.g., a HI- or a U6-derived promoter such that the dsRNA molecule that inhibits expression of the molecule that modulates or regulates, e.g., inhibits, T-cell function is expressed, e.g., is expressed within a the genetically modified cell. In one embodiment the nucleic acid molecule that encodes a dsRNA molecule that inhibits expression of the molecule that modulates or regulates, e.g., inhibits, T-cell function is present on the same vector, e.g., a lentiviral vector, that comprises a nucleic acid molecule that encodes a component, e.g., all of the components, of the chimeric receptor. In such an embodiment the nucleic acid molecule that encodes a dsRNA molecule that inhibits expression of the molecule that modulates or regulates, e.g., inhibits, T-cell function is located on the vector, e.g., the lentiviral vector, 5'- or 3'- to the nucleic acid that encodes a component, e.g., all of the components, of the chimeric receptor. The nucleic acid molecule that encodes a dsRNA molecule that inhibits expression of the molecule that modulates or regulates, e.g., inhibits, T-cell function can be transcribed in the same or different direction as the nucleic acid that encodes a component, e.g., all of the components, of the chimeric receptor. In one embodiment the nucleic acid molecule that encodes a dsRNA molecule that inhibits expression of the molecule that modulates or regulates, e.g., inhibits, T-cell function is present on a vector other than the vector that comprises a nucleic acid molecule that encodes a component, e.g., all of the components, of the chimeric receptor. In one embodiment, the nucleic acid molecule that encodes a dsRNA molecule that inhibits expression of the molecule that modulates or regulates, e.g., inhibits, T-cell function it transiently expressed within the genetically modified cell. In one embodiment, the nucleic acid molecule that encodes a dsRNA molecule that inhibits expression of the molecule that modulates or regulates, e.g., inhibits, T-cell function is stably integrated into the genome of a genetically modified cell of the present disclosure.

In one embodiment, an agent that modulates or regulates, e.g., inhibits, T-cell function can be an antibody or antibody fragment that binds to an inhibitory molecule. For example, the agent can be an antibody or antibody fragment that binds to PD-1, PD-L1, PD-L2 or CTLA4. In one embodiment, the agent is an antibody or antibody fragment that binds to TIM3. In one embodiment, the agent is an antibody or antibody fragment that binds to LAG3.

In some embodiments, the agent which enhances the activity of the genetically modified cell is a CEACAM inhibitor (e.g., CEACAM-1, CEACAM-3, and/or CEACAM-5 inhibitor). In one embodiment, the inhibitor of CEACAM is an anti-CEACAM antibody molecule. In one embodiment, the agent which enhances activity of a genetically modified cell of the present disclosure is miR-17-92. In some embodiments, the agent which enhances the activity of the genetically modified cell is CD40L. In some embodiments, the agent which enhances the activity of the genetically modified cell is GM-CSF. In some embodiments, a genetically modified cell of the present disclosure is further modified to express an antibody or antibody fragment that binds to an inhibitory molecule of the present disclosure.

In one embodiment, the agent which enhances activity of a genetically modified cell of the present disclosure is a cytokine. Cytokines have important functions related to immunoresponsive cell expansion, differentiation, survival, and homeostats. Cytokines that can be administered to the subject receiving a genetically modified cell of the present disclosure include, without limitation, IL-2, IL-4, IL-7, IL-9, IIL-12, L-15, IL-18, and IL-21, or a combination thereof. The cytokine can be administered once a day or more than once a day, e.g., twice a day, three times a day, or four times a day. The cytokine can be administered for more than one day, e.g. the cytokine is administered for 2 days, 3 days, 4 days, 5 days, 6 days, 1 week, 2 weeks, 3 weeks, or 4 weeks. For example, the cytokine is administered once a day for 7 days. In some embodiments, a genetically modified cell of the present disclosure is further modified to express one or more cytokines, such as IL-2, IL-4, IL-7, IL-9, IL-12, L-15, IL-18, and IL-21.

In some embodiments, the cytokine can be administered simultaneously or concurrently with the genetically modified cells, e.g., administered on the same day. The cytokine may be prepared in the same pharmaceutical composition as the genetically modified cells, or may be prepared in a separate pharmaceutical composition. Alternatively, the cytokine can be administered shortly after administration of the genetically modified cells, e.g., 1 day, 2 days, 3 days, 4 days, 5 days, 6 days, or 7 days after administration of the genetically modified cells. In some embodiments where the cytokine is administered in a dosing regimen that occurs over more than one day, the first day of the cytokine dosing regimen can be on the same day as administration with the genetically modified cells, or the first day of the cytokine dosing regimen can be 1 day, 2 days, 3 days, 4 days, 5 days, 6 days, or 7 days after administration of the genetically modified cells. In one embodiment, on the first day, the genetically modified cells are administered to the subject, and on the second day, a cytokine is administered once a day for the next 7 days. In some embodiments, the cytokine is administered for a period of time after administration of the genetically modified cells, e.g., at least 2 weeks, 3 weeks, 4 weeks, 6 weeks, 8 weeks, 10 weeks, 12 weeks, 4 months, 5 months, 6 months, 7 months, 8 months, 9 months, 10 months, 11 months, or 1 year or more after administration of the genetically modified cells. In one embodiment, the cytokine is administered after assessment of the subject's response to the genetically modified cells.

Kits

Certain aspects of the present disclosure relate to kits for the treatment and/or prevention of a myeloid disorder (e.g., AML). In certain embodiments, the kit includes a therapeutic or prophylactic composition comprising an effective amount of one or more chimeric receptors of the present disclosure, isolated nucleic acids of the present disclosure, vectors of the present disclosure, and/or cells of the present disclosure (e.g., immunoresponsive cells). In some embodiments, the kit comprises a sterile container. In some embodiments, such containers can be boxes, ampules, bottles, vials, tubes, bags, pouches, blister-packs, or other suitable container forms known in the art. The container may be made of plastic, glass, laminated paper, metal foil, or other materials suitable for holding medicaments.

In some embodiments, therapeutic or prophylactic composition is provided together with instructions for administering the therapeutic or prophylactic composition to a subject having or at risk of developing a myeloid disorder (e.g., AML). In some embodiments, the instructions may include information about the use of the composition for the treatment and/or prevention of the disorder. In some embodiments, the instructions include, without limitation, a description of the therapeutic or prophylactic composition, a dosage schedule, an administration schedule for treatment or prevention of the disorder or a symptom thereof, precautions, warnings, indications, counter-indications, over-dosage information, adverse reactions, animal pharmacology, clinical studies, and/or references. In some embodiments, the instructions can be printed directly on the container (when present), or as a label applied to the container, or as a separate sheet, pamphlet, card, or folder supplied in or with the container.

ADDITIONAL EMBODIMENTS

The paragraphs below provide additional enumerated embodiments.

1. A chimeric receptor comprising an extracellular antigen-binding domain that binds to an antigen selected from the group consisting of MS4A3, VSTM1, LAT2, MLC1, CD131, GAPT, PRAM1, SLC22A16, SLC17A9, and SPNS3.
2. The chimeric receptor of paragraph 1, wherein the antigen is MS4A3.
3. The chimeric receptor of paragraph 1, wherein the antigen is VSTM1.
4. The chimeric receptor of paragraph 1, wherein the antigen is LAT2.
5. The chimeric receptor of paragraph 1, wherein the antigen is MLC1.
6. The chimeric receptor of paragraph 1, wherein the antigen is CD131.
7. The chimeric receptor of paragraph 1, wherein the antigen is GAPT.
8. The chimeric receptor of paragraph 1, wherein the antigen is PRAM1.
9. The chimeric receptor of paragraph 1, wherein the antigen is SLC22A16.
10. The chimeric receptor of paragraph 1, wherein the antigen is SLC17A9.
11. The chimeric receptor of paragraph 1, wherein the antigen is SPNS3.
12. The chimeric receptor of any one of paragraphs 1-11, wherein the chimeric receptor is a chimeric T cell receptor or a chimeric antigen receptor (CAR).
13. The chimeric receptor of paragraph 12, wherein the chimeric receptor is a CAR.
14. The chimeric receptor of paragraph 13, wherein the CAR comprises one or more intracellular signaling domains, and the one or more intracellular signaling domains are selected from the group consisting of a CD3zeta-chain intracellular signaling domain, a CD97 intracellular signaling domain, a CD11a-CD18 intracellular signaling domain, a CD2 intracellular signaling domain, an ICOS intracellular signaling domain, a CD27 intracellular signaling domain, a CD154 intracellular signaling domain, a CD8 intracellular signaling domain, an OX40 intracellular signaling domain, a 4-1BB intracellular signaling domain, a CD28 intracellular signaling domain, a ZAP40 intracellular signaling domain, a CD30 intracellular signaling domain, a GITR intracellular signaling domain, an HVEM intracellular signaling domain, a DAP10 intracellular signaling domain, a DAP12 intracellular signaling domain, and a MyD88 intracellular signaling domain.

15. The chimeric receptor of paragraph 13 or paragraph 14, wherein the CAR comprises a transmembrane domain, and the transmembrane domain is selected from the group consisting of a CD8 transmembrane domain, a CD28 transmembrane domain a CD3zeta-chain transmembrane domain, a CD4 transmembrane domain, a 4-1BB transmembrane domain, an OX40 transmembrane domain, an ICOS transmembrane domain, a CTLA-4 transmembrane domain, a PD-1 transmembrane domain, a LAG-3 transmembrane domain, a 2B4 transmembrane domain, and a BTLA transmembrane domain.

16. The chimeric receptor of any one of paragraphs 13-15, wherein the CAR comprises a spacer region between the antigen-binding domain and the transmembrane domain, and the spacer region has an amino acid sequence selected from the group consisting of SEQ ID NOs: 55-64.

17. The chimeric receptor of any one of paragraphs 1-16, wherein the antigen-binding domain comprises one or more antibodies, antigen-binding fragments of an antibody, F(ab) fragments, F(ab') fragments, single chain variable fragments (scFvs), or single-domain antibodies (sdAbs).

18. The chimeric receptor of any one of paragraphs 1-16, wherein the antigen-binding domain comprises one or more single chain variable fragments (scFvs).

19. The chimeric receptor of paragraph 18, wherein each of the one or more scFvs comprises a heavy chain variable domain (VH) and a light chain variable domain (VL).

20. The chimeric receptor of paragraph 19, wherein the VH and VL are separated by a peptide linker.

21. The chimeric receptor of paragraph 20, wherein the peptide linker comprises an amino acid sequence of SEQ ID NO: 27.

22. The chimeric receptor of any one of paragraphs 19-21, wherein each of the one or more scFvs comprises the structure VH-L-VL or VL-L-VH, wherein VH is the heavy chain variable domain, L is the peptide linker, and VL is the light chain variable domain.

23. The chimeric receptor of any one of paragraphs 1-22, wherein the antigen-binding domain comprises two single chain variable fragments (scFvs).

24. The chimeric receptor of paragraph 23, wherein each of the two scFvs binds to a distinct epitope on the same antigen.

25. The chimeric receptor of any one of paragraphs 18-24, wherein each of the one or more scFvs is separated by a peptide linker.

26. The chimeric receptor of paragraph 25, wherein the peptide linker comprises the amino acid sequence of GGGGSGGGGSGGGGS (SEQ ID NO: 27) or EAAAKEAAAKEAAAKEAAAK (SEQ ID NO: 74).

27. An isolated cell comprising the chimeric receptor of any one of paragraphs 1-26.

28. The isolated cell of paragraph 27, wherein the chimeric receptor is recombinantly expressed.

29. The isolated cell of paragraph 27 or paragraph 28, wherein the chimeric receptor is expressed from a vector or a selected locus from the genome of the cell.

30. The isolated cell of any one of paragraphs 27-29, wherein the cell selected from the group consisting of a T cell, a Natural Killer (NK) cell, a cytotoxic T lymphocyte (CTL), a regulatory T cell, a Natural Killer T (NKT) cell, a myeloid cell, a macrophage, a human embryonic stem cell (ESC), an ESC-derived cell, a pluripotent stem cell, and induced pluripotent stem cell (iPSC), and an iPSC-derived cell.

31. The isolated cell of any one of paragraphs 27-30, wherein the cell is autologous.

32. The isolated cell of any one of paragraphs 27-30, wherein the cell is allogeneic.

33. An isolated cell comprising:
(a) a first chimeric receptor comprising an extracellular antigen-binding domain that binds to a first antigen, and
(b) a second chimeric receptor comprising an extracellular antigen-binding domain that binds to a second antigen,
wherein each antigen is selected from the group consisting of the antigens listed in Table 1 or the first and second antigens are selected from the group consisting of the antigen pairs listed in Table 3, and
wherein the first antigen is different from the second antigen.

34. An isolated cell comprising:
(a) a first chimeric receptor comprising an extracellular antigen-binding domain that binds to a first antigen, and
(b) a second chimeric receptor comprising an extracellular antigen-binding domain that binds to a second antigen,
wherein each antigen is selected from the group consisting of MS4A3, VSTM1, LAT2, MLC1, CD131, GAPT, PRAM1, SLC22A16, SLC17A9, SPNS3, FLT3, CD33, CLEC12A, ADGRE2, IL3RA, CD117, CD93, IL1RAP, CD244, CCR1, LILRB2, PIEZO1, CD38, EMB, MYADM, LILRA2, CD300LF, and CD70, and
wherein the first antigen is different from the second antigen.

35. The isolated cell of paragraph 33 or paragraph 34, wherein the first antigen is MS4A3 and the second antigen is selected from the group consisting of VSTM1, LAT2, MLC1, CD131, GAPT, PRAM1, SLC22A16, SLC17A9, SPNS3, FLT3, CD33, CLEC12A, ADGRE2, IL3RA, CD117, CD93, IL1RAP, CD244, CCR1, LILRB2, PIEZO1, CD38, EMB, MYADM, LILRA2, CD300LF, and CD70.

36. The isolated cell of paragraph 33 or paragraph 34, wherein the first antigen is VSTM1 and the second antigen is selected from the group consisting of MS4A3, LAT2, MLC1, CD131, GAPT, PRAM1, SLC22A16, SLC17A9, SPNS3, FLT3, CD33, CLEC12A, ADGRE2, IL3RA, CD117, CD93, IL1RAP, CD244, CCR1, LILRB2, PIEZO1, CD38, EMB, MYADM, LILRA2, CD300LF, and CD70.

37. The isolated cell of paragraph 33 or paragraph 34, wherein the first antigen is LAT2 and the second antigen is selected from the group consisting of MS4A3, VSTM1, MLC1, CD131, GAPT, PRAM1, SLC22A16, SLC17A9, SPNS3, FLT3, CD33, CLEC12A, ADGRE2, IL3RA, CD117, CD93, IL1RAP, CD244, CCR1, LILRB2, PIEZO1, CD38, EMB, MYADM, LILRA2, CD300LF, and CD70.

38. The isolated cell of paragraph 33 or paragraph 34, wherein the first antigen is MLC1 and the second antigen is selected from the group consisting of MS4A3, VSTM1, LAT2, CD131, GAPT, PRAM1, SLC22A16, SLC17A9, SPNS3, FLT3, CD33, CLEC12A, ADGRE2, IL3RA, CD117, CD93, IL1RAP, CD244, CCR1, LILRB2, PIEZO1, CD38, EMB, MYADM, LILRA2, CD300LF, and CD70.

39. The isolated cell of paragraph 33 or paragraph 34, wherein the first antigen is CD131 and the second antigen is selected from the group consisting of MS4A3, VSTM1, LAT2, MLC1, GAPT, PRAM1, SLC22A16, SLC17A9, SPNS3, FLT3, CD33, CLEC12A, ADGRE2, IL3RA, CD117, CD93, IL1RAP, CD244, CCR1, LILRB2, PIEZO1, CD38, EMB, MYADM, LILRA2, CD300LF, and CD70.

40. The isolated cell of paragraph 33 or paragraph 34, wherein the first antigen is GAPT and the second antigen is selected from the group consisting of MS4A3, VSTM1, LAT2, MLC1, CD131, PRAM1, SLC22A16, SLC17A9, SPNS3, FLT3, CD33, CLEC12A, ADGRE2, IL3RA, CD117, CD93, IL1RAP, CD244, CCR1, LILRB2, PIEZO1, CD38, EMB, MYADM, LILRA2, CD300LF, and CD70.

41. The isolated cell of paragraph 33 or paragraph 34, wherein the first antigen is PRAM1 and the second antigen is selected from the group consisting of MS4A3, VSTM1, LAT2, MLC1, CD131, GAPT, SLC22A16, SLC17A9, SPNS3, FLT3, CD33, CLEC12A, ADGRE2, IL3RA, CD117, CD93, IL1RAP, CD244, CCR1, LILRB2, PIEZO1, CD38, EMB, MYADM, LILRA2, CD300LF, and CD70.

42. The isolated cell of paragraph 33 or paragraph 34, wherein the first antigen is SLC22A16 and the second antigen is selected from the group consisting of MS4A3, VSTM1, LAT2, MLC1, CD131, GAPT, PRAM1, SLC17A9, SPNS3, FLT3, CD33, CLEC12A, ADGRE2, IL3RA, CD117, CD93, IL1RAP, CD244, CCR1, LILRB2, PIEZO1, CD38, EMB, MYADM, LILRA2, CD300LF, and CD70.

43. The isolated cell of paragraph 33 or paragraph 34, wherein the first antigen is SLC17A9 and the second antigen is selected from the group consisting of MS4A3, VSTM1, LAT2, MLC1, CD131, GAPT, PRAM1, SLC22A16, SPNS3, FLT3, CD33, CLEC12A, ADGRE2, IL3RA, CD117, CD93, IL1RAP, CD244, CCR1, LILRB2, PIEZO1, CD38, EMB, MYADM, LILRA2, CD300LF, and CD70.

44. The isolated cell of paragraph 33 or paragraph 34, wherein the first antigen is SPNS3 and the second antigen is selected from the group consisting of MS4A3, VSTM1, LAT2, MLC1, CD131, GAPT, PRAM1, SLC22A16, SLC17A9, FLT3, CD33, CLEC12A, ADGRE2, IL3RA, CD117, CD93, IL1RAP, CD244, CCR1, LILRB2, PIEZO1, CD38, EMB, MYADM, LILRA2, CD300LF, and CD70.

45. The isolated cell of paragraph 33 or paragraph 34, wherein the first antigen is FLT3.

46. The isolated cell of paragraph 45, wherein the antigen-binding domain that binds to the first antigen comprises a heavy chain variable domain (VH) and a light chain variable domain (VL) selected from the group consisting of:
  (a) a VH comprising the amino acid sequence of SEQ ID NO: 1 or a sequence at least 90% identical thereto and a VL comprising the amino acid sequence of SEQ. ID NO: 2 or a sequence at least 90% identical thereto;
  (b) a VH comprising the amino acid sequence of SEQ ID NO: 3 or a sequence at least 90% identical thereto and a VL comprising the amino acid sequence of SEQ. ID NO: 4 or a sequence at least 90% identical thereto;

(c) a VH comprising the amino acid sequence of SEQ ID NO: 5 or a sequence at least 90% identical thereto and a VL comprising the amino acid sequence of SEQ. ID NO: 6 or a sequence at least 90% identical thereto;
  (d) a VH comprising the amino acid sequence of SEQ ID NO: 7 or a sequence at least 90% identical thereto and a VL comprising the amino acid sequence of SEQ. ID NO: 8 or a sequence at least 90% identical thereto;
  (e) a VH comprising the amino acid sequence of SEQ ID NO: 9 or a sequence at least 90% identical thereto and a VL comprising the amino acid sequence of SEQ. ID NO: 10 or a sequence at least 90% identical thereto;
  (f) a VH comprising the amino acid sequence of SEQ ID NO: 11 or a sequence at least 90% identical thereto and a VL comprising the amino acid sequence of SEQ. ID NO: 12 or a sequence at least 90% identical thereto;
  (g) a VH comprising the amino acid sequence of SEQ ID NO: 13 or a sequence at least 90% identical thereto and a VL comprising the amino acid sequence of SEQ. ID NO: 14 or a sequence at least 90% identical thereto; and
  (h) a VH comprising the amino acid sequence of SEQ ID NO: 15 or a sequence at least 90% identical thereto and a VL comprising the amino acid sequence of SEQ. ID NO: 16 or a sequence at least 90% identical thereto.

47. The isolated cell of paragraph 45 or paragraph 46, wherein the second antigen is CD33.

48. The isolated cell of paragraph 47, wherein the antigen-binding domain that binds to the second antigen comprises a heavy chain variable domain (VH) and a light chain variable domain (VL) selected from the group consisting of:
  (a) a VH comprising the amino acid sequence of SEQ ID NO: 17 or a sequence at least 90% identical thereto and a VL comprising the amino acid sequence of SEQ. ID NO: 18 or a sequence at least 90% identical thereto; and
  (b) a VH comprising the amino acid sequence of SEQ ID NO: 19 or a sequence at least 90% identical thereto and a VL comprising the amino acid sequence of SEQ. ID NO: 20 or a sequence at least 90% identical thereto.

49. The isolated cell of paragraph 45 or paragraph 46, wherein the second antigen is CLEC12A.

50. The isolated cell of paragraph 49, wherein the antigen-binding domain that binds to the second antigen comprises a heavy chain variable domain (VH) and a light chain variable domain (VL) selected from the group consisting of:
  (a) a VH comprising the amino acid sequence of SEQ ID NO: 21 or a sequence at least 90% identical thereto and a VL comprising the amino acid sequence of SEQ. ID NO: 22 or a sequence at least 90% identical thereto;
  (b) a VH comprising the amino acid sequence of SEQ ID NO: 23 or a sequence at least 90% identical thereto and a VL comprising the amino acid sequence of SEQ. ID NO: 24 or a sequence at least 90% identical thereto; and
  (c) a VH comprising the amino acid sequence of SEQ ID NO: 25 or a sequence at least 90% identical thereto and a VL comprising the amino acid sequence of SEQ. ID NO: 26 or a sequence at least 90% identical thereto.

51. The isolated cell of paragraph 33 or paragraph 34, wherein the first antigen is CLEC12A.
52. The isolated cell of paragraph 51, wherein the antigen-binding domain that binds to the first antigen comprises a heavy chain variable domain (VH) and a light chain variable domain (VL) selected from the group consisting of:
    (a) a VH comprising the amino acid sequence of SEQ ID NO: 21 or a sequence at least 90% identical thereto and a VL comprising the amino acid sequence of SEQ. ID NO: 22 or a sequence at least 90% identical thereto;
    (b) a VH comprising the amino acid sequence of SEQ ID NO: 23 or a sequence at least 90% identical thereto and a VL comprising the amino acid sequence of SEQ. ID NO: 24 or a sequence at least 90% identical thereto; and
    (c) a VH comprising the amino acid sequence of SEQ ID NO: 25 or a sequence at least 90% identical thereto and a VL comprising the amino acid sequence of SEQ. ID NO: 26 or a sequence at least 90% identical thereto.
53. The isolated cell of paragraph 51 or paragraph 52, wherein the second antigen is CD33.
54. The isolated cell of paragraph 53, wherein the antigen-binding domain that binds to the second antigen comprises a heavy chain variable domain (VH) and a light chain variable domain (VL) selected from the group consisting of:
    (a) a VH comprising the amino acid sequence of SEQ ID NO: 17 or a sequence at least 90% identical thereto and a VL comprising the amino acid sequence of SEQ. ID NO: 18 or a sequence at least 90% identical thereto; and
    (b) a VH comprising the amino acid sequence of SEQ ID NO: 19 or a sequence at least 90% identical thereto and a VL comprising the amino acid sequence of SEQ. ID NO: 20 or a sequence at least 90% identical thereto.
55. The isolated cell of any one of paragraphs 33-54, wherein the cell is an immunoresponsive cell.
56. The isolated cell of paragraph 55, wherein binding of the first chimeric receptor to the first antigen is capable of activating the immunoresponsive cell.
57. The isolated cell of paragraph 55, wherein binding of the second chimeric receptor to the second antigen is capable of stimulating the immunoresponsive cell.
58. The isolated cell of paragraph 55, wherein binding of the first chimeric receptor to the first antigen and binding of the second chimeric receptor to the second antigen are required for activating the immunoresponsive cell.
59. The isolated cell of paragraph 55, wherein the immunoresponsive cell exhibits a greater degree of cytolytic activity against target cells that are positive for both the first antigen and the second antigen as compared to cytolytic activity against target cells that are positive for only the first antigen or the second antigen.
60. The isolated cell of paragraph 55, wherein binding of the first chimeric receptor to the first antigen or binding of the second chimeric receptor to the second antigen is capable of activating the immunoresponsive cell.
61. The isolated cell of any one of paragraphs 33-60, wherein the first chimeric receptor binds to the first antigen with a low binding affinity.
62. The isolated cell of any one of paragraphs 33-61, wherein the first chimeric receptor binds to the first antigen with a binding affinity that is lower than the binding affinity with which the second chimeric receptor binds to the second antigen.
63. The isolated cell of any one of paragraphs 33-62, wherein the first chimeric receptor binds to the first antigen with a low binding avidity.
64. The isolated cell of any one of paragraphs 33-63, wherein the first chimeric receptor and/or the second chimeric receptor is a chimeric T cell receptor or a chimeric antigen receptor (CAR).
65. The isolated cell of paragraph 64, wherein the first chimeric receptor and/or the second chimeric receptor is a CAR.
66. The isolated cell of paragraph 65, wherein the first chimeric receptor is a first CAR and the second chimeric receptor is a second CAR.
67. The isolated cell of paragraph 65 or paragraph 66, wherein each CAR comprises one or more intracellular signaling domains, and the one or more intracellular signaling domains are selected from the group consisting of a CD3zeta-chain intracellular signaling domain, a CD97 intracellular signaling domain, a CD11a-CD18 intracellular signaling domain, a CD2 intracellular signaling domain, an ICOS intracellular signaling domain, a CD27 intracellular signaling domain, a CD154 intracellular signaling domain, a CD8 intracellular signaling domain, an OX40 intracellular signaling domain, a 4-1BB intracellular signaling domain, a CD28 intracellular signaling domain, a ZAP40 intracellular signaling domain, a CD30 intracellular signaling domain, a GITR intracellular signaling domain, an HVEM intracellular signaling domain, a DAP10 intracellular signaling domain, a DAP12 intracellular signaling domain, a MyD88 intracellular signaling domain, and a 2B4 intracellular signaling domain.
68. The isolated cell of paragraph 67, wherein the one or more intracellular signaling domains of the first CAR are different from the one or more intracellular signaling domains of the second CAR.
69. The isolated cell of paragraph 67, wherein the first CAR and the second CAR each comprise a CD3zeta-chain intracellular signaling domain.
70. The isolated cell of paragraph 69, wherein the first CAR and the second CAR each further comprises an additional intracellular signaling domain selected from the group consisting of a CD97 intracellular signaling domain, a CD11a-CD18 intracellular signaling domain, a CD2 intracellular signaling domain, an ICOS intracellular signaling domain, a CD27 intracellular signaling domain, a CD154 intracellular signaling domain, a CD8 intracellular signaling domain, an OX40 intracellular signaling domain, a 4-1BB intracellular signaling domain, a CD28 intracellular signaling domain, a ZAP40 intracellular signaling domain, a CD30 intracellular signaling domain, a GITR intracellular signaling domain, an HVEM intracellular signaling domain, a DAP10 intracellular signaling domain, a DAP12 intracellular signaling domain, a MyD88 intracellular signaling domain, and a 2B4 intracellular signaling domain.
71. The isolated cell of paragraph 70, wherein the additional intracellular signaling domain of the first CAR is different from the additional intracellular signaling domain of the second CAR.

72. The isolated cell of any one of paragraphs 64-71, wherein each CAR comprises a transmembrane domain, and the transmembrane domain is selected from the group consisting of a CD8 transmembrane domain, a CD28 transmembrane domain a CD3zeta-chain transmembrane domain, a CD4 transmembrane domain, a 4-1BB transmembrane domain, an OX40 transmembrane domain, an ICOS transmembrane domain, a CTLA-4 transmembrane domain, a PD-1 transmembrane domain, a LAG-3 transmembrane domain, a 2B4 transmembrane domain, and a BTLA transmembrane domain.

73. The isolated cell of paragraph 72, wherein the transmembrane domain of the first CAR is different from the transmembrane domain of the second CAR.

74. The isolated cell of any one of paragraphs 64-73, wherein each CAR comprises a spacer region between the antigen-binding domain and the transmembrane domain, and the spacer region has an amino acid sequence selected from the group consisting of SEQ ID NOs: 55-64.

75. The isolated cell of any one of paragraphs 33-74, wherein the antigen-binding domain of the first chimeric receptor and/or the second chimeric receptor comprises one or more antibodies, antigen-binding fragments of an antibody, F(ab) fragments, F(ab') fragments, single chain variable fragments (scFvs), or single-domain antibodies (sdAbs).

76. The isolated cell of any one of paragraphs 33-75, wherein the antigen-binding domain of the first chimeric receptor and the second chimeric receptor comprises one or more single chain variable fragments (scFvs).

77. The isolated cell of paragraph 76, wherein each of the one or more scFvs comprises a heavy chain variable domain (VH) and a light chain variable domain (VL).

78. The isolated cell of paragraph 77, wherein the VH and VL are separated by a peptide linker.

79. The isolated cell of paragraph 78, wherein the peptide linker comprises the amino acid sequence of SEQ ID NO: 27.

80. The isolated cell of any one of paragraphs 77-79, wherein each of the one or more scFvs comprises the structure VH-L-VL or VL-L-VH, wherein VH is the heavy chain variable domain, L is the peptide linker, and VL is the light chain variable domain.

81. The isolated cell of any one of paragraphs 33-80, wherein the antigen-binding domain of the first chimeric receptor and/or the second chimeric receptor comprises two single chain variable fragments (scFvs).

82. The isolated cell of paragraph 81, wherein each of the two scFvs binds to a distinct epitope on the same antigen.

83. The isolated cell of any one of paragraphs 33-80, wherein the first chimeric receptor is recombinantly expressed.

84. The isolated cell of any one of paragraphs 76-83, wherein each of the one or more scFvs is separated by a peptide linker.

85. The isolated cell of paragraph 84, wherein the peptide linker comprises the amino acid sequence of GGGGSGGGGSGGGGS (SEQ ID NO: 27) or EAAAKEAAAKEAAAKEAAAK (SEQ ID NO: 74).

86. The isolated cell of any one of paragraphs 33-85, wherein the first chimeric receptor is expressed from a vector, or a selected locus from the genome of the cell.

87. The isolated cell of any one of paragraphs 33-86, wherein the second chimeric receptor is recombinantly expressed.

88. The isolated cell of any one of paragraphs 33-87, wherein the second chimeric receptor is expressed from a vector, or a selected locus from the genome of the cell.

89. The isolated cell of any one of paragraphs 33-88, wherein the cell further comprises an inhibitory chimeric receptor comprising an antigen-binding domain.

90. The isolated cell of paragraph 89, wherein the inhibitory chimeric receptor inhibits one or more activities of the cell.

91. The isolated cell of paragraph 89 or paragraph 90, wherein the inhibitory chimeric receptor binds an antigen that is not expressed on a tumor cell.

92. The isolated cell of paragraph 89 or paragraph 90, wherein the inhibitory chimeric receptor binds an antigen that is expressed on a non-tumor cell.

93. The isolated cell of paragraph 92, wherein the inhibitory chimeric receptor binds an antigen that is expressed on a non-tumor cell derived from a tissue selected from the group consisting of brain, neuronal tissue, endocrine, bone, bone marrow, immune system, endothelial tissue, muscle, lung, liver, gallbladder, pancreas, gastrointestinal tract, kidney, urinary bladder, male reproductive organs, female reproductive organs, adipose, soft tissue, and skin.

94. The isolated cell of any one of paragraphs 91-93, wherein the tumor cell is an acute myeloid leukemia (AML) cell.

95. The isolated cell of any one of paragraphs 89-94, wherein the inhibitory chimeric receptor comprises an enzymatic inhibitory domain.

96. The isolated cell of paragraph 95, wherein the enzymatic inhibitory domain inhibits immune receptor activation when proximal to an immune receptor.

97. The isolated cell of paragraph 95 or paragraph 96, wherein the enzymatic inhibitory domain comprises an enzyme catalytic domain.

98. The isolated cell of paragraph 97, wherein the enzyme catalytic domain is derived from an enzyme selected from the group consisting of CSK, SHP-1, PTEN, CD45, CD148, PTP-MEG1, PTP-PEST, c-CBL, CBL-b, PTPN22, LAR, PTPH1, SHIP-1, and RasGAP.

99. The isolated cell of any one of paragraphs 89-98, wherein the inhibitory chimeric receptor further comprises one or more intracellular inhibitory co-signaling domains.

100. The isolated cell of paragraph 99, wherein the one or more intracellular inhibitory co-signaling domains are selected from the group consisting of PD-1, CTLA4, TIGIT, LAIR1, GRB-2, Dok-1, Dok-2, SLAP, LAG3, HAVR, BTLA, GITR, and PD-L1.

101. The isolated cell of any one of paragraphs 89-100, where in the inhibitory chimeric receptor binds an antigen selected from the group consisting of EMCN, JAM2, MS4A15, C4BPA, TRPM1, SCTR, SLC2A2, KCNQ2, PERP, WLS, FFAR2, PTPRB, NCKAP1, MPZL2, PLSCR4, TMEM47, ADGRL4, MET, BACE2, ATP8B1, LIFR, ART4, CALCRL, CNTNAP3, PCDH9, IL18R1, SLC8A3, CDH26, TMEM163, ABCA13, CACHD1, CYYR1, ABCB1, ADGRG6, ATP9A, CALN1, CDCP1, IL12RB2, SLC16A14, TMEM136, and TMEM200A.

102. The isolated cell of any one of paragraphs 89-101, wherein the inhibitory chimeric receptor comprises an antigen binding domain derived from an anti-EMCN antibody, an anti-CALN1 antibody, an anti-IL12RB2 antibody, an anti-CDH26 antibody, an anti-IL18R1 antibody, an anti-SLC8A3 antibody, an anti-ABCB1 antibody, an anti-ATP9A antibody, an anti-CDCP1 antibody, an anti-JAM2 antibody, an anti-PCDH9 antibody, an anti-TMEM200A antibody, an anti-ADGRL4 antibody, an anti-ART4 antibody, an anti-BACE2 antibody, an anti-CALCRL antibody, an anti-LIFR antibody, an anti-MET antibody, an anti-MPZL2 antibody, an anti-PTPRB antibody, or an anti-WLS antibody.

103. The isolated cell of paragraph 102, wherein the anti-EMCN antibody is a monoclonal antibody selected from the group consisting of CBFYE-0213, V.7.C7.1, L6H10, L4B1, L5F12, L10B5, L3F12, L6H3, L9H8, and L10F12.

104. The isolated cell of any one of paragraphs 33-103, wherein the cell is selected from the group consisting of a T cell, a Natural Killer (NK) cell, a cytotoxic T lymphocyte (CTL), a regulatory T cell, a Natural Killer T (NKT) cell, a myeloid cell, a macrophage, a human embryonic stem cell (ESC), an ESC-derived cell, a pluripotent stem cell, and induced pluripotent stem cell (iPSC), and an iPSC-derived cell.

105. The isolated cell of any one of paragraphs 33-104, wherein the cell is autologous.

106. The isolated cell of any one of paragraphs 33-104, wherein the cell is allogeneic.

107. A chimeric receptor comprising two or more antigen-binding domains, wherein each of the two or more antigen-binding domains binds to an antigen selected from the group consisting of the antigens listed in Table 1, or wherein two antigen-binding domains of the two or more antigen-bonding domains bind to an antigen pair selected from the group consisting of the antigen pairs listed in Table 3, wherein each antigen-binding domain binds to a distinct antigen.

108. A chimeric receptor comprising two or more antigen-binding domains, wherein each each of the two or more antigen-binding domains binds to an antigen selected from the group consisting of MS4A3, VSTM1, LAT2, MLC1, CD131, GAPT, PRAM1, SLC22A16, SLC17A9, SPNS3, FLT3, CD33, CLEC12A, ADGRE2, IL3RA, CD117, CD93, IL1RAP, CD244, CCR1, LILRB2, PIEZO1, CD38, EMB, MYADM, LILRA2, CD300LF, and CD70, wherein each antigen-binding domain binds to a distinct antigen.

109. The chimeric receptor of paragraph 107 or paragraph 108, wherein one antigen-binding domain binds MS4A3 and a second antigen-binding domain binds to an antigen selected from the group consisting of VSTM1, LAT2, MLC1, CD131, GAPT, PRAM1, SLC22A16, SLC17A9, SPNS3, FLT3, CD33, CLEC12A, ADGRE2, IL3RA, CD117, CD93, IL1RAP, CD244, CCR1, LILRB2, PIEZO1, CD38, EMB, MYADM, LILRA2, CD300LF, and CD70.

110. The chimeric receptor of paragraph 107 or paragraph 108, wherein one antigen-binding domain binds VSTM1 and a second antigen-binding domain binds to an antigen selected from the group consisting of MS4A3, LAT2, MLC1, CD131, GAPT, PRAM1, SLC22A16, SLC17A9, SPNS3, FLT3, CD33, CLEC12A, ADGRE2, IL3RA, CD117, CD93, IL1RAP, CD244, CCR1, LILRB2, PIEZO1, CD38, EMB, MYADM, LILRA2, CD300LF, and CD70.

111. The chimeric receptor of paragraph 107 or paragraph 108, wherein one antigen-binding domain binds LAT2 and a second antigen-binding domain binds to an antigen selected from the group consisting of MS4A3, VSTM1, MLC1, CD131, GAPT, PRAM1, SLC22A16, SLC17A9, SPNS3, FLT3, CD33, CLEC12A, ADGRE2, IL3RA, CD117, CD93, IL1RAP, CD244, CCR1, LILRB2, PIEZO1, CD38, EMB, MYADM, LILRA2, CD300LF, and CD70.

112. The chimeric receptor of paragraph 107 or paragraph 108, wherein one antigen-binding domain binds MLC1 and a second antigen-binding domain binds to an antigen selected from the group consisting of MS4A3, VSTM1, LAT2, CD131, GAPT, PRAM1, SLC22A16, SLC17A9, SPNS3, FLT3, CD33, CLEC12A, ADGRE2, IL3RA, CD117, CD93, IL1RAP, CD244, CCR1, LILRB2, PIEZO1, CD38, EMB, MYADM, LILRA2, CD300LF, and CD70.

113. The chimeric receptor of paragraph 107 or paragraph 108, wherein one antigen-binding domain binds CD131 and a second antigen-binding domain binds to an antigen selected from the group consisting of MS4A3, VSTM1, LAT2, MLC1, GAPT, PRAM1, SLC22A16, SLC17A9, SPNS3, FLT3, CD33, CLEC12A, ADGRE2, IL3RA, CD117, CD93, IL1RAP, CD244, CCR1, LILRB2, PIEZO1, CD38, EMB, MYADM, LILRA2, CD300LF, and CD70.

114. The chimeric receptor of paragraph 107 or paragraph 108, wherein one antigen-binding domain binds GAPT and a second antigen-binding domain binds to an antigen selected from the group consisting of MS4A3, VSTM1, LAT2, MLC1, CD131, PRAM1, SLC22A16, SLC17A9, SPNS3, FLT3, CD33, CLEC12A, ADGRE2, IL3RA, CD117, CD93, IL1RAP, CD244, CCR1, LILRB2, PIEZO1, CD38, EMB, MYADM, LILRA2, CD300LF, and CD70.

115. The chimeric receptor of paragraph 107 or paragraph 108, wherein one antigen-binding domain binds PRAM1 and a second antigen-binding domain binds to an antigen selected from the group consisting of MS4A3, VSTM1, LAT2, MLC1, CD131, GAPT, SLC22A16, SLC17A9, SPNS3, FLT3, CD33, CLEC12A, ADGRE2, IL3RA, CD117, CD93, IL1RAP, CD244, CCR1, LILRB2, PIEZO1, CD38, EMB, MYADM, LILRA2, CD300LF, and CD70.

116. The chimeric receptor of paragraph 107 or paragraph 108, wherein one antigen-binding domain binds SLC22A16 and a second antigen-binding domain binds to an antigen selected from the group consisting of MS4A3, VSTM1, LAT2, MLC1, CD131, GAPT, PRAM1, SLC17A9, SPNS3, FLT3, CD33, CLEC12A, ADGRE2, IL3RA, CD117, CD93, IL1RAP, CD244, CCR1, LILRB2, PIEZO1, CD38, EMB, MYADM, LILRA2, CD300LF, and CD70.

117. The chimeric receptor of paragraph 107 or paragraph 108, wherein one antigen-binding domain binds SLC17A9 and a second antigen-binding domain binds to an antigen selected from the group consisting of MS4A3, VSTM1, LAT2, MLC1, CD131, GAPT, PRAM1, SLC22A16, SPNS3, FLT3, CD33, CLEC12A, ADGRE2, IL3RA, CD117, CD93, IL1RAP, CD244, CCR1, LILRB2, PIEZO1, CD38, EMB, MYADM, LILRA2, CD300LF, and CD70.

118. The chimeric receptor of paragraph 107 or paragraph 108, wherein one antigen-binding domain binds SPNS3 and a second antigen-binding domain binds to an antigen selected from the group consisting of MS4A3, VSTM1, LAT2, MLC1, CD131, GAPT, PRAM1, SLC22A16, SLC17A9, FLT3, CD33, CLEC12A, ADGRE2, IL3RA, CD117, CD93, IL1RAP, CD244, CCR1, LILRB2, PIEZO1, CD38, EMB, MYADM, LILRA2, CD300LF, and CD70.

119. The chimeric receptor of paragraph 107 or paragraph 108, wherein one antigen binding domain binds FLT3.

120. The chimeric receptor of paragraph 119, wherein the antigen-binding domain that binds FLT3 comprises a heavy chain variable domain (VH) and a light chain variable domain (VL) selected from the group consisting of:
 (a) a VH comprising the amino acid sequence of SEQ ID NO: 1 or a sequence at least 90% identical thereto and a VL comprising the amino acid sequence of SEQ. ID NO: 2 or a sequence at least 90% identical thereto;
 (b) a VH comprising the amino acid sequence of SEQ ID NO: 3 or a sequence at least 90% identical thereto and a VL comprising the amino acid sequence of SEQ. ID NO: 4 or a sequence at least 90% identical thereto;
 (c) a VH comprising the amino acid sequence of SEQ ID NO: 5 or a sequence at least 90% identical thereto and a VL comprising the amino acid sequence of SEQ. ID NO: 6 or a sequence at least 90% identical thereto;
 (d) a VH comprising the amino acid sequence of SEQ ID NO: 7 or a sequence at least 90% identical thereto and a VL comprising the amino acid sequence of SEQ. ID NO: 8 or a sequence at least 90% identical thereto;
 (e) a VH comprising the amino acid sequence of SEQ ID NO: 9 or a sequence at least 90% identical thereto and a VL comprising the amino acid sequence of SEQ. ID NO: 10 or a sequence at least 90% identical thereto;
 (f) a VH comprising the amino acid sequence of SEQ ID NO: 11 or a sequence at least 90% identical thereto and a VL comprising the amino acid sequence of SEQ. ID NO: 12 or a sequence at least 90% identical thereto;
 (g) a VH comprising the amino acid sequence of SEQ ID NO: 13 or a sequence at least 90% identical thereto and a VL comprising the amino acid sequence of SEQ. ID NO: 14 or a sequence at least 90% identical thereto; and
 (h) a VH comprising the amino acid sequence of SEQ ID NO: 15 or a sequence at least 90% identical thereto and a VL comprising the amino acid sequence of SEQ. ID NO: 16 or a sequence at least 90% identical thereto.

121. The chimeric receptor of paragraph 119 or paragraph 120, wherein a second a second antigen-binding domain binds CD33.

122. The chimeric receptor of paragraph 121, wherein the second antigen-binding domain that binds CD33 comprises a heavy chain variable domain (VH) and a light chain variable domain (VL) selected from the group consisting of:
 (a) a VH comprising the amino acid sequence of SEQ ID NO: 17 or a sequence at least 90% identical thereto and a VL comprising the amino acid sequence of SEQ. ID NO: 18 or a sequence at least 90% identical thereto; and
 (b) a VH comprising the amino acid sequence of SEQ ID NO: 19 or a sequence at least 90% identical thereto and a VL comprising the amino acid sequence of SEQ. ID NO: 20 or a sequence at least 90% identical thereto.

123. The chimeric receptor of paragraph 119 or paragraph 120, wherein a second antigen-binding domain binds CLEC12A.

124. The chimeric receptor of paragraph 123, wherein the second antigen-binding domain that binds CLEC12A comprises a heavy chain variable domain (VH) and a light chain variable domain (VL) selected from the group consisting of:
 (a) a VH comprising the amino acid sequence of SEQ ID NO: 21 or a sequence at least 90% identical thereto and a VL comprising the amino acid sequence of SEQ. ID NO: 22 or a sequence at least 90% identical thereto;
 (b) a VH comprising the amino acid sequence of SEQ ID NO: 23 or a sequence at least 90% identical thereto and a VL comprising the amino acid sequence of SEQ. ID NO: 24 or a sequence at least 90% identical thereto; and
 (c) a VH comprising the amino acid sequence of SEQ ID NO: 25 or a sequence at least 90% identical thereto and a VL comprising the amino acid sequence of SEQ. ID NO: 26 or a sequence at least 90% identical thereto.

125. The chimeric receptor of paragraph 107 or paragraph 108, wherein one antigen binding domain binds CLEC12A.

126. The chimeric receptor of paragraph 125, wherein the antigen-binding domain that binds CLEC12A comprises a heavy chain variable domain (VH) and a light chain variable domain (VL) selected from the group consisting of:
 (a) a VH comprising the amino acid sequence of SEQ ID NO: 21 or a sequence at least 90% identical thereto and a VL comprising the amino acid sequence of SEQ. ID NO: 22 or a sequence at least 90% identical thereto;
 (b) a VH comprising the amino acid sequence of SEQ ID NO: 23 or a sequence at least 90% identical thereto and a VL comprising the amino acid sequence of SEQ. ID NO: 24 or a sequence at least 90% identical thereto; and
 (c) a VH comprising the amino acid sequence of SEQ ID NO: 25 or a sequence at least 90% identical thereto and a VL comprising the amino acid sequence of SEQ. ID NO: 26 or a sequence at least 90% identical thereto.

127. The chimeric receptor of paragraph 125 or paragraph 126, wherein a second antigen-binding domain binds CD33.

128. The chimeric receptor of paragraph 127, wherein the second antigen-binding domain that binds CD33 comprises a heavy chain variable domain (VH) and a light chain variable domain (VL) selected from the group consisting of:
 (a) a VH comprising the amino acid sequence of SEQ ID NO: 17 or a sequence at least 90% identical thereto and a VL comprising the amino acid sequence of SEQ. ID NO: 18 or a sequence at least 90% identical thereto; and
 (b) a VH comprising the amino acid sequence of SEQ ID NO: 19 or a sequence at least 90% identical thereto and a VL comprising the amino acid sequence of SEQ. ID NO: 20 or a sequence at least 90% identical thereto.

129. The chimeric receptor of any one of paragraphs 107-128, wherein the chimeric receptor is a chimeric T cell receptor or a chimeric antigen receptor (CAR).

130. The chimeric receptor of paragraph 129, wherein the chimeric receptor is a CAR.

131. The chimeric receptor of paragraph 130, wherein the CAR is a bispecific CAR.

132. The chimeric receptor of paragraph 130 or paragraph 131, wherein the CAR comprises one or more intracellular signaling domains, and the one or more intracellular signaling domains are selected from the group consisting of a CD3-zeta chain intracellular signaling domain, a CD97 intracellular signaling domain, a CD11a-CD18 intracellular signaling domain, a CD2 intracellular signaling domain, an ICOS intracellular signaling domain, a CD27 intracellular signaling domain, a CD154 intracellular signaling domain, a CD8 intracellular signaling domain, an OX40 intracellular signaling domain, a 4-1BB intracellular signaling domain, a CD28 intracellular signaling domain, a ZAP40 intracellular signaling domain, a CD30 intracellular signaling domain, a GITR intracellular signaling domain, an HVEM intracellular signaling domain, a DAP10 intracellular signaling domain, a DAP12 intracellular signaling domain, a MyD88 intracellular signaling domain, and a 2B4 intracellular signaling domain.

133. The chimeric receptor of any one of paragraphs 130-132, wherein the CAR comprises a transmembrane domain, and the transmembrane domain is selected from the group consisting of a CD8 transmembrane domain, a CD28 transmembrane domain a CD3zeta-chain transmembrane domain, a CD4 transmembrane domain, a 4-1BB transmembrane domain, an OX40 transmembrane domain, an ICOS transmembrane domain, a CTLA-4 transmembrane domain, a PD-1 transmembrane domain, a LAG-3 transmembrane domain, a 2B4 transmembrane domain, and a BTLA transmembrane domain.

134. The chimeric receptor of any one of paragraphs 120-133, wherein the CAR comprises a spacer region between the antigen-binding domain and the transmembrane domain, and the spacer region has an amino acid sequence selected from the group consisting of SEQ ID NOs: 55-64.

135. The chimeric receptor of any one of paragraphs 107-134, wherein each antigen-binding domain comprises one or more antibodies, antigen-binding fragments of an antibody, F(ab) fragments, F(ab') fragments, single chain variable fragments (scFvs), or single-domain antibodies (sdAbs).

136. The chimeric receptor of any one of paragraphs 107-135, wherein each antigen-binding domain comprises one or more single chain variable fragments (scFvs).

137. The chimeric receptor of paragraph 136, wherein each of the one or more scFvs comprises a heavy chain variable domain (VH) and a light chain variable domain (VL).

138. The chimeric receptor of paragraph 137, wherein the VH and VL are separated by a peptide linker.

139. The chimeric receptor of paragraph 138, wherein the peptide linker comprises the amino acid sequence of SEQ ID NO: 27.

140. The chimeric receptor of any one of paragraphs 137-139, wherein each of the one or more scFvs comprises the structure VH-L-VL or VL-L-VH, wherein VH is the heavy chain variable domain, L is the peptide linker, and VL is the light chain variable domain.

141. The chimeric receptor of any one of paragraphs 107-140, wherein at least one of the antigen-binding domains comprises two single chain variable fragments (scFvs).

142. The chimeric receptor of paragraph 141, wherein each of the two scFvs binds to a distinct epitope on the same antigen.

143. The chimeric receptor of any one of paragraphs 135-142, wherein each of the one or more scFvs is separated by a peptide linker.

144. The chimeric receptor of paragraph 143, wherein the peptide linker comprises the amino acid sequence of GGGGSGGGGSGGGGS (SEQ ID NO: 27) or EAAAKEAAAKEAAAKEAAAK (SEQ ID NO: 74).

145. The chimeric receptor of any one of paragraphs 141-144, wherein at least one of the antigen-binding domains comprises two single chain variable fragments (scFvs), and each of the two scFvs binds to FLT3 and comprises a heavy chain variable domain (VH) and a light chain variable domain (VL) selected from the group consisting of:

(a) a VH comprising the amino acid sequence of SEQ ID NO: 1 or a sequence at least 90% identical thereto and a VL comprising the amino acid sequence of SEQ. ID NO: 2 or a sequence at least 90% identical thereto;

(b) a VH comprising the amino acid sequence of SEQ ID NO: 3 or a sequence at least 90% identical thereto and a VL comprising the amino acid sequence of SEQ. ID NO: 4 or a sequence at least 90% identical thereto;

(c) a VH comprising the amino acid sequence of SEQ ID NO: 5 or a sequence at least 90% identical thereto and a VL comprising the amino acid sequence of SEQ. ID NO: 6 or a sequence at least 90% identical thereto;

(d) a VH comprising the amino acid sequence of SEQ ID NO: 7 or a sequence at least 90% identical thereto and a VL comprising the amino acid sequence of SEQ. ID NO: 8 or a sequence at least 90% identical thereto;

(e) a VH comprising the amino acid sequence of SEQ ID NO: 9 or a sequence at least 90% identical thereto and a VL comprising the amino acid sequence of SEQ. ID NO: 10 or a sequence at least 90% identical thereto;

(f) a VH comprising the amino acid sequence of SEQ ID NO: 11 or a sequence at least 90% identical thereto and a VL comprising the amino acid sequence of SEQ. ID NO: 12 or a sequence at least 90% identical thereto;

(g) a VH comprising the amino acid sequence of SEQ ID NO: 13 or a sequence at least 90% identical thereto and a VL comprising the amino acid sequence of SEQ. ID NO: 14 or a sequence at least 90% identical thereto; and (h) a VH comprising the amino acid sequence of SEQ ID NO: 15 or a sequence at least 90% identical thereto and a VL comprising the amino acid sequence of SEQ. ID NO: 16 or a sequence at least 90% identical thereto.

146. The chimeric receptor of any one of paragraphs 141-145, wherein at least one of the antigen-binding domains comprises two single chain variable fragments (scFvs), and each of the two scFvs binds to CD33 and comprises a heavy chain variable domain (VH) and a light chain variable domain (VL) selected from the group consisting of:
 (a) a VH comprising the amino acid sequence of SEQ ID NO: 17 or a sequence at least 90% identical thereto and a VL comprising the amino acid sequence of SEQ. ID NO: 18 or a sequence at least 90% identical thereto; and
 (b) a VH comprising the amino acid sequence of SEQ ID NO: 19 or a sequence at least 90% identical thereto and a VL comprising the amino acid sequence of SEQ. ID NO: 20 or a sequence at least 90% identical thereto.

147. The chimeric receptor of any one of paragraphs 141-146, wherein at least one of the antigen-binding domains comprises two single chain variable fragments (scFvs), and each of the two scFvs binds to CLEC12A and comprises a heavy chain variable domain (VH) and a light chain variable domain (VL) selected from the group consisting of:
 (a) a VH comprising the amino acid sequence of SEQ ID NO: 21 or a sequence at least 90% identical thereto and a VL comprising the amino acid sequence of SEQ. ID NO: 22 or a sequence at least 90% identical thereto;
 (b) a VH comprising the amino acid sequence of SEQ ID NO: 23 or a sequence at least 90% identical thereto and a VL comprising the amino acid sequence of SEQ. ID NO: 24 or a sequence at least 90% identical thereto; and
 (c) a VH comprising the amino acid sequence of SEQ ID NO: 25 or a sequence at least 90% identical thereto and a VL comprising the amino acid sequence of SEQ. ID NO: 26 or a sequence at least 90% identical thereto.

148. An isolated cell comprising the chimeric receptor of any one of paragraphs 107-147.

149. The isolated cell of paragraph 148, wherein the cell further comprises an additional chimeric receptor comprising an antigen-binding domain.

150. The isolated cell of paragraph 149, wherein the additional chimeric receptor binds to an antigen selected from the group consisting of MS4A3, VSTM1, LAT2, MLC1, CD131, GAPT, PRAM1, SLC22A16, SLC17A9, SPNS3, FLT3, CD33, CLEC12A, ADGRE2, IL3RA, CD117, CD93, IL1RAP, CD244, CCR1, LILRB2, PIEZO1, CD38, EMB, MYADM, LILRA2, CD300LF, and CD70.

151. The isolated cell of paragraph 150, wherein each of the two chimeric receptors binds to distinct antigens.

152. The isolated cell of any one of paragraphs 148-151, wherein the cell is an immunoresponsive cell.

153. The isolated cell of paragraph 152, wherein binding of the chimeric receptor to either of the two antigens is capable of activating the immunoresponsive cell.

154. The isolated cell of paragraph 152, wherein binding of the additional chimeric receptor to its cognate antigen is capable of stimulating the immunoresponsive cell.

155. The isolated cell of paragraph 152, wherein binding of the chimeric receptor to either of the two antigens and binding of the additional chimeric receptor to its cognate antigen are required for activating the immunoresponsive cell.

156. The isolated cell of paragraph 152, wherein the immunoresponsive cell exhibits a greater degree of cytolytic activity against target cells that are positive for either of the two antigens bound by the chimeric receptor and positive for the antigen bound by the additional chimeric receptor, as compared to cytolytic activity against target cells that are only positive for a single antigen.

157. The isolated cell of any one of paragraphs 149-156, wherein the additional chimeric receptor is a chimeric T cell receptor or a chimeric antigen receptor (CAR).

158. The isolated cell of paragraph 157, wherein the additional chimeric receptor is a CAR.

159. The isolated cell of paragraph 157, wherein the chimeric receptor is a first CAR and the additional chimeric receptor is a second CAR.

160. The isolated cell of paragraph 159, wherein the second CAR comprises one or more intracellular signaling domains, and the one or more intracellular signaling domains are selected from the group consisting of a CD3zeta-chain intracellular signaling domain, a CD97 intracellular signaling domain, a CD11a-CD18 intracellular signaling domain, a CD2 intracellular signaling domain, an ICOS intracellular signaling domain, a CD27 intracellular signaling domain, a CD154 intracellular signaling domain, a CD8 intracellular signaling domain, an OX40 intracellular signaling domain, a 4-1BB intracellular signaling domain, a CD28 intracellular signaling domain, a ZAP40 intracellular signaling domain, a CD30 intracellular signaling domain, a GITR intracellular signaling domain, an HVEM intracellular signaling domain, a DAP10 intracellular signaling domain, a DAP12 intracellular signaling domain, a MyD88 intracellular signaling domain, and a 2B4 intracellular signaling domain.

161. The isolated cell of paragraph 160, wherein the one or more intracellular signaling domains of the first CAR are different from the one or more intracellular signaling domains of the second CAR.

162. The isolated cell of paragraph 161, wherein the first CAR and the second CAR each comprise a CD3zeta-chain intracellular signaling domain.

163. The isolated cell of paragraph 162, wherein the first CAR and the second CAR each further comprises an additional intracellular signaling domain selected from the group consisting of a CD97 intracellular signaling domain, a CD11a-CD18 intracellular signaling domain, a CD2 intracellular signaling domain, an ICOS intracellular signaling domain, a CD27 intracellular signaling domain, a CD154 intracellular signaling domain, a CD8 intracellular signaling domain, an OX40 intracellular signaling domain, a 4-1BB intracellular signaling domain, a CD28 intracellular signaling domain, a ZAP40 intracellular signaling domain, a CD30 intracellular signaling domain, a GITR intracellular signaling domain, an HVEM intracellular signaling domain, a DAP10 intracellular signaling domain, a DAP12 intracellular signaling domain, a MyD88 intracellular signaling domain, and a 2B4 intracellular signaling domain.

164. The isolated cell of paragraph 163, wherein the additional intracellular signaling domain of the first CAR is different from the additional intracellular signaling domain of the second CAR.

165. The isolated cell of any one of paragraphs 160-164, wherein the second CAR comprises a transmembrane domain, and the transmembrane domain is selected from the group consisting of a CD8 transmembrane domain, a CD28 transmembrane domain a CD3zeta-chain transmembrane domain, a CD4 transmembrane domain, a 4-1BB transmembrane domain, an OX40 transmembrane domain, an ICOS transmembrane domain, a CTLA-4 transmembrane domain, a PD-1 transmembrane domain, a LAG-3 transmembrane domain, a 2B4 transmembrane domain, and a BTLA transmembrane domain.

166. The isolated cell of paragraph 165, wherein the transmembrane domain of the first CAR is different from the transmembrane domain of the second CAR.

167. The isolated cell of any one of paragraphs 143-166, wherein the second CAR comprises a spacer region between the antigen-binding domain and the transmembrane domain, and the spacer region has an amino acid sequence selected from the group consisting of SEQ ID NOs: 55-64.

168. The isolated cell of any one of paragraphs 146-167, wherein the cell further comprises an inhibitory chimeric receptor comprising an antigen-binding domain.

169. The isolated cell of paragraph 149, wherein the additional chimeric receptor is an inhibitory chimeric receptor comprising an antigen-binding domain.

170. The isolated cell of paragraph 168 or paragraph 169, wherein the inhibitory chimeric receptor inhibits one or more activities of the cell.

171. The isolated cell of any one of paragraphs 168-170, wherein the inhibitory chimeric receptor binds an antigen that is not expressed on a tumor cell.

172. The isolated cell of any one of paragraphs 168-170, wherein the inhibitory chimeric receptor binds an antigen that is expressed on a non-tumor cell.

173. The isolated cell of any one of paragraphs 168-170, wherein the inhibitory chimeric receptor binds an antigen that is expressed on a non-tumor cell derived from a tissue selected from the group consisting of brain, neuronal tissue, endocrine, bone, bone marrow, immune system, muscle, lung, liver, gallbladder, pancreas, gastrointestinal tract, kidney, urinary bladder, male reproductive organs, female reproductive organs, adipose, soft tissue, and skin.

174. The isolated cell of any one of paragraphs 171-173, wherein the tumor cell is an acute myeloid leukemia (AML) cell.

175. The isolated cell of any one of paragraphs 168-174, wherein the inhibitory chimeric receptor comprises an enzymatic inhibitory domain.

176. The isolated cell of paragraph 175, wherein the enzymatic inhibitory domain inhibits immune receptor activation when proximal to an immune receptor.

177. The isolated cell of paragraph 175 or paragraph 176, wherein the enzymatic inhibitory domain comprises an enzyme catalytic domain.

178. The isolated cell of paragraph 177, wherein the enzyme catalytic domain is derived from an enzyme selected from the group consisting of CSK, SHP-1, PTEN, CD45, CD148, PTP-MEG1, PTP-PEST, c-CBL, CBL-b, PTPN22, LAR, PTPH1, SHIP-1, and RasGAP.

179. The isolated cell of any one of paragraphs 168-178, wherein the inhibitory chimeric receptor further comprises one or more intracellular inhibitory co-signaling domains.

180. The isolated cell of paragraph 179, wherein the one or more intracellular inhibitory co-signaling domains are selected from the group consisting of PD-1, CTLA4, TIGIT, LAIR1, GRB-2, Dok-1, Dok-2, SLAP, LAG3, HAVR, BTLA, GITR, and PD-L1.

181. The isolated cell of any one of paragraphs 168-180, where in the inhibitory chimeric receptor binds an antigen selected from the group consisting of EMCN, JAM2, MS4A15, C4BPA, TRPM1, SCTR, SLC2A2, KCNQ2, PERP, WLS, FFAR2, PTPRB, NCKAP1, MPZL2, PLSCR4, TMEM47, ADGRL4, MET, BACE2, ATP8B1, LIFR, ART4, CALCRL, CNTNAP3, PCDH9, IL18R1, SLC8A3, CDH26, TMEM163, ABCA13, CACHD1, CYYR1, ABCB1, ADGRG6, ATP9A, CALN1, CDCP1, IL12RB2, SLC16A14, TMEM136, and TMEM200A.

182. The isolated cell of any one of paragraphs 149-181, wherein the antigen-binding domain of the additional chimeric receptor and/or inhibitory chimeric receptor comprises one or more antibodies, antigen-binding fragments of an antibody, F(ab) fragments, F(ab') fragments, single chain variable fragments (scFvs), or single-domain antibodies (sdAbs).

183. The isolated cell of any one of paragraphs 149-181, wherein the antigen-binding domain of the additional chimeric receptor and/or inhibitory chimeric receptor comprises one or more single chain variable fragments (scFvs).

184. The isolated cell of paragraph 183, wherein the antigen-binding domain of the inhibitory chimeric receptor is derived from an anti-EMCN antibody, an anti-CALN1 antibody, an anti-IL12RB2 antibody, an anti-CDH26 antibody, an anti-IL18R1 antibody, an anti-SLC8A3 antibody, an anti-ABCB1 antibody, an anti-ATP9A antibody, an anti-CDCP1 antibody, an anti-JAM2 antibody, an anti-PCDH9 antibody, an anti-TMEM200A antibody, an anti-ADGRL4 antibody, an anti-ART4 antibody, an anti-BACE2 antibody, an anti-CALCRL antibody, an anti-LIFR antibody, an anti-MET antibody, an anti-MPZL2 antibody, an anti-PTPRB antibody, or an anti-WLS antibody.

185. The isolated cell of paragraph 184, wherein the anti-EMCN antibody is a monoclonal antibody selected from the group consisting of CBFYE-0213, V.7.C7.1, L6H10, L4B1, L5F12, L10B5, L3F12, L6H3, L9H8, and L10F12.

186. The isolated cell of any one of paragraphs 183-185, wherein each of the one or more scFvs comprises a heavy chain variable domain (VH) and a light chain variable domain (VL).

187. The isolated cell of paragraph 186, wherein the VH and VL are separated by a peptide linker.

188. The isolated cell of paragraph 187, wherein the peptide linker comprises the amino acid sequence of SEQ ID NO: 27.

189. The isolated cell of any one of paragraphs 186-188, wherein each of the one or more scFvs comprises the structure VH-L-VL or VL-L-VH, wherein VH is the heavy chain variable domain, L is the peptide linker, and VL is the light chain variable domain.

190. The isolated cell of any one of paragraphs 168-189, wherein the antigen-binding domain of the additional chimeric receptor and/or inhibitory chimeric receptor comprises two single chain variable fragments (scFvs).

191. The isolated cell of paragraph 190, wherein each of the two scFvs binds to a distinct epitope on the same antigen.

192. The isolated cell of any one of paragraphs 182-191, wherein each of the one or more scFvs is separated by a peptide linker.

193. The isolated cell of paragraph 192, wherein the peptide linker comprises the amino acid sequence of GGGGSGGGGSGGGGS (SEQ ID NO: 27) or EAAAKEAAAKEAAAKEAAAK (SEQ ID NO: 74).

194. The isolated cell of any one of paragraphs 146-189 wherein each chimeric receptor is recombinantly expressed.

195. The isolated cell of any one of paragraphs 146-194 wherein each chimeric receptor is expressed from a vector or a selected locus from the genome of the cell.

196. The isolated cell of any one of paragraphs 146-195, wherein the cell selected from the group consisting of a T cell, a Natural Killer (NK) cell, a cytotoxic T lymphocyte (CTL), a regulatory T cell, a Natural Killer T (NKT) cell, a myeloid cell, a macrophage, a human embryonic stem cell (ESC), an ESC-derived cell, a pluripotent stem cell, and induced pluripotent stem cell (iPSC), and an iPSC-derived cell.

197. The isolated cell of any one of paragraphs 146-196, wherein the cell is autologous.

198. The isolated cell of any one of paragraphs 146-196, wherein the cell is allogeneic.

199. An inhibitory chimeric receptor comprising an extracellular antigen-binding domain that binds to an antigen selected from the group consisting of EMCN, JAM2, MS4A15, C4BPA, TRPM1, SCTR, SLC2A2, KCNQ2, PERP, WLS, FFAR2, PTPRB, NCKAP1, MPZL2, PLSCR4, TMEM47, ADGRL4, MET, BACE2, ATP8B1, LIFR, ART4, CALCRL, CNTNAP3, PCDH9, IL18R1, SLC8A3, CDH26, TMEM163, ABCA13, CACHD1, CYYR1, ABCB1, ADGRG6, ATP9A, CALN1, CDCP1, IL12RB2, SLC16A14, TMEM136, and TMEM200A.

200. The inhibitory chimeric receptor of paragraph 199, wherein the antigen is EMCN.

201. The inhibitory chimeric receptor of paragraph 199, wherein the antigen is JAM2.

202. The inhibitory chimeric receptor of paragraph 199, wherein the antigen is MS4A15.

203. The inhibitory chimeric receptor of paragraph 199, wherein the antigen is C4BPA.

204. The inhibitory chimeric receptor of paragraph 199, wherein the antigen is TRPM1.

205. The inhibitory chimeric receptor of paragraph 199, wherein the antigen is SCTR.

206. The inhibitory chimeric receptor of paragraph 199, wherein the antigen is SLC2A2.

207. The inhibitory chimeric receptor of paragraph 199, wherein the antigen is KCNQ2.

208. The inhibitory chimeric receptor of paragraph 199, wherein the antigen is PERP.

209. The inhibitory chimeric receptor of paragraph 199, wherein the antigen is WLS.

210. The inhibitory chimeric receptor of paragraph 199, wherein the antigen is FFAR2.

211. The inhibitory chimeric receptor of paragraph 199, wherein the antigen is PTPRB.

212. The inhibitory chimeric receptor of paragraph 199, wherein the antigen is NCKAP1

213. The inhibitory chimeric receptor of paragraph 199, wherein the antigen is MPZL2.

214. The inhibitory chimeric receptor of paragraph 199, wherein the antigen is PLSCR4.

215. The inhibitory chimeric receptor of paragraph 199, wherein the antigen is TMEM47.

216. The inhibitory chimeric receptor of paragraph 199, wherein the antigen is ADGRL4.

217. The inhibitory chimeric receptor of paragraph 199, wherein the antigen is MET.

218. The inhibitory chimeric receptor of paragraph 199, wherein the antigen is BACE2.

219. The inhibitory chimeric receptor of paragraph 199, wherein the antigen is ATP8B1.

220. The inhibitory chimeric receptor of paragraph 199, wherein the antigen is LIFR.

221. The inhibitory chimeric receptor of paragraph 199, wherein the antigen is ART4.

222. The inhibitory chimeric receptor of paragraph 199, wherein the antigen is CALCRL.

223. The inhibitory chimeric receptor of paragraph 199, wherein the antigen is CNTNAP3.

224. The inhibitory chimeric receptor of paragraph 199, wherein the antigen is PCDH9.

225. The inhibitory chimeric receptor of paragraph 199, wherein the antigen is IL18R1.

226. The inhibitory chimeric receptor of paragraph 199, wherein the antigen is SLC8A3.

227. The inhibitory chimeric receptor of paragraph 199, wherein the antigen is CDH26.

228. The inhibitory chimeric receptor of paragraph 199, wherein the antigen is TMEM163.

229. The inhibitory chimeric receptor of paragraph 199, wherein the antigen is ABCA13.

230. The inhibitory chimeric receptor of paragraph 199, wherein the antigen is CACHD1.

231. The inhibitory chimeric receptor of paragraph 199, wherein the antigen is CYYR1.

232. The inhibitory chimeric receptor of paragraph 199, wherein the antigen is ABCB1.

233. The inhibitory chimeric receptor of paragraph 199, wherein the antigen is ADGRG6.

234. The inhibitory chimeric receptor of paragraph 199, wherein the antigen is ATP9A.

235. The inhibitory chimeric receptor of paragraph 199, wherein the antigen is CALN1.

236. The inhibitory chimeric receptor of paragraph 199, wherein the antigen is CDCP1.

237. The inhibitory chimeric receptor of paragraph 199, wherein the antigen is IL12RB2.

238. The inhibitory chimeric receptor of paragraph 199, wherein the antigen is SLC16A14.

239. The inhibitory chimeric receptor of paragraph 199, wherein the antigen is TMEM136.

240. The inhibitory chimeric receptor of paragraph 199, wherein the antigen is TMEM200A.

241. The inhibitory chimeric receptor of any one of paragraphs 199-240, wherein when expressed on a cell the inhibitory chimeric receptor inhibits one or more activities of the cell.

242. The inhibitory chimeric receptor of any one of paragraphs 199-241, wherein the antigen that is not expressed on a tumor cell.

243. The inhibitory chimeric receptor of any one of paragraphs 199-242, wherein the antigen is expressed on a non-tumor cell.

244. The inhibitory chimeric receptor of paragraph 243, wherein the antigen is expressed on a non-tumor cell derived from a tissue selected from the group consisting of brain, neuronal tissue, endocrine, bone, bone marrow, immune system, muscle, lung, liver, gallbladder, pancreas, gastrointestinal tract, kidney, urinary bladder, male reproductive organs, female reproductive organs, adipose, soft tissue, and skin.

245. The inhibitory chimeric receptor of any one of paragraphs 199-244, wherein the inhibitory chimeric receptor comprises an enzymatic inhibitory domain.

246. The inhibitory chimeric receptor of paragraph 245, wherein the enzymatic inhibitory domain inhibits immune receptor activation when proximal to an immune receptor.
247. The inhibitory chimeric receptor of paragraph 245 or paragraph 246, wherein the enzymatic inhibitory domain comprises an enzyme catalytic domain.
248. The inhibitory chimeric receptor of paragraph 247, wherein the enzyme catalytic domain is derived from an enzyme selected from the group consisting of CSK, SHP-1, PTEN, CD45, CD148, PTP-MEG1, PTP-PEST, c-CBL, CBL-b, PTPN22, LAR, PTPH1, SHIP-1, and RasGAP.
249. The inhibitory chimeric receptor of any one of paragraphs 199-248, wherein the inhibitory chimeric receptor further comprises one or more intracellular inhibitory co-signaling domains.
250. The inhibitory chimeric receptor of paragraph 249, wherein the one or more intracellular inhibitory co-signaling domains are selected from the group consisting of PD-1, CTLA4, TIGIT, LAIR1, GRB-2, Dok-1, Dok-2, SLAP, LAG3, HAVR, BTLA, GITR, and PD-L1.
251. The inhibitory chimeric receptor of any one of paragraphs 199-250, wherein the antigen-binding domain comprises one or more antibodies, antigen-binding fragments of an antibody, F(ab) fragments, F(ab') fragments, single chain variable fragments (scFvs), or single-domain antibodies (sdAbs).
252. The inhibitory chimeric receptor of any of any one of paragraphs 199-251, wherein the antigen-binding domain comprises one or more single chain variable fragments (scFvs).
253. The inhibitory chimeric receptor of paragraph 252, wherein the antigen-binding domain is derived from an anti-EMCN antibody, an anti-CALN1 antibody, an anti-IL12RB2 antibody, an anti-CDH26 antibody, an anti-IL18R1 antibody, an anti-SLC8A3 antibody, an anti-ABCB1 antibody, an anti-ATP9A antibody, an anti-CDCP1 antibody, an anti-JAM2 antibody, an anti-PCDH9 antibody, an anti-TMEM200A antibody, an anti-ADGRL4 antibody, an anti-ART4 antibody, an anti-BACE2 antibody, an anti-CALCRL antibody, an anti-LIFR antibody, an anti-MET antibody, an anti-MPZL2 antibody, an anti-PTPRB antibody, or an anti-WLS antibody.
254. The inhibitory chimeric receptor of paragraph 253, wherein the anti-EMCN antibody is a monoclonal antibody selected from the group consisting of CBFYE-0213, V.7.C7.1, L6H10, L4B1, L5F12, L10B5, L3F12, L6H3, L9H8, and L10F12.
255. The inhibitory chimeric receptor of any one of paragraphs 252-254, wherein each of the one or more scFvs comprises a heavy chain variable domain (VH) and a light chain variable domain (VL).
256. The inhibitory chimeric receptor of paragraph 255, wherein the VH and VL are separated by a peptide linker.
257. The inhibitory chimeric receptor of paragraph 256, wherein the peptide linker comprises the amino acid sequence of SEQ ID NO: 27.
258. The inhibitory chimeric receptor of any one of paragraphs 255-257, wherein each of the one or more scFvs comprises the structure VH-L-VL or VL-L-VH, wherein VH is the heavy chain variable domain, L is the peptide linker, and VL is the light chain variable domain.
259. The inhibitory chimeric receptor of any one of paragraphs 199-258, wherein the antigen-binding domain comprises two single chain variable fragments (scFvs).
260. The inhibitory chimeric receptor of paragraph 259, wherein each of the two scFvs binds to a distinct epitope on the same antigen.
261. The inhibitory chimeric receptor of any one of paragraphs 251-260, wherein each of the one or more scFvs is separated by a peptide linker.
262. The inhibitory chimeric receptor of paragraph 261, wherein the peptide linker comprises the amino acid sequence of GGGGSGGGGSGGGGS (SEQ ID NO: 27) or EAAAKEAAAKEAAAKEAAAK (SEQ ID NO: 74).
263. An isolated cell comprising the inhibitory chimeric receptor of any one of paragraphs 199-262.
264. The isolated cell of paragraph 263, wherein the inhibitory chimeric receptor is recombinantly expressed.
265. The isolated cell of paragraph 263 or paragraph 264, wherein the inhibitory chimeric receptor is expressed from a vector or a selected locus from the genome of the cell.
266. The isolated cell of any one of paragraphs 263-265, wherein the cell further comprises a chimeric receptor comprising an extracellular antigen-binding domain that binds to an antigen selected from the group consisting of FLT3, CD33, CLEC12A, MS4A3, VSTM1, LAT2, MLC1, CD131, GAPT, PRAM1, SLC22A16, SLC17A9, SPNS3, ADGRE2, IL3RA, CD117, CD93, IL1RAP, CD244, CCR1, LILRB2, PIEZO1, CD38, EMB, MYADM, LILRA2, CD300LF, and CD70.
267. An isolated cell comprising:
   (a) an inhibitory chimeric receptor comprising an extracellular antigen-binding domain that binds to a first antigen, wherein the first antigen is selected from the group consisting of EMCN, JAM2, MS4A15, C4BPA, TRPM1, SCTR, SLC2A2, KCNQ2, PERP, WLS, FFAR2, PTPRB, NCKAP1, MPZL2, PLSCR4, TMEM47, ADGRL4, MET, BACE2, ATP8B1, LIFR, ART4, CALCRL, CNTNAP3, PCDH9, IL18R1, SLC8A3, CDH26, TMEM163, ABCA13, CACHD1, CYYR1, ABCB1, ADGRG6, ATP9A, CALN1, CDCP1, IL12RB2, SLC16A14, TMEM136, and TMEM200A, and
   (b) a chimeric receptor comprising one or more extracellular antigen-binding domains, wherein each antigen-binding domain binds to an antigen selected from the group consisting of the antigens listed in Table 1.
268. An isolated cell comprising:
   (a) an inhibitory chimeric receptor comprising an extracellular antigen-binding domain that binds to a first antigen, wherein the first antigen is selected from the group consisting of EMCN, JAM2, MS4A15, C4BPA, TRPM1, SCTR, SLC2A2, KCNQ2, PERP, WLS, FFAR2, PTPRB, NCKAP1, MPZL2, PLSCR4, TMEM47, ADGRL4, MET, BACE2, ATP8B1, LIFR, ART4, CALCRL, CNTNAP3, PCDH9, IL18R1, SLC8A3, CDH26, TMEM163, ABCA13, CACHD1, CYYR1, ABCB1, ADGRG6, ATP9A, CALN1, CDCP1, IL12RB2, SLC16A14, TMEM136, and TMEM200A, and
   (b) a chimeric receptor comprising one or more extracellular antigen-binding domains, wherein each antigen-bind domain binds to an antigen selected from the group consisting of FLT3, CD33, CLEC12A, MS4A3, VSTM1, LAT2, MLC1, CD131, GAPT, PRAM1, SLC22A16, SLC17A9, SPNS3, ADGRE2, IL3RA, CD117, CD93, IL1RAP, CD244, CCR1, LILRB2, PIEZO1, CD38, EMB, MYADM, LILRA2, CD300LF, and CD70.

269. The isolated cell of any one of paragraphs 266-268, wherein the chimeric receptor is a chimeric T cell receptor or a chimeric antigen receptor (CAR).

270. The isolated cell of paragraph 269, wherein the chimeric receptor is a CAR.

271. The isolated cell of paragraph 270, wherein the CAR comprises one or more intracellular signaling domains, and the one or more intracellular signaling domains are selected from the group consisting of a CD3zeta-chain intracellular signaling domain, a CD97 intracellular signaling domain, a CD11a-CD18 intracellular signaling domain, a CD2 intracellular signaling domain, an ICOS intracellular signaling domain, a CD27 intracellular signaling domain, a CD154 intracellular signaling domain, a CD8 intracellular signaling domain, an OX40 intracellular signaling domain, a 4-1BB intracellular signaling domain, a CD28 intracellular signaling domain, a ZAP40 intracellular signaling domain, a CD30 intracellular signaling domain, a GITR intracellular signaling domain, an HVEM intracellular signaling domain, a DAP10 intracellular signaling domain, a DAP12 intracellular signaling domain, a MyD88 intracellular signaling domain, and a 2B4 intracellular signaling domain.

272. The isolated cell of paragraph 270 or paragraph 271, wherein the CAR comprises a transmembrane domain, and the transmembrane domain is selected from the group consisting of a CD8 transmembrane domain, a CD28 transmembrane domain a CD3zeta-chain transmembrane domain, a CD4 transmembrane domain, a 4-1BB transmembrane domain, an OX40 transmembrane domain, an ICOS transmembrane domain, a CTLA-4 transmembrane domain, a PD-1 transmembrane domain, a LAG-3 transmembrane domain, a 2B4 transmembrane domain, and a BTLA transmembrane domain.

273. The isolated cell of any one of paragraphs 208-272, wherein the CAR comprises a spacer region between the antigen-binding domain and the transmembrane domain, and the spacer region has an amino acid sequence selected from the group consisting of SEQ ID NOs: 55-64.

274. The isolated cell of any one of paragraphs 266-273, wherein the antigen-binding domain of the inhibitory chimeric receptor and/or the chimeric receptor comprises one or more antibodies, antigen-binding fragments of an antibody, F(ab) fragments, F(ab') fragments, single chain variable fragments (scFvs), or single-domain antibodies (sdAbs).

275. The isolated cell of any one of paragraphs 266-273, wherein the antigen-binding domain of the inhibitory chimeric receptor and/or the chimeric receptor comprises one or more single chain variable fragments (scFvs).

276. The isolated cell of paragraph 275, wherein the antigen-binding domain of the inhibitory chimeric receptor is derived from an anti-EMCN antibody, an anti-CALN1 antibody, an anti-IL12RB2 antibody, an anti-CDH26 antibody, an anti-IL18R1 antibody, an anti-SLC8A3 antibody, an anti-ABCB1 antibody, an anti-ATP9A antibody, an anti-CDCP1 antibody, an anti-JAM2 antibody, an anti-PCDH9 antibody, an anti-TMEM200A antibody, an anti-ADGRL4 antibody, an anti-ART4 antibody, an anti-BACE2 antibody, an anti-CALCRL antibody, an anti-LIFR antibody, an anti-MET antibody, an anti-MPZL2 antibody, an anti-PTPRB antibody, or an anti-WLS antibody.

277. The inhibitory chimeric receptor of paragraph 276, wherein the anti-EMCN antibody is a monoclonal antibody selected from the group consisting of CBFYE-0213, V.7.C7.1, L6H10, L4B1, L5F12, L10B5, L3F12, L6H3, L9H8, and L10F12.

278. The isolated cell of any one of paragraphs 275-277, wherein each of the one or more scFvs comprises a heavy chain variable domain (VH) and a light chain variable domain (VL).

279. The isolated cell of paragraph 278, wherein the VH and VL are separated by a peptide linker.

280. The isolated cell of paragraph 279, wherein the peptide linker comprises the amino acid sequence of SEQ ID NO: 27.

281. The isolated cell of any one of paragraphs 278-280, wherein each of the one or more scFvs comprises the structure VH-L-VL or VL-L-VH, wherein VH is the heavy chain variable domain, L is the peptide linker, and VL is the light chain variable domain.

282. The isolated cell of any one of paragraphs 266-281, wherein the antigen-binding domain of the inhibitory chimeric receptor and/or the chimeric receptor comprises two single chain variable fragments (scFvs).

283. The isolated cell of paragraph 282, wherein each of the two scFvs binds to a distinct epitope on the same antigen.

284. The isolated cell of any one of paragraphs 274-283, wherein each of the one or more scFvs is separated by a peptide linker.

285. The isolated cell of paragraph 284, wherein the peptide linker comprises the amino acid sequence of GGGGSGGGGSGGGGS (SEQ ID NO: 27) or EAAAKEAAAKEAAAKEAAAK (SEQ ID NO: 74).

286. The isolated cell of any one of paragraphs 267-285, wherein the cell is an immunoresponsive cell.

287. The isolated cell of paragraph 286, wherein binding of the inhibitory chimeric receptor to the first antigen is capable of inhibiting the immunoresponsive cell.

288. The isolated cell of paragraph 286 or paragraph 287, wherein binding of the chimeric receptor to the second antigen is capable of activating the immunoresponsive cell.

289. The isolated cell of any one of paragraphs 267-288, wherein the chimeric receptor binds to the second antigen with a low binding affinity.

290. The isolated cell of any one of paragraphs 267-289, wherein the chimeric receptor binds to the second antigen with a binding affinity that is lower than the binding affinity with which the inhibitory chimeric receptor binds to the first antigen.

291. The isolated cell of any one of paragraphs 267-290, wherein the chimeric receptor binds to the first antigen with a low binding avidity.

292. The isolated cell of any one of paragraphs 266-291, wherein the chimeric receptor is recombinantly expressed.

293. The isolated cell of any one of paragraphs 266-292, wherein the chimeric receptor is expressed from a vector or a selected locus from the genome of the cell.

294. The isolated cell of any one of paragraphs 263-293, wherein the cell selected from the group consisting of a T cell, a Natural Killer (NK) cell, a cytotoxic T lymphocyte (CTL), a regulatory T cell, a Natural Killer T (NKT) cell, a myeloid cell, a macrophage, a human embryonic stem cell (ESC), an ESC-derived cell, a pluripotent stem cell, and induced pluripotent stem cell (iPSC), and an iPSC-derived cell.

295. The isolated cell of any one of paragraphs 263-294, wherein the cell is autologous.

296. The isolated cell of any one of paragraphs 263-294, wherein the cell is allogeneic.

297. An isolated nucleic acid encoding the chimeric receptor of any one of paragraphs 1-22.

298. An isolated nucleic acid encoding the chimeric receptor of any one of paragraphs 107-140.

299. An isolated nucleic acid encoding the inhibitory chimeric receptor of any one of paragraphs 199-258.

300. A vector comprising the nucleic acid of paragraph 297.

301. The vector of paragraph 300, wherein the vector further comprises the nucleic acid of paragraph 298.

302. The vector of paragraph 300 or paragraph 301, wherein the vector further comprises the nucleic acid of paragraph 299.

303. A vector comprising the nucleic acid of paragraph 298.

304. The vector of paragraph 303, wherein the vector further comprises the nucleic acid of paragraph 299.

305. A vector comprising the nucleic acid of paragraph 299.

306. A genetically modified cell comprising the nucleic acid of paragraph 297.

307. The genetically modified cell of paragraph 306, wherein the cell further comprises the nucleic acid of paragraph 298.

308. The genetically modified cell of paragraph 306 or paragraph 307, wherein the cell further comprises the nucleic acid of paragraph 299.

309. A genetically modified cell comprising the nucleic acid of paragraph 298.

310. The genetically modified cell of paragraph 309, wherein the cell further comprises the nucleic acid of paragraph 299.

311. A genetically modified cell comprising the nucleic acid of paragraph 299.

312. A genetically modified cell comprising the vector of any one of paragraphs 300-305.

313. A method of treating a subject in need thereof, the method comprising administering a therapeutically effective dose of any of the isolated cells of any one of paragraphs 24-106, 146-198, 263-296, or 306-312.

314. A method of stimulating a cell-mediated immune response to a tumor cell in a subject, the method comprising administering to a subject having a tumor a therapeutically effective dose of any of the isolated cells of any one of paragraphs 24-106, 146-198, 263-296, or 306-312.

315. A method of providing an anti-tumor immunity in a subject, the method comprising administering to a subject in need thereof a therapeutically effective dose of any of the isolated cells of any one of paragraphs 24-106, 146-198, 263-296, or 306-312.

316. A method of reducing tumor burden in a subject, comprising administering to the subject an effective amount of any of the isolated cells of any one of paragraphs 24-106, 146-198, 263-296, or 306-312.

317. The method of paragraph 316, wherein the method reduces the number of tumor cells.

318. The method of paragraph 316, wherein the method reduces tumor size.

319. The method of paragraph 316, wherein the method reduces tumor volume.

320. The method of paragraph 316, wherein the method eradicates the tumor in the subject.

321. A method of treating a subject having a tumor, the method comprising administering a therapeutically effective dose of any of the cells of any one of paragraphs 24-106, 146-198, 263-296, or 306-312.

322. A method of treating or preventing a myeloid disorder in a subject, comprising administering to the subject an effective amount of any of the isolated cells of any one of paragraphs 24-106, 146-198, 263-296, or 306-312.

323. The method of paragraph 322, wherein the myeloid disorder is myelodysplastic syndromes, myeloproliferative neoplasms, chronic myelomonocytic leukemia, acute myeloid leukemia (AML), acute myeloblastic leukemia, acute promyelocytic leukemia, acute myelomonocytic leukemia, chronic myelocytic leukemia, and polycythemia vera.

324. The method of paragraph 322, wherein the myeloid disorder is acute myeloid leukemia (AML).

325. The method of any one of paragraphs 321-324, wherein the method reduces or eradicates the tumor burden in the subject.

326. A pharmaceutical composition comprising an effective amount of the cell of any one of paragraphs 24-106, 146-198, 263-296, or 306-312 and a pharmaceutically acceptable carrier, pharmaceutically acceptable excipient, or a combination thereof 327. The pharmaceutical composition of paragraph 326, which is for treating and/or preventing a myeloid disorder.

328. A kit for treating and/or preventing a myeloid disorder, comprising the cell of any one of paragraphs 24-106, 146-198, 263-296, or 306-312.

329. The kit of paragraph 328, wherein the kit further comprises written instructions for using the cell for treating and/or preventing a myeloid disorder in a subject.

330. A kit for treating and/or preventing a myeloid disorder, comprising the isolated nucleic acid of any one of paragraphs 297-299.

331. The kit of paragraph 330, wherein the kit further comprises written instructions for using the nucleic acid for producing one or more antigen-specific cells for treating and/or preventing a myeloid disorder in a subject.

332. A kit for treating and/or preventing a myeloid disorder, comprising the vector of any one of paragraphs 300-305.

333. The kit of paragraph 332, wherein the kit further comprises written instructions for using the vector for producing one or more antigen-specific cells for treating and/or preventing a myeloid disorder in a subject.

334. A method of treating and/or preventing a myeloid disorder, comprising administering an effective amount of at least one antibody that binds to an antigen, wherein the antigen is selected from the group consisting of MS4A3, VSTM1, LAT2, MLC1, CD131, GAPT, PRAM1, SLC22A16, SLC17A9, and SPNS3.

335. The method of paragraph 334, wherein the myeloid disorder is selected from the group consisting of myelodysplastic syndromes, myeloproliferative neoplasms, chronic myelomonocytic leukemia, or acute myeloid leukemia (AML), acute myeloblastic leukemia, acute promyelocytic leukemia, acute myelomonocytic leukemia, chronic myelocytic leukemia, and polycythemia vera.

336. The method of paragraph 335, wherein the myeloid disorder is acute myeloid leukemia (AML).

337. The method of any one of paragraphs 334-336, wherein the method reduces or eradicates the tumor burden in the subject.

338. A chimeric antigen receptor (CAR), wherein the CAR comprises an extracellular antigen-binding domain, one or more intracellular signaling domains, a transmembrane domain, and a spacer region between the antigen-binding domain and the transmembrane domain, wherein the spacer region has an amino acid sequence selected from the group consisting of SEQ ID NOs: 55-64.

339. A chimeric receptor comprising an extracellular antigen-binding domain, wherein the antigen-binding domain comprises two or more antibodies, antigen-binding fragments of an antibody, F(ab) fragments, F(ab') fragments, single chain variable fragments (scFvs), or single-domain antibodies (sdAbs).

340. The chimeric receptor of paragraph 339, wherein each of the two or more antibodies, antigen-binding fragments of an antibody, F(ab) fragments, F(ab') fragments, single chain variable fragments (scFvs), or single-domain antibodies (sdAbs) binds to a distinct epitope on the same antigen.

341. The chimeric receptor of paragraph 339 or paragraph 340, wherein the antigen-binding domain comprises two or more single chain variable fragments (scFvs).

342. The chimeric receptor of paragraph 341, wherein each of the two or more scFvs comprises a heavy chain variable domain (VH) and a light chain variable domain (VL).

343. The chimeric receptor of paragraph 342, wherein each VH and VL are separated by a peptide linker.

344. The chimeric receptor of paragraph 343, wherein the peptide linker comprises an amino acid sequence of SEQ ID NO: 27.

345. The chimeric receptor of any one of paragraphs 341-344, wherein each of the two or more scFvs comprises the structure VH-L-VL or VL-L-VH, wherein VH is the heavy chain variable domain, L is the peptide linker, and VL is the light chain variable domain.

346. The chimeric receptor of any one of paragraphs 341-345, wherein each of the two or more scFvs is separated by a peptide linker.

347. The chimeric receptor of paragraph 346, wherein the peptide linker comprises the amino acid sequence of GGGGSGGGGSGGGGS (SEQ ID NO: 27) or EAAAKEAAAKEAAAKEAAAK (SEQ ID NO: 74).

348. The chimeric receptor of any one of paragraphs 339-347, wherein the chimeric receptor is a chimeric T cell receptor or a chimeric antigen receptor (CAR).

349. The chimeric receptor of paragraph 348, wherein the chimeric receptor is a CAR.

350. The chimeric receptor of paragraph 349, wherein the CAR comprises one or more intracellular signaling domains, and the one or more intracellular signaling domains are selected from the group consisting of a CD3zeta-chain intracellular signaling domain, a CD97 intracellular signaling domain, a CD11a-CD18 intracellular signaling domain, a CD2 intracellular signaling domain, an ICOS intracellular signaling domain, a CD27 intracellular signaling domain, a CD154 intracellular signaling domain, a CD8 intracellular signaling domain, an OX40 intracellular signaling domain, a 4-1BB intracellular signaling domain, a CD28 intracellular signaling domain, a ZAP40 intracellular signaling domain, a CD30 intracellular signaling domain, a GITR intracellular signaling domain, an HVEM intracellular signaling domain, a DAP10 intracellular signaling domain, a DAP12 intracellular signaling domain, and a MyD88 intracellular signaling domain.

351. The chimeric receptor of paragraph 349 or paragraph 350, wherein the CAR comprises a transmembrane domain, and the transmembrane domain is selected from the group consisting of a CD8 transmembrane domain, a CD28 transmembrane domain a CD3zeta-chain transmembrane domain, a CD4 transmembrane domain, a 4-1BB transmembrane domain, an OX40 transmembrane domain, an ICOS transmembrane domain, a CTLA-4 transmembrane domain, a PD-1 transmembrane domain, a LAG-3 transmembrane domain, a 2B4 transmembrane domain, and a BTLA transmembrane domain.

352. The chimeric receptor of any one of paragraphs 348-351, wherein the CAR comprises a spacer region between the antigen-binding domain and the transmembrane domain, and the spacer region has an amino acid sequence selected from the group consisting of SEQ ID NOs: 55-64.

353. An isolated cell comprising the chimeric receptor of any one of paragraphs 339-352.

354. The isolated cell of paragraph 353, wherein the chimeric receptor is recombinantly expressed.

355. The isolated cell of paragraph 353 or paragraph 354, wherein the chimeric receptor is expressed from a vector or a selected locus from the genome of the cell.

356. A pharmaceutical composition comprising the isolated cell of any one of paragraphs 353-355 and a pharmaceutically acceptable carrier, pharmaceutically acceptable excipient, or a combination thereof 357. An isolated nucleic acid encoding the chimeric receptor of any one of paragraphs 339-352.

358. A vector comprising the nucleic acid of paragraph 357.

359. A genetically modified cell comprising the nucleic acid of paragraph 357.

EXAMPLES

The following are examples of methods and compositions of the present disclosure. It is understood that various other embodiments may be practiced, given the general description provided herein.

Below are examples of specific embodiments for carrying out the claimed subject matter of the present disclosure. The examples are offered for illustrative purposes only, and are not intended to limit the scope of the present disclosure in any way. Efforts have been made to ensure accuracy with respect to numbers used (e.g., amounts, temperatures, etc.), but some experimental error and deviation should, of course, be allowed for.

Example 1: Bioinformatics Screen for AML Targets

Bioinfomatics Screen Analysis

Microarray data, RNA-seq data and proteomics data from AML and normal hematopoiesis samples as well as data from off-target tissues were analyzed for potential targets associated with AML. Datasets for microarray were obtained from GEO, datasets for RNA-seq were obtained from The Cancer Genome Atlas (TCGA), and datasets for proteomics were obtained from the Human Protein Atlas and the Human Proteome Map. Each data set was initially analyzed for genes and protein targets associated with AML. Data from the initial individual microarray, RNA-seq and proteomics bioinformatics analysis for AML targets was then compared to provide a refined list of AML targets. Putative AML targets were validated in AML cell lines via antibody staining and flow cytometry, and in primary AML samples via antibody staining and flow cytometry. All data was analyzed to provide a final list of AML targets. Bioinformatics analysis combining microarray expression, RNA-seq expression, and HPA toxicity simultaneously allows a more robust pipeline to identify and validate AML antigen targets.

Genes identified in the initial analysis with subcellular localization GO Annotation were removed first. 7806 genes were identified as membrane or cell surface localized. Next, genes with expressed in healthy erythroblasts and T cells as compared to AML hematopoietic cells were removed. Genes with "Supported" or "Enhanced" high immunohistochemistry protein expression in tissues other than bone marrow, spleen, lymph node, appendix, or tonsils were removed. Genes were next positively sorted for those with at least 2-fold higher gene expression in AML tissues as compared to non-hematopoietic tissue expression, based on the RNA-seq expression data. The remaining targets were then screened again with a more stringent requirement to remove genes with medium expression in multiple tissues and only retain genes with at least a 4-fold increase in the putative AML gene, as shown in the RNA-seq dataset, across all AML samples and in FLT3-ITD subpopulations. The remaining genes were then manually filtered for genes with monoclonal human-reactive flow cytometry antibodies availability, known biology, and LSC expression.

Example 2: Logic Gating Strategies

The novel AML antigens identified in Example 1 were then paired for AND and NOT gating.

AND pairs with overlapping tissue toxicities according to either the RNA-seq or HPA databases were removed. Potential targets that could pair with a NOT target were determined by any gene with at least two toxic tissues.

NOT targets were determined using the TCGA RNAseq database using the following criteria: a NOT target had low expression on an AML tissue and a high expression on a desired tissue.

Single or "OR" gating targets determined by this strategy include FLT3, MS4A3, CD33, CLEC12A, ADGRE2, SLC22A16, CD123/IL3RA, MLC1, SPNS3, and GAPT.

Additional AML antigens are described in Table 1. Microarray, RNA-seq and protein expression data for AML antigens are shown in FIGS. 1-25.

"AND/NOT" gating targets determined by this strategy include LAT2, PIEZO1, CD38, EMB, CD131/CSF2RB, LILRA2, CD85H, SLC17A9, MYADM, CD300LF, CD244, CD93, and CD117/c-Kit.

Paired "AND" gating targets are described in Table 3.

"NOT" gating targets determined by this strategy include EMCN, JAM2, MS4A15, C4BPA, TRPM1, SCTR, SLC2A2, KCNQ2, PEPR, WLS, and FFAR. "NOT" are also described in Table 2. Microarray, RNA-seq and protein expression data for NOT antigen gating targets are shown in FIGS. 26-34.

Example 3: T Cells Expressing an FLT3 Chimeric Antigen Receptor

Figure 35A:
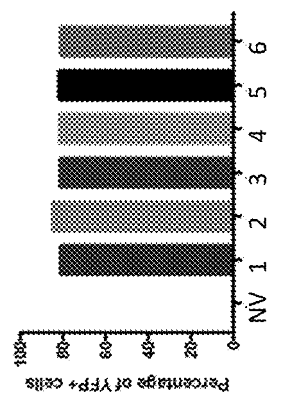
FIG. 35A shows the % cells expressing YFP and the FLT3 CAR from donor 1 for each of the six FLT3 scFvs tested.
Figure 35B:
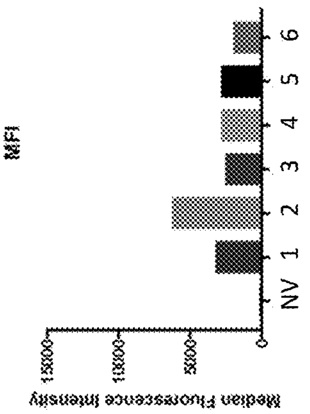
FIG. 35B shows the mean fluorescent intensity of the YFP positive cells from donor 1 for each of the six FLT3 scFvs tested.
Figure 35C:
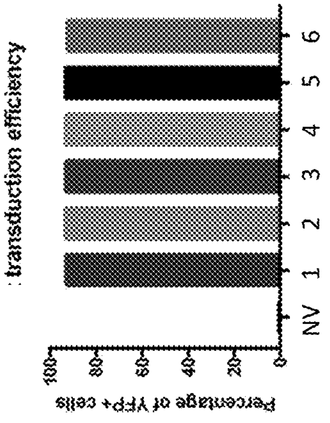
FIG. 35C shows the % cells expressing YFP and the FLT3 CAR from donor 2 for each of the six FLT3 scFvs tested.
Figure 35D:
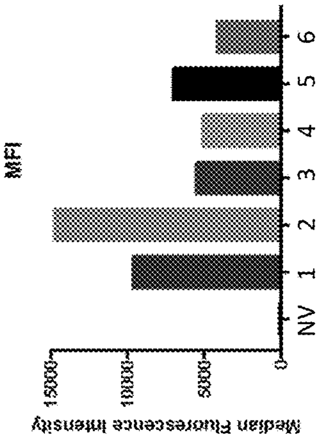
FIG. 35D shows the mean fluorescent intensity of the YFP positive cells from donor 2 for each of the six FLT3 scFvs tested.

T cells from two different donors were genetically modified to express CARs comprised of six different FLT3 scFv polypeptides. The CARS also included a YFP tag as a reporter gene. Expression of the FLT3 CAR in each donor T cell line was quantified via flow cytometry, as determined by expression of the YFP reporter tag. FIG. 35A shows the % cells expressing YFP and the FLT3 CAR from donor 1 for each of the six FLT3 scFvs tested, FIG. 35B shows the mean fluorescent intensity of the YFP positive cells from donor 1 for each of the six FLT3 scFvs tested. FIG. 35C shows the % cells expressing YFP and the FLT3 CAR from donor 2 for each of the six FLT3 scFvs tested, FIG. 35D shows the mean fluorescent intensity of the YFP positive cells from donor 2 for each of the six FLT3 scFvs tested. NV stands for No Vector and is the negative control.

Next, the FLT3 CAR T cells were assessed for killing activity in vitro. FLT3 CARs were mixed at a 1:1 ratio with MOLM13, an AML cell line; SEM, an FLT3+ expression line, and K562, an FLT3-negative cell line as control. T cells and cell lines were co-cultured for 18 hours, and then stained with live/dead stain. Killing efficiency was assessed via flow cytometry.

Figure 36A:
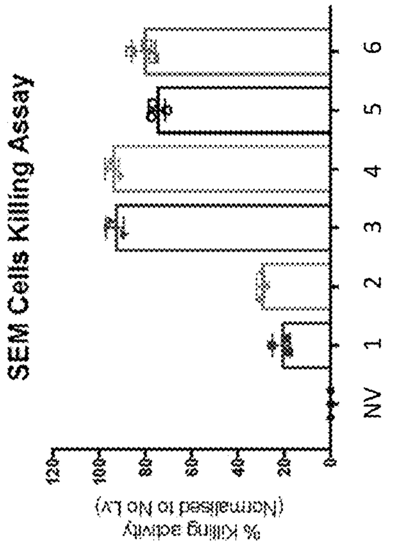
FIG. 36A shows FLT3 CAR T cells from donor 1 induced killing of SEM cells.
Figure 36B:
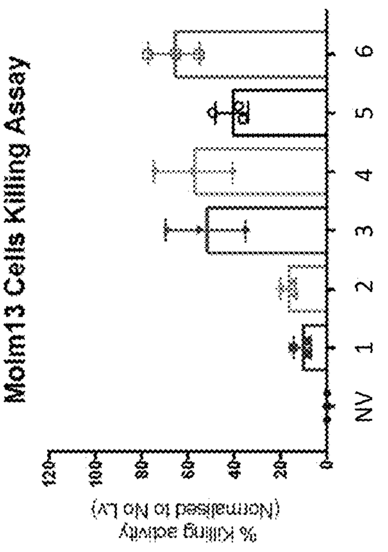
FIG. 36B shows FLT3 CAR T cells from donor 1 induced killing of MOLM13 cells.
Figure 36C:
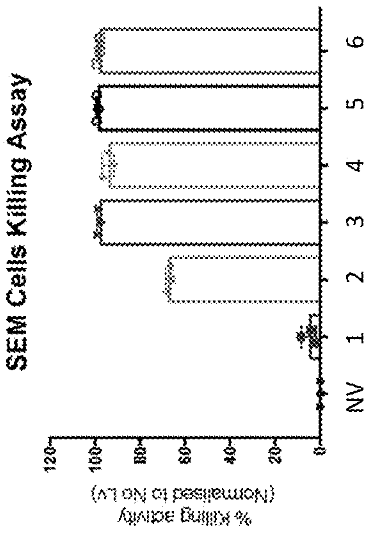
FIG. 36C shows FLT3 CAR T cells from donor 2 induced killing of SEM cells.
Figure 36D:
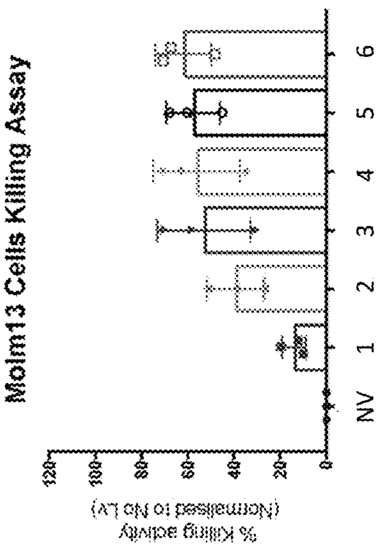
FIG. 36D shows FLT3 CAR T cells from donor 2 induced killing of MOLM13 cells.

As shown in FIG. 36A-D, the FLT3 CAR T cells from both donors killed FLT3 expressing cells. FIGS. 36A and C show killing of SEM cells, FIGS. 36B and D show killing of MOLM13 cells. FIGS. 36A and B are T cells from donor 1, FIG. 36C and D are T cells from donor 2.

Figure 37A:
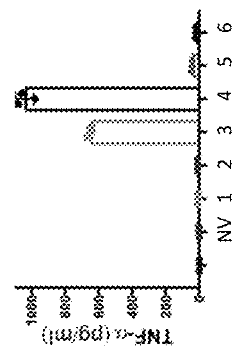
FIG. 37A show TNFα secretion by FLT3 CAR T cells from donor 1 after incubation with SEM cells.
Figure 37B:
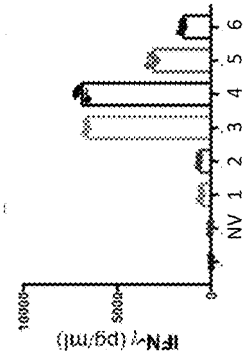
FIG. 37B show IFNγ secretion by FLT3 CAR T cells from donor 1 after incubation with SEM cells.
Figure 37C:
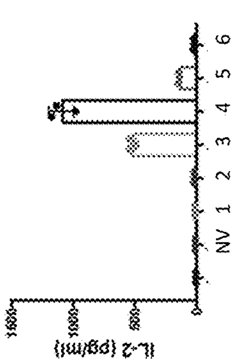
FIG. 37C show IL-2 secretion by FLT3 CAR T cells from donor 1 after incubation with SEM cells.
Figure 37D:
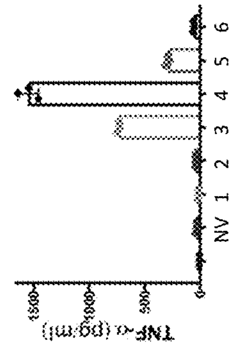
FIG. 37D show TNFα secretion by FLT3 CAR T cells from donor 2 after incubation with SEM cells.
Figure 37E:
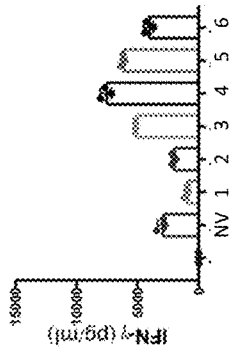
FIG. 37E show IFNγ secretion by FLT3 CAR T cells from donor 2 after incubation with SEM cells.
Figure 37F:
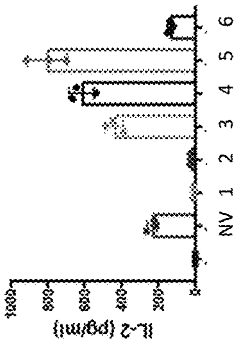
FIG. 37F show IL-2 secretion by FLT3 CAR T cells from donor 1 after incubation with SEM cells.
Figure 38A:
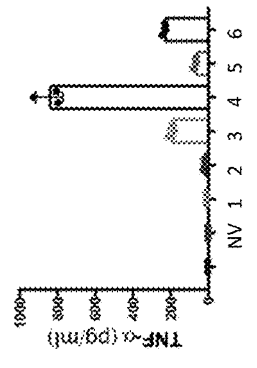
FIG. 38A show TNFα secretion by FLT3 CAR T cells from donor 1 after incubation with MOLM-13 cells.
Figure 38B:
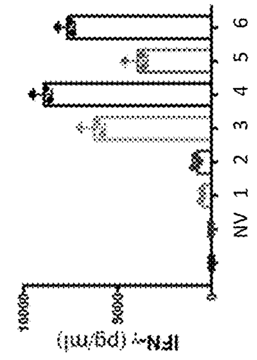
FIG. 38B show IFNγ secretion by FLT3 CAR T cells from donor 1 after incubation with MOLM-13 cells.
Figure 38C:
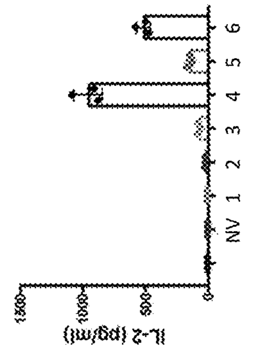
FIG. 38C show IL-2 secretion by FLT3 CAR T cells from donor 1 after incubation with MOLM-13 cells.
Figure 38D:
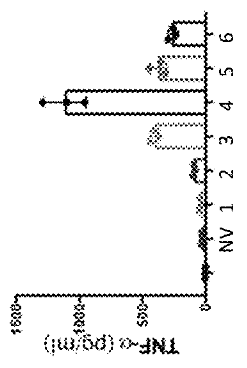
FIG. 38D show TNFα secretion by FLT3 CAR T cells from donor 2 after incubation with MOLM-13 cells.
Figure 38E:
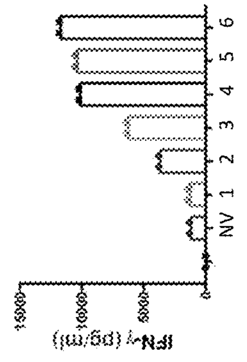
FIG. 38E show IFNγ secretion by FLT3 CAR T cells from donor 2 after incubation with MOLM-13 cells.
Figure 38F:
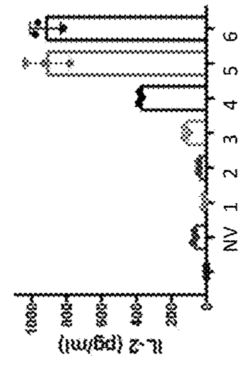
FIG. 38F show IL-2 secretion by FLT3 CAR T cells from donor 1 after incubation with MOLM-13 cells.

Cytokine secretion by the FLT3 CAR T cells after incubation with the SEM or MOLM13 cells was also quantified via ELISA (FIG. 37A-F and FIG. 38A-F). FIGS. 37A-C show the TNF-α, IFN-γ and IL-2 secretion induced in each FLT3 CAR T cell line from donor 1 after incubation with the SEM cells. FIGS. 37D-F show the TNF-α, IFN-γ and IL-2 secretion induced in each FLT3 CAR T cell line from donor 2 after incubation with the SEM cells. FIGS. 38A-C show the TNF-α, IFN-γ and IL-2 secretion induced in each FLT3 CAR T cell line from donor 1 after incubation with the MOLM13 cells. FIGS. 38D-F show the TNF-α, IFN-γ and IL-2 secretion induced in each FLT3 CAR T cell line from donor 2 after incubation with the MOLM13 cells.

Example 4: In Vivo Characterization of T Cells Expressing an FLT3 Chimeric Antigen Receptor Next, FLT3 CAR T cells generated in Example 3 are characterized in vivo in a murine model. Patient-derived tumor cells expressing FLT3, such as MOLM13 and MV411, are xenografted into a mouse. FLT3 CAR T cells are then infused into the xenografted mice. Blood is drawn during the course of the experiment, and spleen, bone marrow, and peripheral blood is collected at the end of the time course. Untreated mice are used as a control. Infusion of FLT3 CAR T cells reduces xenografted tumor cell burden and growth in mice treated with FLT3 CAR T cells as compared to untreated mice.

Example 5: T Cells Expressing FLT3 Chimeric Antigen Receptor and EMCN Chimeric Inhibitory Receptor A T cell is genetically modified to express a CAR that recognizes the AML antigen FLT3 and an inhibitory CAR that recognizes the non AML-antigen EMCN (endomucin). To confirm that the dual modified T cell is functional, T cells are incubated with cells expressing cognate FLT3 antigen and T cell activation is characterized via killing and cytokine production assays as described in Example 3. Briefly, FLT3 CARs are mixed at a 1:1 ratio with MOLM13, an AML cell line; SEM, an FLT3+ expression line, or K562, an FLT3-negative cell line as control. Unmodified T cells are used as a negative control. Dual modified T cells expressing an FLT3 CAR proliferate and produce effector cytokines in response to FLT3 expressing cells.

Next, the dual modified T cells are co-incubated with cells expressing the cognate EMCN antigen and cells expressing the cognate FLT3 antigen. T cell activation is characterized via the killing and cytokine production assays as described above. The cells expressing only the cognate FLT3 antigen are killed, while the cells expressing EMCN antigen only are not killed.

The dual modified FLT3 and EMCN CAR T cells are also characterized in vivo as described in Example 4. Infusion of FLT3 and EMCN CAR T cells reduces xenografted tumor cell burden and growth in treated mice as compared to untreated mice.

Example 6: T Cells Expressing FLT3 Chimeric Antigen Receptor and JAM2 Chimeric Inhibitory Receptor A T cell is genetically modified to express a CAR that recognizes the AML antigen FLT3 and an inhibitory CAR that recognizes the non AML-antigen JAM2. To confirm that the dual modified T cell is functional, T cells are incubated with cells expressing cognate FLT3 antigen and T cell activation is characterized via killing and cytokine production assays as described in Example 3. Briefly, FLT3 CARs are mixed at a 1:1 ratio with MOLM13, an AML cell line; SEM, an FLT3+ expression line, or K562, an FLT3-negative cell line as control. T cells and cell lines are co-cultured for 18 hours, and then stained with live/dead stain. Killing efficiency is assessed via flow cytometry. Unmodified T cells are used as a negative control. Dual modified T cells expressing an FLT3 CAR proliferate and produce effector cytokines in response to FLT3 antigen alone.

Next, the dual modified T cells are co-incubated with cells expressing the cognate JAM2 antigen and cells expressing the cognate FLT3 antigen. T cell activation is characterized via the killing and cytokine production assays as described above. The cells expressing only the cognate FLT3 antigen are killed, while the cells expressing JAM2 antigen only are not killed.

The dual modified FLT3 and JAM2 CAR T cells are also characterized in vivo as described in Example 4. Infusion of FLT3 and JAM2 CAR T cells reduces xenografted tumor cell burden and growth in treated mice as compared to untreated mice.

Example 7: T Cells Expressing CLEC12A Chimeric Antigen Receptor and MS4A15 Chimeric Inhibitory Receptor A T cell is genetically modified to express a CAR that recognizes the AML antigen CLEC12A and an inhibitory CAR that recognizes the non AML-antigen MS4A15. To confirm that the dual modified T cell is functional, T cells are incubated with cells expressing cognate CLEC12A antigen and T cell activation is characterized via killing and cytokine production assays as described in Example 3. Briefly, CLEC12A CARs are mixed at a 1:1 ratio with an AML cell line expressing CLEC12A; a MS4A15+ expression line; or a negative cell line as control. T cells and cell lines are co-cultured for 18 hours, and then stained with live/dead stain. Killing efficiency is assessed via flow cytometry. Unmodified T cells are used as a negative control. Dual modified T cells expressing an CLEC12A CAR proliferate and produce effector cytokines in response to CLEC12A antigen alone.

Next, the dual modified T cells are co-incubated with cells expressing the cognate CLEC12A antigen and cells expressing the cognate MS4A15 antigen. T cell activation is characterized via the killing and cytokine production assays as described above. The cells expressing only the cognate CLEC12A antigen are killed, while the cells expressing MS4A15 antigen only are not killed.

The dual modified CLEC12A and MS4A15 CAR T cells are also characterized in vivo as described in Example 4. Infusion of CLEC12A and MS4A15 CAR T cells reduces xenografted tumor cell burden and growth in treated mice as compared to untreated mice.

Example 8: T Cells Expressing CLEC12A Chimeric Antigen Receptor and SLC34A2 Chimeric Inhibitory Receptor A T cell is genetically modified to express a CAR that recognizes the AML antigen CLEC12A and an inhibitory CAR that recognizes the non AML-antigen SLC34A2. To confirm that the dual modified T cell is functional, T cells are incubated with cells expressing cognate CLEC12A antigen and T cell activation is characterized via killing and cytokine production assays as described in Example 3. Briefly, CLEC12A CARs are mixed at a 1:1 ratio with an AML cell line expressing CLEC12A; a SLC34A2+ expression line; or a negative cell line as control. T cells and cell lines are co-cultured for 18 hours, and then stained with live/dead stain. Killing efficiency is assessed via flow cytometry. Unmodified T cells are used as a negative control. Dual modified T cells expressing an CLEC12A CAR proliferate and produce effector cytokines in response to CLEC12A antigen alone.

Next, the dual modified T cells are co-incubated with cells expressing the cognate CLEC12A antigen and cells expressing the cognate SLC34A2 antigen. T cell activation is characterized via the killing and cytokine production assays as described above. The cells expressing only the cognate CLEC12A antigen are killed, while the cells expressing SLC34A2 antigen only are not killed.

The dual modified CLEC12A and SLC34A2 CAR T cells are also characterized in vivo as described in Example 4. Infusion of CLEC12A and SLC34A2 CAR T cells reduces xenografted tumor cell burden and growth in treated mice as compared to untreated mice.

Example 9: T Cells Expressing IL1RAP Chimeric Antigen Receptor and SLC2A2 Chimeric Inhibitory Receptor A T cell is genetically modified to express a CAR that recognizes the AML antigen IL1RAP and an inhibitory CAR that recognizes the non AML-antigen SLC2A2. To confirm that the dual modified T cell is functional, T cells are incubated with cells expressing cognate, IL1RAP antigen and T cell activation is characterized via killing and cytokine production assays as described in Example 3. Briefly, IL1RAP CARs are mixed at a 1:1 ratio with an AML cell line expressing IL1RAP; a SLC2A2+ expression line; or a negative cell line as control. T cells and cell lines are co-cultured for 18 hours, and then stained with live/dead stain. Killing efficiency is assessed via flow cytometry. Unmodified T cells are used as a negative control. Dual modified T cells expressing an IL1RAP CAR proliferate and produce effector cytokines in response to IL1RAP antigen alone.

Next, the dual modified T cells are co-incubated with cells expressing the cognate IL1RAP antigen and cells expressing the cognate SLC2A2 antigen. T cell activation is characterized via the killing and cytokine production assays as described above. The cells expressing only the cognate IL1RAP antigen are killed, while the cells expressing SLC2A2 antigen only are not killed.

The dual modified IL1RAP and SLC2A2 CAR T cells are also characterized in vivo as described in Example 4. Infusion of IL1RAP and SLC2A2 CAR T cells reduces xenografted tumor cell burden and growth in treated mice as compared to untreated mice.

Example 10: T Cells Expressing CD33 Chimeric Antigen Receptor and TRPM1 Chimeric Inhibitory Receptor A T cell is genetically modified to express a CAR that recognizes the AML antigen CD33 and an inhibitory CAR that recognizes the non AML-antigen TRPM1. To confirm that the dual modified T cell is functional, T cells are incubated with cells expressing cognate CD33 antigen and T cell activation is characterized via killing and cytokine production assays as described in Example 3. Briefly, CD33 CARs are mixed at a 1:1 ratio with an AML cell line expressing CD33; a TRPM1+ expression line; or a negative cell line as control. T cells and cell lines are co-cultured for 18 hours, and then stained with live/dead stain. Killing efficiency is assessed via flow cytometry. Unmodified T cells are used as a negative control. Dual modified T cells expressing an CD33 CAR proliferate and produce effector cytokines in response to CD33 antigen alone.

Next, the dual modified T cells are co-incubated with cells expressing the cognate CD33 antigen and cells expressing the cognate TRPM1 antigen. T cell activation is characterized via the killing and cytokine production assays as described above. The cells expressing only the cognate CD33 antigen are killed, while the cells expressing TRPM1 antigen only are not killed.

The dual modified CD33 and TRPM1 CAR T cells are also characterized in vivo as described in Example 4. Infusion of CD33 and TRPM1 CAR T cells reduces xenografted tumor cell burden and growth in treated mice as compared to untreated mice.

Example 11: T Cells Expressing SLC22A16 Chimeric Antigen Receptor and SCTR Chimeric Inhibitory Receptor A T cell is genetically modified to express a CAR that recognizes the AML antigen SLC22A16 and an inhibitory CAR that recognizes the non AML-antigen SCTR. To confirm that the dual modified T cell is functional, T cells are incubated with cells expressing cognate SLC22A16 antigen and T cell activation is characterized via killing and cytokine production assays as described in Example 3. Briefly, SLC22A16 CARs are mixed at a 1:1 ratio with an AML cell line expressing SLC22A16; a SCTR+ expression line; or a negative cell line as control. T cells and cell lines are co-cultured for 18 hours, and then stained with live/dead stain. Killing efficiency is assessed via flow cytometry. Unmodified T cells are used as a negative control. Dual modified T cells expressing an SLC22A16 CAR proliferate and produce effector cytokines in response to SLC22A16 antigen alone.

Next, the dual modified T cells are co-incubated with cells expressing the cognate SLC22A16 antigen and cells expressing the cognate SCTR antigen. T cell activation is characterized via the killing and cytokine production assays as described above. The cells expressing only the cognate SLC22A16 antigen are killed, while the cells expressing SCTR antigen only are not killed.

The dual modified SLC22A16 and SCTR CAR T cells are also characterized in vivo as described in Example 4. Infusion of SLC22A16 and SCTR CAR T cells reduces xenografted tumor cell burden and growth in treated mice as compared to untreated mice.

Example 12: T Cells Expressing PIEZO1 Chimeric Antigen Receptor and KCNQ2 Chimeric Inhibitory Receptor A T cell is genetically modified to express a CAR that recognizes the AML antigen PIEZO1 and an inhibitory CAR that recognizes the non AML-antigen KCNQ2. To confirm that the dual modified T cell is functional, T cells are incubated with cells expressing cognate PIEZO16 antigen and T cell activation is characterized via killing and cytokine production assays as described in Example 3. Briefly, PIEZO1 CARs are mixed at a 1:1 ratio with an AML cell line expressing PIEZO1; a KCNQ2+ expression line; or a negative cell line as control. T cells and cell lines are co-cultured for 18 hours, and then stained with live/dead stain. Killing efficiency is assessed via flow cytometry. Unmodified T cells are used as a negative control. Dual modified T cells expressing an PIEZO1 CAR proliferate and produce effector cytokines in response to PIEZO1 antigen alone.

Next, the dual modified T cells are co-incubated with cells expressing the cognate PIEZO1 antigen and cells expressing the cognate KCNQ2 antigen. T cell activation is characterized via the killing and cytokine production assays as described above. The cells expressing only the cognate PIEZO1 antigen are killed, while the cells expressing KCNQ2 antigen only are not killed.

The dual modified PIEZO1 and KCNQ2 CAR T cells are also characterized in vivo as described in Example 4. Infusion of PIEZO1 and KCNQ2 CAR T cells reduces xenografted tumor cell burden and growth in treated mice as compared to untreated mice.

Example 13: T Cells Expressing IL3RA Chimeric Antigen Receptor and PERP Chimeric Inhibitory Receptor A T cell is genetically modified to express a CAR that recognizes the AML antigen IL3RA and an inhibitory CAR that recognizes the non AML-antigen PERP. To confirm that the dual modified T cell is functional, T cells are incubated with cells expressing cognate IL3RA antigen and T cell activation is characterized via killing and cytokine production assays as described in Example 3. Briefly, IL3RA CARs are mixed at a 1:1 ratio with an AML cell line expressing IL3RA; a PERP+ expression line; or a negative cell line as control. T cells and cell lines are co-cultured for 18 hours, and then stained with live/dead stain. Killing efficiency is assessed via flow cytometry. Unmodified T cells are used as a negative control. Dual modified T cells expressing an IL3RA CAR proliferate and produce effector cytokines in response to IL3RA antigen alone.

Next, the dual modified T cells are co-incubated with cells expressing the cognate IL3RA antigen and cells expressing the cognate PERP antigen. T cell activation is characterized via the killing and cytokine production assays as described above. The cells expressing only the cognate IL3RA antigen are killed, while the cells expressing PERP antigen only are not killed.

The dual modified IL3RA and PERP CAR T cells are also characterized in vivo as described in Example 4. Infusion of IL3RA and PERP CAR T cells reduces xenografted tumor cell burden and growth in treated mice as compared to untreated mice.

Example 14: Expression of FLT3, CD33, and CLEC12A in AML Cells

Materials and Methods

Bioinformatics analyses identified FLT3, CD33, and CLEC12A as highly expressed in AML. A microarray database was constructed by downloading and normalizing >1100 AML patient-derived and healthy hematopoietic cell samples from NCBI GEO. Using this database, genes with high transcriptional expression in AML cells as compared to healthy hematopoietic cells were selectively identified.

The bioinformatics expression results were confirmed using flow cytometry to analyze FLT3, CD33, and CLEC12A protein levels on the cell surface of AML cells. Cryopreserved AML patient-derived bone marrow mononuclear cells (BMMCs), peripheral blood mononuclear cells (PBMCs), as well as healthy BMMCs and PBMCs (as controls) were thawed on ice and then stained with antibodies recognizing human FLT3, CD33, and CLEC12A proteins. Cells were washed, stained to differentiate between live/dead cells, and analyzed using a Cytoflex flow cytometer and FlowJo software.

Results

Figure 39:
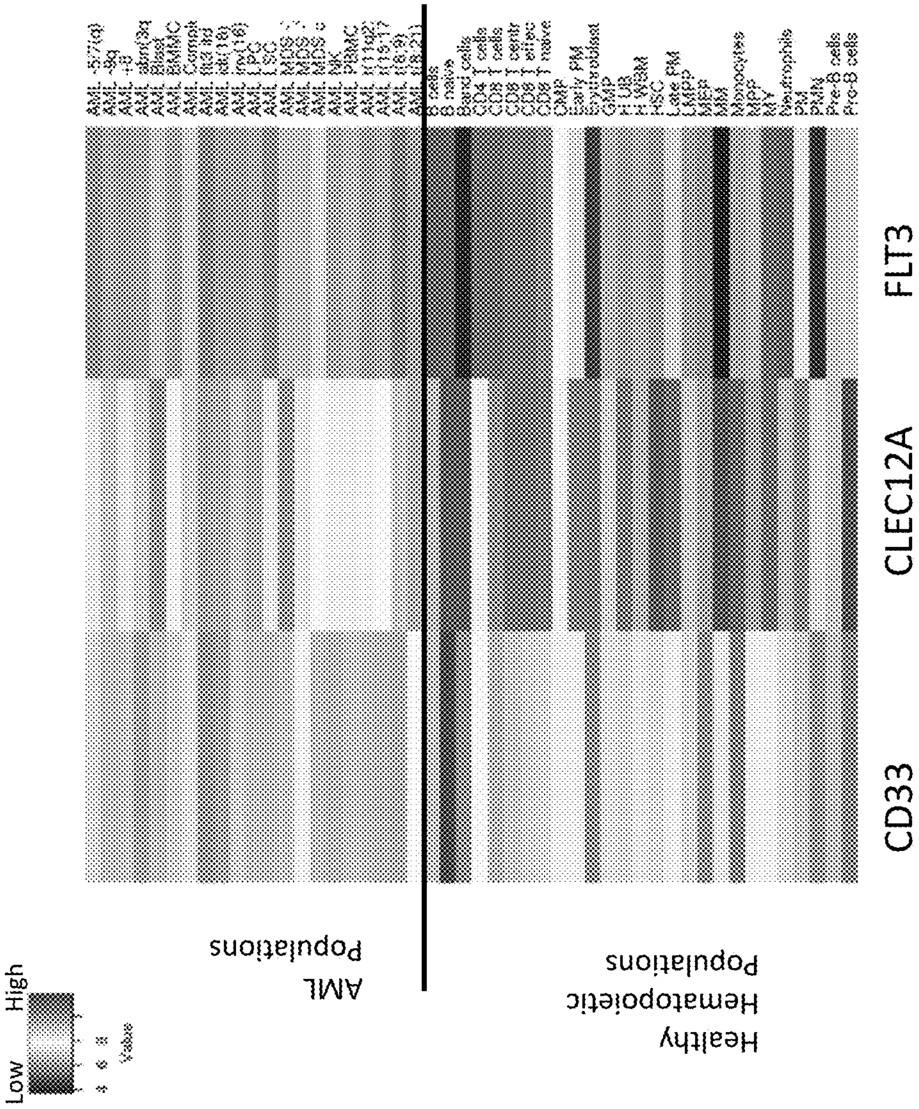
FIG. 39 shows a heat mat of the FLT3, CD33, and CLEC12A microarray expression data in various tissues and/or cell lines.

FLT3, CD33, and CLEC12A are highly expressed in AML patient samples as compared to healthy hematopoietic cells. FIG. 39 shows a heatmap of microarray-based gene expression database containing >1100 healthy and AML patient samples. Cell population in order from top to tottom are: AML −5/7(q), AML −9q, AML+8, AML abn(3q), AML Blast, AML BMMC NK, AML Complex, AML flt3 itd MUT, AML itd(16), AML inv(16)/t(16;16), AML LPC (leukemic progenitor cell), AML LSC (leukemic stem cell), AML MDS −7(q), AML MDS-Y, AML MDS complex, AML NK, AML PBMC NK, AML t(11q23), AML t(15;17), AML t(6;9), AML t(8;21), B cell, B naïve, Band cell, CD4+ T cell, CD8+ T cell, CD8+ T central cell, CD8+ T effector cell, CD8+ T naïve cell, CMP (common myeloid progenitor), Early PM (early promyelocyte), Erythroblasts, GMP (granulocyte macrophage progenitor), H UB (healthy umbilical cord blood), H WBM (healthy whole bone marrow), HSC (hematopoietic stem cell), Late PM (late promyelocyte), LMPP (lymphoid-primed multipotent progenitor), MEP (megakaryocyte erythrocyte progenitor), MM (metamyelocyte), Monocytes, MPP (multipotent progenitor), MY (myelocyte), Neutrophils, PM (promyelocyte), PMN (polymorphonuclear cell), Pre-B cells, Pro-B cells.

The average normalized expression (log 2 expression scale) of FLT3, CD33, and CLEC12A in the indicated primary cells and cell lines are also shown in Table 4. The numbers in brackes indicate the number of samples per group.

TABLE 4

| | AML Samples | | | | | | | | |
|---|---|---|---|---|---|---|---|---|---|
| Gene Symbol | AML +8 [19] | AML −5/7(q) [28] | AML −9q [6] | AML BMMC NK [399] | AML Blast [21] | AML Complex [58] | AML LPC [23] | AML LSC [28] | AML NK [9] |
| FLT3 | 10.0 | 10.3 | 9.7 | 9.6 | 9.1 | 8.8 | 9.8 | 10.3 | 9.7 |
| CD33 | 8.4 | 8.1 | 8.5 | 9.0 | 8.5 | 8.5 | 8.4 | 8.5 | 8.6 |
| CLEC12A | 7.4 | 7.5 | 8.4 | 8.6 | 9.3 | 7.4 | 8.9 | 7.6 | 6.8 |
| Gene Symbol | AML PBMC NK [32] | AML abn(3q) [2] | AML flt3 itd MUT [1] | AML idt(16) [33] | AML inv(16)/t(16; 16) [28] | AML t(11q23) [48] | AML t(15; 17) [58] | AML t(6; 9) [6] | AML t(8; 21) [77] |
| FLT3 | 9.3 | 9.8 | 10.5 | 9.9 | 9.7 | 9.8 | 9.6 | 10.5 | 9.8 |
| CD33 | 9.0 | 9.1 | 9.5 | 9.0 | 9.1 | 9.2 | 9.3 | 8.9 | 7.9 |
| CLEC12A | 7.9 | 8.1 | 9.0 | 8.9 | 9.2 | 8.2 | 7.7 | 8.3 | 9.2 |

| | Healthy Hematopoietic Cells | | | | | | | | |
|---|---|---|---|---|---|---|---|---|---|
| Gene Symbol | Hemato-poietic stem cell (HSC) [22] | Lymphoid-primed multipotent progenitor (LMPP) [7] | Late promye-locyte (Late PM) [3] | Megakary-ocyte erythrocyte progenitor (MEP) [15] | Metamyelocyte (MM) [3] | Multipotent progenitor (MPP) [17] | Myelocyte (MY) [4] | Monocyte [8] | Neutrophil [3] |
| FLT3 | 10.0 | 9.9 | 7.3 | 6.0 | 4.1 | 9.4 | 5.8 | 6.5 | 5.3 |
| CD33 | 7.2 | 8.1 | 7.9 | 5.8 | 7.7 | 7.1 | 8.5 | 10.0 | 6.6 |
| CLEC12A | 4.7 | 8.3 | 11.1 | 5.7 | 12.0 | 5.6 | 11.0 | 10.6 | 8.4 |

TABLE 4-continued

| Gene Symbol | Promyelocyte (PM) [2] | Polymorphonuclear cell (PMN) [3] | Pre-B cell [2] | Pro-B cell [2] | Common myeloid progenitor (CMP) [16] | Early promyelocyte (Early PM) [3] | Erythroblast [7] | Granulocyte macrophage progenitor (GMP) [18] | Healthy umbilical cord blood (H UB) [3] |
|---|---|---|---|---|---|---|---|---|---|
| FLT3 | 7.6 | 4.6 | 7.0 | 8.9 | 7.9 | 8.7 | 4.7 | 9.6 | 9.8 |
| CD33 | 9.1 | 6.6 | 9.4 | 6.3 | 7.4 | 8.0 | 5.2 | 8.2 | 8.0 |
| CLEC12A | 10.4 | 9.0 | 9.3 | 5.7 | 7.6 | 10.6 | 4.6 | 8.6 | 4.7 |

| Gene Symbol | Healthy whole bone marrow (H WBM) | B cell [4] | B naïve [2] | Band cell [4] | CD4 T cell [3] | CD8 T cell [6] | CD8 T central [3] | CD8 T effector [8] | CD8 T naïve [4] |
|---|---|---|---|---|---|---|---|---|---|
| FLT3 | 6.7 | 5.2 | 5.4 | 4.3 | 5.4 | 5.3 | 5.3 | 5.4 | 5.7 |
| CD33 | 8.6 | 6.2 | 5.4 | 6.4 | 7.4 | 6.0 | 6.1 | 6.5 | 6.6 |
| CLEC12A | 9.7 | 5.7 | 5.6 | 11.7 | 7.2 | 4.9 | 4.7 | 4.6 | 4.7 |
| FLT3 | 6.7 | 5.2 | 5.4 | 4.3 | 5.4 | 5.3 | 5.3 | 5.4 | 5.7 |
| CD33 | 8.6 | 6.2 | 5.4 | 6.4 | 7.4 | 6.0 | 6.1 | 6.5 | 6.6 |
| CLEC12A | 9.7 | 5.7 | 5.6 | 11.7 | 7.2 | 4.9 | 4.7 | 4.6 | 4.7 |

| | Endothelial Cells | | | | | | | | |
|---|---|---|---|---|---|---|---|---|---|
| Gene Symbol | Human aortic endothelial cell (HAEC) [2] | Human coronary artery endothelial cell (HCAEC) [2] | Human Microvascular Endothelial Cells (HMVEC) qui [3] | Human Umbilical Artery Endothelial Cell (HUAEC) [5] | Human umbilical vein endothelial cell (HUVEC) [5] | Human Pulmonary Artery Endothelial Cell (PAEC) [6] | Pulmonary microvascular endothelial cell (PMVEC) [6] | Human Umbilical Artery Endothelial Cell (HUAEC) fresh [4] | Human umbilical vein endothelial cell (HUVEC)_fresh [4] | Human umbilical vein endothelial cell (HUVEC) primary [2] |
| FLT3 | 4.4 | 4.6 | 4.4 | 4.4 | 5.1 | 4.6 | 4.6 | 4.3 | 4.7 | 4.9 |
| CD33 | 5.6 | 5.4 | 5.6 | 5.7 | 6.0 | 5.2 | 5.5 | 5.5 | 5.6 | 5.4 |
| CLEC12A | 4.6 | 4.5 | 4.1 | 3.9 | 4.3 | 4.3 | 4.2 | 4.1 | 4.1 | 4.4 |

Flow cytometry analysis of 4 representative AML patient bone marrow mononuclear cells (BMMC) samples demonstrates that a majority of AML blasts express FLT3 and/or CD33 protein (data not shown). Thus, FLT3 "OR" CD33 logic gated CARs can broadly target AML blast populations. Flow cytometry analysis of 4 representative AML patient bone marrow mononuclear cells (BMMC) samples demonstrates that a majority of AML blasts express FLT3 and/or CLEC12A protein (data not shown). Thus, FLT3 "OR" CLEC12A logic gated CARs can broadly target AML blast populations. Flow cytometry analysis of 2 representative AML patient bone marrow mononuclear cells (BMMC) samples demonstrates that a majority of AML leukemic stem cell (LSC)—enriched population expresses FLT3, or, FLT3 and CD33 protein. Thus, FLT3 "OR" CD33 logic gated CAR target can target AML LSC-enriched populations.

Example 15: In Vitro Characterization of FLT3 CAR T Cells

Materials and Methods

Cell Surface Expression

Cell surface expression of FLT3 in MOLM-13, THP-1, and SEM cells was determined by flow cytometry. Cells were stained with a human FLT3 antibody (conjugated to PE-Cy7, clone: BV10A4H2; Biolegend). An isotype control was used as a negative control for background antibody staining. A ratio was determined between the negative and FLT3+ population, confirming MOLM-13, THP-1, and SEM all robustly express the FLT3 receptor.

T Cell Assays

T cells from 1 donor were genetically modified to express CARs with three different FLT3 scFv polypeptides. The FLT3 scFvs used were ml0006, NC7 (SB00819), and D4-3 (SB00816). The CARs had a CD8 signal sequence, a CD8 hinge, a CD8 transmembrane domain, a 4-1BB co-stimulatory domain and a CD3 signaling domain. Each also had a YFP tag on the C terminus.

Primary T cells were isolated from PBMCs and frozen. T cells were thawed and activated with Human T-Activator CD3/CD28 Dynabeads and cultured in CTS OpTmizer T Cell Expansion medium with IL-2 overnight. Next, T cells were transduced with a CAR lentivirus containing a selected CAR vector. CAR expression was assessed via antibody staining and flow cytometry. On day 9 after transduction, T cells and target cells were col-cultured for a cytotoxicity assay (ET ratio: 1:1, 96-well plate, 200 ul total medium volume). The target cells were stained with CellTrace Violet dye to distinguish with T cells.

For cytokine production assays, supernatant was collected after a 5 or 18-hour co-culture and stored at −80 degree for Luminex assay.

For cytotoxicity assays, cells were collected after a 18-20 hour incubation and stained with propidium iodide cell viability dye to distinguish live/dead target cells. Cytotoxicity was assessed by flow cytometry and the data analyzed by FlowJo. The cytotoxicity activity was normalized to a no virus T cell control. In certain cases, data was also normalized with a K562 cytotoxicity control.

The protein and nucleotide sequences of the D4-3 (SB00816) and NC7 (SB00819) FLT3 CARs made are shown in Table 5.

TABLE 5

| SEQ ID NO | Name | Sequence |
|---|---|---|
| 153 | CD8ss_F<br>LT3(D4-<br>3)_CD8<br>hinge_CD8<br>TM_41BB<br>ICD_CD3<br>z_YFP<br>SB00816 | MALPVTALLLPLALLLHAARPDVVMTQSPLSLPVTPGEPASISCRSSQSLLHSNGYNYLDWYLQKPGQSP<br>QLLIYLGSNRASGVPDRFSGSGSGTDFTLKISRVEAEDVGVYYCMQSLQTPFTFGPGTKVDIKGGGGSGG<br>GGSGGGGSEVQLVQSGAEVKKPGASVKVSCKASGYTFTSYYMHWARQAPGQGLEWMGIINPSGGSTSYAQ<br>KFQGRVTMTRDTSTSTVYMELSSLRSEDTAVYYCARVVAAAVADYWGQGTLVTVSSTTTPAPRPPTPAPT<br>IALQPLSLRPEACRPAAGGAVHTRGLDFACDIYIWAPLAGTCGVLLLSLVITKRGRKKLLYIFKQPFMRP<br>VQTTQEEDGCSCRFPEEEEGGCELRVKFSRSADAPAYKQGQNQLYNELNLGRREEYDVLDKRRGRDPEMG<br>GKPRRKNPQEGLYNELQKDKMAEAYSEIGMKGERRRGKGHDGLYQGLSTATKDTYDALHMQALPPRGSSG<br>TGMVSKGEELFTGVVPILVELDGDVNGHKFSVSGEGEGDATYGKLTLKLICTTGKLPVPWPTLVTTLGYG<br>LQCFARYPDHMKQHDFFKSAMPEGYVQERTIFFKDDGNYKTRAEVKFEGDTLVNRIELKGIDFKEDGNIL<br>GHKLEYNYNSHNVYITADKQKNGIKANFKIRHNIEDGGVQLADHYQQNTPIGDGPVLLPDNHYLSYQSAL<br>SKDPNEKRDHMVLLEFVTAAGITLGMDELYK |
| 154 | CD8ss_F<br>LT3(D4-<br>3)_CD8<br>hinge_CD8<br>TM_41BB<br>ICD_CD3<br>z_YFP<br>SB00816 | ACAAAAATTTCAAGGTCGGGTGACAATGACGCGCGACACGTCAACGAGTACAGTGTATATGGAATTGTCT<br>AGCCTGAGGTCCGAGGATACTGCTGTCTATTATTGTGCTCGCGTGGTCGCTGCTGCTGTGGCAGACTACT<br>GGGGTCAGGGTACACTTGTGACGGTAAGCAGCACCACGACGCCGGCGCCCCGGCCTCCCACCCCCGCACC<br>AACGATAGCCCTTCAGCCCTTGAGCCTCCGGCCAGAAGCATGCCGCCCGGCAGCCGGAGGTGCAGTCCAT<br>ACGCGCGGACTGGACTTTGCATGTGACATCTACATATGGGCCCCCCTCGCCGGTACTTGCGGTGTTTTGC<br>TTTTGTCACTGGTGATTACGAAGCGCGGTCGAAAAAAACTCCTCTACATCTTCAAACAACCTTTCATGCG<br>GCCTGTCCAAACAACTCAAGAAGAGGACGGGTGTTCATGCCGCTTTCCAGAGGAAGAGGAAGGTGGCTGT<br>GAACTTAGGGTCAAGTTTAGCAGGTCAGCGGACGCACCAGCTTACAAGCAAGGCCAAAACCAGCTTTATA<br>ACGAATTGAATTTGGGACGCAGGGAAGAATACGATGTGCTCGATAAACGCAGAGGGAGGGACCCGGAAAT<br>GGGAGGAAAGCCAAGGCGGAAAAACCCACAGGAGGGGTTGTACAACGAGCTTCAAAAAGATAAGATGGCG<br>GAAGCATACTCCGAAATAGGAATGAAGGGTGAACGGAGGAGGGGCAAGGGCCACGACGGCCTGTACCAGG<br>GACTCTCAACTGCTACGAAGGATACTTATGATGCTCTTCACATGCAAGCTCTGCCGCCGCGCGGATCGAG<br>TGGCACCGGTATGGTGAGCAAGGGCGAGGAGCTGTTCACCGGGGTGGTGCCCATCCTGGTCGAGCTGGAC<br>GGCGACGTAAACGGCCACAAGTTCAGCGTGTCCGGCGAGGGCGAGGGCGATGCCACCTACGGCAAGCTGA<br>CCCTGAAGCTGATCTGCACCACCGGCAAGCTGCCCGTGCCCTGGCCCACCCTCGTGACCACCCTGGGCTA<br>CGGCCTcCAGTGCTTCGCCCGCTACCCCGACCACATGAAGCAGCACGACTTCTTCAAGTCCGCCATGCCC<br>GAAGGCTACGTCCAGGAGCGCACCATCTTCTTCAAGGACGACGGCAACTACAAGACCCGCGCCGAGGTGA<br>AGTTCGAGGGCGACACCCTGGTGAACCGCATCGAGCTGAAGGGCATCGACTTCAAGGAGGACGGCAACAT<br>CCTGGGGCACAAGCTGGAGTACAACTACAACAGCCACAACGTCTATATCACCGCCGACAAGCAGAAGAAC<br>GGCATCAAGGCCAACTTCAAGATCCGCCACAACATCGAGGACGGCGGCGTGCAGCTCGCCGACCACTACC<br>AGCAGAACACCCCCATCGGCGACGGCCCCGTGCTGCTGCCCGACAACCACTACCTGAGCTACCAGTCCGC<br>CCTGAGCAAAGACCCCAACGAGAAGCGCGATCACATGGTCCTGCTGGAGTTCGTGACCGCCGCCGGGATC<br>ACTCTCGGCATGGACGAGCTGTACAAG |
| 155 | CD8ss_F<br>LT3(NC7)_<br>CD8<br>hinge_CD8<br>TM_41BB<br>ICD_CD3<br>z_YFP<br>SB00819 | MALPVTALLLPLALLLHAARPEVQLVQSGAEVKKPGSSVKVSCKASGGTFSSYAISWVRQAPGQGLEWMG<br>GIIPIFGTANYAQKFQGRVTITADKSTSTAYMELSSLRSEDTAVYYCATFALFGFREQAFDIWGQGTTVT<br>VSSGGGGSGGGGSGGGGSDIQMTQSPSSLSASVGDRVTITCRASQSISSYLNWYQQKPGKAPKLLIYAAS<br>SLQSGVPSRFSGSGSGTDFTLTISSLQPEDLATYYCQQSYSTPFTFGPGTKVDIKTTTPAPRPPTPAPTI<br>ALQPLSLRPEACRPAAGGAVHTRGLDFACDIYIWAPLAGTCGVLLLSLVITKRGRKKLLYIFKQPFMRPV<br>QTTQEEDGCSCRFPEEEEGGCELRVKFSRSADAPAYKQGQNQLYNELNLGRREEYDVLDKRRGRDPEMGG<br>KPRRKNPQEGLYNELQKDKMAEAYSEIGMKGERRRGKGHDGLYQGLSTATKDTYDALHMQALPPRGSSGT<br>GMVSKGEELFTGVVPILVELDGDVNGHKFSVSGEGEGDATYGKLTLKLICTTGKLPVPWPTLVTTLGYGL<br>QCFARYPDHMKQHDFFKSAMPEGYVQERTIFFKDDGNYKTRAEVKFEGDTLVNRIELKGIDFKEDGNILG<br>HKLEYNYNSHNVYITADKQKNGIKANFKIRHNIEDGGVQLADHYQQNTPIGDGPVLLPDNHYLSYQSALS<br>KDPNEKRDHMVLLEFVTAAGITLGMDELYK |
| 156 | CD8ss_F<br>LT3(NC7)_<br>CD8<br>hinge_CD8<br>TM_41BB<br>ICD_CD3<br>z_YFP<br>nucleotide | CAGAAACCTGGGAAAGCGCCGAAGCTCCTTATCTATGCTGCCAGCTCTTTGCAAAGCGGTGTGCCCTCAC<br>GGTTCTCCGGTAGTGGGTCCGGGACCGACTTCACTTTGACCATCAGCAGCCTTCAGCCAGAGGATCTTGC<br>CACTTATTACTGCCAGCAATCTTATAGCACACCGTTTACATTCGGTCCAGGCACAAAGGTAGACATTAAG<br>ACCACGACGCCGGCGCCCCGGCCTCCCACCCCCGCACCAACGATAGCCCTTCAGCCCTTGAGCCTCCGGC<br>CAGAAGCATGCCGCCCGGCAGCCGGAGGTGCAGTCCATACGCGCGGACTGGACTTTGCATGTGACATCTA<br>CATATGGGCCCCCCTCGCCGGTACTTGCGGTGTTTTGCTTTTGTCACTGGTGATTACGAAGCGCGGTCGA<br>AAAAAACTCCTCTACATCTTCAAACAACCTTTCATGCGGCCTGTCCAAACAACTCAAGAAGAGGACGGGT<br>GTTCATGCCGCTTTCCAGAGGAAGAGGAAGGTGGCTGTGAACTTAGGGTCAAGTTTAGCAGGTCAGCGGA<br>CGCACCAGCTTACAAGCAAGGCCAAAACCAGCTTTATAACGAATTGAATTTGGGACGCAGGGAAGAATAC<br>GATGTGCTCGATAAACGCAGAGGGAGGGACCCGGAAATGGGAGGAAAGCCAAGGCGGAAAAACCCACAGG<br>AGGGGTTGTACAACGAGCTTCAAAAAGATAAGATGGCGGAAGCATACTCCGAAATAGGAATGAAGGGTGA<br>ACGGAGGAGGGGCAAGGGCCACGACGGCCTGTACCAGGGACTCTCAACTGCTACGAAGGATACTTATGAT<br>GCTCTTCACATGCAAGCTCTGCCGCCGCGCGGATCGAGTGGCACCGGTATGGTGAGCAAGGGCGAGGAGC<br>TGTTCACCGGGGTGGTGCCCATCCTGGTCGAGCTGGACGGCGACGTAAACGGCCACAAGTTCAGCGTGTC<br>CGGCGAGGGCGAGGGCGATGCCACCTACGGCAAGCTGACCCTGAAGCTGATCTGCACCACCGGCAAGCTG<br>CCCGTGCCCTGGCCCACCCTCGTGACCACCCTGGGCTACGGCCTCCAGTGCTTCGCCCGCTACCCCGACC<br>ACATGAAGCAGCACGACTTCTTCAAGTCCGCCATGCCCGAAGGCTACGTCCAGGAGCGCACCATCTTCTT<br>CAAGGACGACGGCAACTACAAGACCCGCGCCGAGGTGAAGTTCGAGGGCGACACCCTGGTGAACCGCATC<br>GAGCTGAAGGGCATCGACTTCAAGGAGGACGGCAACATCCTGGGGCACAAGCTGGAGTACAACTACAACA<br>GCCACAACGTCTATATCACCGCCGACAAGCAGAAGAACGGCATCAAGGCCAACTTCAAGATCCGCCACAA<br>CATCGAGGACGGCGGCGTGCAGCTCGCCGACCACTACCAGCAGAACACCCCCATCGGCGACGGCCCCGTG<br>CTGCTGCCCGACAACCACTACCTGAGCTACCAGTCCGCCCTGAGCAAAGACCCCAACGAGAAGCGCGATC<br>ACATGGTCCTGCTGGAGTTCGTGACCGCCGCCGGGATCACTCTCGGCATGGACGAGCTGTACAAG |

The FLT3 CAR T cells were assessed for killing activity in vitro. FLT3 CAR with the NC7 or D4-3 FLT3 scFvs were mixed at a 1:1 ratio with MOLM-13, THP-1, or SEM cells. T cells and cell lines were co-cultured for 18 hours, and then stained with live/dead stain. Unmodified T cells were used as a negative control. Killing efficiency was assessed via flow cytometry. Final killing efficiency was calculated by normalizing killing to an FLT3-negative K562 cell line. A dose response assay was also performed. The NC7 FLT3 CAR was mixed with MOLM-13 cells at increasing effector to target cell ratios (1:9, 1:3, 1:1, 3:1, and 9:1 E:T ratios) and the percent killing efficiency was assessed via flow cytometry as previously described.

The FLT3 CAR T cells were assessed for cytokine production in vitro. All three FLT3 CARs (ml006, NC7, and D4-3) were individually mixed at a 1:1 ratio with the AML cell lines MOML-13, MOLM-14, or Eol 1. T cells and cell lines were co-cultured for 18 hours and the supernatants collected for cytokine quantification using the Luminex multiplexed assays. In all cases the cytokine levels were compared to those of an unengineered T cell negative control.

Results

Figures 40A, 40B, 40C:
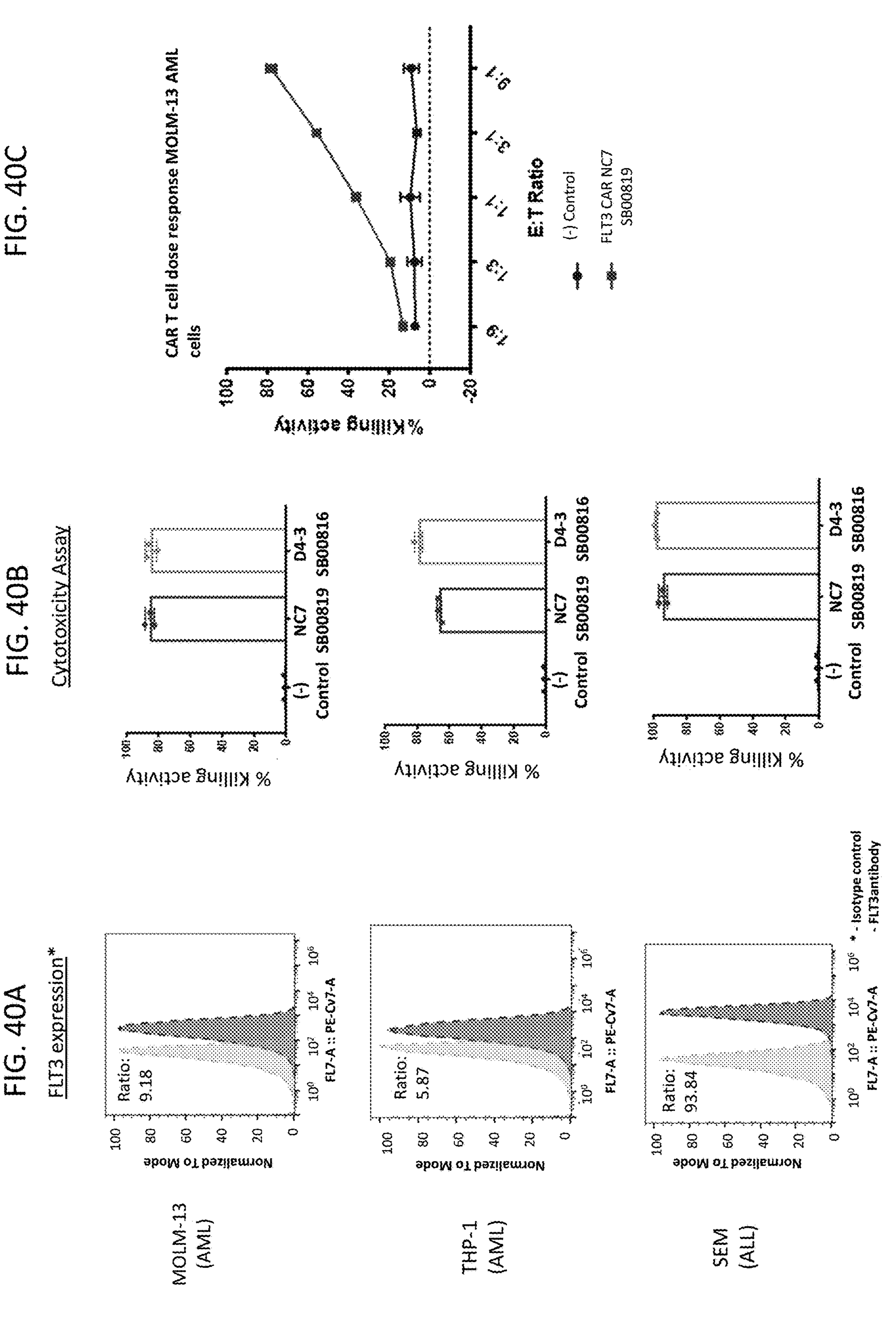
FIG. 40A shows the flow cytometry histogram plots showing expression of FLT3 protein expression (x-axis) in the AML cell lines MOLM-13, THP-1, and the ALL cell line SEM.
FIG. 40B shows that the FLT3 CAR T cells killed MOML-13, THP-1, and SEM human leukemia cells.
FIG. 40C shows a dose dependent FLT3 CAR T cell killing of MOLM-13 AML cells.

NC7 (SB00819) and D4-3 (SB00816) FLT3 CAR T cells show potent cytotoxicity activity against human leukemia cell lines MOLM-13, THP-1, and SEM. FIG. 40A shows the flow cytometry histogram plots showing expression of FLT3 protein expression (x-axis) in the leukemia cell lines. Two FLT3 CAR T cells killed MOML-13 and THP-1 human leukemia cells (E:T ratio of 1:1), as well as SEM cells expressing FLT3 (FIG. 40B).

FIG. 40C shows a dose dependent FLT3 CAR T cell killing of MOLM-13 AML cells. As the ratio of FLT3 T cells increased (E, effector cells) as compared to MOLM-13 cells (T, target cells), the percent killing increased. Thus, FLT3 CAR T cells demonstrate potent in vitro killing activity against human leukemia cells.

Figures 41A, 41B, 41C:
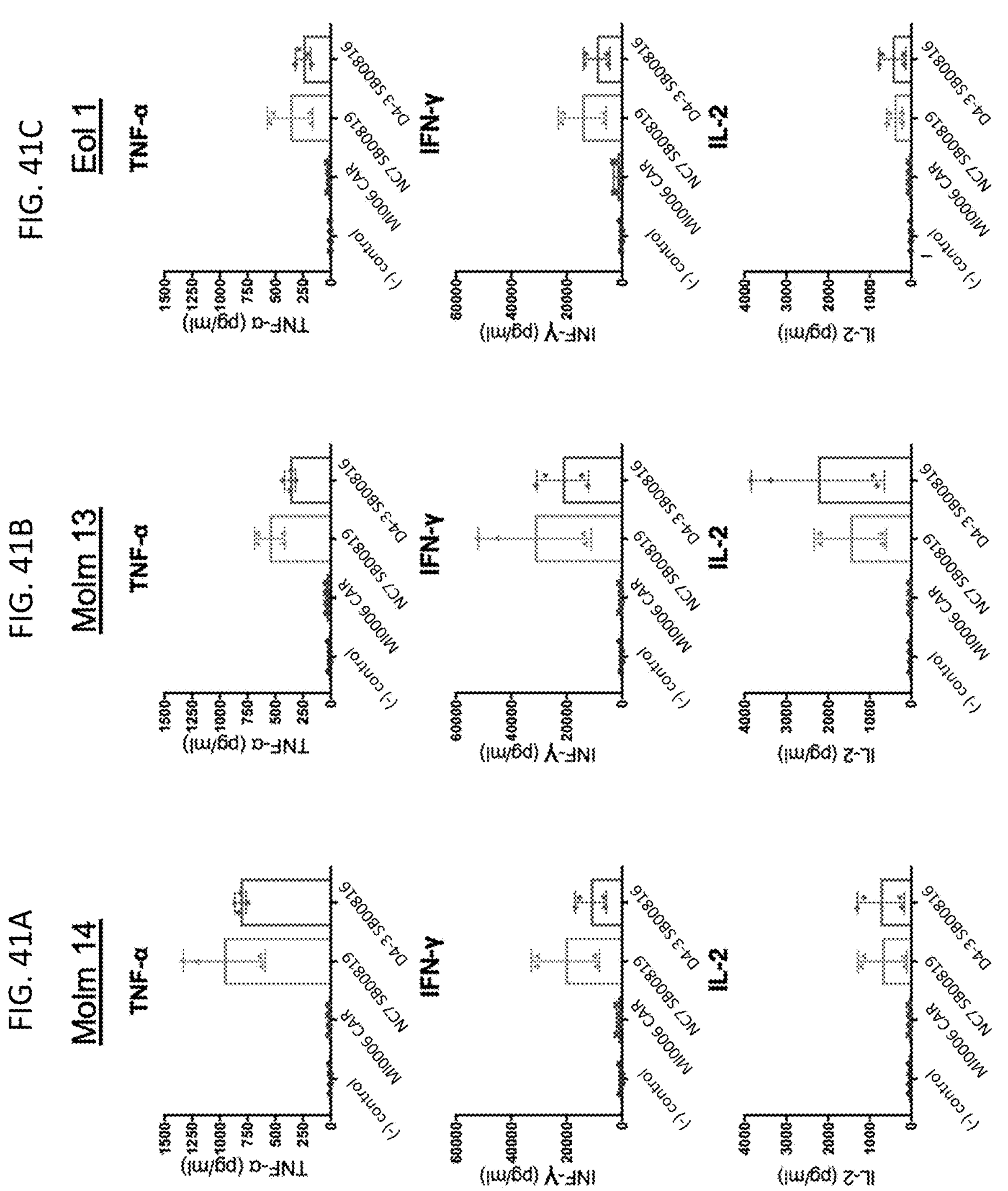
FIG. 41A shows that FLT3 CAR T cells induced TNF-α, IFN-γ, and IL-2 production after incubation with MOLM-14 cells.
FIG. 41B shows that FLT3 CAR T cells induced TNF-α, IFN-γ, and IL-2 production after incubation with MOLM-13 cells.
FIG. 41C shows that FLT3 CAR T cells induced TNF-α, IFN-γ, and IL-2 production after incubation with EOL-1 cells.

In addition, the two of the three FLT3 CAR T cells secreted cytokines when incubated with various FLT3 expressing AML cell lines. The NC7 FLT3 CAR and D4-3 FLT3 CAR both secreted TNFα, IFN-γ, and IL-2 when incubated with MOLM-14 cells (FIG. 41A), MOLM-13 cells (FIG. 41B), and Eol 1 cells (FIG. 41C). Thus, FLT3 CAR T cells demonstrated potent reactivity against various human AML tumor cell lines.

Example 16: In Vitro Characterization of CD33 CAR T Cells

Materials and Methods

Cell Surface Expression

Expression of the CD33 receptor was confirmed MOLM-13, MV4-11, and THP-1 cells using flow cytometry. An isotype control was used as a negative control for background antibody staining, and cells were stained with a human CD33 antibody (conjugated to BV421, clone: WM53; Biolegend), and a ratio was determined between the negative and CD33+ population.

T Cell Assays

T cells from 1 donor were genetically modified to express CARs with two different CD33 scFv polypeptides. The CD33 scFvs used were derived from the hu195 (lintuzumab) and Mylo (gemtuzumab) CD33 antibodies. The CARs had an IgK signal sequence, a FLAG tag, a CD28 hinge, a CD28 transmembrane domain, a CD28 intracellular co-stimulatory domain, and a CD3ζ signaling domain. The protein and nucleotide sequences of the hu195 and Mylo CD33 CARs made are shown in Table 6.

TABLE 6

| SEQ ID NO | Name | Sequence |
|---|---|---|
| 157 | IgKss_Flag_CD33(hu195)_CD28 hinge_CD28 TM_CD28 ICD_CD3z SB01052 | METDTLLLWVLLLWVPGSTGAGGSDYKDDDDKGGSQVQLVQSGAEVKKPGSSVKVSCKASGYTFTDYNMHWVRQAPGQGLEWIGYIYPYNGGTGYNQKFKSKATITADESTNTAYMELSSLRSEDTAVYYCARGRPAMDYWGQGTLVTVSSGGGGSGGGGSGGGGSDIQMTQSPSSLSASVGDRVTITCRASESVDNYGISFMNWFQQKPGKAPKLLIYAASNQGSGVPSRFSGSGSGTDFTLTISSLQPDDFATYYCQQSKEVPWTFGQGTKVEIKSGAAAIEVMYPPPYLDNEKSNGTIIHVKGKHLCPSPLFPGPSKPFWVLVVVGGVLACYSLLVTVAFIIFWVRSKRSRLLHSDYMNMTPRRPGPTRKHYQPYAPPRDFAAYRSRVKFSRSADAPAYKQGQNQLYNELNLGRREEYDVLDKRRGRDPEMGGKPRRKNPQEGLYNELQKDKMAEAYSEIGMKGERRRGKGHDGLYQGLSTATKDTYDALHMQALPPR |
| 158 | IgKss_Flag_CD33(hu195)_CD28 hinge_CD28 TM_CD28 ICD_CD3z SB01052 | ATGGAAACGGATACTCTGCTGCTGTGGGTCCTCTTGCTTTGGGTACCTGGGAGTACCGGCGCTGGCGGGTCCGATTACAAGGACGATGACGACAAAGGGGGTTCTCAGGTTCAGCTGGTTCAGTCTGGCGCCGAAGTGAAGAAACCTGGCAGCAGCGTGAAGGTGTCCTGCAAGGCCAGCGGCTACACCTTTACCGACTACAACATGCACTGGGTCCGACAGGCCCCTGGACAAGGACTTGAGTGGATCGGCTACATCTACCCCTACAATGGCGGCACCGGCTACAACCAGAAGTTCAAGAGCAAGGCCACCATCACCGCCGACGAGAGCACAAACACCGCCTACATGGAACTGAGCAGCCTGAGAAGCGAGGACACCGCCGTGTACTACTGTGCCAGAGGCAGACCCGCCATGGATTATTGGGGACAGGGCACCCTGGTCACCGTTTCTAGCGGAGGCGGAGGATCTGGTGGCGGAGGAAGTGGCGGAGGCGGTTCTGATATCCAGATGACACAGAGCCCCAGCAGCCTGTCTGCCAGCGTGGGAGATAGAGTGACCATCACCTGTAGAGCCAGCGAGAGCGTGGACAACTACGGCATCAGCTTCATGAACTGGTTCCAGCAGAAGCCCGGCAAGGCCCCTAAGCTGCTGATCTACGCCGCCAGCAATCAAGGCAGCGGAGTGCCTAGCAGATTTTCCGGCTCTGGCAGCGGCACCGATTTCACCCTGACAATCTCTAGCCTCCAGCCTGACGACTTCGCCACCTACTACTGCCAGCAGAGCAAAGAGGTGCCCTGGACATTCGGCCAGGGCACAAAGGTGGAAATCACTATCATTCATGTAAAAGGGAAGCATCTTTGTCCTTCTCCCCTTTTCCCCGGTCCGTCTAAACCTTTCAAGAGCGGAGCAGCAGCTATCGAGGTGATGTATCCTCCGCCCTACCTGGATAATGAAAAGAGTAATGGGACTATCATTCATGTAAAAGGGAAGCATCTTTGTCCTTCTCCCCTTTTCCCCGGTCCGTCTAAACCTTTCTGGGTGCTTGTGGTCGTGGGTGGAGTGCTTGCGTGTTACTCCCTGCTGGTGACCGTCGCCTTCATCATTTTCTGGGTCAGGAGCAAACGATCTCGCCTCCTCCATTCTGACTATATGAACATGACTCCTCGCAGACCCGGACCTACGCGGAAACATTACCAACCGTACGCGCCTCCGAGAGACTTCGCCGCGTACAGAAGTAGGGTCAAGTTTAGCAGGTCAGCGGACGCACCAGCTTACAAGCAAGGCCAAAACCAGCTTTATAACGAATTGAATTTGGGACGCAGGGAAGAATACGATGTGCTCGATAAACGCAGAGGGAGGGACCCGGAAATGGGAGGAAAGCCAAGGCGGAAAAACCCACAGGAGGGGTTGTACAACGAGCTTCAAAAAGATAAGATGGCGGAAGCATACTCCGAAATAGGAATGAAGGGTGAACGGAGGAGGGGCAAGGGCCACGACGGCCTGTACCAGGGACTCTCAACTGCTACGAAGGATACTTATGATGCTCTTCACATGCAAGCTCTGCCGCCGCGC |

TABLE 6-continued

| SEQ ID NO | Name | Sequence |
|---|---|---|
| 159 | IgKss_Flag_CD33(Mylo)_CD28 hinge_CD28 TM_CD28 ICD_CD3z SB01056 | METDTLLLWVLLLWVPGSTGAGGSDYKDDDDKGGSEVQLVQSGAEVKKPGSSVKVSCKASGYTITDSNIHWVRQAPGQSLEWIGYIYPYNGGTDYNQKFKNRATLTVDNPTNTAYMELSSLRSEDTAFYYCVNGNPWLAYWGQGTLVTVSSGGGGSGGGGSGGGGSDIQLTQSPSTLSASVGDRVTITCRASESLDNYGIRFLTWFQQKPGKAPKLLMYAASNQGSGVPSRFSGSGSGTEFTLTISSLQPDDFATYYCQQTKEVPWSFGQGTKVEVKRTSSGAAAIEVMYPPPYLDNEKSNGTIIHVKGKHLCPSPLFPGPSKPFWVLVVVGGVLACYSLLVTVAFIIFWVRSKRSRLLHSDYMNMTPRRPGPTRKHYQPYAPPRDFAAYRSRVKFSRSADAPAYKQGQNQLYNELNLGRREEYDVLDKRRGRDPEMGGKPRRKNPQEGLYNELQKDKMAEAYSEIGMKGERRRGKGHDGLYQGLSTATKDTYDALHMQALPPR |
| 160 | IgKss_Flag_CD33(Mylo)_CD28 hinge_CD28 TM_CD28 ICD_CD3z SB01056 | ATGGAAACGGATACTCTGCTGCTGTGGGTCCTCTTGCTTTGGGTACCTGGGAGTACCGGCGCTGGCGGGTCCGATTACAAGGACGATGACGACAAAGGGGGTTCTGAAGTGCAGCTGGTTCAGTCTGGCGCCGAAGTGAAGAAACCTGGCAGCAGCGTGAAGGTGTCCTGCAAGGCCAGCGGCTACACCATCACCGACAGCAACATCCACTGGGTCCGACAGGCTCCAGGCCAGTCTCTTGAGTGGATCGGCTACATCTACCCCTACAACGGCGGCACCGACTACAACCAGAAGTTCAAGAACCGGGCCACACTGACCGTGGACAACCCTACCAATACCGCCTACATGGAACTGAGCAGCCTGCGGAGCGAGGACACCGCCTTTTACTACTGCGTGAACGGCAACCCCTGGCTGGCCTATTGGGGACAGGGAACACTGGTCACAGTGTCTAGCGGAGGCGGAGGATCTGGTGGCGGAGGAAGTGGCGGAGGCGGTTCTGATATTCAGCTGACACAGAGCCCCAGCACACTGTCTGCCTCTGTGGGCGACAGAGTGACCATCACCTGTAGAGCCAGCGAGAGCCTGGACAACTACGGCATCAGATTTCTGACCTGGTTCCAGCAGAAGCCCGGCAAGGCTCCTAAGCTGCTGATGTACGCCGCCAGCAATCAAGGCAGCGGAGTGCCTAGCAGATTTTCCGGCTCTGGCAGCGGCACAGAGTTCACCCTGACAATCTCTAGCCTCCAGCCTGACGACTTCGCCACCTACTACTGCCAGCAGACCAAAGAGGTGCCCTGGTCCTTTGGACAGGGCACCAAGGTGGAAGTGAAGCGGACTAGCTCCGGAGCAGCAGCTATCGAGGTGATGTATCCTCCGCCCTACCTGGATAATGAAAAGAGTAATGGGACTATCATTCATGTAAAAGGGAAGCATCTTTGTCCTTCTCCCCTTTTCCCCGGTCCGTCTAAACCTTTCTGGGTGCTTGTGGTCGTGGGTGGAGTGCTTGCGTGTTACTCCCTGCTGGTGACCGTCGCCTTCATCATTTTCTGGGTCAGGAGCAAACGATCTCGCCTCCTCCATTCTGACTATATGAACATGACTCCTCGCAGACCCGGACCTACGCGGAAACATTACCAACCGTACGCGCCTCCGAGAGACTTCGCCGCGTACAGAAGTAGGGTCAAGTTTAGCAGGTCAGCGGACGCACCAGCTTACAAGCAAGGCCAAAACCAGCTTTATAACGAATTGAATTTGGGACGCAGGGAAGAATACGATGTGCTCGATAAACGCAGAGGGAGGGACCCGGAAATGGGAGGAAAGCCAAGGCGGAAAAACCCACAGGAGGGGTTGTACAACGAGCTTCAAAAAGATAAGATGGCGGAAGCATACTCCGAAATAGGAATGAAGGGTGAACGGAGGAGGGGCAAGGGCCACGACGGCCTGTACCAGGGACTCTCAACTGCTACGAAGGATACTTATGATGCTCTTCACATGCAAGCTCTGCCGCCGCGC |

The CD33 CAR T cells were assessed for killing activity in vitro. CD33 CARs with the hu195 (SB01052) or Mylo (SB01056) CD33 scFvs were mixed at a 1:1 ratio with MOLM-13, MV4-11, or THP-1 cells. T cells and cell lines were co-cultured for 18 hours, and then stained with live/dead stain. Killing efficiency was assessed via flow cytometry. Unmodified T cells were used as a negative control. A dose response assay was also performed with both CD33 CARs in the MOLM-13 and MV4-11 cell lines. The CD33 CARs were mixed with MOLM-13 or MV4-11 cells cells at increasing effector to target cell ratios (1:3, 1:2, 1:1, 2:1, and 3:1 E:T ratios) and the percent killing efficiency was assessed via flow cytometry as previously described. Final killing efficiency was calculated by normalizing killing to a CD33-negative K562 cell line The CD33 CAR T cells were assessed for cytokine production in vitro. Both CD33 CARs were individually mixed at a 1:1 ratio with the AML cell lines MOML-13, MOLM-14, or Eol 1. T cells and cell lines were co-cultured for 18 hours and the supernatants collected for cytokine quantification using the Luminex multiplex assay. In all cases the cytokine levels were compared to those of an unengineered T cell negative control.

Results

CD33 CAR T cells show potent cytotoxicity activity in vitro against multiple human acute myeloid leukemia (AML) cell lines. FIG. 42A shows flow cytometry histogram plots of cell surface expression of CD33 protein expression in the AML cell lines MOLM-13, MV4-11, and THP-1. FIG. 42B shows two different CD33 CAR T cells kill human AML cells in in vitro co-culture cytotoxicity assays. In addition, both CD33 antibodies induced cytotoxicity in a dose dependent manner (FIG. 42C). In vitro cytotoxicity assay showing increased CD33 CAR T cell killing of MOLM-13 and MV4-11 AML cell lines at higher effector to target cell (E:T) ratios.

Figures 43A, 43B, 43C:
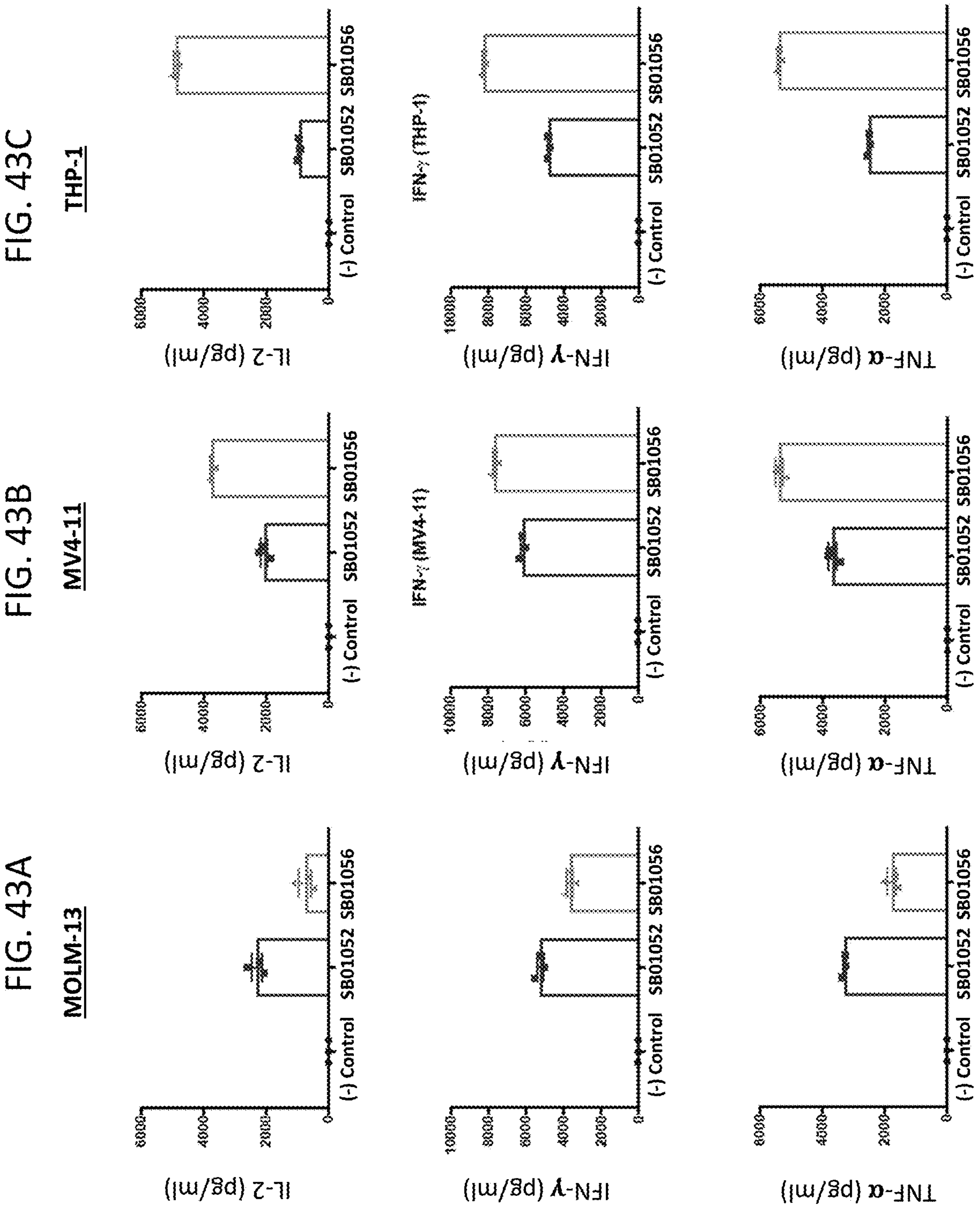
FIG. 43A shows that CD33 CAR T cells induced TNF-α, IFN-γ, and IL-2 production after incubation with MOLM-13 cells.
FIG. 43B shows that CD33 CAR T cells induced TNF-α, IFN-γ, and IL-2 production after incubation with MV4-11 cells.
FIG. 43C shows that CD33 CAR T cells induced TNF-α, IFN-γ, and IL-2 production in THP-1 cells.

CD33 CAR T cells demonstrates potent reactivity against multiple AML tumor cell lines. CD33 CAR T cells show potent cytokine secretion (IL-2, IFN-γ, TNF-α) when co-cultured with human acute myeloid leukemia (AML) cell lines, as detected by Luminex assay. FIG. 43A shows that the two different CD33 CAR T cells (SB01052 and SB01056) secreted IL-2, IFN-γ, and TNF-α after incubation with MOLM-13 cells. FIG. 43B shows that the two different CD33 CAR T cells (SB01052 and SB01056) secreted IL-2, IFN-γ, and TNF-α after incubation with MV4-11 AML cells. FIG. 43C shows two that the two different CD33 CAR T cells (SB01052 and SB01056) secreted IL-2, IFN-γ, and TNF-α after incubation with THP-1 AML cells.

Example 17: In Vitro Characterization of CLEC12A CAR T Cells

Materials and Methods

Cell Surface Expression

Expression of CLEC12A in various AML, leukemia, or lymphoma cell lines (U937, THP-1, HL-60, MV-14, MOLM-14, MOLM-13, Nalm6, Raji, K562, and SEM) was determined by flow cytometry using a PE anti-human CD371 (CLEC12A) antibody (BioLegend, Clone 50C1), and a ratio was determined between the negative and CLEC12A+ population.

T Cell Assays

T cells from 1 donor were genetically modified to express CARs with three different CLEC12A scFv polypeptides. The CLEC12A scFvs used were clones 357, 378, and 161. The CARs had a CD8 signal sequence (CD8ss), a CD8 hinge, a CD8 transmembrane domain, an intracellular CD3ζ signaling domain, and a 4-1BB co-stimulatory domain (4-1BB co-stim). A YFP tag was fused to the C terminus of the CD3ζ signaling domain. The protein and nucleotide sequences of the CLEC12A CARs made are shown in Table 7.

TABLE 7

| SEQ ID NO | Name | Sequence |
|---|---|---|
| 162 | CD8ss_Clec12A(357)_CD8 hinge_CD8 TM_41BB ICD_CD3z_ YFP SB01261 | MALPVTALLLPLALLLHAARPQVQLQESGPGLVKPSETLSLTCVVSGGSISSSNWWSWVRQPPGKGLEW<br>IGEIYHSGSPDYNPSLKSRVTISVDKSRNQFSLKLSSVTAADTAVYYCAKVSTGGFFDYWGQGTLVTVS<br>SGGGGSGGGGSGGGGSEIELTQSPSSLSASVGDRVTITCRASQSISSYLNWYQQKPGKAPKLLIYAASS<br>LQSGVPSRFSGSGSGTDFTLTISSLQPEDFATYYCQQSYSTPPTFGPGTKVEIKTTTPAPRPPTPAPTI<br>ALQPLSLRPEACRPAAGGAVHTRGLDFACDIYIWAPLAGTCGVLLLSLVITKRGRKKLLYIFKQPFMRP<br>VQTTQEEDGCSCRFPEEEEGGCELRVKFSRSADAPAYKQGQNQLYNELNLGRREEYDVLDKRRGRDPEM<br>GGKPRRKNPQEGLYNELQKDKMAEAYSEIGMKGERRRGKGHDGLYQGLSTATKDTYDALHMQALPPRGS<br>SGTGMVSKGEELFTGVVPILVELDGDVNGHKFSVSGEGEGDATYGKLTLKLICTTGKLPVPWPTLVTTL<br>GYGLQCFARYPDHMKQHDFFKSAMPEGYVQERTIFFKDDGNYKTRAEVKFEGDTLVNRIELKGIDFKED<br>GNILGHKLEYNYNSHNVYITADKQKNGIKANFKIRHNIEDGGVQLADHYQQNTPIGDGPVLLPDNHYLS<br>YQSALSKDPNEKRDHMVLLEFVTAAGITLGMDELYK* |
| 163 | CD8ss_Clec12A(357)_CD8 hinge_CD8 TM_41BB ICD_CD3z_ YFP SB01261 | ATGGCCTTACCAGTGACCGCCTTGCTCCTGCCGCTGGCCTTGCTGCTCCACGCCGCCAGGCCGCAGGTG<br>CAGCTGCAGGAGTCGGGCCCAGGACTGGTGAAGCCTTCGGAGACCCTGTCCCTCACCTGCGTTGTCTCT<br>GGTGGCTCCATCAGCAGTAGTAACTGGTGGAGCTGGGTCCGCCAGCCCCCAGGGAAGGGGCTGGAGTGG<br>ATTGGGGAAATCTATCATAGTGGGAGCCCCGACTACAACCCGTCCCTCAAGAGTCGAGTCACCATATCA<br>GTAGACAAGTCCAGGAACCAGTTCTCCCTGAAGCTGAGCTCTGTGACCGCCGCGGACACGGCCGTGTAT<br>TACTGTGCAAAGGTTAGTACTGGTGGTTTCTTTGACTACTGGGGGCAAGGTACCCTGGTCACCGTCTCG<br>AGTGGTGGAGGCGGTTCAGGCGGAGGTGGCTCTGGCGGTGGCGGATCGGAAATTGAGCTCACCCAGTCT<br>CCATCCTCCCTGTCTGCATCTGTAGGAGACAGAGTCACCATCACTTGCCGGGCAAGTCAGAGCATTAGC<br>AGCTACTTAAATTGGTATCAGCAGAAACCAGGGAAAGCCCCTAAGCTCCTGATCTATGCTGCATCCAGT<br>TTGCAAAGTGGGGTCCCATCAAGGTTCAGTGGCAGTGGATCTGGGACAGATTTCACTCTCACCATCAGC<br>AGTCTGCAACCTGAAGATTTTGCAACTTACTACTGTCAACAGAGTTACAGTACCCCTCCAACGTTCGGC<br>CCAGGGACCAAGGTGGAGATCAAAACCACGACGCCGGCGCCCCGGCCTCCCACCCCCGCACCAACGATA<br>GCCCTTCAGCCCTTGAGCCTCCGGCCAGAAGCATGCCGCCCGGCAGCCGGAGGTGCAGTCCATACGCGC<br>GGACTGGACTTTGCATGTGACATCTACATATGGGCCCCCCTCGCCGGTACTTGCGGTGTTTTGCTTTTG<br>TCACTGGTGATTACGAAGCGCGGTCGAAAAAAACTCCTCTACATCTTCAAACAACCTTTCATGCGGCCT<br>GTCCAAACAACTCAAGAAGAGGACGGGTGTTCATGCCGCTTTCCAGAGGAAGAGGAAGGTGGCTGTGAA<br>CTTAGGGTCAAGTTTAGCAGGTCAGCGGACGCACCAGCTTACAAGCAAGGCCAAAACCAGCTTTATAAC<br>GAATTGAATTTGGGACGCAGGGAAGAATACGATGTGCTCGATAAACGCAGAGGGAGGGACCCGGAAATG<br>GGAGGAAAGCCAAGGCGGAAAAACCCACAGGAGGGGTTGTACAACGAGCTTCAAAAAGATAAGATGGCG<br>GAAGCATACTCCGAAATAGGAATGAAGGGTGAACGGAGGAGGGGCAAGGGCCACGACGGCCTGTACCAG<br>GGACTCTCAACTGCTACGAAGGATACTTATGATGCTCTTCACATGCAAGCTCTGCCGCCGCGCGGATCG<br>AGTGGCACCGGTATGGTGAGCAAGGGCGAGGAGCTGTTCACCGGGGTGGTGCCCATCCTGGTCGAGCTG<br>GACGGCGACGTAAACGGCCACAAGTTCAGCGTGTCCGGCGAGGGCGAGGGCGATGCCACCTACGGCAAG<br>CTGACCCTGAAGCTGATCTGCACCACCGGCAAGCTGCCCGTGCCCTGGCCCACCCTCGTGACCACCCTG<br>GGCTACGGCCTCCAGTGCTTCGCCCGCTACCCCGACCACATGAAGCAGCACGACTTCTTCAAGTCCGCC<br>ATGCCCGAAGGCTACGTCCAGGAGCGCACCATCTTCTTCAAGGACGACGGCAACTACAAGACCCGCGCC<br>GAGGTGAAGTTCGAGGGCGACACCCTGGTGAACCGCATCGAGCTGAAGGGCATCGACTTCAAGGAGGAC<br>GGCAACATCCTGGGGCACAAGCTGGAGTACAACTACAACAGCCACAACGTCTATATCACCGCCGACAAG<br>CAGAAGAACGGCATCAAGGCCAACTTCAAGATCCGCCACAACATCGAGGACGGCGGCGTGCAGCTCGCC<br>GACCACTACCAGCAGAACACCCCCATCGGCGACGGCCCCGTGCTGCTGCCCGACAACCACTACCTGAGC<br>TACCAGTCCGCCCTGAGCAAAGACCCCAACGAGAAGCGCGATCACATGGTCCTGCTGGAGTTCGTGACC<br>GCCGCCGGGATCACTCTCGGCATGGACGAGCTGTACAAGTAA |
| 164 | CD8ss_Clec12A(378)_CD8 hinge_CD8 TM_41BB ICD_CD3z_ YFP SB01262 | MALPVTALLLPLALLLHAARPQVQLQESGPGLVKPSETLSLTCVVSGGSISSSNWWSWVRQPPGKGLEW<br>IGEIYHSGSPNYNPSLKSRVTISVDKSKNQFSLKLSSVTAADTAVYYCARSSSGGFFDYWGQGTLVTVS<br>LQSGVPSRFSGSGSGTDFTLTISSLQPEDFATYYCQQSYSTPPTFGQGTKVEIKTTTPAPRPPTPAPTI<br>SGGGGSGGGGSGGGGSEIELTQSPSSLSASVGDRVTITCRASQSISSYLNWYQQKPGKAPKLLIYAASS<br>LQSGVPSRFSGSGSGTDFTLTISSLQPEDFATYYCQQSYSTPPTFGQGTKVEIKTTTPAPRPPTPAPTI<br>ALQPLSLRPEACRPAAGGAVHTRGLDFACDIYIWAPLAGTCGVLLLSLVITKRGRKKLLYIFKQPFMRP<br>VQTTQEEDGCSCRFPEEEEGGCELRVKFSRSADAPAYKQGQNQLYNELNLGRREEYDVLDKRRGRDPEM<br>GGKPRRKNPQEGLYNELQKDKMAEAYSEIGMKGERRRGKGHDGLYQGLSTATKDTYDALHMQALPPRGS<br>SGTGMVSKGEELFTGVVPILVELDGDVNGHKFSVSGEGEGDATYGKLTLKLICTTGKLPVPWPTLVTTL<br>GYGLQCFARYPDHMKQHDFFKSAMPEGYVQERTIFFKDDGNYKTRAEVKFEGDTLVNRIELKGIDFKED<br>GNILGHKLEYNYNSHNVYITADKQKNGIKANFKIRHNIEDGGVQLADHYQQNTPIGDGPVLLPDNHYLS<br>YQSALSKDPNEKRDHMVLLEFVTAAGITLGMDELYK* |
| 165 | CD8ss_Clec12A(378)_CD8 hinge_CD8 TM_41BB ICD_CD3z_ YFP SB01262 | ATGGCCTTACCAGTGACCGCCTTGCTCCTGCCGCTGGCCTTGCTGCTCCACGCCGCCAGGCCGCAGGTG<br>CAGCTGCAGGAGTCGGGCCCAGGACTGGTGAAGCCTTCGGAGACCCTGTCCCTCACCTGCGTTGTCTCT<br>GGTGGCTCCATCAGCAGTAGTAACTGGTGGAGCTGGGTCCGCCAGCCCCCAGGGAAGGGGCTGGAGTGG<br>ATTGGGGAAATCTATCATAGTGGGAGCCCCAACTACAACCCGTCCCTCAAGAGTCGAGTCACCATATCA<br>GTAGACAAGTCCAAGAACCAGTTCTCCCTGAAGCTGAGCTCTGTGACCGCCGCGGACACGGCCGTGTAT<br>TACTGTGCAAGGTCGTCTTCTGGTGGTTTCTTTGACTACTGGGGCCAAGGTACCCTGGTCACCGTCTCG<br>AGTGGTGGAGGCGGTTCAGGCGGAGGTGGCTCTGGCGGTGGCGGATCGGAAATTGAGCTCACCCAGTCT<br>CCATCCTCCCTGTCTGCATCTGTAGGAGACAGAGTCACCATCACTTGCCGGGCAAGTCAGAGCATTAGC<br>AGCTACTTAAATTGGTATCAGCAGAAACCAGGGAAAGCCCCTAAGCTCCTGATCTATGCTGCATCCAGT<br>TTGCAAAGTGGGGTCCCATCAAGGTTCAGTGGCAGTGGATCTGGGACAGATTTCACTCTCACCATCAGC<br>AGTCTGCAACCTGAAGATTTTGCAACTTACTACTGTCAACAGAGTTACAGTACCCCTCCAACGTTCGGC<br>CAAGGGACCAAGGTGGAGATCAAAACCACGACGCCGGCGCCCCGGCCTCCCACCCCCGCACCAACGATA<br>GCCCTTCAGCCCTTGAGCCTCCGGCCAGAAGCATGCCGCCCGGCAGCCGGAGGTGCAGTCCATACGCGC<br>GGACTGGACTTTGCATGTGACATCTACATATGGGCCCCCCTCGCCGGTACTTGCGGTGTTTTGCTTTTG |

TABLE 7-continued

| SEQ ID NO | Name | Sequence |
|---|---|---|
| | | TCACTGGTGATTACGAAGCGCGGTCGAAAAAAACTCCTCTACATCTTCAAACAACCTTTCATGCGGCCT<br>GTCCAAACAACTCAAGAAGAGGACGGGTGTTCATGCCGCTTTCCAGAGGAAGAGGAAGGTGGCTGTGAA<br>CTTAGGGTCAAGTTTAGCAGGTCAGCGGACGCACCAGCTTACAAGCAAGGCCAAAACCAGCTTTATAAC<br>GAATTGAATTTGGGACGCAGGGAAGAATACGATGTGCTCGATAAACGCAGAGGGAGGGACCCGGAAATG<br>GGAGGAAAGCCAAGGCGGAAAAACCCACAGGAGGGGTTGTACAACGAGCTTCAAAAAGATAAGATGGCG<br>GAAGCATACTCCGAAATAGGAATGAAGGGTGAACGGAGGAGGGGCAAGGGCCACGACGGCCTGTACCAG<br>GGACTCTCAACTGCTACGAAGGATACTTATGATGCTCTTCACATGCAAGCTCTGCCGCCGCGCGGATCG<br>AGTGGCACCGGTATGGTGAGCAAGGGCGAGGAGCTGTTCACCGGGGTGGTGCCCATCCTGGTCGAGCTG<br>GACGGCGACGTAAACGGCCACAAGTTCAGCGTGTCCGGCGAGGGCGAGGGCGATGCCACCTACGGCAAG<br>CTGACCCTGAAGCTGATCTGCACCACCGGCAAGCTGCCCGTGCCCTGGCCCACCCTCGTGACCACCCTG<br>GGCTACGGCCTCCAGTGCTTCGCCCGCTACCCCGACCACATGAAGCAGCACGACTTCTTCAAGTCCGCC<br>ATGCCCGAAGGCTACGTCCAGGAGCGCACCATCTTCTTCAAGGACGACGGCAACTACAAGACCCGCGCC<br>GAGGTGAAGTTCGAGGGCGACACCCTGGTGAACCGCATCGAGCTGAAGGGCATCGACTTCAAGGAGGAC<br>GGCAACATCCTGGGGCACAAGCTGGAGTACAACTACAACAGCCACAACGTCTATATCACCGCCGACAAG<br>CAGAAGAACGGCATCAAGGCCAACTTCAAGATCCGCCACAACATCGAGGACGGCGGCGTGCAGCTCGCC<br>GACCACTACCAGCAGAACACCCCCATCGGCGACGGCCCCGTGCTGCTGCCCGACAACCACTACCTGAGC<br>TACCAGTCCGCCCTGAGCAAAGACCCCAACGAGAAGCGCGATCACATGGTCCTGCTGGAGTTCGTGACC<br>GCCGCCGGGATCACTCTCGGCATGGACGAGCTGTACAAGTAA |
| 166 | CD8ss_Cle<br>c12A(161)_<br>CD8<br>hinge_CD8<br>TM_41BB<br>ICD_CD3z_<br>YFP<br>SB01263 | MALPVTALLLPLALLLHAARPQVQLQESGPGLVKPSETLSLTCVVSGGSISSSNWWSWVRQPPGKGLEW<br>IGEIYHSGSPNYNPSLKSRVTISVDKSKNQFSLKLSSVTAADTAVYYCARQTTAGSFDYWGQGTLVTVS<br>SGGGGSGGGGSGGGGSEIELTQSPSSLSASVGDRVTITCRASQSISSYLNWYQQKPGKAPKLLIYAASS<br>LQSGVPSRFSGSGSGTDFTLTISSLQPEDFATYYCQQSYSTPPTFGQGTKVEIKTTTPAPRPPTPAPTI<br>ALQPLSLRPEACRPAAGGAVHTRGLDFACDIYIWAPLAGTCGVLLLSLVITKRGRKKLLYIFKQPFMRP<br>VQTTQEEDGCSCRFPEEEEGGCELRVKFSRSADAPAYKQGQNQLYNELNLGRREEYDVLDKRRGRDPEM<br>GGKPRRKNPQEGLYNELQKDKMAEAYSEIGMKGERRRGKGHDGLYQGLSTATKDTYDALHMQALPPRGS<br>SGTGMVSKGEELFTGVVPILVELDGDVNGHKFSVSGEGEGDATYGKLTLKLICTTGKLPVPWPTLVTTL<br>GYGLQCFARYPDHMKQHDFFKSAMPEGYVQERTIFFKDDGNYKTRAEVKFEGDTLVNRIELKGIDFKED<br>GNILGHKLEYNYNSHNVYITADKQKNGIKANFKIRHNIEDGGVQLADHYQQNTPIGDGPVLLPDNHYLS<br>YQSALSKDPNEKRDHMVLLEFVTAAGITLGMDELYK* |
| 167 | CD8ss_Cle<br>c12A(161)_<br>CD8<br>hinge_CD8<br>TM_41BB<br>ICD_CD3z_<br>YFP<br>SB01263 | ATGGCCTTACCAGTGACCGCCTTGCTCCTGCCGCTGGCCTTGCTGCTCCACGCCGCCAGGCCGCAGGTG<br>CAGCTGCAGGAGTCGGGCCCAGGACTGGTGAAGCCTTCGGAGACCCTGTCCCTCACCTGCGTTGTCTCT<br>GGTGGCTCCATCAGCAGTAGTAACTGGTGGAGCTGGGTCCGCCAGCCCCCAGGGAAGGGGCTGGAGTGG<br>ATTGGGGAAATCTATCATAGTGGGAGCCCCAACTACAACCCGTCCCTCAAGAGTCGAGTCACCATATCA<br>GTAGACAAGTCCAAGAACCAGTTCTCCCTGAAGCTGAGCTCTGTGACCGCCGCGGACACGGCCGTGTAT<br>TACTGTGCAAGGCAGACTACTGCTGGGTCCTTTGACTACTGGGGCCAAGGTACCCTGGTCACCGTCTCG<br>AGTGGTGGAGGCGGTTCAGGCGGAGGTGGCTCTGGCGGTGGCGGATCGGAAATTGAGCTCACCCAGTCT<br>CCATCCTCCCTGTCTGCATCTGTAGGAGACAGAGTCACCATCACTTGCCGGGCAAGTCAGAGCATTAGC<br>AGCTACTTAAATTGGTATCAGCAGAAACCAGGGAAAGCCCCTAAGCTCCTGATCTATGCTGCATCCAGT<br>TTGCAAAGTGGGGTCCCATCAAGGTTCAGTGGCAGTGGATCTGGGACAGATTTCACTCTCACCATCAGC<br>AGTCTGCAACCTGAAGATTTTGCAACTTACTACTGTCAACAGAGTTACAGTACCCCTCCAACGTTCGGC<br>CAAGGGACCAAGGTGGAGATCAAAACCACGACGCCGGCGCCCCGGCCTCCCACCCCCGCACCAACGATA<br>GCCCTTCAGCCCTTGAGCCTCCGGCCAGAAGCATGCCGCCCGGCAGCCGGAGGTGCAGTCCATACGCGC<br>GGACTGGACTTTGCATGTGACATCTACATATGGGCCCCCCTCGCCGGTACTTGCGGTGTTTTGCTTTTG<br>TCACTGGTGATTACGAAGCGCGGTCGAAAAAAACTCCTCTACATCTTCAAACAACCTTTCATGCGGCCT<br>GTCCAAACAACTCAAGAAGAGGACGGGTGTTCATGCCGCTTTCCAGAGGAAGAGGAAGGTGGCTGTGAA<br>CTTAGGGTCAAGTTTAGCAGGTCAGCGGACGCACCAGCTTACAAGCAAGGCCAAAACCAGCTTTATAAC<br>GAATTGAATTTGGGACGCAGGGAAGAATACGATGTGCTCGATAAACGCAGAGGGAGGGACCCGGAAATG<br>GGAGGAAAGCCAAGGCGGAAAAACCCACAGGAGGGGTTGTACAACGAGCTTCAAAAAGATAAGATGGCG<br>GAAGCATACTCCGAAATAGGAATGAAGGGTGAACGGAGGAGGGGCAAGGGCCACGACGGCCTGTACCAG<br>GGACTCTCAACTGCTACGAAGGATACTTATGATGCTCTTCACATGCAAGCTCTGCCGCCGCGCGGATCG<br>AGTGGCACCGGTATGGTGAGCAAGGGCGAGGAGCTGTTCACCGGGGTGGTGCCCATCCTGGTCGAGCTG<br>GACGGCGACGTAAACGGCCACAAGTTCAGCGTGTCCGGCGAGGGCGAGGGCGATGCCACCTACGGCAAG<br>CTGACCCTGAAGCTGATCTGCACCACCGGCAAGCTGCCCGTGCCCTGGCCCACCCTCGTGACCACCCTG<br>GGCTACGGCCTCCAGTGCTTCGCCCGCTACCCCGACCACATGAAGCAGCACGACTTCTTCAAGTCCGCC<br>ATGCCCGAAGGCTACGTCCAGGAGCGCACCATCTTCTTCAAGGACGACGGCAACTACAAGACCCGCGCC<br>GAGGTGAAGTTCGAGGGCGACACCCTGGTGAACCGCATCGAGCTGAAGGGCATCGACTTCAAGGAGGAC<br>GGCAACATCCTGGGGCACAAGCTGGAGTACAACTACAACAGCCACAACGTCTATATCACCGCCGACAAG<br>CAGAAGAACGGCATCAAGGCCAACTTCAAGATCCGCCACAACATCGAGGACGGCGGCGTGCAGCTCGCC<br>GACCACTACCAGCAGAACACCCCCATCGGCGACGGCCCCGTGCTGCTGCCCGACAACCACTACCTGAGC<br>TACCAGTCCGCCCTGAGCAAAGACCCCAACGAGAAGCGCGATCACATGGTCCTGCTGGAGTTCGTGACC<br>GCCGCCGGGATCACTCTCGGCATGGACGAGCTGTACAAGTAA |

The CLEC12A CAR T cells were assessed for killing activity in vitro. CLEC12A CARs were mixed at a 1:1 ratio with U937, THP-1, HL-60, or MOLM-14 cells. T cells and cell lines were co-cultured for 18 hours, and then stained with live/dead stain. Killing efficiency was assessed via flow cytometry. FLT3 CAR T cells expressing SB00819 were used as a comparative benchmark for CAR T cell cytotoxicity and cytokine production. Final killing efficiency was calculated by normalizing killing to an untransduced control T cell sample and unengineered K562 basal killing control using the following formula: % killing=(1−RatioNE)*100%; RatioT:C=% live target cells/% live control cells; RatioNLv=Target/Control of no Lentivirus sample; RatioNE (normalized experimental)=RatioTC/RatioNLv.

Figure 44:
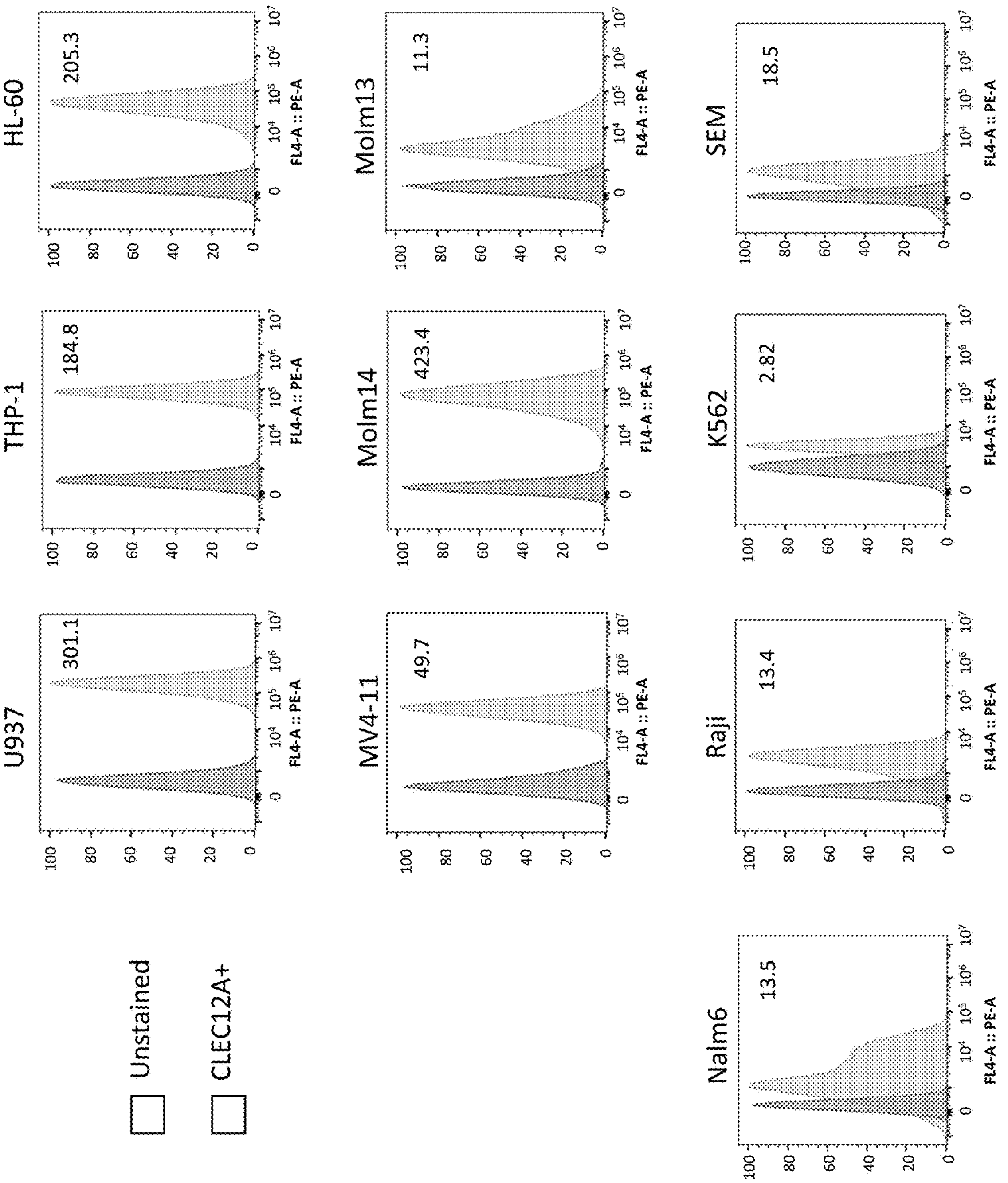
FIG. 44 shows flow cytometry plots of CLEC12A expression in U937, THP-1, HL-60, MV-14, MOLM-14, MOLM-13, Nalm6, Raji, K562, and SEM cell lines.

The CLEC12A CAR T cells were assessed for cytokine production in vitro. All CLEC12A CARs were individually mixed at a 1:1 ratio with the AML cell lines U937, THP-1, HL-60, or MOLM-14. T cells and cell lines were co-cultured for 18 hours and the supernatants collected for IL-2 cytokine quantification using the Luminex multiplex assay. In all cases the cytokine levels were compared to those of an unengineered T cell negative control Results CLEC12A was expressed on the AML, ALL, lymphoma, and leukemia cell lines U937, THP-1, HL-60, MV-14, MOLM-14, MOLM-13, Nalm6, Raji, K562, and SEM. FIG. 44 shows flow cytometry plots of CLEC12A expression in all cell lines tested. The ratio of CLEC12A stained cells to unstained in each cell population are indicated on each graph.

SB01261 has an anti-CLEC12A scFv domain derived from the 357 CLEC12A antibody clone. SB01262 has an anti-CLEC12A scFv domain derived from the 378 CLEC12A antibody clone. SB01263 had an anti-CLEC12A scFv domain derived from the 161 CLEC12A antibody clone.

Figures 45A, 45B, 45C:
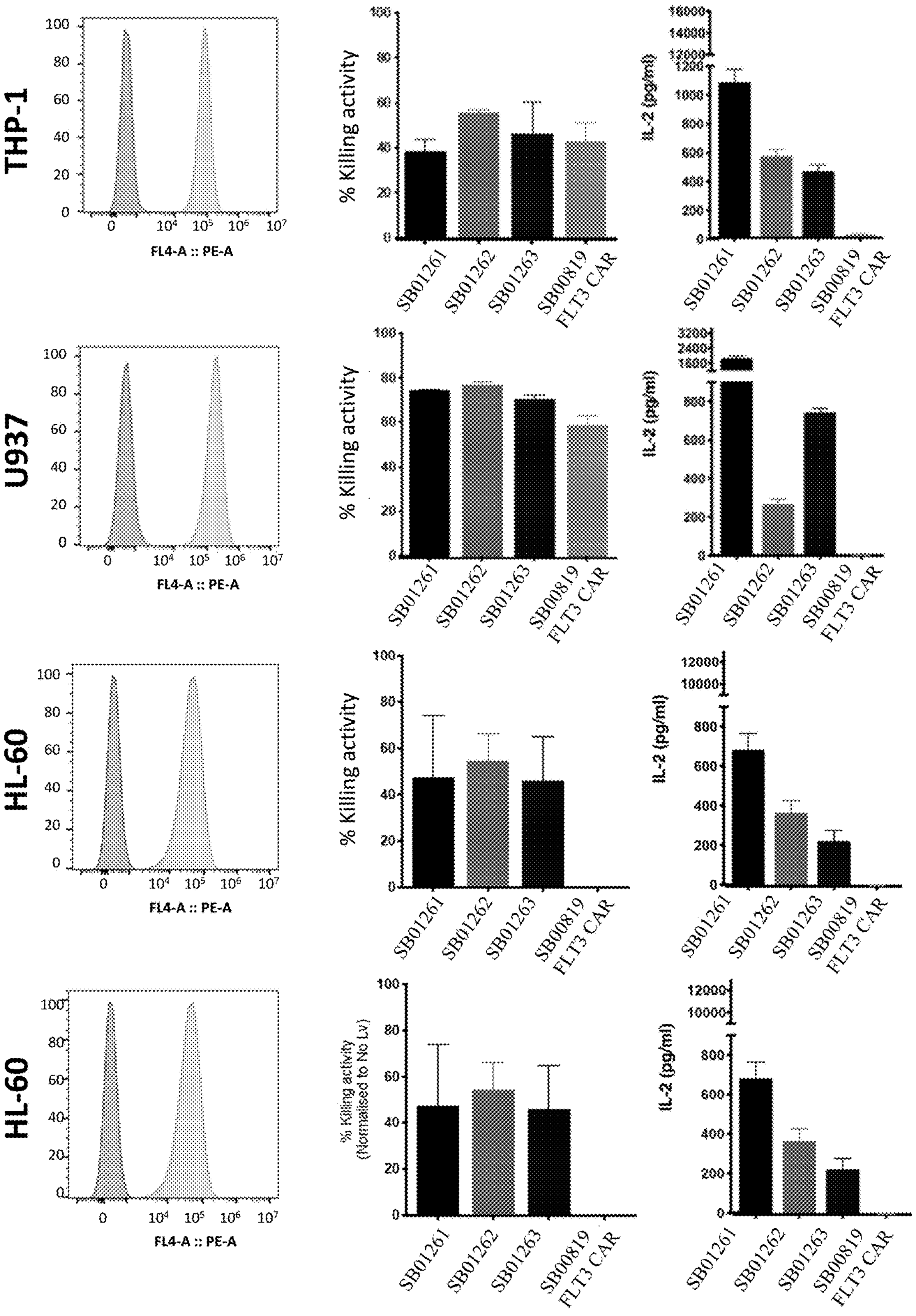
FIG. 45A shows flow cytometry histogram plots showing expression of CLEC12A protein expression in four AML cell lines.
FIG. 45B shows in vitro co-culture cytotoxicity assays showing that CLEC12A CAR T cells kill human AML cells (E:T ratio of 1:1) with percent killing activity on y-axis.
FIG. 45C shows CLEO 2A CAR T cells have potent cytokine secretion (IL-2) when co-cultured with human acute myeloid leukemia (AML) cell lines, as detected by Luminex assay. CAR #1=SB01261, CLEC12A(357) CAR T cell; CAR #2=SB01262, CLEC12A(378) CAR T cells; CAR #3=SB01263, CLEC12A(161) CAR T cells.

FIG. 45A shows flow cytometry histogram plots of cell surface expression of CLEC12A protein expression in the AML cell lines U937, THP-1, HL-60, and MOLM-14. FIG. 45B shows three different CLEC12A CAR T cells kill human AML cells in in vitro co-culture cytotoxicity assays in four different AML cell lines, U937, THP-1, HL-60, or MOLM-14. Thus, CLEC12A CAR T cells showed potent cytotoxicity activity in vitro against multiple human acute myeloid leukemia (AML) cell lines.

CLEC12A CAR T cells show potent IL-2 cytokine secretion when co-cultured with human acute myeloid leukemia (AML) cell lines, as detected by Luminex assay. FIG. 45C shows that three different CLEC12A CAR T cells secreted IL-2 after incubation with U937, THP-1, HL-60, or MOLM-14 cells. Thus, CLEC12A CAR T cells demonstrates potent reactivity against multiple AML tumor cell lines.

An additional CLEC12A CAR using the 378-derived scFv with a FLAG tag in place of the YFP tag (SB01161) was also made and characterized for cytotoxicity and cytokine secretion activity. The FLT3 CAR with an NC-7 scFv and YFP tag (SB00819) and the CD33 CAR with the hu195 scFv and a FLAG tag (SB01052) were used as controls. All six CARs (four CLEC12A CARs, the FLT3 CAR, and the CD33 CAR) were tested against AML cell lines with low CLEC12A expression, MOLM-13 and MV4-11; and AML cell lines with high CLEC12A expression, MOLM-14, U937, THP-1, and HL-60.

Figures 46A, 46B, 46C, 46D, 46E, 46F:
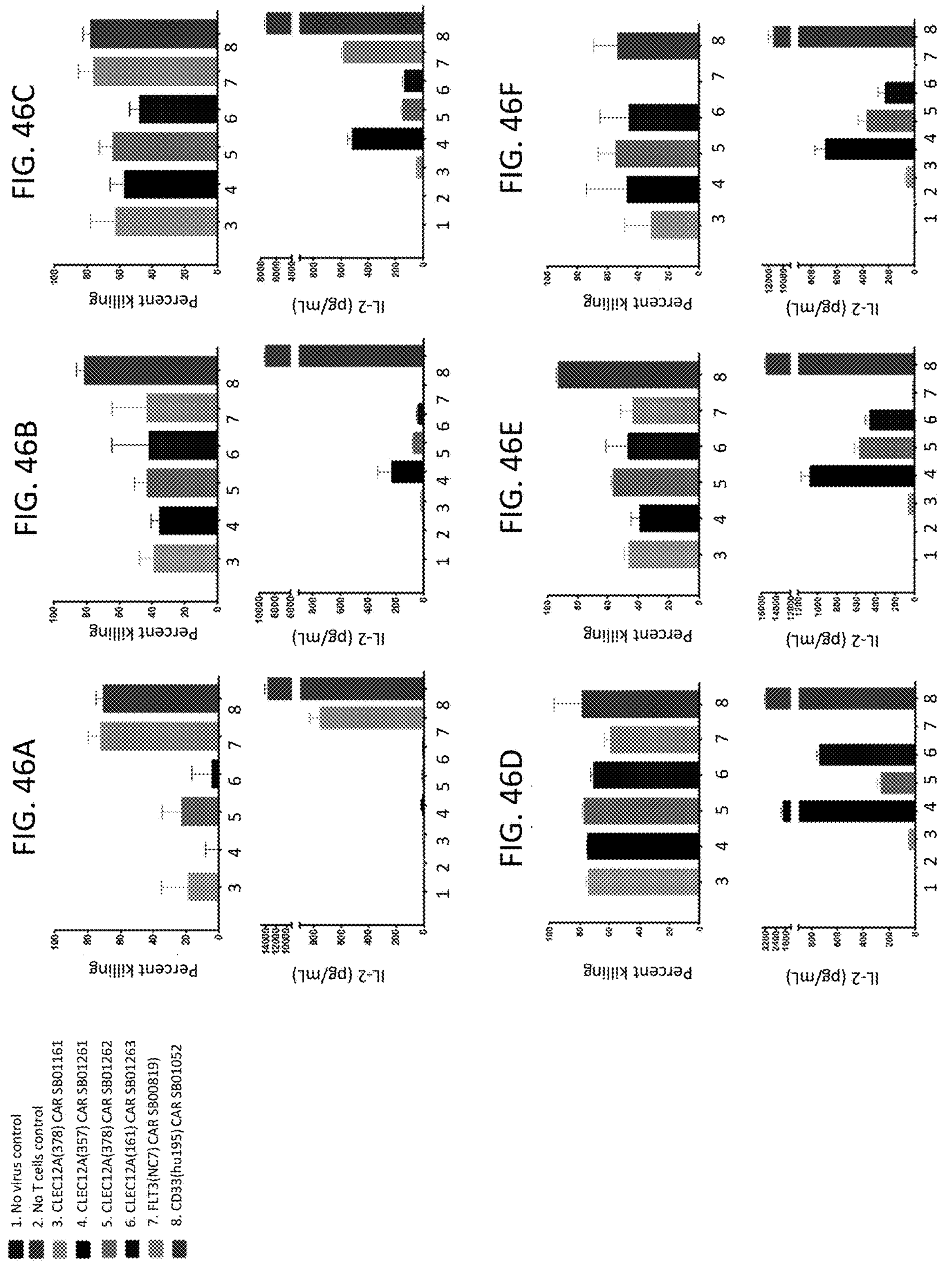
FIG. 46A shows CLEC12A CAR T cells cytotoxicity activity and cytokine production against MOLM-13 (low CLEC12A expression).
FIG. 46B shows CLEC12A CAR T cells cytotoxicity activity and cytokine production against MV4-11 (low CLEC12A expression FIG. 46C shows CLEC12A CAR T cells cytotoxicity activity and cytokine production against MOLM-14 (high CLEC12A expression).
FIG. 46D shows CLEC12A CAR T cells cytotoxicity activity and cytokine production against U937.
FIG. 46E shows CLEC12A CAR T cells cytotoxicity activity and cytokine production against THP-1.
FIG. 46F shows CLEC12A CAR T cells cytotoxicity activity and cytokine production against HL-60. Each CLEC12A CAR had a CD8 hinge and transmembrane domain and 4-1BB and CD3 co-stimulatory domains. The FLT3(NC7) CAR had a 4-1BB co-stimulatory domain. The CD33(hu195) CAR had a CD28 co-stimulatory domain.

The CLEC12A CARs showed cytotoxity and IL-2 production after incubation with cell lines with low CLEC12A expression, MOLM-13 (FIG. 46A) and MV4-11 (FIG. 46B) and high CLEC12A expression, MOLM-14 (FIG. 45C), U937 (FIG. 45D), THP-1 (FIG. 46E), and HL-60 (FIG. 46F). In each figure, the number refers to the sample indicated in the figure legend.

Example 18: In Vitro Characterization of CLEC12A CAR T Cells with Alternative Co-Stimulatory Domains or Secretion Signal Peptide Materials and Methods Three CLEC12A CARs were made with a CD28 co-stimulatory domain, in replacement of the 4-1BB co-stimulatory domain as previously described and shown in Table 6. In addition, three CLEC12A CARs were made with an IgK signal sequence peptide, instead of a CD8 signal sequence peptides. Diagrams of the nine CARs with the various co-stimulatory domains or signal sequence peptides are shown in FIG. 47. The CARs with a CD8 signal sequence included a YFP tag at the C terminus. The CARs with an IgK signal sequence included a FLAG tag between the signal sequence and scFv domains.

Cells were transduced with the three previously made CLEC12A CARs and the six new CLEC12A CARs. The transduction efficiency was determined via flow cytometry after staining with FLAG antibodies (for the IgK signal sequence CARs), or via the YFP expression signal (for the CD8 signal sequence CARs). An FLT3 CAR (SB00819) and a CD33 CAR (SB01052) were used as controls.

T cell cytotoxicity and cytokine production after incubation with HL-60, MOLM14, MV4-11, MOLM-13, and K562 cells were determined as previously described in Example 17.

The protein and nucleotide sequences of the six additional CLEC12A CARs made are shown in Table 8.

TABLE 8

| SEQ ID NO | Name | Sequence |
|---|---|---|
| 168 | CD8ss_Clec12A(357)_CD28 hinge_CD28 TM_CD28 ICD_CD3z_YFP SB01561 | MALPVTALLLPLALLLHAARPQVQLQESGPGLVKPSETLSLTCVVSGGSISSSNWWSWVRQPPGKGLEWIGEIYHSGSPDYNPSLKSRVTISVDKSRNQFSLKLSSVTAADTAVYYCAKVSTGGFFDYWGQGTLVTVSSGGGGSGGGGSGGGGSEIELTQSPSSLSASVGDRVTITCRASQSISSYLNWYQQKPGKAPKLLIYAASSLQSGVPSRFSGSGSGTDFTLTISSLQPEDFATYYCQQSYSTPPTFGPGTKVEIKAAAIEVMYPPPYLDNEKSNGTIIHVKGKHLCPSPLFPGPSKPFWVLVVVGGVLACYSLLVTVAFIIFWVRSKRSRLLHSDYMNMTPRRPGPTRKHYQPYAPPRDFAAYRSRVKFSRSADAPAYKQGQNQLYNELNLGRREEYDVLDKRRGRDPEMGGKPRRKNPQEGLYNELQKDKMAEAYSEIGMKGERRRGKGHDGLYQGLSTATKDTYDALHMQALPPRGSSGTGMVSKGEELFTGVVPILVELDGDVNGHKFSVSGEGEGDATYGKLTLKLICTTGKLPVPWPTLVTTLGYGLQCFARYPDHMKQHDFFKSAMPEGYVQERTIFFKDDGNYKTRAEVKFEGDTLVNRIELKGIDFKEDGNILGHKLEYNYNSHNVYITADKQKNGIKANFKIRHNIEDGGVQLADHYQQNTPIGDGPVLLPDNHYLSYQSALSKDPNEKRDHMVLLEFVTAAGITLGMDELYK* |
| 169 | CD8ss_Clec12A(357)_CD28 hinge_CD2_TM_CD28 ICD_CD3z_YFP SB01561 | ATGGCCTTACCAGTGACCGCCTTGCTCCTGCCGCTGGCCTTGCTGCTCCACGCCGCCAGGCCGCAGGTGCAGCTGCAGGAGTCGGGGCCAGGACTGGTGAAGCCTTCGGAGACCCTGTCCCTCACCTGCGTTGTCTCTGGTGGCTCCATCAGCAGTAGTAACTGGTGGAGCTGGGTCCGCCAGCCCCCAGGGAAGGGGCTGGAGTGGATTGGGGAAATCTATCATAGTGGGAGCCCCGACTACAACCCGTCCCTCAAGAGTCGAGTCACCATATCAGTAGACAAGTCCAGGAACCAGTTCTCCCTGAAGCTGAGCTCTGTGACCGCCGCGGACACGGCCGTGTATTACTGTGCAAAGGTTAGTACTGGTGGTTTCTTTGACTACTGGGGGCAAGGTACCCTGGTCACCGTCTCGAGTGGTGGAGGCGGTTCAGGCGGAGGTGGCTCTGGCGGTGGCGGATCGGAAATTGAGCTCACCCAGTCTCCATCCTCCCTGTCTGCATCTGTAGGAGACAGAGTCACCATCACTTGCCGGGCAAGTCAGAGCATTAGCAGCTACTTAAATTGGTATCAGCAGAAACCAGGGAAAGCCCCTAAGCTCCTGATCTATGCTGCATCCAGTTTGCAAAGTGGGGTCCCATCAAGGTTCAGTGGCAGTGGATCTGGGACAGATTTCACTCTCACCATCAGCAGTCTGCAACCTGAAGATTTTGCAACTTACTACTGTCAACAGAGTTACAGTACCCCTCCAACGTTCGGCCCAGGGACCAAGGTGGAGATCAAAGCAGCAGCTATCGAGGTGATGTATCCTCCGCCCTACCTGGATAATGAAAAGAGTAATGGGACTATCATTCATGTAAAAGGGAAGCATCTTTGTCCTTCTCCCCTTTTCCCCGGT |

TABLE 8-continued

| SEQ ID NO | Name | Sequence |
|---|---|---|
| | | CCGTCTAAACCTTTCTGGGTGCTTGTGGTCGTGGGTGGAGTGCTTGCGTGTTACTCCCTGCTGGTGACC<br>GTCGCCTTCATCATTTTCTGGGTCAGGAGCAAACGATCTCGCCTCCTCCATTCTGACTATATGAACATG<br>ACTCCTCGCAGACCCGGACCTACGCGGAAACATTACCAACCGTACGCGCCTCCGAGAGACTTCGCCGCG<br>TACAGAAGTAGGGTCAAGTTTAGCAGGTCAGCGGACGCACCAGCTTACAAGCAAGGCCAAAACCAGCTT<br>TATAACGAATTGAATTTGGGACGCAGGGAAGAATACGATGTGCTCGATAAACGCAGAGGGAGGGACCCG<br>GAAATGGGAGGAAAGCCAAGGCGGAAAAACCCACAGGAGGGGTTGTACAACGAGCTTCAAAAAGATAAG<br>ATGGCGGAAGCATACTCCGAAATAGGAATGAAGGGTGAACGGAGGAGGGGCAAGGGCCACGACGGCCTG<br>TACCAGGGACTCTCAACTGCTACGAAGGATACTTATGATGCTCTTCACATGCAAGCTCTGCCGCCGCGC<br>GGATCGAGTGGCACCGGTATGGTGAGCAAGGGCGAGGAGCTGTTCACCGGGGTGGTGCCCATCCTGGTC<br>GAGCTGGACGGCGACGTAAACGGCCACAAGTTCAGCGTGTCCGGCGAGGGCGAGGGCGATGCCACCTAC<br>GGCAAGCTGACCCTGAAGCTGATCTGCACCACCGGCAAGCTGCCCGTGCCCTGGCCCACCCTCGTGACC<br>ACCCTGGGCTACGGCCTCCAGTGCTTCGCCCGCTACCCCGACCACATGAAGCAGCACGACTTCTTCAAG<br>TCCGCCATGCCCGAAGGCTACGTCCAGGAGCGCACCATCTTCTTCAAGGACGACGGCAACTACAAGACC<br>CGCGCCGAGGTGAAGTTCGAGGGCGACACCCTGGTGAACCGCATCGAGCTGAAGGGCATCGACTTCAAG<br>GAGGACGGCAACATCCTGGGGCACAAGCTGGAGTACAACTACAACAGCCACAACGTCTATATCACCGCC<br>GACAAGCAGAAGAACGGCATCAAGGCCAACTTCAAGATCCGCCACAACATCGAGGACGGCGGCGTGCAG<br>CTCGCCGACCACTACCAGCAGAACACCCCCATCGGCGACGGCCCCGTGCTGCTGCCCGACAACCACTAC<br>CTGAGCTACCAGTCCGCCCTGAGCAAAGACCCCAACGAGAAGCGCGATCACATGGTCCTGCTGGAGTTC<br>GTGACCGCCGCCGGGATCACTCTCGGCATGGACGAGCTGTACAAGTAA |
| 170 | CD8ss_Cle<br>c12A(378)_<br>CD28<br>hinge_CD28<br>TM_CD28<br>ICD_CD3z_<br>YFP<br>SB01562 | MALPVTALLLPLALLLHAARPQVQLQESGPGLVKPSETLSLTCVVSGGSISSSNWWSWVRQPPGKGLEW<br>IGEIYHSGSPNYNPSLKSRVTISVDKSKNQFSLKLSSVTAADTAVYYCARSSSGGFFDYWGQGTLVTVS<br>SGGGGSGGGGSGGGGSEIELTQSPSSLSASVGDRVTITCRASQSISSYLNWYQQKPGKAPKLLIYAASS<br>LQSGVPSRFSGSGSGTDFTLTISSLQPEDFATYYCQQSYSTPPTFGQGTKVEIKAAAIEVMYPPPYLDN<br>EKSNGTIIHVKGKHLCPSPLFPGPSKPFWVLVVVGGVLACYSLLVTVAFIIFWVRSKRSRLLHSDYMNM<br>TPRRPGPTRKHYQPYAPPRDFAAYRSRVKFSRSADAPAYKQGQNQLYNELNLGRREEYDVLDKRRGRDP<br>EMGGKPRRKNPQEGLYNELQKDKMAEAYSEIGMKGERRRGKGHDGLYQGLSTATKDTYDALHMQALPPR<br>GSSGTGMVSKGEELFTGVVPILVELDGDVNGHKFSVSGEGEGDATYGKLTLKLICTTGKLPVPWPTLVT<br>TLGYGLQCFARYPDHMKQHDFFKSAMPEGYVQERTIFFKDDGNYKTRAEVKFEGDTLVNRIELKGIDFK<br>EDGNILGHKLEYNYNSHNVYITADKQKNGIKANFKIRHNIEDGGVQLADHYQQNTPIGDGPVLLPDNHY<br>LSYQSALSKDPNEKRDHMVLLEFVTAAGITLGMDELYK* |
| 171 | CD8ss_Cle<br>c12A(378)_<br>CD28<br>hinge_CD28<br>TM_CD28<br>ICD_CD3z_<br>YFP<br>SB01562 | ATGGCCTTACCAGTGACCGCCTTGCTCCTGCCGCTGGCCTTGCTGCTCCACGCCGCCAGGCCGCAGGTG<br>CAGCTGCAGGAGTCGGGCCCAGGACTGGTGAAGCCTTCGGAGACCCTGTCCCTCACCTGCGTTGTCTCT<br>GGTGGCTCCATCAGCAGTAGTAACTGGTGGAGCTGGGTCCGCCAGCCCCCAGGGAAGGGGCTGGAGTGG<br>ATTGGGGAAATCTATCATAGTGGGAGCCCCAACTACAACCCGTCCCTCAAGAGTCGAGTCACCATATCA<br>GTAGACAAGTCCAAGAACCAGTTCTCCCTGAAGCTGAGCTCTGTGACCGCCGCGGACACGGCCGTGTAT<br>TACTGTGCAAGGTCGTCTTCTGGTGGTTTCTTTGACTACTGGGGCCAAGGTACCCTGGTCACCGTCTCG<br>AGTGGTGGAGGCGGTTCAGGCGGAGGTGGCTCTGGCGGTGGCGGATCGGAAATTGAGCTCACCCAGTCT<br>CCATCCTCCCTGTCTGCATCTGTAGGAGACAGAGTCACCATCACTTGCCGGGCAAGTCAGAGCATTAGC<br>AGCTACTTAAATTGGTATCAGCAGAAACCAGGGAAAGCCCCTAAGCTCCTGATCTATGCTGCATCCAGT<br>TTGCAAAGTGGGGTCCCATCAAGGTTCAGTGGCAGTGGATCTGGGACAGATTTCACTCTCACCATCAGC<br>AGTCTGCAACCTGAAGATTTTGCAACTTACTACTGTCAACAGAGTTACAGTACCCCTCCAACGTTCGGC<br>CAAGGGACCAAGGTGGAGATCAAAGCAGCAGCTATCGAGGTGATGTATCCTCCGCCCTACCTGGATAAT<br>GAAAAGAGTAATGGGACTATCATTCATGTAAAAGGGAAGCATCTTTGTCCTTCTCCCCTTTTCCCCGGT<br>CCGTCTAAACCTTTCTGGGTGCTTGTGGTCGTGGGTGGAGTGCTTGCGTGTTACTCCCTGCTGGTGACC<br>GTCGCCTTCATCATTTTCTGGGTCAGGAGCAAACGATCTCGCCTCCTCCATTCTGACTATATGAACATG<br>ACTCCTCGCAGACCCGGACCTACGCGGAAACATTACCAACCGTACGCGCCTCCGAGAGACTTCGCCGCG<br>TACAGAAGTAGGGTCAAGTTTAGCAGGTCAGCGGACGCACCAGCTTACAAGCAAGGCCAAAACCAGCTT<br>TATAACGAATTGAATTTGGGACGCAGGGAAGAATACGATGTGCTCGATAAACGCAGAGGGAGGGACCCG<br>GAAATGGGAGGAAAGCCAAGGCGGAAAAACCCACAGGAGGGGTTGTACAACGAGCTTCAAAAAGATAAG<br>ATGGCGGAAGCATACTCCGAAATAGGAATGAAGGGTGAACGGAGGAGGGGCAAGGGCCACGACGGCCTG<br>TACCAGGGACTCTCAACTGCTACGAAGGATACTTATGATGCTCTTCACATGCAAGCTCTGCCGCCGCGC<br>GGATCGAGTGGCACCGGTATGGTGAGCAAGGGCGAGGAGCTGTTCACCGGGGTGGTGCCCATCCTGGTC<br>GAGCTGGACGGCGACGTAAACGGCCACAAGTTCAGCGTGTCCGGCGAGGGCGAGGGCGATGCCACCTAC<br>GGCAAGCTGACCCTGAAGCTGATCTGCACCACCGGCAAGCTGCCCGTGCCCTGGCCCACCCTCGTGACC<br>ACCCTGGGCTACGGCCTCCAGTGCTTCGCCCGCTACCCCGACCACATGAAGCAGCACGACTTCTTCAAG<br>TCCGCCATGCCCGAAGGCTACGTCCAGGAGCGCACCATCTTCTTCAAGGACGACGGCAACTACAAGACC<br>CGCGCCGAGGTGAAGTTCGAGGGCGACACCCTGGTGAACCGCATCGAGCTGAAGGGCATCGACTTCAAG<br>GAGGACGGCAACATCCTGGGGCACAAGCTGGAGTACAACTACAACAGCCACAACGTCTATATCACCGCC<br>GACAAGCAGAAGAACGGCATCAAGGCCAACTTCAAGATCCGCCACAACATCGAGGACGGCGGCGTGCAG<br>CTCGCCGACCACTACCAGCAGAACACCCCCATCGGCGACGGCCCCGTGCTGCTGCCCGACAACCACTAC<br>CTGAGCTACCAGTCCGCCCTGAGCAAAGACCCCAACGAGAAGCGCGATCACATGGTCCTGCTGGAGTTC<br>GTGACCGCCGCCGGGATCACTCTCGGCATGGACGAGCTGTACAAGTAA |
| 172 | CD8ss_Cle<br>c12A(161)_<br>CD28<br>hinge_CD28<br>TM_CD28<br>ICD_CD3z_<br>YFP<br>SB01563 | MALPVTALLLPLALLLHAARPQVQLQESGPGLVKPSETLSLTCVVSGGSISSSNWWSWVRQPPGKGLEW<br>IGEIYHSGSPNYNPSLKSRVTISVDKSKNQFSLKLSSVTAADTAVYYCARQTTAGSFDYWGQGTLVTVS<br>SGGGGSGGGGSGGGGSEIELTQSPSSLSASVGDRVTITCRASQSISSYLNWYQQKPGKAPKLLIYAASS<br>LQSGVPSRFSGSGSGTDFTLTISSLQPEDFATYYCQQSYSTPPTFGQGTKVEIKAAAIEVMYPPPYLDN<br>EKSNGTIIHVKGKHLCPSPLFPGPSKPFWVLVVVGGVLACYSLLVTVAFIIFWVRSKRSRLLHSDYMNM<br>TPRRPGPTRKHYQPYAPPRDFAAYRSRVKFSRSADAPAYKQGQNQLYNELNLGRREEYDVLDKRRGRDP<br>EMGGKPRRKNPQEGLYNELQKDKMAEAYSEIGMKGERRRGKGHDGLYQGLSTATKDTYDALHMQALPPR<br>GSSGTGMVSKGEELFTGVVPILVELDGDVNGHKFSVSGEGEGDATYGKLTLKLICTTGKLPVPWPTLVT<br>TLGYGLQCFARYPDHMKQHDFFKSAMPEGYVQERTIFFKDDGNYKTRAEVKFEGDTLVNRIELKGIDFK<br>EDGNILGHKLEYNYNSHNVYITADKQKNGIKANFKIRHNIEDGGVQLADHYQQNTPIGDGPVLLPDNHY<br>LSYQSALSKDPNEKRDHMVLLEFVTAAGITLGMDELYK* |

TABLE 8-continued

| SEQ ID NO | Name | Sequence |
|---|---|---|
| 173 | CD8ss_Clec12A(161)_CD28 hinge_CD28 TM_CD28 ICD_CD3z_YFP SB01563 | ATGGCCTTACCAGTGACCGCCTTGCTCCTGCCGCTGGCCTTGCTGCTCCACGCCGCCAGGCCGCAGGTG<br>CAGCTGCAGGAGTCGGGCCCAGGACTGGTGAAGCCTTCGGAGACCCTGTCCCTCACCTGCGTTGTCTCT<br>GGTGGCTCCATCAGCAGTAGTAACTGGTGGAGCTGGGTCCGCCAGCCCCCAGGGAAGGGGCTGGAGTGG<br>ATTGGGGAAATCTATCATAGTGGGAGCCCCAACTACAACCCGTCCCTCAAGAGTCGAGTCACCATATCA<br>GTAGACAAGTCCAAGAACCAGTTCTCCCTGAAGCTGAGCTCTGTGACCGCCGCGGACACGGCCGTGTAT<br>TACTGTGCAAGGCAGACTACTGCTGGGTCCTTTGACTACTGGGGCCAAGGTACCCTGGTCACCGTCTCG<br>AGTGGTGGAGGCGGTTCAGGCGGAGGTGGCTCTGGCGGTGGCGGATCGGAAATTGAGCTCACCCAGTCT<br>CCATCCTCCCTGTCTGCATCTGTAGGAGACAGAGTCACCATCACTTGCCGGGCAAGTCAGAGCATTAGC<br>AGCTACTTAAATTGGTATCAGCAGAAACCAGGGAAAGCCCCTAAGCTCCTGATCTATGCTGCATCCAGT<br>TTGCAAAGTGGGGTCCCATCAAGGTTCAGTGGCAGTGGATCTGGGACAGATTTCACTCTCACCATCAGC<br>AGTCTGCAACCTGAAGATTTTGCAACTTACTACTGTCAACAGAGTTACAGTACCCCTCCAACGTTCGGC<br>CAAGGGACCAAGGTGGAGATCAAAGCAGCAGCTATCGAGGTGATGTATCCTCCGCCCTACCTGGATAAT<br>GAAAAGAGTAATGGGACTATCATTCATGTAAAAGGGAAGCATCTTTGTCCTTCTCCCCTTTTCCCCGGT<br>CCGTCTAAACCTTTCTGGGTGCTTGTGGTCGTGGGTGGAGTGCTTGCGTGTTACTCCCTGCTGGTGACC<br>GTCGCCTTCATCATTTTCTGGGTCAGGAGCAAACGATCTCGCCTCCTCCATTCTGACTATATGAACATG<br>ACTCCTCGCAGACCCGGACCTACGCGGAAACATTACCAACCGTACGCGCCTCCGAGAGACTTCGCCGCG<br>TACAGAAGTAGGGTCAAGTTTAGCAGGTCAGCGGACGCACCAGCTTACAAGCAAGGCCAAAACCAGCTT<br>TATAACGAATTGAATTTGGGACGCAGGGAAGAATACGATGTGCTCGATAAACGCAGAGGGAGGGACCCG<br>GAAATGGGAGGAAAGCCAAGGCGGAAAAACCCACAGGAGGGGTTGTACAACGAGCTTCAAAAAGATAAG<br>ATGGCGGAAGCATACTCCGAAATAGGAATGAAGGGTGAACGGAGGAGGGGCAAGGGCCACGACGGCCTG<br>TACCAGGGACTCTCAACTGCTACGAAGGATACTTATGATGCTCTTCACATGCAAGCTCTGCCGCCGCGC<br>GGATCGAGTGGCACCGGTATGGTGAGCAAGGGCGAGGAGCTGTTCACCGGGGTGGTGCCCATCCTGGTC<br>GAGCTGGACGGCGACGTAAACGGCCACAAGTTCAGCGTGTCCGGCGAGGGCGAGGGCGATGCCACCTAC<br>GGCAAGCTGACCCTGAAGCTGATCTGCACCACCGGCAAGCTGCCCGTGCCCTGGCCCACCCTCGTGACC<br>ACCCTGGGCTACGGCCTCCAGTGCTTCGCCCGCTACCCCGACCACATGAAGCAGCACGACTTCTTCAAG<br>TCCGCCATGCCCGAAGGCTACGTCCAGGAGCGCACCATCTTCTTCAAGGACGACGGCAACTACAAGACC<br>CGCGCCGAGGTGAAGTTCGAGGGCGACACCCTGGTGAACCGCATCGAGCTGAAGGGCATCGACTTCAAG<br>GAGGACGGCAACATCCTGGGGCACAAGCTGGAGTACAACTACAACAGCCACAACGTCTATATCACCGCC<br>GACAAGCAGAAGAACGGCATCAAGGCCAACTTCAAGATCCGCCACAACATCGAGGACGGCGGCGTGCAG<br>CTCGCCGACCACTACCAGCAGAACACCCCCATCGGCGACGGCCCCGTGCTGCTGCCCGACAACCACTAC<br>CTGAGCTACCAGTCCGCCCTGAGCAAAGACCCCAACGAGAAGCGCGATCACATGGTCCTGCTGGAGTTC<br>GTGACCGCCGCCGGGATCACTCTCGGCATGGACGAGCTGTACAAGTAA |
| 174 | IgKss_Flag_Clec12A (357)_CD28 hinge_CD28 TM_CD28 ICD_CD3z SB01168 | METDTLLLWVLLLWVPGSTGAGGSDYKDDDDKGGSQVQLQESGPGLVKPSETLSLTCVVSGGSISSSNW<br>WSWVRQPPGKGLEWIGEIYHSGSPDYNPSLKSRVTISVDKSRNQFSLKLSSVTAADTAVYYCAKVSTGG<br>FFDYWGQGTLVTVSSGGGGSGGGGSGGGGSEIELTQSPSSLSASVGDRVTITCRASQSISSYLNWYQQK<br>PGKAPKLLIYAASSLQSGVPSRFSGSGSGTDFTLTISSLQPEDFATYYCQQSYSTPPTFGPGTKVEIKA<br>AAIEVMYPPPYLDNEKSNGTIIHVKGKHLCPSPLFPGPSKPFWVLVVVGGVLACYSLLVTVAFIIFWVR<br>SKRSRLLHSDYMNMTPRRPGPTRKHYQPYAPPRDFAAYRSRVKFSRSADAPAYKQGQNQLYNELNLGRR<br>EEYDVLDKRRGRDPEMGGKPRRKNPQEGLYNELQKDKMAEAYSEIGMKGERRRGKGHDGLYQGLSTATK<br>DTYDALHMQALPPR |
| 175 | IgKss_Flag_Clec12A (357)_CD28 hinge_CD28 TM_CD28 ICD_CD3z SB01168 | ATGGAAACGGATACTCTGCTGCTGTGGGTCCTCTTGCTTTGGGTACCTGGGAGTACCGGCGCTGGCGGG<br>TCCGATTACAAGGACGATGACGACAAAGGGGGTTCTCAGGTGCAGCTGCAGGAGTCGGGGCCAGGACTG<br>GTGAAGCCTTCGGAGACCCTGTCCCTCACCTGCGTTGTCTCTGGTGGCTCCATCAGCAGTAGTAACTGG<br>TGGAGCTGGGTCCGCCAGCCCCCAGGGAAGGGGCTGGAGTGGATTGGGGAAATCTATCATAGTGGGAGC<br>CCCGACTACAACCCGTCCCTCAAGAGTCGAGTCACCATATCAGTAGACAAGTCCAGGAACCAGTTCTCC<br>CTGAAGCTGAGCTCTGTGACCGCCGCGGACACGGCCGTGTATTACTGTGCAAAGGTTAGTACTGGTGGT<br>TTCTTTGACTACTGGGGGCAAGGTACCCTGGTCACCGTCTCGAGTGGTGGAGGCGGTTCAGGCGGAGGT<br>GGCTCTGGCGGTGGCGGATCGGAAATTGAGCTCACCCAGTCTCCATCCTCCCTGTCTGCATCTGTAGGA<br>GACAGAGTCACCATCACTTGCCGGGCAAGTCAGAGCATTAGCAGCTACTTAAATTGGTATCAGCAGAAA<br>CCAGGGAAAGCCCCTAAGCTCCTGATCTATGCTGCATCCAGTTTGCAAAGTGGGGTCCCATCAAGGTTC<br>AGTGGCAGTGGATCTGGGACAGATTTCACTCTCACCATCAGCAGTCTGCAACCTGAAGATTTTGCAACT<br>TACTACTGTCAACAGAGTTACAGTACCCCTCCAACGTTCGGCCCAGGGACCAAGGTGGAGATCAAAGCA<br>GCAGCTATCGAGGTGATGTATCCTCCGCCCTACCTGGATAATGAAAAGAGTAATGGGACTATCATTCAT<br>GTAAAAGGGAAGCATCTTTGTCCTTCTCCCCTTTTCCCCGGTCCGTCTAAACCTTTCTGGGTGCTTGTG<br>AGCAAACGATCTCGCCTCCTCCATTCTGACTATATGAACATGACTCCTCGCAGACCCGGACCTACGCGG<br>GTCGTGGGTGGAGTGCTTGCGTGTTACTCCCTGCTGGTGACCGTCGCCTTCATCATTTTCTGGGTCAGG<br>AGCAAACGATCTCGCCTCCTCCATTCTGACTATATGAACATGACTCCTCGCAGACCCGGACCTACGCGG<br>AAACATTACCAACCGTACGCGCCTCCGAGAGACTTCGCCGCGTACAGAAGTAGGGTCAAGTTTAGCAGG<br>TCAGCGGACGCACCAGCTTACAAGCAAGGCCAAAACCAGCTTTATAACGAATTGAATTTGGGACGCAGG<br>GAAGAATACGATGTGCTCGATAAACGCAGAGGGAGGGACCCGGAAATGGGAGGAAAGCCAAGGCGGAAA<br>AACCCACAGGAGGGGTTGTACAACGAGCTTCAAAAAGATAAGATGGCGGAAGCATACTCCGAAATAGGA<br>ATGAAGGGTGAACGGAGGAGGGGCAAGGGCCACGACGGCCTGTACCAGGGACTCTCAACTGCTACGAAG<br>GATACTTATGATGCTCTTCACATGCAAGCTCTGCCGCCGCGC |
| 176 | IgKss_Flag_Clec12A (378)_CD28 hinge_CD2 TM_CD28 ICD_CD3z SB01169 | METDTLLLWVLLLWVPGSTGAGGSDYKDDDDKGGSQVQLQESGPGLVKPSETLSLTCVVSGGSISSSNW<br>WSWVRQPPGKGLEWIGEIYHSGSPNYNPSLKSRVTISVDKSKNQFSLKLSSVTAADTAVYYCARSSSGG<br>FFDYWGQGTLVTVSSGGGGSGGGGSGGGGSEIELTQSPSSLSASVGDRVTITCRASQSISSYLNWYQQK<br>PGKAPKLLIYAASSLQSGVPSRFSGSGSGTDFTLTISSLQPEDFATYYCQQSYSTPPTFGQGTKVEIKA<br>AAIEVMYPPPYLDNEKSNGTIIHVKGKHLCPSPLFPGPSKPFWVLVVVGGVLACYSLLVTVAFIIFWVR<br>SKRSRLLHSDYMNMTPRRPGPTRKHYQPYAPPRDFAAYRSRVKFSRSADAPAYKQGQNQLYNELNLGRR<br>EEYDVLDKRRGRDPEMGGKPRRKNPQEGLYNELQKDKMAEAYSEIGMKGERRRGKGHDGLYQGLSTATK<br>DTYDALHMQALPPR |

TABLE 8-continued

| SEQ ID NO | Name | Sequence |
|---|---|---|
| 177 | IgKss_Flag_<br>Clec12A<br>(378)_CD28<br>hinge_CD28<br>TM_CD28<br>ICD_CD3z<br>SB01169 | ATGGAAACGGATACTCTGCTGCTGTGGGTCCTCTTGCTTTGGGTACCTGGGAGTACCGGCGCTGGCGGG<br>TCCGATTACAAGGACGATGACGACAAAGGGGGTTCTCAGGTGCAGCTGCAGGAGTCGGGCCCAGGACTG<br>GTGAAGCCTTCGGAGACCCTGTCCCTCACCTGCGTTGTCTCTGGTGGCTCCATCAGCAGTAGTAACTGG<br>TGGAGCTGGGTCCGCCAGCCCCCAGGGAAGGGGCTGGAGTGGATTGGGGAAATCTATCATAGTGGGAGC<br>CCCAACTACAACCCGTCCCTCAAGAGTCGAGTCACCATATCAGTAGACAAGTCCAAGAACCAGTTCTCC<br>CTGAAGCTGAGCTCTGTGACCGCCGCGGACACGGCCGTGTATTACTGTGCAAGGTCGTCTTCTGGTGGT<br>TTCTTTGACTACTGGGGCCAAGGTACCCTGGTCACCGTCTCGAGTGGTGGAGGCGGTTCAGGCGGAGGT<br>GGCTCTGGCGGTGGCGGATCGGAAATTGAGCTCACCCAGTCTCCATCCTCCCTGTCTGCATCTGTAGGA<br>GACAGAGTCACCATCACTTGCCGGGCAAGTCAGAGCATTAGCAGCTACTTAAATTGGTATCAGCAGAAA<br>CCAGGGAAAGCCCCTAAGCTCCTGATCTATGCTGCATCCAGTTTGCAAAGTGGGGTCCCATCAAGGTTC<br>AGTGGCAGTGGATCTGGGACAGATTTCACTCTCACCATCAGCAGTCTGCAACCTGAAGATTTTGCAACT<br>TACTACTGTCAACAGAGTTACAGTACCCCTCCAACGTTCGGCCAAGGGACCAAGGTGGAGATCAAAGCA<br>GCAGCTATCGAGGTGATGTATCCTCCGCCCTACCTGGATAATGAAAAGAGTAATGGGACTATCATTCAT<br>GTAAAAGGGAAGCATCTTTGTCCTTCTCCCCTTTTCCCCGGTCCGTCTAAACCTTTCTGGGTGCTTGTG<br>GTCGTGGGTGGAGTGCTTGCGTGTTACTCCCTGCTGGTGACCGTCGCCTTCATCATTTTCTGGGTCAGG<br>AGCAAACGATCTCGCCTCCTCCATTCTGACTATATGAACATGACTCCTCGCAGACCCGGACCTACGCGG<br>AAACATTACCAACCGTACGCGCCTCCGAGAGACTTCGCCGCGTACAGAAGTAGGGTCAAGTTTAGCAGG<br>TCAGCGGACGCACCAGCTTACAAGCAAGGCCAAAACCAGCTTTATAACGAATTGAATTTGGGACGCAGG<br>GAAGAATACGATGTGCTCGATAAACGCAGAGGGAGGGACCCGGAAATGGGAGGAAAGCCAAGGCGGAAA<br>AACCCACAGGAGGGGTTGTACAACGAGCTTCAAAAAGATAAGATGGCGGAAGCATACTCCGAAATAGGA<br>ATGAAGGGTGAACGGAGGAGGGGCAAGGGCCACGACGGCCTGTACCAGGGACTCTCAACTGCTACGAAG<br>GATACTTATGATGCTCTTCACATGCAAGCTCTGCCGCCGCGC |
| 178 | IgKss_Flag_<br>Clec12A<br>(161)_CD28<br>hinge_CD28<br>TM_CD28<br>ICD_CD3z<br>SB01170 | METDTLLLWVLLLWVPGSTGAGGSDYKDDDDKGGSQVQLQESGPGLVKPSETLSLTCVVSGGSISSSNW<br>WSWVRQPPGKGLEWIGEIYHSGSPNYNPSLKSRVTISVDKSKNQFSLKLSSVTAADTAVYYCARQTTAG<br>SFDYWGQGTLVTVSSGGGGSGGGGSGGGGSEIELTQSPSSLSASVGDRVTITCRASQSISSYLNWYQQK<br>PGKAPKLLIYAASSLQSGVPSRFSGSGSGTDFTLTISSLQPEDFATYYCQQSYSTPPTFGQGTKVEIKA<br>AAIEVMYPPPYLDNEKSNGTIIHVKGKHLCPSPLFPGPSKPFWVLVVVGGVLACYSLLVTVAFIIFWVR<br>SKRSRLLHSDYMNMTPRRPGPTRKHYQPYAPPRDFAAYRSRVKFSRSADAPAYKQGQNQLYNELNLGRR<br>EEYDVLDKRRGRDPEMGGKPRRKNPQEGLYNELQKDKMAEAYSEIGMKGERRRGKGHDGLYQGLSTATK<br>DTYDALHMQALPPR |
| 179 | IgKss_Flag_<br>Clec12A<br>(161)_CD28<br>hinge_CD28<br>TM_CD28<br>ICD_CD3z<br>SB01170 | ATGGAAACGGATACTCTGCTGCTGTGGGTCCTCTTGCTTTGGGTACCTGGGAGTACCGGCGCTGGCGGG<br>TCCGATTACAAGGACGATGACGACAAAGGGGGTTCTCAGGTGCAGCTGCAGGAGTCGGGCCCAGGACTG<br>GTGAAGCCTTCGGAGACCCTGTCCCTCACCTGCGTTGTCTCTGGTGGCTCCATCAGCAGTAGTAACTGG<br>TGGAGCTGGGTCCGCCAGCCCCCAGGGAAGGGGCTGGAGTGGATTGGGGAAATCTATCATAGTGGGAGC<br>CCCAACTACAACCCGTCCCTCAAGAGTCGAGTCACCATATCAGTAGACAAGTCCAAGAACCAGTTCTCC<br>CTGAAGCTGAGCTCTGTGACCGCCGCGGACACGGCCGTGTATTACTGTGCAAGGCAGACTACTGCTGGG<br>TCCTTTGACTACTGGGGCCAAGGTACCCTGGTCACCGTCTCGAGTGGTGGAGGCGGTTCAGGCGGAGGT<br>GGCTCTGGCGGTGGCGGATCGGAAATTGAGCTCACCCAGTCTCCATCCTCCCTGTCTGCATCTGTAGGA<br>GACAGAGTCACCATCACTTGCCGGGCAAGTCAGAGCATTAGCAGCTACTTAAATTGGTATCAGCAGAAA<br>CCAGGGAAAGCCCCTAAGCTCCTGATCTATGCTGCATCCAGTTTGCAAAGTGGGGTCCCATCAAGGTTC<br>AGTGGCAGTGGATCTGGGACAGATTTCACTCTCACCATCAGCAGTCTGCAACCTGAAGATTTTGCAACT<br>TACTACTGTCAACAGAGTTACAGTACCCCTCCAACGTTCGGCCAAGGGACCAAGGTGGAGATCAAAGCA<br>GCAGCTATCGAGGTGATGTATCCTCCGCCCTACCTGGATAATGAAAAGAGTAATGGGACTATCATTCAT<br>GTAAAAGGGAAGCATCTTTGTCCTTCTCCCCTTTTCCCCGGTCCGTCTAAACCTTTCTGGGTGCTTGTG<br>GTCGTGGGTGGAGTGCTTGCGTGTTACTCCCTGCTGGTGACCGTCGCCTTCATCATTTTCTGGGTCAGG<br>AGCAAACGATCTCGCCTCCTCCATTCTGACTATATGAACATGACTCCTCGCAGACCCGGACCTACGCGG<br>AAACATTACCAACCGTACGCGCCTCCGAGAGACTTCGCCGCGTACAGAAGTAGGGTCAAGTTTAGCAGG<br>TCAGCGGACGCACCAGCTTACAAGCAAGGCCAAAACCAGCTTTATAACGAATTGAATTTGGGACGCAGG<br>GAAGAATACGATGTGCTCGATAAACGCAGAGGGAGGGACCCGGAAATGGGAGGAAAGCCAAGGCGGAAA<br>AACCCACAGGAGGGGTTGTACAACGAGCTTCAAAAAGATAAGATGGCGGAAGCATACTCCGAAATAGGA<br>ATGAAGGGTGAACGGAGGAGGGGCAAGGGCCACGACGGCCTGTACCAGGGACTCTCAACTGCTACGAAG<br>GATACTTATGATGCTCTTCACATGCAAGCTCTGCCGCCGCGC |

Results

Figure 48A:
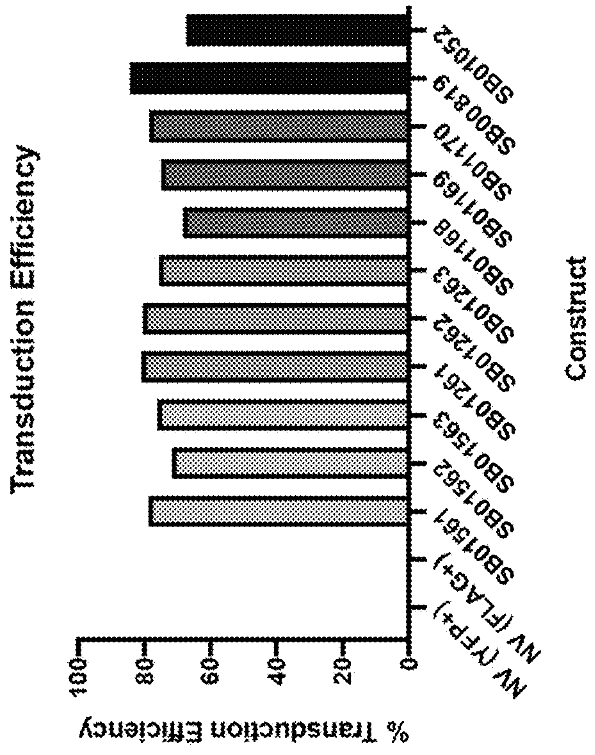
FIG. 48A shows transduction of the indicated CLEC12A CAR in T cells.
Figure 48B:
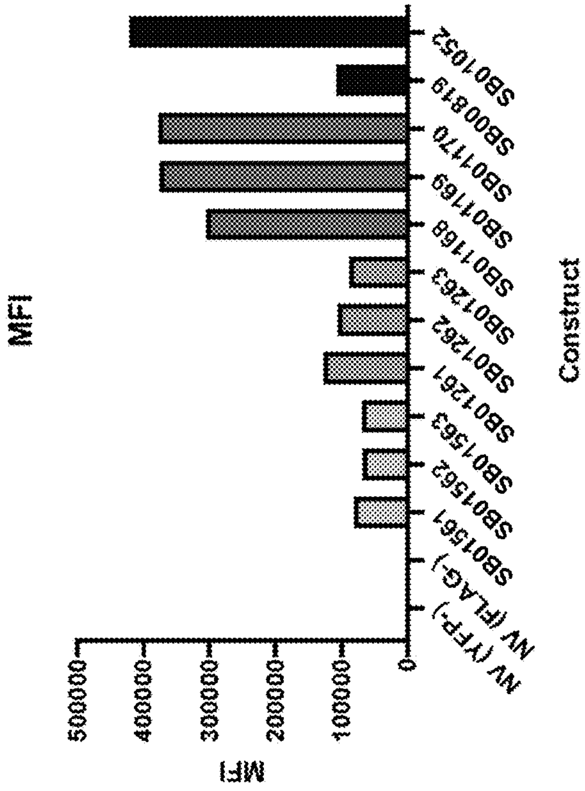
FIG. 48B shows the mean fluorescent intensity (MFI) of the indicated CLEC12A CAR in T cells.

As shown in FIG. 48A, all nine CLEC12A CARs were efficiently transduced into T cells. FIG. 48B shows the mean fluorescent intensity (MFI) of the various CARs.

Figure 49:
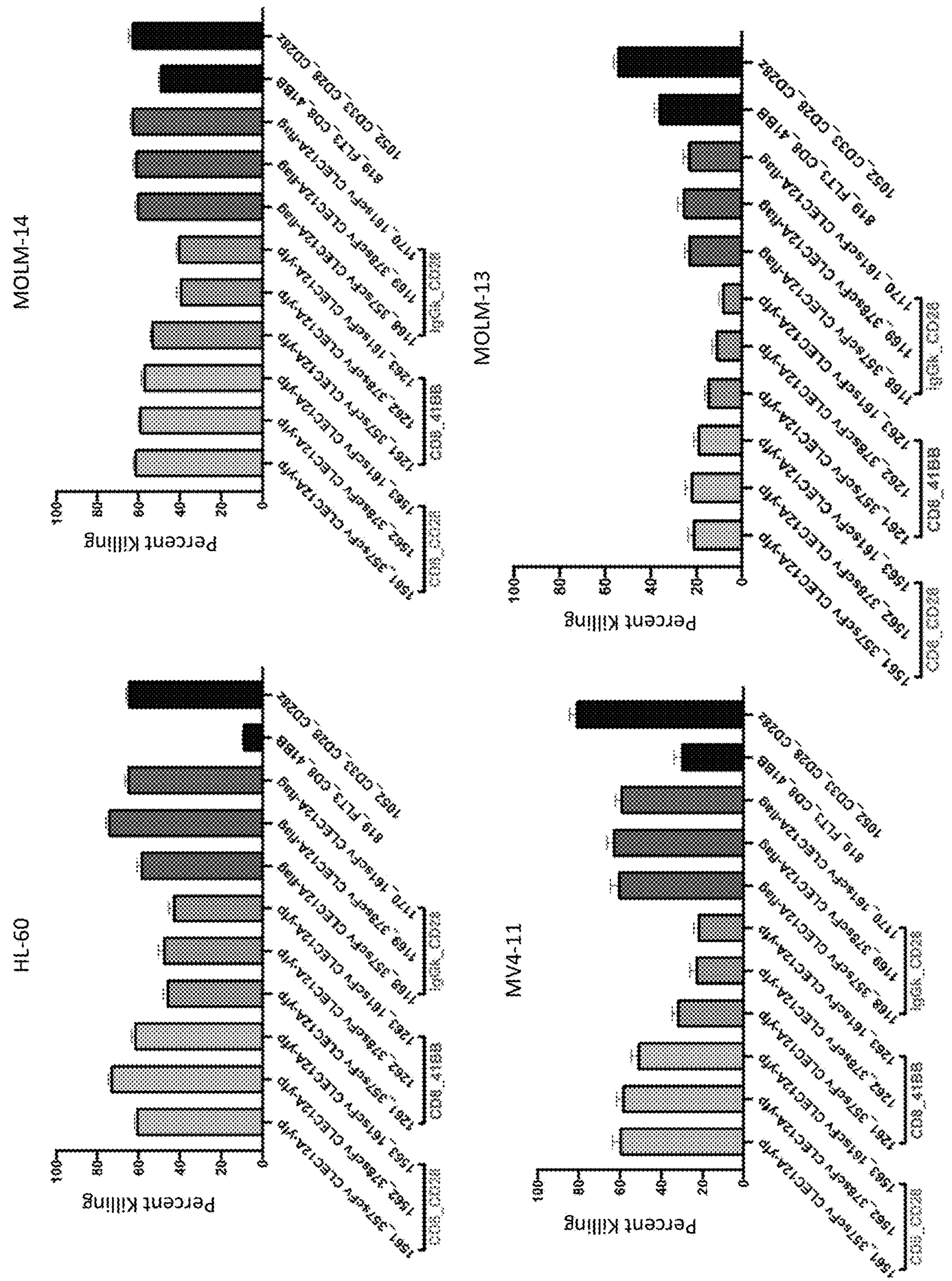
FIG. 49 shows the cytotoxicity of the indicated CLEC12A CAR T cells against HL-60, MOLM14, MV4-11, and MOLM-13 cells as indicated by the percent killing of the cell lines after incubation with the CAR T cells.
Figure 50:
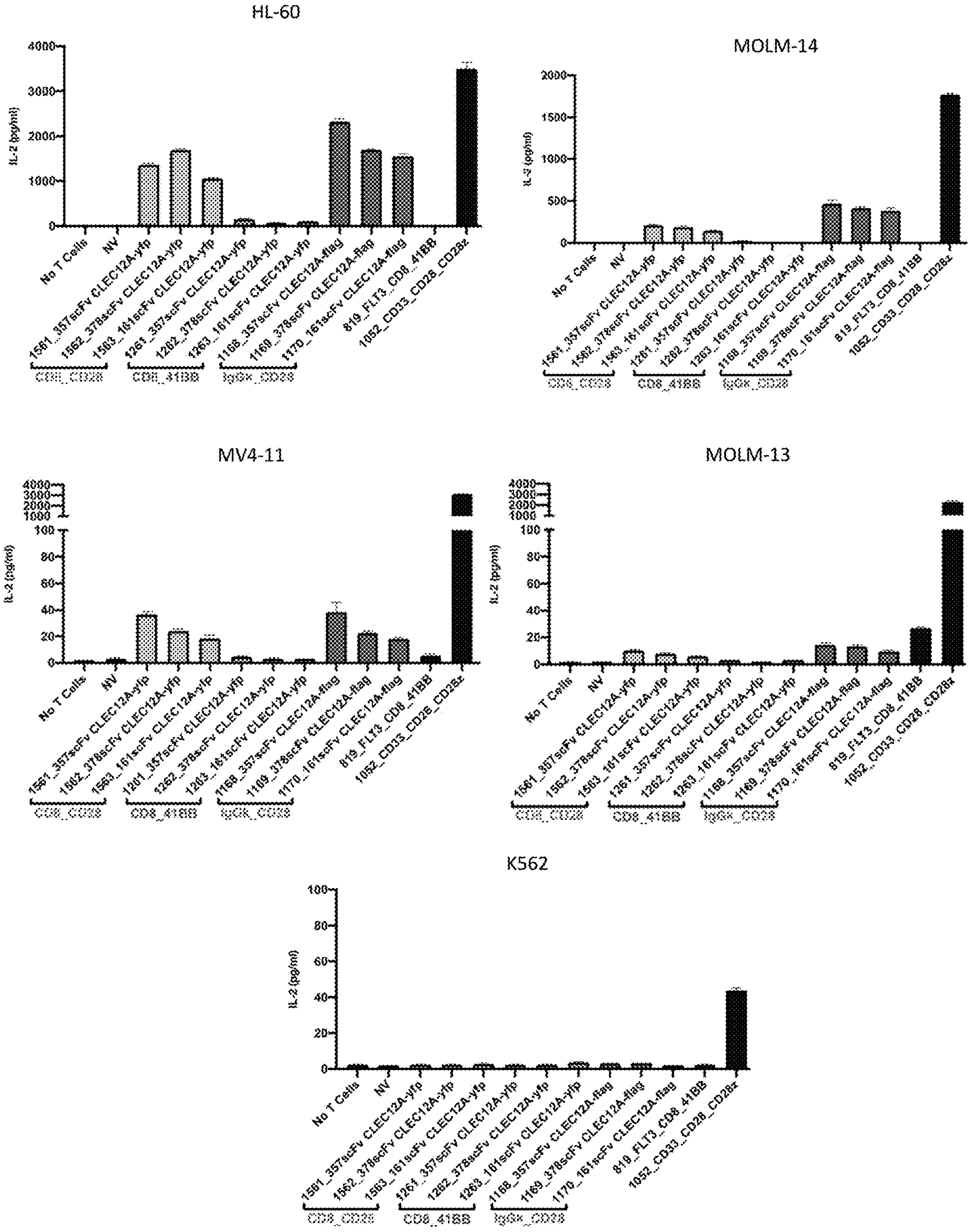
FIG. 50 shows the IL-2 production of the indicated CLEC12A CAR T cells after incubation with HL-60, MOLM14, MV4-11, MOLM-13, and K562 cells.
Figure 51:
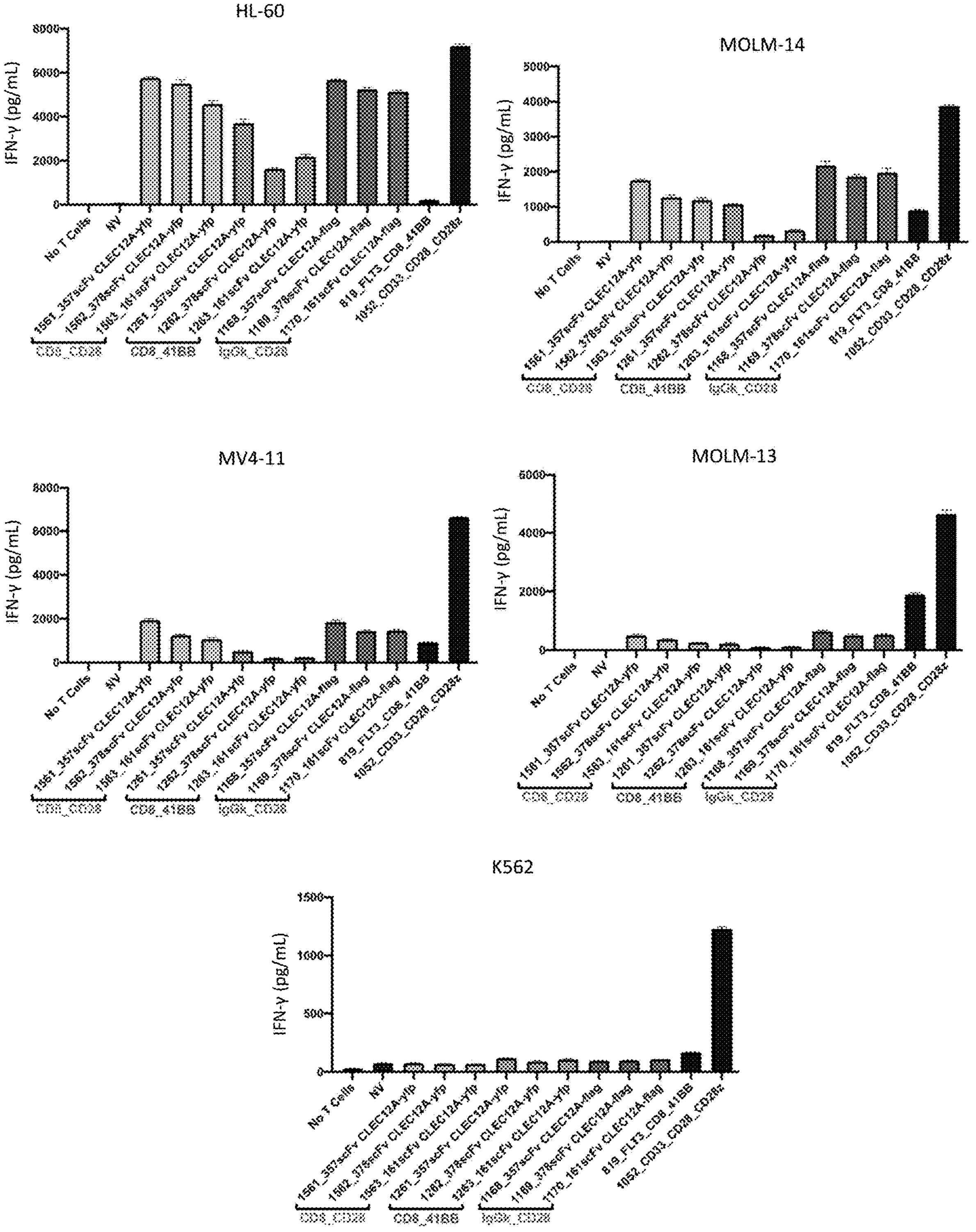
FIG. 51 shows the IFN-γ production of the indicated CLEC12A CAR T cells after incubation with HL-60, MOLM14, MV4-11, MOLM-13, and K562 cells.
Figure 52:
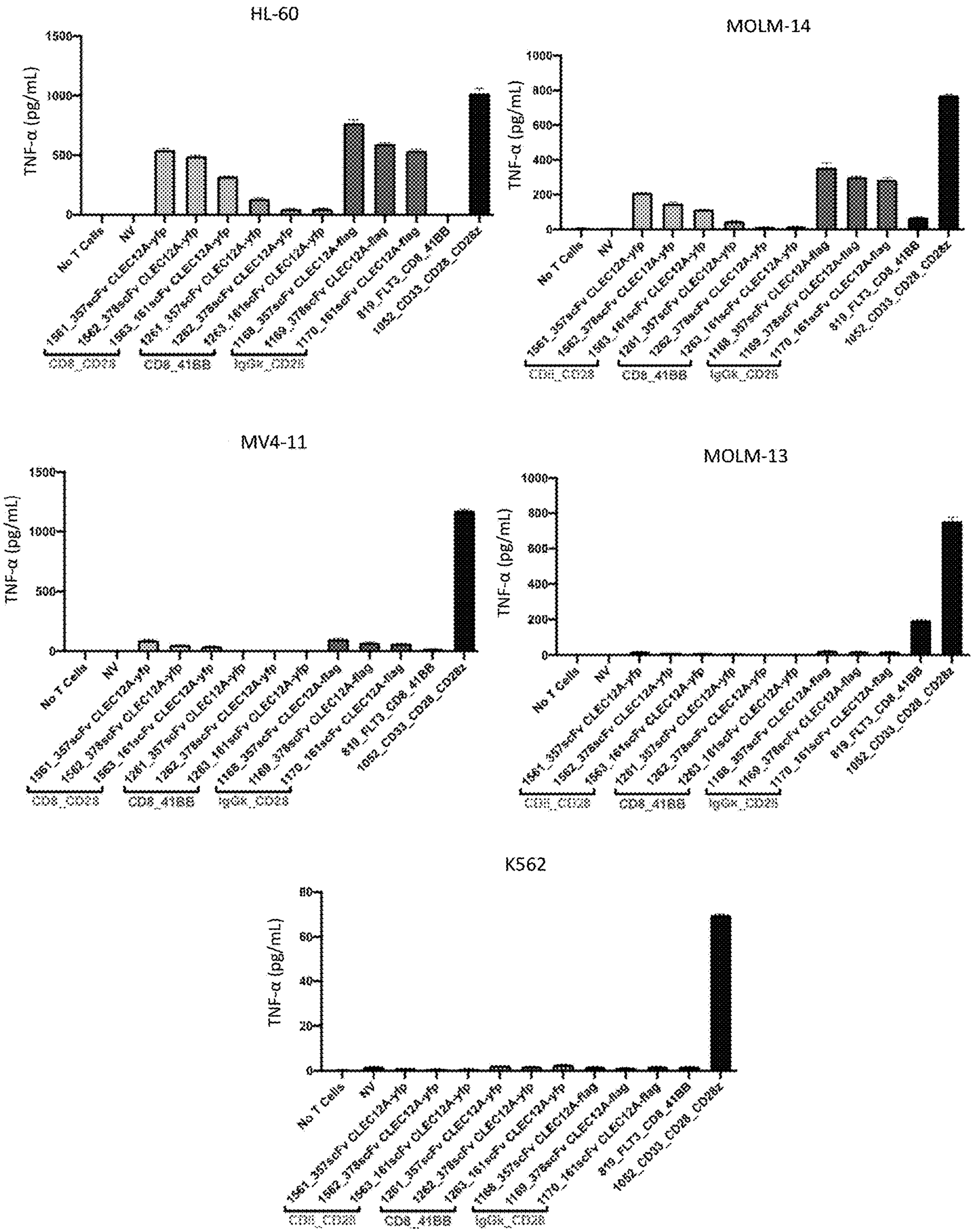
FIG. 52 shows the TNF-α production of the indicated CLEC12A CAR T cells after incubation with HL-60, MOLM14, MV4-11, MOLM-13, and K562 cells.

The CLEC12A-CD28 CAR T cells showed higher cytotoxicity and cytokine production compared to 4-1BB versions in the various cell lines tested (FIGS. 49, 50, 51, and 52). In each case, the CAR construct is referred to by the shortened name, e.g., SB01561 is indicated as 1561. The CLEC12A CARs with a CD28 co-stimulatory domain (SB01561, SB01562, SB01563) demonstrated better cytotoxicity against multiple AML and leukemia cell lines, and increased cytokine secretion (IL-2, IFNg, and TNFa) as compared to the CARs with a 41BB co-stimulatory domain (SB01261, SB01262, SB01263). In additional, the IgGk signaling peptide resulted in similar or better cytotoxity and cytokine production as compared to the CD8 constructs (SB011638, SB01169, SB01170). FIG. 49 shows the cytotoxicity of the indicated CLEC12A CAR T cells against HL-60, MOLM14, MV4-11, and MOLM-13 cells as indicated by the percent killing of the cell lines after incubation with the CAR T cells. FIG. 50 shows the IL-2 production of the indicated CLEC12A CAR T cells after incubation with HL-60, MOLM14, MV4-11, MOLM-13, and K562 cells. FIG. 51 shows the IFN-γ production of the indicated CLEC12A CAR T cells after incubation with HL-60, MOLM14, MV4-11, MOLM-13, and K562 cells. FIG. 52 shows the TNF-α production of the indicated CLEC12A CAR T cells after incubation with HL-60, MOLM14, MV4-11, MOLM-13, and K562 cells.

Example 19: In Vivo Characterization of Anti-FLT3 and Anti-CD33 CAR T Cells

Materials and Methods

CAR Structure

The FLT3 CAR (SB00819) had a CD8 signal sequence, the FLT3 scFv, a CD8 hinge, a CD8 transmembrane domain, a 4-1BB co-stimulatory domain, a CD3ζ signaling domain, and a YFP tag. The FLT3 scFv was derived from FLT3 antibody NC7. The CD33 CAR (SB01052) had an IgGk signal sequence, a FLAG tag, the CD33 scFv, a CD28 hinge, a CD28 transmembrane domain, a CD28 co-stimulatory domain, and a CD3ζ signaling domain. The CD33 scFv was derived from CD33 antibody hu195 (Lintuzumab; hu195; SGN-33; humanized anti-CD33 antibody).

In Vivo Single Dose Experiment Protocol:

The human AML cell line MOLM-13 was chosen as the in vivo AML cell target for testing FLT3 and CD33 CAR T cells due to its robust FLT3 and CD33 surface protein expression. The human AML cell line MOLM-13 was engineered to express a firefly luciferase (fLuc or Luc) reporter (engineered cells denoted MOLM-13-Luc). After injection of these cells into NSG immunocompromised mice, MOLM-13-Luc in vivo tumor engraftment and growth was monitored by injecting the mice with an fLuc substrate (e.g. luciferin) and using a bioluminescence imaging system (AMY HT, by Spectral Instruments Imaging) to quantify the amount of light produced from the luciferase enzyme within the MOLM-13 cells.

$1.0\times10^6$ MOLM-13-Luc AML cells were injected (IV) at Day 0. Post-MOLM-13-Luc injection, $10\times10^6$ CAR+ T cells/mouse were injected (IV) at day 5, or day 8, or day 5+day 12 ($10\times10^6$ cells/mouse on each day). MOLM-13-Luc bioluminescence and mouse weight were assessed twice a week for up to 4 weeks. Total survival was assessed for up to 4 weeks.

The dosing regime and CAR T cells are shown in Table 9 below.

TABLE 9

| Group | n | AML Cell Line | T cell | T cell dose | CAR T regimen |
|---|---|---|---|---|---|
| 1 | 3 | none | Non-engineered T | 10e6 T cells | 5d |
| 2 | 5 | none | FLT3(NC7) CART(SB00819) | 10e6 CAR + T cells | 5d |
| 3 | 5 | none | CD33(hu195) CART (SB01052) | 10e6 CAR + T cells | 5d |
| 4 | 5 | MOLM-13-Luc | Non-engineered T | 10e6 T cells | 5d |
| 5 | 5 | MOLM-13-Luc | FLT3(NC7) CART (SB00819) | 10e6 CAR + T cells | 5d |
| 6 | 5 | MOLM-13-Luc | FLT3(NC7) CART(SB00819) | 10e6 CAR + T cells | 8d |
| 7 | 5 | MOLM-13-Luc | FLT3(NC7) CART(SB00819) | 10e6 CAR + T cells | 5d + 12d |
| 8 | 5 | MOLM-13-Luc | CD33(hu195) CART(SB01052) | 10e6 CAR + T cells | 5d |
| 9 | 5 | MOLM-13-Luc | CD33(hu195) CART(SB01052) | 10e6 CAR + T cells | 8d |
| 10 | 5 | MOLM-13-Luc | CD33(hu195) CART (SB01052) | 10e6 CAR + T cells | 5d + 12d |

Dose Escalation Materials and Methods

For the in vivo dose escalation experiment, on day 0, NSG mice were injected (IV) with human MOLM-13-Luc AML cells (described above). On days 5, mice were injected (IV) with various concentrations of FLT3 CAR T cells or CD33 CAR T cells alone or in combination: $9\times10^6$ or $18\times10^6$ FLT3 CAR T cells; $0.625\times10^6$, $1.25\times10^6$, $2.5\times10^6$, $5\times10^6$, or $10\times10^6$ CD33 CAR T cells; or a combination of $4.5\times10^6$ FLT3 CAR T cells and $2.5\times10^6$ CD33 CAR T cells, $9\times10^6$ FLT3 CAR T cells and $5\times10^6$ CD33 CAR T cells, or $18\times10^6$ FLT3 CAR T cells and $10\times10^6$ CD33 CAR T cells. fLuc bioluminescence, weight, and survival were assessed approximately twice a week for 4 weeks. Mice were sacrificed when endpoint criteria were reached. Two control groups were used: 1. Mice not injected with MOLM-13-Luc or T cells, and 2. Mice injected with $1.0\times10^6$ MOLM-13-Luc cells and $10.0\times10^6$ unengineered T cells.

Results

Figures 53A, 53B, 53C, 53D, 53E, 53F, 53G, 53H, 53I, 53J:
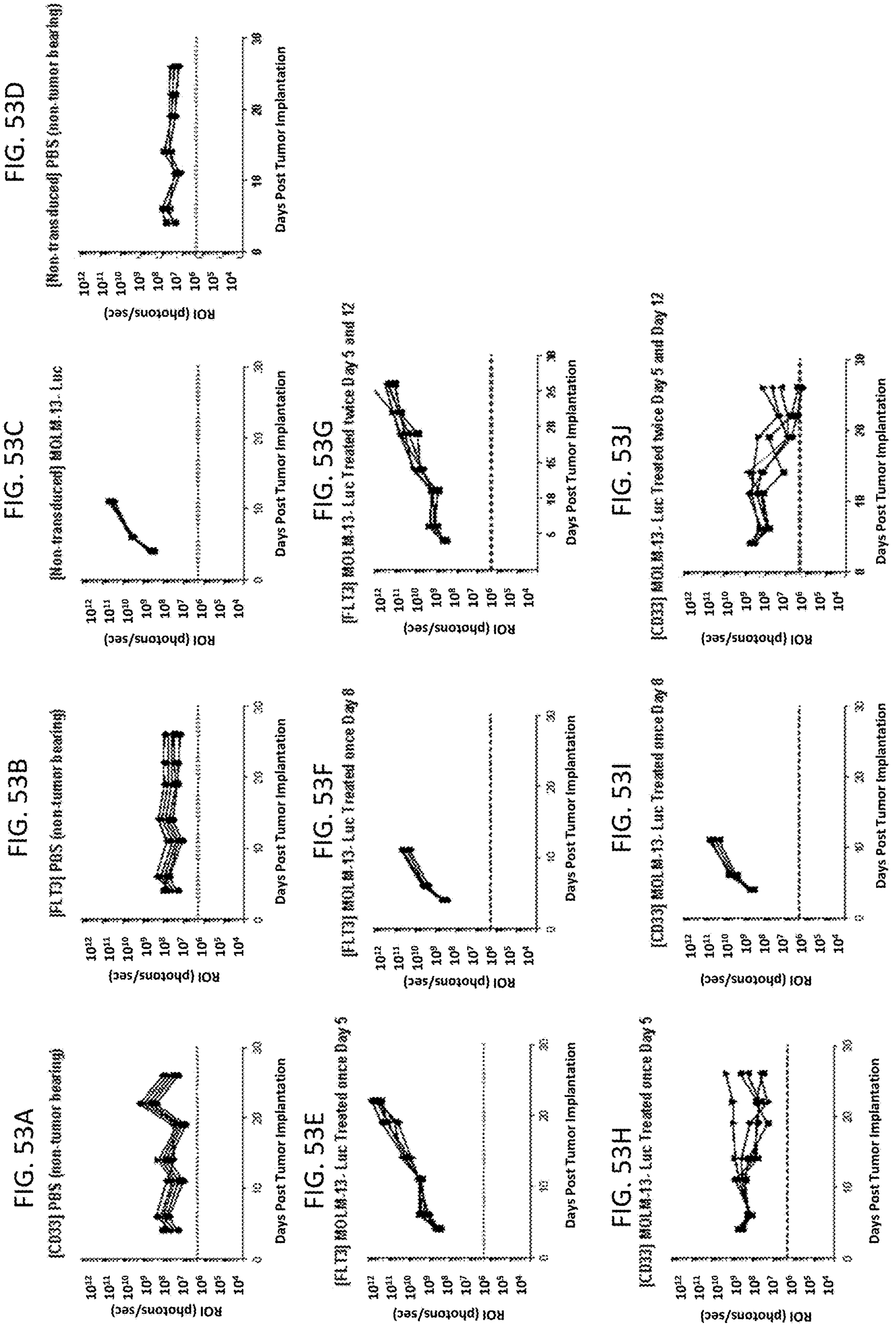
FIG. 53A shows the fLuc bioluminescence in non-tumor bearing mice treated with CD33 CAR T cells.
FIG. 53B shows the fLuc bioluminescence in non-tumor bearing mice treated with FLT3 CAR T cells.
FIG. 53C shows the fLuc bioluminescence in MOLM-13 tumor bearing mice treated with control unengineered T cells. The endpoint criteria was reached on day 14 and the mice sacrificed.
FIG. 53D shows the fLuc bioluminescence in non-tumor bearing mice treated with control unengineered T cells.
FIG. 53E shows the fLuc bioluminescence in MOLM-13 tumor bearing mice treated with FLT3 CAR T cells once on day 5.
FIG. 53F shows the fLuc bioluminescence in MOLM-13 tumor bearing mice treated with FLT3 CAR T cells once on day 8. The endpoint criteria was reached on day 14 and the mice sacrificed.
FIG. 53G shows the fLuc bioluminescence in MOLM-13 tumor bearing mice treated with FLT3 CAR T cells twice on days 5 and 12.
FIG. 53H shows the fLuc bioluminescence in MOLM-13 tumor bearing mice treated with CD33 CAR T cells once on day 5.
FIG. 53I shows the fLuc bioluminescence in MOLM-13 tumor bearing mice treated with CD33 CAR T cells once on day 8. The endpoint criteria was reached on day 14 and the mice sacrificed.
FIG. 53J shows the fLuc bioluminescence in MOLM-13 tumor bearing mice treated with CD33 CAR T cells twice on days 5 and 12.
Figure 53K:
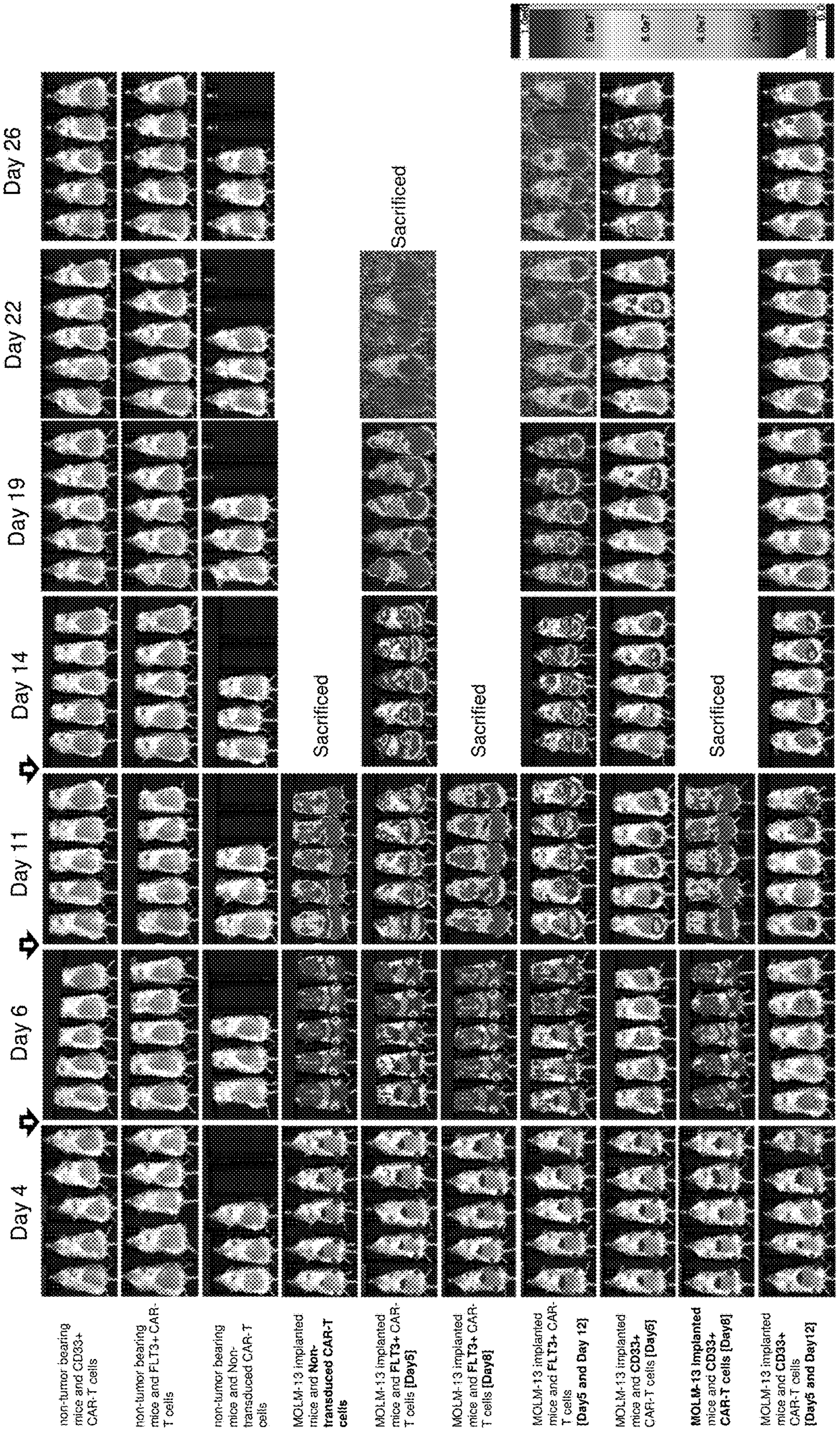
FIG. 53K. provides images of the fLuc bioluminescence in vivo in each treatment group.

FIG. 53A-J provide quantification of the fLuc bioluminescence signal in each mouse group after treatment with FLT3 or CD33 CARs on day 5, day 8, or days 5 and 12. FIG. 53A shows the background fLuc bioluminescence in non-tumor bearing mice treated with CD33 CAR T cells on day 5. FIG. 53B shows the background fLuc bioluminescence in non-tumor bearing mice treated with FLT3 CAR T cells on day 5. FIG. 53C shows the fLuc bioluminescence in untreated MOLM-13-Luc tumor bearing mice. The endpoint criteria was reached on day 14 and the mice sacrificed. FIG. 53D shows background fLuc bioluminescence in non-tumor bearing mice treated with PBS only. FIG. 53E shows the fLuc bioluminescence in MOLM-13-Luc tumor bearing mice treated with FLT3 CAR T cells once on day 5. FIG. 53F shows the fLuc bioluminescence in MOLM-13-Luc tumor bearing mice treated with FLT3 CAR T cells once on day 8. The endpoint criteria was reached on day 14 and the mice sacrificed. FIG. 53G shows the fLuc bioluminescence in MOLM-13-Luc tumor bearing mice treated with FLT3 CAR T cells twice on days 5 and 12. FIG. 53H shows the fLuc bioluminescence in MOLM-13-Luc tumor bearing mice treated with CD33 CAR T cells once on day 5. FIG. 53I shows the fLuc bioluminescence in MOLM-13-Luc tumor bearing mice treated with CD33 CAR T cells once on day 8. The endpoint criteria was reached on day 14 and the mice sacrificed. FIG. 53J shows the fLuc bioluminescence in MOLM-13-Luc tumor bearing mice treated with CD33 CAR T cells twice on days 5 and 12. Images of the fLuc bioluminescence in vivo in each treatment group is shown in FIG. 53K.

Mice treated with FLT3 CAR T cells on day 5 or on day 5 and 7 showed lower tumor burden and survived longer than mice treated with untransduced T cells. Mice treated with CD33 CAR T cells on day 5 or on day 5 and 7 showed lower tumor burden and survived longer than mice treated with untransduced T cells. Thus, both FLT3 and CD33 CAR T cells showed potent in vivo efficacy against MOLM-13-Luc AML cells when injected on day 5 or on days 5+12 after tumor initiation.

Figure 54A:
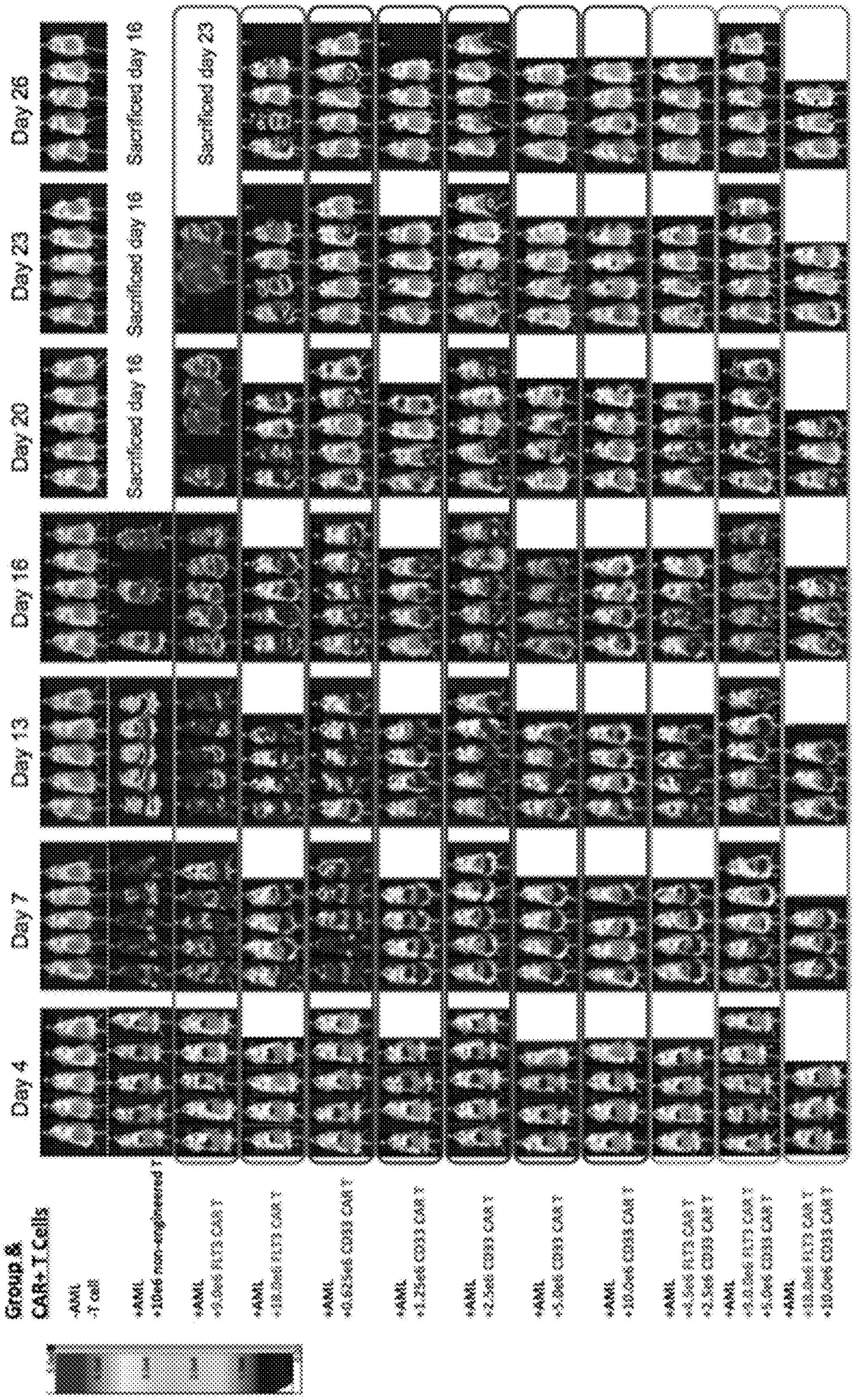
FIG. 54A shows the in vivo image results of a T cell dose escalation assay with FLT3 CAR T cells and CD33 CAR T cells alone or in combination.
Figures 54B, 54C, 54D, 54E, 54F, 54G, 54H, 54I, 54J, 54K, 54L, 54M:
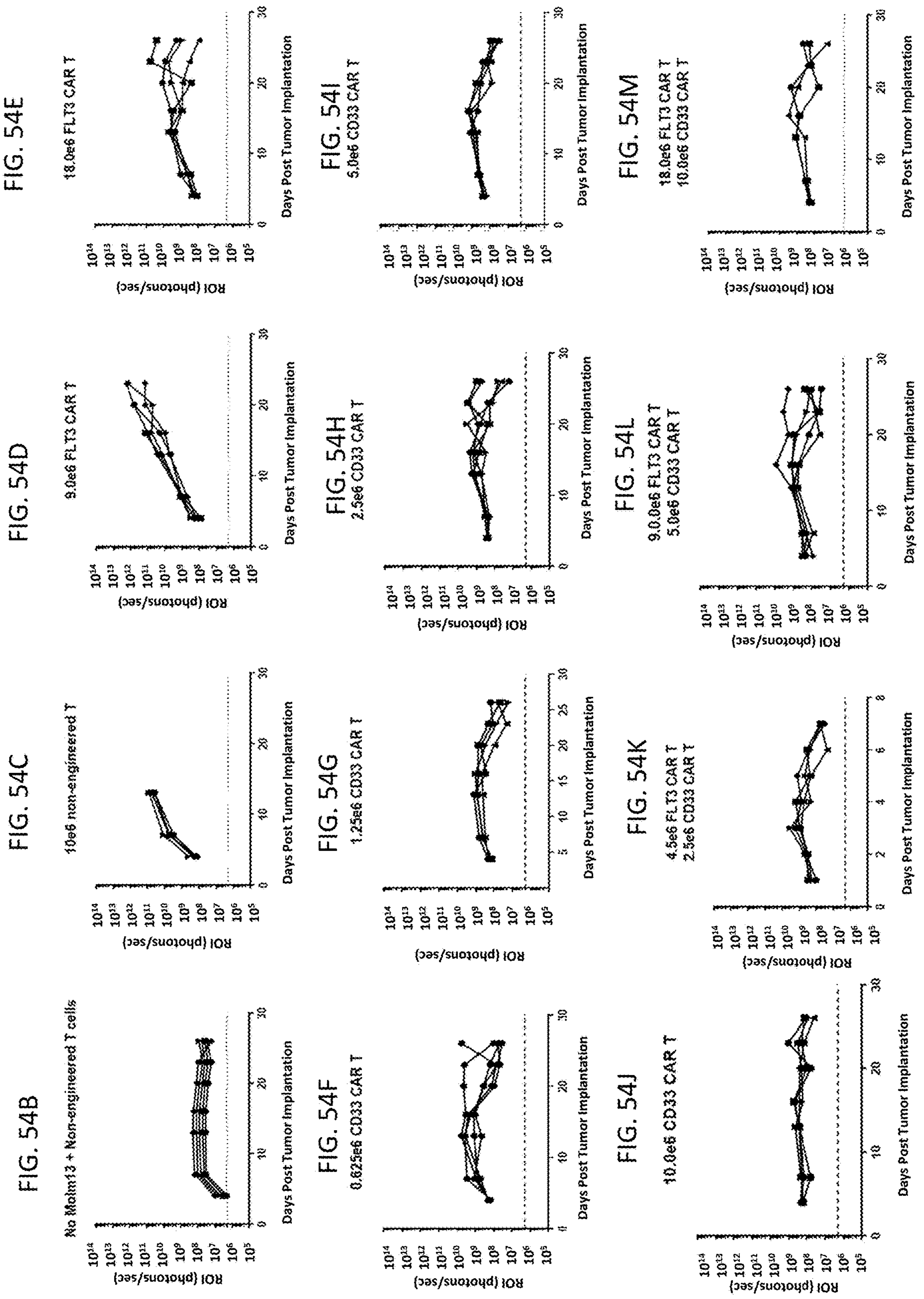
FIG. 54B shows the shows the fLuc bioluminescence in non-tumor bearing mice treated with non-engineered T cells.
FIG. 54C shows the shows the fLuc bioluminescence in MOLM-13 tumor bearing mice treated with non-engineered T cells.
FIG. 54D shows the shows the fLuc bioluminescence in MOLM-13 tumor bearing mice treated with $9\times10^6$ FLT3 T cells.
FIG. 54E shows the shows the fLuc bioluminescence in MOLM-13 tumor bearing mice treated with $18\times10^6$ FLT3 T cells.
FIG. 54F shows the shows the fLuc bioluminescence in MOLM-13 tumor bearing mice treated with $0.625\times10^6$ CD33 T cells.
FIG. 54G shows the shows the fLuc bioluminescence in MOLM-13 tumor bearing mice treated with $1.25\times10^6$ CD33 T cells.
FIG. 54H shows the shows the fLuc bioluminescence in MOLM-13 tumor bearing mice treated with $2.5\times10^6$ CD33 T cells.
FIG. 54I shows the shows the fLuc bioluminescence in MOLM-13 tumor bearing mice treated with $5\times10^6$ CD33 T cells.
FIG. 54J shows the shows the fLuc bioluminescence in MOLM-13 tumor bearing mice treated with $10\times10^6$ CD33 T cells.
FIG. 54K shows the shows the fLuc bioluminescence in MOLM-13 tumor bearing mice treated with $4.5\times10^6$ FLT3 CAR T cells and $2.5\times10^6$ CD33 T cells.
FIG. 54L shows the shows the fLuc bioluminescence in MOLM-13 tumor bearing mice treated with $9\times10^6$ FLT3 CAR T cells and $5\times10^6$ CD33 T cells.
FIG. 54M shows the shows the fLuc bioluminescence in MOLM-13 tumor bearing mice treated with $18\times10^6$ FLT3 CAR T cells and $10\times10^6$ CD33 T cells.

The results of the CAR T cell dose escalation study are shown in FIG. 54. Images of the fLuc bioluminescence in vivo in each treatment group are shown. The mice injected with MOLM-13-Luc cells and unengineered T cells were sacrificed on day 16. Mice treated with $9\times10^6$ FLT3 CAR T cells were sacrificed on day 23. No other treatment groups were sacrificed before the end of the time course on day 26 (FIG. 54A). FIG. 54B-M provide quantification of the fLuc bioluminescence signal in each mouse group. FIG. 54B shows the shows the fLuc bioluminescence in non-tumor bearing mice treated with non-engineered T cells. FIG. 54C shows the shows the fLuc bioluminescence in MOLM-13 tumor bearing mice treated with non-engineered T cells. FIG. 54D shows the shows the fLuc bioluminescence in MOLM-13 tumor bearing mice treated with $9\times10^6$ FLT3 T cells. FIG. 54E shows the shows the fLuc bioluminescence in MOLM-13 tumor bearing mice treated with $18\times10^6$ FLT3 T cells. FIG. 54F shows the shows the fLuc bioluminescence in MOLM-13 tumor bearing mice treated with $0.625\times10^6$ CD33 T cells. FIG. 54G shows the shows the fLuc bioluminescence in MOLM-13 tumor bearing mice treated with $1.25\times10^6$ CD33 T cells. FIG. 54H shows the shows the fLuc bioluminescence in MOLM-13 tumor bearing mice treated with $2.5\times10^6$ CD33 T cells. FIG. 54I shows the shows the fLuc bioluminescence in MOLM-13 tumor bearing mice treated with $5\times10^6$ CD33 T cells. FIG. 54J shows the shows the fLuc bioluminescence in MOLM-13 tumor bearing mice treated with $10\times10^6$ CD33 T cells. FIG. 54K shows the shows the fLuc bioluminescence in MOLM-13 tumor bearing mice treated with $4.5\times10^6$ FLT3 CAR T cells and $2.5\times10^6$ CD33 T cells. FIG. 54L shows the shows the fLuc bioluminescence in MOLM-13 tumor bearing mice treated with $9\times10^6$ FLT3 CAR T cells and $5\times10^6$ CD33 T cells. FIG. 54M shows the shows the fLuc bioluminescence in MOLM-13 tumor bearing mice treated with $18\times10^6$ FLT3 CAR T cells and $10\times10^6$ CD33 T cells.)

Mice treated with CD33 CAR T cells alone or in combination with FLT3 CAR T cells showed a significant reduction in the MOLM-13-Luc bioluminescence signal. Thus, FLT3 and CD33 CAR T cells showed potent in vivo activity against MOLM-13-Luc AML cells at different doses.

Example 20: In Vivo Characterization of Anti-CLEC12A CAR T Cells

Materials and Methods

CAR Structure

Six CLEC12A CARs were made using the three CLEC12A binders derived from the 357, 378, and 161 CLEC12A antibodies and either a CD28 (SB01561, SB01562, SB01563) or a 4-1BB co-stimulatory domain (SB01261, SB01262, SB01263). The CARs also had a CD8 signal sequence, a CD8 hinge, a CD8 transmembrane domain, a CD3ζ signaling domain, and a YFP tag. The CLEC12A CARs are listed in Table 5 below. 28z refers to a CD28 co-stimulatory domain, BBz refers for a 4-1BB co-stimulatory domain. FLT3 CAR T cells with an NC7 scFv and CD33 CAR T cells with a hu195 scFv were used as controls.

Single Dose Experiment Protocol:

The human AML cell line MOLM-14 was chosen as the in vivo AML cell target for testing CLEC12A CAR T cells due to its robust CLEC12A surface expression (See FIG. 44-45A). MOLM-14 AML cells were engineered to express a firefly luciferase (referred to as fLuc or Luc) reporter (engineered cells denoted MOLM-14-Luc or MOLM-14-fLuc After injection of these cells into NSG immunocompromised mice, MOLM-14-Luc in vivo tumor engraftment and growth was monitored by injecting the mice with an fLuc substrate (e.g. luciferin) and using a bioluminescence imaging system (AMY HT, by Spectral Instruments Imaging) to quantify the amount of light produced from the luciferase enzyme within the MOLM-13 cells.

$1.0\times10^6$ MOLM-14-Luc AML cells were injected (IV) at Day 0. Post-MOLM-14-Luc injection, $10\times10^6$ CAR+ T cells/mouse were injected (IV) at day 5. MOLM-14-Luc bioluminescence and mouse weight were assessed twice a week for up to 4 weeks. Total survival was assessed for up to 4 weeks.

The dosing regime and CAR T cells used are shown in the Table 10 below.

TABLE 10

| Group | n | AML Cells | CAR T cell | T cell dose | CAR T regimen |
|---|---|---|---|---|---|
| 1 | 5 | MOLM-14-Luc | Non-engineered T | 10e6 T cells | 5d |
| 2 | 5 | MOLM-14-Luc | Clec12a-28z (357) CAR T (SB01561) | 10.0e6 CAR + T cells | 5d |
| 3 | 5 | MOLM-14-Luc | Clec12a-28z (378) CAR T (SB01562) | 10.0e6 CAR + T cells | 5d |
| 4 | 5 | MOLM-14-Luc | Clec12a-28z (161) CAR T (SB01563) | 10.0e6 CAR + T cells | 5d |
| 5 | 5 | MOLM-14-Luc | Clec12a-BBz (357) CAR T (SB01261) | 10.0e6 CAR + T cells | 5d |
| 6 | 5 | MOLM-14-Luc | Clec12a-BBz (378) CAR T (SB01262) | 10.0e6 CAR + T cells | 5d |
| 7 | 5 | MOLM-14-Luc | Clec12a-BBz (161) CAR T (SB01263) | 10.0e6 CAR + T cells | 5d |
| 8 | 5 | MOLM-14-Luc | FLT3(NC7) CAR T (SB00819) | 10.0e6 CAR + T cells | 5d |
| 9 | 5 | MOLM-14-Luc | CD33(hu195) CAR T (SB01052) | 10.0e6 CAR + T cells | 5d |

Results

Figure 55B:
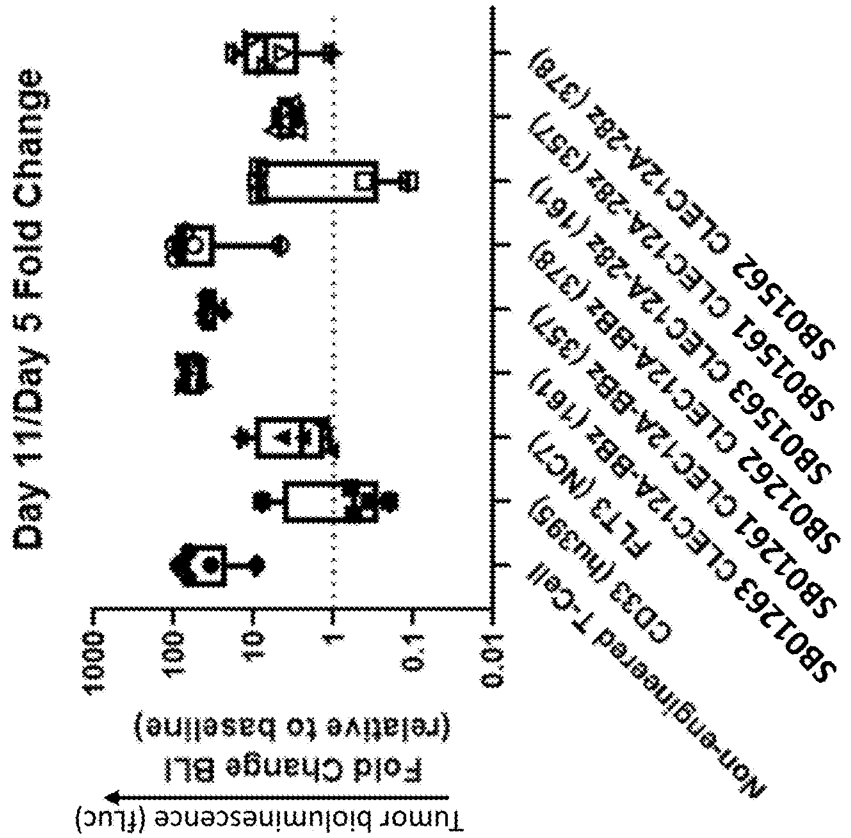
FIG. 55B shows the fold change on day 11 in the relative bioluminescence of tumor MOLM-14 cells in vivo after treatment with the indicated CAR.
Figure 55A:
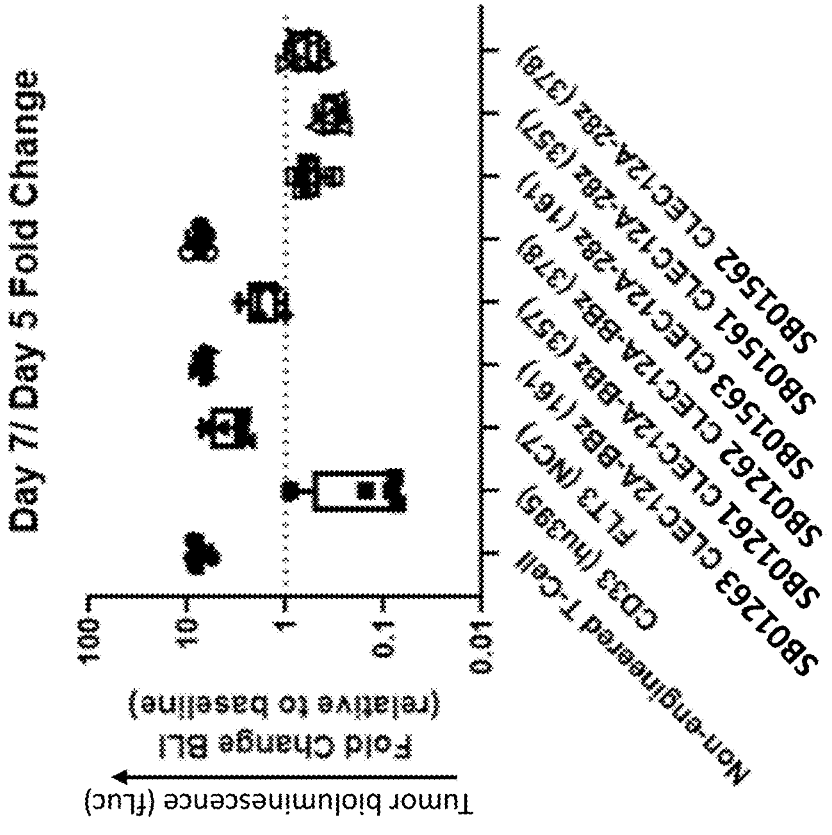
FIG. 55A shows the fold change on day 7 in the relative bioluminescence of tumor MOLM-14 cells in vivo after treatment with the indicated CAR.
Figure 55C:
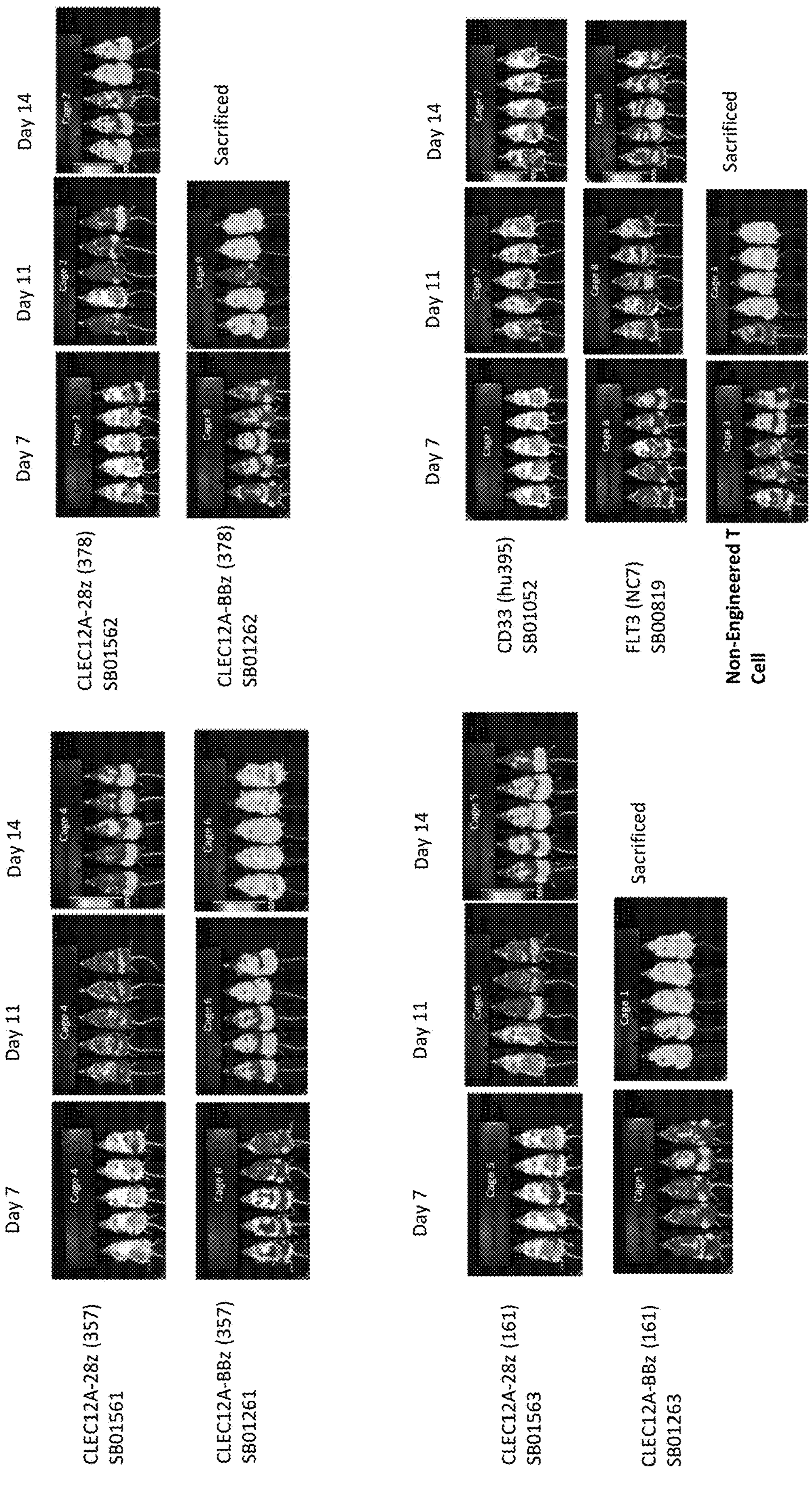
FIG. 55C shows the bioluminescence of tumor MOLM-14 cells in vivo after treatment with the indicated CAR.

The results of the in vivo efficacy study are shown in FIGS. 55A, 55B, and 55C. The relative tumor bioluminescence of each mouse group are shown as a comparison of Day 7/Day5 (FIG. 55A) and Day 11/Day 5 (FIG. 55B). The fold change in the MOLM-14 tumor cell bioluminescent signal (fLuc) relative to the day 5 fLuc is shown on the y-axis. Thus, increases in tumor bioluminescence from Day 5 to Day 7 or Day 11 are shown as an increase in the luminescence signal, while decreases in tumor bioluminescence from Day 5 to Day 7 or Day 11 are shown as a decrease of the bioluminescence signal. Treatment with the CD33 and FLT3 CAR T cells reduced the tumor burden, as did the CLEC12A CAR T cells with the CD28 co-stimulatory domain on Day 7 and Day 11 (FIGS. 55A and 55B). In most case, the CARs with the CD28 co-stimulatory domain were more efficacious in reducing tumor burden or extending mouse survival time than the CARs with the 4-1BB co-stimulatory domain. The 357 CLEC12A CAR with a 4-1BB co-stimulatory domain (SB01261) also resulted in reduced tumor burden on Day 7 as compared to Day 5 (FIG. 55A). Images of the bioluminescence in vivo in each treatment group is shown in FIG. 55C.

Thus, CLEC12A CARs with the CD28 co-stimulatory domains were more effective than the CARS with the 4-1BBz configuration at limiting MOLM-14 tumor growth.

Example 21: In Vitro and In Vivo FLT3 CAR Hinge Optimization

Materials and Methods

In Vitro Assays

Figures 56A, 56B, 56C, 56D, 56E:
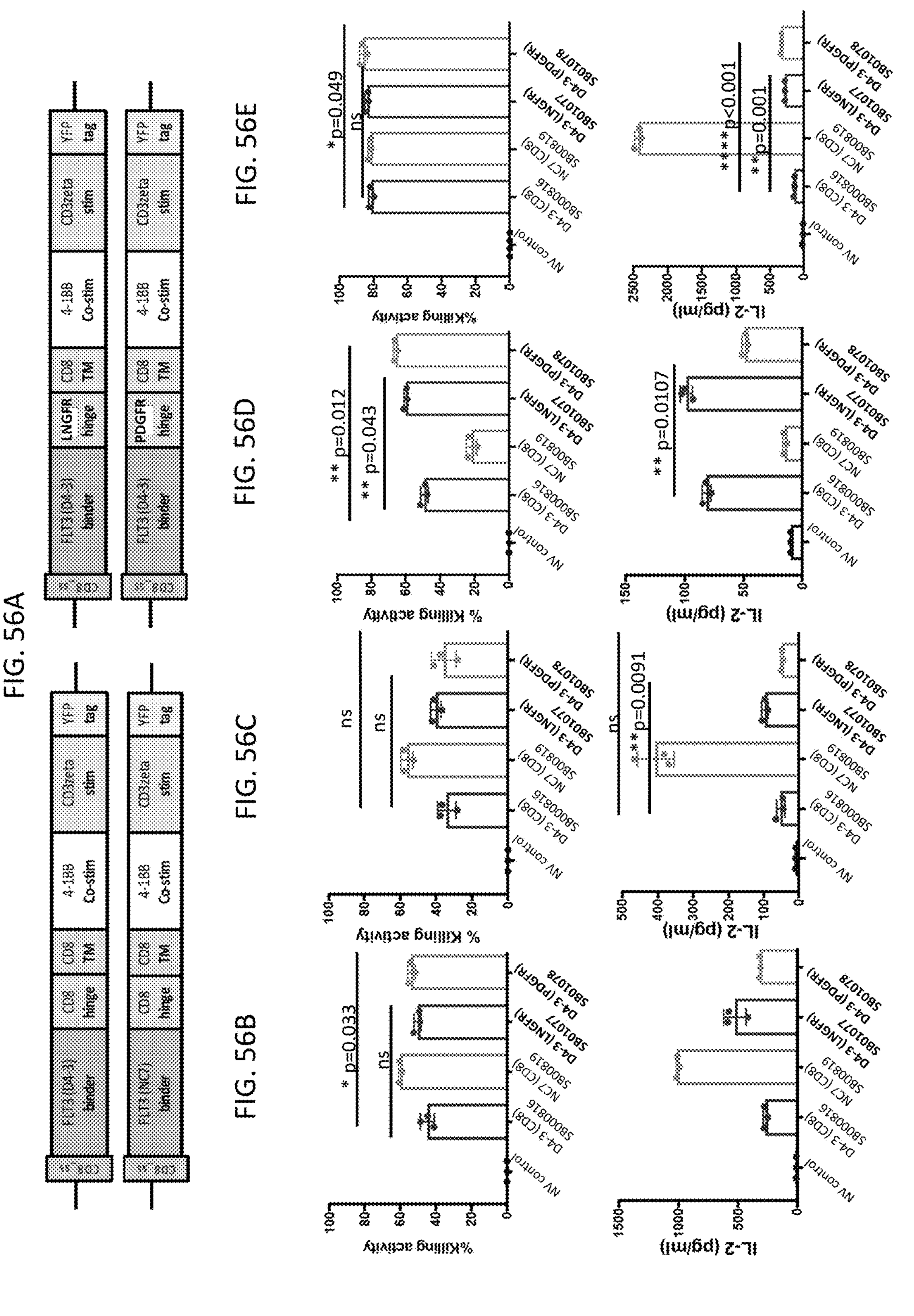
FIG. 56A provides schematics of indicated CARs with alternative hinge sequences.
FIG. 56B shows the cytotoxicity and IL-2 production of the indicated CAR after incubation with MOLM-13 cells.
FIG. 56C shows the cytotoxicity and IL-2 production of the indicated CAR after incubation with MOLM-14 cells.
FIG. 56D shows the cytotoxicity and IL-2 production of the indicated CAR after incubation with MV4-11 cells.
FIG. 56E shows the cytotoxicity and IL-2 production of the indicated CAR after incubation with SEM cells.

To optimize and increase FLT3 (D4-3) CAR T cell activity, an in vitro and in vivo functional screen of alternate hinges was performed. Efforts to optimize the FLT3 (D4-3) hinge region included: a D4-3 FLT3 CAR with a CD8 hinge (standard D4-3 hinge) (SB00816), an NC7 FLT3 CAR with a CD8 hinge (positive control for robust CAR activity) (SB00819), a D4-3 FLT3 CAR with an LNGFR (low-affinity nerve growth factor receptor) hinge (SB1076), a D4-3 FLT3 CAR with a truncated LNGFR (tLNGFR) hinge (SB1077), and a D4-3 FLT3 CAR with a PDGFR (platelet-derived growth factor receptor) hinge (SB01078) were synthesized. A diagram of the D4-3 FLT3 CARs with different hinges is shown in FIG. 56A.

Additional hinges were also assessed in the D4-3 FLT3 CAR. CARs with an IgG4 minimal linker (SB01071), an IgG4 minimal linker without disulfides (SB01072), an IgG4 minimal linker with enhanced disulfides (SB01073), and IgG1 minimal linker (SB01074) were synthesized. These CARs were also assessed for T cell cytotoxicity and IL2, IFN-γ, and TNF-α production and compared to the original D4-3 Car sequence and the CARs with the LNGFR and PDGFR hinge sequences.

T cell cytotoxicity and cytokine production after incubation with MOLM14, MV4-11, MOLM-13, and SEM cells were determined as previously described in Example 15.

The protein and nucleotide sequences of the FLT3 CARs produced are shown in Table 11.

TABLE 11

| SEQ ID NO | Name | Sequence |
|---|---|---|
| 180 | CD8ss_FLT3<br>(D4-3)_LNGFR<br>hingeCD8<br>TM_41BB<br>ICD_CD3z_YFP<br>SB01076 | MALPVTALLLPLALLLHAARPDVVMTQSPLSLPVTPGEPASISCRSSQSLLHSNGYNYLDWYLQKPGQS<br>PQLLIYLGSNRASGVPDRFSGSGSGTDFTLKISRVEAEDVGVYYCMQSLQTPFTFGPGTKVDIKGGGGS<br>GGGGSGGGGSEVQLVQSGAEVKKPGASVKVSCKASGYTFTSYYMHWARQAPGQGLEWMGIINPSGGSTS<br>YAQKFQGRVTMTRDTSTSTVYMELSSLRSEDTAVYYCARVVAAAVADYWGQGTLVTVSSACPTGLYTHS<br>GECCKACNLGEGVAQPCGANQTVCEPCLDSVTFSDVVSATEPCKPCTECVGLQSMSAPCVEADDAVCRC<br>AYGYYQDETTGRCEACRVCEAGSGLVFSCQDKQNTVCEECPDGTYSDEADAECIYIWAPLAGTCGVLLL<br>SLVITKRGRKKLLYIFKQPFMRPVQTTQEEDGCSCRFPEEEEGGCELRVKFSRSADAPAYKQGQNQLYN<br>ELNLGRREEYDVLDKRRGRDPEMGGKPRRKNPQEGLYNELQKDKMAEAYSEIGMKGERRRGKGHDGLYQ<br>GLSTATKDTYDALHMQALPPRGSSGTGMVSKGEELFTGVVPILVELDGDVNGHKFSVSGEGEGDATYGK<br>LTLKLICTTGKLPVPWPTLVTTLGYGLQCFARYPDHMKQHDFFKSAMPEGYVQERTIFFKDDGNYKTRA<br>EVKFEGDTLVNRIELKGIDFKEDGNILGHKLEYNYNSHNVYITADKQKNGIKANFKIRHNIEDGGVQLA<br>DHYQQNTPIGDGPVLLPDNHYLSYQSALSKDPNEKRDHMVLLEFVTAAGITLGMDELYK |
| 181 | CD8ss_FLT3<br>(D4-3)_LNGFR<br>hingeCD8<br>TM_41BB<br>ICD_CD3z_YFP<br>SB01076 | ATGGCCTTACCAGTGACCGCCTTGCTCCTGCCGCTGGCCTTGCTGCTCCACGCCGCCAGGCCGGACGTA<br>GTTATGACACAGTCTCCACTGTCATTGCCAGTAACACCAGGTGAGCCCGCCTCCATCTCATGTAGATCC<br>TCCCAATCTCTCCTTCATTCAAACGGGTATAATTATCTCGACTGGTATTTGCAGAAACCGGGCCAGAGC<br>CCTCAACTGCTCATCTATTTGGGGAGCAACCGGGCCTCTGGTGTCCCTGATAGATTCTCCGGGAGTGGA<br>TCAGGTACGGATTTTACACTGAAGATCAGCAGGGTGGAAGCAGAAGATGTTGGTGTGTATTACTGTATG<br>CAATCACTCCAGACCCCGTTTACCTTTGGGCCTGGAACAAAGGTAGATATTAAAGGCGGAGGGGGATCA<br>GGGGGTGGGGGGTCAGGTGGCGGTGGAAGTGAAGTGCAACTTGTTCAGAGCGGGGCAGAAGTTAAGAAG<br>CCAGGCGCTTCCGTCAAGGTGAGTTGCAAGGCAAGTGGATACACCTTTACGAGTTATTATATGCACTGG<br>GCACGGCAGGCCCCTGGTCAGGGCCTCGAATGGATGGGGATTATAAATCCTTCTGGCGGGTCAACCAGC<br>TACGCACAAAAATTTCAAGGTCGGGTGACAATGACGCGCGACACGTCAACGAGTACAGTGTATATGGAA<br>TTGTCTAGCCTGAGGTCCGAGGATACTGCTGTCTATTATTGTGCTCGCGTGGTCGCTGCTGCTGTGGCA<br>GACTACTGGGGTCAGGGTACACTTGTGACGGTAAGCAGCGCCTGCCCGACCGGGCTCTACACTCATAGC<br>GGGGAATGTTGTAAGGCATGTAACTTGGGTGAGGGCGTCGCACAGCCCTGCGGAGCTAACCAAACAGTG<br>TGCGAACCCTGCCTCGATAGTGTGACGTTCTCTGATGTTGTATCAGCTACAGAGCCTTGCAAACCATGT<br>ACTGAGTGCGTTGGACTTCAGTCAATGAGCGCTCCATGTGTGGAGGCAGATGATGCGGTCTGTCGATGT<br>GCTTACGGATACTACCAAGACGAGACAACAGGGCGGTGCGAGGCCTGTAGAGTTTGTGAGGCGGGCTCC<br>GGGCTGGTGTTTTCATGTCAAGACAAGCAAAATACGGTCTGTGAAGAGTGCCCTGATGGCACCTACTCA<br>GACGAAGCAGATGCAGAATGCATCTACATATGGGCCCCCCTCGCCGGTACTTGCGGTGTTTTGCTTTTG<br>TCACTGGTGATTACGAAGCGCGGTCGAAAAAAACTCCTCTACATCTTCAAACAACCTTTCATGCGGCCT<br>GTCCAAACAACTCAAGAAGAGGACGGGTGTTCATGCCGCTTTCCAGAGGAAGAGGAAGGTGGCTGTGAA<br>CTTAGGGTCAAGTTTAGCAGGTCAGCGGACGCACCAGCTTACAAGCAAGGCCAAAACCAGCTTTATAAC<br>GAATTGAATTTGGGACGCAGGGAAGAATACGATGTGCTCGATAAACGCAGAGGGAGGGACCCGGAAATG<br>GGAGGAAAGCCAAGGCGGAAAAACCCACAGGAGGGGTTGTACAACGAGCTTCAAAAAGATAAGATGGCG<br>GAAGCATACTCCGAAATAGGAATGAAGGGTGAACGGAGGAGGGGCAAGGGCCACGACGGCCTGTACCAG<br>GGACTCTCAACTGCTACGAAGGATACTTATGATGCTCTTCACATGCAAGCTCTGCCGCCGCGCGGATCG<br>AGTGGCACCGGTATGGTGAGCAAGGGCGAGGAGCTGTTCACCGGGGTGGTGCCCATCCTGGTCGAGCTG<br>GACGGCGACGTAAACGGCCACAAGTTCAGCGTGTCCGGCGAGGGCGAGGGCGATGCCACCTACGGCAAG<br>CTGACCCTGAAGCTGATCTGCACCACCGGCAAGCTGCCCGTGCCCTGGCCCACCCTCGTGACCACCCTG<br>GGCTACGGCCTcCAGTGCTTCGCCCGCTACCCCGACCACATGAAGCAGCACGACTTCTTCAAGTCCGCC<br>ATGCCCGAAGGCTACGTCCAGGAGCGCACCATCTTCTTCAAGGACGACGGCAACTACAAGACCCGCGCC<br>GAGGTGAAGTTCGAGGGCGACACCCTGGTGAACCGCATCGAGCTGAAGGGCATCGACTTCAAGGAGGAC<br>GGCAACATCCTGGGGCACAAGCTGGAGTACAACTACAACAGCCACAACGTCTATATCACCGCCGACAAG<br>CAGAAGAACGGCATCAAGGCCAACTTCAAGATCCGCCACAACATCGAGGACGGCGGCGTGCAGCTCGCC<br>GACCACTACCAGCAGAACACCCCCATCGGCGACGGCCCCGTGCTGCTGCCCGACAACCACTACCTGAGC<br>TACCAGTCCGCCCTGAGCAAAGACCCCAACGAGAAGCGCGATCACATGGTCCTGCTGGAGTTCGTGACC<br>GCCGCCGGGATCACTCTCGGCATGGACGAGCTGTACAAG |

TABLE 11-continued

| SEQ ID NO | Name | Sequence |
|---|---|---|
| 182 | CD8ss_FLT3<br>(D4-3)_trunc<br>LNGFR<br>hinge_CD8<br>TM_41BB<br>ICD_CD3z_YFP<br>SB01077 | MALPVTALLLPLALLLHAARPDVVMTQSPLSLPVTPGEPASISCRSSQSLLHSNGYNYLDWYLQKPGQS<br>PQLLIYLGSNRASGVPDRFSGSGSGTDFTLKISRVEAEDVGVYYCMQSLQTPFTFGPGTKVDIKGGGGS<br>GGGGSGGGGSEVQLVQSGAEVKKPGASVKVSCKASGYTFTSYYMHWARQAPGQGLEWMGIINPSGGSTS<br>YAQKFQGRVTMTRDTSTSTVYMELSSLRSEDTAVYYCARVVAAAVADYWGQGTLVTVSSACPTGLYTHS<br>GECCKACNLGEGVAQPCGANQTVCIYIWAPLAGTCGVLLLSLVITKRGRKKLLYIFKQPFMRPVQTTQE<br>EDGCSCRFPEEEEGGCELRVKFSRSADAPAYKQGQNQLYNELNLGRREEYDVLDKRRGRDPEMGGKPRR<br>KNPQEGLYNELQKDKMAEAYSEIGMKGERRRGKGHDGLYQGLSTATKDTYDALHMQALPPRGSSGTGMV<br>SKGEELFTGVVPILVELDGDVNGHKFSVSGEGEGDATYGKLTLKLICTTGKLPVPWPTLVTTLGYGLQC<br>FARYPDHMKQHDFFKSAMPEGYVQERTIFFKDDGNYKTRAEVKFEGDTLVNRIELKGIDFKEDGNILGH<br>KLEYNYNSHNVYITADKQKNGIKANFKIRHNIEDGGVQLADHYQQNTPIGDGPVLLPDNHYLSYQSALS<br>KDPNEKRDHMVLLEFVTAAGITLGMDELYK |
| 183 | CD8ss_FLT3<br>(D4-3)_trunc<br>LNGFR<br>hinge_CD8<br>TM_41BB<br>ICD_CD3z_YFP<br>SB01077 | ATGGCCTTACCAGTGACCGCCTTGCTCCTGCCGCTGGCCTTGCTGCTCCACGCCGCCAGGCCGGACGTA<br>GTTATGACACAGTCTCCACTGTCATTGCCAGTAACACCAGGTGAGCCCGCCTCCATCTCATGTAGATCC<br>TCCCAATCTCTCCTTCATTCAAACGGGTATAATTATCTCGACTGGTATTTGCAGAAACCGGGCCAGAGC<br>CCTCAACTGCTCATCTATTTGGGGAGCAACCGGGCCTCTGGTGTCCCTGATAGATTCTCCGGGAGTGGA<br>TCAGGTACGGATTTTACACTGAAGATCAGCAGGGTGGAAGCAGAAGATGTTGGTGTGTATTACTGTATG<br>CAATCACTCCAGACCCCGTTTACCTTTGGGCCTGGAACAAAGGTAGATATTAAAGGCGGAGGGGGATCA<br>GGGGGTGGGGGGTCAGGTGGCGGTGGAAGTGAAGTGCAACTTGTTCAGAGCGGGGCAGAAGTTAAGAAG<br>CCAGGCGCTTCCGTCAAGGTGAGTTGCAAGGCAAGTGGATACACCTTTACGAGTTATTATATGCACTGG<br>GCACGGCAGGCCCCTGGTCAGGGCCTCGAATGGATGGGGATTATAAATCCTTCTGGCGGGTCAACCAGC<br>TACGCACAAAAATTTCAAGGTCGGGTGACAATGACGCGCGACACGTCAACGAGTACAGTGTATATGGAA<br>TTGTCTAGCCTGAGGTCCGAGGATACTGCTGTCTATTATTGTGCTCGCGTGGTCGCTGCTGCTGTGGCA<br>GACTACTGGGGTCAGGGTACACTTGTGACGGTAAGCAGCGCCTGCCCTACAGGACTCTACACGCATAGC<br>GGTGAGTGTTGTAAAGCATGCAACCTCGGGGAAGGTGTAGCCCAGCCATGCGGGGCTAACCAAACCGTT<br>TGCATCTACATATGGGCCCCCCTCGCCGGTACTTGCGGTGTTTTGCTTTTGTCACTGGTGATTACGAAG<br>CGCGGTCGAAAAAAACTCCTCTACATCTTCAAACAACCTTTCATGCGGCCTGTCCAAACAACTCAAGAA<br>GAGGACGGGTGTTCATGCCCGCTTTCCAGAGGAAGAGGAAGGTGGCTGTGAACTTAGGGTCAAGTTTAGC<br>AGGTCAGCGGACGCACCAGCTTACAAGCAAGGCCAAAACCAGCTTTATAACGAATTGAATTTGGGACGC<br>AGGGAAGAATACGATGTGCTCGATAAACGCAGAGGGAGGGACCCGGAAATGGGAGGAAAGCCAAGGCGG<br>AAAAACCCACAGGAGGGGTTGTACAACGAGCTTCAAAAAGATAAGATGGCGGAAGCATACTCCGAAATA<br>GGAATGAAGGGTGAACGGAGGAGGGGCAAGGGCCACGACGGCCTGTACCAGGGACTCTCAACTGCTACG<br>AAGGATACTTATGATGCTCTTCACATGCAAGCTCTGCCGCCGCGCGGATCGAGTGGCACCGGTATGGTG<br>AGCAAGGGCGAGGAGCTGTTCACCGGGGTGGTGCCCATCCTGGTCGAGCTGGACGGCGACGTAAACGGC<br>CACAAGTTCAGCGTGTCCGGCGAGGGCGAGGGCGATGCCACCTACGGCAAGCTGACCCTGAAGCTGATC<br>TGCACCACCGGCAAGCTGCCCGTGCCCTGGCCCACCCTCGTGACCACCCTGGGCTACGGCCTCCAGTGC<br>TTCGCCCGCTACCCCGACCACATGAAGCAGCACGACTTCTTCAAGTCCGCCATGCCCGAAGGCTACGTC<br>CAGGAGCGCACCATCTTCTTCAAGGACGACGGCAACTACAAGACCCGCGCCGAGGTGAAGTTCGAGGGC<br>GACACCCTGGTGAACCGCATCGAGCTGAAGGGCATCGACTTCAAGGAGGACGGCAACATCCTGGGGCAC<br>AAGCTGGAGTACAACTACAACAGCCACAACGTCTATATCACCGCCGACAAGCAGAAGAACGGCATCAAG<br>GCCAACTTCAAGATCCGCCACAACATCGAGGACGGCGGCGTGCAGCTCGCCGACCACTACCAGCAGAAC<br>ACCCCCATCGGCGACGGCCCCGTGCTGCTGCCCGACAACCACTACCTGAGCTACCAGTCCGCCCTGAGC<br>AAAGACCCCAACGAGAAGCGCGATCACATGGTCCTGCTGGAGTTCGTGACCGCCGCCGGGATCACTCTC<br>GGCATGGACGAGCTGTACAAG |
| 184 | CD8ss_FLT3<br>(D4-3)_PDGFRb<br>hinge_CD8<br>TM_41BB<br>ICD_CD3z_YFP<br>SB01078 | MALPVTALLLPLALLLHAARPDVVMTQSPLSLPVTPGEPASISCRSSQSLLHSNGYNYLDWYLQKPGQS<br>PQLLIYLGSNRASGVPDRFSGSGSGTDFTLKISRVEAEDVGVYYCMQSLQTPFTFGPGTKVDIKGGGGS<br>GGGGSGGGGSEVQLVQSGAEVKKPGASVKVSCKASGYTFTSYYMHWARQAPGQGLEWMGIINPSGGSTS<br>YAQKFQGRVTMTRDTSTSTVYMELSSLRSEDTAVYYCARVVAAAVADYWGQGTLVTVSSAVGQDTQEVI<br>VVPHSLPFKVIYIWAPLAGTCGVLLLSLVITKRGRKKLLYIFKQPFMRPVQTTQEEDGCSCRFPEEEEG<br>GCELRVKFSRSADAPAYKQGQNQLYNELNLGRREEYDVLDKRRGRDPEMGGKPRRKNPQEGLYNELQKD<br>KMAEAYSEIGMKGERRRGKGHDGLYQGLSTATKDTYDALHMQALPPRGSSGTGMVSKGEELFTGVVPIL<br>VELDGDVNGHKFSVSGEGEGDATYGKLTLKLICTTGKLPVPWPTLVTTLGYGLQCFARYPDHMKQHDFF<br>KSAMPEGYVQERTIFFKDDGNYKTRAEVKFEGDTLVNRIELKGIDFKEDGNILGHKLEYNYNSHNVYIT<br>ADKQKNGIKANFKIRHNIEDGGVQLADHYQQNTPIGDGPVLLPDNHYLSYQSALSKDPNEKRDHMVLLE<br>FVTAAGITLGMDELYK |
| 185 | CD8ss_FLT3<br>(D4-3)_PDGFRb<br>hinge_CD8<br>TM_41BB<br>ICD_CD3z_YFP<br>SB01078 | ATGGCCTTACCAGTGACCGCCTTGCTCCTGCCGCTGGCCTTGCTGCTCCACGCCGCCAGGCCGGACGTA<br>GTTATGACACAGTCTCCACTGTCATTGCCAGTAACACCAGGTGAGCCCGCCTCCATCTCATGTAGATCC<br>TCCCAATCTCTCCTTCATTCAAACGGGTATAATTATCTCGACTGGTATTTGCAGAAACCGGGCCAGAGC<br>CCTCAACTGCTCATCTATTTGGGGAGCAACCGGGCCTCTGGTGTCCCTGATAGATTCTCCGGGAGTGGA<br>TCAGGTACGGATTTTACACTGAAGATCAGCAGGGTGGAAGCAGAAGATGTTGGTGTGTATTACTGTATG<br>CAATCACTCCAGACCCCGTTTACCTTTGGGCCTGGAACAAAGGTAGATATTAAAGGCGGAGGGGGATCA<br>GGGGGTGGGGGGTCAGGTGGCGGTGGAAGTGAAGTGCAACTTGTTCAGAGCGGGGCAGAAGTTAAGAAG<br>CCAGGCGCTTCCGTCAAGGTGAGTTGCAAGGCAAGTGGATACACCTTTACGAGTTATTATATGCACTGG<br>GCACGGCAGGCCCCTGGTCAGGGCCTCGAATGGATGGGGATTATAAATCCTTCTGGCGGGTCAACCAGC<br>TACGCACAAAAATTTCAAGGTCGGGTGACAATGACGCGCGACACGTCAACGAGTACAGTGTATATGGAA<br>TTGTCTAGCCTGAGGTCCGAGGATACTGCTGTCTATTATTGTGCTCGCGTGGTCGCTGCTGCTGTGGCA<br>GACTACTGGGGTCAGGGTACACTTGTGACGGTAAGCAGCGCTGTGGGCCAGGACACGCAGGAGGTCATC<br>GTGGTGCCACACTCCTTGCCCTTTAAGGTGATCTACATATGGGCCCCCCTCGCCGGTACTTGCGGTGTT<br>TTGCTTTTGTCACTGGTGATTACGAAGCGCGGTCGAAAAAAACTCCTCTACATCTTCAAACAACCTTTC<br>ATGCGGCCTGTCCAAACAACTCAAGAAGAGGACGGGTGTTCATGCCCGCTTTCCAGAGGAAGAGGAAGGT<br>GGCTGTGAACTTAGGGTCAAGTTTAGCAGGTCAGCGGACGCACCAGCTTACAAGCAAGGCCAAAACCAG<br>CTTTATAACGAATTGAATTTGGGACGCAGGGAAGAATACGATGTGCTCGATAAACGCAGAGGGAGGGAC<br>CCGGAAATGGGAGGAAAGCCAAGGCGGAAAAACCCACAGGAGGGGTTGTACAACGAGCTTCAAAAAGAT |

TABLE 11-continued

| SEQ ID NO | Name | Sequence |
|---|---|---|
| | | AAGATGGCGGAAGCATACTCCGAAATAGGAATGAAGGGTGAACGGAGGAGGGGCAAGGGCCACGACGGC<br>CTGTACCAGGGACTCTCAACTGCTACGAAGGATACTTATGATGCTCTTCACATGCAAGCTCTGCCGCCG<br>CGCGGATCGAGTGGCACCGGTATGGTGAGCAAGGGCGAGGAGCTGTTCACCGGGGTGGTGCCCATCCTG<br>GTCGAGCTGGACGGCGACGTAAACGGCCACAAGTTCAGCGTGTCCGGCGAGGGCGAGGGCGATGCCACC<br>TACGGCAAGCTGACCCTGAAGCTGATCTGCACCACCGGCAAGCTGCCCGTGCCCTGGCCCACCCTCGTG<br>ACCACCCTGGGCTACGGCCTCCAGTGCTTCGCCCGCTACCCCGACCACATGAAGCAGCACGACTTCTTC<br>AAGTCCGCCATGCCCGAAGGCTACGTCCAGGAGCGCACCATCTTCTTCAAGGACGACGGCAACTACAAG<br>ACCCGCGCCGAGGTGAAGTTCGAGGGCGACACCCTGGTGAACCGCATCGAGCTGAAGGGCATCGACTTC<br>AAGGAGGACGGCAACATCCTGGGGCACAAGCTGGAGTACAACTACAACAGCCACAACGTCTATATCACC<br>GCCGACAAGCAGAAGAACGGCATCAAGGCCAACTTCAAGATCCGCCACAACATCGAGGACGGCGGCGTG<br>CAGCTCGCCGACCACTACCAGCAGAACACCCCCATCGGCGACGGCCCCGTGCTGCTGCCCGACAACCAC<br>TACCTGAGCTACCAGTCCGCCCTGAGCAAAGACCCCAACGAGAAGCGCGATCACATGGTCCTGCTGGAG<br>TTCGTGACCGCCGCCGGGATCACTCTCGGCATGGACGAGCTGTACAAG |
| 186 | CD8ss_FLT3 (D4-3)_IgG4 min hinge_CD8 TM_41BB ICD_CD3z_YFP SB01071 | MALPVTALLLPLALLLHAARPDVVMTQSPLSLPVTPGEPASISCRSSQSLLHSNGYNYLDWYLQKPGQS<br>PQLLIYLGSNRASGVPDRFSGSGSGTDFTLKISRVEAEDVGVYYCMQSLQTPFTFGPGTKVDIKGGGGS<br>GGGGSGGGGSEVQLVQSGAEVKKPGASVKVSCKASGYTFTSYYMHWARQAPGQGLEWMGIINPSGGSTS<br>YAQKFQGRVTMTRDTSTSTVYMELSSLRSEDTAVYYCARVVAAAVADYWGQGTLVTVSSESKYGPPCPS<br>CPIYIWAPLAGTCGVLLLSLVITKRGRKKLLYIFKQPFMRPVQTTQEEDGCSCRFPEEEEGGCELRVKF<br>SRSADAPAYKQGQNQLYNELNLGRREEYDVLDKRRGRDPEMGGKPRRKNPQEGLYNELQKDKMAEAYSE<br>IGMKGERRRGKGHDGLYQGLSTATKDTYDALHMQALPPRGSSGTGMVSKGEELFTGVVPILVELDGDVN<br>GHKFSVSGEGEGDATYGKLTLKLICTTGKLPVPWPTLVTTLGYGLQCFARYPDHMKQHDFFKSAMPEGY<br>VQERTIFFKDDGNYKTRAEVKFEGDTLVNRIELKGIDFKEDGNILGHKLEYNYNSHNVYITADKQKNGI<br>KANFKIRHNIEDGGVQLADHYQQNTPIGDGPVLLPDNHYLSYQSALSKDPNEKRDHMVLLEFVTAAGIT<br>LGMDELYK |
| 187 | CD8ss_FLT3 (D4-3)_IgG4 min hinge_CD8 TM_41BB ICD_CD3z_YFP SB01071 | ATGGCCTTACCAGTGACCGCCTTGCTCCTGCCGCTGGCCTTGCTGCTCCACGCCGCCAGGCCGGACGTA<br>GTTATGACACAGTCTCCACTGTCATTGCCAGTAACACCAGGTGAGCCCGCCTCCATCTCATGTAGATCC<br>TCCCAATCTCTCCTTCATTCAAACGGGTATAATTATCTCGACTGGTATTTGCAGAAACCGGGCCAGAGC<br>CCTCAACTGCTCATCTATTTGGGGAGCAACCGGGCCTCTGGTGTCCCTGATAGATTCTCCGGGAGTGGA<br>TCAGGTACGGATTTTACACTGAAGATCAGCAGGGTGGAAGCAGAAGATGTTGGTGTGTATTACTGTATG<br>CAATCACTCCAGACCCCGTTTACCTTTGGGCCTGGAACAAAGGTAGATATTAAAGGCGGAGGGGGATCA<br>GGGGGTGGGGGGTCAGGTGGCGGTGGAAGTGAAGTGCAACTTGTTCAGAGCGGGGCAGAAGTTAAGAAG<br>CCAGGCGCTTCCGTCAAGGTGAGTTGCAAGGCAAGTGGATACACCTTTACGAGTTATTATATGCACTGG<br>GCACGGCAGGCCCCTGGTCAGGGCCTCGAATGGATGGGGATTATAAATCCTTCTGGCGGGTCAACCAGC<br>TACGCACAAAAATTTCAAGGTCGGGTGACAATGACGCGCGACACGTCAACGAGTACAGTGTATATGGAA<br>TTGTCTAGCCTGAGGTCCGAGGATACTGCTGTCTATTATTGTGCTCGCGTGGTCGCTGCTGCTGTGGCA<br>GACTACTGGGGTCAGGGTACACTTGTGACGGTAAGCAGCGAAAGCAAGTACGGTCCACCTTGCCCTAGC<br>TGTCCGATCTACATATGGGCCCCCCTCGCCGGTACTTGCGGTGTTTTGCTTTTGTCACTGGTGATTACG<br>AAGCGCGGTCGAAAAAAACTCCTCTACATCTTCAAACAACCTTTCATGCGGCCTGTCCAAACAACTCAA<br>GAAGAGGACGGGTGTTCATGCCGCTTTCCAGAGGAAGAGGAAGGTGGCTGTGAACTTAGGGTCAAGTTT<br>AGCAGGTCAGCGGACGCACCAGCTTACAAGCAAGGCCAAAACCAGCTTTATAACGAATTGAATTTGGGA<br>CGCAGGGAAGAATACGATGTGCTCGATAAACGCAGAGGGAGGGACCCGGAAATGGGAGGAAAGCCAAGG<br>CGGAAAAACCCACAGGAGGGGTTGTACAACGAGCTTCAAAAAGATAAGATGGCGGAAGCATACTCCGAA<br>ATAGGAATGAAGGGTGAACGGAGGAGGGGCAAGGGCCACGACGGCCTGTACCAGGGACTCTCAACTGCT<br>ACGAAGGATACTTATGATGCTCTTCACATGCAAGCTCTGCCGCCGCGCGGATCGAGTGGCACCGGTATG<br>GTGAGCAAGGGCGAGGAGCTGTTCACCGGGGTGGTGCCCATCCTGGTCGAGCTGGACGGCGACGTAAAC<br>GGCCACAAGTTCAGCGTGTCCGGCGAGGGCGAGGGCGATGCCACCTACGGCAAGCTGACCCTGAAGCTG<br>ATCTGCACCACCGGCAAGCTGCCCGTGCCCTGGCCCACCCTCGTGACCACCCTGGGCTACGGCCTCCAG<br>TGCTTCGCCCGCTACCCCGACCACATGAAGCAGCACGACTTCTTCAAGTCCGCCATGCCCGAAGGCTAC<br>GTCCAGGAGCGCACCATCTTCTTCAAGGACGACGGCAACTACAAGACCCGCGCCGAGGTGAAGTTCGAG<br>GGCGACACCCTGGTGAACCGCATCGAGCTGAAGGGCATCGACTTCAAGGAGGACGGCAACATCCTGGGG<br>CACAAGCTGGAGTACAACTACAACAGCCACAACGTCTATATCACCGCCGACAAGCAGAAGAACGGCATC<br>AAGGCCAACTTCAAGATCCGCCACAACATCGAGGACGGCGGCGTGCAGCTCGCCGACCACTACCAGCAG<br>AACACCCCCATCGGCGACGGCCCCGTGCTGCTGCCCGACAACCACTACCTGAGCTACCAGTCCGCCCTG<br>AGCAAAGACCCCAACGAGAAGCGCGATCACATGGTCCTGCTGGAGTTCGTGACCGCCGCCGGGATCACT<br>CTCGGCATGGACGAGCTGTACAAG |
| 188 | CD8ss_FLT3 (D4-3)_IgG4 min hinge no disulfides_CD8 TM_41BB ICD_CD3z_YFP SB01072 | MALPVTALLLPLALLLHAARPDVVMTQSPLSLPVTPGEPASISCRSSQSLLHSNGYNYLDWYLQKPGQS<br>PQLLIYLGSNRASGVPDRFSGSGSGTDFTLKISRVEAEDVGVYYCMQSLQTPFTFGPGTKVDIKGGGGS<br>GGGGSGGGGSEVQLVQSGAEVKKPGASVKVSCKASGYTFTSYYMHWARQAPGQGLEWMGIINPSGGSTS<br>YAQKFQGRVTMTRDTSTSTVYMELSSLRSEDTAVYYCARVVAAAVADYWGQGTLVTVSSESKYGPPAPS<br>APIYIWAPLAGTCGVLLLSLVITKRGRKKLLYIFKQPFMRPVQTTQEEDGCSCRFPEEEEGGCELRVKF<br>SRSADAPAYKQGQNQLYNELNLGRREEYDVLDKRRGRDPEMGGKPRRKNPQEGLYNELQKDKMAEAYSE<br>IGMKGERRRGKGHDGLYQGLSTATKDTYDALHMQALPPRGSSGTGMVSKGEELFTGVVPILVELDGDVN<br>GHKFSVSGEGEGDATYGKLTLKLICTTGKLPVPWPTLVTTLGYGLQCFARYPDHMKQHDFFKSAMPEGY<br>VQERTIFFKDDGNYKTRAEVKFEGDTLVNRIELKGIDFKEDGNILGHKLEYNYNSHNVYITADKQKNGI<br>KANFKIRHNIEDGGVQLADHYQQNTPIGDGPVLLPDNHYLSYQSALSKDPNEKRDHMVLLEFVTAAGIT<br>LGMDELYK |

TABLE 11-continued

| SEQ ID NO | Name | Sequence |
|---|---|---|
| 189 | CD8ss_FLT3 (D4-3)_IgG4 min hinge no disulfides_CD8 TM_41BB ICD_CD3z_YFP SB01072 | ATGGCCTTACCAGTGACCGCCTTGCTCCTGCCGCTGGCCTTGCTGCTCCACGCCGCCAGGCCGGACGTA<br>GTTATGACACAGTCTCCACTGTCATTGCCAGTAACACCAGGTGAGCCCGCCTCCATCTCATGTAGATCC<br>TCCCAATCTCTCCTTCATTCAAACGGGTATAATTATCTCGACTGGTATTTGCAGAAACCGGGCCAGAGC<br>CCTCAACTGCTCATCTATTTGGGGAGCAACCGGGCCTCTGGTGTCCCTGATAGATTCTCCGGGAGTGGA<br>TCAGGTACGGATTTTACACTGAAGATCAGCAGGGTGGAAGCAGAAGATGTTGGTGTGTATTACTGTATG<br>CAATCACTCCAGACCCCGTTTACCTTTGGGCCTGGAACAAAGGTAGATATTAAAGGCGGAGGGGGATCA<br>GGGGGTGGGGGGTCAGGTGGCGGTGGAAGTGAAGTGCAACTTGTTCAGAGCGGGGCAGAAGTTAAGAAG<br>CCAGGCGCTTCCGTCAAGGTGAGTTGCAAGGCAAGTGGATACACCTTTACGAGTTATTATATGCACTGG<br>GCACGGCAGGCCCCTGGTCAGGGCCTCGAATGGATGGGGATTATAAATCCTTCTGGCGGGTCAACCAGC<br>TACGCACAAAAATTTCAAGGTCGGGTGACAATGACGCGCGACACGTCAACGAGTACAGTGTATATGGAA<br>TTGTCTAGCCTGAGGTCCGAGGATACTGCTGTCTATTATTGTGCTCGCGTGGTCGCTGCTGCTGTGGCA<br>GACTACTGGGGTCAGGGTACACTTGTGACGGTAAGCAGCGAATCCAAGTACGGCCCCCCAGCGCCTAGT<br>GCCCCAATCTACATATGGGCCCCCCTCGCCGGTACTTGCGGTGTTTTGCTTTTGTCACTGGTGATTACG<br>AAGCGCGGTCGAAAAAAACTCCTCTACATCTTCAAACAACCTTTCATGCGGCCTGTCCAAACAACTCAA<br>GAAGAGGACGGGTGTTCATGCCGCTTTCCAGAGGAAGAGGAAGGTGGCTGTGAACTTAGGGTCAAGTTT<br>AGCAGGTCAGCGGACGCACCAGCTTACAAGCAAGGCCAAAACCAGCTTTATAACGAATTGAATTTGGGA<br>CGCAGGGAAGAATACGATGTGCTCGATAAACGCAGAGGGAGGGACCCGGAAATGGGAGGAAAGCCAAGG<br>CGGAAAAACCCACAGGAGGGGTTGTACAACGAGCTTCAAAAAGATAAGATGGCGGAAGCATACTCCGAA<br>ATAGGAATGAAGGGTGAACGGAGGAGGGGCAAGGGCCACGACGGCCTGTACCAGGGACTCTCAACTGCT<br>ACGAAGGATACTTATGATGCTCTTCACATGCAAGCTCTGCCGCCGCGCGGATCGAGTGGCACCGGTATG<br>GTGAGCAAGGGCGAGGAGCTGTTCACCGGGGTGGTGCCCATCCTGGTCGAGCTGGACGGCGACGTAAAC<br>GGCCACAAGTTCAGCGTGTCCGGCGAGGGCGAGGGCGATGCCACCTACGGCAAGCTGACCCTGAAGCTG<br>ATCTGCACCACCGGCAAGCTGCCCGTGCCCTGGCCCACCCTCGTGACCACCCTGGGCTACGGCCTCCAG<br>TGCTTCGCCCGCTACCCCGACCACATGAAGCAGCACGACTTCTTCAAGTCCGCCATGCCCGAAGGCTAC<br>GTCCAGGAGCGCACCATCTTCTTCAAGGACGACGGCAACTACAAGACCCGCGCCGAGGTGAAGTTCGAG<br>GGCGACACCCTGGTGAACCGCATCGAGCTGAAGGGCATCGACTTCAAGGAGGACGGCAACATCCTGGGG<br>CACAAGCTGGAGTACAACTACAACAGCCACAACGTCTATATCACCGCCGACAAGCAGAAGAACGGCATC<br>AAGGCCAACTTCAAGATCCGCCACAACATCGAGGACGGCGGCGTGCAGCTCGCCGACCACTACCAGCAG<br>AACACCCCCATCGGCGACGGCCCCGTGCTGCTGCCCGACAACCACTACCTGAGCTACCAGTCCGCCCTG<br>AGCAAAGACCCCAACGAGAAGCGCGATCACATGGTCCTGCTGGAGTTCGTGACCGCCGCCGGGATCACT<br>CTCGGCATGGACGAGCTGTACAAG |
| 190 | CD8ss_FLT3 (D4-3)_IgG4 S228P min hinge_CD8 TM_41BB ICD_CD3z_YFP SB01073 | MALPVTALLLPLALLLHAARPDVVMTQSPLSLPVTPGEPASISCRSSQSLLHSNGYNYLDWYLQKPGQS<br>PQLLIYLGSNRASGVPDRFSGSGSGTDFTLKISRVEAEDVGVYYCMQSLQTPFTFGPGTKVDIKGGGGS<br>GGGGSGGGGSEVQLVQSGAEVKKPGASVKVSCKASGYTFTSYYMHWARQAPGQGLEWMGIINPSGGSTS<br>YAQKFQGRVTMTRDTSTSTVYMELSSLRSEDTAVYYCARVVAAAVADYWGQGTLVTVSSESKYGPPCPP<br>CPIYIWAPLAGTCGVLLLSLVITKRGRKKLLYIFKQPFMRPVQTTQEEDGCSCRFPEEEEGGCELRVKF<br>SRSADAPAYKQGQNQLYNELNLGRREEYDVLDKRRGRDPEMGGKPRRKNPQEGLYNELQKDKMAEAYSE<br>IGMKGERRRGKGHDGLYQGLSTATKDTYDALHMQALPPRGSSGTGMVSKGEELFTGVVPILVELDGDVN<br>GHKFSVSGEGEGDATYGKLTLKLICTTGKLPVPWPTLVTTLGYGLQCFARYPDHMKQHDFFKSAMPEGY<br>VQERTIFFKDDGNYKTRAEVKFEGDTLVNRIELKGIDFKEDGNILGHKLEYNYNSHNVYITADKQKNGI<br>KANFKIRHNIEDGGVQLADHYQQNTPIGDGPVLLPDNHYLSYQSALSKDPNEKRDHMVLLEFVTAAGIT<br>LGMDELYK |
| 191 | CD8ss_FLT3 (D4-3)_IgG4 S228P min hinge_CD8 TM_41BB ICD_CD3z_YFP SB01073 | ATGGCCTTACCAGTGACCGCCTTGCTCCTGCCGCTGGCCTTGCTGCTCCACGCCGCCAGGCCGGACGTA<br>GTTATGACACAGTCTCCACTGTCATTGCCAGTAACACCAGGTGAGCCCGCCTCCATCTCATGTAGATCC<br>TCCCAATCTCTCCTTCATTCAAACGGGTATAATTATCTCGACTGGTATTTGCAGAAACCGGGCCAGAGC<br>CCTCAACTGCTCATCTATTTGGGGAGCAACCGGGCCTCTGGTGTCCCTGATAGATTCTCCGGGAGTGGA<br>TCAGGTACGGATTTTACACTGAAGATCAGCAGGGTGGAAGCAGAAGATGTTGGTGTGTATTACTGTATG<br>CAATCACTCCAGACCCCGTTTACCTTTGGGCCTGGAACAAAGGTAGATATTAAAGGCGGAGGGGGATCA<br>GGGGGTGGGGGGTCAGGTGGCGGTGGAAGTGAAGTGCAACTTGTTCAGAGCGGGGCAGAAGTTAAGAAG<br>CCAGGCGCTTCCGTCAAGGTGAGTTGCAAGGCAAGTGGATACACCTTTACGAGTTATTATATGCACTGG<br>GCACGGCAGGCCCCTGGTCAGGGCCTCGAATGGATGGGGATTATAAATCCTTCTGGCGGGTCAACCAGC<br>TACGCACAAAAATTTCAAGGTCGGGTGACAATGACGCGCGACACGTCAACGAGTACAGTGTATATGGAA<br>TTGTCTAGCCTGAGGTCCGAGGATACTGCTGTCTATTATTGTGCTCGCGTGGTCGCTGCTGCTGTGGCA<br>GACTACTGGGGTCAGGGTACACTTGTGACGGTAAGCAGCGAATCTAAATATGGCCCGCCATGCCCGCCT<br>TGCCCAATCTACATATGGGCCCCCCTCGCCGGTACTTGCGGTGTTTTGCTTTTGTCACTGGTGATTACG<br>AAGCGCGGTCGAAAAAAACTCCTCTACATCTTCAAACAACCTTTCATGCGGCCTGTCCAAACAACTCAA<br>GAAGAGGACGGGTGTTCATGCCGCTTTCCAGAGGAAGAGGAAGGTGGCTGTGAACTTAGGGTCAAGTTT<br>AGCAGGTCAGCGGACGCACCAGCTTACAAGCAAGGCCAAAACCAGCTTTATAACGAATTGAATTTGGGA<br>CGCAGGGAAGAATACGATGTGCTCGATAAACGCAGAGGGAGGGACCCGGAAATGGGAGGAAAGCCAAGG<br>CGGAAAAACCCACAGGAGGGGTTGTACAACGAGCTTCAAAAAGATAAGATGGCGGAAGCATACTCCGAA<br>ATAGGAATGAAGGGTGAACGGAGGAGGGGCAAGGGCCACGACGGCCTGTACCAGGGACTCTCAACTGCT<br>ACGAAGGATACTTATGATGCTCTTCACATGCAAGCTCTGCCGCCGCGCGGATCGAGTGGCACCGGTATG<br>GTGAGCAAGGGCGAGGAGCTGTTCACCGGGGTGGTGCCCATCCTGGTCGAGCTGGACGGCGACGTAAAC<br>GGCCACAAGTTCAGCGTGTCCGGCGAGGGCGAGGGCGATGCCACCTACGGCAAGCTGACCCTGAAGCTG<br>ATCTGCACCACCGGCAAGCTGCCCGTGCCCTGGCCCACCCTCGTGACCACCCTGGGCTACGGCCTCCAG<br>TGCTTCGCCCGCTACCCCGACCACATGAAGCAGCACGACTTCTTCAAGTCCGCCATGCCCGAAGGCTAC<br>GTCCAGGAGCGCACCATCTTCTTCAAGGACGACGGCAACTACAAGACCCGCGCCGAGGTGAAGTTCGAG<br>GGCGACACCCTGGTGAACCGCATCGAGCTGAAGGGCATCGACTTCAAGGAGGACGGCAACATCCTGGGG<br>CACAAGCTGGAGTACAACTACAACAGCCACAACGTCTATATCACCGCCGACAAGCAGAAGAACGGCATC<br>AAGGCCAACTTCAAGATCCGCCACAACATCGAGGACGGCGGCGTGCAGCTCGCCGACCACTACCAGCAG<br>AACACCCCCATCGGCGACGGCCCCGTGCTGCTGCCCGACAACCACTACCTGAGCTACCAGTCCGCCCTG<br>AGCAAAGACCCCAACGAGAAGCGCGATCACATGGTCCTGCTGGAGTTCGTGACCGCCGCCGGGATCACT<br>CTCGGCATGGACGAGCTGTACAAG |

TABLE 11-continued

| SEQ ID NO | Name | Sequence |
|---|---|---|
| 192 | CD8ss_FLT3 (D4-3)_IgG1 min hinge_CD8 TM_41BB ICD_CD3z_YFP SB01074 | MALPVTALLLPLALLLHAARPDVVMTQSPLSLPVTPGEPASISCRSSQSLLHSNGYNYLDWYLQKPGQSPQLLIYLGSNRASGVPDRFSGSGSGTDFTLKISRVEAEDVGVYYCMQSLQTPFTFGPGTKVDIKGGGGSGGGGSGGGGSEVQLVQSGAEVKKPGASVKVSCKASGYTFTSYYMHWARQAPGQGLEWMGIINPSGGSTSYAQKFQGRVTMTRDTSTSTVYMELSSLRSEDTAVYYCARVVAAAVADYWGQGTLVTVSSEPKSCDKTHTCPIYIWAPLAGTCGVLLLSLVITKRGRKKLLYIFKQPFMRPVQTTQEEDGCSCRFPEEEEGGCELRVKFSRSADAPAYKQGQNQLYNELNLGRREEYDVLDKRRGRDPEMGGKPRRKNPQEGLYNELQKDKMAEAYSEIGMKGERRRGKGHDGLYQGLSTATKDTYDALHMQALPPRGSSGTGMVSKGEELFTGVVPILVELDGDVNGHKFSVSGEGEGDATYGKLTLKLICTTGKLPVPWPTLVTTLGYGLQCFARYPDHMKQHDFFKSAMPEGYVQERTIFFKDDGNYKTRAEVKFEGDTLVNRIELKGIDFKEDGNILGHKLEYNYNSHNVYITADKQKNGIKANFKIRHNIEDGGVQLADHYQQNTPIGDGPVLLPDNHYLSYQSALSKDPNEKRDHMVLLEFVTAAGITLGMDELYK |
| 193 | CD8ss_FLT3 (D4-3)_IgG1 min hinge_CD8 TM_41BB ICD_CD3z_YFP SB01074 | ATGGCCTTACCAGTGACCGCCTTGCTCCTGCCGCTGGCCTTGCTGCTCCACGCCGCCAGGCCGGACGTAGTTATGACACAGTCTCCACTGTCATTGCCAGTAACACCAGGTGAGCCCGCCTCCATCTCATGTAGATCCTCCCAATCTCTCCTTCATTCAAACGGGTATAATTATCTCGACTGGTATTTGCAGAAACCGGGCCAGAGCCCTCAACTGCTCATCTATTTGGGGAGCAACCGGGCCTCTGGTGTCCCTGATAGATTCTCCGGGAGTGGATCAGGTACGGATTTTACACTGAAGATCAGCAGGGTGGAAGCAGAAGATGTTGGTGTGTATTACTGTATGCAATCACTCCAGACCCCGTTTACCTTTGGGCCTGGAACAAAGGTAGATATTAAAGGCGGAGGGGGATCAGGGGGTGGGGGGTCAGGTGGCGGTGGAAGTGAAGTGCAACTTGTTCAGAGCGGGGCAGAAGTTAAGAAGCCAGGCGCTTCCGTCAAGGTGAGTTGCAAGGCAAGTGGATACACCTTTACGAGTTATTATATGCACTGGGCACGGCAGGCCCCTGGTCAGGGCCTCGAATGGATGGGGATTATAAATCCTTCTGGCGGGTCAACCAGCTACGCACAAAAATTTCAAGGTCGGGTGACAATGACGCGCGACACGTCAACGAGTACAGTGTATATGGAATTGTCTAGCCTGAGGTCCGAGGATACTGCTGTCTATTATTGTGCTCGCGTGGTCGCTGCTGCTGTGGCAGACTACTGGGGTCAGGGTACACTTGTGACGGTAAGCAGCGAACCGAAGTCTTGTGATAAAACTCATACGTGCCCGATCTACATATGGGCCCCCCTCGCCGGTACTTGCGGTGTTTTGCTTTTGTCACTGGTGATTACGAAGCGCGGTCGAAAAAAACTCCTCTACATCTTCAAACAACCTTTCATGCGGCCTGTCCAAACAACTCAAGAAGAGGACGGGTGTTCATGCCGCTTTCCAGAGGAAGAGGAAGGTGGCTGTGAACTTAGGGTCAAGTTTAGCAGGTCAGCGGACGCACCAGCTTACAAGCAAGGCCAAAACCAGCTTTATAACGAATTGAATTTGGGACGCAGGGAAGAATACGATGTGCTCGATAAACGCAGAGGGAGGGACCCGGAAATGGGAGGAAAGCCAAGGCGGAAAAACCCACAGGAGGGGTTGTACAACGAGCTTCAAAAAGATAAGATGGCGGAAGCATACTCCGAAATAGGAATGAAGGGTGAACGGAGGAGGGGCAAGGGCCACGACGGCCTGTACCAGGGACTCTCAACTGCTACGAAGGATACTTATGATGCTCTTCACATGCAAGCTCTGCCGCCGCGCGGATCGAGTGGCACCGGTATGGTGAGCAAGGGCGAGGAGCTGTTCACCGGGGTGGTGCCCATCCTGGTCGAGCTGGACGGCGACGTAAACGGCCACAAGTTCAGCGTGTCCGGCGAGGGCGAGGGCGATGCCACCTACGGCAAGCTGACCCTGAAGCTGATCTGCACCACCGGCAAGCTGCCCGTGCCCTGGCCCACCCTCGTGACCACCCTGGGCTACGGCCTCCAGTGCTTCGCCCGCTACCCCGACCACATGAAGCAGCACGACTTCTTCAAGTCCGCCATGCCCGAAGGCTACGTCCAGGAGCGCACCATCTTCTTCAAGGACGACGGCAACTACAAGACCCGCGCCGAGGTGAAGTTCGAGGGCGACACCCTGGTGAACCGCATCGAGCTGAAGGGCATCGACTTCAAGGAGGACGGCAACATCCTGGGGCACAAGCTGGAGTACAACTACAACAGCCACAACGTCTATATCACCGCCGACAAGCAGAAGAACGGCATCAAGGCCAACTTCAAGATCCGCCACAACATCGAGGACGGCGGCGTGCAGCTCGCCGACCACTACCAGCAGAACACCCCCATCGGCGACGGCCCCGTGCTGCTGCCCGACAACCACTACCTGAGCTACCAGTCCGCCCTGAGCAAAGACCCCAACGAGAAGCGCGATCACATGGTCCTGCTGGAGTTCGTGACCGCCGCCGGGATCACTCTCGGCATGGACGAGCTGTACAAG |

In Vivo Assays

Mouse Materials and Methods

The MOLM-13 cell line expressing firefly luciferase (fLuc or Luc) was used in the in vivo experiments as described in Example 19.

$1.0\times10^6$ MOLM-13-Luc AML cells were injected (IV) at Day 0. Post-MOLM-13-Luc injection, $10\times10^6$ CAR+ T cells/mouse were injected (IV) at day 5 ($10\times10^6$ cells/mouse on each day). MOLM-13-Luc bioluminescence and mouse weight were assessed twice a week for up to 4 weeks. Total survival was assessed for up to 4 weeks.

The dosing regime and CAR T cells used are shown in the Table 12 below.

TABLE 12

| Group | n | AML | T cell | T cell dose | CAR T regimen |
|---|---|---|---|---|---|
| 1 | 3 | none | none | N/A | N/A |
| 2 | 3 | none | Non-engineered T | 20e6 T cells | 5d |
| 3 | 5 | MOLM-13-Luc | none | N/A | N/A |
| 3 | 5 | MOLM-13-Luc | Non-engineered T | 20e6 T cells | 5d |
| 4 | 5 | MOLM-13-Luc | FLT3(NC7 + CD8hinge) CAR T (SB00819) | 19.2e6 CAR + T cells | 5d |
| 5 | 5 | MOLM-13-Luc | FLT3(D4-3 + CD8hinge) CAR T (SB00816) | 17.2e6 CAR + T cells | 5d |
| 6 | 5 | MOLM-13-Luc | FLT3(D4-3 + LNGFRhinge) CAR T (SB01077) | 12.4e6 CAR + T cells | 5d |
| 7 | 5 | MOLM-13-Luc | FLT3(D4-3 + PDGFRhinge) CAR T (SB01078) | 14.4e6 CAR + T cells | 5d |

Results

In Vitro Assays

The FLT3 hinge optimization resulted in statistically significant increase in FLT3 CAR activity when using LNGFR and PDGFR hinges (SB1077 and SB1078, respectively). The use of an LNGFR or PDGFR hinge in the D4-3 CAR resulted in increased cytotoxity and IL-2 production after incubation with MOLM-13 cells (FIG. 56B), MOLM-14 cells (FIG. 56C) MV4-11 cells (FIG. 56D), and SEM cells (FIG. 56E) as compared to the CD8 hinge. In each of FIG. 56B-E, the top panel shows the cytotoxity of each CAR after incubation with the indicated cell line and the bottom panel shows the IL-2 production of each CAR after incubation with the indicated cell line.

Figure 57A:
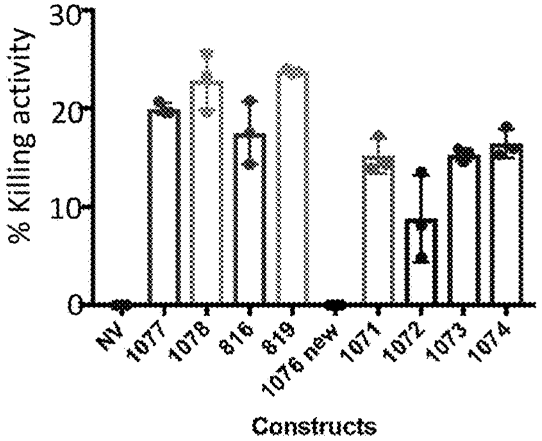
FIG. 57A shows the percent killing, as normalized to non-transduced CAR T cells by the indicated CAR T cells after incubation with MOLM-13 cells.
Figure 57B:
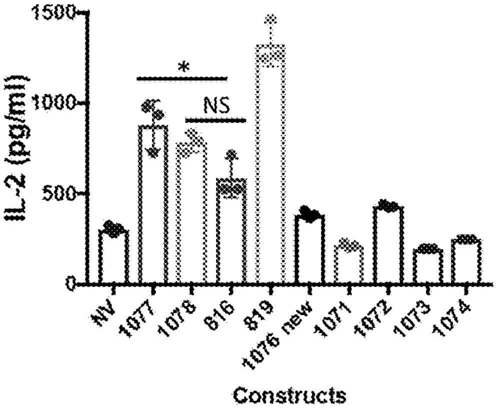
FIG. 57B shows the IL-2 production of the indicated CAR after incubation with MOLM-13 cells.
Figure 57C:
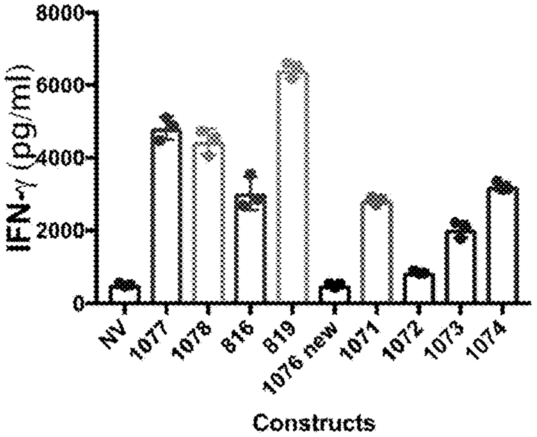
FIG. 57C shows the production of IFN-γ by the indicated CAR T cells after incubation with MOLM-13 cells.
Figure 57D:
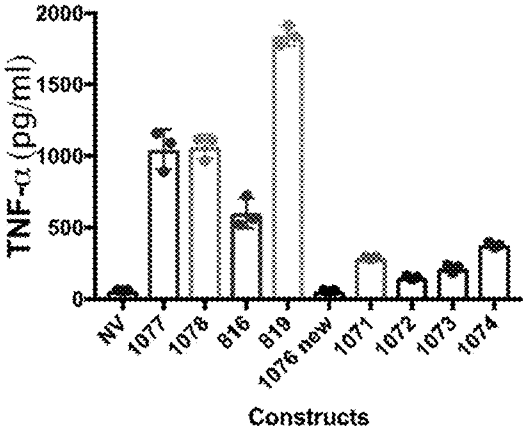
FIG. 57D shows the production of TNF-α by the indicated CAR T cells after incubation with MOLM-13 cells.

Similar results were observed with the other hinge sequences. FIG. 57A shows the percent killing, as normalized to non-transduced CAR T cells. FIG. 57B-D show the production of IL-2 (FIG. 57B), IFN-γ (FIG. 57C), and TNF-α (FIG. 57D) by the indicated CAR T cells after incubation with MOLM-13 cells.

In Vitro Assays

Figure 58A:
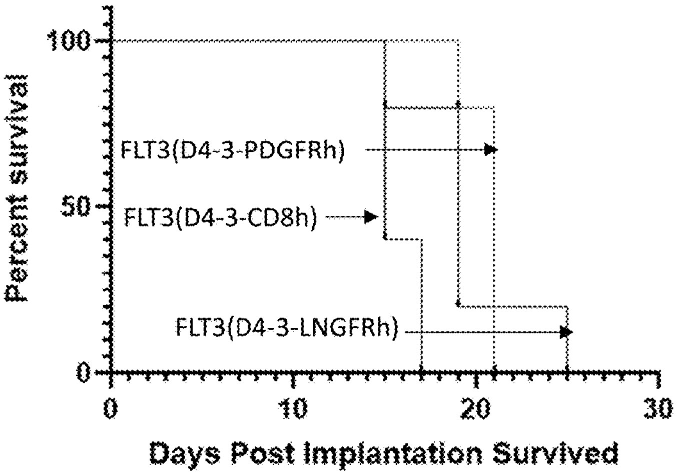
FIG. 58A shows in vivo survival after treatment with the indicated CAR T cells in the MOLM-13 model.
Figure 58B:
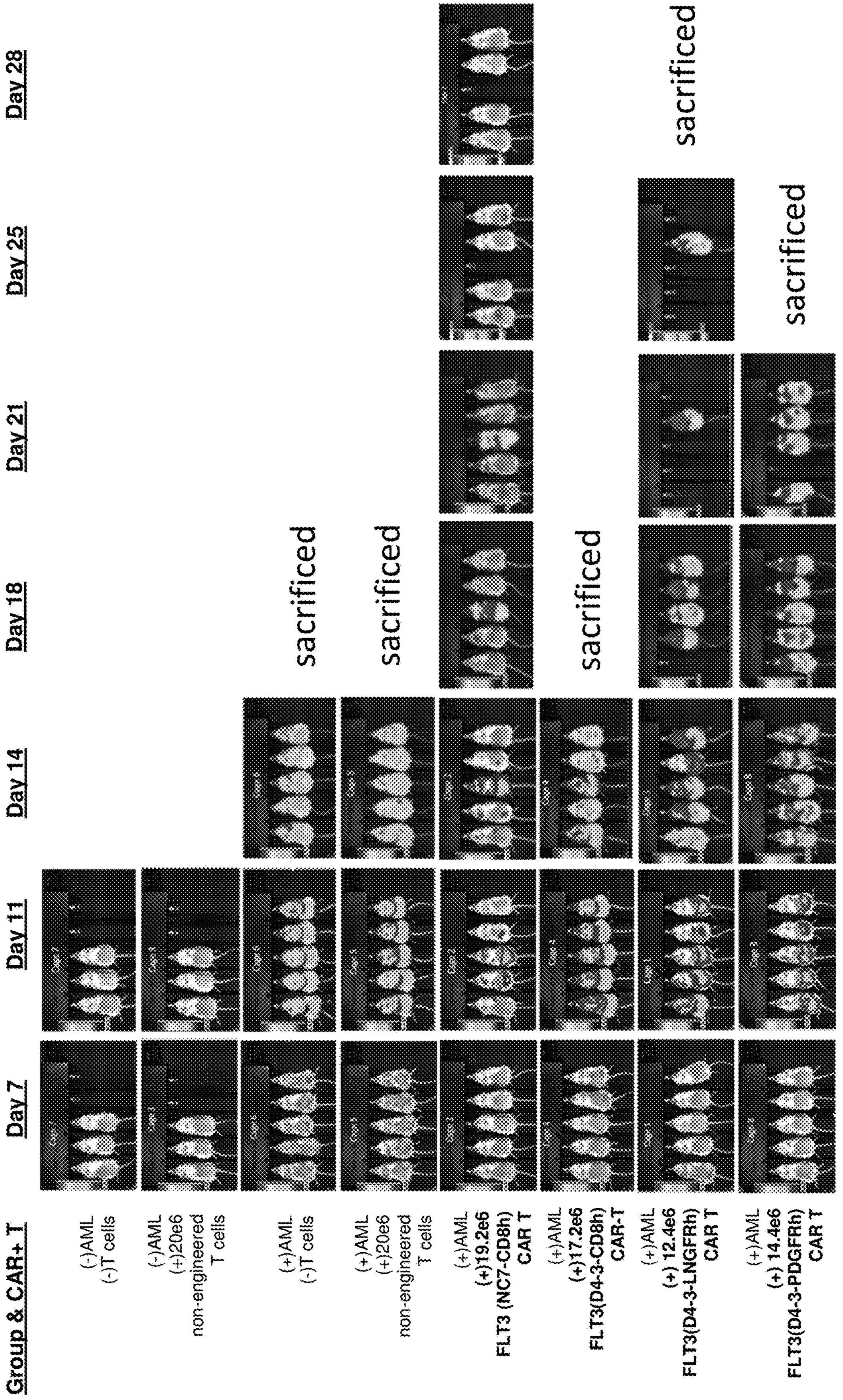
FIG. 58B shows the bioluminescence of tumor MOLM-13 cells in vivo after treatment with the indicated CAR.

FLT3 (D4-3) CARs constructed with LNGFR or PDGFR hinges demonstrated increased in vivo potency of the CAR T cell against MOLM-13 AML cells compared to the D4-3 FLT3 CAR with CD8 hinge, as shown by the increased mouse survival (FIG. 58A). FIG. 58B shows the bioluminescence of tumor MOLM-13 cells in vivo after treatment with the indicated CAR. Thus, D4-3 FLT3 CARs with LNGFR or PDGFR hinges were more effective in both in vitro and in vivo AML models than D4-3 FLT3 CAR with CD8 hinge.

Example 22: In Vitro Characterization of Bicistronic FLT3 OR CD33 CAR T Cells Materials and Methods Four different bicistronic FLT3 and CD33 CARs were made using a CD33 hu195 scFv and a FLT3 NC7 scFv, SB01658, SB01659, SB01530, and SB01266.

The SB01658 CAR is a CD33 "OR" FLT3 bicistronic CAR with the structure: CD8 signal sequence-FLAG-CD33 (hu195)scFv-CD28 hinge-CD28 transmembrane-CD28 co-stimulatory domain-CD3ζ stimulatory domain—T2A-E2A—CD8 signal sequence-FLT3(NC7)scFv-CD8 hinge-CD8 transmembrane-4-1BB co-stimulatory domain-CD3 signaling domain-YFP.

The SB01659 CAR is a CD33 "OR" FLT3 bicistronic CAR with the structure: CD8 signal sequence-FLAG-CD33 (hu195)scFv-CD28 hinge-CD28 transmembrane-CD28 co-stimulatory domain-CD3ζ stimulatory domain—E2A-T2A—CD8 signal sequence-FLT3(NC7)scFv-CD8 hinge-CD8 transmembrane-4-1BB co-stimulatory domain-CD3ζ signaling domain-YFP.

The SB01530 CAR is a CD33 "OR" FLT3 bicistronic CAR with the structure: CD8 signal sequence-FLAG-CD33 (hu195)scFv-CD28 hinge-CD28 transmembrane-CD28 co-stimulatory domain-CD3ζ stimulatory domain—T2A—CD8 signal sequence-FLT3(NC7)scFv-CD8 hinge-CD8 transmembrane-4-1BB co-stimulatory domain-CD3ζ signaling domain-YFP.

The SB01266 CAR is a CD33 "OR" FLT3 bicistronic CAR with the structure: CD8 signal sequence-FLAG-CD33 (hu195)scFv-CD28 hinge-CD28 transmembrane-CD28 co-stimulatory domain-CD3ζ stimulatory domain-T2A-CD8 signal sequence-FLT3(NC7)scFv-CD8 hinge-CD8 transmembrane-4-1BB co-stimulatory domain-CD3ζ signaling domain-YFP SB01530 is a codon optimized version of SB01266.

The protein and nucleotide sequences of the bicistronic FLT3 and CD33 CARs produced are shown in Table 13.

TABLE 13

| SEQ ID NO | Name | Sequence |
|---|---|---|
| 194 | CD8ss_Flag_CD33 (hu195)_CD28 hinge_CD28 TM_CD28 ICD_CD3z_T2A_E2A_-CD8ss_NC7_CD8 hinge_CD8 TM_41BB ICD-CD3z_YFP SB01658 | MALPVTALLLPLALLLHAARPAGGSDYKDDDDKGGGGSGGGGQVQLVQSGAEVKKPGSSVKVSCKASGYTFTDYNMHWVRQAPGQGLEWIGYIYPYNGGTGYNQKFKSKATITADESTNTAYMELSSLRSEDTAVYYCARGRPAMDYWGQGTLVTVSSGGGGSGGGGSGGGGSDIQMTQSPSSLSASVGDRVTITCRASESVDNYGISFMNWFQQKPGKAPKLLIYAASNQGSGVPSRFSGSGSGTDFTLTISSLQPDDFATYYCQQSKEVPWTFGQGTKVEIKSGAAAIEVMYPPPYLDNEKSNGTIIHVKGKHLCPSPLFPGPSKPFWVLVVVGGVLACYSLLVTVAFIIFWVRSKRSRLLHSDYMNMTPRRPGPTRKHYQPYAPPRDFAAYRSRVKFSRSADAPAYKQGQNQLYNELNLGRREEYDVLDKRRGRDPEMGGKPRRKNPQEGLYNELQKDKMAEAYSEIGMKGERRRGKGHDGLYQGLSTATKDTYDALHMQALPPRGSGEGRGSLLTCGDVEENPGPGSGQCTNYALLKLAGDVESNPGPMALPVTALLLPLALLLHAARPEVQLVQSGAEVKKPGSSVKVSCKASGGTFSSYAISWVRQAPGQGLEWMGGIIPIFGTANYAQKFQGRVTITADKSTSTAYMELSSLRSEDTAVYYCATFALFGFREQAFDIWGQGTTVTVSSGGGGSGGGGSGGGGSDIQMTQSPSSLSASVGDRVTITCRASQSISSYLNWYQQKPGKAPKLLIYAASSLQSGVPSRFSGSGSGTDFTLTISSLQPEDLATYYCQQSYSTPFTFGPGTKVDIKTTTPAPRPPTPAPTIALQPLSLRPEACRPAAGGAVHTRGLDFACDIYIWAPLAGTCGVLLLSLVITKRGRKKLLYIFKQPFMRPVQTTQEEDGCSCRFPEEEEGGCELRVKFSRSADAPAYKQGQNQLYNELNLGRREEYDVLDKRRGRDPEMGGKPRRKNPQEGLYNELQKDKMAEAYSEIGMKGERRRGKGHDGLYQGLSTATKDTYDALHMQALPPRGSSGTGMVSKGEELFTGVVPILVELDGDVNGHKFSVSGEGEGDATYGKLTLKLICTTGKLPVPWPTLVTTLGYGLQCFARYPDHMKQHDFFKSAMPEGYVQERTIFFKDDGNYKTRAEVKFEGDTLVNRIELKGIDFKEDGNILGHKLEYNYNSHNVYITADKQKNGIKANFKIRHNIEDGGVQLADHYQQNTPIGDGPVLLPDNHYLSYQSALSKDPNEKRDHMVLLEFVTAAGITLGMDELYK* |
| 195 | CD8ss_Flag_CD33 (hu195)_CD28 hinge_CD28 TM_CD28 ICD_CD3z_T2A_E2A_- | ATGGCTCTGCCTGTGACAGCTCTGCTGCTGCCTCTGGCTCTGCTTCTGCATGCTGCTAGACCTGCCGGCGGAAGCGACTACAAGGACGACGATGACAAAGGCGGCGGAGGATCTGGTGGCGGAGGACAGGTTCAGCTGGTTCAGTCTGGCGCCGAAGTGAAGAAACCTGGCAGCAGCGTGAAGGTGTCCTGCAAGGCCAGCGGCTACACCTTTACCGACTACAACATGCACTGGGTCCGACAGGCCCCTGGACAAGGACTTGAGTGGATCGGCTACATCTACCCCTACAATGGCGGCACCGGCTACAACCAGAAGTTCAAGAGCAAGGCCACCAT |

TABLE 13-continued

| SEQ ID NO | Name | Sequence |
|---|---|---|
| | CD8ss_NC7_CD8 hinge_CD8 TM_41BB ICD_CD3z_YFP SB01658 | CACCGCCGACGAGAGCACAAACACCGCCTACATGGAACTGAGCAGCCTGAGAAGCGAGGACACCGCCGTGTACTACTGCGCTAGAGGCAGACCCGCCATGGATTATTGGGGCCAGGGAACCCTGGTCACCGTTTCTAGCGGAGGCGGAGGTAGTGGTGGTGGCGGTAGTGGCGGAGGTGGAAGCGATATCCAGATGACACAGAGCCCCAGCAGCCTGTCTGCCAGCGTGGGAGATAGAGTGACCATCACCTGTAGAGCCAGCGAGAGCGTGGACAACTACGGCATCAGCTTCATGAACTGGTTCCAGCAGAAGCCCGGCAAGGCCCCTAAGCTGCTGATCTACGCCGCCAGCAATCAAGGCAGCGGAGTGCCTAGCAGATTTTCCGGCTCTGGCAGCGGCACCGATTTCACCCTGACCATCAGTAGCCTGCAGCCTGACGACTTCGCCACCTACTACTGCCAGCAGAGCAAAGAGGTGCCCTGGACATTTGGACAGGGCACCAAGGTGGAAATCAAGAGCGGAGCCGCCGCTATCGAAGTGATGTACCCTCCTCCTTACCTGGACAACGAGAAGTCCAACGGCACCATCATCCACGTGAAGGGCAAGCACCTGTGTCCTTCTCCACTGTTCCCCGGACCTAGCAAGCCTTTCTGGGTGCTCGTTGTTGTTGGCGGCGTGCTGGCCTGTTACTCTCTGCTGGTTACCGTGGCCTTCATCATCTTTTGGGTCCGAAGCAAGCGGAGCAGACTGCTGCACTCCGACTACATGAACATGACCCCTAGACGGCCCGGACCAACCAGAAAGCACTACCAGCCTTACGCTCCTCCTAGAGATTTCGCCGCCTACCGGTCCAGAGTGAAGTTCAGCAGATCCGCCGATGCTCCCGCCTATAAGCAGGGCCAGAATCAGCTGTACAACGAGCTGAATCTGGGGCGCAGAGAAGAGTACGACGTGCTGGATAAGCGGAGAGGCAGAGATCCTGAGATGGGCGGCAAGCCCAGACGGAAGAATCCTCAAGAGGGCCTGTATAATGAGCTGCAGAAAGACAAGATGGCCGAGGCCTACAGCGAGATCGGAATGAAGGGCGAACGCAGAAGAGGCAAGGGCCACGATGGACTGTATCAGGGCCTGAGCACCGCCACAAAGGACACCTATGATGCCCTGCACATGCAGGCCCTGCCTCCAAGAGGTTCTGGCGAGGGACGCGGGAGTCTACTGACGTGTGGAGACGTGGAGGAAAACCCTGGACCTGGCTCTGGCCAGTGCACCAATTATGCCCTGCTGAAACTGGCCGGCGACGTGGAATCTAACCCAGGACCTATGGCACTGCCCGTCACTGCACTGCTGCTTCCGCTCGCACTTCTGCTGCATGCCGCAAGACCAGAAGTGCAGCTCGTCCAGTCAGGGGCTGAAGTGAAAAAGCCAGGCTCCTCCGTGAAAGTGTCTTGTAAAGCCTCCGGCGGCACCTTCAGCAGCTACGCCATTTCTTGGGTTCGACAAGCTCCAGGCCAGGGCCTCGAATGGATGGGAGGAATCATCCCCATCTTCGGCACCGCCAACTACGCCCAGAAATTCCAGGGACGCGTGACAATCACAGCCGACAAGTCTACCAGCACAGCTTATATGGAACTGTCTAGCCTGCGCTCCGAGGATACAGCTGTGTACTATTGTGCCACATTCGCCCTGTTCGGCTTCAGAGAGCAGGCCTTCGATATCTGGGGCCAAGGCACCACAGTGACAGTGTCCTCTGGCGGTGGTGGATCTGGCGGAGGCGGTTCTGGCGGCGGTGGCAGTGATATTCAAATGACCCAGTCTCCATCCAGCCTGAGCGCCTCTGTTGGCGACAGAGTGACAATTACATGCCGGGCCAGCCAGAGCATCAGCTCCTACCTGAATTGGTATCAGCAGAAACCAGGCAAAGCTCCCAAACTCCTGATCTATGCTGCCTCCAGCCTGCAGAGTGGCGTGCCCTCTAGATTTTCTGGAAGCGGCTCCGGCACCGACTTTACACTCACCATAAGCTCCCTGCAGCCAGAAGATCTGGCCACATATTACTGTCAGCAGTCCTACAGCACCCCTTTCACATTCGGCCCAGGCACAAAAGTGGACATTAAGACCACCACACCAGCTCCTCGGCCTCCAACTCCTGCTCCTACAATTGCTCTGCAGCCCCTGTCTCTGAGGCCCGAAGCTTGTAGACCTGCTGCTGGCGGAGCCGTGCATACAAGAGGACTGGATTTCGCCTGCGACATCTACATCTGGGCTCCTCTGGCCGGAACATGCGGAGTGTTGCTGCTGAGCCTGGTCATCACCAAGCGGGGCAGAAAGAAGCTGCTGTACATCTTCAAGCAGCCCTTCATGCGGCCCGTGCAGACCACACAAGAGGAAGATGGCTGCTCCTGCAGATTCCCCGAGGAAGAAGAAGGCGGCTGCGAGCTGCGCGTGAAGTTTTCTAGAAGCGCTGACGCCCCTGCCTACAAACAGGGACAAAACCAGCTCTACAATGAACTGAACCTCGGCAGACGCGAGGAATATGATGTGCTGGACAAAAGACGCGGCAGGGACCCTGAAATGGGAGGGAAGCCTCGGCGGAAAAACCCACAAGAAGGACTGTATAACGAACTCCAAAAGGATAAGATGGCAGAAGCCTATTCCGAGATTGGCATGAAGGGCGAGCGTCGGAGAGGAAAAGGACACGACGGCCTCTACCAGGGCCTGTCTACAGCCACCAAGGATACTTACGACGCACTCCATATGCAGGCTCTCCCACCTAGAGGCTCTAGCGGCACTGGCATGGTGTCCAAGGGCGAAGAACTGTTCACAGGCGTGGTGCCCATCCTGGTGGAACTGGACGGGGATGTGAACGGCCACAAGTTTAGCGTTAGCGGCGAAGGCGAAGGGGATGCCACATACGGAAAGCTGACACTGAAACTGATCTGCACCACCGGCAAGCTGCCTGTGCCATGGCCTACACTGGTTACCACACTCGGCTACGGCCTGCAGTGCTTCGCCAGATATCCCGACCATATGAAGCAGCACGACTTCTTCAAGAGCGCCATGCCTGAGGGCTACGTGCAAGAGAGAACCATCTTCTTCAAAGACGACGGCAACTACAAGACCCGGGCAGAAGTGAAGTTTGAGGGCGACACCCTCGTGAACCGGATCGAGCTGAAGGGCATCGACTTCAAAGAGGATGGAAACATCCTGGGCCACAAGCTCGAGTACAACTACAACAGCCACAACGTGTACATTACCGCCGACAAGCAGAAGAACGGCATCAAGGCCAACTTCAAGATCCGGCACAACATCGAGGATGGCGGGGTGCAGCTGGCCGATCATTACCAGCAGAATACCCCTATCGGCGACGGCCCTGTTCTGCTGCCCGATAATCACTACCTGAGCTACCAGAGCGCCCTGAGCAAGGACCCCAATGAGAAGAGGGACCACATGGTGCTGCTGGAATTCGTGACAGCCGCCGGAATCACCCTCGGCATGGACGAACTGTACAAGTGA |
| 196 | CD8ss_Flag_CD33 (hu195)_CD28 hinge_CD28 TM_CD28 ICD_CD3z_E2A_T2A_- CD8ss_NC7_CD8 hinge_CD8 TM_41BB ICD_CD3z_YFP SB01659 | MALPVTALLLPLALLLHAARPAGGSDYKDDDDKGGGGSGGGGQVQLVQSGAEVKKPGSSVKVSCKASGYTFTDYNMHWVRQAPGQGLEWIGYIYPYNGGTGYNQKFKSKATITADESTNTAYMELSSLRSEDTAVYYCARGRPAMDYWGQGTLVTVSSGGGGSGGGGSGGGGSDIQMTQSPSSLSASVGDRVTITCRASESVDNYGISFMNWFQQKPGKAPKLLIYAASNQGSGVPSRFSGSGSGTDFTLTISSLQPDDFATYYCQQSKEVPWTFGQGTKVEIKSGAAAIEVMYPPPYLDNEKSNGTIIHVKGKHLCPSPLFPGPSKPFWVLVVVGGVLACYSLLVTVAFIIFWVRSKRSRLLHSDYMNMTPRRPGPTRKHYQPYAPPRDFAAYRSRVKFSRSADAPAYKQGQNQLYNELNLGRREEYDVLDKRRGRDPEMGGKPRRKNPQEGLYNELQKDKMAEAYSEIGMKGERRRGKGHDGLYQGLSTATKDTYDALHMQALPPRGSGQCTNYALLKLAGDVESNPGPGSGEGRGSLLTCGDVEENPGPMALPVTALLLPLALLLHAARPEVQLVQSGAEVKKPGSSVKVSCKASGGTFSSYAISWVRQAPGQGLEWMGGIIPIFGTANYAQKFQGRVTITADKSTSTAYMELSSLRSEDTAVYYCATFALFGFREQAFDIWGQGTTVTVSSGGGGSGGGGSGGGGSDIQMTQSPSSLSASVGDRVTITCRASQSISSYLNWYQQKPGKAPKLLIYAASSLQSGVPSRFSGSGSGTDFTLTISSLQPEDLATYYCQQSYSTPFTFGPGTKVDIKTTTPAPRPPTPAPTIALQPLSLRPEACRPAAGGAVHTRGLDFACDIYIWAPLAGTCGVLLLSLVITKRGRKKLLYIFKQPFMRPVQTTQEEDGCSCRFPEEEEGGCELRVKFSRSADAPAYKQGQNQLYNELNLGRREEYDVLDKRRGRDPEMGGKPRRKNPQEGLYNELQKDKMAEAYSEIGMKGERRRGKGHDGLYQGLSTATKDTYDALHMQALPPRGSSGTGMVSKGEELFTGVVPILVELDGDVNGHKFSVSGEGEGDATYGKLTLKLICTTGKLPVPWPTLVTTLGYGLQCFARYPDHMKQHDFFKSAMPEGYVQERTIFFKDDGNYKTRAEVKFEGDTLVNRIELKGIDFKEDGNILGHKLEYNYNSHNVYITADKQKNGIKANFKIRHNIEDGGVQLADHYQQNTPIGDGPVLLPDNHYLSYQSALSKDPNEKRDHMVLLEFVTAAGITLGMDELYK* |

TABLE 13-continued

| SEQ ID NO | Name | Sequence |
|---|---|---|
| 197 | CD8ss_Flag_CD33 (hu195)_CD28 hinge_CD28 TM_CD28 ICD_CD3z_E2A_T2A_-CD8ss_NC7_CD8 hinge_CD8 TM_41BB ICD_CD3z_YFP SB01659 | ATGGCTCTGCCTGTGACAGCTCTGCTGCTGCCTCTGGCTCTGCTTCTGCATGCTGCTAGACCTGCCG<br>GCGGAAGCGACTACAAGGACGACGATGACAAAGGCGGCGGAGGATCTGGTGGCGGAGGACAGGTTCA<br>GCTGGTTCAGTCTGGCGCCGAAGTGAAGAAACCTGGCAGCAGCGTGAAGGTGTCCTGCAAGGCCAGC<br>GGCTACACCTTTACCGACTACAACATGCACTGGGTCCGACAGGCCCCTGGACAAGGACTTGAGTGGA<br>TCGGCTACATCTACCCCTACAATGGCGGCACCGGCTACAACCAGAAGTTCAAGAGCAAGGCCACCAT<br>CACCGCCGACGAGAGCACAAACACCGCCTACATGGAACTGAGCAGCCTGAGAAGCGAGGACACCGCC<br>GTGTACTACTGCGCTAGAGGCAGACCCGCCATGGATTATTGGGGCCAGGGAACCCTGGTCACCGTTT<br>CTAGCGGAGGCGGAGGTAGTGGTGGTGGCGGTAGTGGCGGAGGTGGAAGCGATATCCAGATGACACA<br>GAGCCCCAGCAGCCTGTCTGCCAGCGTGGGAGATAGAGTGACCATCACCTGTAGAGCCAGCGAGAGC<br>GTGGACAACTACGGCATCAGCTTCATGAACTGGTTCCAGCAGAAGCCCGGCAAGGCCCCTAAGCTGC<br>TGATCTACGCCGCCAGCAATCAAGGCAGCGGAGTGCCTAGCAGATTTTCCGGCTCTGGCAGCGGCAC<br>CGATTTCACCCTGACCATCAGTAGCCTGCAGCCTGACGACTTCGCCACCTACTACTGCCAGCAGAGC<br>AAAGAGGTGCCCTGGACATTTGGACAGGGCACCAAGGTGGAAATCAAGAGCGGAGCCGCCGCTATCG<br>AAGTGATGTACCCTCCTCCTTACCTGGACAACGAGAAGTCCAACGGCACCATCATCCACGTGAAGGG<br>CAAGCACCTGTGTCCTTCTCCACTGTTCCCCGGACCTAGCAAGCCTTTCTGGGTGCTCGTTGTTGTT<br>GGCGGCGTGCTGGCCTGTTACTCTCTGCTGGTTACCGTGGCCTTCATCATCTTTTGGGTCCGAAGCA<br>AGCGGAGCAGACTGCTGCACTCCGACTACATGAACATGACCCCTAGACGGCCCGGACCAACCAGAAA<br>GCACTACCAGCCTTACGCTCCTCCTAGAGATTTCGCCGCCTACCGGTCCAGAGTGAAGTTCAGCAGA<br>TCCGCCGATGCTCCCGCCTATAAGCAGGGCCAGAATCAGCTGTACAACGAGCTGAATCTGGGGCGCA<br>GAGAAGAGTACGACGTGCTGGATAAGCGGAGAGGCAGAGATCCTGAGATGGGCGGCAAGCCCAGACG<br>GAAGAATCCTCAAGAGGGCCTGTATAATGAGCTGCAGAAAGACAAGATGGCCGAGGCCTACAGCGAG<br>ATCGGAATGAAGGGCGAACGCAGAAGAGGCAAGGGCCACGATGGACTGTATCAGGGCCTGAGCACCG<br>CCACAAAGGACACCTATGATGCCCTGCACATGCAGGCCCTTCCACCTAGAGGTAGCGGCCAGTGTAC<br>CAACTACGCCCTGCTGAAACTGGCCGGCGACGTGGAATCTAATCCTGGACCTGGATCTGGCGAGGGA<br>CGCGGGAGTCTACTGACGTGTGGAGACGTGGAGGAAAACCCTGGACCTATGGCACTGCCAGTCACTG<br>CCCTGCTGCTTCCACTTGCACTGTTGCTGCACGCCGCTAGACCAGAAGTGCAGCTCGTTCAAAGCGG<br>AGCTGAAGTGAAAAAGCCCGGCTCCTCCGTGAAAGTGTCTTGTAAAGCCTCCGGCGGCACCTTCAGC<br>AGCTACGCCATTTCTTGGGTTCGACAAGCTCCAGGCCAGGGCCTCGAATGGATGGGAGGAATCATCC<br>CCATCTTCGGCACCGCCAATTACGCCCAGAAATTCCAGGGACGCGTGACAATCACAGCCGACAAGTC<br>TACCAGCACAGCTTATATGGAACTGTCTAGCCTGCGCTCCGAGGATACAGCTGTGTACTATTGTGCC<br>ACATTCGCCCTGTTCGGCTTCAGAGAGCAGGCCTTCGATATCTGGGGCCAAGGCACCACAGTGACAG<br>TGTCCTCTGGCGGTGGTGGTTCAGGTGGCGGTGGCTCTGGCGGAGGCGGTTCTGATATTCAGATGAC<br>CCAGTCTCCATCCAGCCTGAGCGCCTCTGTTGGCGACAGAGTGACAATTACATGCCGGGCCAGCCAG<br>AGCATCAGCTCCTACCTGAATTGGTATCAGCAGAAACCAGGCAAAGCTCCCAAACTCCTGATCTATG<br>CTGCCTCCAGCCTGCAGAGTGGCGTGCCCTCTAGATTTTCTGGAAGCGGCTCCGGCACCGACTTTAC<br>ACTCACCATAAGCTCCCTGCAGCCAGAAGATCTGGCCACATATTACTGTCAGCAGTCCTACAGCACC<br>CCTTTCACATTCGGCCCAGGCACAAAAGTGGACATTAAGACCACCACACCAGCTCCTCGGCCTCCAA<br>CTCCTGCTCCTACAATTGCTCTGCAGCCCCTGTCTCTGAGGCCCGAAGCTTGTAGACCTGCTGCTGG<br>CGGAGCCGTGCATACAAGAGGACTGGATTTCGCCTGCGACATCTACATCTGGGCTCCTCTGGCCGGA<br>ACATGCGGAGTGTTGCTGCTGAGCCTGGTCATCACCAAGCGGGGCAGAAAGAAGCTGCTGTACATCT<br>TCAAGCAGCCCTTCATGCGGCCCGTGCAGACCACACAAGAGGAAGATGGCTGCTCCTGCAGATTCCC<br>CGAGGAAGAAGAAGGCGGCTGCGAACTGCGCGTGAAGTTCTCTAGAAGCGCTGACGCCCCTGCCTAC<br>AAACAGGGACAAAACCAGCTCTACAATGAACTGAACCTCGGCAGACGCGAGGAATATGATGTGCTGG<br>ACAAAAGACGCGGCAGGGACCCTGAAATGGGAGGGAAGCCTCGGCGGAAAAACCCACAAGAAGGACT<br>GTATAACGAACTCCAAAAGGATAAGATGGCAGAAGCCTATTCCGAGATTGGCATGAAGGGCGAGCGT<br>CGGAGAGGAAAAGGACACGACGGCCTCTACCAGGGCCTGTCTACAGCCACCAAGGATACTTACGACG<br>CACTCCATATGCAGGCTCTGCCACCACGAGGCAGCTCTGGAACTGGCATGGTGTCCAAGGGCGAAGA<br>ACTGTTCACAGGCGTGGTGCCCATCCTGGTTGAACTGGATGGCGACGTGAACGGCCACAAGTTTAGC<br>GTTAGCGGAGAAGGCGAAGGCGACGCCACATACGGAAAGCTGACACTGAAACTGATCTGCACCACCG<br>GCAAGCTGCCTGTGCCATGGCCTACACTGGTTACCACACTCGGCTACGGCCTGCAGTGCTTCGCCAG<br>ATATCCCGACCATATGAAGCAGCACGACTTCTTCAAGAGCGCCATGCCTGAGGGCTACGTGCAAGAG<br>AGAACCATCTTCTTCAAAGACGACGGCAACTACAAGACCCGGGCAGAAGTGAAGTTTGAGGGCGACA<br>CCCTCGTGAACCGGATCGAGCTGAAGGGCATCGACTTCAAAGAGGATGGAAACATCCTGGGCCACAA<br>GCTCGAGTACAACTACAACAGCCACAACGTGTACATTACCGCCGACAAGCAGAAGAACGGCATCAAG<br>GCCAACTTCAAGATCCGGCACAACATCGAGGATGGCGGGGTGCAGCTGGCCGATCATTACCAGCAGA<br>ATACCCCTATCGGCGACGGCCCTGTTCTGCTGCCCGATAATCACTACCTGAGCTACCAGAGCGCCCT<br>GAGCAAGGACCCCAATGAGAAGAGGGACCACATGGTGCTGCTGGAATTCGTGACAGCCGCCGGAATC<br>ACCCTCGGCATGGACGAGCTGTATAAGTGA |
| 198 | CD8ss_Flag_CD33 (hu195)_CD28 hinge_CD28 TM_CD28 ICD_CD3z_T2A_-CD8ss_NC7_CD8 hinge_CD8 TM_41BB ICD_CD3z_YFP SB01266 | MALPVTALLLPLALLLHAARPAGGSDYKDDDDKGGGGSGGGGQVQLVQSGAEVKKPGSSVKVSCKAS<br>GYTFTDYNMHWVRQAPGQGLEWIGYIYPYNGGTGYNQKFKSKATITADESTNTAYMELSSLRSEDTA<br>VYYCARGRPAMDYWGQGTLVTVSSGGGGSGGGGSGGGGSDIQMTQSPSSLSASVGDRVTITCRASES<br>VDNYGISFMNWFQQKPGKAPKLLIYAASNQGSGVPSRFSGSGSGTDFTLTISSLQPDDFATYYCQQS<br>KEVPWTFGQGTKVEIKSGAAAIEVMYPPPYLDNEKSNGTIIHVKGKHLCPSPLFPGPSKPFWVLVVV<br>GGVLACYSLLVTVAFIIFWVRSKRSRLLHSDYMNMTPRRPGPTRKHYQPYAPPRDFAAYRSRVKFSR<br>SADAPAYKQGQNQLYNELNLGRREEYDVLDKRRGRDPEMGGKPRRKNPQEGLYNELQKDKMAEAYSE<br>IGMKGERRRGKGHDGLYQGLSTATKDTYDALHMQALPPRRRKRGSGEGRGSLLTCGDVEENPGPMAL<br>PVTALLLPLALLLHAARPEVQLVQSGAEVKKPGSSVKVSCKASGGTFSSYAISWVRQAPGQGLEWMG<br>GIIPIFGTANYAQKFQGRVTITADKSTSTAYMELSSLRSEDTAVYYCATFALFGFREQAFDIWGQGT<br>TVTVSSGGGGGGGGSGGGGSDIQMTQSPSSLSASVGDRVTITCRASQSISSYLNWYQQKPGKAPKL<br>LIYAASSLQSGVPSRFSGSGSGTDFTLTISSLQPEDLATYYCQQSYSTPFTFGPGTKVDIKTTTPAP<br>RPPTPAPTIALQPLSLRPEACRPAAGGAVHTRGLDFACDIYIWAPLAGTCGVLLLSLVITKRGRKKL<br>LYIFKQPFMRPVQTTQEEDGCSCRFPEEEEGGCELRVKFSRSADAPAYKQGQNQLYNELNLGRREEY<br>DVLDKRRGRDPEMGGKPRRKNPQEGLYNELQKDKMAEAYSEIGMKGERRRGKGHDGLYQGLSTATKD<br>TYDALHMQALPPRGSSGTGMVSKGEELFTGVVPILVELDGDVNGHKFSVSGEGEGDATYGKLTLKLI |

TABLE 13-continued

| SEQ ID NO | Name | Sequence |
|---|---|---|
| | | CTTGKLPVPWPTLVTTLGYGLQCFARYPDHMKQHDFFKSAMPEGYVQERTIFFKDDGNYKTRAEVKF<br>EGDTLVNRIELKGIDFKEDGNILGHKLEYNYNSHNVYITADKQKNGIKANFKIRHNIEDGGVQLADH<br>YQQNTPIGDGPVLLPDNHYLSYQSALSKDPNEKRDHMVLLEFVTAAGITLGMDELYK* |
| 199 | CD8ss_Flag_CD33<br>(hu195)_CD28<br>hinge_CD28<br>TM_CD28<br>ICD_CD3z_T2A_-<br>CD8ss_NC7_CD8<br>hinge_CD8<br>TM_41BB<br>ICD_CD3z_YFP<br>SB01266 | ATGGCCTTACCAGTGACCGCCTTGCTCCTGCCGCTGGCCTTGCTGCTCCACGCCGCCAGGCCGGCTG<br>GCGGGTCCGATTACAAGGACGATGACGACAAAGGTGGCGGAGGAAGCGGGGGAGGCGGCCAGGTTCA<br>GCTGGTTCAGTCTGGCGCCGAAGTGAAGAAACCTGGCAGCAGCGTGAAGGTGTCCTGCAAGGCCAGC<br>GGCTACACCTTTACCGACTACAACATGCACTGGGTCCGACAGGCCCCTGGACAAGGACTTGAGTGGA<br>TCGGCTACATCTACCCCTACAATGGCGGCACCGGCTACAACCAGAAGTTCAAGAGCAAGGCCACCAT<br>CACCGCCGACGAGAGCACAAACACCGCCTACATGGAACTGAGCAGCCTGAGAAGCGAGGACACCGCC<br>GTGTACTACTGTGCCAGAGGCAGACCCGCCATGGATTATTGGGGACAGGGCACCCTGGTCACCGTTT<br>CTAGCGGAGGCGGAGGATCTGGTGGCGGAGGAAGTGGCGGAGGCGGTTCTGATATCCAGATGACACA<br>GAGCCCCAGCAGCCTGTCTGCCAGCGTGGGAGATAGAGTGACCATCACCTGTAGAGCCAGCGAGAGC<br>GTGGACAACTACGGCATCAGCTTCATGAACTGGTTCCAGCAGAAGCCCGGCAAGGCCCCTAAGCTGC<br>TGATCTACGCCGCCAGCAATCAAGGCAGCGGAGTGCCTAGCAGATTTTCCGGCTCTGGCAGCGGCAC<br>CGATTTCACCCTGACAATCTCTAGCCTCCAGCCTGACGACTTCGCCACCTACTACTGCCAGCAGAGC<br>AAAGAGGTGCCCTGGACATTCGGCCAGGGCACAAAGGTGGAAATCAAGAGCGGAGCAGCAGCTATCG<br>AGGTGATGTATCCTCCGCCCTACCTGGATAATGAAAAGAGTAATGGGACTATCATTCATGTAAAAGG<br>GAAGCATCTTTGTCCTTCTCCCCTTTTCCCCGGTCCGTCTAAACCTTTCTGGGTGCTTGTGGTCGTG<br>GGTGGAGTGCTTGCGTGTTACTCCCTGCTGGTGACCGTCGCCTTCATCATTTTCTGGGTCAGGAGCA<br>AACGATCTCGCCTCCTCCATTCTGACTATATGAACATGACTCCTCGCAGACCCGGACCTACGCGGAA<br>ACATTACCAACCGTACGCGCCTCCGAGAGACTTCGCCGCGTACAGAAGTAGGGTCAAGTTTAGCAGG<br>TCAGCGGACGCACCAGCTTACAAGCAAGGCCAAAACCAGCTTTATAACGAATTGAATTTGGGACGCA<br>GGGAAGAATACGATGTGCTCGATAAACGCAGAGGGAGGGACCCGGAAATGGGAGGAAAGCCAAGGCG<br>GAAAAACCCACAGGAGGGGTTGTACAACGAGCTTCAAAAAGATAAGATGGCGGAAGCATACTCCGAA<br>ATAGGAATGAAGGGTGAACGGAGGAGGGGCAAGGGCCACGACGGCCTGTACCAGGGACTCTCAACTG<br>CTACGAAGGATACTTATGATGCTCTTCACATGCAAGCTCTGCCGCCGCGCCGCAGGAAAAGAGGAAG<br>CGGCGAAGGTCGAGGCTCTTTGCTCACATGCGGCGATGTGGAAGAAAATCCGGGCCCAATGGCGCTC<br>CCGGTGACAGCACTTCTCTTGCCTCTTGCCCTGCTGTTGCATGCCGCGCGCCCAGAGGTTCAACTGG<br>TACAAAGCGGAGCCGAGGTAAAGAAACCAGGGAGTAGCGTCAAAGTGTCCTGCAAAGCCTCAGGCGG<br>CACATTCAGTAGCTATGCTATTTCATGGGTACGCCAAGCACCAGGACAGGGGCTGGAGTGGATGGGC<br>GGGATTATCCCCATCTTCGGTACGGCAAACTATGCACAAAAGTTCCAGGGACGAGTCACCATCACGG<br>CTGATAAGTCCACCTCCACCGCCTATATGGAGCTGAGTTCCCTTCGGAGCGAGGATACTGCTGTGTA<br>TTATTGTGCCACGTTCGCACTGTTCGGTTTTCGGGAGCAGGCGTTTGATATTTGGGGACAAGGCACA<br>ACGGTCACGGTCAGTTCAGGCGGAGGGGGATCAGGGGGTGGGGGGTCAGGTGGCGGTGGAAGTGACA<br>TTCAGATGACCCAGAGTCCCTCTTCATTGAGTGCGAGCGTCGGTGATCGGGTTACGATAACCTGTAG<br>GGCCTCCCAAAGTATATCATCATATTTGAACTGGTACCAACAGAAACCTGGGAAAGCGCCGAAGCTC<br>CTTATCTATGCTGCCAGCTCTTTGCAAAGCGGTGTGCCCTCACGGTTCTCCGGTAGTGGGTCCGGGA<br>CCGACTTCACTTTGACCATCAGCAGCCTTCAGCCAGAGGATCTTGCCACTTATTACTGCCAGCAATC<br>TTATAGCACACCGTTTACATTCGGTCCAGGCACAAAGGTAGACATTAAGACCACGACGCCGGCGCCC<br>CGGCCTCCCACCCCCGCACCAACGATAGCCCTTCAGCCCTTGAGCCTCCGGCCAGAAGCATGCCGCC<br>CGGCAGCCGGAGGTGCAGTCCATACGCGCGGACTGGACTTTGCATGTGACATCTACATATGGCCCC<br>CCTCGCCGGTACTTGCGGTGTTTTGCTTTTGTCACTGGTGATTACGAAGCGCGGTCGAAAAAAACTC<br>CTCTACATCTTCAAACAACCTTTCATGCGGCCTGTCCAAACAACTCAAGAAGAGGACGGGTGTTCAT<br>GCCGCTTTCCAGAGGAAGAGGAAGGTGGCTGTGAACTTAGGGTCAAGTTTAGCAGGTCAGCGGACGC<br>ACCAGCTTACAAGCAAGGCCAAAACCAGCTTTATAACGAATTGAATTTGGGACGCAGGGAAGAATAC<br>GATGTGCTCGATAAACGCAGAGGGAGGGACCCGGAAATGGGAGGAAAGCCAAGGCGGAAAAACCCAC<br>AGGAGGGGTTGTACAACGAGCTTCAAAAAGATAAGATGGCGGAAGCATACTCCGAAATAGGAATGAA<br>GGGTGAACGGAGGAGGGGCAAGGGCCACGACGGCCTGTACCAGGGACTCTCAACTGCTACGAAGGAT<br>ACTTATGATGCTCTTCACATGCAAGCTCTGCCGCCGCGCGGATCGAGTGGCACCGGTATGGTGAGCA<br>AGGGCGAGGAGCTGTTCACCGGGGTGGTGCCCATCCTGGTCGAGCTGGACGGCGACGTAAACGGCCA<br>CAAGTTCAGCGTGTCCGGCGAGGGCGAGGGCGATGCCACCTACGGCAAGCTGACCCTGAAGCTGATC<br>TGCACCACCGGCAAGCTGCCCGTGCCCTGGCCCACCCTCGTGACCACCCTGGGCTACGGCCTCCAGT<br>GCTTCGCCCGCTACCCCGACCACATGAAGCAGCACGACTTCTTCAAGTCCGCCATGCCCGAAGGCTA<br>CGTCCAGGAGCGCACCATCTTCTTCAAGGACGACGGCAACTACAAGACCCGCGCCGAGGTGAAGTTC<br>GAGGGCGACACCCTGGTGAACCGCATCGAGCTGAAGGGCATCGACTTCAAGGAGGACGGCAACATCC<br>TGGGGCACAAGCTGGAGTACAACTACAACAGCCACAACGTCTATATCACCGCCGACAAGCAGAAGAA<br>CGGCATCAAGGCCAACTTCAAGATCCGCCACAACATCGAGGACGGCGGCGTGCAGCTCGCCGACCAC<br>TACCAGCAGAACACCCCCATCGGCGACGGCCCCGTGCTGCTGCCCGACAACCACTACCTGAGCTACC<br>AGTCCGCCCTGAGCAAAGACCCCAACGAGAAGCGCGATCACATGGTCCTGCTGGAGTTCGTGACCGC<br>CGCCGGGATCACTCTCGGCATGGACGAGCTGTACAAGTAA |
| 200 | CD8ss_Flag_CD33<br>(hu195)_CD28<br>hinge_CD28<br>TM_CD28<br>ICD_CD3z_T2A_-<br>CD8ss_NC7_CD8<br>hinge_CD8<br>TM_41BB<br>ICD_CD3z_YFP<br>SB01530 | MALPVTALLLPLALLLHAARPAGGSDYKDDDDKGGGGSGGGGQVQLVQSGAEVKKPGSSVKVSCKAS<br>GYTFTDYNMHWVRQAPGQGLEWIGYIYPYNGGTGYNQKFKSKATITADESTNTAYMELSSLRSEDTA<br>VYYCARGRPAMDYWGQGTLVTVSSGGGGSGGGGSGGGGSDIQMTQSPSSLSASVGDRVTITCRASES<br>VDNYGISFMNWFQQKPGKAPKLLIYAASNQGSGVPSRFSGSGSGTDFTLTISSLQPDDFATYYCQQS<br>KEVPWTFGQGTKVEIKSGAAAIEVMYPPPYLDNEKSNGTIIHVKGKHLCPSPLFPGPSKPFWVLVVV<br>GGVLACYSLLVTVAFIIFWVRSKRSRLLHSDYMNMTPRRPGPTRKHYQPYAPPRDFAAYRSRVKFSR<br>SADAPAYKQGQNQLYNELNLGRREEYDVLDKRRGRDPEMGGKPRRKNPQEGLYNELQKDKMAEAYSE<br>IGMKGERRRGKGHDGLYQGLSTATKDTYDALHMQALPPRRRKRGSGEGRGSLLTCGDVEENPGPMAL<br>PVTALLLPLALLLHAARPEVQLVQSGAEVKKPGSSVKVSCKASGGTFSSYAISWVRQAPGQGLEWMG<br>GIIPIFGTANYAQKFQGRVTITADKSTSTAYMELSSLRSEDTAVYYCATFALFGFREQAFDIWGQGT<br>TVTVSSGGGGSGGGGSGGGGSDIQMTQSPSSLSASVGDRVTITCRASQSISSYLNWYQQKPGKAPKL<br>LIYAASSLQSGVPSRFSGSGSGTDFTLTISSLQPEDLATYYCQQSYSTPFTFGPGTKVDIKTTTPAP<br>RPPTPAPTIALQPLSLRPEACRPAAGGAVHTRGLDFACDIYIWAPLAGTCGVLLLSLVITKRGRKKL<br>LYIFKQPFMRPVQTTQEEDGCSCRFPEEEEGGCELRVKFSRSADAPAYKQGQNQLYNELNLGRREEY |

TABLE 13-continued

| SEQ ID NO | Name | Sequence |
|---|---|---|
| | | DVLDKRRGRDPEMGGKPRRKNPQEGLYNELQKDKMAEAYSEIGMKGERRRGKGHDGLYQGLSTATKD<br>TYDALHMQALPPRGSSGTGMVSKGEELFTGVVPILVELDGDVNGHKFSVSGEGEGDATYGKLTLKLI<br>CTTGKLPVPWPTLVTTLGYGLQCFARYPDHMKQHDFFKSAMPEGYVQERTIFFKDDGNYKTRAEVKF<br>EGDTLVNRIELKGIDFKEDGNILGHKLEYNYNSHNVYITADKQKNGIKANFKIRHNIEDGGVQLADH<br>YQQNTPIGDGPVLLPDNHYLSYQSALSKDPNEKRDHMVLLEFVTAAGITLGMDELYK* |
| 201 | CD8ss_Flag_CD33<br>(hu195)_CD28<br>hinge_CD28<br>TM_CD28<br>ICD_CD3z_T2A_-<br>CD8ss_NC7_CD8<br>hinge_CD8<br>TM_41BB<br>ICD_CD3z_YFP<br>SB01530 | ATGGCTCTGCCTGTGACAGCTCTGCTGCTGCCTCTGGCTCTGCTTCTGCATGCTGCTAGACCTGCCG<br>GCGGAAGCGACTACAAGGACGACGATGACAAAGGCGGCGGAGGATCTGGTGGCGGAGGACAGGTTCA<br>GCTGGTTCAGTCTGGCGCCGAAGTGAAGAAACCTGGCAGCAGCGTGAAGGTGTCCTGCAAGGCCAGC<br>GGCTACACCTTTACCGACTACAACATGCACTGGGTCCGACAGGCCCCTGGACAAGGACTTGAGTGGA<br>TCGGCTACATCTACCCCTACAATGGCGGCACCGGCTACAACCAGAAGTTCAAGAGCAAGGCCACCAT<br>CACCGCCGACGAGAGCACAAACACCGCCTACATGGAACTGAGCAGCCTGAGAAGCGAGGACACCGCC<br>GTGTACTACTGCGCTAGAGGCAGACCCGCCATGGATTATTGGGGCCAGGGAACCCTGGTCACCGTTT<br>CTAGCGGAGGCGGAGGTAGTGGTGGTGGCGGTAGTGGCGGAGGTGGAAGCGATATCCAGATGACACA<br>GAGCCCCAGCAGCCTGTCTGCCAGCGTGGGAGATAGAGTGACCATCACCTGTAGAGCCAGCGAGAGC<br>GTGGACAACTACGGCATCAGCTTCATGAACTGGTTCCAGCAGAAGCCCGGCAAGGCCCCTAAGCTGC<br>TGATCTACGCCGCCAGCAATCAAGGCAGCGGAGTGCCTAGCAGATTTTCCGGCTCTGGCAGCGGCAC<br>CGATTTCACCCTGACCATCAGTAGCCTGCAGCCTGACGACTTCGCCACCTACTACTGCCAGCAGAGC<br>AAAGAGGTGCCCTGGACATTTGGACAGGGCACCAAGGTGGAAATCAAGAGCGGAGCCGCCGCTATCG<br>AAGTGATGTACCCTCCTCCTTACCTGGACAACGAGAAGTCCAACGGCACCATCATCCACGTGAAGGG<br>CAAGCACCTGTGTCCTTCTCCACTGTTCCCCGGACCTAGCAAGCCTTTCTGGGTGCTCGTTGTTGTT<br>GGCGGCGTGCTGGCCTGTTACTCTCTGCTGGTTACCGTGGCCTTCATCATCTTTTGGGTCCGAAGCA<br>AGCGGAGCAGACTGCTGCACTCCGACTACATGAACATGACCCCTAGACGGCCCGGACCAACCAGAAA<br>GCACTACCAGCCTTACGCTCCTCCTAGAGATTTCGCCGCCTACCGGTCCAGAGTGAAGTTCAGCAGA<br>TCCGCCGATGCTCCCGCCTATAAGCAGGGCCAGAATCAGCTGTACAACGAGCTGAATCTGGGGCGCA<br>GAGAAGAGTACGACGTGCTGGATAAGCGGAGAGGCAGAGATCCTGAGATGGGCGGCAAGCCCAGACG<br>GAAGAATCCTCAAGAGGGCCTGTATAATGAGCTGCAGAAAGACAAGATGGCCGAGGCCTACAGCGAG<br>ATCGGAATGAAGGGCGAACGCAGAAGAGGCAAGGGCCACGATGGACTGTATCAGGGCCTGAGCACCG<br>CCACAAAGGACACCTATGATGCCCTGCACATGCAGGCCCTGCCACCTCGGAGAAGAAAAAGAGGCTC<br>TGGCGAAGGCAGAGGCTCCCTGCTTACATGTGGCGACGTGGAAGAGAACCCTGGACCTATGGCACTG<br>CCAGTCACTGCCCTGCTGCTTCCACTTGCACTGTTGCTGCACGCCGCTAGACCAGAAGTGCAGCTCG<br>TTCAAAGCGGAGCTGAAGTGAAAAAGCCCGGCTCCTCCGTGAAAGTGTCTTGTAAAGCCTCCGGCGG<br>CACCTTCAGCAGCTACGCCATTTCTTGGGTTCGACAAGCTCCAGGCCAGGGCCTCGAATGGATGGGA<br>GGAATCATCCCCATCTTCGGCACCGCCAACTACGCCCAGAAATTCCAGGGACGCGTGACAATCACAG<br>CCGACAAGTCTACCAGCACAGCTTATATGGAACTGTCTAGCCTGCGCTCCGAGGATACAGCTGTGTA<br>CTATTGTGCCACATTCGCCCTGTTCGGCTTCAGAGAGCAGGCCTTCGATATCTGGGGCCAAGGCACC<br>ACAGTGACAGTGTCCTCTGGCGGTGGTGGATCTGGCGGAGGCGGTTCTGGCGGCGGTGGCAGTGATA<br>TTCAAATGACCCAGTCTCCATCCAGCCTGAGCGCCTCTGTTGGCGACAGAGTGACAATTACATGCCG<br>GGCCAGCCAGAGCATCAGCTCCTACCTGAATTGGTATCAGCAGAAACCAGGCAAAGCTCCCAAACTC<br>CTGATCTATGCTGCCTCCAGCCTGCAGAGTGGCGTGCCCTCTAGATTTTCTGGAAGCGGCTCCGGCA<br>CCGACTTTACACTCACCATAAGCTCCCTGCAGCCAGAAGATCTGGCCACATATTACTGTCAGCAGTC<br>CTACAGCACCCCTTTCACATTCGGCCCAGGCACAAAAGTGGACATTAAGACCACCACACCAGCTCCT<br>CGGCCTCCAACTCCTGCTCCTACAATTGCTCTGCAGCCCCTGTCTCTGAGGCCCGAAGCTTGTAGAC<br>CTGCTGCTGGCGGAGCCGTGCATACAAGAGGACTGGATTTCGCCTGCGACATCTACATCTGGGCTCC<br>TCTGGCCGGAACATGCGGAGTGTTGCTGCTGAGCCTGGTCATCACCAAGCGGGGCAGAAAGAAGCTG<br>CTGTACATCTTCAAGCAGCCCTTCATGCGGCCCGTGCAGACCACACAAGAGGAAGATGGCTGCTCCT<br>GCAGATTCCCCGAGGAAGAAGAAGGCGGCTGCGAACTGCGCGTGAAGTTCTCTAGAAGCGCTGACGC<br>CCCTGCCTACAAACAGGGACAAAACCAGCTCTACAATGAACTGAACCTCGGCAGACGCGAGGAATAT<br>GATGTGCTGGACAAAAGACGCGGCAGGGACCCTGAAATGGGAGGGAAGCCTAGAAGAAAGAACCCAC<br>AAGAAGGCCTTTACAACGAACTGCAAAAGGATAAGATGGCAGAAGCTTACTCCGAGATTGGCATGAA<br>GGGCGAGCGTCGGAGAGGAAAAGGACACGACGGCCTCTACCAGGGCCTGTCTACAGCCACCAAGGAT<br>ACTTACGACGCACTCCATATGCAGGCTCTCCCACCAAGAGGCAGCTCTGGCACTGGCATGGTGTCCA<br>AGGGCGAAGAACTGTTCACAGGCGTGGTGCCCATCCTGGTGGAACTGGACGGGGATGTGAACGGCCA<br>CAAGTTTAGCGTTAGCGGAGAAGGCGAAGGCGACGCCACATACGGAAAGCTGACACTGAAACTGATC<br>TGCACCACCGGCAAGCTGCCTGTGCCATGGCCTACACTGGTTACCACACTCGGCTACGGCCTGCAGT<br>GCTTCGCTAGATACCCCGACCATATGAAGCAGCACGACTTCTTCAAGAGCGCCATGCCTGAGGGCTA<br>CGTGCAAGAGAGAACCATCTTCTTCAAAGACGACGGCAACTACAAGACCCGGGCAGAAGTGAAGTTT<br>GAGGGCGACACCCTCGTGAACCGGATCGAGCTGAAGGGCATCGACTTCAAAGAGGATGGAAACATCC<br>TGGGCCACAAGCTCGAGTACAACTACAACAGCCACAACGTGTACATTACCGCCGACAAGCAGAAGAA<br>CGGCATCAAGGCCAACTTCAAGATCCGGCACAACATCGAGGATGGCGGGGTGCAGCTGGCCGATCAT<br>TACCAGCAGAATACCCCTATCGGCGACGGCCCTGTTCTGCTGCCCGATAATCACTACCTGAGCTACC<br>AGAGCGCCCTGAGCAAGGACCCCAATGAGAAGAGGGACCACATGGTGCTGCTGGAATTCGTGACAGC<br>CGCCGGAATCACCCTCGGCATGGACGAGCTGTATAAGTGA |

K562 Cell Engineering $1\times10^6$ K5672 target cells were transduced with an FLT3- or CD33-expressing lentivirus with a puromycin resistant gene. FLT3 or CD33 expression was assessed 72 hours after transduction using a Cytoflex flow cytometer. Transduced cells were selected with 4 ug/ml puromycin for 3 weeks. FLT3 and CD33 expression was determined using flow cytometry after 3-weeks of puromycin selection. The engineered cells were cultured for one week in complete medium without puromycin. Engineered cells were frozen in cryopreservation medium and stored in liquid nitrogen.

Bicistronic CAR T Cell Assay with Engineered K526 Cells

T cell cytotoxicity and cytokine production after incubation with MV4-11, MOLM-13, and SEM cells were determined as previously described in Examples 15-17.

The monocistronic FLT3 CAR had an NC7 scFv and a 4-1BB co-stimulatory domain (SB00819). The monocistronic CD33 CAR had a hu195 scFv with a CD28 co-stimulatory domain (SB01052). The bicistronic FLT3 and CD33 CAR was SB01659 as described above.

Results

Figures 59A, 59B, 59C, 59D:
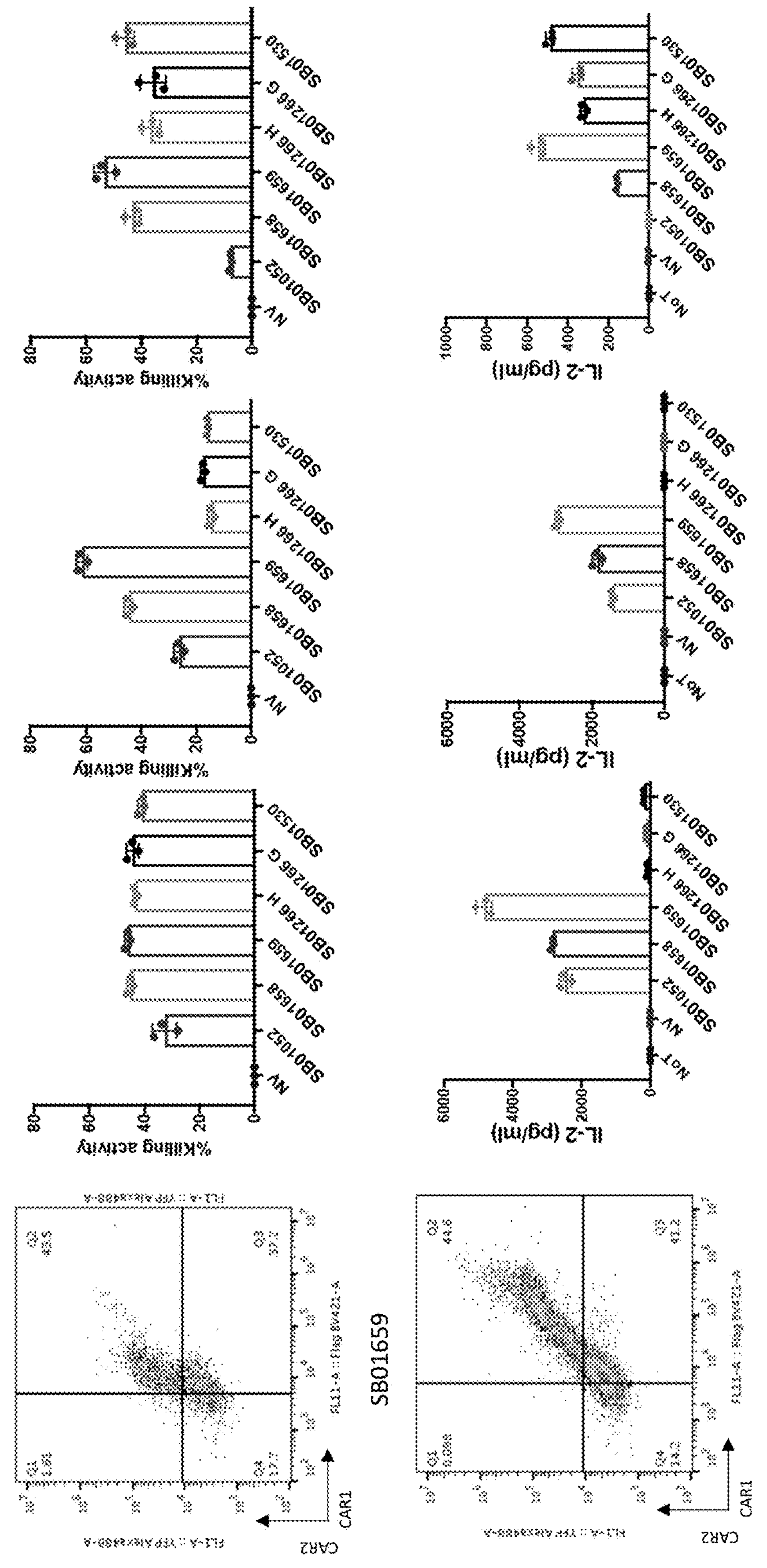
FIG. 59A shows expression of two bicistronic FLT3 and CD33 CARs in T cells, SB01266 and SB01659.
FIG. 59B shows the cytotoxicity and IL-2 production of the indicated CAR after incubation with MOLM-13 cells.
FIG. 59C shows the cytotoxicity and IL-2 production of the indicated CAR after incubation with MV4-11 cells.
FIG. 59D shows the cytotoxicity and IL-2 production of the indicated CAR after incubation with SEM cells.

The SB01659 bicistronic CAR had better expression in T cells as compared to the SB01266 bicistronic CAR (FIG. 59A). The SB01659 bicistronic CAR also demonstrated superior cytotoxity and IL-2 production after incubation with MOLM-13 cells (FIG. 59B), MV4-11 cells (FIG. 59C), and SEM cells (FIG. 59D) as compared to the CD33 monocistronic Car (SB01052) and other bicistronic CARs (SB01658, SB01266, and SB01530, FIGS. 59B, 59C, and 59D). In each case, the CAR construct is referred to by the shortened name, e.g., SB01659 is indicated as 1659. NoT indicates samples without added T cells, NV indicates samples with untransduced T cells. SB01266H and SB01266G were two separate preparations of the SB01266 CAR.

Figures 60A, 60B, 60C:
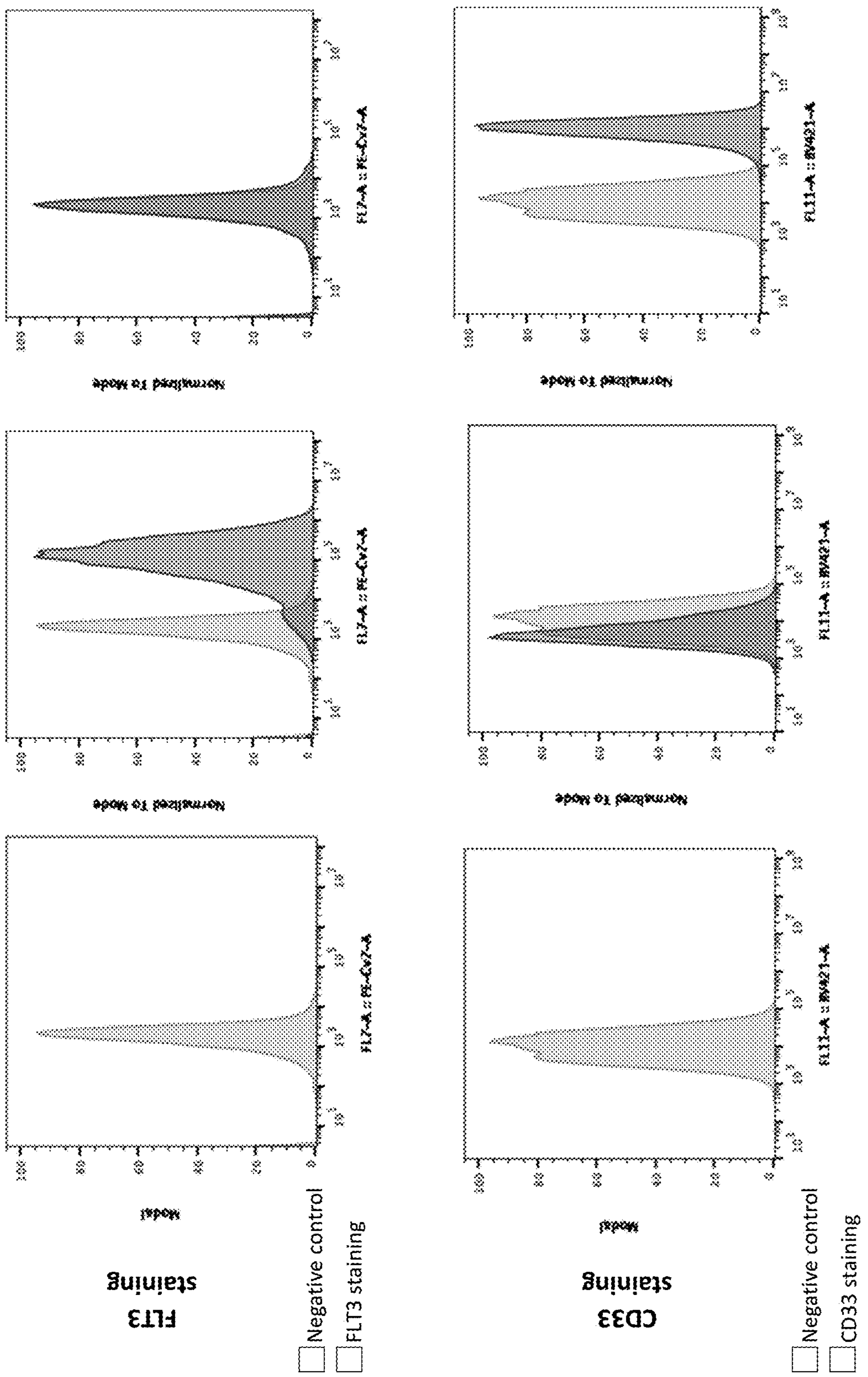
FIG. 60A shows FLT3 and CD33 staining in unengineered K562 cells.
FIG. 60B shows FLT3 and CD33 staining in K562 cells engineered to express FLT3.
FIG. 60C shows FLT3 and CD33 staining in K562 cells engineered to express CD33.

The K562 cells were engineered to over express either FLT3 or CD33. Unengineered K562 cells expressing neither FLT3 or CD33 are shown in FIG. 60A. K562 cells expressing FLT3 are shown in FIG. 60B. K562 cells expressing CD33 are shown in FIG. 60C.

Figure 61:
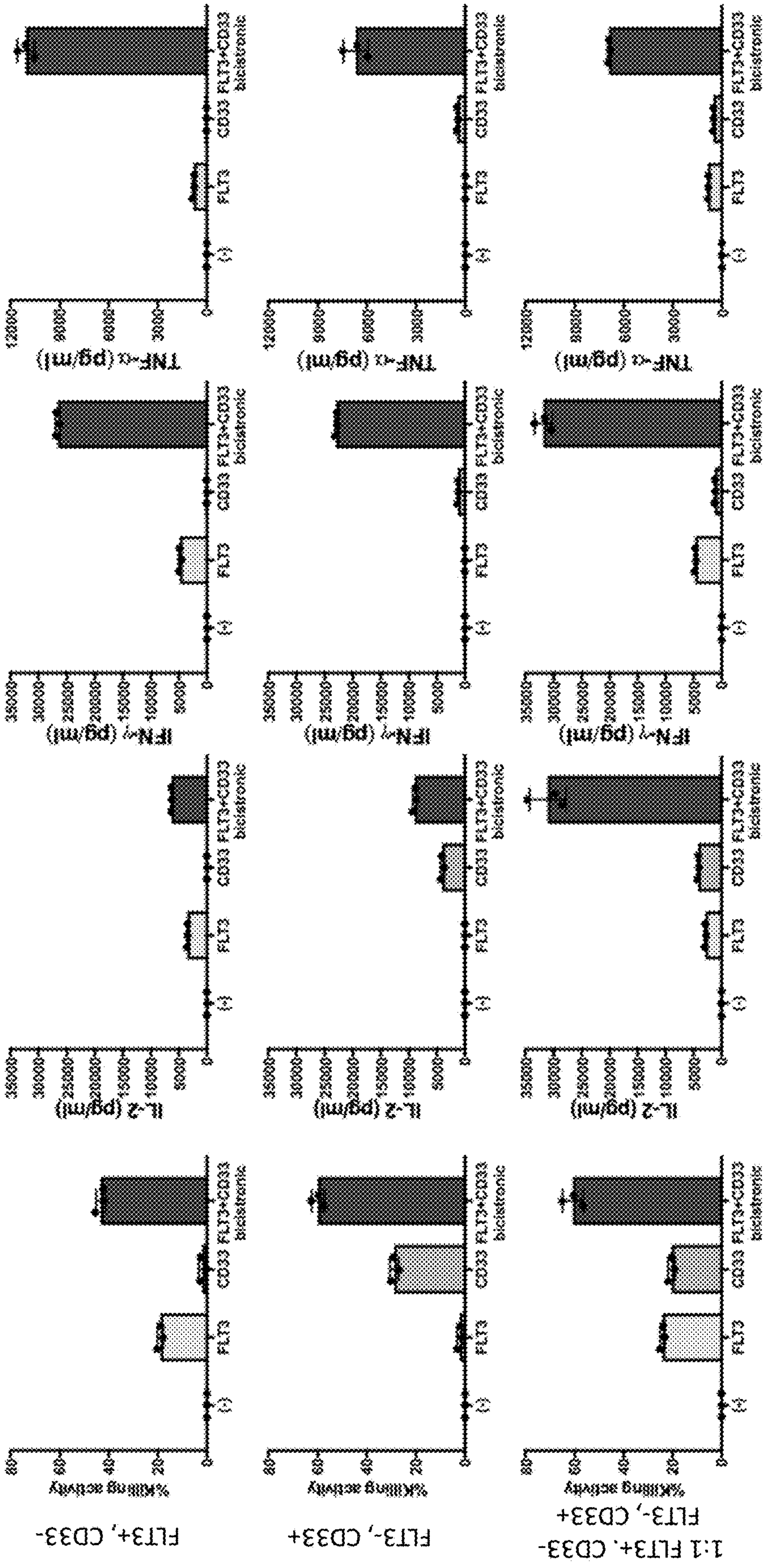
FIG. 61 shows the cytotoxity, IL-2 production, IFN-γ production, and TNF-α production by monovalent FLT3 CAR T cells, monovalent CD33 CAR T cells, and bicistronic FLT3 and CD33 CAR T cells incubated with K562 cells expressing FLT3 (upper panels), CD33 (middle panels), or a 1:1 mix of FLT3 and CD33 expressing cells (bottom panels).

The CD33 "OR" FLT3 bicistronic CAR SB01659 outperformed the CD33 and FLT3 monocistronic CARs against engineered K562 cells (FIG. 61). The top row panels show the T cell cytotoxicity, IL-2 production, IFN-γ, TNF-α in the FLT+, CD33− K562 cells. The middle row panels show the T cell cytotoxicity, IL-2 production, IFN-γ, TNF-α in FLT−, CD33+K562 cells. The bottom row panels show the T cell cytotoxicity, IL-2 production, IFN-γ, TNF-α in a 1:1 mixture of FLT3+, CD33− and FLT−, CD33+ K562 cells. The negative control (−) are non-transduced T cells. In each condition, the FLT3/CD33 bicistronic CAR T cells demonstrated better activation and stimulation than the monocistronic FLT3 or CD33 CAR T cells.

Figure 62:
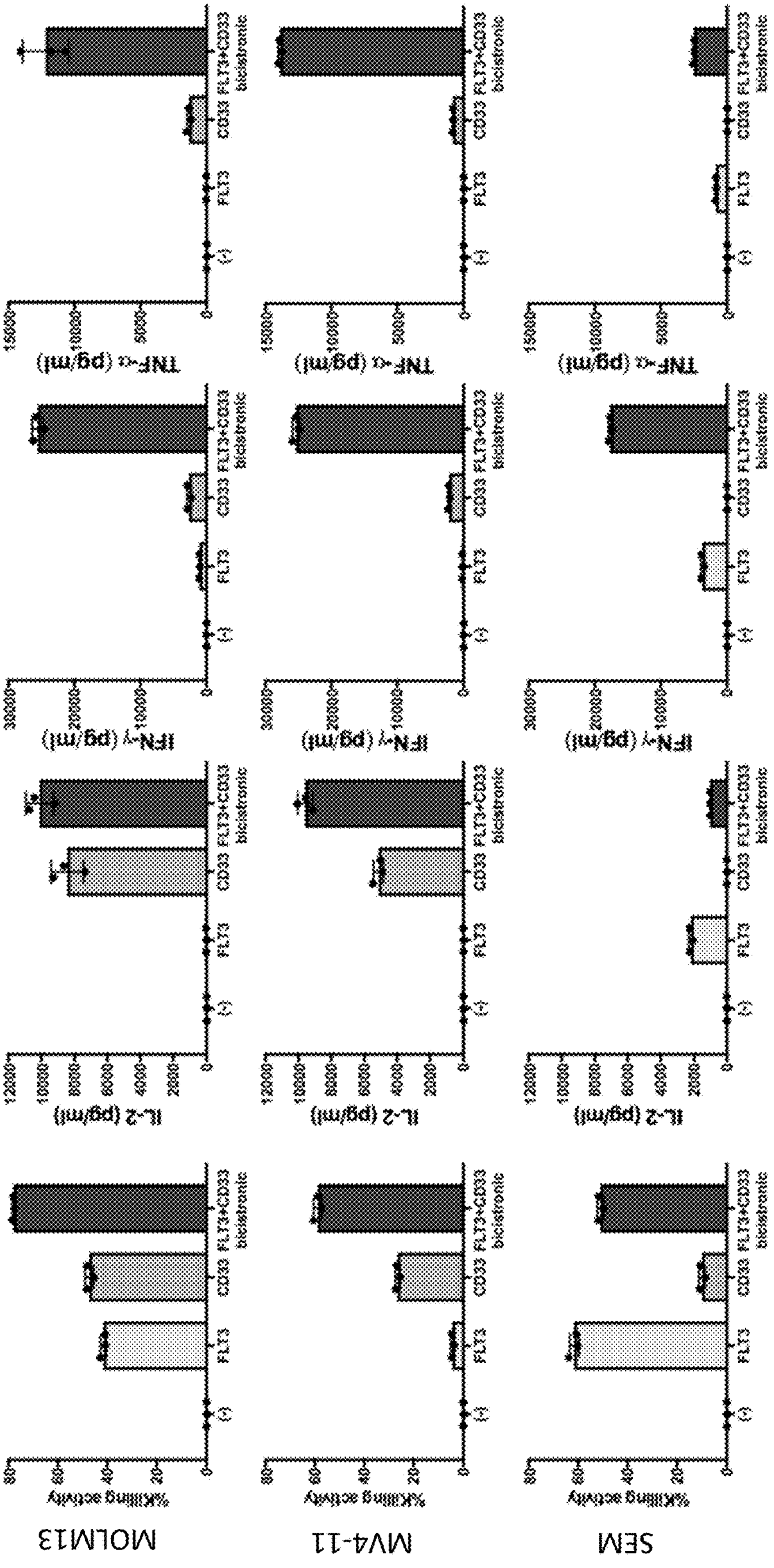
FIG. 62 shows the cytotoxity, IL-2 production, IFN-γ production, and TNF-α production by monovalent FLT3 CAR T cells, monovalent CD33 CAR T cells, and bicistronic FLT3 and CD33 CAR T cells incubated with MOLM-13 cells (upper panels), MV4-11 cells (middle panels), or SEM cells (bottom panels).

The CD33 "OR" FLT3 bicistronic CAR SB01659 outperformed the CD33 and FLT3 monocistronic CARs against leukemia cell lines (FIG. 62). The top row panels show the T cell cytotoxicity, IL-2 production, IFN-γ, TNF-α after incubation with the MOLM-13 cells, which have high FLT3 and high CD33 expression. The middle row panels show the T cell cytotoxicity, IL-2 production, IFN-γ, TNF-α after incubation with MV4-11 cells, which have lower FLT3 expression and higher CD33 expression. The bottom row panels show the T cell cytotoxicity, IL-2 production, IFN-γ, TNF-α after incubation with SEM cells, which have higher FLT3 expression and lower CD33 expression. The negative control (−) are non-transduced T cells. In most cell lines, the FLT3/CD33 bicistronic CAR T cells demonstrated better activation and stimulation than the monocistronic FLT3 or CD33 CAR T cells, with the exception of cytotoxicity and IL-2 production in the SEM cell line. However, the biscistronic FLT3/CD33 CAR T cells still induced significant cytotoxicity in the SEM cells (greater than 50%, and greater than the monocistronic CD33 CAR T cells) and superior IFN-γ and TNF-α production in the SEM cells.

Example 23: In Vitro Characterization of Bivalent FLT3 CAR CAR T Cells

Materials and Methods

Two bivalent FLT3 CARs were synthesized, with either a loop scFv (SB01861) or a tandem scFv (SB01862) with the NC7 and D4-3 scFvs. The structure of the loop scFv is shown in FIG. 63A. The structure of the tandem scFv is shown in FIG. 63B.

The monovalent FLT3 CAR used as a control was SB00819 with the NC7 scFv.

T cell cytotoxicity and cytokine production after incubation with MV4-11 and SEM cells were determined as previously described in Examples 15-17.

The protein and nucleotide sequences of the FLT3 CARs produced are shown in Table 14.

TABLE 14

| SEQ ID NO | Name | Sequence |
|---|---|---|
| 202 | CD8ss_D43<br>VL_linker_NC7<br>VH_linker_NC7<br>VL_linker_D43<br>VH_CD8<br>hinge_CD8<br>TM_41BB<br>ICD_CD3z<br>ICD_YFP<br>SB01861 | MALPVTALLLPLALLLHAARPDVVMTQSPLSLPVTPGEPASISCRSSQSLLHSNGYNYLDWYLQKPGQ<br>SPQLLIYLGSNRASGVPDRFSGSGSGTDFTLKISRVEAEDVGVYYCMQSLQTPFTFGPGTKVDIKGGG<br>GSEVQLVQSGAEVKKPGSSVKVSCKASGGTFSSYAISWVRQAPGQGLEWMGGIIPIFGTANYAQKFQG<br>RVTITADKSTSTAYMELSSLRSEDTAVYYCATFALFGFREQAFDIWGQGTTVTVSSGSTSGSGKPGSG<br>EGSTKGDIQMTQSPSSLSASVGDRVTITCRASQSISSYLNWYQQKPGKAPKLLIYAASSLQSGVPSRF<br>SGSGSGTDFTLTISSLQPEDLATYYCQQSYSTPFTFGPGTKVDIKGGGGSEVQLVQSGAEVKKPGASV<br>KVSCKASGYTFTSYYMHWARQAPGQGLEWMGIINPSGGSTSYAQKFQGRVTMTRDTSTSTVYMELSSL<br>RSEDTAVYYCARVVAAAVADYWGQGTLVTVSSTTTPAPRPPTPAPTIALQPLSLRPEACRPAAGGAVH<br>TRGLDFACDIYIWAPLAGTCGVLLLSLVITKRGRKKLLYIFKQPFMRPVQTTQEEDGCSCRFPEEEEG<br>GCELRVKFSRSADAPAYKQGQNQLYNELNLGRREEYDVLDKRRGRDPEMGGKPRRKNPQEGLYNELQK<br>DKMAEAYSEIGMKGERRRGKGHDGLYQGLSTATKDTYDALHMQALPPRGSSGTGMVSKGEELFTGVVP<br>ILVELDGDVNGHKFSVSGEGEGDATYGKLTLKLICTTGKLPVPWPTLVTTLGYGLQCFARYPDHMKQH<br>DFFKSAMPEGYVQERTIFFKDDGNYKTRAEVKFEGDTLVNRIELKGIDFKEDGNILGHKLEYNYNSHN<br>VYITADKQKNGIKANFKIRHNIEDGGVQLADHYQQNTPIGDGPVLLPDNHYLSYQSALSKDPNEKRDH<br>MVLLEFVTAAGITLGMDELYK* |
| 203 | CD8ss_D43<br>VL_linker_NC7<br>VH_linker_NC7<br>VL_linker_D43<br>VH_CD8<br>hinge_CD8<br>TM_41BB<br>ICD_CD3z<br>ICD_YFP<br>SB01861 | ATGGCTCTGCCTGTTACAGCTCTGCTGCTGCCTCTGGCTCTGCTTCTGCATGCCGCCAGACCTGACGT<br>GGTCATGACACAGTCTCCACTGAGCCTGCCTGTGACACCTGGCGAACCTGCCAGCATCAGCTGTAGAA<br>GCAGCCAGAGCCTGCTGCACAGCAACGGCTACAACTACCTGGACTGGTATCTGCAGAAGCCCGGCCAG<br>TCTCCTCAGCTGCTGATCTACCTGGGCTCCAATAGAGCCAGCGGCGTGCCCGATAGATTTTCTGGCAG<br>CGGCAGCGGAACCGACTTCACCCTGAAGATCTCCAGAGTGGAAGCCGAGGACGTGGGCGTGTACTACT<br>GTATGCAGTCCCTGCAGACCCCTTTCACCTTCGGACCTGGCACCAAGGTGGACATCAAAGGCGGCGGA<br>GGATCTGAGGTGCAGCTGGTTCAATCTGGCGCCGAAGTGAAGAAACCCGGCAGCTCTGTGAAGGTGTC<br>CTGCAAAGCTAGCGGCGGCACCTTTAGCAGCTACGCCATCTCTTGGGTCCGACAGGCTCCTGGACAAG<br>GCCTGGAATGGATGGGCGGCATCATCCCTATCTTCGGCACCGCCAATTACGCCCAGAAATTCCAGGGC<br>AGAGTGACCATCACCGCCGACAAGAGCACAAGCACCGCCTACATGGAACTGAGCAGCCTGAGAAGCGA<br>GGACACCGCCGTGTACTATTGCGCCACATTCGCCCTGTTCGGCTTCAGAGAGCAGGCCTTCGATATCT<br>GGGGCCAGGGCACAACCGTGACAGTGTCTAGCGGCAGCACAAGCGGCTCTGGCAAACCTGGATCTGGC<br>GAGGGAAGCACCAAGGGCGATATCCAGATGACACAGAGCCCCAGCAGCCTGTCTGCCTCTGTGGGAGA |

TABLE 14-continued

| SEQ ID NO | Name | Sequence |
|---|---|---|
| | | CAGAGTGACAATTACCTGCCGGGCCAGCCAGTCCATCAGCTCCTACCTGAATTGGTATCAGCAAAAAC |
| | | CTGGCAAGGCCCCTAAGCTGCTCATCTATGCCGCTAGCAGTCTGCAGAGCGGAGTGCCCTCAAGATTC |
| | | AGCGGATCTGGATCCGGCACCGATTTCACACTGACCATAAGCTCACTGCAGCCCGAGGACCTGGCCAC |
| | | CTACTATTGTCAGCAGTCCTACAGCACCCCGTTCACATTTGGCCCAGGCACAAAAGTCGATATCAAAG |
| | | GTGGTGGCGGCAGCGAAGTCCAGCTGGTGCAAAGCGGAGCTGAAGTGAAAAAGCCAGGCGCCAGCGTG |
| | | AAAGTGTCTTGCAAGGCCTCCGGCTACACATTCACCAGCTACTACATGCACTGGGCCAGACAGGCACC |
| | | AGGACAGGGACTTGAGTGGATGGGCATCATCAATCCTTCCGGCGGCTCCACAAGCTACGCCCAAAAGT |
| | | TTCAAGGCCGCGTGACCATGACCAGAGACACCAGCACCTCCACCGTGTATATGGAACTGTCTAGCCTG |
| | | CGCTCCGAGGATACAGCCGTCTACTACTGTGCCAGAGTGGTGGCTGCTGCCGTGGCCGATTATTGGGG |
| | | ACAGGGAACACTGGTCACCGTGTCCAGCACAACAACCCCTGCTCCTAGACCTCCTACACCAGCTCCAA |
| | | CCATTGCTCTGCAGCCCCTGTCTCTGAGGCCAGAGGCTTGTAGACCTGCTGCTGGCGGAGCCGTGCAT |
| | | ACAAGAGGACTGGATTTCGCCTGCGACATCTACATCTGGGCCCCTCTGGCTGGAACATGTGGCGTGTT |
| | | GCTGCTGAGCCTGGTCATCACCAAGCGGGGCAGAAAGAAGCTGCTGTACATCTTCAAGCAGCCCTTCA |
| | | TGCGGCCCGTGCAGACCACACAAGAGGAAGATGGCTGCTCCTGCAGATTCCCCGAGGAAGAAGAAGGC |
| | | GGCTGCGAACTGAGAGTGAAGTTCAGCAGAAGCGCCGACGCTCCCGCCTATAAGCAGGGACAGAACCA |
| | | GCTCTACAACGAGCTGAACCTGGGGAGAAGAGAAGAGTACGACGTGCTGGATAAGCGGAGAGGCAGAG |
| | | ATCCTGAGATGGGCGGAAAGCCCAGACGGAAGAATCCTCAAGAGGGCCTGTACAATGAGCTGCAGAAA |
| | | GACAAGATGGCCGAGGCCTACAGCGAGATCGGAATGAAGGGCGAGCGCAGAAGAGGCAAGGGACACGA |
| | | TGGACTGTACCAGGGCCTGAGCACCGCCACCAAGGATACCTATGATGCCCTGCACATGCAGGCCCTGC |
| | | CTCCAAGAGGATCTAGCGGAACAGGCATGGTGTCCAAAGGCGAGGAACTGTTCACAGGCGTGGTGCCC |
| | | ATTCTGGTGGAACTGGATGGCGACGTGAACGGCCACAAGTTTAGCGTTAGCGGAGAAGGCGAAGGCGA |
| | | CGCCACATACGGAAAGCTGACCCTGAAGCTGATCTGCACCACCGGCAAACTGCCTGTGCCTTGGCCTA |
| | | CACTCGTGACCACACTCGGCTATGGCCTGCAGTGCTTCGCCAGATATCCCGACCATATGAAGCAGCAC |
| | | GACTTCTTCAAGAGCGCCATGCCTGAGGGCTACGTGCAAGAGCGGACCATCTTCTTTAAGGACGACGG |
| | | CAACTACAAGACCCGGGCAGAAGTGAAGTTTGAGGGCGACACCCTGGTCAACCGGATCGAGCTGAAGG |
| | | GCATCGACTTCAAAGAGGACGGCAACATCCTGGGCCACAAGCTCGAGTACAACTACAACAGCCACAAC |
| | | GTGTACATCACGGCCGATAAGCAGAAGAACGGCATCAAGGCCAACTTCAAGATCCGCCACAACATCGA |
| | | GGATGGCGGCGTTCAGCTGGCCGATCACTACCAGCAGAATACCCCTATCGGCGACGGACCTGTGCTGC |
| | | TCCCCGATAATCACTACCTGAGCTACCAGAGCGCCCTGAGCAAGGACCCCAACGAGAAGAGGGATCAC |
| | | ATGGTGCTGCTGGAATTCGTGACCGCTGCCGGCATCACCCTCGGCATGGATGAACTGTACAAGTGA |
| 204 | CD8ss_NC7 | MALPVTALLLPLALLLHAARPEVQLVQSGAEVKKPGSSVKVSCKASGGTFSSYAISWVRQAPGQGLEW |
| | VH_linker_NC7 | MGGIIPIFGTANYAQKFQGRVTITADKSTSTAYMELSSLRSEDTAVYYCATFALFGFREQAFDIWGQG |
| | VL_linker_D43 | TTVTVSSGGGGSGGGGSGGGGSDIQMTQSPSSLSASVGDRVTITCRASQSISSYLNWYQQKPGKAPKL |
| | VL_linker_D43 | LIYAASSLQSGVPSRFSGSGSGTDFTLTISSLQPEDLATYYCQQSYSTPFTFGPGTKVDIKGGGGSGG |
| | VH_CD8 | GGSGGGGSGGGGSGGGGSDVVMTQSPLSLPVTPGEPASISCRSSQSLLHSNGYNYLDWYLQKPGQSPQ |
| | hinge_CD8 | LLIYLGSNRASGVPDRFSGSGSGTDFTLKISRVEAEDVGVYYCMQSLQTPFTFGPGTKVDIKGGGGSG |
| | TM_41BB | GGGSGGGGSEVQLVQSGAEVKKPGASVKVSCKASGYTFTSYYMHWARQAPGQGLEWMGIINPSGGSTS |
| | ICD_CD3z | YAQKFQGRVTMTRDTSTSTVYMELSSLRSEDTAVYYCARVVAAAVADYWGQGTLVTVSSTTTPAPRPP |
| | ICD_YFP | TPAPTIALQPLSLRPEACRPAAGGAVHTRGLDFACDIYIWAPLAGTCGVLLLSLVITKRGRKKLLYIF |
| | SB01862 | KQPFMRPVQTTQEEDGCSCRFPEEEEGGCELRVKFSRSADAPAYKQGQNQLYNELNLGRREEYDVLDK |
| | | RRGRDPEMGGKPRRKNPQEGLYNELQKDKMAEAYSEIGMKGERRRGKGHDGLYQGLSTATKDTYDALH |
| | | MQALPPRGSSGTGMVSKGEELFTGVVPILVELDGDVNGHKFSVSGEGEGDATYGKLTLKLICTTGKLP |
| | | VPWPTLVTTLGYGLQCFARYPDHMKQHDFFKSAMPEGYVQERTIFFKDDGNYKTRAEVKFEGDTLVNR |
| | | IELKGIDFKEDGNILGHKLEYNYNSHNVYITADKQKNGIKANFKIRHNIEDGGVQLADHYQQNTPIGD |
| | | GPVLLPDNHYLSYQSALSKDPNEKRDHMVLLEFVTAAGITLGMDELYK* |
| 205 | CD8ss_NC7 | ATGGCTCTGCCTGTTACAGCTCTGCTGCTGCCTCTGGCTCTGCTTCTGCATGCCGCTAGACCTGAAGT |
| | VH_linker_NC7 | GCAGCTGGTTCAGTCTGGCGCCGAAGTGAAGAAACCTGGCAGCAGCGTGAAGGTGTCCTGCAAAGCTT |
| | VL_linker_D43 | CTGGCGGCACCTTCAGCAGCTACGCCATCTCTTGGGTTCGACAGGCCCCTGGACAAGGCCTGGAATGG |
| | VL_linker_D43 | ATGGGAGGCATCATCCCCATCTTCGGCACCGCCAATTACGCCCAGAAATTCCAGGGCAGAGTGACCAT |
| | VH_CD8 | CACCGCCGACAAGAGCACAAGCACCGCCTACATGGAACTGAGCAGCCTGAGAAGCGAGGACACCGCCG |
| | hinge_CD8 | TGTACTACTGCGCCACATTTGCCCTGTTCGGCTTCAGAGAGCAGGCCTTCGATATCTGGGGCCAGGGC |
| | TM_41BB | ACAACCGTGACCGTTTCTAGCGGAGGCGGAGGATCTGGTGGCGGAGGAAGTGGCGGAGGCGGTTCTGA |
| | ICD_CD3z | TATCCAGATGACACAGAGCCCCAGCAGCCTGTCTGCCTCTGTGGGAGACAGAGTGACAATTACCTGCC |
| | ICD_YFP | GGGCCAGCCAGAGCATCAGCTCCTACCTGAACTGGTATCAGCAGAAGCCCGGCAAGGCCCCTAAGCTG |
| | SB01862 | CTGATCTATGCTGCCTCCAGTCTGCAGAGCGGCGTGCCATCTAGATTTTCTGGCAGCGGCTCCGGCAC |
| | | CGACTTCACCCTGACAATATCTAGCCTGCAGCCAGAGGACCTGGCCACCTACTACTGTCAGCAGTCCT |
| | | ACAGCACCCCTTTCACCTTCGGACCTGGCACCAAGGTGGACATCAAAGGTGGTGGTGGCAGTGGTGGC |
| | | GGTGGCTCAGGTGGCGGCGGATCAGGCGGTGGTGGTTCTGGCGGCGGTGGATCTGATGTGGTTATGAC |
| | | CCAGTCTCCTCTGAGCCTGCCTGTGACACCTGGCGAACCTGCCAGCATCTCCTGTAGAAGCAGCCAGT |
| | | CTCTGCTGCACAGCAACGGCTACAACTACCTGGATTGGTATCTCCAGAAACCAGGACAGTCCCCTCAG |
| | | CTCCTCATCTACCTGGGCAGCAATAGAGCCTCTGGCGTGCCCGATAGATTCAGCGGCTCTGGAAGCGG |
| | | CACAGATTTCACACTGAAGATCTCCAGAGTGGAAGCCGAGGACGTGGGCGTGTACTATTGCATGCAGA |
| | | GCCTGCAGACCCCATTCACATTTGGCCCAGGCACAAAAGTCGATATCAAAGGCGGCGGAGGTTCCGGC |
| | | GGTGGCGGAAGCGGAGGTGGTGGCTCTGAAGTTCAGCTCGTGCAAAGCGGAGCTGAAGTGAAAAAGCC |
| | | AGGCGCCTCCGTGAAAGTGTCTTGTAAAGCCAGCGGCTACACCTTTACCAGCTACTACATGCACTGGG |
| | | CCAGACAGGCACCAGGCCAGGGACTTGAGTGGATGGGCATCATCAATCCTAGCGGCGGCAGCACAAGC |
| | | TACGCCCAAAAGTTTCAAGGCCGCGTGACCATGACCAGAGACACCAGCACCTCCACCGTGTATATGGA |
| | | ACTGTCCTCTCTGCGGAGCGAAGATACAGCCGTGTATTATTGTGCCAGAGTGGTGGCCGCTGCCGTGG |
| | | CCGATTATTGGGGACAGGGAACACTGGTCACCGTGTCCAGCACAACAACCCCTGCTCCTAGACCTCCT |
| | | ACACCAGCTCCAACCATTGCTCTGCAGCCCCTGTCTCTGAGGCCAGAGGCCTGTAGACCTGCTGCTGG |
| | | CGGAGCTGTGCATACAAGAGGCCTGGATTTCGCCTGCGACATCTACATCTGGGCTCCTCTGGCCGGAA |
| | | CATGCGGAGTGTTGCTGCTGAGCCTGGTCATCACCAAGCGGGGCAGAAAGAAGCTGCTGTACATCTTC |
| | | AAGCAGCCCTTCATGCGGCCCGTGCAGACCACACAAGAGGAAGATGGCTGCTCCTGCAGATTCCCCGA |
| | | GGAAGAAGAAGGCGGCTGCGAACTGAGAGTGAAGTTTAGCAGAAGCGCCGACGCTCCCGCCTATAAGC |

TABLE 14-continued

| SEQ ID NO | Name | Sequence |
|---|---|---|
| | | AGGGACAGAATCAGCTGTACAATGAGCTGAACCTGGGGCGCAGAGAAGAGTACGACGTGCTGGATAAG<br>CGGAGAGGCAGAGATCCTGAGATGGGCGGCAAGCCCAGACGGAAGAATCCTCAAGAGGGCCTGTATAA<br>CGAGCTGCAGAAAGACAAGATGGCCGAGGCCTACAGCGAGATCGGAATGAAGGGCGAACGCAGAAGAG<br>GCAAGGGCCACGATGGACTGTATCAGGGCCTGTCCACAGCCACCAAGGACACCTATGATGCCCTGCAC<br>ATGCAGGCCCTGCCTCCAAGAGGATCTTCTGGCACAGGCATGGTGTCCAAGGGCGAAGAACTGTTCAC<br>AGGCGTGGTGCCCATCCTGGTGGAACTGGACGGGGATGTGAACGGCCACAAGTTTAGCGTTAGCGGCG<br>AAGGCGAAGGGGATGCCACATACGGAAAGCTGACCCTGAAGCTGATCTGCACCACCGGCAAACTGCCA<br>GTGCCTTGGCCTACACTCGTGACCACACTCGGCTATGGCCTGCAGTGCTTCGCCAGATATCCCGACCA<br>TATGAAGCAGCACGACTTCTTCAAGAGCGCCATGCCTGAGGGCTACGTGCAAGAGAGAACCATCTTCT<br>TTAAGGACGACGGCAACTACAAGACCCGGGCAGAAGTGAAGTTCGAGGGCGACACCCTGGTCAACCGG<br>ATCGAGCTGAAGGGCATCGACTTCAAAGAGGACGGCAACATCCTGGGCCACAAGCTCGAGTACAACTA<br>CAACAGCCACAACGTGTACATCACGGCCGATAAGCAGAAGAACGGCATCAAGGCCAACTTCAAGATCC<br>GGCACAACATCGAGGATGGCGGCGTTCAGCTGGCCGATCACTACCAGCAGAATACCCCTATCGGCGAC<br>GGACCTGTCCTGCTGCCTGACAATCACTACCTGAGCTACCAGAGCGCCCTGAGCAAGGACCCCAACGA<br>GAAGAGGGATCACATGGTGCTGCTGGAATTCGTGACCGCCGCTGGCATCACCCTCGGCATGGATGAGC<br>TGTATAAGTGA |

Results

The novel bivalent CAR designs significantly improved killing of low target antigen density cells. The FLT3 bivalent CARs SB01861 and SB01862 killed MV4-11 cells (low FLT3 expression) at 2 to 2.5-fold greater efficiencies than the monovalent FLT3 CAR SB00819 (FIG. 63C upper panel).

Figure 63C:
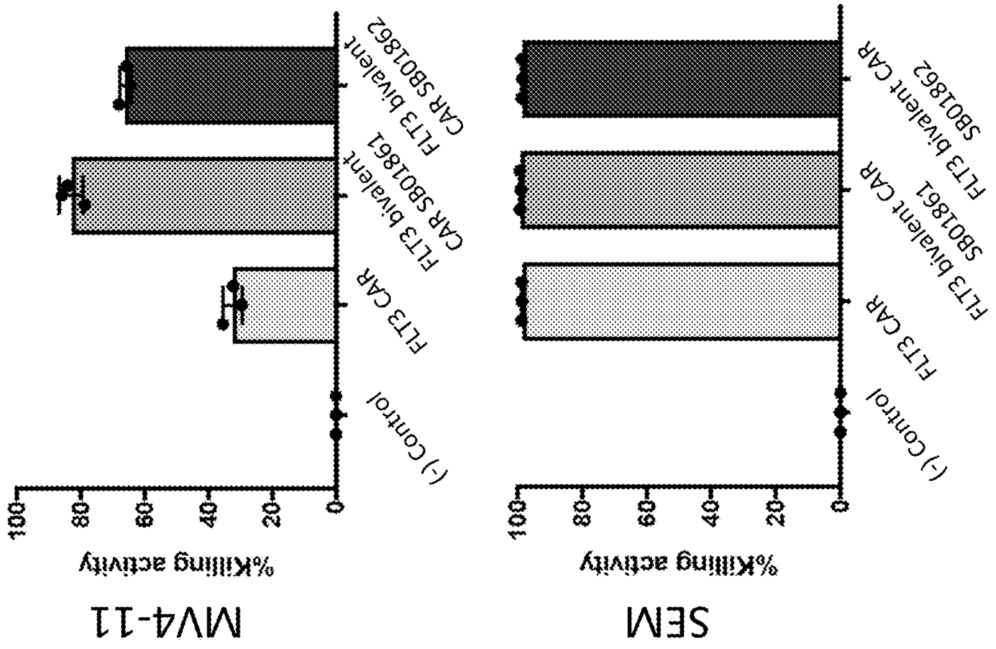
FIG. 63C shows the cytotoxicity of a monovalent FLT3 CAR T cell, the loop bivalent FLT3 CAR T cell, and the tandem FLT3 CAR T cell after incubation with MV4-11 cells (top) or SEM cells (bottom).
Figure 63B:
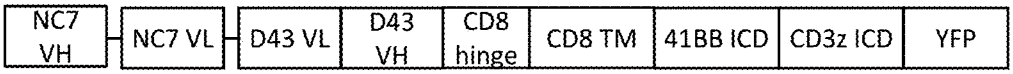
FIG. 63B shows a schematic of a tandem FLT3 bivalent CAR.
Figure 63A:
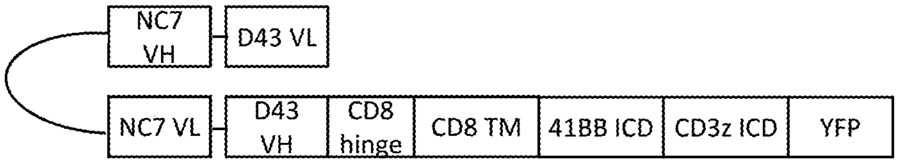
FIG. 63A shows a schematic of a loop FLT3 bivalent CAR.

In addition, the FLT3 bivalent CARs killed SEM cells (high FLT3 expression) with similar efficiencies as the monovalent FLT3 CAR (FIG. 63C lower panel). Thus, bivalent CAR design architecture can be exploited to build more potent CAR circuits with the greater capacity to respond to low target densities than monovalent CARs.

Example 24: Optimization of Hinge and Transmembrane Domains for Use with a CD28 Co-Stimulatory Domain Materials and Methods CD33 CARs with the hu195 scFv and CD8 hinge and transmembrane sequences were synthesized. The CARs also comprised a CD28 co-stimulatory domain and a CD3 stimulatory domain.

T cell cytotoxicity and cytokine production after incubation with MV4-11, MOLM-13, and K562 CD33 expressing cells were determined as previously described in Examples 15-17.

CD8 hinge and transmembrane protein and nucleotide sequences are shown in Table 15. The protein and nucleotide sequences for CAR constructs SB01364, SB01373, and SB01374 are also provided.

TABLE 15

| SEQ ID NO | Name | Sequence |
|---|---|---|
| 206 | CD8 Hinge Sequence 1 | TTTPAPRPPTPAPTIALQPLSLRPEACRPAAGGAVHTRGLDFACD |
| 207 | CD8 Hinge Sequence 2 Fitzer-Attas | ALSNSIMYFSHFVPVFLPAKPTTTPAPRPPTPAPTIASQPLSLRPEACRPAAGGAVHTRGLDFA<br>CD |
| 208 | CD8 Hinge Sequence 3 | FVPVFLPAKPTTTPAPRPPTPAPTIALQPLSLRPEACRPAAGGAVHTRGLDFACD |
| 209 | CD8 TM Sequence 1 | IYIWAPLAGTCGVLLLSLVIT |
| 210 | CD8 TM Sequence 2 Fitzer-Attas | IYIWAPLAGTCGVLLLSLVITLYCNHR |
| 211 | CD8 TM Sequence 3 | IYIWAPLAGTCGVLLLSLVITLYCNHRN |
| 212 | GMCSFss_CD33(hu195)_CD8 hinge_CD8 TM_CD28 ICD_CD3z_YFP SB01364 | MLLLVTSLLLCELPHPAFLLIPQVQLVQSGAEVKKPGSSVKVSCKASGYTFTDYNMHWVRQAPG<br>QGLEWIGYIYPYNGGTGYNQKFKSKATITADESTNTAYMELSSLRSEDTAVYYCARGRPAMDYW<br>GQGTLVTVSSGGGGSGGGGSGGGGSDIQMTQSPSSLSASVGDRVTITCRASESVDNYGISFMNW<br>FQQKPGKAPKLLIYAASNQGSGVPSRFSGSGSGTDFTLTISSLQPDDFATYYCQQSKEVPWTFG<br>QGTKVEIKSGTTTPAPRPPTPAPTIALQPLSLRPEACRPAAGGAVHTRGLDFACDIYIWAPLAG<br>TCGVLLLSLVITRSKRSRLLHSDYMNMTPRRPGPTRKHYQPYAPPRDFAAYRSRVKFSRSADAP<br>AYKQGQNQLYNELNLGRREEYDVLDKRRGRDPEMGGKPRRKNPQEGLYNELQKDKMAEAYSEIG<br>MKGERRRGKGHDGLYQGLSTATKDTYDALHMQALPPRGSSGTGMVSKGEELFTGVVPILVELDG |

TABLE 15-continued

| SEQ ID NO | Name | Sequence |
|---|---|---|
| | | DVNGHKFSVSGEGEGDATYGKLTLKLICTTGKLPVPWPTLVTTLGYGLQCFARYPDHMKQHDFFKSAMPEGYVQERTIFFKDDGNYKTRAEVKFEGDTLVNRIELKGIDFKEDGNILGHKLEYNYNSHNVYITADKQKNGIKANFKIRHNIEDGGVQLADHYQQNTPIGDGPVLLPDNHYLSYQSALSKDPNEKRDHMVLLEFVTAAGITLGMDELYK* |
| 213 | GMCSFss_CD33(hu195)_CD8 hinge_CD8 TM_CD28 ICD_CD3z_YFP SB01364 | ATGCTCCTTCTCGTGACCTCTTTGCTTCTTTGTGAACTCCCACACCCAGCATTCCTCTTGATCCCCCAAGTACAACTCGTCCAATCCGGGGCAGAGGTCAAGAAGCCCGGGAGTTCAGTCAAAGTCTCATGTAAAGCGTCTGGATATACTTTCACTGATTATAATATGCATTGGGTGAGACAAGCACCCGGCCAGGGGCTGGAATGGATTGGGTATATTTATCCATATAACGGTGGAACAGGGTATAATCAGAAATTCAAATCTAAAGCTACTATTACAGCGGATGAAAGTACGAATACAGCTTATATGGAGTTGTCCTCACTCAGGTCCGAAGATACAGCAGTATATTATTGCGCTAGGGGTCGGCCTGCAATGGACTACTGGGGCCAAGGTACTCTCGTGACTGTGTCAAGTGGCGGTGGCGGCAGCGGCGGCGGCGGCTCCGGTGGTGGTGGAAGTGACATTCAAATGACGCAATCCCCATCTAGTCTCAGCGCTTCCGTTGGGGACCGCGTAACAATTACTTGCAGGGCATCAGAATCCGTTGATAATTATGGGATTTCCTTTATGAATTGGTTTCAACAAAAGCCGGGGAAAGCACCAAAACTCCTCATTTATGCAGCTTCCAACCAGGGGTCAGGGGTCCCGTCCCGTTTCAGCGGTTCAGGGAGTGGTACAGACTTTACGCTTACAATTTCCAGTCTCCAACCCGATGATTTTGCAACATATTATTGTCAACAATCCAAGGAAGTTCCTTGGACGTTTGGGCAAGGTACCAAAGTTGAGATAAAATCTGGAACAACAACCCCTGCACCACGGCCCCCTACCCCCGCACCAACCATTGCACTCCAACCCTTGTCCTTGCGCCCCGAGGCCTGCAGGCCCGCCGCCGGTGGTGCAGTTCACACTAGGGGCTTGGACTTTGCTTGTGATATATATATATATGGGCTCCACTCGCAGGGACTTGCGGAGTCCTTTTGCTGTCACTTGTGATTACACGAAGTAAAAGATCTCGGCTTTTGCATTCAGATTATATGAATATGACTCCACGCAGGCCTGGGCCCACACGAAAACATTATCAACCGTATGCACCCCCACGCGACTTTGCTGCTTATAGGAGCCGGGTCAAATTTTCCCGGAGCGCAGACGCCCCAGCTTACAAACAAGGTCAAAATCAACTTTATAATGAACTCAATTTGGGCCGGCGGGAAGAATATGATGTCCTTGATAAAAGACGTGGGCGCGACCCGGAAATGGGCGGGAAACCACGTCGCAAGAACCCGCAGGAAGGTTTGTACAACGAACTCCAAAAGGATAAAATGGCTGAAGCTTATTCCGAAATAGGGATGAAAGGTGAACGGCGCCGCGGTAAAGGCCATGACGGCTTGTATCAAGGTCTTAGTACAGCAACAAAAGACACATACGACGCTCTCCATATGCAAGCACTCCCACCGCGCGGATCGAGTGGCACCGGTATGGTTTCTAAAGGAGAGGAGCTCTTTACTGGTGTCGTCCCTATATTGGTCGAGCTCGATGGCGACGTTAATGGTCATAAATTCAGTGTGTCAGGAGAGGGAGAAGGCGACGCTACGTATGGCAAATTGACATTGAAGTTGATATGTACAACGGGTAAACTCCCAGTTCCCTGGCCGACGCTCGTAACAACGCTGGGTTATGGACTTCAATGTTTTGCTCGTTACCCTGATCACATGAAACAACATGATTTCTTTAAATCTGCTATGCCCGAAGGGTATGTCCAGGAACGGACTATCTTCTTCAAAGATGATGGAAATTATAAAACTCGCGCAGAGGTGAAATTCGAAGGGGATACTCTTGTGAATCGAATTGAACTTAAAGGTATTGATTTCAAGGAAGATGGGAACATACTCGGGCATAAACTTGAATATAATTATAACAGCCATAATGTTTACATCACCGCAGATAAACAGAAGAATGGAATTAAAGCGAATTTTAAAATTCGCCATAATATTGAAGACGGCGGGGTGCAACTCGCTGATCACTATCAACAAAACACTCCAATTGGAGATGGTCCGGTCCTGCTCCCGGACAACCATTATCTTTCTTATCAATCCGCTCTCTCCAAAGATCCTAATGAAAAGCGGGACCATATGGTCTTGCTTGAGTTTGTCACTGCAGCCGGGATAACTCTGGGGATGGATGAACTCTACAAATAA |
| 214 | GMCSFss_Flag_CD33(hu195)_Fitzer-Attas CD8 hinge_Fitzer-Attas CD8 TM_CD28 ICD_CD3z SB01373 | MLLLVTSLLLCELPHPAFLLIPAGGSDYKDDDDKGGGGSGGGGQVQLVQSGAEVKKPGSSVKVSCKASGYTFTDYNMHWVRQAPGQGLEWIGYIYPYNGGTGYNQKFKSKATITADESTNTAYMELSSLRSEDTAVYYCARGRPAMDYWGQGTLVTVSSGGGGSGGGGSGGGGSDIQMTQSPSSLSASVGDRVTITCRASESVDNYGISFMNWFQQKPGKAPKLLIYAASNQGSGVPSRFSGSGSGTDFTLTISSLQPDDFATYYCQQSKEVPWTFGQGTKVEIKSGALSNSIMYFSHFVPVFLPAKPTTTPAPRPPTPAPTIASQPLSLRPEACRPAAGGAVHTRGLDFACDIYIWAPLAGTCGVLLLSLVITLYCNHRRSKRSRLLHSDYMNMTPRRPGPTRKHYQPYAPPRDFAAYRSRVKFSRSADAPAYKQGQNQLYNELNLGRREEYDVLDKRRGRDPEMGGKPRRKNPQEGLYNELQKDKMAEAYSEIGMKGERRRGKGHDGLYQGLSTATKDTYDALHMQALPPR |
| 215 | GMCSFss_Flag_CD33(hu195)_Fitzer-Attas CD8 hinge_Fitzer-Attas CD8 TM_CD28 ICD_CD3z SB01373 | ATGTTGCTGCTGGTTACCTCTCTCCTCTTGTGTGAGCTTCCGCACCCTGCCTTTCTCCTGATACCGGCTGGCGGATCTGACTACAAGGACGACGATGACAAAGGCGGCGGCGGGTCCGGAGGAGGTGGACAGGTCCAGCTCGTACAGTCTGGTGCAGAAGTGAAGAAACCCGGTTCATCAGTTAAGGTTTCTTGCAAAGCCAGTGGCTACACATTTACCGACTACAACATGCACTGGGTCAGACAGGCCCCCGGCCAAGGCTTGGAGTGGATCGGGTACATATACCCTTACAATGGCGGTACTGGATACAACCAGAAATTCAAGAGCAAGGCCACGATTACCGCGGATGAGAGCACAAACACAGCCTATATGGAACTGTCATCTTTGCGAAGCGAGGACACCGCCGTTTATTATTGTGCCAGAGGACGTCCCGCGATGGATTATTGGGGTCAGGGGACACTCGTCACAGTGAGCAGCGGCGGCGGTGGCAGTGGCGGAGGAGGCTCAGGCGGCGGCGGATCTGATATTCAAATGACCCAATCACCATCTTCCCTTTCTGCTAGTGTGGGAGATAGGGTGACTATCACATGTAGAGCTAGCGAATCCGTAGACAACTACGGCATCAGCTTCATGAACTGGTTCCAGCAAAAGCCTGGCAAGGCCCCAAAGTTGCTCATTTACGCGGCCAGCAATCAAGGCAGTGGTGTGCCCAGCAGATTTTCCGGATCAGGCAGCGGAACCGATTTCACCTTGACCATTTCTTCTCTGCAGCCTGACGACTTTGCCACGTACTACTGCCAACAGTCTAAAGAGGTTCCTTGGACTTTTGGGCAGGGAACAAAAGTCGAAATAAAGTCCGGCGCCTTGAGCAACTCTATCATGTACTTTAGCCACTTCGTGCCGGTGTTTCTTCCTGCCAAGCCTACAACTACACCAGCCCCAAGACCCCCAACTCCAGCGCCAACAATCGCGTCCCAGCCCTTGTCTCTGAGACCAGAAGCCTGTAGACCCGCTGCAGGCGGAGCCGTTCATACTCGGGGACTGGATTTCGCATGCGACATTTACATCTGGGCCCCACTGGCTGGCACGTGTGGGGTCCTGCTTCTGTCTCTGGTAATCACCCTTTATTGCAACCACAGGAGATCCAAGAGGAGCCGCCTGTTGCACTCAGACTACATGAACATGACACCTAGGCGGCCAGGTCCTACTCGAAAACACTATCAACCTTACGCTCCCCCTCGGGATTTCGCGGCTTACCGAAGCAGAGTGAAATTCAGCAGATCCGCTGATGCACCGGCTTATAAGCAGGGCCAAAATCAACTGTACAACGAGCTGAATCTGGGGAGACGGGAAGAGTACGACGTCCTGGACAAGCGCAGGGGAAGAGACCCTGAGATGGGCGGGAAGCCACGTAGGAAGAACCCACAAGAGGGCCTGTATAATGAGCTGCAGAAAGACAAGATGGCAGAGGCTTACAGTGAGATTGGAATGAAGGGTGAAAGGCGGCGGGGAAAGGGCCATGACGGCCTCTATCAGGGACTGTCCACAGCAACTAAGGACACCTATGATGCACTCCACATGCAGGCCCTGCCCCCGAGA |

TABLE 15-continued

| SEQ ID NO | Name | Sequence |
|---|---|---|
| 216 | CD8ss_Flag_CD33(hu195)_Fitzer-Attas CD8 hinge_Fitzer-Attas CD8 TM_CD28 ICD_CD3z SB01374 | MALPVTALLLPLALLLHAARPAGGSDYKDDDDKGGGGSGGGGQVQLVQSGAEVKKPGSSVKVSC<br>KASGYTFTDYNMHWVRQAPGQGLEWIGYIYPYNGGTGYNQKFKSKATITADESTNTAYMELSSL<br>RSEDTAVYYCARGRPAMDYWGQGTLVTVSSGGGGSGGGGSGGGGSDIQMTQSPSSLSASVGDRV<br>TITCRASESVDNYGISFMNWFQQKPGKAPKLLIYAASNQGSGVPSRFSGSGSGTDFTLTISSLQ<br>PDDFATYYCQQSKEVPWTFGQGTKVEIKSGTTTPAPRPPTPAPTIASQPLSLRPEACRPAAGGA<br>VHTRGLDFACDIYIWAPLAGTCGVLLLSLVITLYCNHRRSKRSRLLHSDYMNMTPRRPGPTRKH<br>YQPYAPPRDFAAYRSRVKFSRSADAPAYKQGQNQLYNELNLGRREEYDVLDKRRGRDPEMGGKP<br>RRKNPQEGLYNELQKDKMAEAYSEIGMKGERRRGKGHDGLYQGLSTATKDTYDALHMQALPPR |
| 217 | CD8ss_Flag_CD33(hu195)_Fitzer-Attas CD8 hinge_Fitzer-Attas CD8 TM_CD28 ICD_CD3z SB01374 | ATGGCCCTGCCCGTCACCGCATTGTTGCTCCCCCTCGCGTTGCTGCTCCACGCCGCGCGTCCCG<br>CTGGTGGCTCTGATTATAAAGATGATGACGATAAAGGGGGGGGCGGTAGCGGCGGTGGTGGTCA<br>AGTCCAACTCGTGCAAAGCGGTGCTGAGGTCAAGAAGCCCGGATCAAGTGTAAAAGTAAGCTGT<br>AAAGCTTCCGGGTATACATTCACTGATTATAATATGCATTGGGTGCGTCAAGCTCCCGGGCAGG<br>GTCTCGAATGGATTGGGTATATATATCCTTATAACGGCGGGACAGGGTATAATCAGAAATTTAA<br>ATCTAAAGCAACAATAACGGCGGATGAATCTACCAATACTGCTTATATGGAGCTTTCCTCTCTC<br>CGCAGTGAAGATACTGCTGTCTATTATTGTGCACGGGGACGCCCTGCAATGGACTACTGGGGAC<br>AAGGCACACTTGTGACAGTCAGCTCTGGTGGTGGTGGATCCGGCGGAGGAGGCTCAGGTGGTGG<br>CGGGAGTGACATTCAAATGACTCAAAGTCCTTCCTCTCTTAGCGCAAGTGTCGGTGACCGCGTC<br>ACAATTACGTGCCGGGCAAGTGAATCAGTCGATAATTATGGTATTTCATTTATGAATTGGTTTC<br>AACAAAAGCCCGGAAAAGCTCCAAAACTGTTGATATATGCAGCTTCAAACCAGGGAAGTGGCGT<br>CCCCTCACGCTTCTCTGGAAGCGGGTCTGGTACTGACTTTACTCTCACAATTTCCTCTCTCCAA<br>CCCGATGATTTTGCAACGTATTATTGTCAACAATCCAAGGAAGTACCTTGGACCTTCGGCCAAG<br>GGACAAAAGTTGAGATTAAATCCGGGACAACAACCCCCGCTCCGCGCCCACCCACACCAGCACC<br>AACAATTGCATCCCAACCATTGAGTCTCAGACCCGAGGCATGCCGACCAGCCGCAGGCGGTGCA<br>GTTCACACTCGCGGTCTCGACTTTGCGTGTGATATATATATTTGGGCACCCCTCGCCGGCACCT<br>GCGGTGTTCTTTTGCTCTCCCTCGTGATTACTCTTTATTGTAATCATCGTAGAAGTAAAAGGTC<br>CCGTTTGCTTCATTCTGATTATATGAATATGACTCCAAGGCGCCCTGGCCCCACACGGAAACAT<br>TATCAACCATATGCCCCACCCCGGGACTTTGCTGCATATAGAAGCCGCGTCAAATTTTCACGGT<br>CAGCAGACGCACCTGCTTACAAACAAGGACAAAACCAATTGTATAATGAACTTAACCTCGGAAG<br>GCGCGAGGAATATGATGTCTTGGATAAAAGGCGCGGGCGGGATCCCGAAATGGGCGGGAAACCT<br>CGGCGCAAGAATCCCCAGGAAGGTCTTTACAACGAACTCCAAAAGGATAAAATGGCAGAAGCTT<br>ATTCAGAAATTGGGATGAAAGGGGAGCGGCGCCGAGGCAAAGGGCATGATGGTCTCTACCAAGG<br>ACTTTCCACCGCTACAAAAGATACATACGACGCATTGCATATGCAAGCTTTGCCACCCCGT |

Results

CD8 hinge and transmembrane domains were tested in combination with CARS comprising CD28 co-stimulatory domains. The CD8 hinge and transmembrane sequences were used in place of the CD28 hinge and transmembrane domains used in previous CAR constructs. CAR constructs SB01364, SB01372, SB01373, and SB01374 demonstrated high expression in T cells (data not shown). SB01364 has CD8 hinge sequence 1 (SEQ ID NO: 206), CD8 transmembrane sequence 1 (SEQ ID NO: 209), and a GMCSF signal sequence; SB01372 has CD8 hinge sequence 2 (SEQ ID NO: 207), CD8 transmembrane sequence 2 (SEQ ID NO: 210), and a CD8 signal sequence; SB01373 has CD8 hinge sequence 2 (SEQ ID NO: 207), CD8 transmembrane sequence 2 (SEQ ID NO: 210), and a GMCSF signal sequence; SB01374 has CD8 hinge sequence 1 (SEQ ID NO: 206), CD8 transmembrane sequence 2 (SEQ ID NO: 210), and a CD8 signal sequence.

Figure 64A:
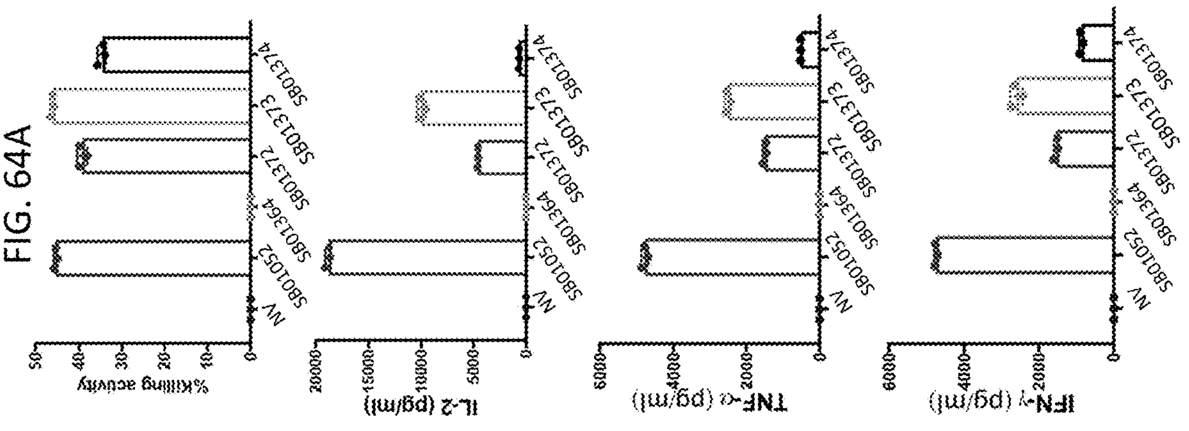
FIG. 64A shows the cytotoxity and IL-2, IFN-γ, and TNF-α secretion of the indicated CAR constructs after incubation with MOLM-13 cells.
Figure 64B:
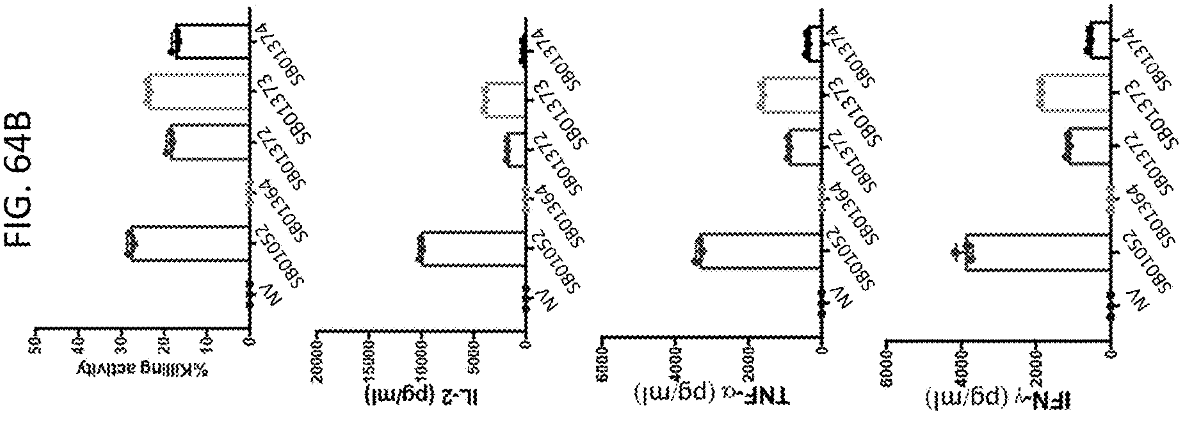
FIG. 64B shows the cytotoxity and IL-2, IFN-γ, and TNF-α secretion of the indicated CAR constructs after incubation with MV4-11 cells.

FIG. 64A shows the cytotoxity and IL-2, IFN-γ, and TNF-α secretion of the indicated CAR constructs after incubation with MOLM-13 cells. FIG. 64B shows the cytotoxity and IL-2, IFN-γ, and TNF-α secretion of the indicated CAR constructs after incubation with MV4-11 cells. FIG. 64A shows the cytotoxity and IL-2, IFN-γ, and TNF-α secretion of the CAR indicated constructs after incubation with K563 CD33 expressing cells. The CD33 CAR SB01052 was used as a control. Untransduced T cells were used as a negative control (NV). In each case, the CAR construct is referred to by the shortened name, e.g., SB01372 is indicated as 1372.

Killing and cytokine assays (FIG. 64A-C) demonstrate that the CD8 hinge 2 and transmembrane 2, used together in SB01373, was successfully used in place of a CD28 hinge and CD28 transmembrane configuration in the CAR and preserved the CAR activity.

Example 25: Identification of Inhibitory Chimeric Receptor Targets on HSCs

Additional NOT targets expressed on hematopoietic stem cells were identified using the bioinformatics screening described in Examples 1 and 2. In short, 7,860 HSC membrane-associated genes were identified via annotation as "cell surface" or "membrane" genes according to GO and Human Protein Atlas. Expression of the identified HSC proteins was determined in healthy HSCs and AML cells via microarray data and 115 genes were identified. Genes that were confirmed to be highly expressed on HSCs were then confirmed to be lowly expressed in AML cells via RNA-seq, resulting in 15 genes with high expression on HSCs and low expression on AML cells. The resulting hits were confirmed for protein expression in HSCs. 10 genes with confirmed membrane expression were identified and shown in Table 16.

TABLE 16

| Gene symbol | Gene name | Function |
|---|---|---|
| (1.) EMCN | Endomucin | Type I transmembrane mucin-like sialoglycoprotein that interferes with cell-cell and -ECM interactions |
| (2.) PCDH9 | Protocadherin 9 | Type I transmembrane protein that mediates cell adhesion in presence of calcium |
| (3.) JAM2 | Junctional adhesion molecule 2 | Type I transmembrane protein that mediates cell-cell interactions |
| (4.) IL18R1 | Interleukin 18 receptor 1 | Type I transmembrane protein and interleukin 18 (IL-18) cytokine receptor |
| (5.) SLC8A3 | Solute carrier family 8 member A3 | Multi-pass (11) transmembrane sodium/calcium exchanger integral membrane protein |
| (6.) CDH26 | Cadherin 26 | Type I transmembrane protein involved in cell interactions, migration, and differentiation |
| (7.) TMEM163 | Transmembrane protein 163 | Multi-pass (6) transmembrane protein that binds divalent cations |
| (8.) ABCA13 | ATP Binding Cassette Transporter A13 | Multi-pass (14) ATP-binding transmembrane protein |
| (9.) CACHD1 | Cache Domain Containing 1 | Type I transmembrane voltage-dependent calcium channel |
| (10.) CYYR1 | Cysteine And Tyrosine Rich 1 | Type I transmembrane protein |

Figure 64C:
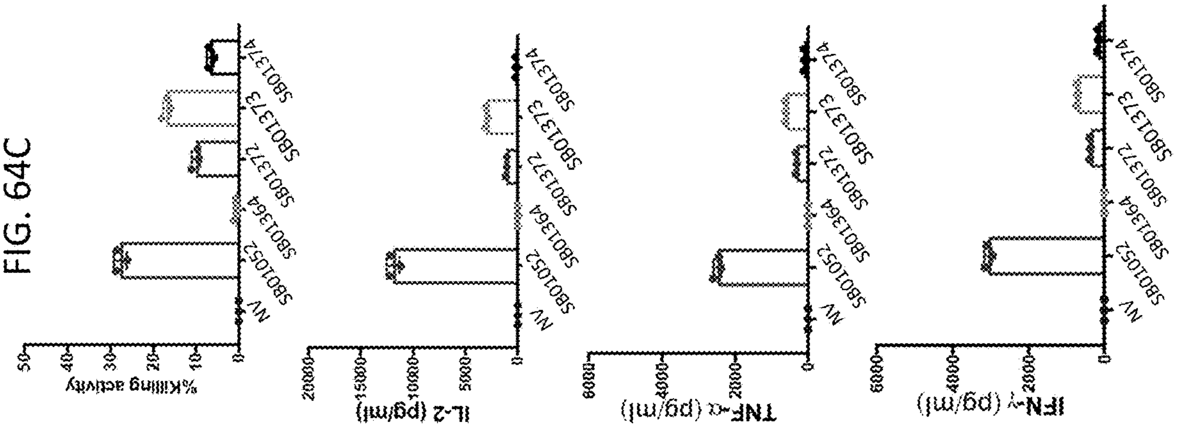
FIG. 64C shows the cytotoxity and IL-2, IFN-γ, and TNF-α secretion of the indicated CAR constructs after incubation with K562 cells expressing CD33.
Figure 65B:
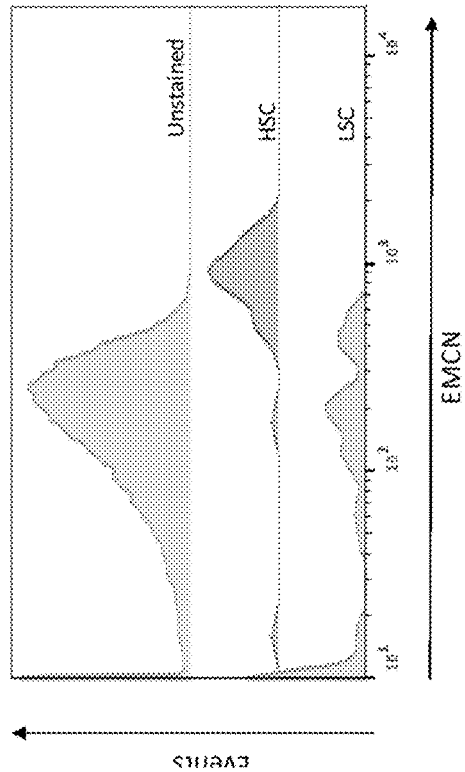
FIG. 65B shows EMCN expression on HSCs and LSCs.
Figure 65A:
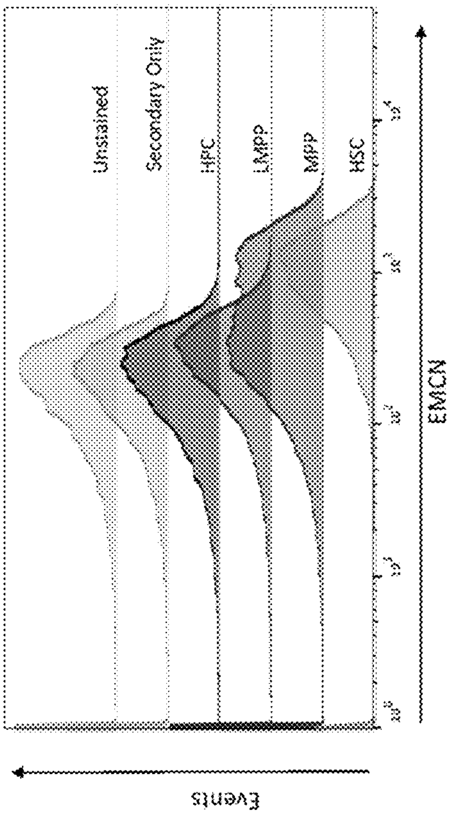
FIG. 65A shows EMCN expression on the indicated cell types.

EMCN is highly expressed in the hematopoietic stem cell (HSC) subset and lowly expressed in leukemia stem cells (FIG. 64A-C). Bone Marrow Mononuclear Cells from a healthy donor and an AML patient were enriched for CD34+ cells. The CD34 fraction was separated via flow cytometry for CD90 and CD45RA positive cells. The HSCs (CD45+, Lin−, CD34+, CD38−, CD90+, CD45RA−), MPP (CD45+, Lin−, CD34+, CD38−, CD90−, CD45RA−), and LMPP (CD45+, Lin−, CD34+, CD38−, CD90−, CD45RA+) were stained with anti-EMCN antibody (L6H10) and expression of EMCN on the various cell populations was determined. As shown in FIG. 65A, EMCN is expressed on HSCs.

Figure 65C:
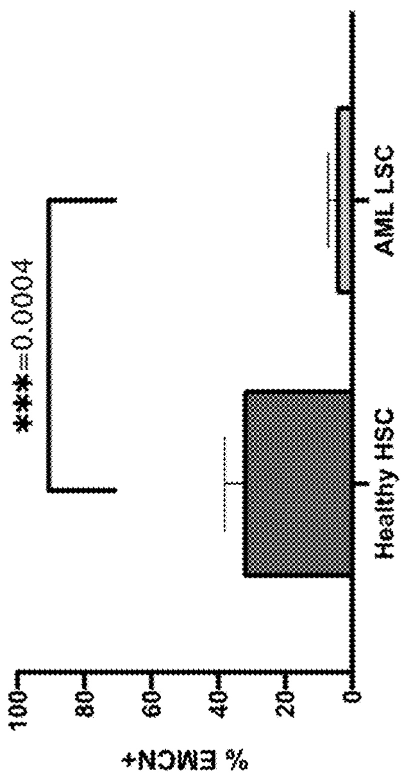
FIG. 65C shows a summary of EMCN expression on HSCs and LSCs from multiple donors.

HSCs and LSCs also showed differential expression of EMCN. Bone Marrow Mononuclear Cells from a healthy donor and an AML patient were enriched for CD34+ cells. The CD34 fraction was separated via flow cytometry for CD90 and CD45RA positive cells. The HSCs (CD45+, Lin−, CD34+, CD38−, CD90+, CD45RA−) and LSCs (CD45+, Lin−, CD34+CD38−, CD90−, CD45RA+) were stained with anti-EMCN antibody and expression of EMCN on the two cell types was compared. As shown in FIG. 65B, EMCN is expressed on HSCs but lowly expressed on LSCs. A summary of the EMCN expression on HSCs from 11 donors and LSCs from 7 AML patients is shown in FIG. 65C.

JAM2 was also determined to be expressed on HSCs and progenitor cells and only lowly on AML cells. JAM2 was expressed on 8.78% of HSCs, 10.4% on MPPs, and 9.52 on LMPP cells (data not shown).

A second screening approach was also used to identify NOT targets. 298 genes with expression profiles similar to EMCN were identified using the Gene Expression Commons platform (Seita J, Sahoo D, Rossi D J, Bhattacharya D, Serwold T, Inlay M A, et al. (2012) Gene Expression Commons: An Open Platform for Absolute Gene Expression Profiling. PLoS ONE 7(7): e40321. doi.org/10.1371/journal.pone.0040321). 17 genes were predicted to have cell surface expression after manual curation. 9 genes were confirmed to have high expression in HSCs and low expression in AML cells. The nine additional genes are shown in Table 17.

TABLE 17

| Gene Symbol | Gene Name |
|---|---|
| (11.) ABCB1 | ATP Binding Cassette Subfamily B Mem. 1 |
| (12.) ADGRG6 | Adhesion G Protein-Coupled Receptor G6 |
| (13.) ATP9A | ATPase Phospholipid Transporting 9A |
| (14.) CALNI | Calneuron 1 |
| (15.) CDCP1 | CUB Domain Containing Protein 1 |
| (16.) IL12RB2 | Interleukin 12 Receptor Subunit Beta 2 |
| (17.) SLC16A14 | Solute Carrier Family 16 Member 14 |
| (18.) TMEM136 | Transmembrane Protein 136 |
| (19.) TMEM200A | Transmembrane Protein 200A |

Example 26: Identification of Endothelial Safety Target Antigens

Endothelial safety targets were identified using the bioinformatics screening described in Examples 1 and 2 on the U133 blood samples microarray dataset. The U133 dataset includes 39 endothelial cell samples (10 fresh sample and 29 from cultured endothelial cells) and 876 AML samples. Briefly, genes with GO-annotated or Affy-annotated surface expression (9885) were identified. Genes with strong evidence for non-surface or membrane localization in Human Protein Atlas were removed, with 7860 genes remaining. These genes were assessed for higher expression in endothelial samples as compared to AML samples, resulting in 32 genes.

Next, the protein expression of each gene was confirmed in the Human Protein Atlas, surface expression in Genecards, and the size of extracellular domain (ECD) in Uniprot, leaving 16 potential target genes.

Table 18 provides a list of the endothelial safety target antigens and their fold change (log 2 expression scale) in endothelial cells as compared to AML cells.

TABLE 18

| Gene | Fold change in endothelial/AML cells |
|---|---|
| ADGRG6 | 7.263917592 |
| PTPRB | 7.224113221 |
| NCKAP1 | 6.568049829 |
| MPZL2 | 6.543630634 |
| PLSCR4 | 6.540126087 |
| TMEM47 | 6.476813823 |
| WLS | 6.406909834 |
| ADGRL4 | 6.277799777 |
| MET | 6.132032353 |
| BACE2 | 5.685994648 |
| ATP8B1 | 5.636851301 |
| LIFR (225575) | 5.521001536 |
| EMCN | 5.43255665 |
| ART4 | 5.314938365 |
| CALCRL | 5.312163738 |
| LIFR (225571) | 5.083770824 |
| CNTNAP3 /// CNTNAP3B | 5.031224128 |

Next, expression of previously identified HSC NOT target antigens was assessed on endothelial cells. Such dual targets can be used to protect both HSCs and endothelial cells from AML targeting CARs. The 19 genes identified in Example 25 were assessed for endothelial expression. 12 genes with dual expression were identified: EMCN, PCDH9, JAM2, CACHD1, CYYR1, ABCB1, ADGRG6, ATP9A, CDCP1, SLC16A14, TMEM136, and TMEM200A. Thus, the endothelial targets identified can be used to protect healthy endothelial cells from CAR immune cells that may possess on-target off-tissue toxicity against endothelial cells. In addition, the twelve identified dual endothelial and HSCs target antigens an be used as single "NOT" target antigens to concurrently protect healthy endothelial cells and hematopoietic stem cells (HSCs) from CAR immune cells that might possess on-target off-tissue toxicity against against healthy HSCs or endothelial cells.

Gene expression quantification of the identified AML, hematopoietic, and endothelial targets in various cell lines and sample tissues are provided in Tables 18-20. Table 18 shows gene expression in AML samples. Table 19 shows gene expression in healthy hematapoietic samples. Table 20 shows gene expression in endothelial cells.

CALN1, IL12RB2, ABCA13, CDH26, IL18R1, SLC8A3, TMEM163 are highly expressed in healthy hemaopoietic cells and thus can be used as HSC safety NOT targets. ADGRL4, ART4, ATP8B1, BACE2, CALCRL, CNTNAP3, LIFR, MET, MPZL2, NCKAP1, PLSCR4, PTPRB, TMEM47, and WLS are highly expressed in endothelial cells and thus can be used as endothelial safety NOT targets. ABCB1, ADGRG6, ATP9A, CACHD1, CDCP1, CYYR1, EMCN, JAM2, PCDH9, SLC16A14, TMEM136, and TMEM200A are highly expressed in healthy hemaopoietic cells and endothelial cells and thus can be used as HSC and endothelial safety NOT targets.

Table 19. Gene Expression in AML Sample

TABLE 19

| Gene expression in AML Samples | | | | | | | | | |
|---|---|---|---|---|---|---|---|---|---|
| Gene Symbol | AML +8 [19] | AML −5/7(q) [28] | AML −9q [6] | AML BMMC NK [399] | AML Blast [21] | AML Complex [58] | AML LPC [23] | AML LSC [28] | AML NK [9] |
| CALN1 | 3.5 | 4.1 | 3.8 | 3.9 | 3.6 | 4.4 | 3.8 | 4.2 | 3.5 |
| IL12RB2 | 4.2 | 4.5 | 4.2 | 4.3 | 4.5 | 4.6 | 4.5 | 4.5 | 4.1 |
| ABCA13 | 3.2 | 3.2 | 3.2 | 4.3 | 3.6 | 4.2 | 3.5 | 3.6 | 4.0 |
| CDH26 | 4.1 | 4.1 | 4.3 | 5.2 | 4.9 | 5.0 | 5.1 | 5.1 | 4.9 |
| IL18R1 | 4.6 | 4.6 | 4.9 | 5.2 | 4.9 | 5.5 | 4.8 | 5.0 | 5.2 |
| SLC8A3 | 5.8 | 5.8 | 5.8 | 5.0 | 5.6 | 5.2 | 5.8 | 5.9 | 5.2 |
| TMEM163 | 5.0 | 5.1 | 4.5 | 4.8 | 4.7 | 4.9 | 5.1 | 5.5 | 5.4 |
| ABCB1 | 5.3 | 5.6 | 5.6 | 4.8 | 5.0 | 5.0 | 5.2 | 5.4 | 4.7 |
| ADGRG6 | 4.3 | 3.7 | 3.7 | 3.9 | 4.3 | 4.2 | 4.5 | 4.8 | 4.8 |
| ATP9A | 5.5 | 6.1 | 5.7 | 5.7 | 5.9 | 6.4 | 6.1 | 6.6 | 7.1 |
| CACHD1 | 4.8 | 4.9 | 4.8 | 5.0 | 4.8 | 4.7 | 5.1 | 5.3 | 6.0 |
| CDCP1 | 5.4 | 5.7 | 5.4 | 5.6 | 6.0 | 5.6 | 6.5 | 6.7 | 5.7 |
| CYYR1 | 3.9 | 4.2 | 4.9 | 4.0 | 4.0 | 5.1 | 4.3 | 4.4 | 4.1 |
| EMCN | 4.3 | 4.4 | 4.3 | 4.3 | 4.3 | 4.3 | 4.4 | 4.6 | 4.4 |
| JAM2 | 5.3 | 5.4 | 5.4 | 5.2 | 5.1 | 5.3 | 5.2 | 5.4 | 5.7 |
| PCDH9 | 4.7 | 5.1 | 4.7 | 5.2 | 4.6 | 5.1 | 4.8 | 5.5 | 6.5 |
| SLC16A14 | 4.2 | 4.3 | 4.2 | 4.6 | 3.9 | 5.0 | 4.0 | 4.2 | 4.3 |
| TMEM136 | 3.8 | 3.8 | 3.7 | 4.0 | 4.1 | 4.0 | 4.1 | 4.2 | 4.2 |
| TMEM200A | 3.5 | 3.8 | 3.4 | 3.7 | 3.9 | 3.7 | 3.8 | 4.6 | 4.0 |
| ADGRL4 | 3.5 | 3.5 | 3.4 | 3.8 | 3.4 | 3.8 | 3.3 | 3.4 | 3.6 |
| ART4 | 3.9 | 3.8 | 3.7 | 3.9 | 4.0 | 4.1 | 3.6 | 3.6 | 3.8 |
| ATP8B1 | 3.6 | 3.8 | 3.7 | 3.6 | 3.5 | 3.5 | 3.6 | 3.7 | 3.4 |
| BACE2 | 3.1 | 3.2 | 3.1 | 3.3 | 3.9 | 3.4 | 3.7 | 3.6 | 4.2 |
| CALCRL | 4.8 | 5.3 | 4.6 | 4.4 | 4.1 | 4.6 | 4.2 | 4.4 | 4.2 |
| CNTNAP3 | 3.8 | 3.7 | 3.7 | 3.7 | 3.4 | 3.7 | 3.5 | 3.6 | 3.7 |
| LIFR | 3.5 | 3.5 | 3.5 | 3.7 | 3.5 | 3.6 | 3.6 | 3.6 | 3.7 |
| MET | 3.8 | 3.8 | 3.8 | 4.0 | 3.9 | 4.0 | 4.0 | 3.9 | 3.9 |
| MPZL2 | 3.4 | 3.5 | 3.2 | 3.3 | 4.0 | 3.3 | 3.8 | 4.1 | 3.9 |
| NCKAP1 | 3.6 | 3.6 | 3.5 | 3.8 | 3.7 | 4.0 | 3.7 | 3.7 | 3.7 |
| PLSCR4 | 3.6 | 4.3 | 4.0 | 4.0 | 4.2 | 4.5 | 3.9 | 4.1 | 3.8 |
| PTPRB | 3.4 | 3.4 | 3.4 | 3.5 | 3.4 | 3.5 | 3.4 | 3.5 | 3.5 |
| TMEM47 | 3.3 | 3.3 | 3.4 | 3.5 | 3.6 | 3.5 | 3.5 | 3.6 | 3.7 |
| WLS | 4.3 | 4.2 | 4.1 | 4.0 | 4.0 | 4.2 | 4.0 | 3.9 | 3.9 |

TABLE 19-continued

| Gene expression in AML Samples | | | | | | | | | |
|---|---|---|---|---|---|---|---|---|---|
| Gene Symbol | AML PBMC NK [32] | AML abn(3q) [2] | AML flt3 itd MUT [1] | AML idt(16) [33] | AML inv(16)/ t(16; 16) [28] | AML t(11q23) [48] | AML t(15; 17) [58] | AML t(6; 9) [6] | AML t(8; 21) [77] |
| CALN1 | 4.0 | 3.3 | 3.3 | 3.6 | 4.2 | 3.8 | 3.5 | 3.8 | 3.8 |
| IL12RB2 | 4.3 | 4.3 | 3.9 | 4.3 | 4.2 | 5.4 | 4.1 | 4.2 | 4.1 |
| ABCA13 | 3.9 | 3.5 | 3.2 | 3.2 | 3.8 | 3.5 | 3.7 | 3.6 | 3.9 |
| CDH26 | 4.9 | 3.8 | 4.5 | 4.3 | 5.0 | 4.6 | 6.3 | 4.3 | 6.0 |
| IL18R1 | 5.5 | 4.9 | 4.4 | 4.5 | 5.1 | 4.9 | 5.1 | 4.6 | 5.2 |
| SLC8A3 | 5.2 | 5.8 | 5.6 | 5.7 | 5.3 | 5.1 | 5.1 | 5.6 | 5.2 |
| TMEM163 | 5.1 | 5.8 | 4.7 | 4.9 | 5.0 | 4.6 | 4.5 | 5.0 | 4.5 |
| ABCB1 | 4.8 | 5.2 | 4.8 | 4.9 | 4.7 | 4.6 | 4.7 | 4.8 | 5.1 |
| ADGRG6 | 3.8 | 4.0 | 3.5 | 3.7 | 3.5 | 5.8 | 3.6 | 3.6 | 3.6 |
| ATP9A | 6.1 | 5.2 | 6.8 | 5.1 | 5.2 | 5.6 | 6.7 | 5.1 | 5.7 |
| CACHD1 | 5.2 | 4.8 | 4.6 | 4.6 | 4.4 | 5.1 | 4.5 | 4.7 | 4.9 |
| CDCP1 | 5.8 | 5.3 | 5.7 | 5.3 | 5.4 | 5.5 | 5.3 | 5.2 | 5.3 |
| CYYR1 | 4.0 | 4.1 | 3.9 | 3.8 | 3.7 | 3.8 | 3.9 | 3.8 | 3.8 |
| EMCN | 4.3 | 4.5 | 4.0 | 4.3 | 4.2 | 4.3 | 4.2 | 4.2 | 4.3 |
| JAM2 | 5.2 | 5.4 | 5.0 | 5.1 | 5.0 | 5.2 | 5.2 | 5.1 | 5.2 |
| PCDH9 | 5.4 | 4.5 | 4.3 | 4.7 | 4.6 | 6.0 | 4.7 | 4.7 | 4.6 |
| SLC16A14 | 4.3 | 4.4 | 3.9 | 4.0 | 4.2 | 4.1 | 4.2 | 4.1 | 4.0 |
| TMEM136 | 4.0 | 3.6 | 3.4 | 3.7 | 3.9 | 4.0 | 3.8 | 3.6 | 4.0 |
| TMEM200A | 3.9 | 3.4 | 3.4 | 3.4 | 3.4 | 3.6 | 3.5 | 3.4 | 3.4 |
| ADGRL4 | 3.6 | 3.6 | 3.3 | 3.5 | 3.6 | 3.6 | 3.6 | 3.5 | 3.6 |
| ART4 | 3.7 | 4.0 | 3.6 | 3.6 | 3.7 | 3.7 | 3.8 | 3.7 | 3.7 |
| ATP8B1 | 3.5 | 3.5 | 3.4 | 3.9 | 3.8 | 3.5 | 3.7 | 3.6 | 3.5 |
| BACE2 | 3.6 | 3.1 | 3.0 | 3.2 | 3.3 | 3.3 | 3.2 | 3.2 | 3.3 |
| CALCRL | 4.6 | 4.7 | 4.2 | 4.7 | 4.2 | 4.2 | 4.1 | 4.8 | 4.2 |
| CNTNAP3 | 3.6 | 3.9 | 3.6 | 3.6 | 3.5 | 3.8 | 3.8 | 4.3 | 3.7 |
| LIFR | 3.6 | 3.5 | 3.2 | 3.4 | 3.5 | 3.6 | 3.6 | 3.5 | 3.5 |
| MET | 3.8 | 3.8 | 3.6 | 3.8 | 3.8 | 3.9 | 3.9 | 3.8 | 3.9 |
| MPZL2 | 3.7 | 3.5 | 3.2 | 3.3 | 3.2 | 3.4 | 3.2 | 3.2 | 3.1 |
| NCKAP1 | 3.8 | 3.7 | 3.4 | 3.5 | 3.6 | 3.6 | 3.6 | 3.5 | 3.6 |
| PLSCR4 | 4.1 | 4.1 | 3.4 | 3.5 | 3.6 | 3.6 | 3.7 | 3.5 | 3.6 |
| PTPRB | 3.5 | 3.4 | 3.3 | 3.4 | 3.4 | 3.4 | 3.4 | 3.4 | 3.4 |
| TMEM47 | 3.5 | 3.4 | 3.4 | 3.4 | 3.4 | 3.4 | 3.5 | 3.3 | 3.4 |
| WLS | 4.0 | 4.5 | 3.9 | 4.1 | 3.8 | 4.0 | 4.4 | 4.1 | 4.0 |

Table 20. Gene Expression in Healthy Hematopoietic Cells

TABLE 20

| Gene expression in Healthy Hematopoietic Cells | | | | | | | | | | | | | | |
|---|---|---|---|---|---|---|---|---|---|---|---|---|---|---|
| Gene Symbol | Hematopoietic stem cell (HSC) [22] | Lymphoid-primed multipotent progenitor (LMPP) [7] | Late promyelocyte (PM) [3] | Megakaryocyte erythrocyte progenitor (MEP) [15] | Metamyelocyte (MM) [3] | Multipotent progenitor (MPP) [17] | Myelocyte (MY) [4] | Monocyte [8] | Neutrophil [3] | Promyelocyte (PM) [2] | Polymorphonuclear cell (PMN) [3] | Pre-B cell [2] | Pro-B cell [2] | Common myeloid progenitor (CMP) [16] |
| CALN1 | 8.4 | 5.7 | 3.6 | 4.3 | 3.5 | 7.7 | 3.5 | 3.5 | 3.6 | 3.5 | 3.4 | 3.7 | 4.1 | 5.4 |
| IL12RB2 | 7.3 | 6.3 | 4.0 | 4.9 | 3.7 | 6.8 | 3.9 | 4.2 | 4.3 | 4.1 | 3.8 | 4.5 | 6.9 | 5.6 |
| ABCA13 | 6.6 | 4.2 | 7.0 | 3.4 | 9.2 | 5.6 | 9.5 | 3.3 | 3.3 | 8.4 | 3.7 | 5.7 | 3.5 | 3.8 |
| CDH26 | 6.4 | 7.0 | 5.9 | 5.0 | 5.3 | 6.4 | 5.0 | 4.6 | 4.8 | 6.6 | 6.0 | 5.3 | 4.5 | 6.0 |
| IL18R1 | 6.4 | 5.0 | 4.1 | 4.2 | 6.9 | 5.9 | 6.4 | 4.5 | 7.6 | 4.1 | 9.6 | 7.0 | 4.1 | 4.7 |
| SLC8A3 | 7.9 | 6.2 | 4.1 | 6.3 | 3.7 | 7.6 | 4.5 | 5.4 | 5.7 | 5.4 | 4.0 | 4.9 | 4.9 | 6.5 |
| TMEM163 | 7.6 | 5.9 | 4.2 | 4.7 | 4.3 | 7.0 | 4.0 | 4.6 | 4.4 | 4.3 | 4.2 | 4.1 | 4.7 | 5.8 |
| ABCB1 | 7.8 | 6.6 | 4.6 | 5.0 | 4.8 | 7.2 | 4.5 | 4.7 | 4.6 | 4.3 | 4.7 | 4.9 | 4.4 | 5.5 |
| ADGRG6 | 9.9 | 7.9 | 4.0 | 4.3 | 3.4 | 9.0 | 3.6 | 3.8 | 3.5 | 3.6 | 3.6 | 3.9 | 3.9 | 6.2 |
| ATP9A | 9.5 | 7.4 | 6.8 | 5.7 | 9.7 | 8.8 | 7.9 | 5.2 | 5.6 | 6.2 | 8.5 | 5.9 | 5.9 | 6.8 |
| CACHD1 | 7.1 | 6.4 | 4.2 | 4.6 | 4.3 | 6.9 | 4.4 | 4.5 | 4.5 | 4.4 | 5.1 | 4.5 | 4.8 | 5.4 |
| CDCP1 | 7.8 | 7.8 | 4.9 | 5.7 | 4.8 | 7.7 | 5.0 | 5.2 | 5.6 | 5.6 | 4.7 | 5.1 | 6.0 | 6.2 |
| CYYR1 | 7.5 | 7.0 | 8.6 | 6.5 | 7.8 | 7.0 | 7.2 | 3.8 | 4.2 | 7.6 | 4.8 | 4.0 | 5.8 | 6.2 |
| EMCN | 8.7 | 6.0 | 4.0 | 4.4 | 4.2 | 6.9 | 4.1 | 4.6 | 4.6 | 4.2 | 4.0 | 4.6 | 5.1 | 4.8 |
| JAM2 | 8.5 | 8.2 | 5.6 | 5.5 | 5.0 | 7.7 | 4.9 | 4.9 | 5.0 | 5.0 | 5.4 | 5.1 | 6.5 | 6.6 |
| PCDH9 | 10.5 | 7.8 | 4.4 | 7.0 | 4.1 | 10.0 | 4.4 | 4.7 | 4.7 | 5.0 | 4.6 | 7.5 | 8.4 | 8.9 |
| SLC16A14 | 7.0 | 7.6 | 5.1 | 4.3 | 8.4 | 6.4 | 8.0 | 4.2 | 5.2 | 5.1 | 4.1 | 5.9 | 7.3 | 5.0 |
| TMEM136 | 6.2 | 4.6 | 3.7 | 4.2 | 3.8 | 5.4 | 3.7 | 3.8 | 3.9 | 3.7 | 3.9 | 4.1 | 4.0 | 4.8 |
| TMEM200A | 8.0 | 7.4 | 3.9 | 3.8 | 3.6 | 7.1 | 3.5 | 3.3 | 3.5 | 3.4 | 3.5 | 4.6 | 5.6 | 4.0 |
| ADGRL4 | 3.4 | 3.4 | 3.3 | 3.5 | 3.4 | 3.4 | 3.4 | 3.5 | 3.6 | 3.4 | 3.4 | 3.4 | 3.5 | 3.4 |
| ART4 | 3.5 | 3.6 | 3.4 | 3.7 | 3.7 | 3.6 | 3.5 | 3.6 | 3.8 | 3.8 | 3.5 | 3.2 | 3.4 | 3.7 |

TABLE 20-continued

Gene expression in Healthy Hematopoietic Cells

| | | | | | | | | | | | | | | |
|---|---|---|---|---|---|---|---|---|---|---|---|---|---|---|
| ATP8B1 | 3.8 | 4.0 | 4.0 | 3.6 | 3.6 | 3.7 | 3.7 | 3.5 | 3.6 | 3.3 | 3.7 | 3.3 | 3.5 | 3.6 |
| BACE2 | 3.8 | 3.3 | 3.5 | 4.1 | 3.3 | 3.9 | 3.4 | 3.1 | 3.6 | 3.6 | 3.2 | 3.4 | 3.2 | 5.3 |
| CALCRL | 4.5 | 4.1 | 3.9 | 4.3 | 4.1 | 4.3 | 4.0 | 4.9 | 4.2 | 4.2 | 3.9 | 4.7 | 4.1 | 4.3 |
| CNTNAP3 | 3.5 | 3.5 | 3.4 | 3.4 | 6.4 | 3.5 | 5.2 | 3.7 | 7.8 | 3.6 | 7.2 | 3.7 | 3.6 | 3.6 |
| LIFR | 3.6 | 3.6 | 3.7 | 3.7 | 3.5 | 3.7 | 3.6 | 3.4 | 3.5 | 3.6 | 3.6 | 3.5 | 3.6 | 3.7 |
| MET | 3.9 | 3.9 | 3.6 | 4.0 | 4.0 | 3.8 | 3.7 | 3.7 | 3.8 | 4.1 | 3.9 | 3.8 | 3.8 | 4.0 |
| MPZL2 | 4.7 | 3.8 | 3.1 | 3.3 | 3.5 | 3.9 | 3.7 | 4.9 | 5.1 | 3.2 | 5.6 | 4.8 | 3.2 | 3.4 |
| NCKAP1 | 4.7 | 3.7 | 3.5 | 4.4 | 3.6 | 4.4 | 3.5 | 3.4 | 3.4 | 3.7 | 3.6 | 3.7 | 3.7 | 3.9 |
| PLSCR4 | 7.6 | 5.7 | 4.6 | 5.8 | 3.2 | 7.1 | 3.8 | 3.5 | 3.5 | 4.2 | 3.8 | 3.5 | 4.2 | 5.7 |
| PTPRB | 3.4 | 3.4 | 3.3 | 3.4 | 3.3 | 3.5 | 3.4 | 3.5 | 3.5 | 3.3 | 3.3 | 3.5 | 3.4 | 3.5 |
| TMEM47 | 3.6 | 3.5 | 3.5 | 3.5 | 3.3 | 3.6 | 3.3 | 3.5 | 3.4 | 3.4 | 3.4 | 3.4 | 3.3 | 3.6 |
| WLS | 3.9 | 3.8 | 4.5 | 4.0 | 6.3 | 3.8 | 6.5 | 7.2 | 8.2 | 4.0 | 9.3 | 6.8 | 3.8 | 4.0 |

| Gene Symbol | Early pro-mye-locyte (PM) [3] | Erythro-blast [7] | Granulocyte macro-phage progenitor (GMP) [18] | Healthy umbi-lical cord blood (H UB) [3] | Healthy whole bone marrow (H WBM) [74] | B cell [4] | B naïve [2] | Band cell [4] | CD4 T cell [3] | CD8 T cell [5] | CD8 T central [3] | CD8 T effector [8] | CD8 T naïve [3] |
|---|---|---|---|---|---|---|---|---|---|---|---|---|---|
| CALN1 | 3.7 | 3.5 | 4.9 | 6.8 | 3.6 | 3.6 | 3.5 | 3.8 | 3.5 | 3.5 | 3.4 | 3.4 | 3.5 |
| IL12RB2 | 4.6 | 4.3 | 5.5 | 6.2 | 4.3 | 4.3 | 4.1 | 3.9 | 5.0 | 4.7 | 4.5 | 4.4 | 4.6 |
| ABCA13 | 4.8 | 3.1 | 3.6 | 8.9 | 7.8 | 3.2 | 4.1 | 3.9 | 3.2 | 3.3 | 3.2 | 3.2 | 3.2 |
| CDH26 | 6.0 | 3.9 | 6.5 | 7.2 | 5.2 | 4.3 | 4.5 | 5.5 | 4.4 | 4.5 | 4.2 | 4.3 | 4.4 |
| IL18R1 | 3.8 | 4.4 | 5.3 | 5.0 | 6.3 | 4.7 | 4.9 | 9.7 | 5.6 | 5.9 | 5.8 | 5.3 | 5.2 |
| SLC8A3 | 3.8 | 5.3 | 5.2 | 6.7 | 5.0 | 5.9 | 4.9 | 3.8 | 5.4 | 5.8 | 5.3 | 5.3 | 5.5 |
| TMEM163 | 4.5 | 4.4 | 5.1 | 5.5 | 4.6 | 4.5 | 4.9 | 4.2 | 4.6 | 4.8 | 4.5 | 4.7 | 4.6 |
| ABCB1 | 4.4 | 4.5 | 4.9 | 7.3 | 4.7 | 5.1 | 4.7 | 4.8 | 4.9 | 5.7 | 6.7 | 7.3 | 6.3 |
| ADGRG6 | 5.0 | 3.7 | 6.2 | 9.0 | 3.9 | 3.8 | 3.6 | 3.5 | 4.0 | 4.0 | 3.7 | 3.7 | 3.6 |
| ATP9A | 7.1 | 5.5 | 6.8 | 9.6 | 6.7 | 5.7 | 5.1 | 10.5 | 5.4 | 5.7 | 5.4 | 5.2 | 5.0 |
| CACHD1 | 4.2 | 4.3 | 5.2 | 5.9 | 4.5 | 4.6 | 4.2 | 6.0 | 4.7 | 4.9 | 4.7 | 4.9 | 4.8 |
| CDCP1 | 4.5 | 5.1 | 6.4 | 8.4 | 5.3 | 5.2 | 5.4 | 5.1 | 5.2 | 5.2 | 5.2 | 5.2 | 5.1 |
| CYYR1 | 8.0 | 3.8 | 6.2 | 5.9 | 5.1 | 4.2 | 3.7 | 6.8 | 3.9 | 3.9 | 4.1 | 4.1 | 4.3 |
| EMCN | 4.0 | 4.5 | 4.5 | 7.4 | 4.3 | 4.7 | 4.3 | 4.1 | 4.9 | 4.9 | 4.6 | 4.5 | 4.5 |
| JAM2 | 5.1 | 4.8 | 7.1 | 8.2 | 5.2 | 5.3 | 6.6 | 5.0 | 5.0 | 5.1 | 5.0 | 5.3 | 5.3 |
| PCDH9 | 4.2 | 4.6 | 6.1 | 7.7 | 6.1 | 9.0 | 9.9 | 4.2 | 4.8 | 5.5 | 4.5 | 4.6 | 4.5 |
| SLC16A14 | 4.3 | 4.1 | 5.9 | 8.1 | 6.7 | 4.7 | 5.7 | 4.5 | 4.7 | 4.5 | 4.2 | 3.9 | 4.0 |
| TMEM136 | 3.7 | 3.8 | 4.7 | 4.9 | 3.9 | 4.0 | 4.0 | 4.0 | 3.9 | 3.9 | 3.8 | 3.7 | 3.8 |
| TMEM200A | 3.6 | 3.4 | 5.0 | 10.0 | 3.7 | 3.5 | 3.7 | 3.4 | 4.0 | 3.9 | 4.2 | 3.9 | 3.7 |
| ADGRL4 | 3.3 | 3.5 | 3.6 | 3.4 | 3.8 | 3.6 | 3.3 | 3.6 | 3.5 | 3.8 | 3.5 | 3.4 | 3.4 |
| ART4 | 3.3 | 5.7 | 3.7 | 3.7 | 4.9 | 3.8 | 3.5 | 3.6 | 3.6 | 3.7 | 3.8 | 3.8 | 3.7 |
| ATP8B1 | 4.2 | 3.7 | 3.7 | 3.4 | 3.4 | 3.6 | 3.4 | 3.8 | 3.6 | 3.7 | 3.5 | 3.4 | 3.4 |
| BACE2 | 3.3 | 3.3 | 3.4 | 3.2 | 3.4 | 3.8 | 5.7 | 3.3 | 3.1 | 3.2 | 3.3 | 3.2 | 3.2 |
| CALCRL | 4.2 | 4.3 | 4.5 | 4.7 | 4.0 | 4.1 | 3.9 | 4.0 | 4.5 | 4.4 | 4.1 | 4.2 | 4.2 |
| CNTNAP3 | 3.4 | 3.8 | 3.6 | 3.6 | 4.1 | 3.7 | 3.5 | 7.4 | 3.5 | 3.7 | 3.9 | 3.9 | 3.8 |
| LIFR | 3.7 | 3.4 | 3.7 | 3.6 | 3.7 | 3.7 | 3.3 | 3.6 | 3.6 | 3.7 | 3.5 | 3.5 | 3.6 |
| MET | 3.8 | 3.8 | 4.1 | 3.8 | 3.9 | 4.0 | 3.7 | 3.9 | 4.0 | 4.0 | 3.8 | 3.8 | 3.7 |
| MPZL2 | 3.1 | 3.1 | 3.8 | 4.8 | 3.4 | 3.1 | 3.2 | 4.7 | 3.3 | 3.3 | 3.1 | 3.1 | 3.1 |
| NCKAP1 | 3.3 | 4.1 | 3.7 | 3.5 | 4.1 | 3.6 | 3.5 | 3.4 | 3.8 | 3.7 | 4.9 | 4.3 | 4.4 |
| PLSCR4 | 4.5 | 6.7 | 5.4 | 6.3 | 4.8 | 3.5 | 3.3 | 3.5 | 3.5 | 3.6 | 3.6 | 3.5 | 3.5 |
| PTPRB | 3.3 | 3.3 | 3.5 | 3.4 | 3.4 | 3.5 | 3.5 | 3.4 | 3.5 | 3.5 | 3.4 | 3.4 | 3.5 |
| TMEM47 | 3.3 | 3.4 | 3.7 | 3.8 | 3.4 | 3.5 | 3.4 | 3.4 | 3.4 | 3.6 | 3.5 | 3.6 | 3.6 |
| WLS | 4.7 | 4.2 | 4.1 | 3.9 | 4.9 | 4.5 | 4.1 | 7.7 | 4.3 | 4.2 | 4.3 | 4.2 | 4.3 |

Table 21. Gene Expression in Endothelial Cells

TABLE 21

Gene Expression in Endothelial Cells

| Gene Symbol | Human aortic endo-thelial cell (HAEC) [2] | Human coronary artery endo-thelial cell (HCAEC) [2] | Human Microvascular Endothelial Cells (HMVEC)_qui [3] | Human Umbilical Artery Endo-thelial Cell (HUAEC) [5] | Human umbilical vein endo-thelial cell (HUVEC) [5] | Human Pulmonary Artery Endo-thelial Cell (PAEC) [6] | Pulmonary micro-vascular endo-thelial cell (PMVEC) [6] | Human Umbilical Artery Endothelial Cell (HUAEC)_fresh [4] | Human umbilical vein endothelial cell (HUVEC)_fresh [4] | Human umbilical vein endothelial cell (HUVEC)_pri-mary [2] |
|---|---|---|---|---|---|---|---|---|---|---|
| CALN1 | 3.3 | 3.5 | 3.3 | 3.3 | 3.4 | 3.4 | 3.5 | 3.3 | 3.4 | 3.4 |
| IL12RB2 | 3.8 | 4.0 | 3.8 | 4.0 | 4.1 | 3.9 | 3.9 | 4.0 | 4.0 | 4.6 |
| ABCA13 | 3.2 | 3.2 | 3.2 | 3.4 | 3.7 | 3.2 | 3.2 | 3.2 | 3.3 | 3.2 |
| CDH26 | 4.0 | 3.9 | 3.8 | 3.7 | 4.0 | 3.9 | 3.8 | 4.1 | 4.5 | 3.7 |
| IL18R1 | 5.3 | 6.4 | 3.9 | 5.5 | 5.1 | 4.2 | 4.3 | 6.7 | 8.3 | 6.4 |
| SLC8A3 | 4.8 | 5.0 | 4.7 | 4.9 | 5.2 | 4.9 | 4.9 | 4.8 | 4.9 | 4.6 |

TABLE 21-continued

Gene Expression in Endothelial Cells

| Gene Symbol | Human aortic endo-thelial cell (HAEC) [2] | Human coronary artery endo-thelial cell (HCAEC) [2] | Human Microvascular Endothelial Cells (HMVEC)_qui [3] | Human Umbilical Artery Endo-thelial Cell (HUAEC) [5] | Human umbilical vein endo-thelial cell (HUVEC) [5] | Human Pulmonary Artery Endo-thelial Cell (PAEC) [6] | Pulmonary micro-vascular endo-thelial cell (PMVEC) [6] | Human Umbilical Artery Endothelial Cell (HUAEC)_fresh [4] | Human umbilical vein endothelial cell (HUVEC)_fresh [4] | Human umbilical vein endothelial cell (HUVEC)_pri-mary [2] |
|---|---|---|---|---|---|---|---|---|---|---|
| TMEM163 | 5.3 | 5.7 | 5.0 | 4.3 | 4.6 | 4.4 | 4.4 | 4.2 | 4.4 | 4.4 |
| ABCB1 | 7.0 | 5.2 | 4.3 | 5.6 | 5.0 | 4.3 | 4.3 | 4.6 | 4.4 | 4.6 |
| ADGRG6 | 6.0 | 8.6 | 6.4 | 8.8 | 7.7 | 5.8 | 5.4 | 12.2 | 11.2 | 9.5 |
| ATP9A | 9.9 | 10.2 | 9.0 | 10.3 | 9.6 | 9.5 | 9.7 | 10.0 | 9.4 | 8.1 |
| CACHD1 | 6.4 | 6.6 | 7.3 | 6.7 | 6.6 | 7.9 | 7.8 | 6.8 | 7.6 | 6.9 |
| CDCP1 | 5.4 | 6.9 | 5.4 | 6.7 | 6.8 | 5.2 | 5.4 | 5.2 | 5.2 | 5.8 |
| CYYR1 | 8.7 | 7.2 | 4.9 | 6.4 | 6.7 | 7.5 | 7.6 | 9.2 | 9.9 | 3.9 |
| EMCN | 11.2 | 9.8 | 10.4 | 10.3 | 9.6 | 10.9 | 10.9 | 9.5 | 11.6 | 6.8 |
| JAM2 | 5.7 | 6.2 | 5.0 | 6.8 | 7.0 | 4.9 | 5.0 | 10.1 | 9.5 | 4.6 |
| PCDH9 | 9.0 | 7.3 | 8.5 | 6.6 | 6.4 | 5.6 | 5.3 | 5.5 | 6.4 | 5.6 |
| SLC16A14 | 6.8 | 3.9 | 3.9 | 4.5 | 4.3 | 3.7 | 4.0 | 9.1 | 7.7 | 3.9 |
| TMEM136 | 5.8 | 6.0 | 5.5 | 6.1 | 5.8 | 5.2 | 5.3 | 5.9 | 5.7 | 4.8 |
| TMEM200A | 3.6 | 6.3 | 3.6 | 8.3 | 7.9 | 3.4 | 3.4 | 8.0 | 3.7 | 5.5 |
| ADGRL4 | 10.8 | 10.6 | 10.3 | 9.7 | 8.9 | 10.7 | 10.8 | 10.6 | 9.6 | 9.2 |
| ART4 | 9.5 | 7.1 | 7.0 | 9.2 | 6.1 | 9.3 | 9.3 | 9.8 | 10.1 | 6.0 |
| ATP8B1 | 10.6 | 9.8 | 9.0 | 10.6 | 9.1 | 7.2 | 6.9 | 9.8 | 8.9 | 8.8 |
| BACE2 | 9.2 | 8.2 | 8.0 | 8.8 | 6.6 | 10.8 | 11.0 | 10.6 | 8.9 | 6.3 |
| CALCRL | 8.0 | 7.8 | 9.1 | 5.6 | 4.7 | 9.7 | 9.8 | 9.6 | 10.0 | 6.5 |
| CNTNAP3 | 9.7 | 8.9 | 7.8 | 7.3 | 7.2 | 8.9 | 9.0 | 9.1 | 9.4 | 6.6 |
| LIFR | 7.5 | 7.7 | 7.2 | 7.2 | 5.8 | 8.3 | 8.3 | 9.1 | 10.5 | 6.7 |
| MET | 9.3 | 9.9 | 9.2 | 9.6 | 7.9 | 9.1 | 9.1 | 9.4 | 10.6 | 10.4 |
| MPZL2 | 8.7 | 9.3 | 9.1 | 5.9 | 4.9 | 6.1 | 5.7 | 10.3 | 10.2 | 8.5 |
| NCKAP1 | 10.6 | 10.2 | 9.7 | 10.5 | 9.3 | 9.4 | 9.5 | 10.8 | 10.1 | 9.7 |
| PLSCR4 | 11.1 | 10.2 | 10.6 | 11.0 | 9.4 | 12.5 | 12.4 | 11.2 | 11.6 | 6.9 |
| PTPRB | 10.8 | 9.5 | 10.1 | 9.4 | 7.7 | 8.9 | 9.0 | 12.7 | 11.7 | 4.7 |
| TMEM47 | 9.7 | 10.0 | 9.0 | 10.6 | 8.9 | 6.5 | 6.3 | 10.9 | 10.5 | 7.0 |
| WLS | 9.0 | 8.6 | 9.2 | 7.8 | 7.8 | 8.1 | 7.9 | 8.7 | 8.5 | 8.3 |

Example 27: Characterization of Monovalent and Bicistronic FTL3 and CD33 CAR Natural Killer (NK) Cells Materials and Methods CAR Expression in NK Cells Primary NK cells were isolated from PBMCs and frozen. Frozen NK cells were thawed and activated with CD335 (NKp46)-Biotin, CD2-Biotin, and MACS Anti-Biotin MACSiBead Particles. Activated NK cells were expanded in NK MACS Medium with IL-2 and frozen on day 15. When ready, the expanded NK cells were thawed and rested in complete medium overnight. NK cells were transduced with selected CAR lentivirus, to produce FLT3 CAR (SB00819) NK cells, CD33 CAR (SB01052) NK cells, or bicistronic FLT3 and CD33 CAR (SB01659) NK cells. CAR expression was assessed on day 6 after transfection.

NK Cell Cytotoxicity Assay

An NK cell cytotoxicity assay and cytokine production assay were performed as described in Examples 15-18, using SEM cells and an ET ration of 1:2. CAR NK cells were incubated with the SEM target cells for 20 hours and the cell supernatant was collected for cytokine production. Cytotoxicity and cytokine production was assessed by flow cytometry and Luminex assay as previously described. Cytotoxicity percentage was normalized to a target cell only control. Non-engineered NK cells expressing EGFP were used as a negative control.

An NK cell cytotoxicity assay was performed as described in Examples 15-18, using PL-21 AML cells. PL-21 AML cells are known to express FLT3 and CD33 (Reiter K, et al, Leukemia (2018) 32, 313-322 shows FLT3 expression in PL-21 cells and Kearney C J, et al, OncoImmunology, 5:8, e1196308, DOI: 10.1080/2162402X.2016.1196308 shows CD33 expression in PL-21 cells, both of which are incorporated by reference).

Results

NK cells show up to 45% CAR expression at day 6 after lentivirus transduction. The FLT3 CAR NK cells were 28.8% positive for the FLT3 CAR (data not shown). The CD33 CAR NK cells were 25.8% positive for the CD33 CAR (data not shown). The bicistronic FLT3/CD33 CAR NK cells were 3.9% positive for the FLT3 CAR and 26.9% positive for CD33 (data not shown).

Figure 66A:
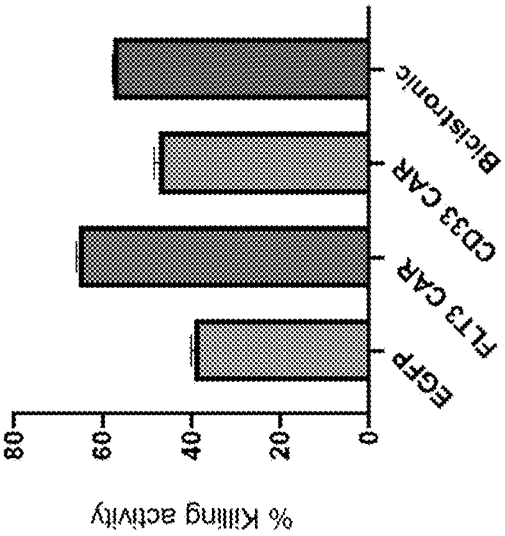
FIG. 66A shows FLT3, CD33, and FLT3/CD33 CAR NK cell killing of SEM cells.
Figure 66B:
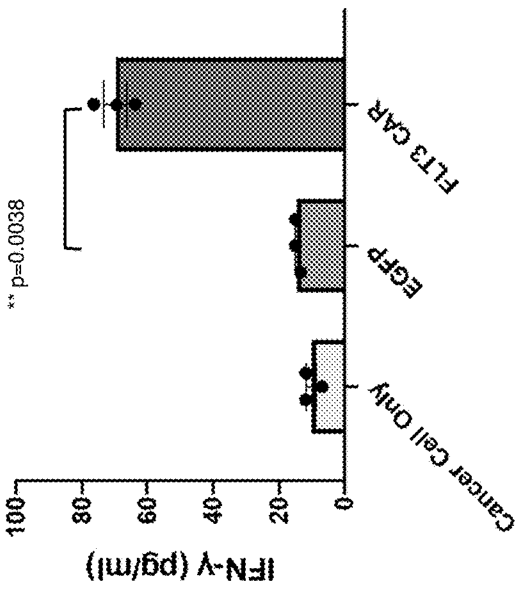
FIG. 66B shows IFN-γ secretion by FLT3 CAR NK cells after incubation with SEM cells.
Figure 66C:
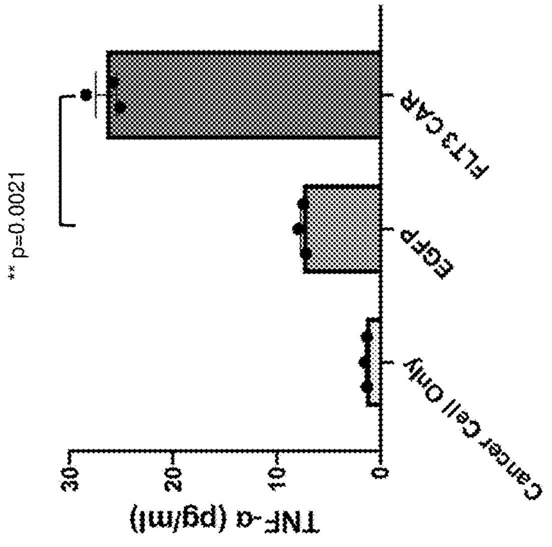
FIG. 66C shows TNF-α secretion by FLT3 CAR NK cells after incubation with SEM cells.

CAR NK cells demonstrated significant cytotoxicity and cytokine production against SEM cells. The FLT3 CAR NK cells (SB00819), the CD33 CAR NK cells (SB01052), and the FLT3 OR CD33 bicistronic CAR NK cells (SB01659) demonstrated statistically significant killing activity of SEM cells as compared to the EGFP negative control NK cells (FIG. 66A). The FLT3 CAR NK cells showed significantly greater IFN-γ (FIG. 66B) and TNF-α (FIG. 66C) cytokine secretion compared to EGFP negative control NK cells after co-culture with SEM cells.

Figure 66D:
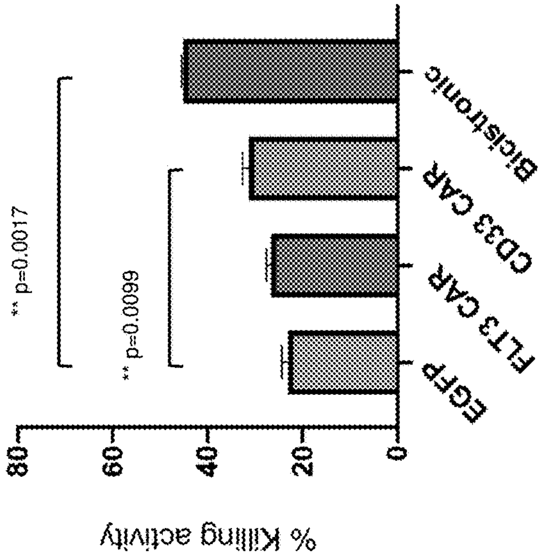
FIG. 66D shows FLT3, CD33, and FLT3/CD33 CAR NK cell killing of PL-21 cells.

The FLT3, CD33, and FLT3/CD33 CAR NK cells also demonstrated significant cytotoxicity against PL-21 cells. The CD33 CAR NK cells (SB01052), and the FLT3 OR CD33 bicistronic CAR NK cells (SB01659) show significant cytotoxicity against PL-21 AML cells as compared to EGFP control NK cells (FIG. 66D). The FLT3 CAR NK cells (SB00819) showed a trend towards increased killing of PL-21 cells compared to EGFP control NK cells.

Thus, monovalent FLT3 CAR NK cells, monovalent CD33 CAR NK cells, and bicistronic FLT3/CD33 CAR NK cells were effective in killing two different AML target cells and secreting cytokines.

INCORPORATION BY REFERENCE

All publications, patents, patent applications and other documents cited in this application are hereby incorporated by reference in their entireties for all purposes to the same extent as if each individual publication, patent, patent application or other document were individually indicated to be incorporated by reference for all purposes.

EQUIVALENTS

While various specific embodiments have been illustrated and described, the above specification is not restrictive. It will be appreciated that various changes can be made without departing from the spirit and scope of the present disclosure(s). Many variations will become apparent to those skilled in the art upon review of this specification.

What is claimed is:

1. A method of treating a subject having acute myeloid leukemia (AML), wherein the method comprises delivering to the subject an autologous or an allogeneic T cell or Natural Killer (NK) cell comprising:

(a) an anti-FLT3 chimeric antigen receptor (CAR) comprising a FLT3-binding domain and an anti-CD33 CAR comprising a CD33-binding domain, or a bivalent CAR comprising a FLT3-binding domain and a CD33-binding domain, wherein the FLT3-binding domain comprises a heavy chain variable domain (VH) comprising a CDR-H1 sequence comprising the amino acid sequence of SEQ ID NO: 81, a CDR-H2 sequence comprising the amino acid sequence of SEQ ID NO: 82, and a CDR-H3 sequence comprising the amino acid sequence of SEQ ID NO: 83 and a light chain variable domain (VL) comprising a CDR-L1 sequence comprising the amino acid sequence of SEQ ID NO: 84, a CDR-L2 sequence comprising the amino acid sequence of SEQ ID NO: 85, and a CDR-L3 sequence comprising the amino acid sequence of SEQ ID NO: 86, and wherein the CD33-binding domain comprises VH comprising a CDR-H1 sequence comprising the amino acid sequence of SEQ ID NO: 123, a CDR-H2 sequence comprising the amino acid sequence of SEQ ID NO: 124, and a CDR-H3 sequence comprising the amino acid sequence of SEQ ID NO: 125 and a VL comprising a CDR-L1 sequence comprising the amino acid sequence of SEQ ID NO: 126, a CDR-L2 sequence comprising the amino acid sequence of SEQ ID NO: 127, and a CDR-L3 sequence comprising the amino acid sequence of SEQ ID NO: 128; and (b) an inhibitory chimeric receptor comprising an extracellular antigen-binding domain that binds to EMCN.

2. The method of claim 1, wherein the T cell or the NK cell comprises the bivalent CAR.

3. The method of claim 1, wherein the anti-FLT3 CAR and the anti-CD33 CAR, or the bivalent CAR comprises a CD3zeta-chain intracellular signaling domain and one or more additional intracellular signaling domains selected from the group consisting signaling domain, a CD2 intracellular signaling domain, an ICOS intracellular signaling domain, a CD27 intracellular signaling domain, a CD154 intracellular signaling domain, a CD8 intracellular signaling domain, an OX40 intracellular signaling domain, a 4-1BB intracellular signaling domain, a CD28 intracellular signaling domain, a ZAP40 intracellular signaling domain, a CD30 intracellular signaling domain, a GITR intracellular signaling domain, an HVEM intracellular signaling domain, a DAP10 intracellular signaling domain, a DAP12 intracellular signaling domain, a MyD88 intracellular signaling domain, and a 2B4 intracellular signaling domain.

4. The method of claim 3, wherein the anti-FLT3 CAR and the anti-CD33 CAR, or the bivalent CAR comprises a transmembrane domain selected from the group consisting of: a CD8 transmembrane domain, a CD28 transmembrane domain a CD3zeta-chain transmembrane domain, a CD4 transmembrane domain, a 4-1BB transmembrane domain, an OX40 transmembrane domain, an ICOS transmembrane domain, a CTLA-4 transmembrane domain, a PD-1 transmembrane domain, a LAG-3 transmembrane domain, a 2B4 transmembrane domain, and a BTLA transmembrane domain.

5. The method of claim 4, wherein the anti-FLT3 CAR and the anti-CD33 CAR, or the bivalent CAR comprises a spacer region between the antigen-binding domain and the transmembrane domain, and the spacer region has an amino acid sequence selected from the group consisting of the amino acid sequences of: SEQ ID NOs: 55-64.

6. The method of claim 1, wherein the inhibitory chimeric receptor comprises a scFv, and wherein the scFv comprises an antigen binding domain obtained from an anti-EMCN antibody.

7. The method of claim 1, wherein the FLT3-binding domain comprises an scFv and the CD33-binding domain comprises an scFv.

8. The method of claim 7, wherein the T cell or the NK cell comprises the bivalent CAR and wherein the scFvs are separated from each other by a peptide linker, and wherein the peptide linker comprises the amino acid sequence of SEQ ID NO: 27 or SEQ ID NO: 74.

9. The method of claim 8, wherein each of the scFvs comprises a VH and a VL, the VH and the VL are separated by a peptide linker, and wherein the peptide linker comprises the amino acid sequence of SEQ ID NO: 27.

10. The method of claim 1, wherein the T cell or the NK cell is allogeneic.

11. The method of claim 1, wherein the delivering comprises intravenous (IV) administration.

12. The method of claim 1, wherein the AML expresses CD33.

13. The method of claim 1, wherein the AML expresses FLT3.

14. The method of claim 1, wherein the AML expresses both CD33 and FLT3.

15. A method of providing an anti-tumor immunity in a subject, wherein the anti-tumor immunity comprises targeting AML, the method comprising administering to the subject in need thereof a therapeutically effective dose of an autologous or an allogeneic T cell or NK cell comprising:

(a) an anti-FLT3 CAR comprising a FLT3-binding domain and an anti-CD33 CAR comprising a CD33-binding domain, or a bivalent CAR comprising a FLT3-binding domain and a CD33-binding domain, wherein the FLT3-binding domain comprises a VH comprising a CDR-H1 sequence comprising the amino acid sequence of SEQ ID NO: 81, a CDR-H2 sequence comprising the amino acid sequence of SEQ ID NO: 82, and a CDR-H3 sequence comprising the amino acid sequence of SEQ ID NO: 83 and a VL comprising a CDR-L1 sequence comprising the amino acid sequence of SEQ ID NO: 84, a CDR-L2 sequence comprising the amino acid sequence of SEQ ID NO: 85, and a CDR-L3 sequence comprising the amino acid sequence of SEQ ID NO: 86, and wherein the CD33-binding domain comprises a VH comprising a CDR-H1 sequence comprising the amino acid sequence of SEQ ID NO: 123, a CDR-H2 sequence comprising the amino acid sequence of SEQ ID NO: 124, and a CDR-H3 sequence comprising the amino acid sequence of SEQ ID NO: 125 and a VL comprising a CDR-L1 sequence comprising the amino acid sequence of SEQ ID NO: 126, a CDR-L2 sequence comprising the amino acid sequence of SEQ ID NO: 127, and a CDR-L3 sequence comprising the amino acid sequence of SEQ ID NO: 128; and (b) an inhibitory chimeric receptor comprising an extracellular antigen-binding domain that binds to EMCN.

16. The method of claim 15, wherein the T cell or the NK cell comprises the bivalent CAR.

17. The method of claim 15, wherein the anti-FLT3 CAR and the anti-CD33 CAR, or the bivalent CAR comprises a CD3zeta-chain intracellular signaling domain and one or more additional intracellular signaling domains selected from the group consisting of: a CD97 intracellular signaling domain, a CD11a-CD18 intracellular signaling domain, a CD2 intracellular signaling domain, an ICOS intracellular signaling domain, a CD27 intracellular signaling domain, a CD154 intracellular signaling domain, a CD8 intracellular signaling domain, an OX40 intracellular signaling domain, a 4-1BB intracellular signaling domain, a CD28 intracellular signaling domain, a ZAP40 intracellular signaling domain, a CD30 intracellular signaling domain, a GITR intracellular signaling domain, an HVEM intracellular signaling domain, a DAP10 intracellular signaling domain, a DAP12 intracellular signaling domain, a MyD88 intracellular signaling domain, and a 2B4 intracellular signaling domain.

18. The method of claim 17, wherein the anti-FLT3 CAR and the anti-CD33 CAR, or the bivalent CAR comprises a transmembrane domain selected from the group consisting of: a CD8 transmembrane domain, a CD28 transmembrane domain a CD3zeta-chain transmembrane domain, a CD4 transmembrane domain, a 4-1BB transmembrane domain, an OX40 transmembrane domain, an ICOS transmembrane domain, a CTLA-4 transmembrane domain, a PD-1 transmembrane domain, a LAG-3 transmembrane domain, a 2B4 transmembrane domain, and a BTLA transmembrane domain.

19. The method of claim 18, wherein the anti-FLT3 CAR and the anti-CD33 CAR, or the bivalent CAR comprises a spacer region between the antigen-binding domain and the transmembrane domain, and the spacer region has an amino acid sequence selected from the group consisting of the amino acid sequences of: SEQ ID NOs: 55-64.

20. The method of claim 15, wherein the inhibitory chimeric receptor comprises a scFv, and wherein the scFv comprises an antigen binding domain obtained from an anti-EMCN antibody.

21. The method of claim 15, wherein the FLT3-binding domain comprises an scFv and the CD33-binding domain comprises an scFv.

22. The method of claim 21, wherein the T cell or the NK cell comprises the bivalent CAR and wherein the scFvs are separated from each other by a peptide linker, and wherein the peptide linker comprises the amino acid sequence of SEQ ID NO: 27 or SEQ ID NO: 74.

23. The method of claim 22, wherein each of the scFvs comprises a VH and a VL, the VH and the VL are separated by a peptide linker, and wherein the peptide linker comprises the amino acid sequence of SEQ ID NO: 27.

24. The method of claim 15, wherein the T cell or the NK cell is allogeneic.

25. The method of claim 15, wherein the administering comprises IV administration.

26. The method of claim 15, wherein the AML expresses CD33.

27. The method of claim 15, wherein the AML expresses FLT3.

28. The method of claim 15, wherein the AML expresses both CD33 and FLT3.

* * * * *

UNITED STATES PATENT AND TRADEMARK OFFICE
CERTIFICATE OF CORRECTION

PATENT NO.         : 12,005,081 B2
APPLICATION NO.    : 17/338528
DATED              : June 11, 2024
INVENTOR(S)        : Garrison et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 10 days.

Signed and Sealed this
Fifteenth Day of July, 2025

Coke Morgan Stewart
*Acting Director of the United States Patent and Trademark Office*